(12) United States Patent
Zhang et al.

(10) Patent No.: US 11,278,608 B2
(45) Date of Patent: Mar. 22, 2022

(54) NICOTINE NANOVACCINES AND USES THEREOF

(71) Applicant: VIRGINIA TECH INTELLECTUAL PROPERTIES, INC., Blacksburg, VA (US)

(72) Inventors: Chenming Zhang, Blacksburg, VA (US); Zongmin Zhao, Blacksburg, VA (US); Yun Hu, Blacksburg, VA (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 123 days.

(21) Appl. No.: 16/476,252

(22) PCT Filed: Jan. 5, 2017

(86) PCT No.: PCT/US2017/012269
§ 371 (c)(1),
(2) Date: Jul. 5, 2019

(87) PCT Pub. No.: WO2018/128610
PCT Pub. Date: Jul. 12, 2018

(65) Prior Publication Data
US 2019/0351037 A1 Nov. 21, 2019

(51) Int. Cl.
| | |
|---|---|
| *A61K 39/00* | (2006.01) |
| *A61K 39/39* | (2006.01) |
| *A61K 47/00* | (2006.01) |
| *A61K 45/06* | (2006.01) |
| *A61K 9/14* | (2006.01) |
| *A61P 25/34* | (2006.01) |
| *A61K 9/51* | (2006.01) |
| *A61K 39/385* | (2006.01) |

(52) U.S. Cl.
CPC ........ *A61K 39/0013* (2013.01); *A61K 9/5123* (2013.01); *A61K 9/5153* (2013.01); *A61K 39/385* (2013.01); *A61P 25/34* (2018.01); *A61K 2039/55505* (2013.01); *A61K 2039/55544* (2013.01); *A61K 2039/55555* (2013.01); *A61K 2039/55561* (2013.01); *A61K 2039/55572* (2013.01); *A61K 2039/55588* (2013.01); *A61K 2039/6081* (2013.01); *A61K 2039/6093* (2013.01)

(58) Field of Classification Search
CPC ........ A61P 37/04; A61P 35/00; A61P 31/00; A61P 37/02; A61K 39/39
See application file for complete search history.

(56) References Cited

U.S. PATENT DOCUMENTS

| | | |
|---|---|---|
| 8,932,595 B2 | 1/2015 | Iannacone et al. |
| 8,980,276 B2 | 3/2015 | Brown et al. |
| 2010/0092425 A1* | 4/2010 | Von Andrian .......... A61P 25/34 424/85.2 |
| 2010/0233251 A1 | 9/2010 | Von Andrian et al. |
| 2014/0037736 A1 | 2/2014 | Shi et al. |
| 2014/0127301 A1 | 5/2014 | Alexis et al. |

FOREIGN PATENT DOCUMENTS

| | | |
|---|---|---|
| AU | 2014210682 B2 | 10/2015 |
| CN | 102933237 A | 2/2013 |

OTHER PUBLICATIONS

International Search Report and Written Opinion issued by the United States International Searching Authority dated Apr. 20, 2017 for PCT/US2017/012269.
Hu, Yun et al., "The next-generation nicotine vaccine: a novel and potent hybrid nanoparticle-based nicotine vaccine," Biomaterials, vol. 106, pp. 228-239, Aug. 18, 2016.
Extended European Search Report issued by the European Patent Office dated Jun. 25, 2020 for counterpart European Application No. 17890825.7.
Hu, et al., "The next-generation nicotine vaccine: a novel and potent hybrid nanoparticle based nicotine vaccine", Biomaterials, Elsevier, Amsterdam, NL, vol. No. 106,, Aug. 18, 2016, pp. 228-239.
Zhao, et al., "A Nanoparticle-Based Nicotine Vaccine and the Influence of Particle Size on Its Immunogenicity and Efficacy", Nanomedicine: Nanotechnology, Biology and Medicine, vol. 13, Issue 2, Feb. 1, 2017, pp. 443-454.
Zhao, et al., "Hybrid nanoparticle-based nicotine nanovaccines: Boosting the immunological efficacy by conjugation of potent carrier proteins", Nanomedicine: Nanotechnology, Biology and Medicine, vol. 14, Issue 5, Apr. 30, 2018, pp. 1655-1665.
Papisov, M.I., "Acyclic Polyacetals from Polysaccharides: Biomimetic Biomedical "Stealth" Polymers," ACS Symposium Series, vol. 786, pp. 301-314, 2001.
Kabanov, et al., "DNA Complexes with Polycations for the Delivery of Genetic Material into Cells," Bioconjugate Chem., vol. 6, No. 1, pp. 7-20, Received: Jul. 22, 1994.
Boussif, et al., "A versatile vector for gene and oligonucleotide transfer into cells in culture and in vivo: Polyethylenimine," Proc. Natl. Acad. Sci. USA, vol. 92, pp. 7297-7301, Aug. 1995.
Kukowska-Latallo, et al., "Efficient transfer of genetic material into mammalian cells using Starburst polyamidoamine dendrimers," Proc. Natl. Acad. Sci., USA, Genetics, vol. 93, pp. 4897-4902, May 1996.
Tang, et al., "In Vitro Gene Delivery by Degraded Polyamidoamine Dendrimers," Bioconjugate Chem., vol. 7, No. 6, pp. 703-174, Received: Jul. 25, 1996.
Haensler, et al., "Polyamidoamine Cascade Polymers Mediate Efficient Transfection of Cells in Culture," Bioconjugate Chem., vol. 4, pp. 372-379, Received: May 7, 1993.
Putnam, et al., "Poly(4-hydroxy-L-proline ester): Low-Temperature Polycondensation and Plasmid DNA Complexation," Macromolecules, vol. 32, pp. 3658-3662, Received: Mar. 23, 1999.

(Continued)

*Primary Examiner* — Barry A Chestnut
(74) *Attorney, Agent, or Firm* — Carin R. Miller, Esq.; Johnson, Marcou, Isaacs & Nix, LLC

(57) ABSTRACT

Provided herein are nicotine polymer-stabilized nanoparticles, formulations thereof, and vaccines. Also provided herein are methods of treating and/or preventing nicotine addiction in a subject in need thereof.

20 Claims, 112 Drawing Sheets

(56) References Cited

OTHER PUBLICATIONS

Barrera, et al., Synthesis and RGD Peptide Modification of a New Biodegradable Copolymer: Poly(lactic acid-co-lysine), J. Am. Chem. Soc., vol. 115, pp. 11010-11011, Received: Jun. 21, 1993.
Kwon, et al., "Pseudopoly (amino acids): A Study of the Synthesis and Characterization of Poly(trans-4-hydroxy-iV-acyl-L-proline esters)," Macromolecules, vol. 22, pp. 3250-3255, Revised Manuscript Received: Jan. 3, 1989.
Lim, et al., "A Self-Destroying Polycationic Polymer: Biodegradable Poly(4-hydroxy-L-proline ester)," J. Am. Chem. Soc., vol. 121, No. 24, pp. 5633-5639, Received: Nov. 20, 1998.
Zhou, et al., "Preparation of Poly(L-serine ester): A Structural Analogue of Conventional Poly(L-serine)," Macromolecules, vol. 23, pp. 3399-3406, Revised Manuscript Received: Jan. 4, 1990.
Gao, et al., "In vivo molecular and cellular imaging with quantum dots,", Curr. Op. Biotechnol., vol. 16, pp. 63-72, Available online: Dec. 8, 2004.
Benowitz, NL., "Nicotine addiction," N Engl J Med., vol. 362, No. 24, pp. 2295-2303, Jun. 17, 2010.
Prochaska, et al., "The Past, Present, and Future of Nicotine Addiction Therapy," Annu Rev Med., vol. 67, pp. 467-486, Nov. 21, 2016.
Paolini, et al., "Mechanistic insights into nicotine withdrawal," Biochem Pharmacol., vol. 82, No. 8, pp. 996-1007, Oct. 15, 2011.
Stead LF, et al.,"Nicobrevin for smoking cessation (Review)," Cochrane Db Syst Rev. 2013.
Piper ME, et al., "Efficacy of bupropion alone and in combination with nicotine gum," Nicotine Tob Res., vol. 9, No. 9, pp. 947-954, Sep. 2007.
Koegelenberg CFN, et al., "Efficacy of Varenicline Combined With Nicotine Replacement Therapy vs Varenicline Alone for Smoking Cessation A Randomized Clinical Trial," Jama-J Am Med Assoc., vol. 312, No. 2, pp. 155-161, Jul. 9, 2014.
Pentel PR, LeSage MG., "New Directions in Nicotine Vaccine Design and Use," Adv Pharmacol., vol. 69, pp. 553-580, Jun. 6, 2014.
Raupach T., et al., "Nicotine vaccines to assist with smoking cessation:current status of research," Drugs., vol. 72, No. 4, pp. e1-16, 2012.
Goniewicz ML, et al., "Nicotine vaccines to treat tobacco dependence," Hum Vacc Immunother., vol. 9, No. 1, pp. 13-25, Accepted: Sep. 1, 2012.
Keyler DE, et al., "Enhanced immunogenicity of a bivalent nicotine vaccine," Int Immunopharmacol. vol. 8, No. 11, pp. 1589-1594, Nov. 2008.
McCiuskie MJ., et al., "Molecular attributes of conjugate antigen influence function of antibodies induced by anti-nicotine vaccine in mice and non-human primates," Int Immunopharmacol., vol. 25, pp. 518-527, Available online: Feb. 28, 2015.
Miller KD, et al., "Novel Anti-Nicotine Vaccine Using a Trimeric Coiled-Coil Hapten Carrier," Plos One, vol. 9, pp. 1-19, Dec. 10, 2014.
De Blasi M., et al., "Scientific overview: 2013 BBC plenary symposium on tobacco addiction," Drug Alcohol Depen., vol. 141, pp. 107-117, Aug. 2014.
Hatsukami DK, et al., "Immunogenicity and Smoking-Cessation Outcomes for a Novel Nicotine Immunotherapeutic," Clin Pharmacol Ther., vol. 89, No. 3, pp. 392-399, Mar. 2011.
Cornuz J.,et al., "A Vaccine against Nicotine for Smoking Cessation: A Randomized Controlled Trial," Plos One, vol. 3, No. 6, e2547, pp. 1-10, Jun. 2008.
Pryde DC, et al., "Selection of a Novel Anti-Nicotine Vaccine: Influence of Antigen Design on Antibody Function in Mice," Plos One, vol. 8, No. 10, e76557, pp. 1-16, Oct. 2013.
De Villiers SHL, et al., "Nicotine hapten structure, antibody selectivity and effect relationships: Results from a nicotine vaccine screening procedure," Vaccine, vol. 28, pp. 2161-2168, Available online: Jan. 7, 2010.
Chen XY, et al., "High immunogenicity of nicotine vaccines obtained by intradermal delivery with safe adjuvants," Vaccine, vol. 31, No. 1, pp. 159-164, Dec. 17, 2012.
McCiuskie MJ, et al., "Enhancing immunogenicity of a 3' aminomethylnicotine-DT-conjugate anti-nicotine vaccine with CpG adjuvant in mice and non-human primates," Int Immunopharmacol., vol. 16, pp. 50-56, Available online: Apr. 2, 2013.
Lockner JW, et al., "A Conjugate Vaccine Using Enantiopure Hapten Imparts Superior Nicotine-Binding Capacity," J Med Chem., vol. 58, pp. 1005-1011, Published: Dec. 10, 2014.
Collins KC, et al., "Investigating Hapten Clustering as a Strategy to Enhance Vaccines against Drugs of Abuse," Bioconjug Chem., vol. 25, pp. 593-600, Published: Feb. 12, 2014.
Hu Y, et al., "A novel and efficient nicotine vaccine using nano-lipoplex as a delivery vehicle," Hum Vacc Immunother., vol. 10, No. 1, pp. 64-72, Accepted: Sep. 26, 2013.
Zheng, H., et al., "Negatively Charged Carbon Nanohorn Supported Cationic Liposome Nanoparticles: A Novel Delivery Vehicle for Anti-Nicotine Vaccine," J Biomed Nanotechnol., vol. 11, No. 12, pp. 2197-2210, Dec. 2015.
Zhao Z., et al., "A nanoparticle-based nicotine vaccine and the influence of particle size on its immunogenicity and efficacy," Nanomed-Nanotechnol., vol. 13, No. 2, pp. 443-454, Feb. 2017.
Jacob NT, et al., "Investigations of Enantiopure Nicotine Haptens Using an Adjuvanting Carrier in Anti-Nicotine Vaccine Development," J Med Chem., vol. 59, pp. 2523-2529, Published: Feb. 26, 2016.
Parra J, et al., "Carbon nanotube-protein carriers enhance size-dependent self-adjuvant antibody response to haptens," J Control Release., vol. 170, No. 2, pp. 242-251, Sep. 10, 2013.
Sloat BR, et al., "Strong antibody responses induced by protein antigens conjugated onto the surface of lecithin-based nanoparticles," J Control Release, vol. 141, No. 1, pp. 93-100, Jan. 4, 2010.
Jalah R, et al., "Efficacy, but not antibody titer or affinity, of a heroin hapten conjugate vaccine correlates with increasing hapten densities on tetanus toxoid, but not on CRM197 carriers," Bioconjug Chem., vol. 26, No. 6, pp. 1041-1053, Jun. 17, 2015.
Pravetoni M, et al., "Structurally distinct nicotine immunogens elicit antibodies with non-overlapping specificities," Biochem Pharmacol., vol. 83, No. 4, pp. 543-550, Feb. 15, 2012.
De Villiers SHL, et al., "Increased efficacy of a trivalent nicotine vaccine compared to a dose-matched monovalent vaccine when formulated with alum," Vaccine. vol. 31, No. 52, pp. 6185-6193, Dec. 16, 2013.
Thangavel S, et al., "Redox nanoparticle increases the chemotherapeutic efficiency of pioglitazone and suppresses its toxic side effects," Biomaterials., vol. 99, pp. 109-123, Available online: May 13, 2016.
Liu, et al., "Multifunctional aptamer-based nanoparticles for targeted drug delivery to circumvent cancer resistance," Biomaterials., vol. 91, pp. 44-56, Available online: Mar. 10, 2016.
Qian Y, et al., "Targeting dendritic cells in lymph node with an antigen peptide-based nanovaccine for cancer immunotherapy," Biomaterials., vol. 98, pp. 171-183, Available online: May 5, 2016.
Yan SY, et al., "Polarized immune responses modulated by layered double hydroxides nanoparticle conjugated with CpG," Biomaterials., vol. 35, pp. 9508-9516, Available online: Aug. 19, 2014.
Rosalia RA, et al., "CD40-targeted dendritic cell delivery of PLGA-nanoparticle vaccines induce potent anti-tumor responses," Biomaterials., vol. 40, pp. 88-97, Available online: Nov. 26, 2014.
Chen MC, et al., "A review of the prospects for polymeric nanoparticle platforms in oral insulin delivery," Biomaterials, vol. 32, pp. 9826-9838, Available online: Sep. 17, 2011.
Mandai B.,et al., "Core-shell-type lipid-polymer hybrid nanoparticles as a drug delivery platform," Nanomed-Nanotechnol., vol. 9, No. 4, pp. 474-491, May 2013.
Park K., "Controlled drug delivery systems: Past forward and future back," J Control Release., vol. 190, pp. 3-8, Sep. 28, 2014.
Zhang LF, et al., "How to stabilize phospholipid liposomes (using nanoparticles)", Nano Lett., vol. 6, pp. 694-698, Received: Dec. 12, 2005.

(56) References Cited

OTHER PUBLICATIONS

Zhao PF, et al., "Improving drug accumulation and photothermal efficacy in tumor depending on size of ICG loaded lipid-polymer nanoparticles," Biomaterials., vol. 35, pp. 6037-6046, Available online: Apr. 26, 2014.
Mueller M, et al., "Coencapsulation of tumor lysate and CpG-ODB in PLGA-microspheres enables successful immunotherapy of prostate carcinoma in TRAMP mice," J Control Release, vol. 62, pp. 159-166, 2012.
Wang Q, et al., "Time course study of the antigen-specific immune response to a PLGA microparticle vaccine formulation," Biomaterials., vol. 35, pp. 8385-8393, Available online: Jun. 27, 2014.
Ibricevic A, et al., "PEGylation of cationic, shell-crosslinked-knedel-like nanoparticles modulates inflammation and enhances cellular uptake in the lung," Nanomed-Nanotechnol., vol. 9, No. 7, pp. 912-922, Oct. 2013.
Pelaz B, et al., "Surface Functionalization of Nanoparticles with Polyethylene Glycol: Effects on Protein Adsorption and Cellular Uptake," Acs Nano., vol. 9, No. 7, pp. 6996-7008, Published online: Jun. 16, 2015.
Mickler FM, et al., "Effect of integrin targeting and PEG shielding on polyplex micelle internalization studied by live-cell imaging," J Control Release, vol. 156, pp. 364-373, Available online: Aug. 6, 2011.
Moser M, et al., "Dendritic cell regulation of TH1-TH2 development," Nat Immunol., vol. 1, No. 3, pp. 199-205, Sep. 2000.
McCarthy, D. E., et al., "A randomized controlled clinical trial of bupropion SR and individual smoking cessation counseling," Nicotine Tob Res., vol. 10, No. 4, pp. 717-729, Accepted: Jul. 23, 2007.
Stapleton, J. A., et al., "Varenicline in the routine treatment of tobacco dependence: a pre-post comparison with nicotine replacement therapy and an evaluation in those with mental illness," Addiction, vol. 103, pp. 146-154, Accepted: Oct. 24, 2007.
Carpenter, M. J.,et al., "Clinical Strategies to Enhance the Efficacy of Nicotine Replacement Therapy for Smoking Cessation: A Review of the Literature," Drugs, vol. 73, No. 5, pp. 407-426, Apr. 2013.
Shen, X. Y., et al., "Vaccines Against Drug Abuse," Clin Pharmacol. Ther., vol. 91, No. 1, pp. 60-70.
Hieda, Y., et al., "Active immunization alters the plasma nicotine concentration in rats," J Pharmacol Exp Ther, vol. 283, pp. 1076-1081, Accepted for publication: Aug. 8, 1997.
Pravetoni, M., et al., "Vaccination against nicotine alters the distribution of nicotine delivered via cigarette smoke inhalation to rats," Biochem Pharmacol, vol. 81, No. 9, pp. 1164-1170, May 1, 2011.
Meijler, M. M., et al., "A new strategy for improved nicotine vaccines using conformationally constrained haptens," J Am Chem Soc, vol. 125, pp. 7164-7165, Published on Web: May 21, 2003.
Lockner, J. W., et al., "Enhancing nicotine vaccine immunogenicity with liposomes," Bioorg Med Chem Lett, vol. 23, No. 4, pp. 975-978, Feb. 15, 2013.
Cornish, K. E., et al., "Immunogenicity of Individual Vaccine Components in a Bivalent Nicotine Vaccine Differ According to Vaccine Formulation and Administration Conditions," Plos One, vol. 8, No. 2, e82557, Published: Dec. 2, 2013.
Pejawar-Gaddy, S., et al., "Design of Lipid Nanocapsule Delivery Vehicles for Multivalent Display of Recombinant Env Trimers in HIV Vaccination," Bioconjugate Chem, vol. 25, 1470-1478, Published: Jul. 14, 2014.
Daglioglu, C., et al., "Synthesis and Characterization of AICAR and DOX Conjugated Multifunctional Nanoparticles as a Platform for Synergistic Inhibition of Cancer Cell Growth," Bioconjugate Chem, vol. 27, pp. 1098-1111, Published: Mar. 20, 2016.
Kim, C. S., et al., "Co-Delivery of Protein and Small Molecule Therapeutics Using Nanoparticle-Stabilized Nanocapsules," Bioconjugate Chem, vol. 26, No. 5, pp. 950-954, May 20, 2015.
McCluskie, M. J., et al., "Molecular attributes of conjugate antigen influence function of antibodies induced by anti-nicotine vaccine in mice and non-human primates," International Immunopharmacology, vol. 25, pp. 518-527, Available online: Feb. 28, 2015.

Foged, C., et al., "Particle size and surface charge affect particle uptake by human dendritic cells in an in vitro model," Int J Pharm, vol. 298, No. 2, pp. 315-322, Jul. 25, 2005.
Harris, J. R., et al., "Keyhole limpet hemocyanin (KLH): a biomedical review," Micron, vol. 30, pp. 597-623, Dec. 1999.
Bachmann, M. F., et al., "Vaccine delivery: a matter of size, geometry, kinetics and molecular patterns," Nat Rev Immunol, vol. 10, pp. 787-796, Published online: Oct. 15, 2010.
Reddy, S. T., et al., "Exploiting lymphatic transport and complement activation in nanoparticle vaccines," Nat Biotechnol, vol. 25, No. 10, pp. 1159-1164, Oct. 2007.
Oussoren, C., et al., "Lymphatic uptake and biodistribution of liposomes after subcutaneous injection. II. Influence of liposomal size, lipid compostion and lipid dose," Biochim Biophys Acta, vol. 1328, pp. 261-272, Accepted: May 21, 1997.
Banchereau, J., et al., "Dendritic cells and the control of immunity," Nature, vol. 392, pp. 245-252, Mar. 19, 1998.
Maurer, P., et al., "Frontline: a therapeutic vaccine for nicotine dependence: preclinical efficacy, and phase I safety and immunogenicity," Eur J Immunol., vol. 35, pp. 2031-2040, Accepted: May 27, 2005.
Liu, X. W., et al., "A DNA Nanostructure Platform for Directed Assembly of Synthetic Vaccines," Nano Lett, vol. 12, No. 8, pp. 4254-4259, Aug. 8, 2012.
Visciano, M. L., et al., "Effects of adjuvants on IgG subclasses elicited by virus-like Particles," J Transl Med, vol. 10, No. 4, pp. 1-8, 2012.
Hu, Y., et al., "In vitro performance of lipid-PLGA hybrid nanoparticles as an antigen delivery system: lipid composition matters,"Nanoscale Res Lett., vol. 9, pp. 1-10, 2014.
Polosa R, et al., "Treatment of nicotine addiction: present therapeutic options and pipeline developments," Trends Pharmacol Sci., vol. 32, No. 5, pp. 281-289, May 2011.
Moreno AY, et al, "Immunopharmacotherapy: Vaccination strategies as a treatment for drug abuse and dependence," Pharmacology Biochemistry and Behavior, vol. 92, No. 2, pp. 199-205, Apr. 2009.
Hu, Y., et al., "The next-generation nicotine vaccine: a novel and potent hybrid nanoparticle-based nicotine vaccine," Biomaterials., vol. 106, pp. 228-239, Nov. 2016.
Zhong TY, et al., "Hemocyanins Stimulate Innate Immunity by Inducing Different Temporal Patterns of Proinflammatory Cytokine Expression in Macrophages," Journal of Immunology., vol. 196, pp. 4650-4662, 2016.
McCluskie MJ, et al., "Anti-nicotine vaccines: Comparison of adjuvanted CRM197 and Qb-VLP conjugate formulations for immunogenicity and function in non-human primates," International Immunopharmacology., vol. 29, pp. 663-671, Available online: Sep. 26, 2015.
Haile CN, et al., "Altered Methamphetamine Place Conditioning in Mice Vaccinated With a Succinyl-Methamphetamine-Tetanus-Toxoid Vaccine," American Journal on Addictions, vol. 24, No. 8, pp. 748-755, Nov. 19, 2015.
Benne N, et al., "Orchestrating immune responses: How size, shape and rigidity affect the immunogenicity of particulate vaccines," J Control Release., vol. 234, pp. 124-134, Jul. 28, 2016.
Zheng MB, et al., "Single-Step Assembly of DOX/ICG Loaded Lipid-Polymer Nanoparticles for Highly Effective Chemo-photothermal Combination Therapy," Acs Nano., vol. 7, pp. 2056-2067, Published online: Feb. 15, 2013.
Zhang LF, et al., "Self-assembled lipid-polymer hybrid nanoparticles: A robust drug delivery platform," Acs Nano., vol. 2, No. 2, pp. 1696-1702, Aug. 2008.
Hu Y, et al., "Engineering the lipid layer of lipid-PLGA hybrid nanoparticles for enhanced in vitro cellular uptake and improved stability," Acta Biomater. , vol. 28, pp. 149-159, Dec. 2015.
Hu Y, et al., "In vitro controlled release of antigen in dendritic cells using pH-sensitive liposome-polymeric hybrid nanoparticles," Polymer, vol. 80, pp. 171-1719, Dec. 2, 2015.
Hadinoto K, et al., "Lipid-polymer hybrid nanoparticles as a new generation therapeutic delivery platform: A review," Eur J Pharm Biopharm., vol. 85, No. 3, pp. 427-443, Nov. 2013.
Broker M, et al., "Biochemical and biological characteristics of cross-reacting material 197 (CRM197), a non-toxic mutant of

(56) References Cited

OTHER PUBLICATIONS diphtheria toxin: Use as a conjugation protein in vaccines and other potential clinical applications," Biologicals, vol. 39, pp. 195-204, Accepted: May 24, 2011.
Pichichero ME., "Protein carriers of conjugate vaccines Characteristics, development, and clinical trials," Hum Vacc Immunother., vol. 9, No. 12, pp. 2505-2523, Dec. 2013.
Skolnick P., "Biologic Approaches to Treat Substance-Use Disorders," Trends Pharmacol Sci., vol. 36, pp. 628-635, Oct. 2015.
Cerny, E.H. et al., "Vaccines against nicotine," Hum Vaccine, vol. 5, pp. 200-205, Published online: Apr. 1, 2009.
McCluskie, M.J. et al., "Enhancing immunogenicity of a 3'aminomethylnicotine-DT-conjugate anti-nicotine vaccine with CpG adjuvant in mice and non-human primates," Int Immunopharmacol., vol. 16, pp. 50-56, Available online: Apr. 2, 2013.
LeSage, et al., "Current status of immunologic approaches to treating tobacco dependence: vaccines and nicotine-specific antibodies," AAPS Journal, vol. 8, No. 1, pp. E65-E75, 2006.
Mata-Haro, V. et al., "The vaccine adjuvant monophosphoryl lipid A as a TRIF-biased agonist of TLR4," Science, vol. 316, pp. 1628-1632, Jun. 15, 2007.
Jain, R.A., "The manufacturing techniques of various drug loaded biodegradable poly(lactide-co-glycolide) (PLGA) devices," Biomaterials, vol. 21, No. 23, pp. 2475-2490, Dec. 1, 2000.
Sliwinska-Mosson, et al., "New trends in the treatment of nicotine addiction," Acta Pol Pharm., vol. 71, No. 4, pp. 525-530, 2014.
Hartmann-Boyce, et al., "Nicotine vaccines for smoking cessation," Cochrane Database Syst Rev., Issue 8, CD007072, pp. 1-38, 2012.
Singh, et al., "Synthesis and characterization of hapten-protein conjugates for antibody production against small molecules," Bioconjug Chem., vol. 15, No. 1, pp. 168-173, 2004.
Moreno, et al., "A critical evaluation of a nicotine vaccine within a self-administration behavioral model," Mol Pharm., vol. 7, pp. 431-441, Jan. 27, 2010.
Coffman, et al., "Vaccine adjuvants: putting innate immunity to work," Immunity, vol. 33, pp. 492-503, Oct. 29, 2010.
De Jong, et al., "Encapsulation in liposomal nanoparticles enhances the immunostimulatory, adjuvant and anti-tumor activity of subcutaneously administered CpG ODN," Cancer Immunol Immunother., vol. 56, pp. 1251-1264, Published online: Jan. 23, 2007.
Cheng, J., et al., "Formulation of functionalized PLGA-PEG nanoparticles for in vivo targeted drug delivery," Biomaterials, vol. 28, No. 5, pp. 869-876, Feb. 2007.
Chang, et al., "Clinical development of liposome-based drugs: formulation, characterization, and therapeutic efficacy," Int J Nanomedicine, vol. 7, pp. 49-60, Dec. 29, 2011.
Lu, et al., "Current advances in research and clinical applications of PLGA-based nanotechnology," Expert Rev Mol Diagn., vol. 9, No. 4, pp. 325-341, May 2009.
Miles, et al., "Phase III multicenter clinical trial of the sialyl-TN (STn)-keyhole limpet hemocyanin (KLH) vaccine for metastatic breast cancer," Oncologist, vol. 16, pp. 1092-1100, May 14, 2011.
Duthie, et al., "Use of defined TLR ligands as adjuvants within human vaccines," Immunol Rev., vol. 239, No. 1, pp. 178-196, Jan. 2011.
Mansourian, et al., "Effective induction of anti-tumor immunity using p5 HER-2/neu derived peptide encapsulated in fusogenic DOTAP cationic liposomes co-administrated with CpG-ODN," Immunol Lett, vol. 162, pp. 87-93, Available online Jul. 30, 2014.
Reddy, et al., "Targeting dendritic cells with biomaterials: developing the next generation of vaccines," Trends Immunol., vol. 27, No. 12 pp. 573-579, Available online: Oct. 16, 2006.
Reddy, et al., "In vivo targeting of dendritic cells in lymph nodes with poly(propylene sulfide) nanoparticles," J Control Release, vol. 112, No. 1, pp. 26-34, May 1, 2006.
Kool, et al., "Alum adjuvant: some of the tricks of the oldest adjuvant," J Med Microbiol., vol. 61, pp. 927-934, 2012.
Casella, T.C. Mitchell., "Putting endotoxin to work for us: monophosphoryl lipid A as a safe and effective vaccine adjuvant," Cell Mol Life Sci., vol. 65, pp. 3231-3240, Oct. 2008.
Tomljenovic, et al., "Aluminum vaccine adjuvants: are they safe?" Curr Med Chem., vol. 18, No. 17, pp. 2630-2637, 2011.
Cruz, et al., "The influence of PEG chain length and targeting moiety on antibody-mediated delivery of nanoparticle vaccines to human dendritic cells," Biomaterials, vol. 32, pp. 6791-803, Available online Jul. 2, 2011.
Shahbazi, et al., "Surface chemistry dependent immunostimulative potential of porous silicon nanoplatforms," Biomaterials, vol. 35, pp. 9224-9235, Available online Aug. 12, 2014.
Moingeon, J. Haensler, A. Lindberg., "Towards the rational design of Th1 adjuvants," Vaccine, vol. 19, No. 31, pp. 4363-4372, Aug. 14, 2001.
Sarti, et al., "In vivo evidence of oral vaccination with PLGA nanoparticles containing the immunostimulant monophosphoryl lipid A," Biomaterials, vol. 32, pp. 4052-4057, Available online Mar. 4, 2011.
Chan, et al., "PLGA-lecithin-PEG core-shell nanoparticles for controlled drug delivery," Biomaterials, vol. 30, pp. 1627-1634, Available online Dec. 25, 2008.
Kamphuis, et al., "Immunogenicity and protective capacity of a virosomal respiratory syncytial virus vaccine adjuvanted with monophosphoryl lipid A in mice," PLoS One, vol. 7, No. 5, e36812, May 2012.
Dong, et al., "Methoxy poly(ethylene glycol)-poly(lactide) (MPEG-PLA) nanoparticles for controlled delivery of anticancer drugs," Biomaterials, vol. 25, pp. 2843-2849, Accepted Sep. 15, 2003.
Cahill, S. Stevens, R. Perera, T. Lancaster., "Pharmacological interventions for smoking cessation: an overview and network meta-analysis," Cochrane Database Syst Rev, vol. 5 (2013), pp. CD009329, pp. 1-48.
Brito, et al., "Vaccine adjuvant formulations: a pharmaceutical perspective," Semin Immunol, vol. 25, pp. 130-145, 2013.
Oleszycka, et al., "Immunomodulatory properties of the vaccine adjuvant alum," Curr Opin Immunol., vol. 28, pp. 1-5, 2014.
Petrovsky, et al., "Vaccine adjuvants: current state and future trends," Immunol Cell Biol., vol. 82 (2004), pp. 488-496.
Tomljenovic, et al., "Mechanisms of aluminum adjuvant toxicity and autoimmunity in pediatric populations," Lupus, vol. 21, pp. 223-230, Jan. 2012.
Shaw, L. et al., "Aluminum in the central nervous system (CNS): toxicity in humans and animals, vaccine adjuvants, and autoimmunity," Immunol Res., vol. 56, pp. 304-316, 2013.
De Gregorio, et al., "Alum adjuvanticity: unraveling a century old mystery," Eur J Immunol, vol. 38, pp. 2068-2071, 2008.
Bode, et al., "CpG Dna as a vaccine adjuvant," Expert Rev Vaccines, vol. 10, No. 4, pp. 499-511, Apr. 2011.
Klinman, et al., "Immunotherapeutic uses of CpG oligodeoxynucleotides," Nat Rev Immunol., vol. 4, pp. 249-258, Apr. 2004.
Roda, et al., "CpG-containing oligodeoxynucleotides act through TLR9 to enhance the NK cell cytokine response to antibody-coated tumor cells," J Immunol., vol. 175, pp. 1619-1627, 2005.
Krishnamachari, et al., "Nanoparticle delivery systems in cancer vaccines," Pharm Res, vol. 28, No. 2, pp. 215-236, Feb. 2011.
Khan, et al., "Immunological principles regulating immunomodulation with biomaterials," Acta Biomater., vol. 10 (2014), pp. 1720-1727, Available online: Dec. 14, 2013.
Tonstad, et al., "Niccine(R), a nicotine vaccine, for relapse prevention: a phase II, randomized, placebo-controlled, multicenter clinical trial," Nicotine Tob Res., vol. 15, pp. 1492-1501, accepted Jan. 2, 2013.
Danhier, et al., "PLGA-based nanoparticles: an overview of biomedical applications," J Control Release, vol. 161, No. 2, pp. 505-522, Jul. 20, 2012.
Cohen-Sela, et al., "A new double emulsion solvent diffusion technique for encapsulating hydrophilic molecules in PLGA nanoparticles," J Control Release, vol. 133, pp. 90-95, Available online Sep. 24, 2008.
Schwendener, et al., "Liposomes as vaccine delivery systems: a review of the recent advances," Ther Adv Vaccines, vol. 2, No. 6, pp. 159-182.
Lian, et al., "Trends and developments in liposome drug delivery systems," J Pharm Sci., vol. 90, No. 6pp. 667-680, Jun. 1, 2001.

(56) References Cited

OTHER PUBLICATIONS

Otsuka, et al., "PEGylated nanoparticles for biological and pharmaceutical applications," Adv Drug Deliv Rev, vol. 55, No. 3, pp. 403-419, Feb. 24, 2003.
Pasut, et al., "Polyethylene glycol (PEG)-dendron phospholipids as innovative constructs for the preparation of super stealth liposomes for anticancer therapy," J Control Release, vol. 199, pp. 106-113, Available online Dec. 9, 2014.
Salmaso, et al., "Stealth properties to improve therapeutic efficacy of drug nanocarriers," J Drug Deliv, vol. 2013, Article ID 374252, 19 pages, Accepted Feb. 6, 2013.
Liu, et al., "High epitope density in a single protein molecule significantly enhances antigenicity as well as immunogenicity: a novel strategy for modern vaccine development and a preliminary investigation about B cell discrimination of monomeric proteins," Eur J Immunol, vol. 35 (2005), pp. 505-514.
Cruz, et al., "Targeted PLGA nano- but not microparticles specifically deliver antigen to human dendritic cells via DC-SIGN in vitro," J Control Release, vol. 144, pp. 118-126, Available online Feb. 13, 2010.
Shirota, et al., "Recent progress concerning CpG DNA and its use as a vaccine adjuvant," Expert Rev Vaccines, vol. 13, pp. 299-312, Feb. 2014.
Sahdev, et al., "Biomaterials for nanoparticle vaccine delivery systems," Pharm Res, vol. 31, pp. 2563-2582, Oct. 2014.
Salvador-Morales,et al., "Immunocompatibility properties of lipid-polymer hybrid nanoparticles with heterogeneous surface functional groups," Biomaterials, vol. 30, pp. 2231-2240, Available online Jan. 23, 2009.
Lima, et al., "Vaccine adjuvant: it makes the difference," Vaccine, vol. 22 (2004), pp. 2374-2379, Available online Apr. 9, 2004.
Gupta, et al., "Aluminum compounds as vaccine adjuvants," Adv Drug Deliv Rev, vol. 32, pp. 155-172, accepted Oct. 20, 1997.
Marshall, et al., "Identification of a novel CpG DNA class and motif that optimally stimulate B cell and plasmacytoid dendritic cell functions," J Leukoc Biol, vol. 73 (2003), pp. 781-792.
Chuang, et al., "Development of CpG-oligodeoxynucleotides for effective activation of rabbit TLR9 mediated immune responses," PLoS One, vol. 9 (2014), pp. e108808.
Kosten, et al., "Attenuation of cocaine-induced locomotor activity in male and female mice by active immunization," Am J Addict, vol. 23 (2014), pp. 604-607.
Wang, et al., "A noticeable phenomenon: thiol terminal PEG enhances the immunogenicity of PEGylated emulsions injected intravenously or subcutaneously into rats," Eur J Pharm Biopharm, vol. 85 (2013), pp. 744-751.
Silva, et al., "PLGA particulate delivery systems for subunit vaccines: linking particle properties to immunogenicity," Hum Vaccin Immunother, vol. 12, No. 4, 1056-1069, 2016.
Van Schayck, et al., "Nicotine vaccination—does it have a future?" Addiction, vol. 109 (2014), pp. 1223-1225.
Kinsey. "Vaccines against drugs of abuse: where are we now?"Ther. Adv. Vaccines, vol. 2 (2014), pp. 106-117.
Lockyer, F. Gao, J.P. Derrick, B. Bolgiano. Structural correlates of carrier protein recognition in tetanus toxoid-conjugated bacterial polysaccharide vaccines. Vaccine, vol. 33, pp. 1345-1352, Available online Jan. 29, 2015.
Shinefield. "Overview of the development and current use of CRM(197) conjugate vaccines for pediatric use," Vaccine, vol. 28 (2010), pp. 4335-4339.
Sanchez Vallecillo, et al., "Adjuvant activity of CpG-ODN formulated as a liquid crystal," Biomaterials, vol. 35, pp. 2529-2542, Available online Dec. 30, 2013.
Patil, et al., "Evaluation of monophosphoryl lipid A as adjuvant for pulmonary delivered influenza vaccine," J. Control. Release, vol. 174, pp. 51-62, Jan. 28, 2014.
Siefert, et al., "Artificial bacterial biomimetic nanoparticles synergize pathogen-associated molecular patterns for vaccine efficacy," Biomaterials, vol. 97 (2016), pp. 85-96.

Joshi, et al., "Biodegradable particles as vaccine delivery systems: size matters," AAPS J., vol. 15 (2013), pp. 85-94.
Thrane, et al., "Bacterial superglue enables easy development of efficient virus-like particle based vaccines," J. Nanobiotechnology, vol. 14 (2016), pp. 30.
Kim, et al., "Doxorubicin-loaded porous PLGA microparticles with surface attached TRAIL for the inhalation treatment of metastatic lung cancer," Biomaterials, vol. 34 (2013), pp. 6444-6453.
Cahill, L.F. Stead, T. Lancaster., "Nicotine receptor partial agonists for smoking cessation," Cochrane Database Syst. Rev., (2010), pp. CD006103.
Raupach, et al., "Pharmacotherapy for smoking cessation: current advances and research topics," CNS Drugs, vol. 25 (2011), pp. 371-378.
Gursel, et al., "Development of CpG ODN Based Vaccine Adjuvant Formulations," Methods Mol. Biol., vol. 1404 (2016), pp. 289-98.
Matyas, et al., "Liposomes containing monophosphoryl lipid A: a potent adjuvant system for inducing antibodies to heroin hapten analogs," Vaccine, vol. 31 (2013), pp. 2804-2810.
Butcher, et al., "Drug delivery: Unravelling the stealth effect," Nat. Nanotechnol., vol. 11 (2016), pp. 310-311.
Yang, et al., "Polyethylene glycol-polyamidoamine dendritic micelle as solubility enhancer and the effect of the length of polyethylene glycol arms on the solubility of pyrene in water," J. Colloid. Interface Sci., vol. 273 (2004), pp. 148-154.
Moffatt, et al., "Uptake characteristics of NGR-coupled stealth PEI/pDNA nanoparticles loaded with PLGA-PEG-PLGA tri-block copolymer for targeted delivery to human monocyte-derived dendritic cells," Int. J. Pharm., vol. 321 (2006), pp. 143-154.
Garbuzenko, et al., "Effect of grafted PEG on liposome size and on compressibility and packing of lipid bilayer," Chem. Phys. Lipids, vol. 135 (2005), pp. 117-129.
Sriwongsitanont, et. al., "Physicochemical properties of PEG-grafted liposomes," Chem. Pharm. Bull. (Tokyo), vol. 50 (2002), pp. 1238-1244.
Tuse, et al., "Clinical Safety and Immunogenicity of Tumor-Targeted, Plant-Made Id-KLH Conjugate Vaccines for Follicular Lymphoma," Biomed. Res. Int., vol. 2015, pp. 648143, Accepted Apr. 12, 2015.
De Groot AS, Martin W., "Reducing risk, improving outcomes: bioengineering less immunogenic protein therapeutics," Clinical immunology. May 2009, vol. 131, No. 2, pp. 189-201.
Alving, et al., "Adjuvants for human vaccines." Current opinion in immunology., Jun. 2012, vol. 24, No. 3, pp. 310-315.
Mbow ML, et al., "New adjuvants for human vaccines." Current opinion in immunology, vol. 22, pp. 411-416, Available online May 11, 2010.
Morefield GL, et al., "Role of aluminum-containing adjuvants in antigen internalization by dendritic cells in vitro," vol. 23, pp. 1588-1595, Available online Oct. 31, 2004.
Marrack P, McKee AS, Munks MW., "Towards an understanding of the adjuvant action of aluminium," Nature reviews Immunology., vol. 9, pp. 287-293, Apr. 2009.
Goto N, Akama K., "Histopathological studies of reactions in mice injected with aluminum-adsorbed tetanus toxoid," Microbiology and immunology., vol. 26, No. 12, pp. 1121-1132, Accepted for publication, Oct. 15, 1982.
Rosalie RA, et al., "CD40-targeted dendritic cell delivery of PLGA-nanoparticle vaccines induce potent anti-tumor responses," Biomaterials., vol. 40, pp. 88-97, Available online Nov. 26, 2014.
Pentel PR, et al., "A nicotine conjugate vaccine reduces nicotine distribution to brain and attenuates its behavioral and cardiovascular effects in rats," Pharmacology, biochemistry, and behavior, 2000, vol. 65, No. 1, pp. 191-198.
Baylor, et al., "Aluminum salts in vaccines—US perspective," Vaccine. vol. 20, Suppl 3, pp. S18-S23, May 31, 2002.
Kwon, et al., "Enhanced antigen presentation and immunostimulation of dendritic cells using acid-degradable cationic nanoparticles," Journal of controlled release, vol. 105, pp. 199-212, Available online: Jun. 1, 2005.
Hamdy, et al., "Enhanced antigen-specific primary CD4+ and CD8+ responses by codelivery of ovalbumin and toll-like receptor ligand

(56) References Cited

OTHER PUBLICATIONS monophosphoryl lipid A in poly(D,L-lactic-co-glycolic acid) nanoparticles," Journal of biomedical materials research Part A. vol. 81, pp. 652-662.

Mi FL, et al., "Porous chitosan microsphere for controlling the antigen release of Newcastle disease vaccine: preparation of antigen-adsorbed microsphere and in vitro release," Biomaterials., vol. 20, No. 17, pp. 1603-1612, Sep. 1999.

Hanson MC, et al., "Antigen delivery by lipid-enveloped PLGA microparticle vaccines mediated by in situ vesicle shedding," Biomacromolecules., vol. 15, pp. 2475-2481, Published: Jun. 4, 2014.

Moon JJ, et al., Antigen-displaying lipidenveloped PLGA nanoparticles as delivery agents for a Plasmodium vivax malaria vaccine, PloS one., vol. 7, No. 2, e31472, Feb. 2012.

Gnjatic, et al., "Toll-like receptor agonists: are they good adjuvants?" Cancer journal., vol. 16, No. 4, pp. 382-391, 2010.

Ishii KJ, Akira S., "Toll or toll-free adjuvant path toward the optimal vaccine development," Journal of clinical immunology., vol. 27, No. 4, pp. 363-371, Jul. 2007.

Li X, Aldayel AM, Cui Z., "Aluminum hydroxide nanoparticles show a stronger vaccine adjuvant activity than traditional aluminum hydroxide microparticles," Journal of controlled release, vol. 173, pp. 148-57, Jan. 2014.

"Office Action and Search Report" issued by the Chinese National Intellectual Property Administrations Peoples Republic of China dated Nov. 3, 2021 for counterpart Application No. 201780088068.1.

\* cited by examiner

| Naovaccines | PDI | KLH/Nic-KLH conjugation efficiency (%) | Nic-hapten density (#/x10$^4$/NP) |
|---|---|---|---|
| LPKN | 0.11±0.02 | 82.3±5.4 | 6.32±0.39 |
| LPNK | 0.15±0.03 | 85.3±7.4 | 5.89±0.67 |
| LPNKN | 0.14±0.03 | 80.2±6.7 | 6.02±0.53 |

Antigen conjugation efficiency and hapten density of nanovaccines

FIG. 23

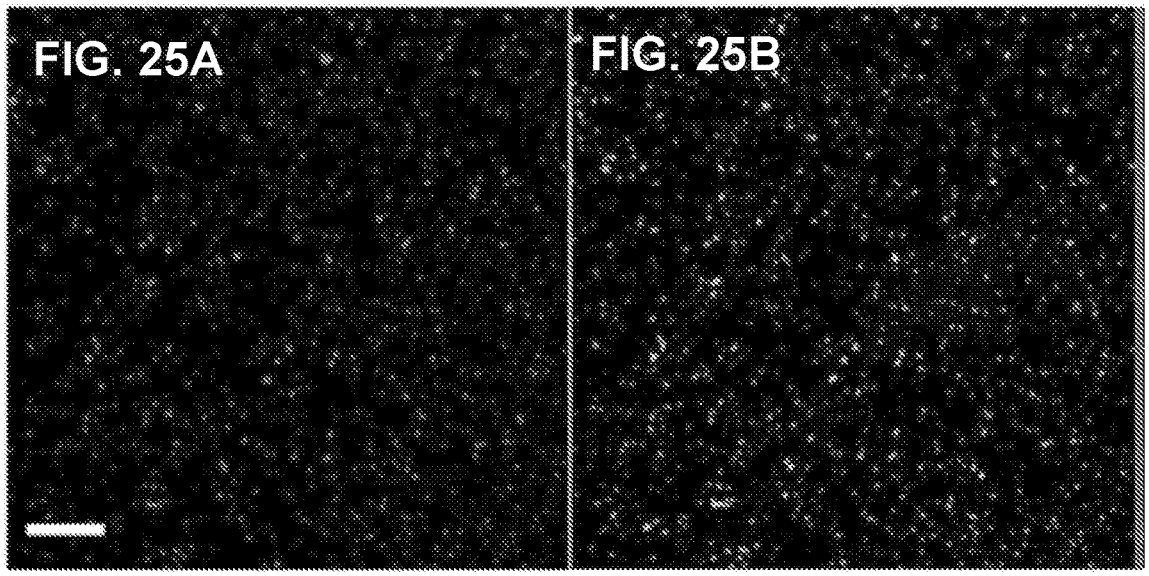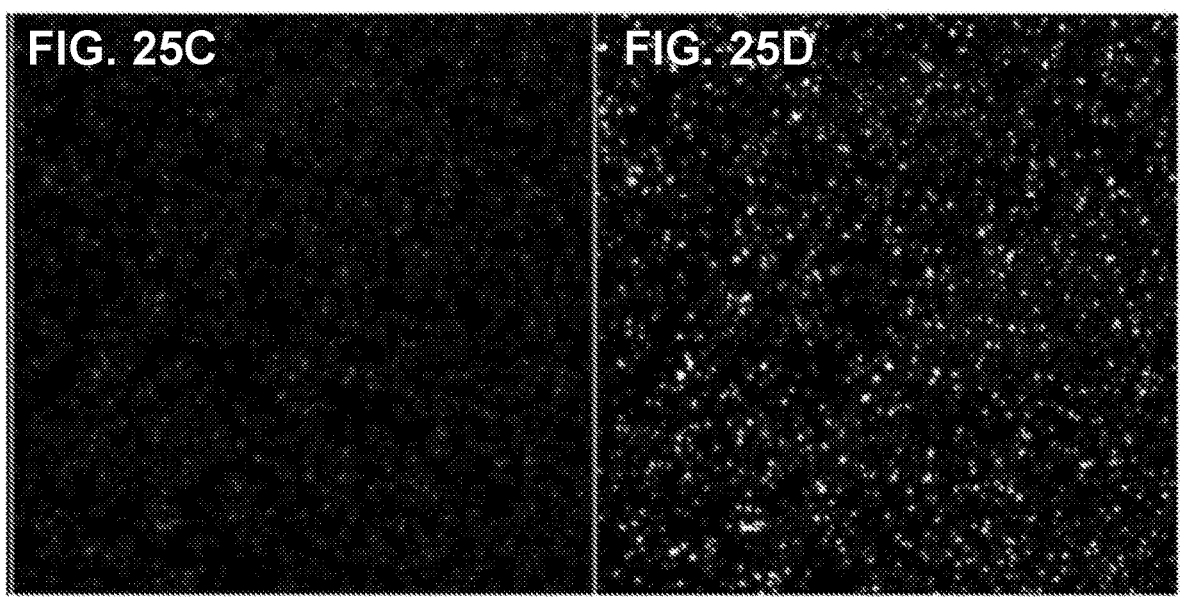

Physiochemical properties and hapten density of nanovaccine NPs

| NPs | Size (d. nm) | Zeta potential (mv) | PDI | Nic-KLH association efficiency (%) | Hapten density (#x10³/NP) |
|---|---|---|---|---|---|
| NKLP-C (low-density) | 121.3±7.9 | 4.16±0.14 | 0.22±0.02 | 86.4±0.97 | 29.4±9.2 |
| NKLP-F (medium-density) | 123.8±6.1 | 3.92±0.23 | 0.24±0.03 | 87.9±1.02 | 145.6±18.1 |
| NKLP-I (high-density) | 121.2±4.2 | 3.86±0.12 | 0.21±0.02 | 86.7±0.45 | 318.6±18.2 |

FIG. 32

| | Negative control | Nic-KLH with Alum | Low density | Low density with Alum | Medium density | Medium density with Alum | High density | High density with Alum |
|---|---|---|---|---|---|---|---|---|
| Th1/Th2 index | - | 0.092± 0.056 | 0.151± 0.054 | 0.120± 0.075 | 0.126± 0.030 | 0.108± 0.027 | 0.105± 0.014 | 0.0989± 0.020 |

FIG. 48

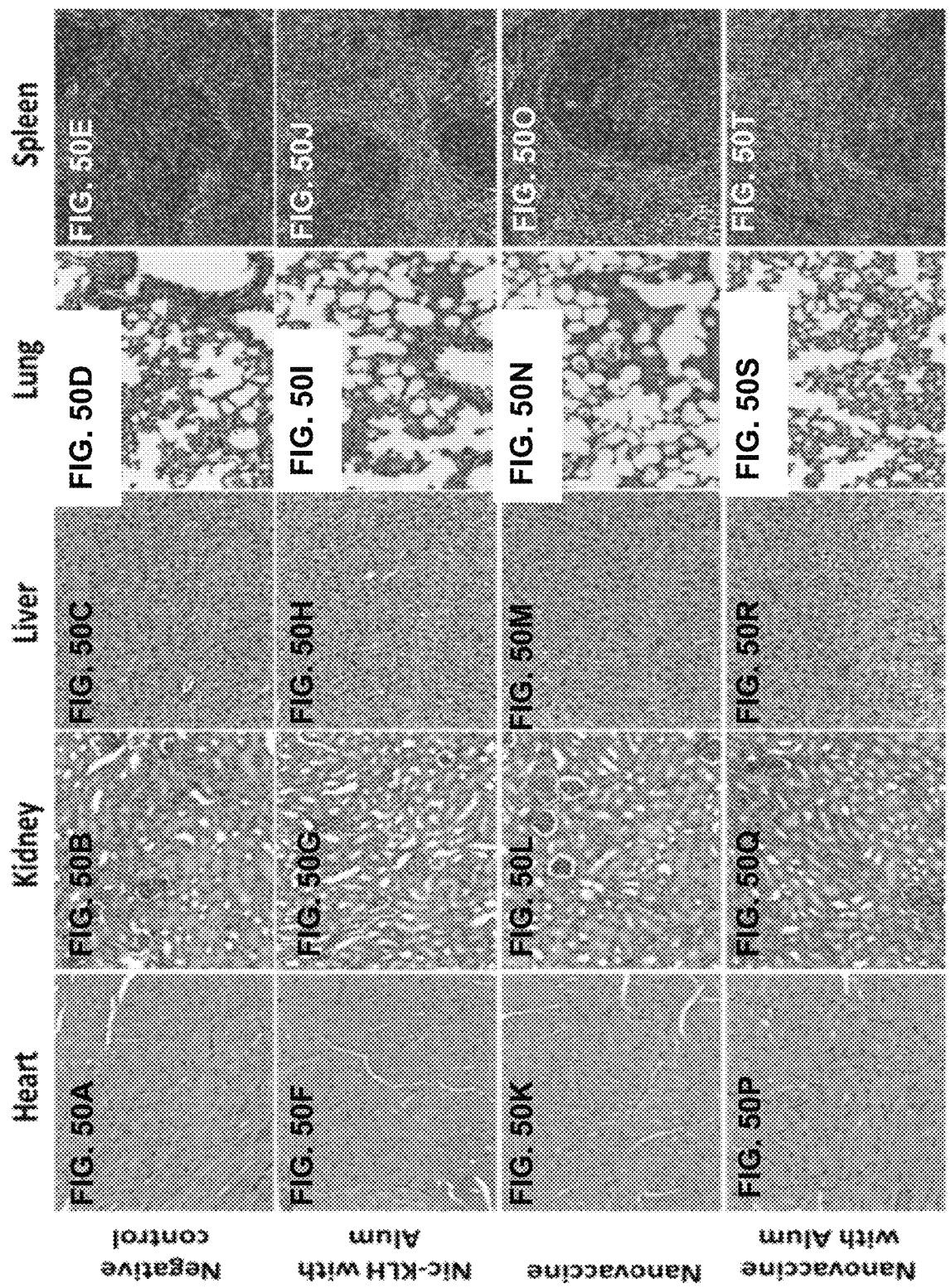

FIG. 53A  AF-350 (TT)

FIG. 53B  NBD (lipids)

FIG. 53C  Nile Red (PLGA)

FIG. 53D  Merged

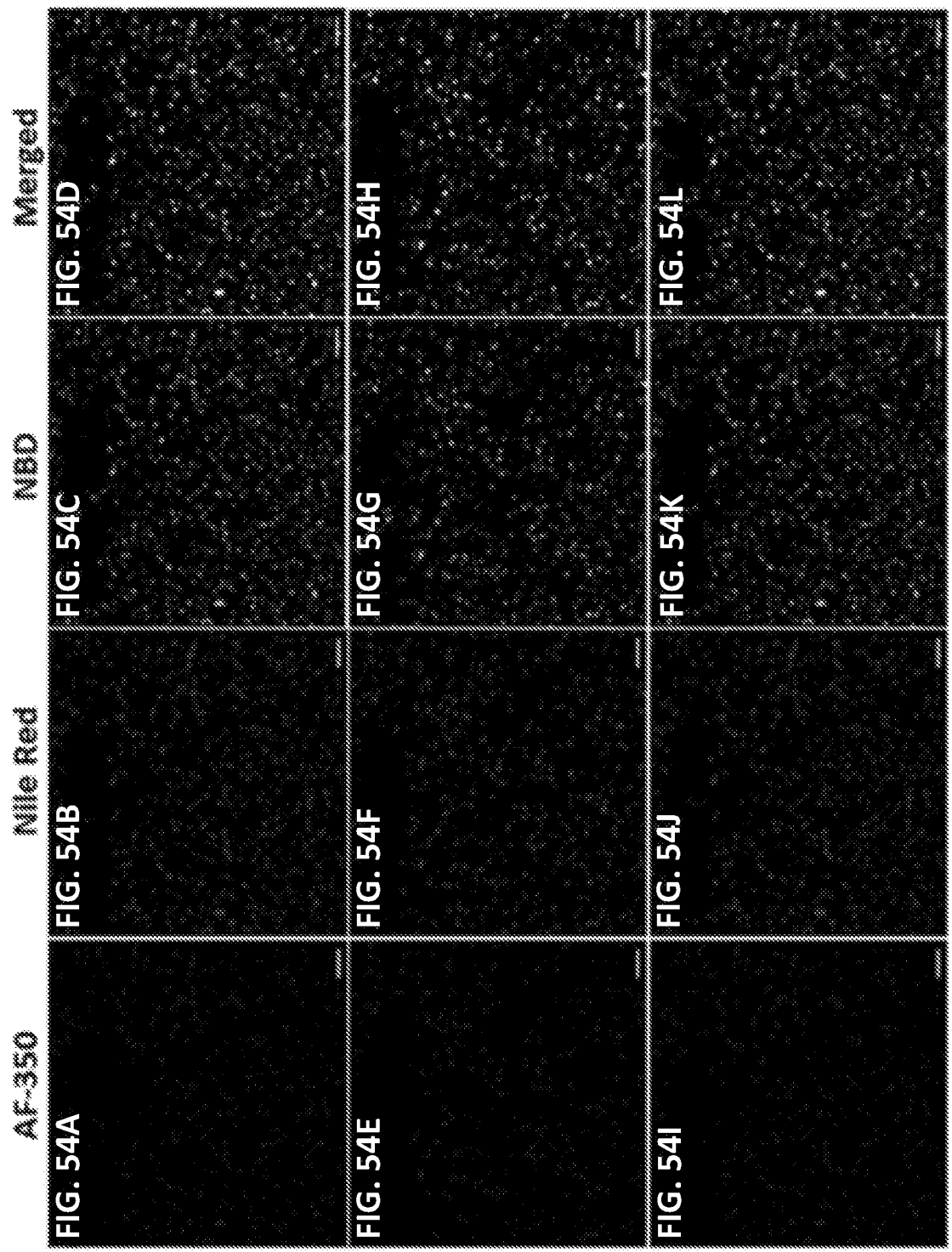

| | Nicotine | Cotinine | Nornicotine | Nicotine-N-oxide | Acetylcholine |
|---|---|---|---|---|---|
| Nano-KLH-Nic | 100 | <1 | <1 | <1 | <1 |
| Nano-KS-Nic | 100 | <1 | 2.9 | <1 | <1 |
| Nano-CRM197-Nic | 100 | 1.5 | 5.7 | <1 | <1 |
| Nano-TT-Nic | 100 | <1 | 2.8 | <1 | <1 |
| Nic-TT + alum | 100 | 1.4 | 6.1 | <1 | <1 |

| | Heart | Kidney | Liver | Spleen | Lung |
|---|---|---|---|---|---|
| Blank (PBS) | FIG. 71A | FIG. 71B | FIG. 71C | FIG. 71D | FIG. 71E |
| Nano-KLH-Nic | FIG. 71F | FIG. 71G | FIG. 71H | FIG. 71I | FIG. 71J |
| Nano-KS-Nic | FIG. 71K | FIG. 71L | FIG. 71M | FIG. 71N | FIG. 71O |
| Nano-CRM$_{197}$-Nic | FIG. 71P | FIG. 71Q | FIG. 71R | FIG. 71S | FIG. 71T |
| Nano-TT-Nic | FIG. 71U | FIG. 71V | FIG. 71W | FIG. 71X | FIG. 71Y |

| NanoNicVac | Size (d. nm) | Zeta-potential (mV) | PDI | Conjugation efficiency (%) | Hapten loading (μg Nic/mg NP) |
|---|---|---|---|---|---|
| Nano-KLH-Nic | 167.2 ± 9.7 | -11.00 ± 0.98 | 0.256 ± 0.067 | 87.6 ± 7.9 | 0.88 ± 0.07 |
| Nano-KS-Nic | 153.2 ± 10.2 | -11.80 ± 0.93 | 0.271 ± 0.076 | 83.2 ± 11.3 | 0.91 ± 0.12 |
| Nano-CRM$_{197}$-Nic | 125.2 ± 13.5 | -12.50 ± 0.75 | 0.230 ± 0.066 | 90.0 ± 7.6 | 0.86 ± 0.07 |
| Nano-TT-Nic | 136.6 ± 7.4 | -11.20 ± 2.07 | 0.218 ± 0.045 | 84.3 ± 9.4 | 0.81 ± 0.09 |

Data were expressed as means ± standard deviation (n=3).

FIG. 72

|  | PBS | Nic-KLH + Alum | NanoNiccine + Alum | NanoNiccine + MPLA | NanoNiccine + MPLA & Alum |
|---|---|---|---|---|---|
| Heart | FIG. 81A | FIG. 81B | FIG. 81C | FIG. 81D | FIG. 81E |
| Lung | FIG. 81F | FIG. 81G | FIG. 81H | FIG. 81I | FIG. 81J |
| Kidney | FIG. 81K | FIG. 81L | FIG. 81M | FIG. 81N | FIG. 81O |
| Spleen | FIG. 81P | FIG. 81Q | FIG. 81R | FIG. 81S | FIG. 81T |
| Stomach | FIG. 81U | FIG. 81V | FIG. 81W | FIG. 81X | FIG. 81Y |
| Liver | FIG. 81Z | FIG. 81AA | FIG. 81BB | FIG. 81CC | FIG. 81DD |

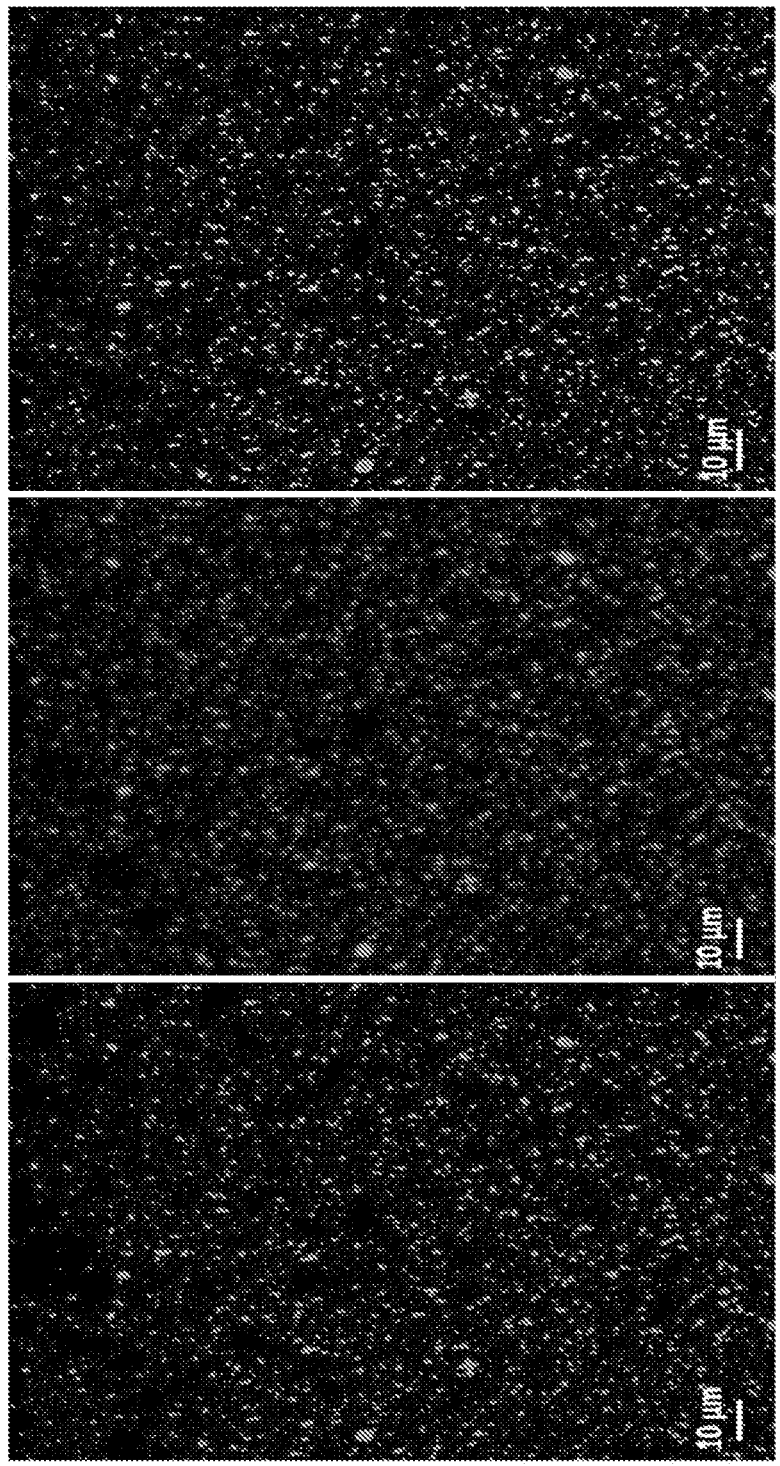

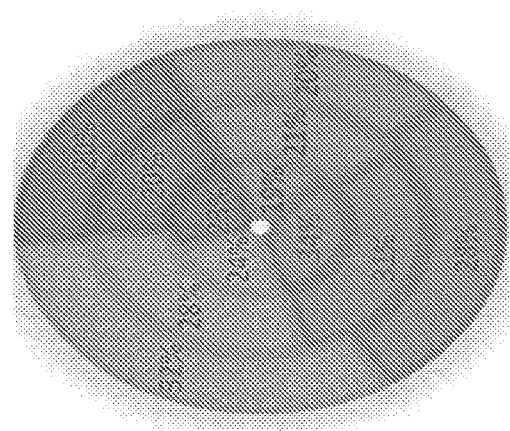
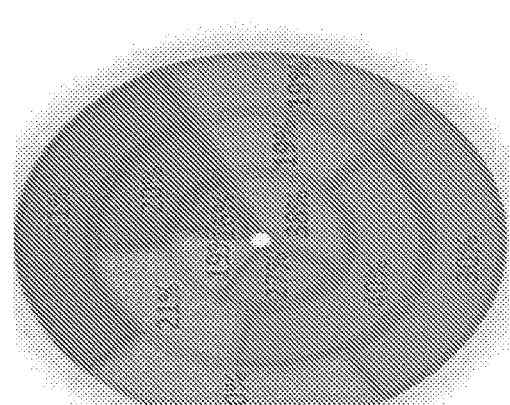
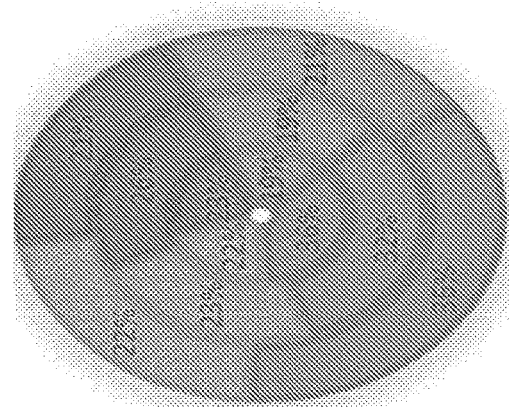
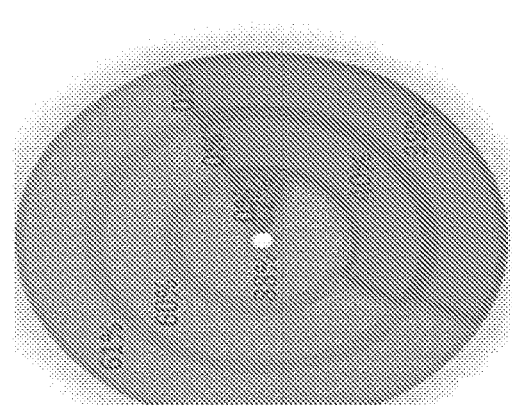
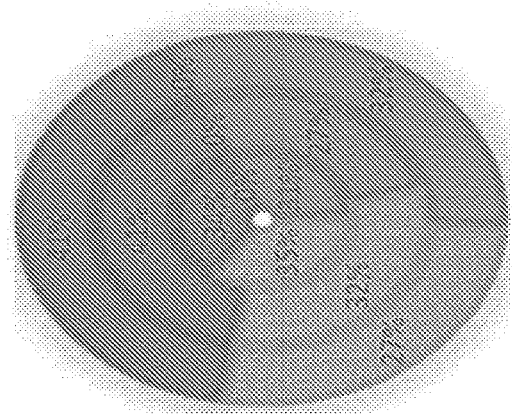
FIG. 88

FIGS. 89A-89JJ

FIG. 107A 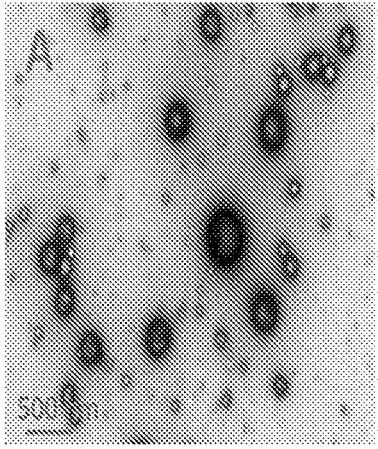 FIG. 107B 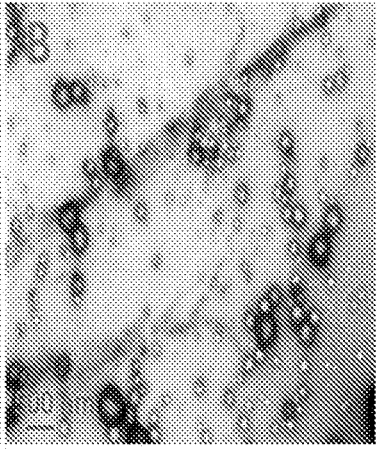 FIG. 107C 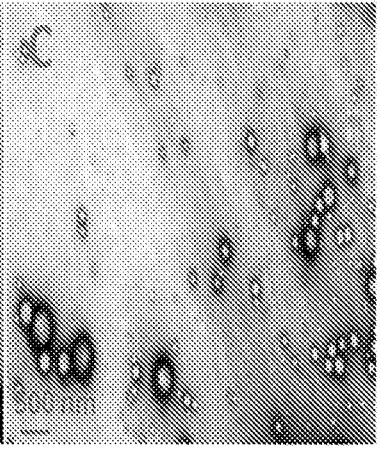
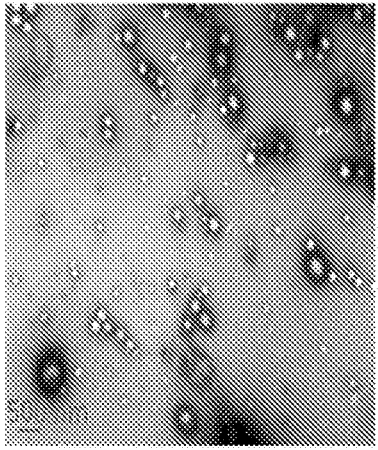 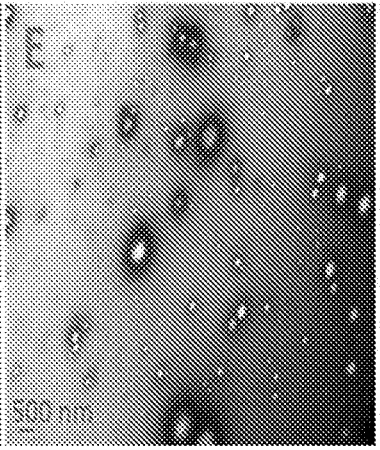
FIG. 107D FIG. 107E

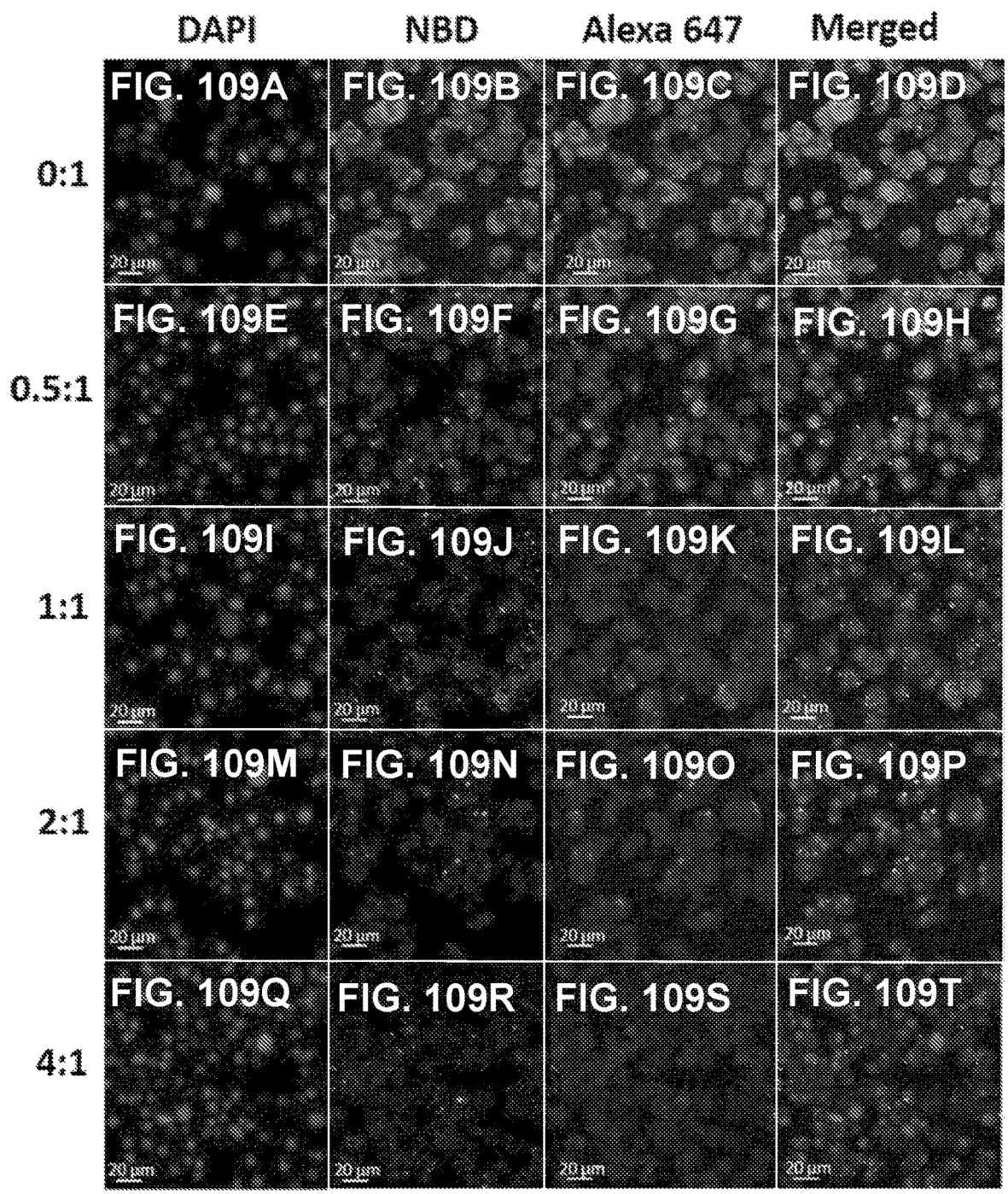

NICOTINE NANOVACCINES AND USES THEREOF

STATEMENT REGARDING FEDERALLY SPONSORED RESEARCH OR DEVELOPMENT

This invention was made with government support under grant number U01DA036850 awarded by the National Institute on Drug Abuse. The government has certain rights to the invention.

CROSS REFERENCE TO RELATED APPLICATIONS

This application is the U.S. National Stage Application under 35 U.S.C. § 371 of Patent Cooperation Treaty Application No.: PCT/US2017/012269, filed on Jan. 5, 2017, entitled "NICOTINE NANOVACCINES AND USES THEREOF," the contents of which is incorporated by reference herein in its entirety.

BACKGROUND

The U.S. Surgeon General has commented that stopping smoking represents the single most important step that smokers can take to enhance the length and quality of their lives. Despite the well evidenced improvement to health and quality of life, smokers can have severe difficulty smoking due the physical addiction to nicotine contained in cigarettes and other smoking products, including e-cigarettes. While many modalities ranging from mental health therapies to nicotine replacement therapy, the failure rate in overcoming nicotine addiction is still high. As such, there exists a need for improved therapies that can assist with stopping and/or preventing nicotine addiction.

SUMMARY

Provided herein are nanoparticles that can contain a poly(lactic-co-glycolic acid) core; a lipid shell, wherein the lipid shell can encapsulate the polymer core; a first stimulating molecule, wherein the first stimulating molecule can be encapsulated in the lipid shell; a second stimulating molecule, wherein the second stimulating molecule can be attached to the outer surface of the lipid shell via a lipid-polyethylene glycol linker, wherein the stimulating protein can be enclosed inside the polymer core, a first nicotine-hapten antigen, wherein the first nicotine-hapten antigen can be attached directly to the second stimulating protein; and a second nicotine-hapten antigen, wherein the second nicotine-hapten antigen can be attached to the outer surface of the lipid shell via a lipid-polyethylene glycol linker, wherein the second nicotine-hapten antigen is not attached to the second stimulating molecule.

Provided herein are nanoparticles that can contain a polymer core; a lipid shell, wherein the lipid shell can encapsulate the polymer core; a first stimulating protein, wherein the first stimulating protein can be attached to the outer surface of the lipid shell, a first nicotine-hapten antigen, wherein the first nicotine-hapten antigen can be attached to the first stimulating protein; and a second nicotine-hapten antigen, wherein the second nicotine-hapten antigen can be attached to the outer surface of the lipid shell and wherein the second nicotine-hapten antigen is not attached to the first stimulating protein. The polymer core can contain or be composed of poly(lactic-co-glycolic acid). The lipid shell can contain a cationic lipid. The lipid shell can, in some embodiments, conatin a lipid selected from the group of: DOTAP (dioleoyl trimethylammonium propane) or a derivative thereof, cholesterol, DSPE (1,2-Distearoylphosphatidylethanolamine)-PEG (polyethylene glycol)-maleimide, and DSPE-PEG-amine, a DSPE-PEG having at least one reactive terminal group, and any combination thereof. The polymer core further can include a second stimulating molecule, wherein the second stimulating molecule can be attached to or enclosed in a polymer of the polymer core. In some embodiments, the second stimulating molecule can be selected from the group of: keyhole limpet hemocyanin (KLH) multimer, KLH subunit, tetanus toxoid (TT), cross-reacting material 197 ($CRM_{197}$), bovine serum albumin (BSA), Human papillomavirus (HPV) proteins, recombinant *P. aeruginosa* exoprotein A, recombinant cholera toxin B, outer protein capsid of bacteriophage Qb, a peptide, and any combination thereof. In some embodiments, the first stimulating molecule can be selected from the group consisting of: keyhole limpet hemocyanin (KLH) multimer, KLH subunit, tetanus toxoid (TT), cross-reacting material 197 ($CRM_{197}$), bovine serum albumin (BSA), Human papillomavirus (HPV) proteins, recombinant *P. aeruginosa* exoprotein A, recombinant cholera toxin B, outer protein capsid of bacteriophage Qb, a peptide, and any combination thereof. In some embodiments, the first nicotine-hapten and the second nicotine hapten can be different. In some embodiments, first nicotine-hapeten and the second nicotine hapten can be the same. The nanoparticles can contain a second stimulating molecule, wherein the second stimulating molecule is encapsulated in the lipid shell. In some embodiments, the total density of the first nicotine-hapten and the second nicotine-hapten can range from about 52 to about 115 nicotine-hapten molecules per nanoparticle. In some embodiments, the molar percentage of DSPE-PEG-amine in the lipid portion can range from about 1 to about 99 molar percent. In embodiments, the diameter of the nanoparticle can range from about 1 nm to 999 nm.

Provided herein are vaccine formulations that can contain one or more nanoparticles, wherein the nanoparticle(s) can contain a poly(lactic-co-glycolic acid) core; a lipid shell, wherein the lipid shell can encapsulate the polymer core; a first stimulating molecule, wherein the first stimulating molecule can be encapsulated in the lipid shell; a second stimulating molecule, wherein the second stimulating molecule can be attached to the outer surface of the lipid shell via a lipid-polyethylene glycol linker, wherein the stimulating protein can be enclosed inside the polymer core, a first nicotine-hapten antigen, wherein the first nicotine-hapten antigen can be attached directly to the second stimulating protein; a second nicotine-hapten antigen, wherein the second nicotine-hapten antigen can be attached to the outer surface of the lipid shell via a lipid-polyethylene glycol linker, wherein the second nicotine-hapten antigen is not attached to the second stimulating molecule, and a pharmaceutically acceptable carrier.

Provided herein are vaccine formulations that can contain a nanoparticle, wherein the nanoparticle can contain a polymer core; a lipid shell, wherein the lipid shell can encapsulate the polymer core; a first stimulating protein, wherein the first stimulating protein can be attached to the outer surface of the lipid shell, a first nicotine-hapten antigen, wherein the first nicotine-hapten antigen can be attached to the first stimulating protein; a second nicotine-hapten antigen, wherein the second nicotine-hapten antigen can be attached to the outer surface of the lipid shell and wherein the second nicotine-hapten antigen is not attached to the first stimulating protein, and a pharmaceutically acceptable carrier. The vaccine formulations can further include a second stimulating molecule, wherein the first stimulating molecule is encapsulated in the lipid shell. The vaccine formulations provided herein can further include one or more adjuvants. In embodiments, the adjuvant can be a Toll-like receptor agonist. The adjuvant(s) can be covalently or noncovalently incorporated into the polymer core and/or the lipid shell. The polymer core can contain or be composed of poly(lactic-co-glycolic acid). The lipid shell can contain a cationic lipid. The lipid shell can, in some embodiments, conatin a lipid selected from the group of: DOTAP (dioleoyl trimethylammonium propane) or a derivative thereof, cholesterol, DSPE (1,2-Distearoylphosphatidylethanolamine)-PEG (polyethylene glycol)-maleimide, and DSPE-PEG-amine, a DSPE-PEG having at least one reactive terminal group, and any combination thereof. The polymer core further contain a second stimulating molecule, wherein the second stimulating molecule can be attached to and/or be encapsulated by a polymer of the polymer core. In some embodiments, the second stimulating molecule can be selected from the group of: keyhole limpet hemocyanin (KLH) multimer, KLH subunit, tetanus toxoid (TT), cross-reacting material 197 ($CRM_{197}$), bovine serum albumin (BSA), Human papillomavirus (HPV) proteins, recombinant *P. aeruginosa* exoprotein A, recombinant cholera toxin B, outer protein capsid of bacteriophage Qb, a peptide, and any combination thereof. The first stimulating molecule can be selected from the group of: keyhole limpet hemocyanin (KLH) multimer, KLH subunit, tetanus toxoid (TT), cross-reacting material 197 ($CRM_{197}$), bovine serum albumin (BSA), Human papillomavirus (HPV) proteins, recombinant *P. aeruginosa* exoprotein A, recombinant cholera toxin B, outer protein capsid of bacteriophage Qb, a peptide, and any combination thereof. In some embodiments, the first nicotine-hapten and the second nicotine hapten can be different. In some embodiments, first nicotine-hapten and the second nicotine-hapten can be the same. In some embodiments, the total density of the first nicotine-hapten and the second nicotine-hapten can range from about 52 to about 115 nicotine-hapten molecules per nanoparticle. In some embodiments, the molar percentage of DSPE-PEG-amine in the lipid portion can range from about 1 to about 99 molar percent. In embodiments, the diameter of the nanoparticle can range from about 1 nm to 999 nm. In some embodiments, the diameter of the nanoparticle can range from about 20 nm to about 200 nm. In some embodiments, the vaccine formulation does not contain alum.

Provided herein are methods of treating nicotine addiction or a symptom thereof in a subject in need thereof, the method including the step of administering a nanoparticle provided herein or formulation thereof to the subject in need thereof.

Provided herein are methods of treating nicotine addition or a symptom thereof in a subject in need thereof, the method including the step of administering a vaccine formulation that can contain a nanoparticle as provided herein to the subject in need thereof.

BRIEF DESCRIPTION OF THE DRAWINGS

Further aspects of the present disclosure will be readily appreciated upon review of the detailed description of its various embodiments, described below, when taken in conjunction with the accompanying drawings.

FIG. 19A shows a graph demonstrating the time-course of anti-nicotine antibody's affinity induced by immunization with nicotine nanovaccines. FIG. 19B shows a graph demonstrating the endpoint comparison of antibody's affinity among different hapten localization nanovaccine groups on day 40. Significantly different: * $p<0.05$,  $p<0.01$, * $p<0.001$.

(FIG. 20E) Th1/Th2 index induced by immunization with nicotine nanovaccines. Th1/Th2 index=(IgG2a+IgG3)/2/IgG1. Significantly different: * $p<0.05$, *** $p<0.001$.

FIG. 23 shows a table demonstrating antigen conjugation efficiency and hapten density of nanovaccines.

FIGS. 25A-25D show CLSM images demonstrating validation of the successful assembly of nanovaccine NPs. The PLGA and lipid layer were labeled by Nile red and NBD, respectively, and AF350 was used as a model of Nic hapten attached on KLH. The scale bar represents 10 μm.

FIG. 32 shows a table demonstrating the physicochemical properties and hapten density of nanovaccine NPs.

FIG. 48 shows a table demonstrating Th1/Th2 indexes of the immune responses induced by nicotine vaccines. All the Th1/Th2 indexes were significantly lower than 1 ($p<0.001$) and no significant differences were present among all vaccine groups.

FIGS. 50A-50T show representative histopathological images of mouse tissues after administration of the negative control, Nic-KLH with alum, high-density nanovaccine, and highdensity nanovaccine with alum. No lesions were observed in mouse organs of all the representative groups.

FIGS. 53A-53D show CLSM images demonstrating the co-localization of TT stimulating protein (FIG. 53A), lipid shell (FIG. 53B), PLGA core (FIG. 53C), and an image merge (FIG. 53D), which were labeled by AF-350, NBD, and Nile Red, respectively. Scale bars represent 10 μm.

FIGS. 54A-54L show CLSM images demonstrating formation of nanovaccine nanoparticles with different stimulating proteins. PLGA core, lipid shell, and stimulating protein (KLH, KS, and $CRM_{197}$) were labeled by Nile Red, NBD, and AF-350, respectively. Scale bars represent 10 μm.

FIGS. 71A-71Y show representative histopathological images demonstrating the relative safety of NanoNicVac conjugated with different stimulating proteins. Organs of mice from groups of PBS blank group (FIGS. 71A-71E), Nano-KLH-Nic (FIGS. 71F-71J), Nano-KS-Nic (FIGS. 71K-71O), Nano-$CRM_{197}$-Nic (FIGS. 71P-71T), and Nano-TT-Nic (FIGS. 71U-71Y) were processed by H&E staining and imaged.

FIG. 72 shows a table demonstrating the physiochemical properties of NanoNicVac nanoparticles conjugated with different stimulating proteins.

(FIG. 75A) KLH containing PLGA nanoparticles; (FIG. 75B) liposomes; and (FIG. 75C) NanoNiccine particles. Freshly synthesized nanoparticles were negatively stained and images were acquired via JEOL JEM 1400 TEM.

FIGS. 81A-81DD show H&E staining of the sections of main organs including heart, lung, kidney, spleen, stomach and liver harvested from the mice immunized with different nicotine vaccines. Mice were sacrificed on day 57 and their major organs were stored in 10% formalin before H&E staining. Scale bars represent 200 µm.

FIGS. 84A-84C show confocal images of NanoNiccine particles, in which the lipid layer was stained with NBD (FIG. 84A) and PLGA core was labeled with Alexa 647 (FIG. 84B). The merged image is shown in FIG. 84C. Scale bars represent 10 µm.

FIG. 88 shows percentages of subclass anti-Nic IgGs in the mice immunized with NanoNiccines. Mice were administered with NanoNiccine, NanoNiccine 1555, NanoNiccine 1826, NanoNiccine MixL, and NanoNiccine H, respectively. Titers of subclass anti-Nic IgGs, including IgG1, IgG2a, IgG2b, and IgG3 were measured using ELISA and their relative percentages were calculated for serum from days 13 (Inner circle), 28 (Middle circle), and 35 (outer circle).

Figures 89A, 89B, 89C, 89D, 89E, 89F, 89G, 89H, 89I, 89J:
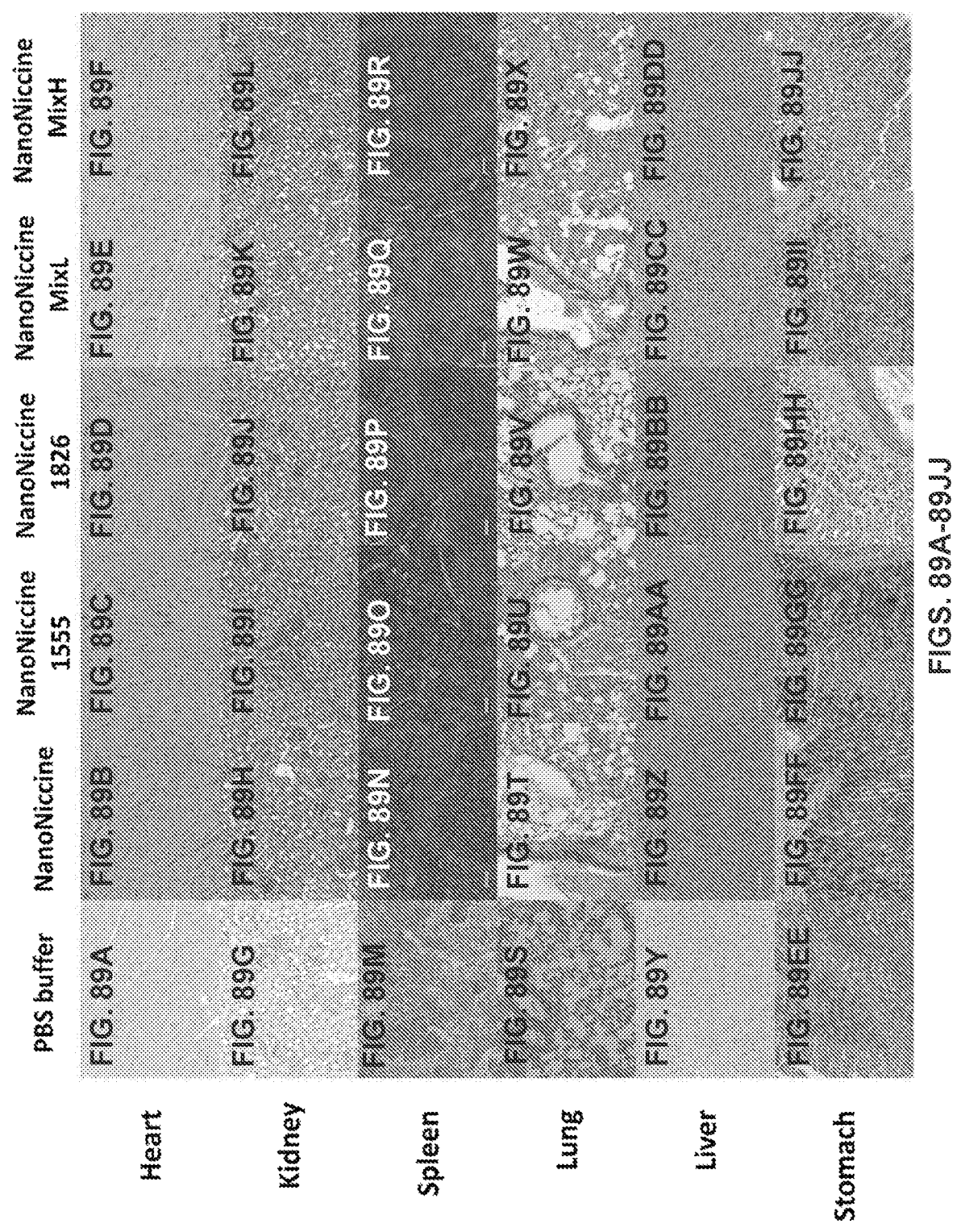

FIGS. 89A-89JJ show histopathological examination of organs from mice, which were immunized with NanoNiccine, NanoNiccine 1555, NanoNiccine 1826, NanoNiccine MixL, and NanoNiccine MixH, respectively. Organs from mice, which were injected with PBS buffer, were used as control. Scale bars represent 200 µm

FIGS. 107A-107E show TEM images of NanoNiccine that were released from NanoNiccine-Alum mixture. Newly prepare NanoNiccine was thoroughly mixed with Alum at Alum/NanoNiccine mass ratios of (FIG. 107A) 0:1, (FIG. 107B) 0.5:1, (FIG. 107C) 1:1, (FIG. 107D) 2:1, and (FIG. 107E) 4:1. The mixtures were incubated for 48 h, followed by recovery of NanoNiccine via centrifugation (washed 3 times with H2O). The morphologies of the released NanoNiccine were captured using a TEM. The scale bars represent 500 nm.

FIGS. 109A-109T show confocal microscopy images demonstrating uptake of NanoNiccine by DCs. NanoNiccine that were labeled with NBD an Alexa 647 was thoroughly mixed with Alum at Alum/NanoNiccine mass ratios of 0:1, 0.5:1, 1:1, 2:1, and 4:1. The NanoNiccine-Alum mixture that contained 100 µg NanoNiccine was incubated with $7 \times 10^5$ cells for 180 min. The scale bars represent 20 µm.

DETAILED DESCRIPTION

Figure 1:
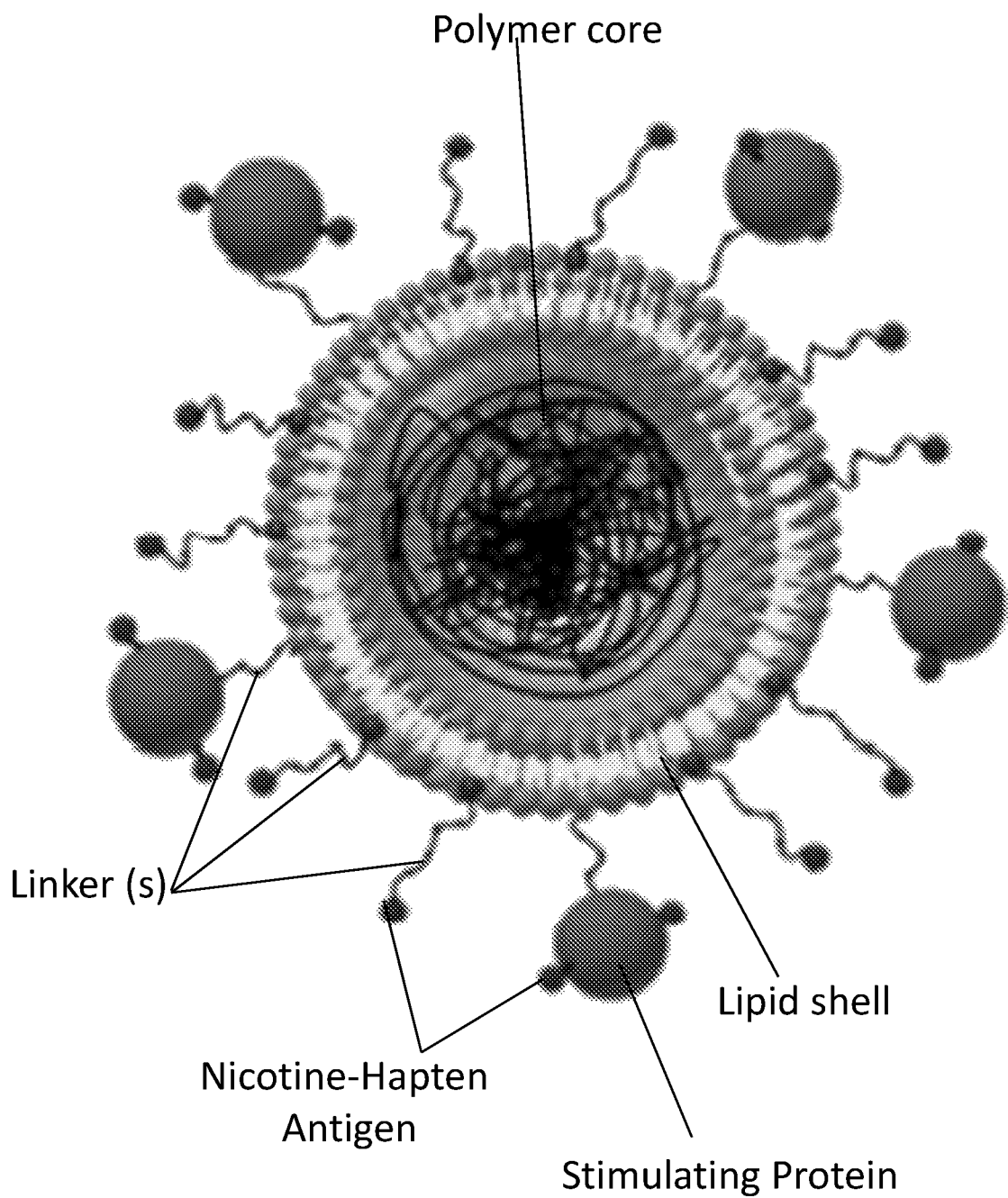
FIG. 1 shows a schematic illustration generally depicting embodiments of a nicotine lipid-polymeric nanoparticle.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of molecular biology, microbiology, nanotechnology, organic chemistry, biochemistry, biotechnology, immunology, bioconjugate chemistry and the like, which are within the skill of the art. Such techniques are explained fully in the literature.

Definitions

As used herein, "about," "approximately," and the like, when used in connection with a numerical variable, can generally refers to the value of the variable and to all values of the variable that are within the experimental error (e.g., within the 95% confidence interval for the mean) or within +/−10% of the indicated value, whichever is greater.

As used herein, "active agent" or "active ingredient" can refer to a substance, compound, or molecule, which is biologically active or otherwise, induces a biological or physiological effect on a subject to which it is administered to. In other words, "active agent" or "active ingredient" refers to a component or components of a composition to which the whole or part of the effect of the composition is attributed.

As used herein, "addiction" can be used to refer to a pathological (physical and/or mental) state, involving the progression of acute substance use to the development of substance-seeking behavior, the vulnerability to relapse, and the decreased, slowed ability to respond to naturally rewarding stimuli. The Diagnostic and Statistical Manual of Mental Disorders, Fourth Edition (DSM-IV) has categorized three stages of addiction: preoccupation/anticipation, bingeintoxication, and withdrawal/negative affect. These stages are characterized, respectively, everywhere by constant cravings and preoccupation with obtaining the substance; using more of the substance than necessary to experience the intoxicating effects; and experiencing tolerance, withdrawal symptoms, and decreased motivation for normal life activities. By the American Society of Addiction Medicine definition, substance addiction differs from substance dependence and substance tolerance. The term substance addiction is also used as a category which can include the same persons who can be given the diagnosis of substance dependence or substance abuse.

As used herein, "additive effect" can refer to an effect arising between two or more molecules, compounds, substances, factors, or compositions that is equal to or the same as the sum of their individual effects.

As used herein, "administering" can refer to an administration that is oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation, by catheters, stents or via an implanted reservoir or other device that administers, either actively or passively (e.g. by diffusion) a composition the perivascular space and adventitia. The term "parenteral" can include subcutaneous, intravenous, intramuscular, intra-articular, intra-synovial, intrasternal, intrathecal, intrahepatic, intralesional, and intracranial injections or infusion techniques.

As used herein, "adjuvant" can refer to an additional compound, composition, or ingredient that can facilitate stimulation an immune response in addition to the main antigen of a composition, formulation, or vaccine. Generally, an adjuvant can increase the immune response of an antigen as compared to the antigen alone. This can improve and/or facilitate any protective immunity developed in the recipient subject in response to the antigen. "Adjuvant" as used herein can refer to a component that potentiates the immune responses to an antigen and/or modulates it towards the desired immune response(s).

As used herein, "antibody" can refer to a glycoprotein containing at least two heavy (H) chains and two light (L) chains inter-connected by disulfide bonds, or an antigen binding portion thereof. Each heavy chain is comprised of a heavy chain variable region (abbreviated herein as VH) and a heavy chain constant region. Each light chain is comprised of a light chain variable region and a light chain constant region. The VH and VL regions retain the binding specificity to the antigen and can be further subdivided into regions of hypervariability, termed complementarity determining regions (CDR). The CDRs are interspersed with regions that are more conserved, termed framework regions (FR). Each VH and VL is composed of three CDRs and four framework regions, arranged from amino-terminus to carboxy-terminus in the following order: FR1, CDR1, FR2, CDR2, FR3, CDR3, and FR4. The variable regions of the heavy and light chains contain a binding domain that interacts with an antigen.

As used herein, "antigen" can refer to a molecule with one or more epitopes that stimulate a host's immune system to make a secretory, humoral and/or cellular antigen-specific response, or to a DNA molecule that is capable of producing such an antigen in a vertebrate. The term is also used interchangeably with "immunogen." For example, a specific antigen can be complete protein, portions of a protein, peptides, fusion proteins, glycosylated proteins and combinations thereof.

As used herein, "anti-infective" can refer to compounds or molecules that can either kill an infectious agent or inhibit it from spreading. Anti-infectives include, but are not limited to, antibiotics, antibacterials, antifungals, antivirals, and anti protozoans.

As used herein, "aptamer" can refer to single-stranded DNA or RNA molecules that can bind to pre-selected targets including proteins with high affinity and specificity. Their specificity and characteristics are not directly determined by their primary sequence, but instead by their tertiary structure.

As used herein, "attached," "attachment" and the like can refer to the formation of a covalent or non-covalent association (e.g. a bond) between two or more molecules or conjugation of two or more molecules. As used herein, "attached," "attachment" and the like can refer to direct association of two or more molecules together with no intermediate molecules between those that are attached together or to the indirect attachment of two or more molecules together that is mediated via one or more linkers. Where the association is non-covalent, this can encompass charge interactions, affinity interactions, metal coordination, physical adsorption, host-guest interactions, hydrophobic interactions, TT stacking interactions, hydrogen bonding interactions, van der Waals interactions, magnetic interactions, electrostatic interactions, dipole-dipole interactions, and/or combinations thereof. Where the association is covalent, this can encompases bonds where a pair of electrons is shared between one or more atoms in each molecule involved.

As used herein, "concentrated" can refer to a molecule or population thereof, including but not limited to a polynucleotide, peptide, polypeptide, protein, antibody, or fragments thereof, that is distinguishable from its naturally occurring counterpart in that the concentration or number of molecules per volume is greater than that of its naturally occurring counterpart.

As used herein, "control" can refer to an alternative subject or sample used in an experiment for comparison purpose and included to minimize or distinguish the effect of variables other than an independent variable.

As used herein, "chemotherapeutic agent" or "chemotherapeutic" can refer to a therapeutic agent utilized to prevent or treat cancer.

As used herein, "culturing" can refer to maintaining cells under conditions in which they can proliferate and avoid senescence as a group of cells. "Culturing" can also include conditions in which the cells also or alternatively differentiate.

As used herein, "deoxyribonucleic acid (DNA)" and "ribonucleic acid (RNA)" can generally refer to any polyribonucleotide or polydeoxribonucleotide, which may be unmodified RNA or DNA or modified RNA or DNA. RNA may be in the form of a tRNA (transfer RNA), snRNA (small nuclear RNA), rRNA (ribosomal RNA), mRNA (messenger RNA), anti-sense RNA, RNAi (RNA interference construct), siRNA (short interfering RNA), or ribozymes.

As used herein, "DNA molecule" can include nucleic acids/polynucleotides that are made of DNA.

As used herein, "derivative" can refer to any compound having the same or a similar core structure to the compound but having at least one structural difference, including substituting, deleting, and/or adding one or more atoms or functional groups. The term "derivative" does not mean that the derivative is synthesized from the parent compound either as a starting material or intermediate, although this may be the case. The term "derivative" can include prodrugs, or metabolites of the parent compound. Derivatives include compounds in which free amino groups in the parent compound have been derivatized to form amine hydrochlorides, p-toluene sulfoamides, benzoxycarboamides, t-butyloxycarboamides, thiourethane-type derivatives, trifluoroacetylamides, chloroacetylamides, or formamides. Derivatives include compounds in which carboxyl groups in the parent compound have been derivatized to form methyl and ethyl esters, or other types of esters or hydrazides. Derivatives include compounds in which hydroxyl groups in the parent compound have been derivatized to form O-acyl or O-alkyl derivatives. Derivatives include compounds in which a hydrogen bond donating group in the parent compound is replaced with another hydrogen bond donating group such as OH, NH, or SH. Derivatives include replacing a hydrogen bond acceptor group in the parent compound with another hydrogen bond acceptor group such as esters, ethers, ketones, carbonates, tertiary amines, imine, thiones, sulfones, tertiary amides, and sulfides. "Derivatives" also includes extensions of the replacement of the cyclopentane ring with saturated or unsaturated cyclohexane or other more complex, e.g., nitrogen-containing rings, and extensions of these rings with side various groups.

As used herein, "dose," "unit dose," or "dosage" can refer to physically discrete units suitable for use in a subject, each unit containing a predetermined quantity of the nicotine nanovaccine and/or a pharmaceutical formulation thereof calculated to produce the desired response or responses in association with its administration.

As used herein, "effective amount" can refer to the amount of a compound provided herein that is sufficient to effect beneficial or desired biological, emotional, medical, or clinical response of a cell, tissue, system, animal, or human. An effective amount can be administered in one or more administrations, applications, or dosages. The term also includes within its scope amounts effective to enhance or restore to substantially normal physiological function. The "effective amount" can refer to the amount of a nicotine nanovaccine and nicotine lipid-polymeric nanoparticles as provided herein that can stimulate a B cell and/or T cell response, can elicit a Th2-skewed response in a subject that a control, can stimulate production of nicotine specific antibodies in a subject, can increase the amount of nicotine in the serum of a subject, can promote the enzymatic degradation of nicotine in the serum, can reduce the amout of nicotine present in the brain of a subject, can inhibit, reduce and/or eliminate one ore more symptoms of nicotine additicion in a subject and/or any combination thereof.

As used herein, the terms "Fc portion," "Fc region," and the like are used interchangeably herein and can refer to the fragment crystallizable region of an antibody that interacts with cell surface receptors called Fc receptors and some proteins of the complement system. The IgG Fc region is composed of two identical protein fragments that are derived from the second and third constant domains of the IgG antibody's two heavy chains.

As used herein, "immunomodulator," can refer to an agent, such as a therapeutic agent, which is capable of modulating or regulating one or more immune function or response.

As used herein, "immune response" can refer to the reaction of the molecules, components, pathways, organs, fluids and/or cells of the body to the presence of a substance that is foreign or recognized by the body as foreign to the body.

As used herein, "isolated" means separated from constituents, cellular and otherwise, in which the polynucleotide, peptide, polypeptide, protein, antibody, or fragments thereof, are normally associated with in nature. A non-naturally occurring polynucleotide, peptide, polypeptide, protein, antibody, or fragments thereof, do not require "isolation" to distinguish it from its naturally occurring counterpart.

As used herein, "mammal," for the purposes of treatments, can refer to any animal classified as a mammal, including human, domestic and farm animals, nonhuman primates, and zoo, sports, or pet animals, such as, but not limited to, dogs, horses, cats, and cows. As used herein, "modulate or modulation of the immune response" can refer to change in the immune response that results from the introduction of a composition, vaccine, or other compound or formulation described herein in a recipient subject as compared to a suitable control.

The term "molecular weight", as used herein, can generally refer to the mass or average mass of a material. If a polymer or oligomer, the molecular weight can refer to the relative average chain length or relative chain mass of the bulk polymer. In practice, the molecular weight of polymers and oligomers can be estimated or characterized in various ways including gel permeation chromatography (GPC) or capillary viscometry. GPC molecular weights are reported as the weight-average molecular weight ($M_w$) as opposed to the number-average molecular weight ($M_n$). Capillary viscometry provides estimates of molecular weight as the inherent viscosity determined from a dilute polymer solution using a particular set of concentration, temperature, and solvent conditions.

As used herein, "negative control" can refer to a "control" that is designed to produce no effect or result, provided that all reagents are functioning properly and that the experiment is properly conducted. Other terms that are interchangeable with "negative control" include "sham," "placebo," and "mock."

As used herein, nicotine uless indicated otherwise, throughout this disclosure can include the terms "nicotine," "nicotine moiety," and "nicotine hapten", all which can be used interchangeably herein, and are intended to include nicotine per se (i.e., (S)-(−)-, (R)-(−)-, or a combination thereof) as well as metabolites, derivatives, analogues, and haptens thereof. Metabolites of nicotine include any compound that is the product of metabolic processing of nicotine, such as cotinine, continine N'-oxide (CNO), 5'-hydroxycotinine (5HC), 3'-hydroxycotinine (3HC), 5-hydroxycotinine (5HC), 5-hydroxycotinine-N-oxide, 3-hydroxycotinine glucuronide, norcotinine, nornicotine, nicotine-N-oxide (NNO), (S)-nicotine-N—B-glucuronide (Nicotine-Gluc), and Cotinine-glucuronide (Cotinine-Gluc). Derivatives of nicotine include conjugates of nicotine covalently bonded to another species (such as a polymer, oligomer, or small molecule). Analogues include, for example, nicotine wherein the N-methyl group has been replaced with a higher order alkyl group. Similarly, the term "anti-nicotine antibody" refers to an antibody typically created in a biological organism (such as an animal) that binds to nicotine and/or metabolites, derivatives, or analogues thereof.

As used herein, "nucleic acid" and "polynucleotide" generally refer to a string of at least two base-sugar-phosphate combinations and refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. "Polynucleotide" and "nucleic acids" also encompasses such chemically, enzymatically or metabolically modified forms of polynucleotides, as well as the chemical forms of DNA and RNA characteristic of viruses and cells, including simple and complex cells, inter alia. For instance, the term polynucleotide includes DNAs or RNAs as described above that contain one or more modified bases. Thus, DNAs or RNAs comprising unusual bases, such as inosine, or modified bases, such as tritylated bases, to name just two examples, are polynucleotides as the term is used herein. "Polynucleotide" and "nucleic acids" also includes PNAs (peptide nucleic acids), phosphorothioates, and other variants of the phosphate backbone of native nucleic acids. Natural nucleic acids have a phosphate backbone, artificial nucleic acids may contain other types of backbones, but contain the same bases. Thus, DNAs or RNAs with backbones modified for stability or for other reasons are "nucleic acids" or "polynucleotide" as that term is intended herein. As used herein, "nucleic acid sequence" and "oligonucleotide" also encompasses a nucleic acid and polynucleotide as defined above.

As used herein, "nicotine addiction" can refer to addiction to nicotine and products and other compositions that contain nicotine (nicotine containing products). Example compositions and products containing nicotine include, but are not limited to tobacco and tobacco containing products, electronic cigarettes, vegetables belonging to the family Solanacea, and pharmaceutical nicotine replacement products.

As used herein, "organism", "host", and "subject" refers to any living entity comprised of at least one cell. A living organism can be as simple as, for example, a single isolated eukaryotic cell or cultured cell or cell line, or as complex as a mammal, including a human being, and animals (e.g., vertebrates, amphibians, fish, mammals, e.g., cats, dogs, horses, pigs, cows, sheep, rodents, rabbits, squirrels, bears, primates (e.g., chimpanzees, gorillas, and humans). "Subject" may also be a cell, a population of cells, a tissue, an organ, or an organism, preferably to human and constituents thereof.

As used herein, a "particle" can refer to any entity having a diameter of less than 10 microns (μm). Typically, particles have a longest dimension (e.g., diameter) of 1000 nm or less. In some embodiments, particles have a diameter of 300 nm or less. Particles include microparticles, nanoparticles, and picoparticles. In some embodiments, nanoparticles can have a diameter of 200 nm or less. In some embodiments, nanoparticles have a diameter of 100 nm or less. In some embodiments, nanoparticles have a diameter of 50 nm or less. In some embodiments, nanoparticles have a diameter of 30 nm or less. In some embodiments, nanoparticles have a diameter of 20 nm or less. In some embodiments, nanoparticles have a diameter of 10 nm or less. In some embodiments, particles can be a matrix of polymers. In some embodiments, particles can be a non-polymeric particle (e.g., a metal particle, quantum dot, ceramic, inorganic material, bone, etc.). Particles may also be liposomes and/or micelles. As used herein, the term "nanoparticle" refers to any particle having a diameter of less than 1000 nm.

As used herein, "patient" refers to an organism, host, or subject in need of treatment. As used herein "peptide" refers to chains of at least 2 amino acids that are short, relative to a protein or polypeptide.

As used herein, "pharmaceutical formulation" refers to the combination of an active agent, compound, or ingredient with a pharmaceutically acceptable carrier or excipient, making the composition suitable for diagnostic, therapeutic, or preventive use in vitro, in vivo, or ex vivo.

As used herein, "pharmaceutically acceptable carrier or excipient" can refer to a carrier or excipient that is useful in preparing a pharmaceutical formulation that is generally safe, non-toxic, and is neither biologically or otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

As used herein, "pharmaceutically acceptable salt" can refer to any acid or base addition salt whose counter-ions are non-toxic to the subject to which they are administered in pharmaceutical doses of the salts.

As used herein, "positive control" can refer to a "control" that is designed to produce the desired result, provided that all reagents are functioning properly and that the experiment is properly conducted.

As used herein, "preventative" and "prevent" can refer to hindering or stopping a disease or condition before it occurs, even if undiagnosed, or while the disease or condition is still in the sub-clinical phase.

As used herein, "protein" as used herein can refer to a molecule composed of one or more chains of amino acids in a specific order. The term protein is used interchangeable with "polypeptide." The order is determined by the base sequence of nucleotides in the gene coding for the protein. Proteins are required for the structure, function, and regulation of the body's cells, tissues, and organs.

As used herein, "purified" or "purify" can be used in reference to a nucleic acid sequence, peptide, or polypeptide that has increased purity relative to the natural environment.

As used herein, "separated" can refer to the state of being physically divided from the original source or population such that the separated compound, agent, particle, or molecule can no longer be considered part of the original source or population.

As used interchangeably herein, "subject," "individual," or "patient," refers to a vertebrate and/or a mammal. Mammals include, but are not limited to, murines, simians, humans, farm animals, sport animals, and pets. The term "pet" includes a dog, cat, guinea pig, mouse, rat, rabbit, ferret, and the like. The term farm animal includes a horse, sheep, goat, chicken, pig, cow, donkey, llama, alpaca, turkey, and the like.

As used herein, "substantially pure" can mean an object species is the predominant species present (i.e., on a molar basis it is more abundant than any other individual species in the composition), and preferably a substantially purified fraction is a composition wherein the object species comprises about 50 percent of all species present. Generally, a substantially pure composition will comprise more than about 80 percent of all species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single species.

As used herein, the term "specific binding" can refer to non-covalent physical association of a first and a second moiety wherein the association between the first and second moieties is at least 2 times as strong, at least 5 times as strong as, at least 10 times as strong as, at least 50 times as strong as, at least 100 times as strong as, or stronger than the association of either moiety with most or all other moieties present in the environment in which binding occurs. Binding of two or more entities may be considered specific if the equilibrium dissociation constant, Kd, is $10^{-3}$ M or less, $10^{-4}$ M or less, $10^{-5}$ M or less, $10^{-6}$ M or less, $10^{-7}$ M or less, $10^{-8}$ M or less, $10^{-9}$ M or less, $10^{-10}$ M or less, $10^{-11}$ M or less, or $10^{-12}$ M or less under the conditions employed, e.g., under physiological conditions such as those inside a cell or consistent with cell survival. In some embodiments, specific binding can be accomplished by a plurality of weaker interactions (e.g., a plurality of individual interactions, wherein each individual interaction is characterized by a Kd of greater than $10^{-3}$ M). In some embodiments, specific binding, which can be referred to as "molecular recognition," is a saturable binding interaction between two entities that is dependent on complementary orientation of functional groups on each entity. Examples of specific binding interactions include aptamer-aptamer target interactions, antibody-antigen interactions, avidin-biotin interactions, ligand-receptor interactions, metal-chelate interactions, hybridization between complementary nucleic acids, etc.

As used herein, the terms "T cell antigen" can refer to any antigen that is recognized by and triggers an immune response in a T cell (e.g., an antigen that is specifically recognized by a T cell receptor on a T cell via presentation of the antigen or portion thereof bound to a major histocompatibility complex molecule (MHC). In some embodiments, an antigen that is a T cell antigen is also a B cell antigen. In other embodiments, the T cell antigen is not also a B cell antigen. T cells antigens generally are proteins or peptides. T cell antigens may be an antigen that stimulates a CD8+ T cell response, a CD4+ T cell response, or both. The nanocarriers, therefore, in some embodiments can effectively stimulate both types of responses.

As used herein, "therapeutic" can refer to treating, healing, and/or ameliorating a disease, disorder, condition, or side effect, or to decreasing in the rate of advancement of a disease, disorder, condition, or side effect. A "therapeutically effective amount" can therefore refer to an amount of a compound that can yield a therapeutic effect.

As used herein, the terms "treating" and "treatment" can refer generally to obtaining a desired pharmacological and/or physiological effect. The effect can be, but does not necessarily have to be, prophylactic in terms of preventing or partially preventing a disease, symptom or condition thereof, such as ephorial feeling acquired from smoking. The term "treatment" as used herein covers any treatment of nicotine addiction in a mammal, particularly a human and can include any one or more of the following: (a) preventing the disease from occurring in a subject which may be predisposed to the disease but has not yet been diagnosed as having it; (b) inhibiting the disease, i.e., arresting its development; and/or (c) relieving the disease, i.e., mitigating or ameliorating the disease and/or its symptoms or conditions. The term "treatment" as used herein can refer to therapeutic treatment alone, prophylactic treatment alone, or both therapeutic and prophylactic treatment. Those in need of treatment (subjects in need thereof) can include those already with the disorder and/or those in which the disorder is to be prevented. Efficacy can be measured using objective or subjective techniques. For example, efficacy can be measured via determining antibody titers and comparing them to a standard and/or control. Efficacy can be measured by measuring the occurrence of nicotine use and comparing the amount of use to a standard, control, and/or over a period of time. Efficacy can be measured by querying the subject and determining if cravings for nicotine and/or nicotine product have been reduced, remained the same, or increased. Efficacy can be measured by querying the subject and determining any changes in euphoric feeling attained after nicotine consumption. Efficacy can be determined by measuring a metabolite or other molecule (e.g. a neurotransmitter) in the subject and comparing the amount measured to a standard and/or a control. Other methods of determining efficacy will be appreciated by those of skill in the art.

As used herein, "vaccine" can refer to a compound, molecule, compositions, and formulations that are capable of inducing an immune response in a subject. The term "vaccine" can also be used to refer to a compound, molecule, compositions, and formulations that are capable of providing protective immunity against an organism. The vaccine may provide protection or immunization against a compound, such as nicotine. The vaccine can be capable of stimulating a B cell immune response specific to nicotine.

Unless otherwise defined herein, all technical and scientific terms used herein have the same meaning as commonly understood by one of ordinary skill in the art.

Discussion

Tobacco smoking is a large public health threat the world, resulting in approximately 6 million premature deaths worldwide. Despite strong desire to quit smoking, the majority of unassisted smokers usually relapse within the first month, and only 3-5% of them remain abstinent after 6 months. Even with the help of pharmacological interventions, including nicotine replacement therapy, varenidine, and bupropion, the long-term smoking cessation rate at one year is disappointingly low (about 10-25%). Nicotine is the primary agent in tobacco and tobacco-based and related products that generates addiction to tobacco products. Nicotine is an alkaloid derived from the tobacco plant that is responsible for smoking's psychoactive and addictive effects. Nicotine is formed of two rings linked together by a single bond: an aromatic six-membered ring (pyridine) and an aliphatic five-membered ring (pyrrolidine). The pyrrolidine is N-methylated and linked through its carbon-2 to the carbon-3 of pyridine. Thus, the carbon-2 is chiral, and there is virtually free rotation around the single bond linking the two rings. It has been established that the absolute configuration of carbon-2 is S. Thus, the natural configuration of nicotine is (S)-(−)-nicotine.

There have been attempts to generate nicotine vaccines to immunize a user to nicotine and thus its addictive effects. Early nicotine vaccines used the conventional conjugate vaccine approach with a carrier protein (e.g. keyhole lymphocyte hemocyanin) conjugated to a hapten-nicotine. These conjugate nicotine vaccines suffer from a variety of shortfalls, such as fast degradation, low nicotine loading capacity, low bioavailability, and poor recognition and uptake by immune cells, which has limited their immunological efficacy. More recent approaches include nanoparticle based vaccines that are core and core-shell nanoparticle based. Current nanoparticle-based nicotine vaccines are not without their shortcomings and have failed to generate sufficient immunogenicity and have failed to demonstrate clinical efficacy.

With that said, described herein are lipid-polymeric nanoparticles that can be capable of functioning as a nicotine vaccine. The lipid-polymeric nanoparticles provided herein can include a polymer core surrounded by a lipid shell. The lipid-polymeric nanoparticles provided herein can have a hapten-nicotine that can be directly conjugated to a stimulating protein that can be in turn conjugated the surface of and/or integrated into the lipid shell and can have a hapten-nicotine that is conjugated to the lipid shell directly to the lipid shell or indirectly via a linker. The polymer core can contain additional molecules, such as additional immune stimulating molecules and proteins. The nicotine lipid-polymeric nanoparticles provided herein can be formulated as pharmaceutical formulations and/or vaccines. The nicotine lipid-polymeric nanoparticles provided herein can be administered to a subject in need thereof for treatment and/or prevention of nicotine addiction and/or use of a nicotine product, such as tobacco.

The nicotine lipid-polymeric nanoparticles can be capable of stimulating an immune response in B cells and/or T cells. The nicotine lipid-polymeric nanoparticles can be capable of stimulating the production of anti-nicotine antibodies in a subject. The nicotine lipid-polymeric nanoparticles provided herein can provide increased immunogenicity, induce a lower anti-stimulating protein antibody response, and/or a more Th2 skewed immune response as compared to current nanoparticle-based nicotine vaccines. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Nicotine Lipid-Polymeric Nanoparticles

Provided herein are nicotine lipid-polymeric nanoparticles. As generally shown in FIG. 1, the nicotine lipid-polymeric nanoparticles can have a general core-shell structure with a polymer core and a lipid shell. The lipid shell can encapsulate the polymer core. The nicotine lipid-polymeric nanoparticles can include a first nicotine-hapten that is attached to a simulating protein that is attached to the outer surface of the lipid shell or otherwise integrated in the lipid shell. The stimulating protein can be attached to the outer surface of the lipid shell indirectly via a linker as shown in FIG. 1. The nicotine lipid-polymeric nanoparticles can also include a second nicotine-hapten antigen that is attached to the outer surface of the lipid shell and is not attached to the stimulating protein. The second nicotine-hapten antigen can be indirectly attached to the outer surface of the lipid membrane via a linker.

The nicotine lipid-polymeric nanoparticles can have a greatest dimension (e.g., diameter) of less than 100, 10, 5, or 1 microns (μm). The nicotine lipid-polymeric nanoparticles can have a greatest dimension (e.g., diameter) of less than 900 nm, 800 nm, 700 nm, 600 nm, 500 nm, 400 nm, 300 nm, 200 nm, or 100 nm. The nicotine lipid-polymeric nanoparticles can have a greatest dimension (e.g., diameter) of 300 nm or less. The nicotine lipid-polymeric nanoparticles can have a greatest dimension (e.g., diameter) of 250 nm or less. The nicotine lipid-polymeric nanoparticles can have a greatest dimension (e.g., diameter) of 200 nm or less. The nicotine lipid-polymeric nanoparticles can have a greatest dimension (e.g., diameter) of 150 nm or less. The nicotine lipid-polymeric nanoparticles can have a greatest dimension (e.g., diameter) of 100 nm or less. The nicotine lipid-polymeric nanoparticles can have a greatest dimension (e.g., diameter) ranging between 20 nm and 200 nm. As used herein "greatest dimension" can refer to the largest dimension of a nanoparticle herein as measured along any axis of the nanoparticle. As used herein "minimum dimensions" can refer to the smallest dimension of a nanoparticle herein as measured along any axis of the nanoparticle.

A population of nicotine lipid-polymeric nanoparticles can have a mean geometric diameter that is less than 500 nm. A population of the nicotine lipid-polymeric nanoparticles can have a mean geometric diameter that is greater than 20 nm but less than 500 nm. The nicotine lipid-polymeric nanoparticles can have a mean geometric diameter of a population of nanocarriers is about 20 nm, 60 nm, 75 nm, 100 nm, 125 nm, 150 nm, 175 nm, 200 nm, 225 nm, 250 nm, 275 nm, 300 nm, 325 nm, 350 nm, 375 nm, 400 nm, 425 nm, 450 nm, or 475 nm. In some embodiments, the mean geometric diameter can be between 100-400 nm, 100-300 nm, 100-250 nm, or 100-200 nm. In some embodiments, the mean geometric diameter can be between 20-400 nm, 20-350 nm, 20-300 nm, 20-250 nm, or 20-200 nm. In some embodiments, the mean geometric diameter can be between 20-200 nm.

In certain embodiments, the nicotine nanoparticles are greater in size than the renal excretion limit (e.g., nanoparticles having diameters of greater than 6 nm). In certain embodiments, the nicotine nanoparticles are small enough to avoid clearance of nanocarriers from the bloodstream by the liver (e.g., nanoparticles having diameters of less than 1000 nm). In general, physiochemical features of nanocarriers can allow a nanocarrier to circulate longer in plasma by decreasing renal excretion and liver clearance.

A population of the nicotine nanoparticles can be generally uniform in terms of of size, shape, and/or composition so that each nicotine nanoparticle has similar properties. For example, at least 80%, at least 90%, or at least 95% of the nicotine nanoparticles can have a diameter or greatest dimension that falls within 5%, 10%, or 20% of the average diameter or greatest dimension. In some embodiments, a population of nicotine nanoparticles can be heterogeneous with respect to size, shape, and/or composition. In some embodiments, 30%, 40%, 50%, 60%, 70%, 80%, 90%, or more of the nicotine nanoparticles of a population of nicotine nanoparticles can have a diameter that is less than 500, 300, 200, 100, 50, or 25 nm. In some embodiments, 10%, 20%, 30%, 40%, 50%, 60%, 70%, 80%, 90%, or more of the nanocarriers of a population of nicotine nanoparticles have a diameter that is greater than 20 nm but less than 200 nm. In some embodiments, 10%, 20%, 30%, 40%, 50%, 60%, 70%, 80%, 90%, or more of the nicotine nanoparticles of a population of nicotine nanoparticles have a diameter of about 20 nm, 50, nm, 60 nm, 75 nm, 100 nm, 125 nm, 150 nm, 175 nm, 200 nm, 225 nm, 250 nm, 275 nm, 300 nm, 325 nm, 350 nm, 375 nm, 400 nm, 425 nm, 450 nm, or 475 nm. In some embodiments, 10%, 20%, 30%, 40%, 50%, 60%, 70%, 80%, 90%, or more of the nicotine nanoparticles of a population of nicotine nanoparticles can have a diameter that is between 100-400 nm, 100-300 nm, 100-250 nm, or 100-200 nm. In some embodiments, 10%, 20%, 30%, 40%, 50%, 60%, 70%, 80%, 90%, or more of the nicotine nanoparticles of a population of n nicotine nanoparticles have a diameter that is between 20-400 nm, 20-350 nm, 20-300 nm, 20-250 nm, or 20-200 nm.

The nicotine lipid-polymeric nanoparticles can have a core/shell structure, wherein the core is one layer (e.g. a polymeric core) and the shell is a second layer (e.g. a lipid bilayer or monolayer). The nicotine lipid-polymeric nanoparticles can have any shape. The nicotine lipid-polymeric nanoparticles can be spheres or spheroids. The nicotine lipid-polymeric nanoparticles can be flat or plate-shaped. The nicotine lipid-polymeric nanoparticles can be cubes or cuboids. The nicotine lipid-polymeric nanoparticles can be ovals or ellipses. The nicotine lipid-polymeric nanoparticles can be cylinders, cones, or pyramids. The nicotine lipid-polymeric nanoparticles can have one or more inner and outer surfaces (e.g. the core can have a surface and the shell can have an inner and an outer surface), and at least one of the one or more surfaces comprises an immunofeature surface.

Zeta potential is a measurement of surface potential of a particle. The nicotine nanoparticles can have a positive zeta potential. In some embodiments, the nicotine nanoparticles can have a zeta potential ranging between −50 mV and +50 mV. In some embodiments, the nicotine nanoparticles can have a zeta potential ranging between −25 mV and +25 mV. In some embodiments, the nicotine nanoparticles can have a zeta potential ranging between −10 mV and +10 mV. In some embodiments, the nicotine nanoparticles can have a zeta potential ranging between −5 mV and +5 mV. In some embodiments, the nicotine nanoparticles can have a zeta potential ranging between 0 mV and +50 mV. In some embodiments, the nicotine nanoparticles can have a zeta potential ranging between 0 mV and +25 mV. In some embodiments, the nicotine nanoparticles can have a zeta potential ranging between 0 mV and +10 mV. In some embodiments, the nicotine nanoparticles can have a zeta potential ranging between 0 mV and +5 mV. In some embodiments, the nicotine nanoparticles can have a zeta potential ranging between −50 mV and 0 mV. In some embodiments, the nicotine nanoparticles can have a zeta potential ranging between −25 mV and 0 mV. In some embodiments, the nicotine nanoparticles can have a zeta potential ranging between −10 mV and 0 mV. In some embodiments, the nicotine nanoparticles can have a zeta potential ranging between −5 mV and 0 mV. In some embodiments, the nicotine nanoparticles can have a substantially neutral zeta potential (i.e. approximately 0 mV). In some embodiments, nicotine nanoparticles can have a negative charge. In some embodiments, nicotine nanoparticles can have a positive charge. In some embodiments, nicotine nanoparticles can be electrically neutral. The overall zeta potential of the lipid-polymeric nanoparticles can range from about −100 mV to about 100 mV.

The nicotine lipid-polymeric nanoparticles, or any component thereof, can be biodegradable and/or biocompatible. In general, a biocompatible substance is not toxic to cells. A substance can be considered to be biocompatible if its addition to cells results in less than a certain threshold of cell death (e.g. less than 50%, 20%, 10%, 5%, or less cell death). A substance can be considered to be biocompatible if its addition to cells does not induce adverse effects. In general, a biodegradable substance can be one that undergoes breakdown under physiological conditions over the course of a therapeutically relevant time period (e.g., weeks, months, or years). A biodegradable substance can be a substance that can be broken down by cellular machinery. A biodegradable substance is a substance that can be broken down by chemical processes. The nicotine lipid-polymeric nanoparticles or a component thereof can be both biocompatible and biodegradable. The nicotine lipid-polymeric nanoparticles or a component thereof can be biocompatible, but not biodegradable. The nicotine lipid-polymeric nanoparticles or a component thereof can be that is biodegradable, but not biocompatible.

The nicotine lipid-polymeric nanoparticles can be prepared using any method known in the art. For example, particulate nicotine lipid-polymeric nanoparticles formulations can be formed by methods such as nanoprecipitation, flow focusing fluidic channels, spray drying, single and double emulsion solvent evaporation, solvent extraction, phase separation, milling, microemulsion procedures, nanoprinting, microfabrication, nanofabrication, sacrificial layers, simple and complex coacervation, as well as other methods well known to those of ordinary skill in the art. Alternatively or additionally, aqueous and organic solvent syntheses for monodisperse semiconductor, conductive, magnetic, organic, and other nanoparticles may be utilized. In some embodiments, nicotine lipid-polymeric nanoparticles can be made by self-assembly. As an example, lipids are mixed with a lipophilic component that can contain a nicotine and then formed into thin films on a solid surface. A hydrophilic component dissolved in an aqueous solution, which can be added to the lipid films to hydrolyze lipids under vortex. Liposomes with lipophilic components and hydrophilic components inside the liposome lumen can be spontaneously assembled. In certain embodiments, pre-formulated polymeric nanoparticles (e.g. polymeric core nanoparticles) can be mixed with small liposomes under gentle vortex to induce liposome fusion onto polymeric nanoparticle surface. The nanoparticles can be manufactured under sterile conditions. Other assembly methods will be appreciated by those of ordinary skill in the art in view of the present disclosure.

Polymer Core. The nicotine lipid-polymeric nanoparticles can have a polymer core. A wide variety of polymers and methods for forming polymeric matrices therefrom are known in the art of drug delivery. In general, a polymeric matrix can be composed of one or more polymers. Any suitable polymer can be used in the polymer core. In some embodiments, one, more than one, or all of the polymer(s) present in the polymer core can be biodegradable. The polymers can be natural or unnatural (synthetic) polymers. The polymers can be homopolymers or copolymers composed of two or more monomers. In terms of sequence, copolymers can be random, block, or comprise a combination of random and block sequences. The polymers can be organic polymers. The polymers can be synthetic polymers. The polymers can be dendritic polymers or blends of polymers. Non-limiting examples of suitable core polymers include polyethylenes, polycarbonates (e.g. poly(1,3-dioxan-2one)), polyanhydrides (e.g. poly(sebacic anhydride)), polyhydroxyacids (e.g. poly(β-hydroxyalkanoate)), polypropylfumerates, polycaprolactones, polyamides (e.g. polycaprolactam), polyacetals, polyethers, polyesters (e.g. polylactide, polyglycolide), poly(orthoesters), polycyanoacrylates, polyvinyl alcohols, polyurethanes, polyphosphazenes, polyacrylates, polymethacrylates, polyureas, polystyrenes, and polyamines.

Suitable polymers also include those which have been approved for use in humans by the U.S. Food and Drug Administration (FDA) under 21 C.F.R. § 177.2600, including but not limited to polyesters (e.g., polylactic acid, poly(lactic-co-glycolic acid), polycaprolactone, polyvalerolactone, poly(1,3-dioxan-2one)); polyanhydrides (e.g., poly (sebacic anhydride)); polyethers (e.g., polyethylene glycol); polyurethanes; polymethacrylates; polyacrylates; and polycyanoacrylates.

The polymer(s) can be hydrophilic. For example, polymers can include anionic groups (e.g., phosphate group, sulphate group, carboxylate group); cationic groups (e.g., quaternary amine group); or polar groups (e.g., hydroxyl group, thiol group, amine group). The polymer core can be a hydrophilic polymeric matrix which generates a hydrophilic environment within the nicotine nanoparticle. In some embodiments, additional hydrophilic immunomodulatory agents and/or immunostimulatory agents may be associated with hydrophilic polymeric matrix core.

The polymer(s) can be hydrophobic. A hydrophobic polymeric matrix can generate a hydrophobic environment within the core of the nicotine nanoparticle. In some embodiments, hydrophobic immunomodulatory agents and/or immunostimulatory agents can be associated with hydrophobic polymeric matrix core.

The polymers can be modified with one or more moieties and/or functional groups. Any moiety or functional group can be used. In some embodiments, polymers can be modified with polyethylene glycol (PEG), with a carbohydrate, and/or with acyclic polyacetals derived from polysaccharides (Papisov, 2001, ACS Symposium Series, 786:301; incorporated herein by reference).

The polymers can be modified with a lipid or fatty acid group, properties of which are described in further detail below. In some embodiments, a fatty acid group may be one or more of butyric, caproic, caprylic, capric, lauric, myristic, palmitic, stearic, arachidic, behenic, or lignoceric acid. In some embodiments, a fatty acid group may be one or more of palmitoleic, oleic, vaccenic, linoleic, alpha-linoleic, gamma-linoleic, arachidonic, gadoleic, arachidonic, eicosapentaenoic, docosahexaenoic, or erucic acid.

The polymers can be polyesters, including copolymers including lactic acid and glycolic acid units, such as poly (lactic acid-co-glycolic acid) and poly(lactide-co-glycolide), collectively referred to herein as "PLGA"; and homopolymers including glycolic acid units, referred to herein as "PGA," and lactic acid units, such as poly-L-lactic acid, poly-D-lactic acid, poly-D,L-lactic acid, poly-L-lactide, poly-D-lactide, and poly-D,L-lactide, collectively referred to herein as "PLA." In some embodiments, exemplary polyesters include, for example, polyhydroxyacids; PEG copolymers and copolymers of lactide and glycolide (e.g., PLA-PEG copolymers, PGA-PEG copolymers, PLGA-PEG copolymers, and derivatives thereof. In some embodiments, polyesters include, for example, polyanhydrides, poly(ortho ester), poly(ortho ester)-PEG copolymers, poly(caprolactone), poly(caprolactone)-PEG copolymers, polylysine, polylysine-PEG copolymers, poly(ethylene imine), poly (ethylene imine)-PEG copolymers, poly(L-lactide-co-L-lysine), poly(serine ester), poly(4-hydroxy-L-proline ester), poly[α-(4-aminobutyl)-L-glycolic acid], and derivatives thereof.

The polymers can be one or more acrylic polymers. Acrylic polymers can include, for example, acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolymer, poly(methyl methacrylate), poly(methacrylic acid anhydride), methyl methacrylate, polymethacrylate, poly (methyl methacrylate) copolymer, polyacrylamide, aminoalkyl methacrylate copolymer, glycidyl methacrylate copolymers, polycyanoacrylates, and combinations comprising one or more of the foregoing polymers. The acrylic polymer may comprise fully-polymerized copolymers of acrylic and methacrylic acid esters with a low content of quaternary ammonium groups.

The polymers can be cationic polymers. In general, cationic polymers can condense and/or protect negatively charged strands of nucleic acids (e.g. DNA, RNA, or derivatives thereof). Amine-containing polymers such as poly (lysine) (Zauner et al., 1998, Adv. Drug Del. Rev., 30:97; and Kabanov et al., 1995, Bioconjugate Chem., 6:7; both of which are incorporated herein by reference), poly(ethylene imine) (PEI; Boussif et al., 1995, Proc. Natl. Acad. Sci., USA, 1995, 92:7297; incorporated herein by reference), and poly(amidoamine) dendrimers (Kukowska-Latallo et al., 1996, Proc. Natl. Acad. Sci., USA, 93:4897; Tang et al., 1996, Bioconjugate Chem., 7:703; and Haensler et al., 1993, Bioconjugate Chem., 4:372; all of which are incorporated herein by reference) are positively-charged at physiological pH, form ion pairs with nucleic acids, and mediate transfection in a variety of cell lines.

The polymers can be degradable polyesters bearing cationic side chains (Putnam et al., 1999, Macromolecules, 32:3658; Barrera et al., 1993, J. Am. Chem. Soc., 115:11010; Kwon et al., 1989, Macromolecules, 22:3250; Lim et al., 1999, J. Am. Chem. Soc., 121:5633; and Zhou et al., 1990, Macromolecules, 23:3399; all of which are incorporated herein by reference). Examples of these polyesters include poly(L-lactide-co-L-lysine) (Barrera et al., 1993, J. Am. Chem. Soc., 115:11010; incorporated herein by reference), poly(serine ester) (Zhou et al., 1990, Macromolecules, 23:3399; incorporated herein by reference), poly(4-hydroxy-L-proline ester) (Putnam et al., 1999, Macromolecules, 32:3658; and Lim et al., 1999, J. Am. Chem. Soc., 121:5633; both of which are incorporated herein by reference), and poly(4-hydroxy-L-proline ester) (Putnam et al., 1999, Macromolecules, 32:3658; and Lim et al., 1999, J. Am. Chem. Soc., 121:5633; both of which are incorporated herein by reference).

The polymers can be carbohydrates, properties of which are described in further detail below. In some embodiments, a carbohydrate may be a polysaccharide comprising simple sugars (or their derivatives) connected by glycosidic bonds, as known in the art. In some embodiments, a carbohydrate may be one or more of pullulan, cellulose, microcrystalline cellulose, hydroxypropyl methylcellulose, hydroxycellulose, methylcellulose, dextran, cyclodextran, glycogen, starch, hydroxyethylstarch, carageenan, glycon, amylose, chitosan, N,O-carboxylmethylchitosan, algin and alginic acid, starch, chitin, heparin, konjac, glucommannan, pustulan, heparin, hyaluronic acid, curdlan, and xanthan.

The polymer can be a protein or peptide, properties of which are described in further detail below. Exemplary proteins that may be used in accordance with the present invention include, but are not limited to, albumin, collagen, a poly(amino acid) (e.g., polylysine), an antibody, etc.

The polymer can be a nucleic acid (i.e., polynucleotide), properties of which are described in further detail below. Exemplary polynucleotides that may be used in accordance with the present invention include, but are not limited to, DNA, RNA, etc.

The polymer core can have a greatest dimension between 1 nm and 1000 nm. The polymer core can have a greatest dimension of less than 900 nm, 800 nm, 700 nm, 600 nm, 500 nm, 400 nm, 300 nm, 200 nm, or 100 nm. The polymer core can have a greatest dimension (e.g., diameter) of 300 nm or less. The polymer core can have a greatest dimension (e.g., diameter) of 250 nm or less. The polymer core can have a greatest dimension (e.g., diameter) of 200 nm or less. The polymer core can have a greatest dimension (e.g., diameter) of 150 nm or less. The polymer core can have a greatest dimension (e.g., diameter) of 100 nm or less. The polymer core can have a greatest dimension (e.g., diameter) of 50 nm or less. The polymer core can have a greatest dimension ranging between 20 nm and 200 nm.

The ratio of polymer(s) in the polymer core can range from 0:100 to 100:0 for the first two polymers. Each additional polymers can be included such that the first polymer can be present at about 0 to about 100% w/w or v/v, the second polymer can be present at about 0 to about 100% w/w or v/v, and each additional polymer can be present at about 0 to about 100% w/w or v/v. The ratio of each polymer present can be determined from the amount present. For example. If there are three polymers present in the polymer core and the first polymer is present at 25% w/w, the second polymer is present at 25% w/w, and the third polymer is present at 50% w/w, the ratio can be said to be 25:25:50 or 1:1:2.

In some embodiments, the polymer can be PLGA. PLGA is a biocompatible and biodegradable co-polymer of lactic acid and glycolic acid, and various forms of PLGA are characterized by the ratio of lactic acid:glycolic acid. Lactic acid can be L-lactic acid, D-lactic acid, or D,L-lactic acid. The degradation rate of PLGA can be adjusted by altering the lactic acid:glycolic acid ratio. In some embodiments, PLGA to be used in accordance with the present invention is characterized by a lactic acid:glycolic acid ratio of any value, such as approximately 100:0, approximately 85:15, approximately 75:25, approximately 60:40, approximately 50:50, approximately 40:60, approximately 25:75, approximately 15:85, or approximately 0:100.

The core can include optional additional immunostimulatory agents that can be attached to or otherwise integrated with the polymer in the core. Optional additional immunostimulatory agents are discussed in detail elsewhere herein.

Lipid Shell

The nicotine lipid-polymeric nanoparticles can have a shell that can be composed of one or more lipids. The lipid shell can be such that the nicotine lipid-polymeric nanoparticles is a liposome. The lipid shell can be a lipid monolayer, a lipid bilayer, and/or multiple lipid bilayers. For example, a lipid bilayer may form the exterior surface of a nanocarrier, in which case the nicotine lipid-polymeric nanoparticles having a lipid bilayer shell can be referred to as a liposome. The liposome nanoparticles can have relatively moldable surfaces, and the nanoparticles can take on a variety of shapes (e.g., spherical, oblong, cylindrical, etc.) depending on environmental factors. It will be appreciated, therefore, that the maximum diameter of such nanocarriers may change in different environments. The lipid shell can contain one or more types of phospholipids. In some embodiments, the lipid shell can be a lipid monolayer. In some embodiments the nicotine lipid-polymeric nanoparticles can be refer to as a micelle. The lipid shell can be composed of one or more amphiphilic lipids (i.e., lipids that possess both hydrophilic and hydrophobic properties). In some embodiments, an amphiphilic lipid can promote the production of the nicotine lipid-polymeric nanoparticles with increased stability, improved uniformity, and/or increased viscosity.

When the lipid shell includes a lipid bilayer, the lipid bilayer can be oriented such that the interior and the exterior of the nicotine nanoparticles are hydrophilic and the lumen of the nicotine nanoparticles are hydrophobic. In other embodiments, the the lipid bilayer can be oriented such that the interior and the exterior of the nicotine nanoparticles are hydrophobic and the lumen of the nicotine nanoparticles are hydrophilic. One of skill in the art will appreciate the general nature of the compositions of the lipid shell and core that would facilitate such orientations of a lipid bilayer shell.

The percent of lipid in nicotine-nanoparticles (when considered as a whole) can range from 0.0001% to 99% by weight, from 10% to 99% by weight, from 25% to 99% by weight, from 50% to 99% by weight, or from 75% to 99% by weight. In some embodiments, the percent of lipid in nicotine-nanoparticles can range from 0.0001% to 75% by weight, from 0% to 50% by weight, from 0.0001% to 25% by weight, or from 0.0001% to 10% by weight. In some embodiments, the percent of lipid in nicotine-nanoparticles can be approximately 1% by weight, approximately 2% by weight, approximately 3% by weight, approximately 4% by weight, approximately 5% by weight, approximately 10% by weight, approximately 15% by weight, approximately 20% by weight, approximately 25% by weight, approximately 40% by weight, approximately 50% by weight, or approximately 60% by weight.

The lipid shell can include one or more oils. In general, any oil known in the art can be included in the lipid shell. In some embodiments, an oil can be composed of one or more fatty acid groups or salts thereof. A fatty acid group can include digestible, long chain (e.g., $C_8$-$C_{50}$), substituted or unsubstituted hydrocarbons. A fatty acid group can be a $C_{10}$-$C_{20}$ fatty acid or salt thereof. In some embodiments, a fatty acid group can be a $C_{15}$-$C_{20}$ fatty acid or salt thereof. A fatty acid group may be a $C_{15}$-$C_{25}$ fatty acid or salt thereof. In some embodiments, a fatty acid group may be unsaturated. A fatty acid group can be monounsaturated. A fatty acid group can be polyunsaturated. A double bond of an unsaturated fatty acid group can be in the cis conformation. A double bond of an unsaturated fatty acid can be in the trans conformation. A fatty acid group can be one or more of butyric, caproic, caprylic, capric, lauric, myristic, palmitic, stearic, arachidic, behenic, or lignoceric acid. A fatty acid group can be one or more of palmitoleic, oleic, vaccenic, linoleic, alpha-linolenic, gamma-linoleic, arachidonic, gadoleic, arachidonic, eicosapentaenoic, docosahexaenoic, or erucic acid. The oil can be a liquid triglyceride.

Suitable oils that can be used in the lipid shell include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, jojoba, kukui nut, lavandin, lavender, lemon, *Litsea cubeba*, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

The lipid shell can include a hormone (e.g. estrogen, testosterone), steroid (e.g., cholesterol, bile acid), vitamin (e.g. vitamin E), phospholipid (e.g. phosphatidyl choline), sphingolipid (e.g. ceramides), lipopolysaccharide (e.g. monophosphoryl lipid A), or lipoprotein (e.g. apolipoprotein). The lipid shell can include any molecular adjuvants, such as toll-like receptor (TLR) agonists. Exemplary toll-like receptor agonists include, but are not limited to, triacylated lipopetides, peptidoglycans, bacterial lipoproteins, lipoteichoic acid, lipopolysaccharides, GPI-anchor proteins, neisserial porins, hemagglutinin, pospholipomannan, LAM, viral ssRNA, viral dsRNA, F-protein, mannan, glycoinositolphospholipids, viral envelope proteins, flagellin, pheno-soluble modulin, diacylated lipopeptides, LTA, zymosan, hemozoin, and unmethylated CpG DNA.

The lipid shell can include one or more amphiphilic molecules (also refered to herein as "amphiphilic entities"). Any amphiphilic entity known in the art is suitable for use in making nanocarriers in accordance with the present invention. Such amphiphilic entities include, but are not limited to, phosphoglycerides; phosphatidylcholines; dipalmitoyl phosphatidylcholine (DPPC); dioleylphosphatidyl ethanolamine (DOPE); dioleyloxypropyltriethylammonium (DOTMA); dioleoylphosphatidylcholine; cholesterol; cholesterol ester; diacylglycerol; diacylglycerolsuccinate; diphosphatidyl glycerol (DPPG); hexanedecanol; fatty alcohols such as polyethylene glycol (PEG); polyoxyethylene-9-lauryl ether; a surface active fatty acid, such as palmitic acid or oleic acid; fatty acids; fatty acid monoglycerides; fatty acid diglycerides; fatty acid amides; sorbitan trioleate (Span®85) glycocholate; sorbitan monolaurate (Span®20); polysorbate 20 (Tween®20); polysorbate 60 (Tween®60); polysorbate 65 (Tween® 65); polysorbate 80 (Tween® 80); polysorbate 85 (Tween® 85); polyoxyethylene monostearate; surfactin; a poloxomer; a sorbitan fatty acid ester such as sorbitan trioleate; lecithin; lysolecithin; phosphatidylserine; phosphatidylinositol; sphingomyelin; phosphatidylethanolamine (cephalin); cardiolipin; phosphatidic acid; cerebrosides; dicetylphosphate; dipalmitoylphosphatidylglycerol; stearylamine; dodecylamine; hexadecyl-amine; acetyl palmitate; glycerol ricinoleate; hexadecyl sterate; isopropyl myristate; tyloxapol; poly(ethylene glycol)5000-phosphatidylethanolamine; poly(ethylene glycol)400-monostearate; phospholipids; synthetic and/or natural detergents having high surfactant properties; deoxycholates; cyclodextrins; chaotropic salts; ion pairing agents; and combinations thereof. An amphiphilic entity component may be a mixture of different amphiphilic entities. These amphiphilic entities may be extracted and purified from a natural source or may be prepared synthetically in a laboratory. In certain specific embodiments, amphiphilic entities are commercially available.

The lipid(s) of the lipid shell can be a lipid-polymer conjugate (i.e. a conjugate molecule having a lipid component and a polymer component). The lipids provided above can be conjugated to a suitable polymer to form a lipid-polymer conjugate. Suitable polymers for a lipid-polymer conjugated include polyethelye glycol (PEG), polynucleotides, polypeptides, polysaccrides, or any kind of polymer. The molecular weight of the PEG can rage from 300 to 10,000,000 g/mol. The molecular weight of the PEG can be indicicated herein as a number following "PEG". For example, a PEG having a molecular weight of about 2000 can be abbreviated as PEG2000. The lipid-polymer conjgates can also function as linkers, which are described in greated detail elsewhere herein.

The lipid shell can be PEGlayted, in addition to the incluseion of a lipid-PEG conjugate. Methods of PEGylating lipid shelled-nanoparticles are generally known in the art.

The lipid shell can be positively charged, negatively charged, or electrically neutral. The lipid shell can include one ore more molecules. The lipid shell can include one or more compounds that can effect the surface charge of the lipid shell. These can include, but are not limited to, -palmitoyl-2-oleoyl-sn-glycero-3-phosphocholine (POPC), 1,2-dioleoyl-3-trimethylammonium-propane, chloride salt (DOTAP), monosialoganglioside GM3, 1,2-di hexadecanoyl-sn-glycero-3-phospho-L-serine, sodium salt (DPPS), monophosphoryl Lipid A (MPLA), cholesterol (CHOL), and N-4-nitrobenzo-2-oxa-1,3-diazole phosphatidylethanolamine (NBD-PE).

The stimulating protein to which the first nicotine-hapten is conjugated to can be attached to the lipid shell via a lipid-polymer conjugate in the lipid shell and/or via a PEG molecule that is attached to the lipid shell. The second nicotine-hapten can be conjugated directly to a lipid-polymer conjugate in the lipid shell and/or via a PEG molecule that is attached to the lipid shell.

In some embodiments the lipid shell can include DOTAP, cholesterol, DSPE-PEG-maleimide, and DSPE-PEG-amine, or DSPE-PEG with any reactive terminal groups. The PEG in the DSPE-PEG-maleimide and/or the DSPE-PEG-amine can be PEG2000. The weight percent of DOTAP in the lipid shell can range from 1% w/w to about 99% w/w. The weight percent of DSPE-PEG-maleimide in the lipid shell can range from 1% w/w to about 100% w/w. The weight percent of cholesterol in the lipid shell can range from 5% w/w to about 20% w/w.

The molar ratio of DOTAP:cholesterol can range from 3.5 to 18. The ratio of DOTAP:DSPE-PEG-maleimide can range from 14 to 18. The molarratio of DSPE-PEG-maleimide: cholesterol can range from 0.25 to 3.

Nicotine-Haptens

The nicotine lipid-polymeric nanoparticles provided herein contains at least two nicotine-haptens that are each localized or attached to a different structure of the the nicotine lipid-polymeric nanoparticle. The nicotine-haptens can be capable of stimulating B cells. As shown in FIG. 1, a first nicotine-hapten can be attached to a stimulating protein that is attached to, directly or indirectly via a linker, or is otherwise integrated with the outer surface of the lipid shell. The second nicotine-hapten is not attached to a stimulating protein and can can be attached to, directly or indirectly via a linker, or is otherwise integrated directly with the outer surface of the lipid shell. The nicotine lipid-polymeric nanoparticles provided herein can contain further nicotine-haptens at additional locations on the nanoparticles, such as the core. The nicotine-haptens can each be the same or different. Other compounds that can be used as a nicotine-hapten include, but are not limited to, nicotine-polymer conjugates and any metabolite, derivative, or analogue of nicotine. Additional examples of derivatives of nicotine can be found, for example, in U.S. Pat. No. 6,232,082 (to Ennifar et al.) and U.S. Pat. No. 6,932,971 (to Bachmann et al.), the relevant portions of the disclosures of which are incorporated herein by reference. The nicotine-hapten can include a chemically derivatized nicotine. For example, nicotine may be chemically derivatized at the 3' position to provide a hydroxyl residue that is suitable for reaction with reagents such as succinic anhydride to form O-succinyl-3'-hydroxymethyl-nicotine. This nicotine derivative may be coupled to amino acids of the core particle, such as lysine, using the activation reagent EDC. The O-succinyl-3'-hydroxymethyl-nicotine can be activated with EDC and the resulting activated carboxylic group is stabilized by N-hydroxysuccinimide. In other embodiments, nicotine derivatives can be produced by acylation of nornicotine with succinic anhydride in methylene chloride in the presence of two equivalents of diisopropylethylamine. Such a nicotine hapten can be then coupled to a stimulating protein, such as one on the surface of the lipid shell, via an activating reagent e.g. HATU.

The first and the second nicotine-haptens can each be independently selected from the group of: O-succinyl-3'-hydromethyl-(±)-nicotine, 6-(carboxymethyl ureido)-(6)-nicotine, 3-aminomethyl-nicotine, nicotine 6-hexanoic acid, 5-aminoethoxy-nicotine, (2S)—N,N'-(disulfanediyldiethane-2,1-diyl)bis[4-(2-pyridin-3-ylpyrrolidin-1-yl)butanamide], and any nicotine derivatives.

The density (i.e., the total number of nicotine-haptens per nanoparticle) of the nicotine lipid-polymeric nanoparticle can be low-density (i.e. ranging from about $2.0\times10^4$ to about $3.9\times10^4$ nicotine-haptens/nanoparticle. The density of the nicotine lipid-polymeric nanoparticle can be medium-density (i.e. ranging from about $12.7\times10^4$ to about $16.3\times10^4$ nicotine-haptens/nanoparticle. The density of the nicotine lipid-polymeric nanoparticle can be high-density (i.e. ranging from about $30.0\times10^4$ to about $33.6\times10^4$ nicotine-haptens/nanoparticle. The nicotine lipid-polymeric nanoparticles can each include less than less than 90% by weight, less than 75% by weight, less than 50% by weight, less than 40% by weight, less than 30% by weight, less than 20% by weight, less than 15% by weight, less than 10% by weight, less than 5% by weight, less than 1% by weight, less than 0.5%, less than 0.1%, less than 0.01%, or less than 0.001% by weight of the first and/or the second nicotine-haptens.

Stimulating Molecules

The nicotine lipid-polymeric nanoparticles can include one or more stimulating molecules. In some embodiments, the stimulating molecule(s) can be a stimulating protein(s). As discussed elsewhere, the first nicotine-hapten(s) can be attached to one or more stimulating molecules. The density of the nicotine-haptens on the stimulating molecule(s) can be low density (ranging from 2 nicotine haptens to 11 nicotine haptens per stimulating molecule), medium density (ranging from 11 nicotine haptens to 52 nicotine haptens per stimulating molecule), or high density (ranging from 52 nicotine haptens to 115 nicotine haptens per stimulating molecule). The stimulating molecules can be attached to, either directly or indirectly via a linker, to the outer surface of the lipid shell. In embodiments, the linker can be a lipid-polymer conjugate that is incorporated into the lipid shell (see e.g. FIG. 1). Suitable stimulating molecules include, but are not limited to, keyhole limpet hemocyanin (KLH) multimer, KLH subunit, tetanus toxoid (TT), cross-reacting material $CRM_{197}$, bovine serum albumin (BSA), Human papillomavirus (HPV) proteins, recombinant *P. aeruginosa* exoprotein A, recombinant cholera toxin B, outer protein capsid of bacteriophage Qb, peptides, or any molecules that can stimulate immune cells.

Linkers

The stimulating protein (which is attached to the first nicotine-hapten) and/or the second nicotine hapten can be indirectly attached to the outer surface of the lipid shell via a linker. In some embodiments, the linker is a lipid-polymer conjugate molecule that has the lipid portion of the conjugate molecule incorporated into the lipid shell. Suitable lipid-polymer conjugates are discussed in greater detail elsewhere herein with respect to the lipid shell. In some embodiments, the linker can be a polymer (e.g. PEG) that is otherwise attached to the outer surface of the lipid shell. The linker can be a PEG molecule attached to DOTAP or DSPE that is part of the lipid shell.

Any suitable linker can be used in the nicotine nanoparticles provided herein. Linkers can be used to form amide linkages, ester linkages, disulfide linkages, etc. Linkers can contain carbon atoms or heteroatoms (e.g., nitrogen, oxygen, sulfur, etc.). Linkers can be 1 to 50 atoms long, 1 to 40 atoms long, 1 to 25 atoms long, 1 to 20 atoms long, 1 to 15 atoms long, 1 to 10 atoms long, or 1 to 10 atoms long. Linkers can be substituted with various substituents including, but not limited to, hydrogen atoms, alkyl, alkenyl, alkynyl, amino, alkylamino, dialkylamino, trialkylamino, hydroxyl, alkoxy, halogen, aryl, heterocyclic, aromatic heterocyclic, cyano, amide, carbamoyl, carboxylic acid, ester, thioether, alkylthioether, thiol, and ureido groups. As would be appreciated by one of skill in this art, each of these groups may in turn be substituted.

The linker can be an aliphatic or heteroaliphatic linker. The linker can be a polyalkyl linker. The linker can be a polyether linker. The linker can be a polyethylene linker. The linker can be a polyethylene glycol (PEG) linker.

The linker can be uncleavable or cleavable. To give but a few examples, cleavable linkers include protease cleavable peptide linkers, nuclease sensitive nucleic acid linkers, lipase sensitive lipid linkers, glycosidase sensitive carbohydrate linkers, pH sensitive linkers, hypoxia sensitive linkers, photo-cleavable linkers, heat-labile linkers, enzyme cleavable linkers (e.g. esterase cleavable linker), ultrasound-sensitive linkers, x-ray cleavable linkers, etc. In some embodiments, the linker is not a cleavable linker.

Any of a variety of methods can be used to associate a linker with a vaccine nanocarrier. General strategies include passive adsorption (e.g., via electrostatic interactions), multivalent chelation, high affinity non-covalent binding between members of a specific binding pair, covalent bond formation, etc. (Gao et al., 2005, Curr. Op. Biotechnol., 16:63; incorporated herein by reference). In some embodiments, click chemistry can be used to associate a linker with a particle.

Polypeptides can conveniently be attached to the nanoparticles via amine or thiol groups in lysine or cysteine side chains respectively, or by an N-terminal amino group. Nucleic acids such as RNAs can be synthesized with a terminal amino group. A variety of coupling reagents (e.g., succinimidyl 3-(2-pyridyldithio)propionate (SPDP) and sulfosuccinimidyl-4-(N-maleimidomethyl)cyclohexane-1-carboxylate (sulfo-SMCC) may be used to associate the various components of vaccine nanocarriers. Nicotine nanoparticles can be prepared with functional groups, e.g., amine or carboxyl groups, available at the surface to facilitate association with a biomolecule.

Non-covalent specific binding interactions can be employed. For example, either a particle or a biomolecule can be functionalized with biotin with the other being functionalized with streptavidin. These two moieties specifically bind to each other non-covalently and with a high affinity, thereby associating the particle and the biomolecule. Other specific binding pairs could be similarly used. Alternately, histidine-tagged biomolecules can be associated with particles conjugated to nickel-nitrolotriaceteic acid (Ni-NTA).

The linker can further include an additaionl pacer. The spacer can be, for example, a short peptide chain, e.g., between 1 and 10 amino acids in length, e.g., 1, 2, 3, 4, or 5 amino acids in length, a nucleic acid, an alkyl chain, etc.

Additional Immunostimulatory Agents

In addition to the nicotine-haptens, the nicotine lipid-polymeric nanoparticles can optionally contain one or more additional immunostimulatory agents. The additional immunostimulatory agent(s) can be capable of stimulating B cells and/or T cells. Assays to determine T cell, B cell, or other immune system component are generally known in the art. The additional immunostimulatory agent(s) can be attached, directly or indirectly, to the outer and/or inner surface of the lipid shell, the polymeric core, the stimulating protein, and/or any combination thereof. The additional immunostimulatory agents can be all the same immunostimulatory agent or can be a mixture of two or more species of immunostimulatory agents. Where two or more species of immunostimulatory agents are present, the two or more species can be segregated to different locations (e.g. species one can be attached to the surface of the lipid shell and species two can be attached to the core) or can be non-discriminatorily dispersed on various structures (e.g. all species present can be attached to the core and/or outer surface of the lipid shell). One of ordinary skill in the art will recognize that the preceding examples are only representative of the many different ways in which the optional additional immunostimulatory agent(s) can be associated with different locales of the nicotine lipid-polymeric nanoparticles.

Suitable additional immunostimulatory agents can include, without limitation, adjuvants, haptens (including nicotine and non-nicotine haptens), carrier proteins, natural or synthetic Toll-like receptor (TLR) agonists, dendritic cell surface molecule agonists, NOD-like receptor agonists, cytokines, proinflammatory stimulating molecules, complement cascade moleclues, activated components of immue complexes, antigen presenting cell agonists, T-cell receptor agonists, glcyoproteins, glycopolypeptides, proteins, peptides, small molecules, toxins and/or combinstions thereof. Specifc non-limiting examples of suitable immunostimulatory agents can include, without limitation, CpG oligodeoxynucleotides, bacterial lipopolyaacharides, VSV-G viral protein, HMGB-1, additional TLR agonists (e.g. TLR-1TLR-2, TLR-3, TLR-4, TLR-5, TLR-6, TLR-7, TLR-8, TLR-9, and TLR-10 agonists, urate crystals, CD21 and its agonists, CD35 and its agonists, CD40 agonsits, KLH, tetanus toxoid, alum, and any combination thereof.

Pharmaceutical Formulations

Also within the scope of this disclosure are pharmaceutical formulations (which include vaccine formulations) that can contain an amount of a nicotine lipid-polymeric nanoparticles as provided elsewhere herein. The nicotine lipid-polymeric nanoparticles described herein can be provided to a subject in need thereof alone or as such as an active ingredient, in a pharmaceutical formulation. In some embodiments, the pharmaceutical formulations contain an effective amount of a nicotine lipid-polymeric nanoparticles. The pharmaceutical formulations described herein can be administered to a subject in need thereof. The subject in need thereof can have a nicotine addiction. In some embodiments, the subject can be a human. In other embodiments, the nicotine lipid-polymeric nanoparticles can be used in the manufacture of a medicament for the treatment or prevention of nicotine addiction in a subject. The term pharmaceutical formulation also encompasses pharmaceutically acceptable salts of the pharmaceutical formulations and/or active ingredients provided herein.

Pharmaceutically Acceptable Carriers and Auxiliary Ingredients and Agents

The pharmaceutical formulations containing an effective amount of a nicotine lipid-polymeric nanoparticles described herein can further include a pharmaceutically acceptable carrier. Suitable pharmaceutically acceptable carriers include, but are not limited to, water, salt solutions, alcohols, gum arabic, vegetable oils, benzyl alcohols, polyethylene glycols, gelatin, carbohydrates such as lactose, amylose or starch, magnesium stearate, talc, silicic acid, viscous paraffin, perfume oil, fatty acid esters, hydroxy methylcellulose, and polyvinyl pyrrolidone, which do not deleteriously react with the active composition.

The pharmaceutical formulations can be sterilized, and if desired, mixed with auxiliary agents, such as lubricants, preservatives, stabilizers, wetting agents, emulsifiers, salts for influencing osmotic pressure, buffers, coloring, flavoring and/or aromatic substances, and the like which do not deleteriously react with the active composition.

In addition to the effective amount of a nicotine lipid-polymeric nanoparticles described herein, the pharmaceutical formulation can also include an effective amount of an auxiliary active agent, including but not limited to, DNA, RNA, amino acids, peptides, polypeptides, antibodies, aptamers, ribozymes, guide sequences for ribozymes that inhibit translation or transcription of essential tumor proteins and genes, hormones, immunomodulators, antipyretics, anxiolytics, antipsychotics, analgesics, antispasmodics, anti-inflammatories, anti-histamines, anti-infectives, chemotherapeutics, antihypertensives, anticoagulants, and antiarrhythmics.

The pharmaceutical formulations can optionally include one ore more suitable adjuvants. Suitable adjuvants are generally known in the art and can include, but are not limited to aluminum salts (e.g, aluminum phosphate and aluminum hydroxide), organic adjuvants (e.g. squalene), and oil-based (e.g., MF59), CpG oligodeoxynucleotides, resiquimod, flagellin, gardiquimod, imiquimod, monophosphoryl lipid A, poly(I:C), and chitosan.

Effective Amounts of the Nicotine Lipid-Polymeric Nanoparticles and Auxiliary Agents The pharmaceutical formulations can contain an effective amount of a Nicotine lipid-polymeric nanoparticles, and optionally, a therapeutically effective amount of an auxiliary agent. In some embodiments, the effective amount of the nicotine lipid-polymeric nanoparticles can range from about 0.3 mg/kg body weight to about 30 mg/kg. The effective amount of the nicotine lipid-polymeric nanoparticles can range from about 1 mg to about 10 g. For liquid formulations, some embodiments, the effective amount of the Nicotine lipid-polymeric nanoparticles or pharmaceutical formulation containing a nicotine lipid-polymeric nanoparticles can range from about 10 µL to about 10 mL. One of skill in the art will appreciate that the exact volume will depend on, inter alia, the age and size of the subject, as well as the location of administration. The effective concentration of the nicotine lipid-polymeric nanoparticles can range from about 1 nM to 1M.

In embodiments where an optional auxiliary active agent is included in the pharmaceutical formulation, the therapeutically effective amount of the auxiliary active agent will vary depending on the auxiliary active agent. In some embodiments, the therapeutically effective amount of the optional auxiliary active agent can range from 0.001 micrograms to about 1000 milligram. In other embodiments, the therapeutically effective amount of the optional auxiliary active agent can range from about 0.01 IU to about 1000 IU. In further embodiments, the therapeutically effective amount of the auxiliary active agent can range from 0.001 mL to about 1 mL. In yet other embodiments, the therapeutically effective amount of the optional auxiliary active agent can range from about 1% w/w to about 50% w/w of the total pharmaceutical formulation. In additional embodiments, the therapeutically effective amount of the optional auxiliary active agent ranges from about 1% v/v to about 50% v/v of the total pharmaceutical formulation. In still other embodiments, the therapeutically effective amount of the optional auxiliary active agent ranges from about 1% w/v to about 50% w/v of the total pharmaceutical formulation.

Dosage Forms

In some embodiments, the pharmaceutical formulations described herein can be in a dosage form. The dosage forms can be adapted for administration by any appropriate route. Appropriate routes include, but are not limited to, oral (including buccal or sublingual), rectal, epidural, intracranial, intraocular, inhaled, intranasal, topical (including buccal, sublingual, or transdermal), vaginal, intraurethral, parenteral, intracranial, subcutaneous, intramuscular, intravenous, intraperitoneal, intradermal, intraosseous, intracardiac, intraarticular, intracavernous, intrathecal, intravireal, intracerebral, and intracerebroventricular and intradermal. Such formulations can be prepared by any method known in the art.

Dosage forms adapted for oral administration can be discrete dosage units such as capsules, pellets or tablets, powders or granules, solutions, or suspensions in aqueous or non-aqueous liquids; edible foams or whips, or in oil-in-water liquid emulsions or water-in-oil liquid emulsions. In some embodiments, the pharmaceutical formulations adapted for oral administration also include one or more agents which flavor, preserve, color, or help disperse the pharmaceutical formulation. Dosage forms prepared for oral administration can also be in the form of a liquid solution that can be delivered as foam, spray, or liquid solution. In some embodiments, the oral dosage form can contain about 10 mg to 10 g of a pharmaceutical formulation containing an effective amount or an appropriate fraction thereof of the nicotine lipid-polymeric nanoparticles. The oral dosage form can be administered to a subject in need thereof by a suitable administration method.

Where appropriate, the dosage forms described herein can be microencapsulated. The dosage form can also be prepared to prolong or sustain the release of any ingredient. In some embodiments, the nicotine lipid-polymeric nanoparticles can be the ingredient whose release is delayed. In other embodiments, the release of an optionally included auxiliary ingredient is delayed. Suitable methods for delaying the release of an ingredient include, but are not limited to, coating or embedding the ingredients in material in polymers, wax, gels, and the like. Delayed release dosage formulations can be prepared as described in standard references such as "Pharmaceutical dosage form tablets," eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995). These references provide information on excipients, materials, equipment, and processes for preparing tablets and capsules and delayed release dosage forms of tablets and pellets, capsules, and granules. The delayed release can be anywhere from about an hour to about 3 months or more.

Examples of suitable coating materials include, but are not limited to, cellulose polymers such as cellulose acetate phthalate, hydroxypropyl cellulose, hydroxypropyl methylcellulose, hydroxypropyl methylcellulose phthalate, and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Coatings may be formed with a different ratio of water soluble polymer, water insoluble polymers, and/or pH dependent polymers, with or without water insoluble/water soluble non polymeric excipient, to produce the desired release profile. The coating is either performed on the dosage form (matrix or simple) which includes, but is not limited to, tablets (compressed with or without coated beads), capsules (with or without coated beads), beads, particle compositions, "ingredient as is" formulated as, but not limited to, suspension form or as a sprinkle dosage form.

Dosage forms adapted for topical administration can be formulated as ointments, creams, suspensions, lotions, powders, solutions, pastes, gels, sprays, aerosols, or oils. In some embodiments for treatments of the eye or other external tissues, for example the mouth or the skin, the pharmaceutical formulations are applied as a topical ointment or cream. When formulated in an ointment, the nicotine lipid-polymeric nanoparticles, optional auxiliary active ingredient, and/or pharmaceutically acceptable salt thereof can be formulated with a paraffinic or water-miscible ointment base. In other embodiments, the active ingredient can be formulated in a cream with an oil-in-water cream base or a water-in-oil base. Dosage forms adapted for topical administration in the mouth include lozenges, pastilles, and mouth washes.

Dosage forms adapted for nasal or inhalation administration include aerosols, solutions, suspension drops, gels, or dry powders. In some embodiments, the nicotine lipid-polymeric nanoparticles, the composition containing a nicotine lipid-polymeric nanoparticles, auxiliary active ingredient, and/or pharmaceutically acceptable salt thereof in a dosage form adapted for inhalation is in a particle-size-reduced form that is obtained or obtainable by micronization. In some embodiments, the particle size of the size reduced (e.g. micronized) compound or salt or solvate thereof, is defined by a D50 value of about 0.5 to about 10 microns as measured by an appropriate method known in the art. Dosage forms adapted for administration by inhalation also include particle dusts or mists. Suitable dosage forms wherein the carrier or excipient is a liquid for administration as a nasal spray or drops include aqueous or oil solutions/suspensions of an active ingredient, which may be generated by various types of metered dose pressurized aerosols, nebulizers, or insufflators.

In some embodiments, the dosage forms are aerosol formulations suitable for administration by inhalation. In some of these embodiments, the aerosol formulation contains a solution or fine suspension of the nicotine lipid-polymeric nanoparticles and/or pharmaceutically acceptable salt thereof, and a pharmaceutically acceptable aqueous or non-aqueous solvent. Aerosol formulations can be presented in single or multi-dose quantities in sterile form in a sealed container. For some of these embodiments, the sealed container is a single dose or multi-dose nasal or an aerosol dispenser fitted with a metering valve (e.g. metered dose inhaler), which is intended for disposal once the contents of the container have been exhausted.

Where the aerosol dosage form is contained in an aerosol dispenser, the dispenser contains a suitable propellant under pressure, such as compressed air, carbon dioxide, or an organic propellant, including but not limited to a hydrofluorocarbon. The aerosol formulation dosage forms in other embodiments are contained in a pump-atomizer. The pressurized aerosol formulation can also contain a solution or a suspension of a nicotine lipid-polymeric nanoparticles or a pharmaceutical formulation thereof. In further embodiments, the aerosol formulation also contains co-solvents and/or modifiers incorporated to improve, for example, the stability and/or taste and/or fine particle mass characteristics (amount and/or profile) of the formulation. Administration of the aerosol formulation can be once daily or several times daily, for example 2, 3, 4, or 8 times daily, in which 1, 2, or 3 doses or more are delivered each time.

For some dosage forms suitable and/or adapted for inhaled administration, the pharmaceutical formulation is a dry powder inhalable formulation. In addition to the nicotine lipid-polymeric nanoparticles, an optional auxiliary active ingredient, and/or pharmaceutically acceptable salt thereof, such a dosage form can contain a powder base such as lactose, glucose, trehalose, manitol, and/or starch. In some of these embodiments, the Nicotine lipid-polymeric nanoparticles, optional auxiliary active ingredient, and/or pharmaceutically acceptable salt thereof is in a particle-size reduced form. In further embodiments, a performance modifier, such as L-leucine or another amino acid, cellobiose octaacetate, and/or metals salts of stearic acid, such as magnesium or calcium stearate.

In some embodiments, the aerosol formulations are arranged so that each metered dose of aerosol contains a predetermined amount of an active ingredient, such as the one or more of the nicotine lipid-polymeric nanoparticles described herein.

Dosage forms adapted for vaginal administration can be presented as pessaries, tampons, creams, gels, pastes, foams, or spray formulations. Dosage forms adapted for rectal administration include suppositories or enemas.

Dosage forms adapted for parenteral administration and/or adapted for any type of injection (e.g. intravenous, intraocular, intraperitoneal, subcutaneous, intramuscular, intradermal, intraosseous, epidural, intracardiac, intraarticular, intracavernous, intrathecal, intravitreal, intracerebral, and intracerebroventricular) can include aqueous and/or non-aqueous sterile injection solutions, which can contain anti-oxidants, buffers, bacteriostats, solutes that render the composition isotonic with the blood of the subject, and aqueous and non-aqueous sterile suspensions, which can include suspending agents and thickening agents. The dosage forms adapted for parenteral administration can be presented in a single-unit dose or multi-unit dose containers, including but not limited to sealed ampoules or vials. The doses can be lyophilized and resuspended in a sterile carrier to reconstitute the dose prior to administration. Extemporaneous injection solutions and suspensions can be prepared in some embodiments, from sterile powders, granules, and tablets.

Dosage forms adapted for ocular administration can include aqueous and/or non-aqueous sterile solutions that can optionally be adapted for injection, and which can optionally contain anti-oxidants, buffers, bacteriostats, solutes that render the composition isotonic with the eye or fluid contained therein or around the eye of the subject, and aqueous and non-aqueous sterile suspensions, which can include suspending agents and thickening agents.

For some embodiments, the dosage form contains a predetermined amount of the nicotine lipid-polymeric nanoparticles per unit dose. In an embodiment, the predetermined amount of the nicotine lipid-polymeric nanoparticles is an effective amount of the nicotine lipid-polymeric nanoparticles. In other embodiments, the predetermined amount of the nicotine lipid-polymeric nanoparticles can be an appropriate fraction of the effective amount of the active ingredient. Such unit doses may therefore be administered once or more than once a day. Such pharmaceutical formulations may be prepared by any of the methods well known in the art.

Methods of Using the Nicotine Lipid-Polymeric Nanoparticles

The formulations, vaccines, and nicotine lipid-polymeric nanoparticles provided herein can be used to induce an immune response, particularly a B cell response specific to nicotine. The formulations, vaccines, and nicotine lipidpolymeric nanoparticles provided herein can be used to prevent and/or treat a nicotine addiction or symptom thereof in a subject.

The method can include the step of administering an amount, such as an effective amount, to a subject. The subject can be suffering from a nicotine addiction or a healthy subject (one who has not suffered from a nicotine addiction). The method can include the step of administering an amount, such as an effective amount, to a subject such that a B cell and/or T cell response is stimulated. In some embodiments, the B cell response is the generation of antibodies that can specifically bind nicotine. The antibodies can interact with nicotine in a subject system and result in neutralization and/or clearance of the nicotine from the body. In this way, the amount of nicotine reaching nicotinic receptors can be reduced and/or eliminated and thus break the biochemical cycle that can result in addiction. The amount of the nicotine lipid-polymeric nanoparticles administered can be effective to decrease the amount of nicotine in the brain as compared to a control and/or before administration of the nicotine lipid-polymeric nanoparticles. The amount of the nicotine lipid-polymeric nanoparticles administered can be effective to increase the amount of nicotine in the serum as compared to a control and/or before administration of the nicotine lipid-polymeric nanoparticles. The amount of the nicotine lipid-polymeric nanoparticles administered can result in a more Th2 skewed response in the subject immunized with current nicotine vaccines. A Th2 skewed response can result in an improved response to treatment and/or improved outcome after treatment. The amount of the nicotine lipid-polymeric nanoparticles can result in an enhanced immune response in the subject as compared to currently available nicotine vaccines.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

Introduction

Tobacco smoking is one of the largest public health threats the world has ever faced; approximately, 6 millions of premature deaths are attributed to tobacco use each year in the world.[1-3] Despite the strong desires to quit smoking, the majority of unassisted smokers usually relapse within the first month, and only 3-5% of them remain abstinent after 6 months.[4] Even with the help of pharmacological interventions, including nicotine replacement therapy, varenidine, and bupropion, the long-term smoking cessation rate at one year is disappointingly low (10-25%).[5-8]

Nicotine vaccines are an attractive approach for smoking cessation.[9, 10] Promisingly, some conjugate nicotine vaccines were successful in inducing strong immunogenicity as well as achieving high pharmacokinetic efficacy in preclinical and early-stage clinical trials.[11-14] However, no current nicotine vaccine has demonstrated an overall enhanced smoking cessation rate over placebo, mainly due to the highly-variable and insufficient antibody titers.[15-17] Although great efforts have been made to improve their immunogenicity by modulating multiple factors [13, 18-23], conjugate nicotine vaccines bear some intrinsic shortfalls, such as fast degradation, low nicotine loading capacity, low bioavailability, and poor recognition and uptake by immune cells, which has limited their immunological efficacy.

To circumvent these disadvantages of conjugate nicotine vaccines, in previous work, a next generation nicotine nanovaccines were designed using nanoparticles (NPs) as delivery vehicles for antigen presentation. [24-26] Particularly, a lipid-polymeric hybrid nanoparticle (NP)-based nicotine nanovaccine was demonstrated to induce significantly higher immunogenicity over the conjugate vaccine and resulted in prominent pharmacokinetic efficacy in mice. [26]

Figure 2A:
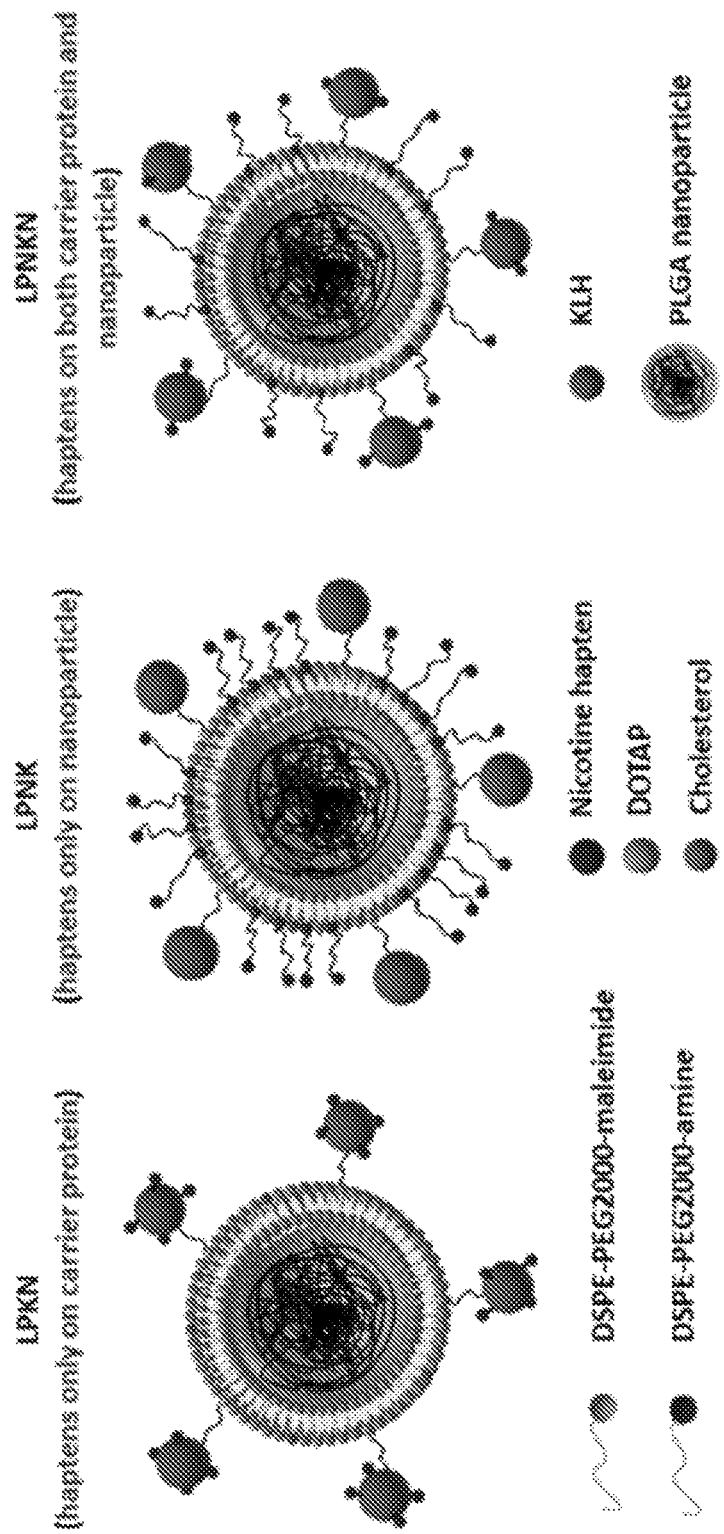
FIGS. 2A-2B show a schematic illustration demonstrating embodiments of the structure (FIG. 2A) and synthetic scheme (FIG. 2B) of hybrid NP-based nicotine nanovaccines with different hapten localizations.
Figure 2B:
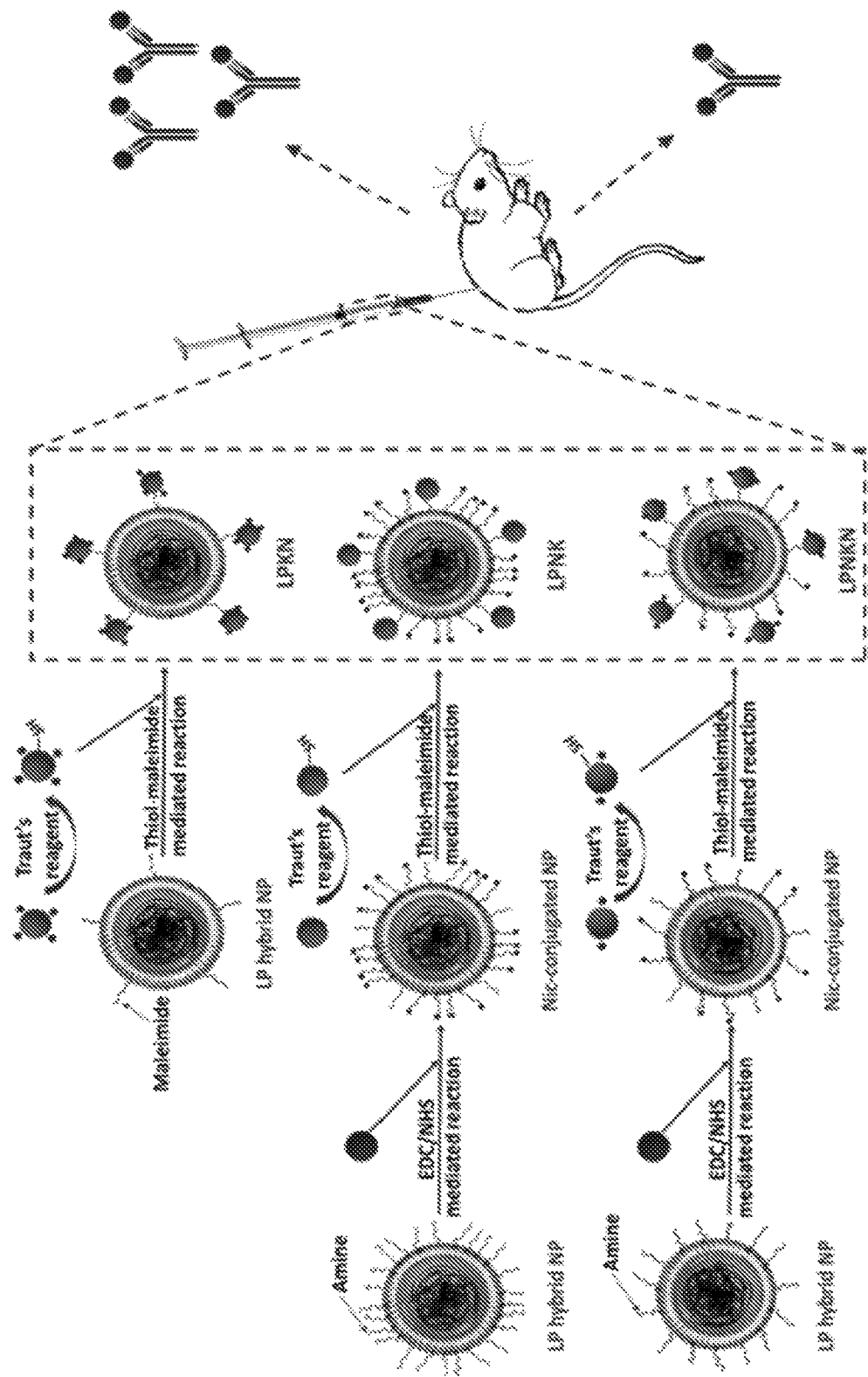
Figures 3A, 3B, 3C, 3D, 3E, 3F, 3G, 3H:
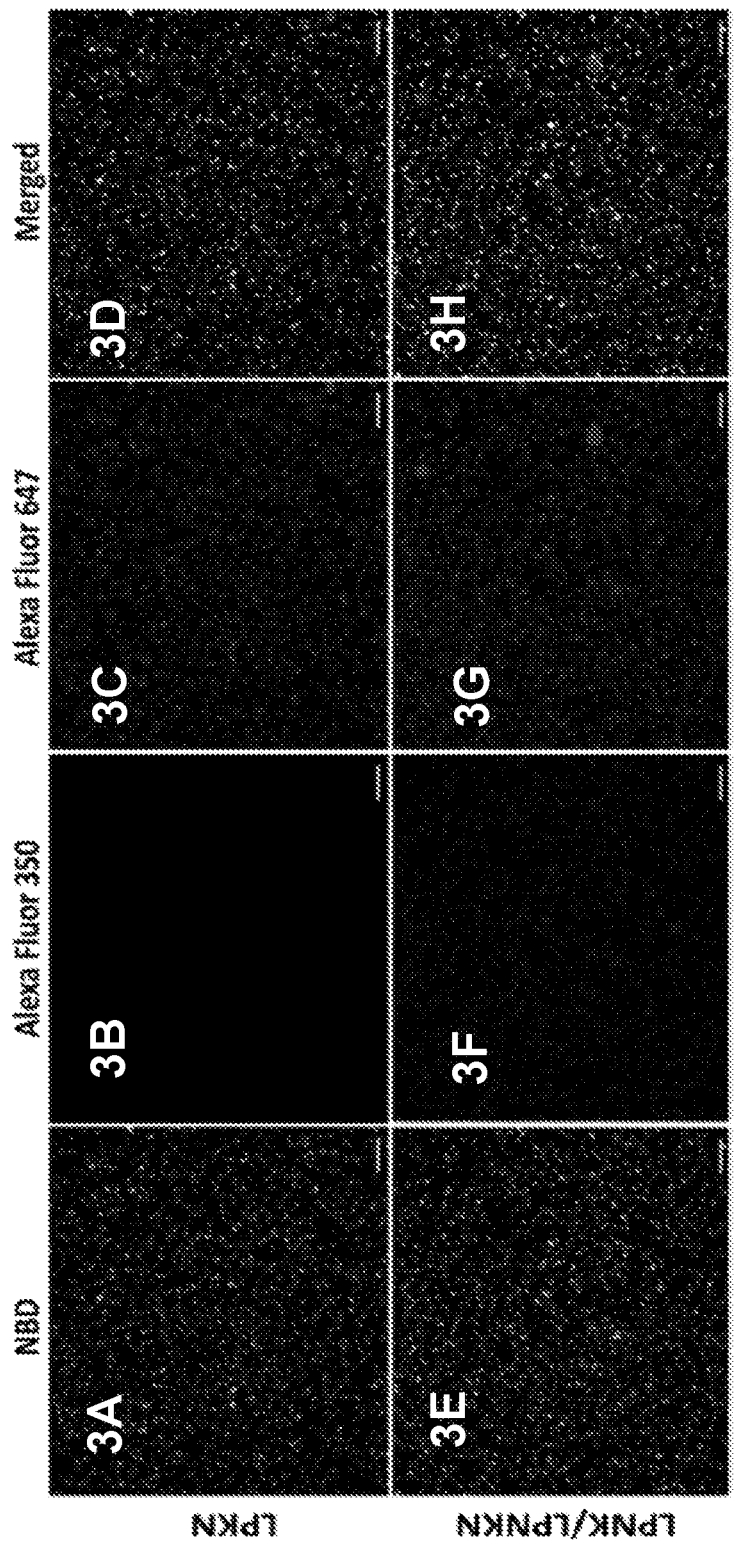
FIGS. 3A-3H show confocal laser scanning microscopy (CLSM) images demonstrating the co-localization of model hapten dyes with hybrid NPs. Scale bars represent 10 μm.

Nicotine hapten is such a small molecule and thus can only elicit an immune response when attached to a carrier, such as another protein or nanoparticle. [9]. Additionally, a stimulating protein is typically necessary in an NP-based nanoparticle vaccine to stimulate helper T-cell formation that is involved in B cell maturation [9, 27]. Meanwhile, conjugating protein antigen to the surface of NPs could promote its delivery and presentation. [28, 29]. In prior nanovaccine designs, hapten was conjugated to the surface of protein antigens. [26] As the localization of haptens on vaccine NPs can unpredictably affect the recognition of antigens by immune cells, in this Example, a hybrid NP-based nicotine was designed utilizing a different hapten localization and the impact of hapten localization on its immunogenicity, avidity, and pharmacokinetic efficacy was evaluated. As shown in FIGS. 2A-2B, three nanovaccines, which had haptens localized only on stimulating protein (LPKN), only on NP surface (LPNK), or on both (LPNKN), were synthesized. The immunogenicity, avidity, and pharmacokinetic efficacy of nanovaccines were tested in mice.

Materials and Methods

Lactel® polymer (50:50 poly(lactic-co-glycolic acid) (PLGA) was purchased from Durect Corporation (Cupertino, Calif., USA). Keyhole limpet hemocyanin (KLH) was purchased from Stellar Biotechnologies (Port Hueneme, Calif., USA). Alexa Fluor 647 NHS ester (AF647), Alexa Fluor 350 NHS ester (AF350), 1-Ethyl-3-[3-dimethylaminopropyl] carbodiimide hydrochloride (EDC), and N-hydroxysulfosuccinimide (Sulfo-NHS) were purchased from Thermo Fisher Scientific (Rockford, Ill., USA).1,2-Dioleoyl-3-trimethylammonium-propane (DOTAP), cholesterol (CHOL), 1,2-diphytanoyl-sn-glycero-3-phosphoethanolamine-N-(7-nitro-2-1,3-benzoxadiazol-4-yl) (ammonium salt) (NBD-PE), 1,2-distearoyl-sn-glycero-3-phosphoethanolamine-N-[maleimide(polyethylene glycol)-2000] (ammonium salt) (DSPE-PEG2000-maleimide), and 1,2-distearoyl-sn-glycero-3-phosphoethanolamine-N-[amino (polyethylene glycol)-2000] (ammonium salt) (DSPE-PEG2000-amine) were purchased from Avanti Polar Lipids (Alabaster, Ala., USA). O-Succinyl-3'-hydroxymethyl-(±)-nicotine (Nic) was purchased from Toronto Research Chemicals (North York, ON, Canada). All other chemicals were of analytical grade.

Fabrication of PLGA-NPs by Nanoprecipitation

PLGA NPs were fabricated by a nanoprecipitation method. In brief, 20 mg of PLGA was dissolved in 2 mL of acetone. The PLGA-in-acetone organic solution was injected into 10 mL of 0.5% PVA aqueous phase by a vertically mounted syringe pump with magnetic stir agitation (1200 rpm). The resultant suspension was placed under vacuum for 6 hours to eliminate the organic solvent. PLGA NPs were collected by centrifugation at 10,000 g, 4° C. for 30 min.

Fabrication of Lipid-Polymeric Hybrid NPs

Lipid-polymeric hybrid NPs were fabricated with a previously reported hydration-sonication method. [26] In brief, 2.5 mg of lipid mixture consisting of DOTAP, DSPE-PEG2000-maleimide, DSPE-PEG2000-amine, and CHOL, was evaporated to form a lipid film. The Molar ratios of DOTAP:DSPE-PEG2000-maleimide:DSPE-PEG2000-amine:CHOL for LPKN (and negative control), LPNK, and LPNKN were 90:5:0:5, 70:5:20:5, and 80:5:10:5, respectively. The lipid film was hydrated with 0.01M phosphate buffer saline (PBS) and sonicated for 2 min to form a liposome suspension. Lipid-polymeric hybrid NPs were assembled by coating liposomes to PLGA NPs (PLGA:lipids=10:1(w/w)) via sonication for 10 min. Lipid-polymeric hybrid NPs were collected by centrifugation at 10,000 g, 4° C. for 30 min. The PLGA cores were labeled by Nile Red, and the number of NPs per mg was estimated by flow cytometry using an Amnis ImageStreamX Mark 2 imaging flow cytometer.

Synthesis of Nic-KLH Conjugates

Nic-KLH conjugates were synthesized by an EDC/NHS-mediated reaction as reported previously. [26] Specifically, the Nic-KLH conjugates used for preparing LPKN or LPNKN nanovaccines were synthesized by reacting 1.2 mg or 2.4 mg of Nic hapten with 5 mg of KLH. Hapten densities of Nic-KLH conjugates were estimated by a 2,4,6-trinitrobenzene sulfonic acid-based method as reported previously. [30] The Nic-BSA conjugate was synthesized using the same method.

Preparation of Nanovaccine NPs

LPKN nanovaccine NPs were assembled with the method reported previously. [26] In brief, an appropriate amount of Traut's reagent was added into 2 mg of Nic-KLH conjugate in 0.5 mL of PBS and reacted for 1 hour to form thiolated Nic-KLH. One mg of thiolated Nic-KLH was conjugated to 30 mg of lipid-polymeric hybrid NPs by reacting the thiolated Nic-KLH with maleimide groups in the lipid layer of NPs for 2 hours. Unconjugated Nic-KLH was separated by centrifugation at 10,000 g, 4° C. for 30 min, and quantified by the bicinchoninic acid assay. Negative control was prepared following a similar procedure, except that KLH, instead of Nic-KLH, was conjugated to NP surface.

For LPNK and LPNKN synthesis, Nic-haptens were conjugated to the surfaces of hybrid NPs via an EDC/NHS-mediated reaction. In brief, an aliquot of Nic-haptens (Nic:DSPE-PEG2000-amine=1:2) was activated for 30 min in 0.3 mL of activation buffer (0.1M MES, 0.5 M NaCl, pH 6.0) by adding EDC and NHS (Nic:EDC:NHS=1:10:10). Nic-hapten-conjugated hybrid NPs (LPN) were synthesized by reacting the activated Nic-haptens with 30 mg of hybrid NPs in 2 mL of coupling buffer (0.1M sodium phosphate, 0.15 M NaCl, pH7.2) for 10 hours. Unconjugated Nic-haptens were eliminated by dialysis and quantified by HPLC using a Luna C18 (2) reverse phased chromatography column and a UV detector (at 254 nm). LPNK and LPNKN NPs were assembled by conjugating KLH or Nic-KLH to LPN NPs with the same method as LPKN nanovaccine. Nanovaccine NPs were collected by centrifugation at 10,000 g, 4° C. for 30 min, and stored at 2° C. for later use.

Characterization of NPs

Size and zeta potential of NPs were measured on a Nano ZS Zetasizer (Malvern Instruments, Worcestershire, United Kingdom) at 25° C. The morphology of NPs was characterized by transmission electron microscopy (TEM) on a JEM 1400 transmission electron microscope (JEOL, Tokyo, Japan). Fluorescent nanovaccine NPs, in which the lipid layer was labeled by NBD, and AF647 and AF350 were conjugated to KLH and NP surface, respectively, were imaged on a Zeiss LSM 510 laser scanning microscope (Carl Zeiss, Oberkochen, Germany). The Fourier transform infrared (FT-IR) spectra of NPs were recorded on a Thermo Nicolet 6700 FT-IR spectrometer (Thermo Fisher Scientific, Waltham, Mass.).

Cellular Uptake of Nanovaccine NPs in Dendritic Cells (DCs)

The uptake of nanovaccine NPs by DCs was studied by flow cytometry assay (FCA). NBD-labelled LPKN, LPNK, and LPNKN NPs were prepared by adding 2.5% of NBD into lipid mixture. JAWSII (ATCC® CRL-11904™) immature DCs ($2 \times 10^6$/well) were seeded into 24-well plates and cultured overnight. Cells were treated with 20 µg of NBD-labelled nanovaccine NPs for 15 min or 2 h. After being washed 3 times with PBS, cells were detached from the culture plates using trypsin/EDTA solution and collected by centrifugation at 200 g for 10 min. Cell pellets were re-suspended in PBS. Samples were immediately analyzed on a flow cytometer (FACSAria I, BD Biosciences, Franklin Lakes, N.J., USA).

The cellular uptake and processing of nanovaccine NPs were analyzed by confocal laser scanning microscopy (CLSM). AF647- and NBD-labeled NPs were prepared according to the method described above, except that AF647-KLH was conjugated to hybrid NPs and 2.5% of NBD was added into lipids for labeling. Cells ($2 \times 10^5$/chamber) were seeded into 2-well chamber slides and cultured overnight. Cells were treated with 20 µg of AF647- and NBD-labeled nanovaccine NPs for 15 min or 2 h. Cells were then washed using PBS and fixed with freshly prepared 4% (w/v) paraformaldehyde for 10 min. The membrane of cells was permeabilized by adding 0.5 mL of 0.1% (v/v) Triton™ X-100 for 10 min. Cell nuclei were stained by 4',6-diamidino-2-phenylindole (DAPI). The intracellular distribution of NPs was visualized on a Zeiss LSM 510 laser scanning microscope.

Immunization of Mice with Nicotine-Nanovaccines

Female Balb/c mice (6-7 weeks of age, 16-20 g, 6 per group) were immunized subcutaneously with a total volume of 200 µL of nicotine vaccines containing 25 µg of Nic-KLH/KLH immunogen on days 0, 14, and 28. For the negative control group, mice were immunized with KLH associated hybrid NPs without Nic-hapten conjugation containing 25 µg of KLH. For the blank group, mice were injected with 200 µL of sterilized PBS. Blood was collected from the retro-orbital plexus under isoflurane anesthesia on days 0, 12, 26, and 40.

Measurement of Anti-Nicotine Antibody Affinity

The relative avidity of anti-nicotine antibody induced by nicotine nanovaccines was measured by a competition ELISA method. [31] In brief, serum samples were diluted to achieve absorbance values of around 1.0 at 450 nm. Nicotine was serially diluted from $10^{-2}$ M to $10^{-7}$ M. One hundred µL of nicotine solutions were added into Nic-BSA coated plates, and 100 µL of serum samples were subsequently added to plates. The other steps were the same as in measuring anti-nicotine antibody titers. Percent inhibition was calculated at each nicotine concentration and plotted against log nicotine concentration. The concentration at which 50% inhibition was achieved ($IC_{50}$) was extrapolated for each sample.

Pharmacokinetic Study in Mice

The pharmacokinetic study was conducted using a method reported previously. [26] In brief, mice were administered 0.06 mg/kg nicotine subcutaneously two weeks after the second booster immunization (on day 42). Brain and serum samples were collected 3 min post nicotine dosing. Nicotine concentration in the brain and serum was measured by GC/MS as reported previously. [32]

Histopathological Analysis

Histopathological analysis was conducted to detect lesions of mouse organs caused by the immunization with nicotine vaccines following a method reported previously. [26] Tissue blocks were stained with hematoxylin and eosin (H&E) and imaged on a Nikon Eclipse E600 light microscope.

Statistical Analyses

Data are expressed as means±standard deviation unless specified. Comparisons among multiple groups were conducted using one-way ANOVA followed by Tukey's HSD test. Differences were considered significant when the p-values were less than 0.05.

Results

Verification of Nic-Hapten-Conjugate Chemistry

CLSM was employed to verify the Nic-hapten conjugate chemistry. AF350-NHS and AF647-NHS, two models of Nic-hapten that have same reactive groups, were used to conjugate to NP surface and KLH, respectively. Hybrid NPs were labeled by NBD. The co-localization of AF647 with NBD suggested the successful conjugation of model hapten to KLH (see FIGS. 3A-3D). This verified the conjugate chemistry for LPKN synthesis. Meanwhile, the overlapping of AF350, AF647, and NBD indicated the efficient conjugation of model hapten to NP surface and the successful association of model hapten-KLH conjugate to NPs (see FIGS. 3E-3H). This verified the conjugate chemistry for LPNK and LPNKN synthesis.

Figure 4:
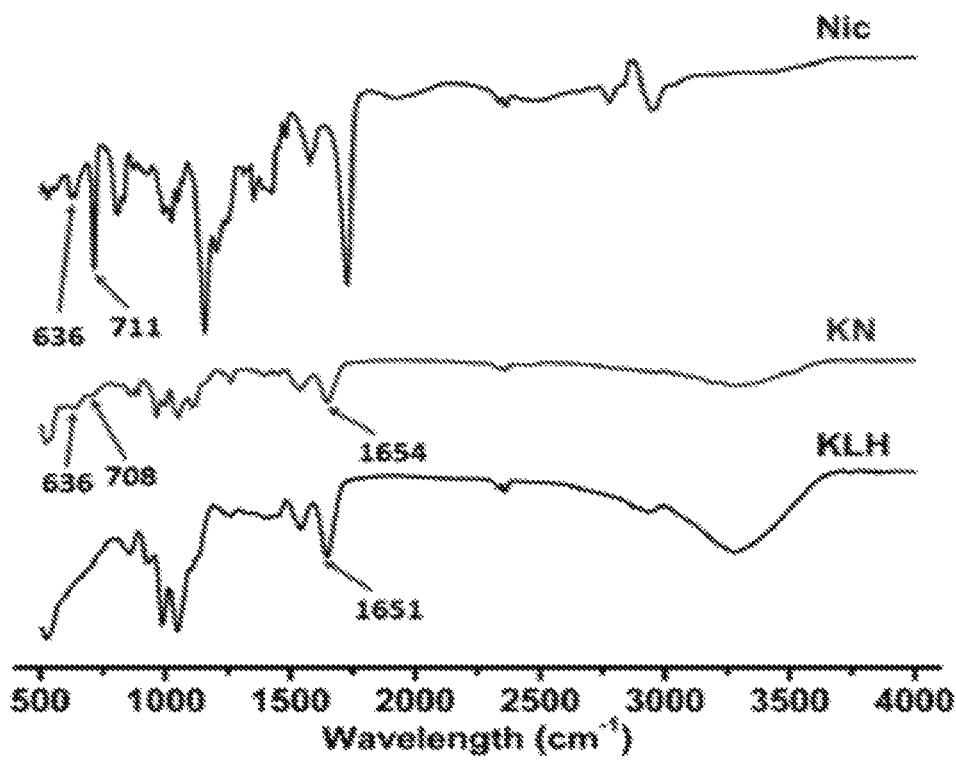
FIG. 4 shows a graph demonstrating the FT-IR spectra of Nic-hapten, KLH, Nic-KLH conjugate.
Figure 5:
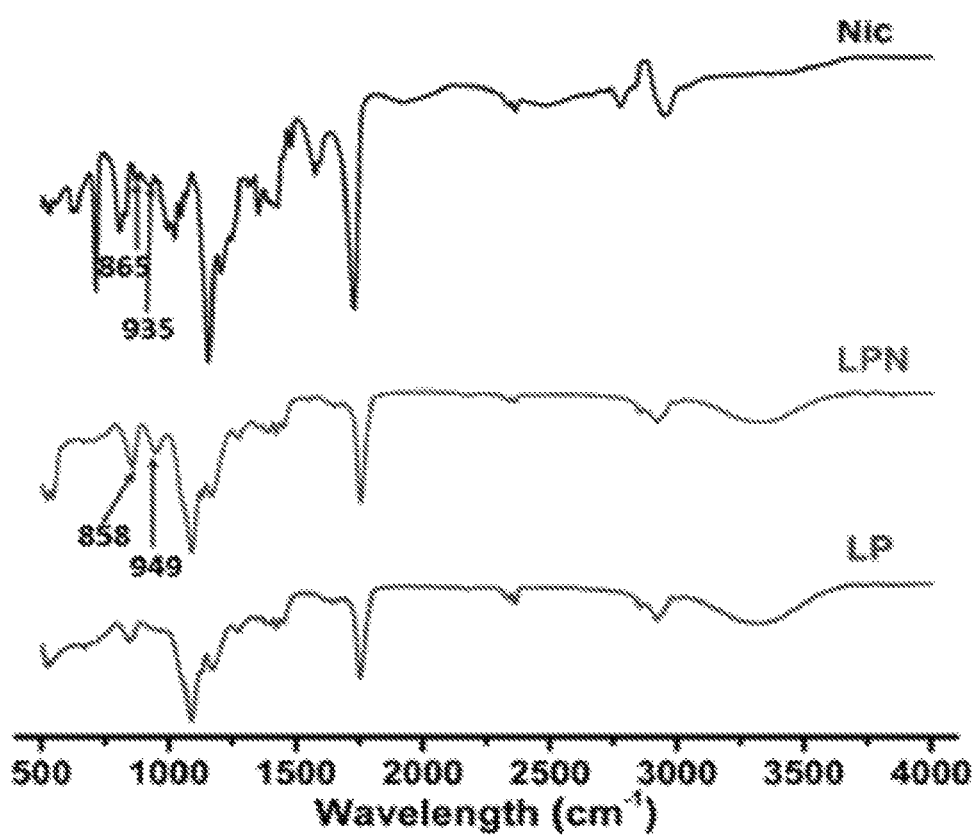
FIG. 5 shows a graph demonstrating the FT-IR spectra of hybrid Nic-hapten-conjugated LPN NPs.
Figure 6:
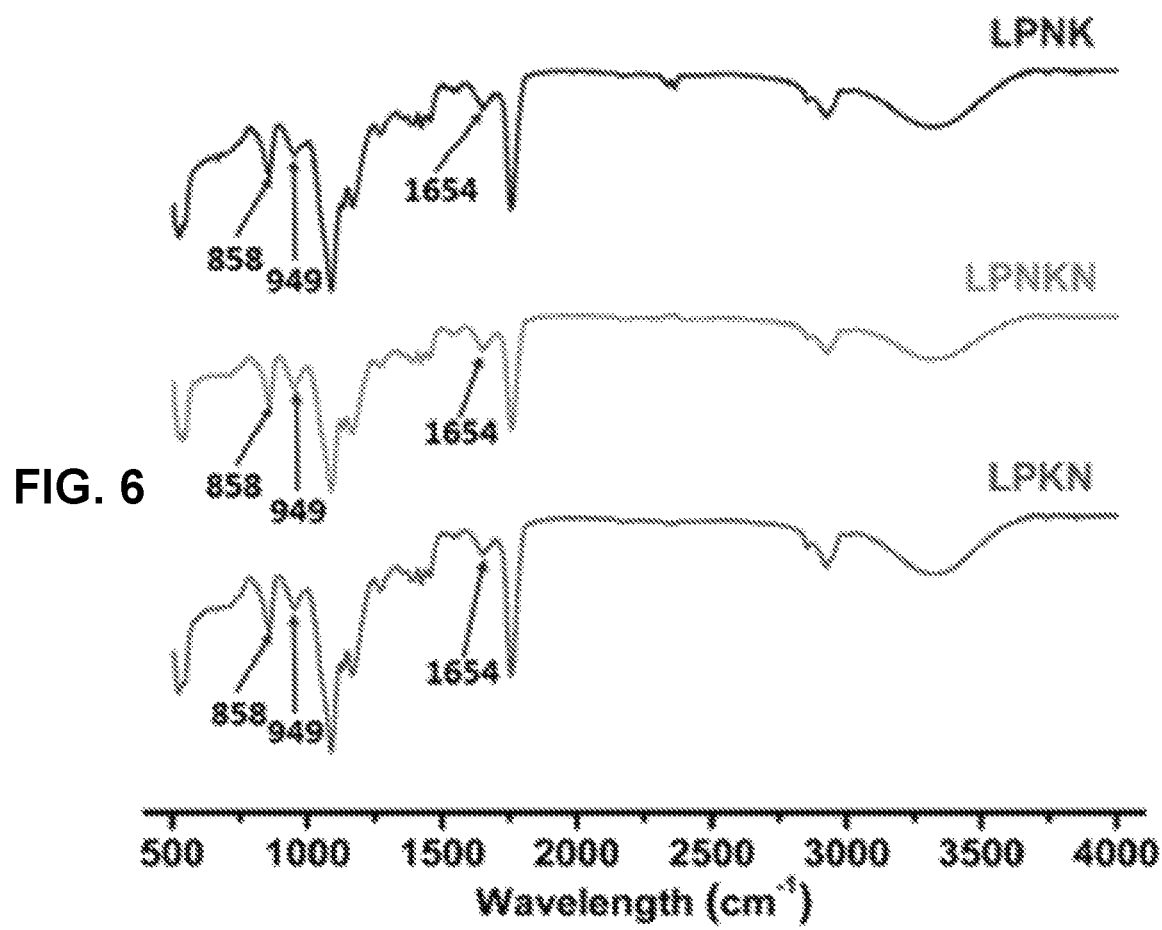
FIG. 6 shows a graph demonstrating the FT-IR spectra of LPKN, LPNK, and LPNKN.
Figures 7A, 7B, 7C, 7D, 7E, 7F:
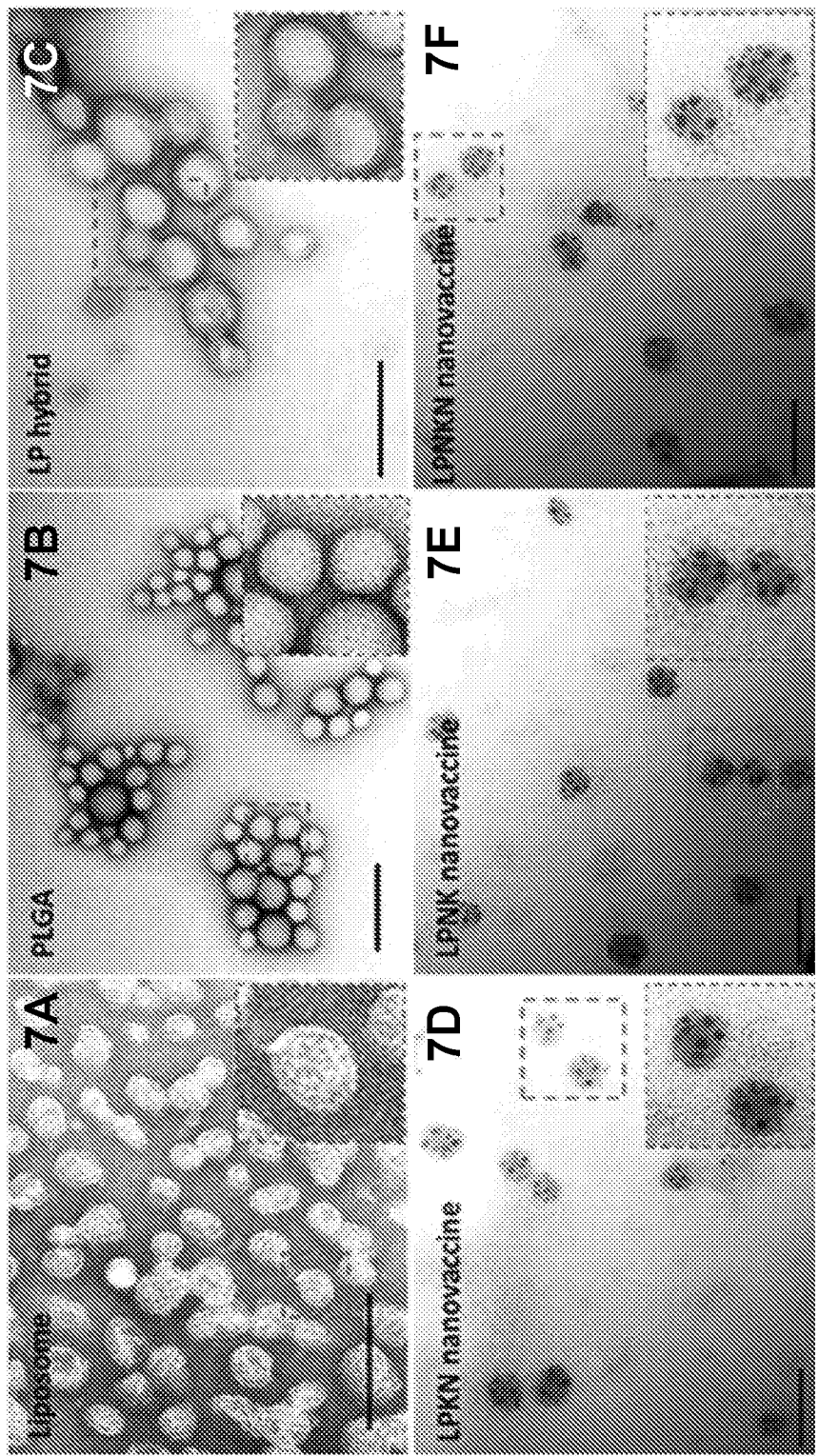
FIGS. 7A-7F show transmission electron microscopy (TEM) images demonstrating the morphological characteristics of various NPs provided herein. Scale bars represent 200 nm.

FT-IR was further used to validate the conjugate chemistry for nanovaccine synthesis. Specific peaks of both Nic-hapten (636 and 708 $cm^{-1}$ and KLH (1654 $cm^{-1}$ showed in the spectrum of Nic-KLH conjugate (FIG. 4), suggesting the efficient conjugation of Nic-hapten to KLH. Similarly, characteristic peaks of Nic-hapten (858 and 949 $cm^{-1}$ appeared in the spectrum of LPN NPs (FIG. 5). This revealed the successful attachment of Nic-hapten to NP surface. In addition, the spectra of all three nanovaccines included characteristic peaks of both Nic-hapten and KLH/Nic-KLH (FIG. 6), indicating the successful synthesis of nanovaccines.

Characterization of Nanovaccine NPs

Nanovaccine NPs were characterized morphologically using TEM (FIGS. 7A-7F). A core-shell structure was clearly shown on hybrid NPs, which was displayed as a bright core and dark shell. All three nanovaccine NPs had similar morphological features. Specifically, multiple black dots that were KLH/Nic-KLH showed on the surface of NPs. This further suggested the successful conjugation of protein antigens to hybrid NP surface. The conjugation efficiency of Nic-KLH/KLH was 82.3±5.4%, 85.3±7.4%, and 80.2±6.7%, for LPKN, LPNK, and LPNKN, respectively (FIG. 23). The Nic-hapten densities of LPKN, LPNK, and LPNKN were (6.32±0.39)×$10^4$/NP, (5.89±0.67)×$10^4$/NP, and (6.02±0.53)×$10^4$/NP, respectively (FIG. 23). This suggested the three nanovaccines with different hapten localizations had similar overall hapten densities.

Figure 8:
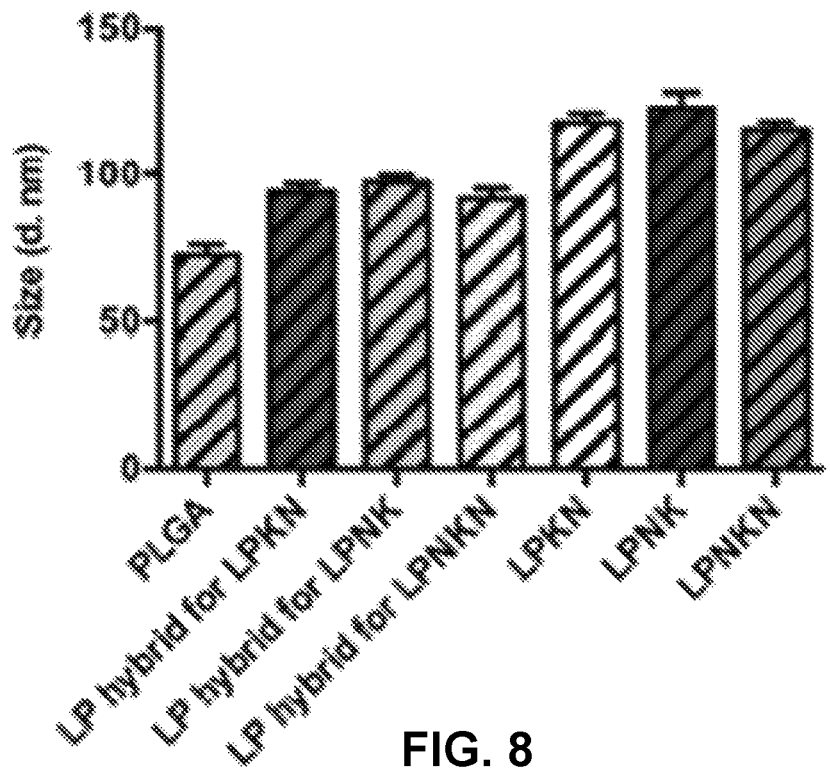
FIG. 8 shows a graph demonstrating the average size of LPKN, LPNK, and LPNKN NPs.
Figure 9:
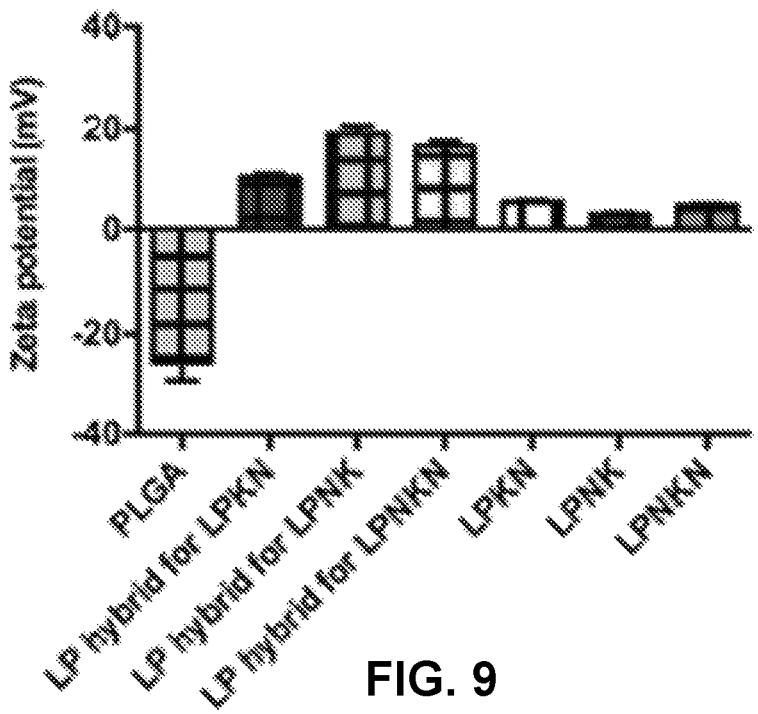
FIG. 9 shows a graph demonstrating the zeta potential of LPKN, LPNK, and LPNKN NPs.
Figure 10:
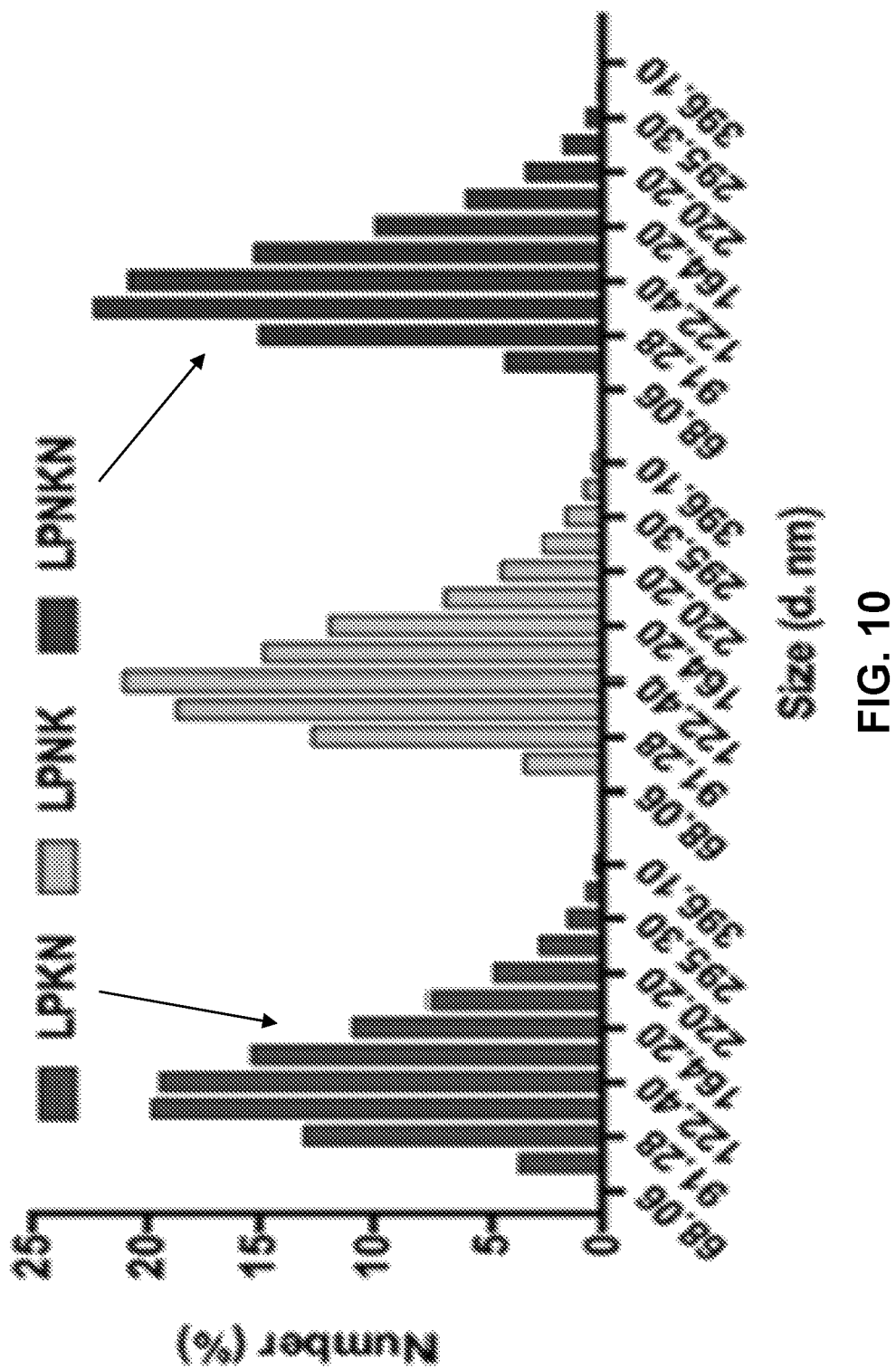
FIG. 10 shows a graph demonstrating the size distribution of LPKN, LPNK, and LPNKN NPs.

Physicochemical properties of NPs were characterized. The three nanovaccines exhibited similar average diameters, which was 118.1, 122.8, and 115.7 nm for LPKN, LPNK, and LPNKN nanovaccines, respectively (FIG. 8). Consistent with the uniform size in TEM images (FIGS. 7A-7F) and low polydispersity index (P01) (FIG. 23), dynamic light scattering data revealed that all three nanovaccines had similarly narrow size distributions, with most particles being smaller than 200 nm (FIG. 10). The zeta-potentials were 5.46±0.25, 2.85±0.23, and 4.69±0.24 mV, for LPKN, LPNK, and LPNKN, respectively (FIG. 9). This revealed that the nanovaccines were still positively charged after conjugation of the negatively charged Nic-hapten and protein antigens.

Figure 11:
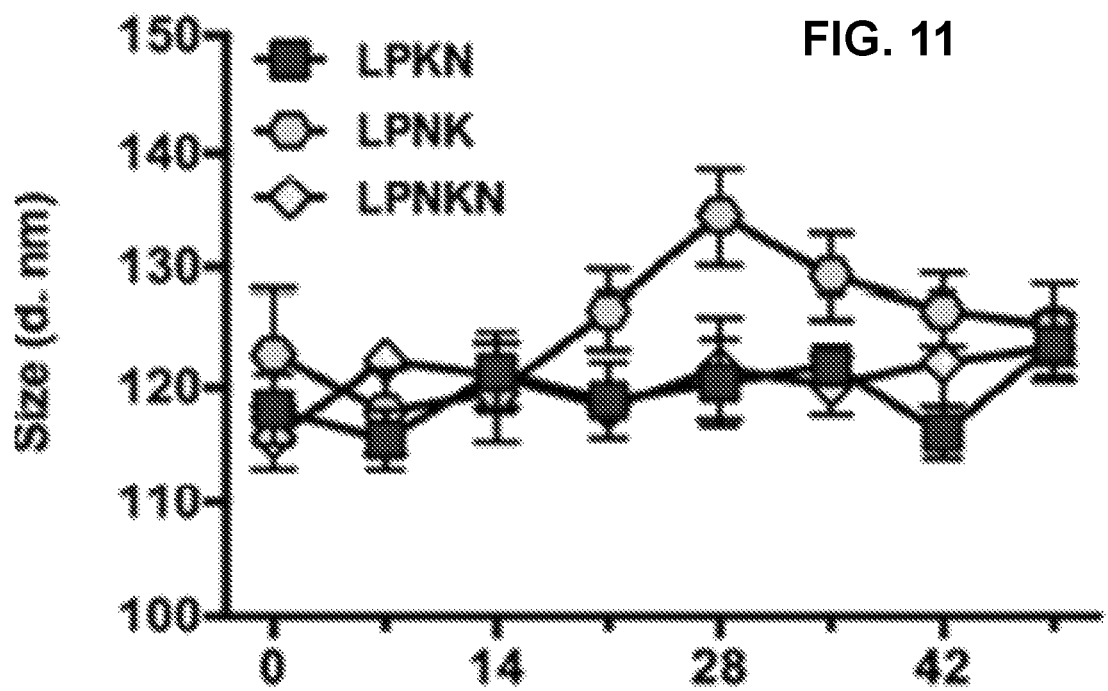
FIG. 11 shows a graph demonstrating the stability of the nanovaccines in phosphate buffered saline (PBS).
Figure 12:
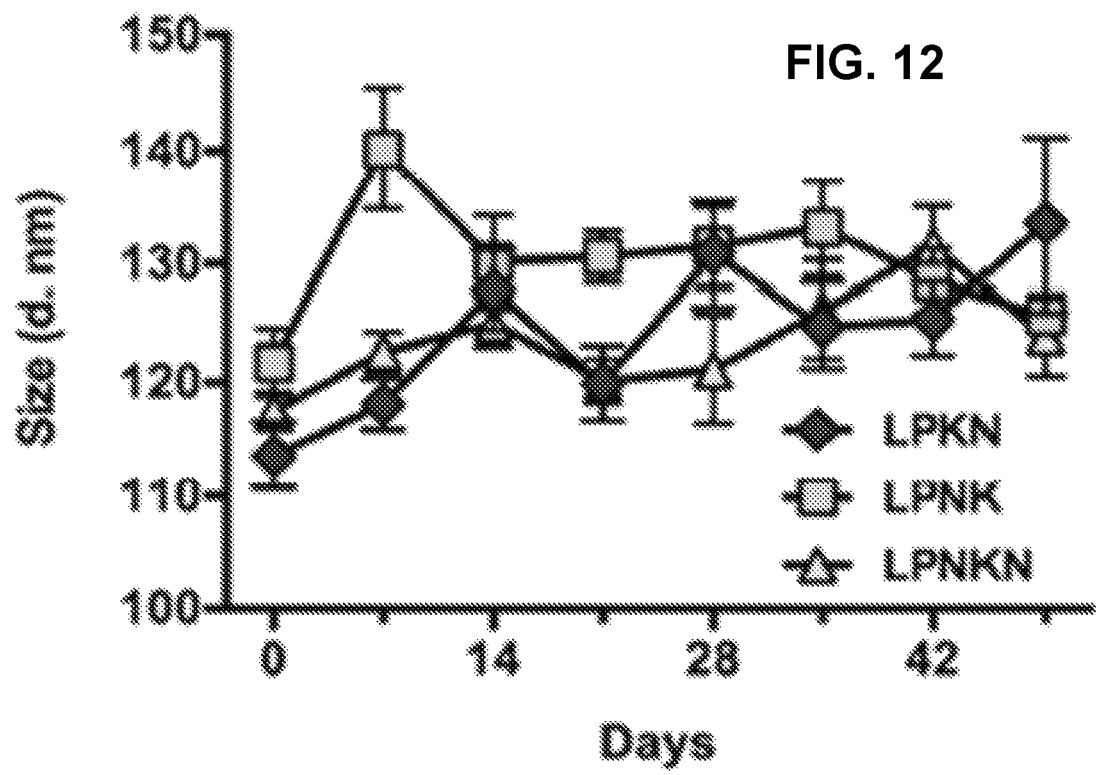
FIG. 12 shows a graph demonstrating the stability of the nanovaccines in deionized (DI) water.
Figures 13A, 13B:
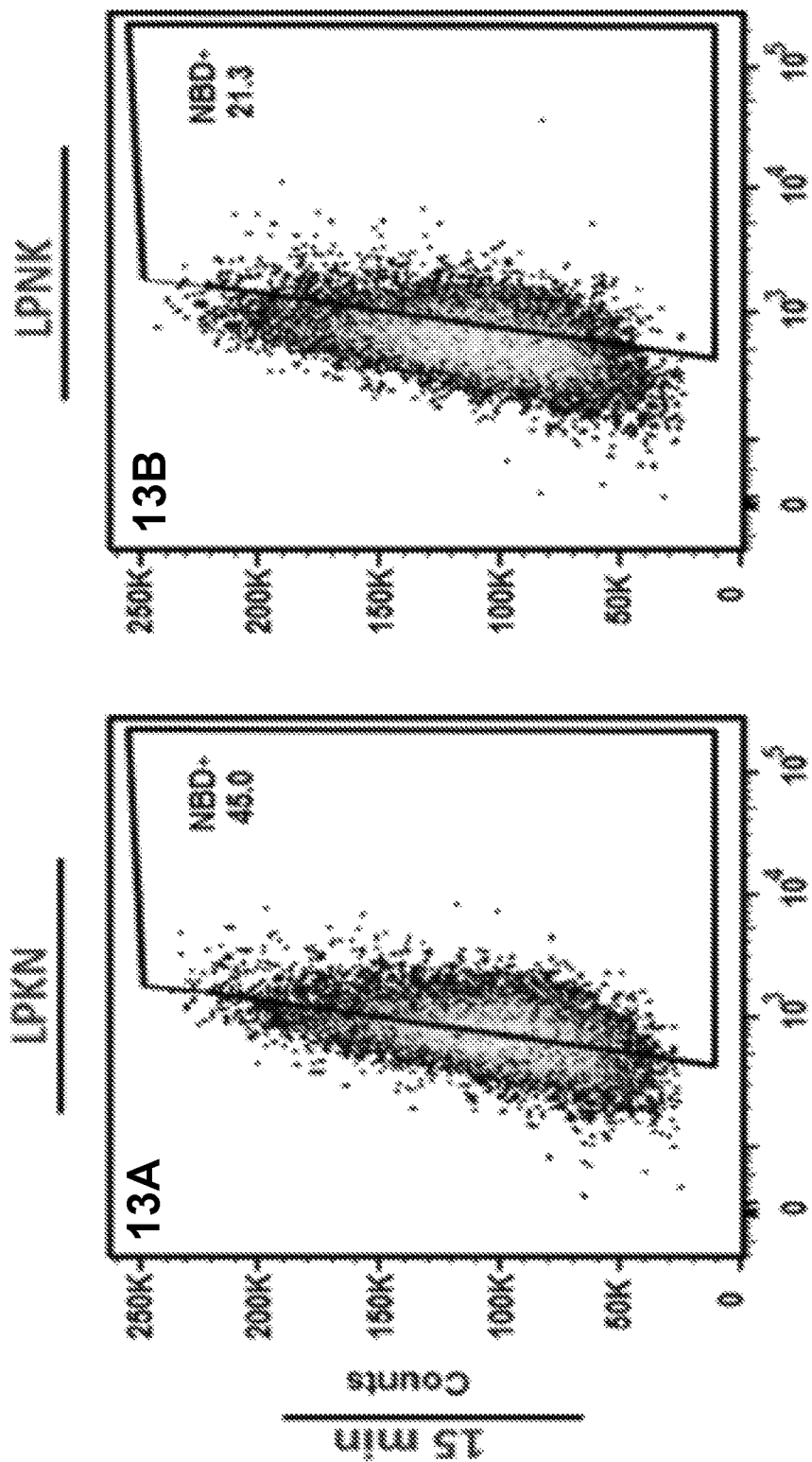
FIGS. 13A-13F show results of a flow cytometry assay demonstrating the uptake of nanovaccine NPs by dendritic cells, and more specifically, the population distribution of cells treated with 20 μg of the nanovaccine NPs for 15 min (FIGS. 13A-13C) or 120 min (FIGS. 13D-13F).
Figures 13C, 13D:
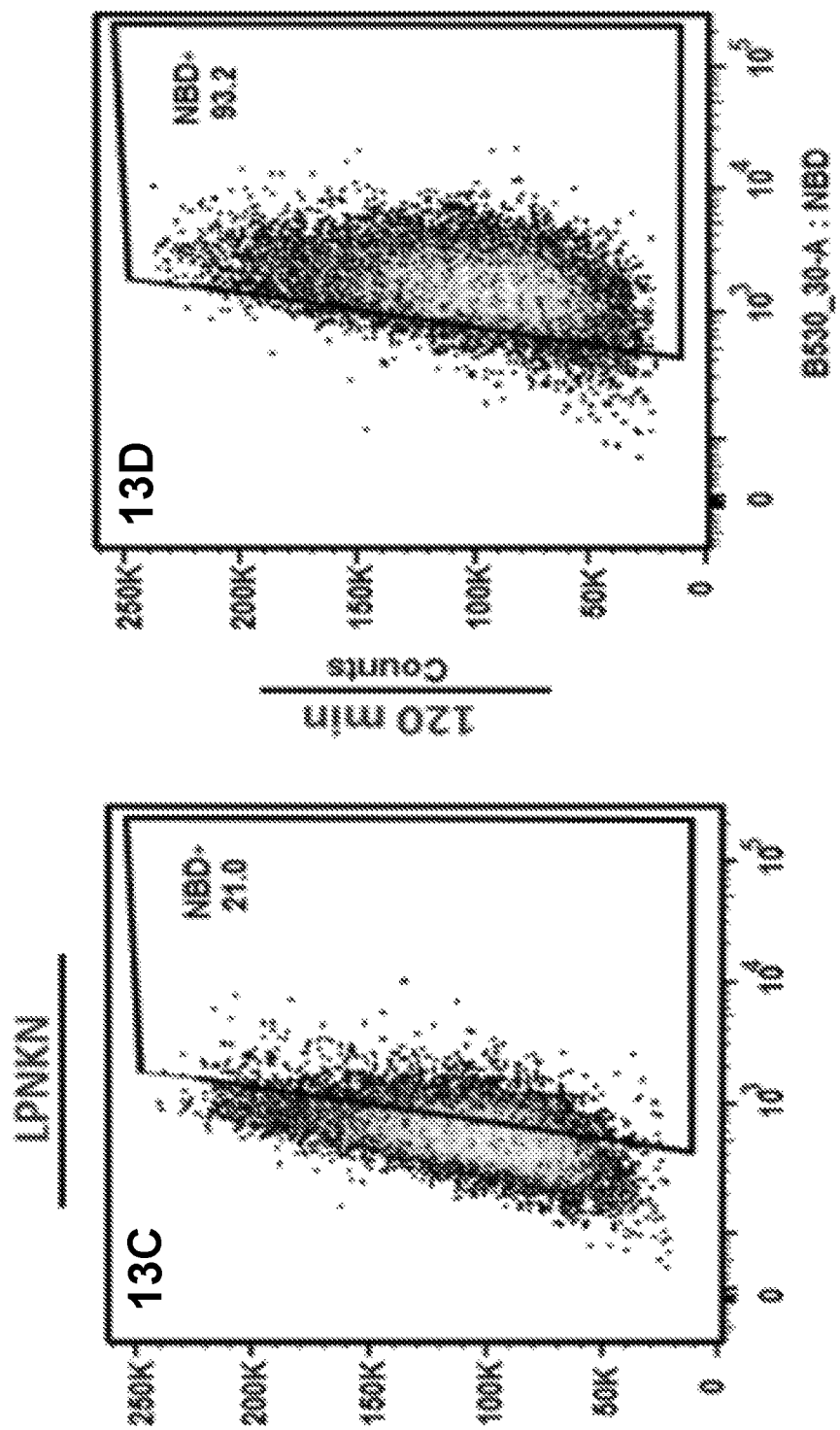
Figures 13E, 13F:
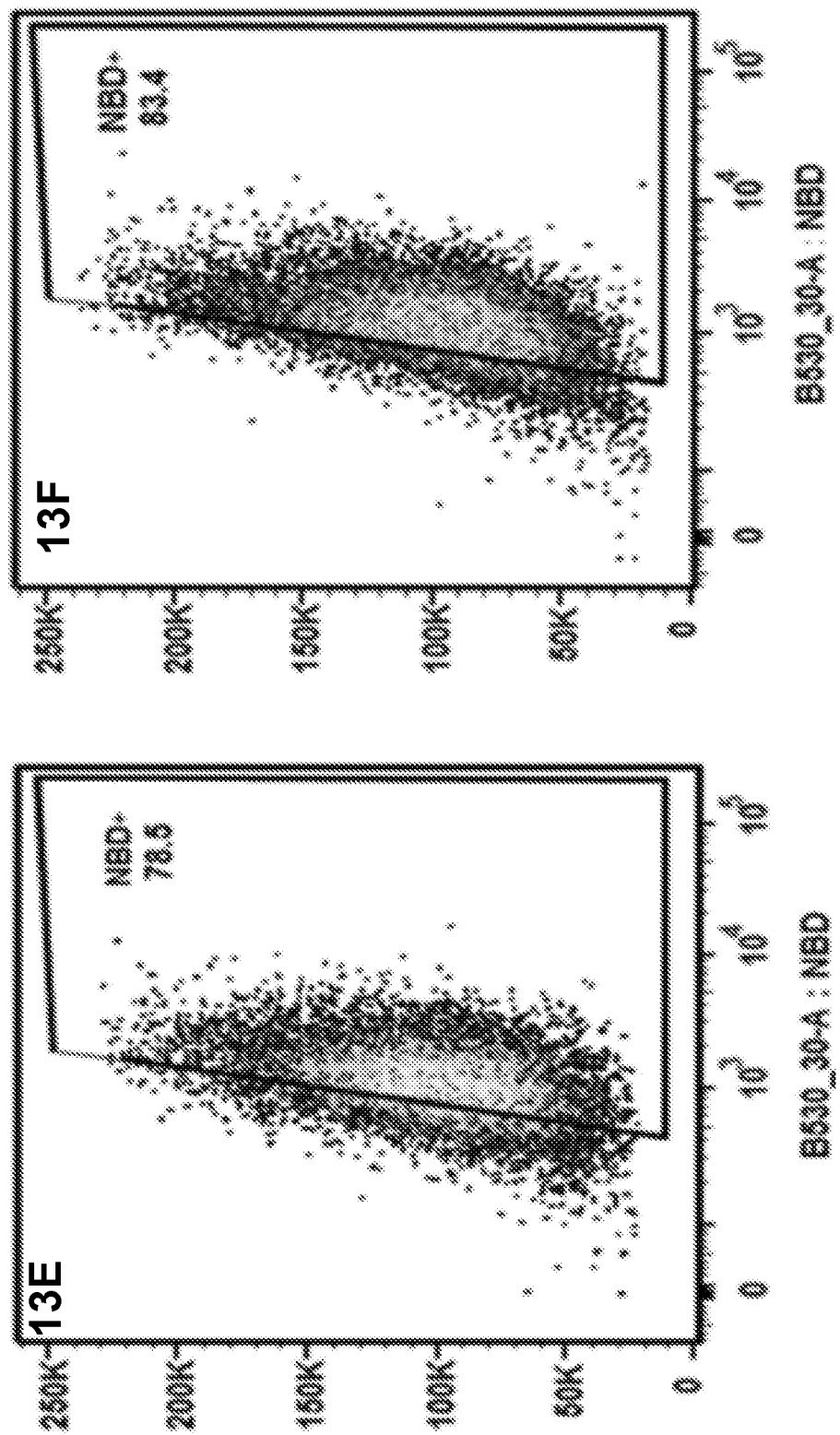

The stability of nanovaccines, indicated by size change, was tested in PBS and DI water for up to 49 days. The size change of all three nanovaccines was less than 20 nm in PBS over the entire study period (FIG. 11), suggesting the nanovaccines were highly stable in PBS for up to 49 days. The nanovaccines appeared to be less stable in water. The size change of nanovaccines was still less than 30 nm for up to 49 days in DI water (FIG. 12).

Cellular Uptake of Nanovaccine NPs

Figure 14:
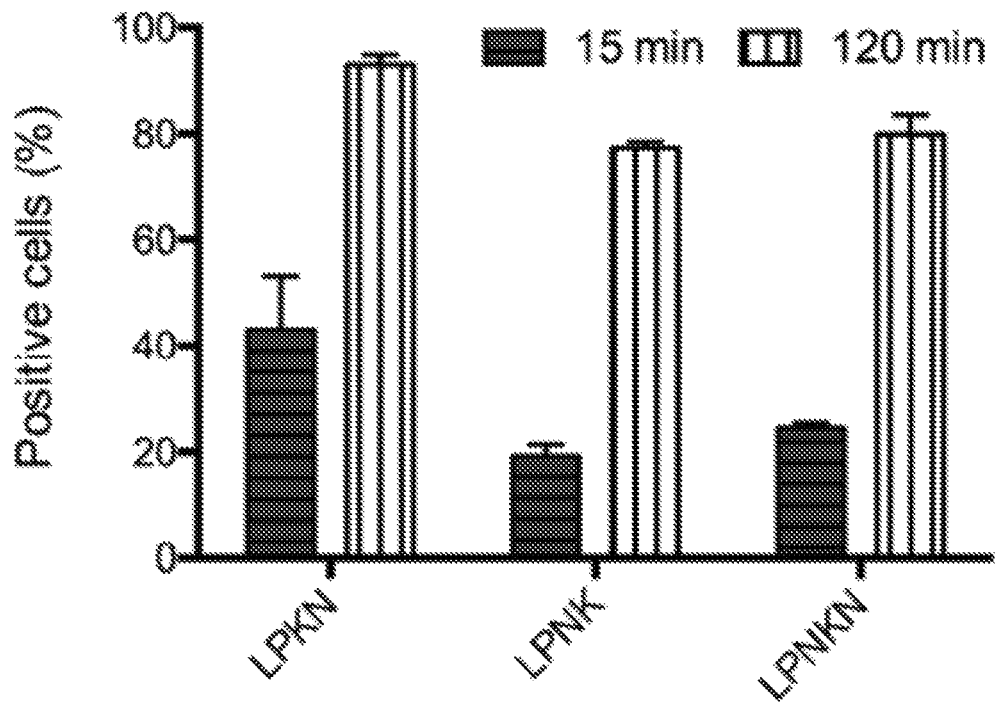
FIG. 14 shows a graph demonstrating the results of the flow cytometry assay, and more specifically, demonstrating the percentage of NBD-positive cells.
Figure 15:
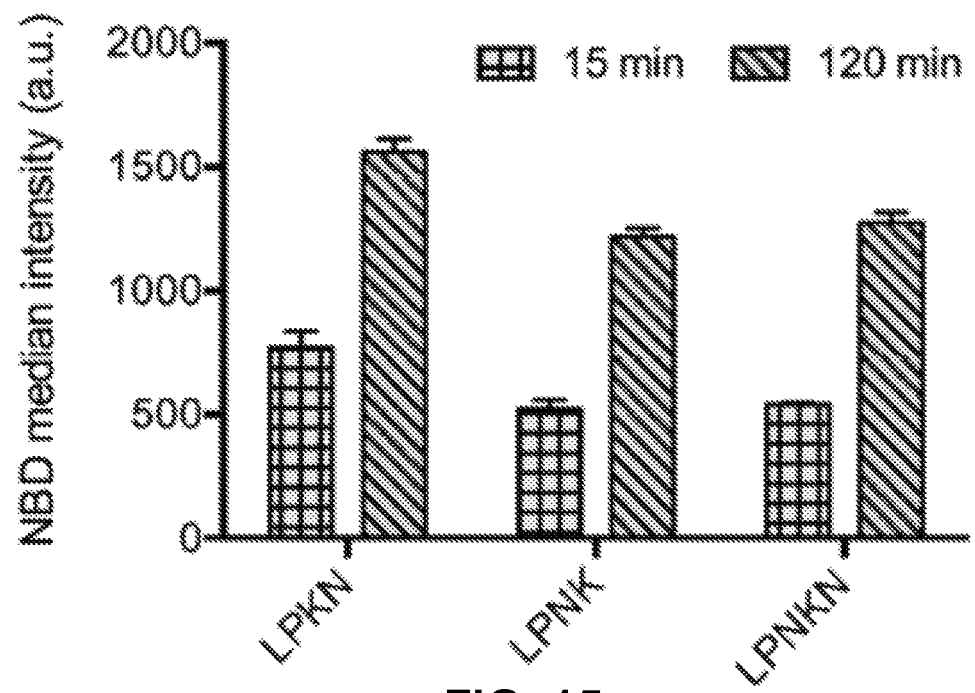
FIG. 15 shows a graph demonstrating the results of the flow cytometry assay, and more specifically, demonstrating the NBD median intensity in cells.
Figures 16A, 16B, 16C, 16D, 16E, 16F, 16G, 16H, 16I, 16J, 16K, 16L:
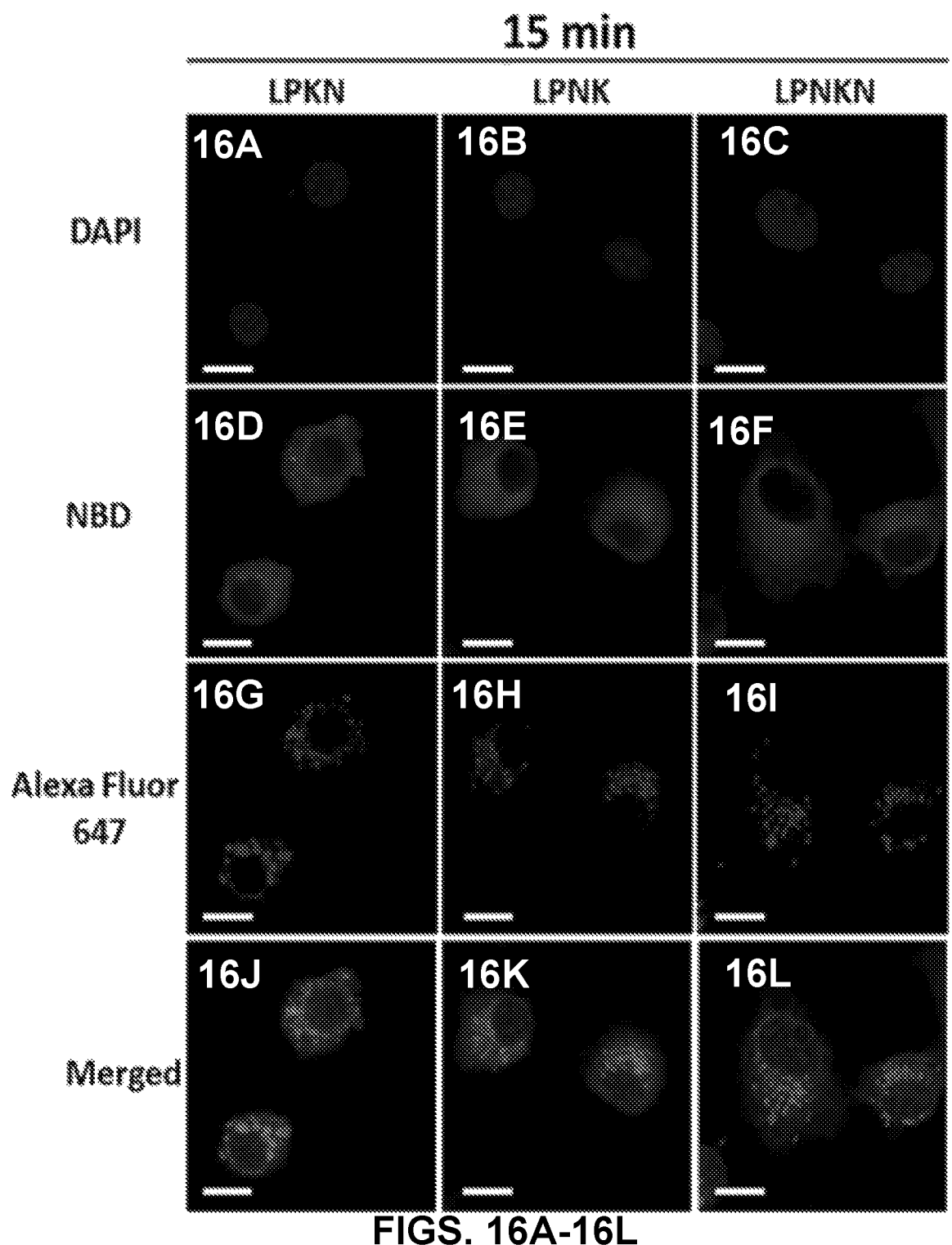
FIGS. 16A-16L show CLSM images demonstrating uptake of nanovaccine NPs by dendritic cells. The lipid layer of hybrid NPs was labeled by NBD. Nic-hapten on KLH was substituted with AF647 to provide fluorescence. Cells were treated with 20 μg of nanovaccine NPs for 15 min. Scale bars represent 10 μm.
Figures 17A, 17B, 17C, 17D, 17E, 17F, 17G, 17H, 17I, 17J, 17K, 17L:
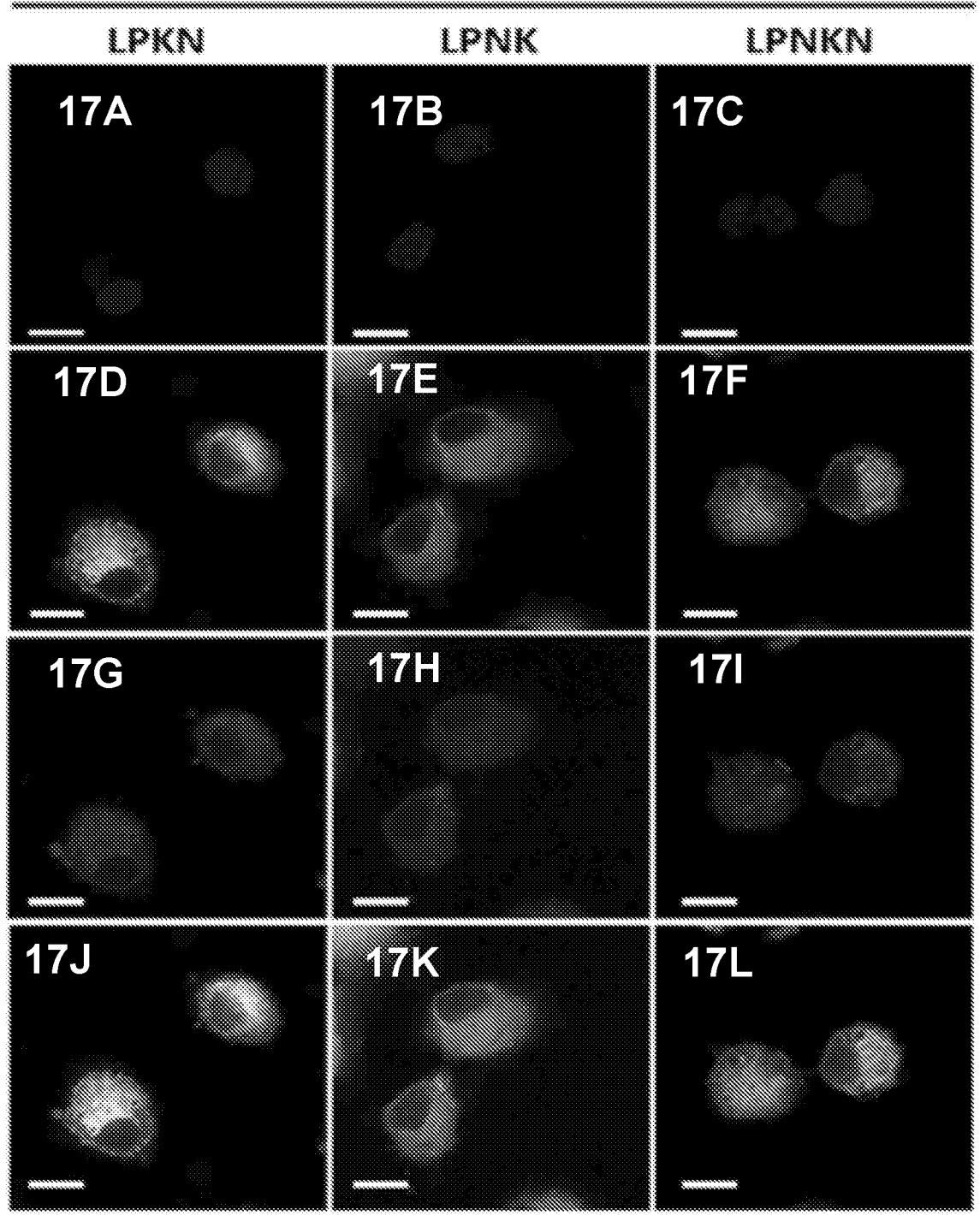
FIGS. 17A-17L show CLSM images demonstrating uptake of nanovaccine NPs by dendritic cells. The lipid layer of hybrid NPs was labeled by NBD. Nic-hapten on KLH was substituted with AF647 to provide fluorescence. Cells were treated with 20 μg of nanovaccine NPs for 120 min. Scale bars represent 10 μm.

The cellular uptake of nanovaccine NPs was studied in DCs by FCA. The uptake of nanovaccines displayed a time-dependent manner. After 15 min's incubation, except for LPKN, only small portions of cells had taken up NPs (FIGS. 13A-13F and 14). The percentages of NBD-positive cells were 43.0±8.3%, 19.2±1.76%, and 24.5±0.8% for LPKN, LPNK, and LPNKN, respectively (FIG. 14). The corresponding median NBD intensity was 773±52, 522±30, and S40±6, respectively (FIG. 15). After a 120 min incubation, more NPs were internalized for all three nanovaccines. Particularly, the percentages of NBD-positive cells were 93.0±1.4%, 77.3±0.9%, and 84.3±3.0%, for LPKN, LPNK, and LPNKN, respectively (FIG. 14); and the median NBD intensity was 1560±44, 1217±28, and 1237±34, respectively (FIG. 15). The data of both NBD-positive cells and NBD median intensity revealed that LPKN were taken up by dendritic cells more rapidly than LPNK and LPNKN.

The uptake and processing of nanovaccines were further studied by CLSM. Consistent with the FCA data, the uptake of nanovaccine NPs was time-dependent (FIGS. 16A-16L and 17A-17L). After 15 min's incubation, dim NBD and AF647 fluorescences were shown in cells (FIGS. 16A-16L). This suggested cells had taken up small amounts of nanovaccine NPs within 15 min. In contrast, the fluorescence of NBD and AF647 was very bright in cells after a 120 min incubation (FIGS. 16A-16L), indicating more NPs were taken up with time. Interestingly, the processing of the nanovaccines appeared to be step-wise in the cells. After 15 min, NBD fluorescence widely distributed in cells, while AF647 fluorescence displayed as individual particles (FIGS. 16A-16L). This indicated that the lipid-layer was removed from the hybrid NPs to release protein antigens, but the protein antigens had not been efficiently processed. After 120 min, both NBD and AF647 fluorescence widely distributed in cells (FIGS. 17A-17L), revealing that protein antigens had been effectively processed to small peptides. Moreover, consistent with the FCA data, LPKN was observed to be more efficiently taken up by dendritic cells than LPNK and LPNKN, as both NBD and AF647 fluorescence were brighter in LPKN group, especially at 120 min.

Immunogenicity of Nanovaccines Against Nicotine and Stimulating Protein

Figure 18A:
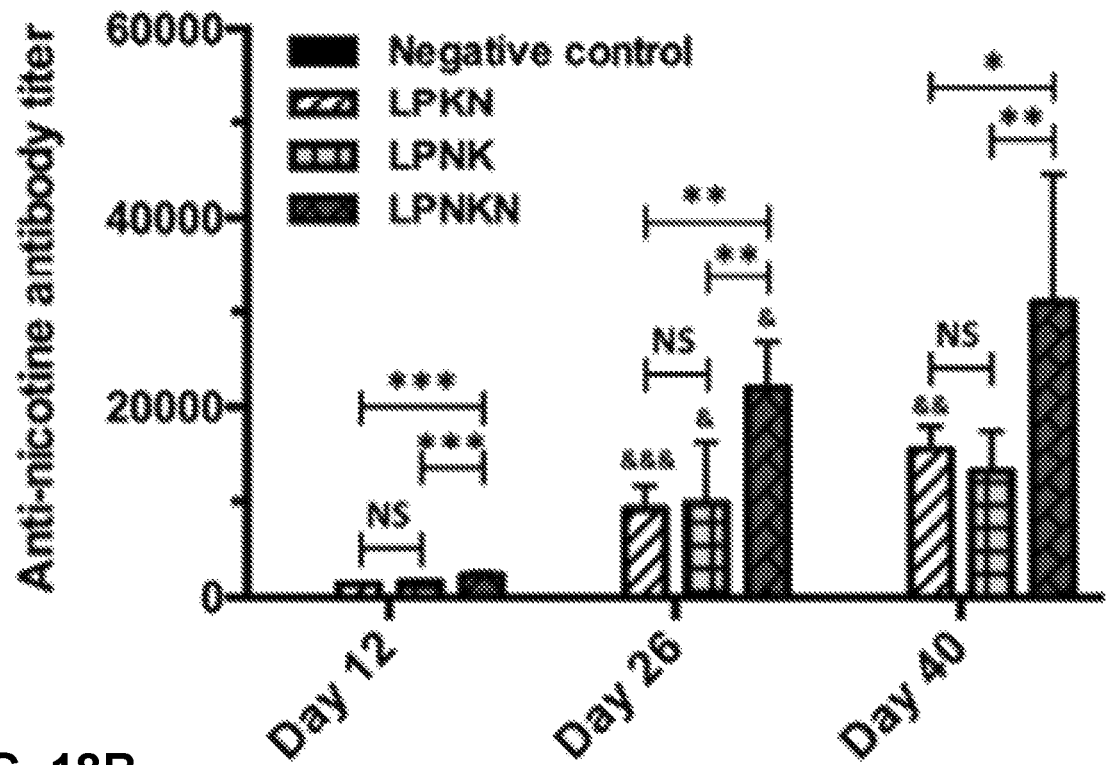
FIGS. 18A-18B show graphs demonstrating the anti-nicotine antibody titers (FIG. 18A) and anti-KLH antibody titers (FIG. 18B) determined by ELISA. Significantly different as compared to the previous studied day: & $p<0.05$, && $p<0.01$, &&& $p<0.001$. Significantly different compared to the other three groups on the same studied day: ## $p<0.01$, ### $p<0.001$. Significantly different: * $p<0.05$,  $p<0.01$, * $p<0.001$.

The immunogenicity of nanovaccines against nicotine was evaluated in mice, and the results are shown in FIG. 18A. No anti-nicotine antibody titers were detected in the negative control group on all days in which mice were immunized with KLH associated hybrid NPs without hapten conjugation. After the primary immunization, the anti-nicotine antibody titers of LPKN, LPNK, and LPNKN on day 12 were $(1.3\pm0.1)\times10^3$, $(1.6\pm0.2)\times10^3$ and $(2.3\pm0.3)\times10^3$, respectively. After the first booster immunization, anti-nicotine antibody titers on day 26 were significantly increased over that on day 12. The titers were $(9.2\pm2.2)\times10^3$, $(9.8\pm6.0)\times10^3$, and $(21.9\pm4.5)\times10^3$ for LPKN, LPNK, and LPNKN, respectively. After the second booster immunization, anti-nicotine antibody titers were further considerably ascended on day 40, which were $(15.5\pm2.3)\times10^3$, $(13.1\pm4.1)\times10^3$, and $(31.0\pm12.4)\times10^3$ for LPKN, LPNK, and LPNKN, respectively. Statistical analysis suggested that LPNKN generated significantly higher anti-nicotine antibody titers than LPKN and LPNK ($p<0.05$), while LPKN and LPNK induced comparable titers ($p>0.95$), on all the studied days.

Figure 18B:
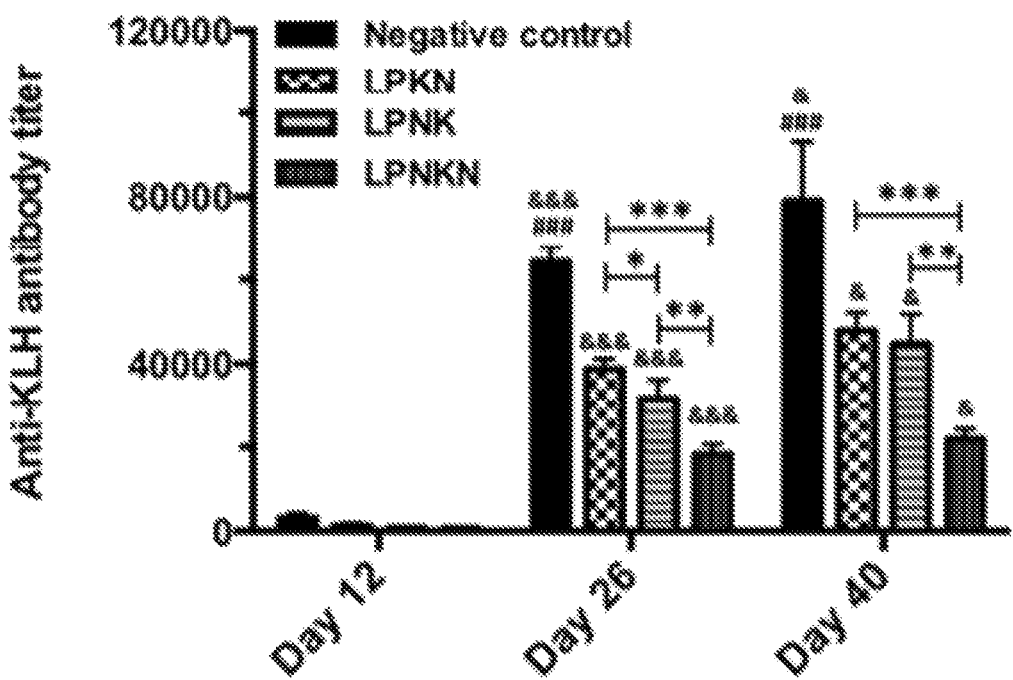

Titers of anti-KLH antibody were also monitored. The results are shown in FIG. 18B. Similar to anti-nicotine antibody titers, anti-KLH antibody titers significantly increased after each immunization. On all the studied days, the negative control induced the highest level of anti-KLH antibody. For the nanovaccines with different hapten localizations, the anti-KLH antibody titers were in the order of LPKN>LPNK>LPNKN for all of the studied days. The differences among different nanovaccine groups were significant ($p<0.05$) on days 26 and 40, except for LPKN and LPNK. Specifically, end-point titers of $(79.1\pm14.1)\times10^3$ $(47.9\pm4.3)\times10^3$ $(44.7\pm7.1)\times10^3$ and $(21.8\pm2.6)\times10^3$ were detected in the negative control, LPKN, LPNK, and LPNKN groups, respectively.

Avidity of Anti-Nicotine Antibodies Induced by Nanovaccines

Figure 19A:
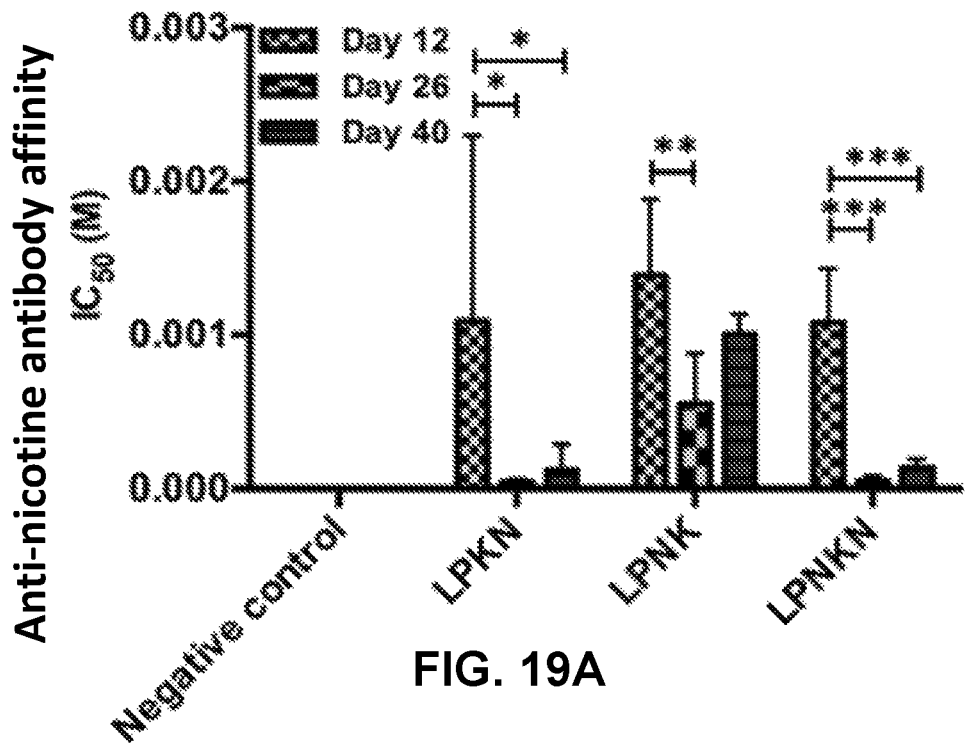
FIGS. 19A-19B show graphs demonstrating anti-nicotine antibody affinity estimated by competition ELISA.
Figure 19B:
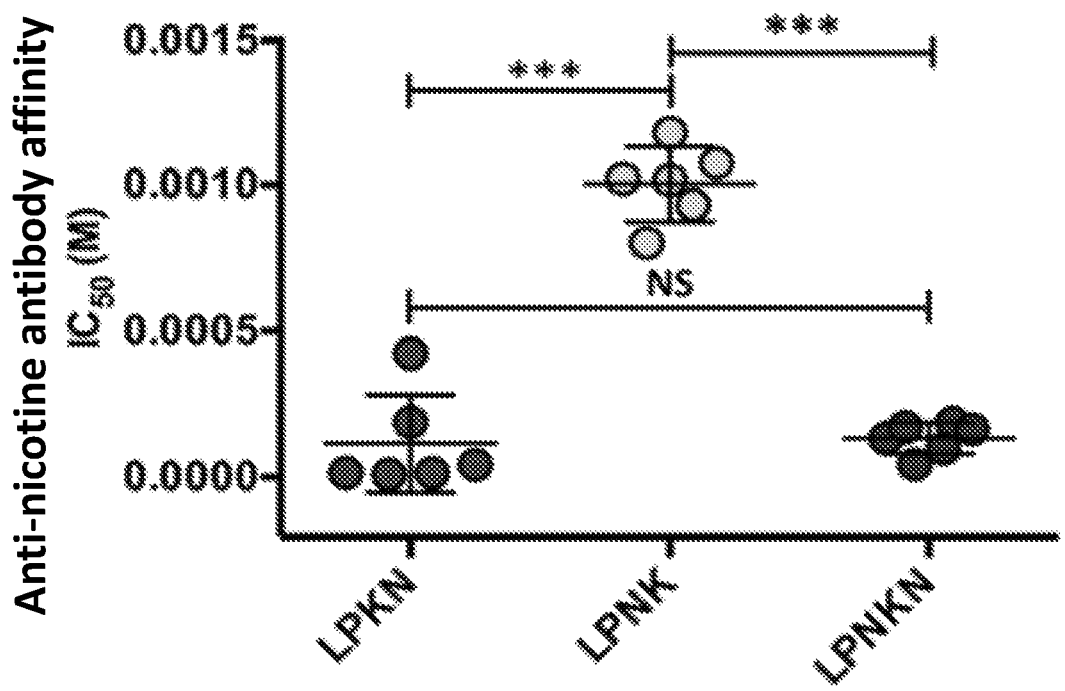
Figure 20A:
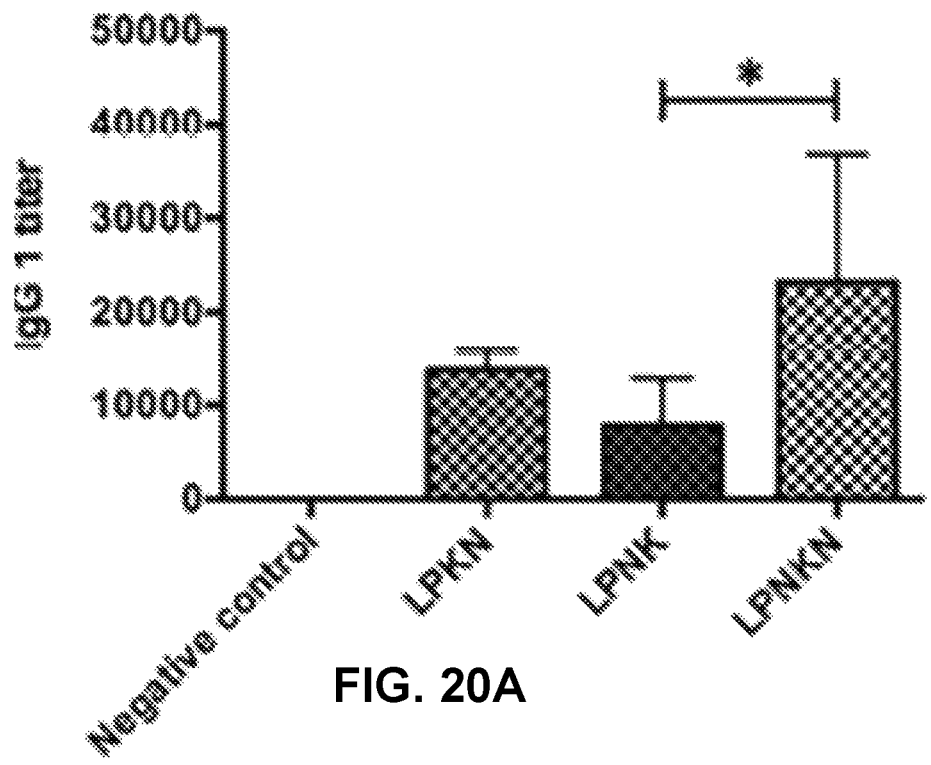
FIGS. 20A-20E show graphs demonstrating anti-nicotine subclass antibody titers of (FIG. 20A) IgG 1, (FIG. 20B) IgG 2a, (FIG. 20C) IgG 2b, and (FIG. 20D) IgG 3.
Figure 20B:
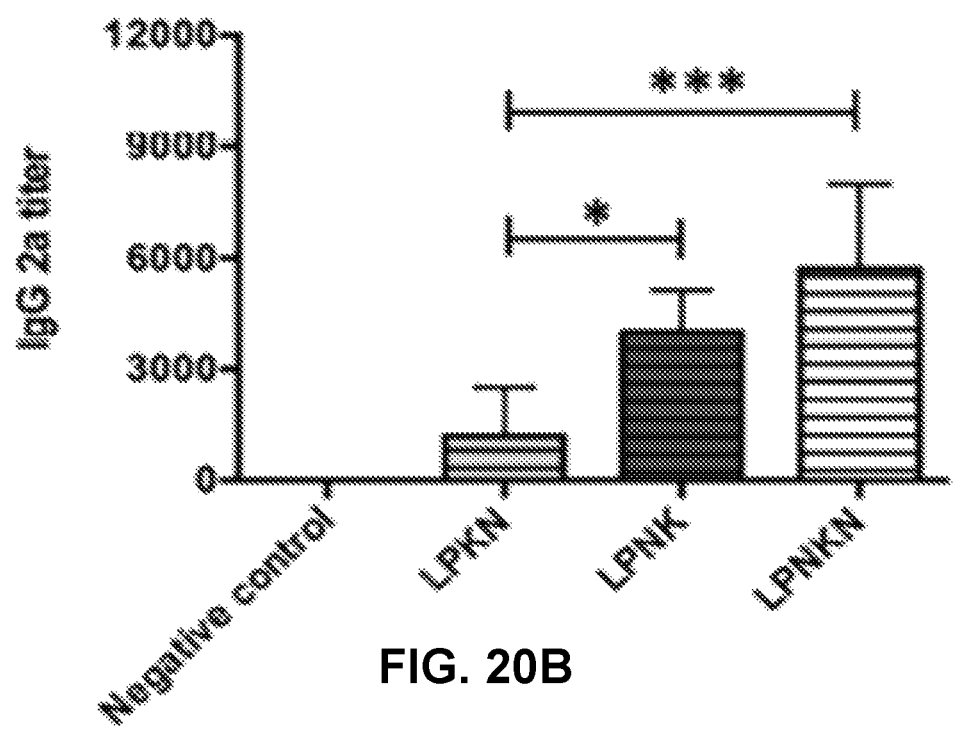
Figure 20C:
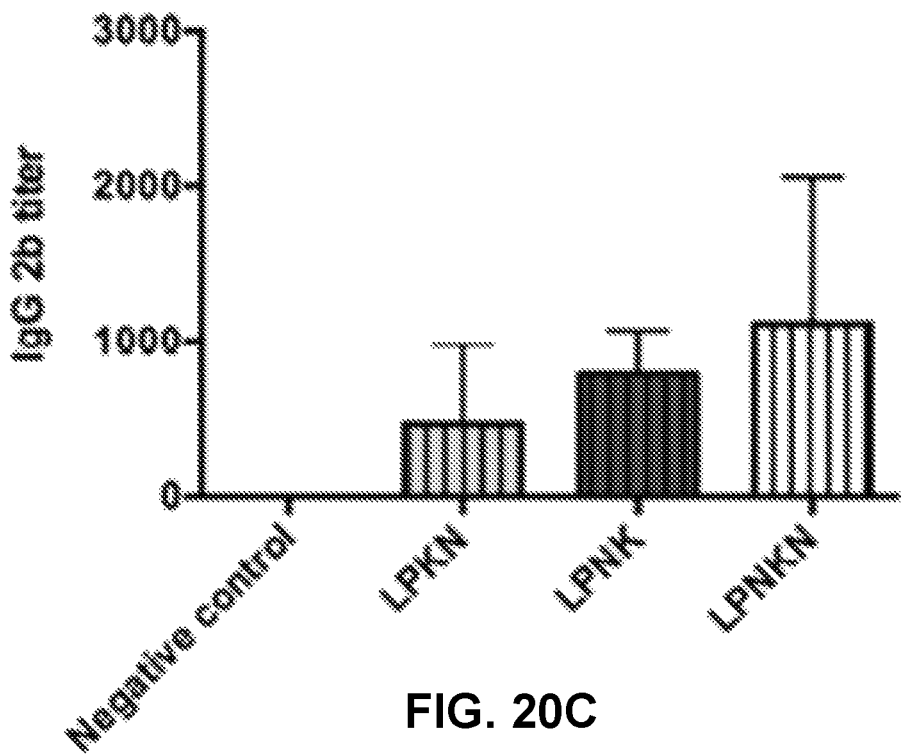
Figure 20D:
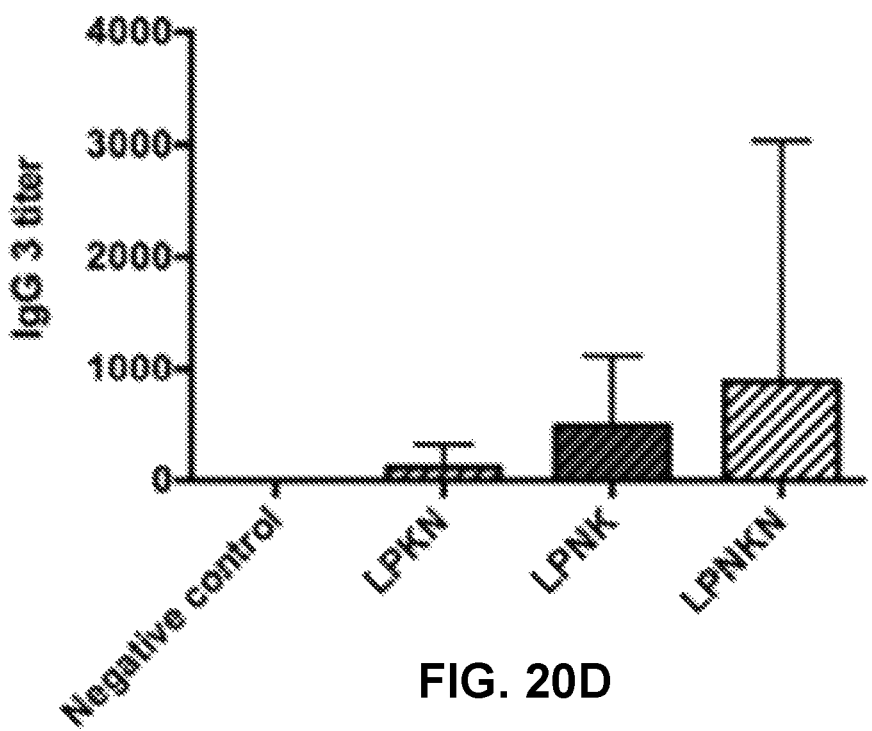
Figure 20E:
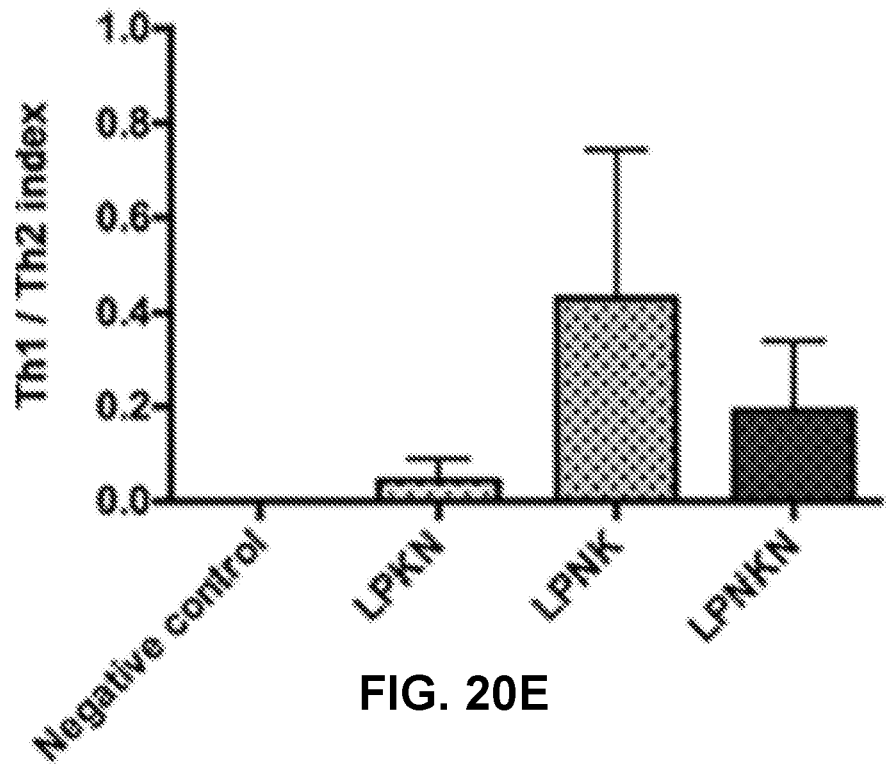

Avidity of anti-nicotine antibodies elicited by nanovaccines was estimated by competition ELISA, and the time-course of antibody avidity on days 12, 26, and 40 was shown in FIG. 19A. On day 12, $IC_{50}$ for LPKN, LPNK, and LPNKN was $1085\pm1103$, $1380\pm460$, and $1077\pm319$ μM, respectively. On day 26, $IC_{50}$ decreased to be $29\pm19$, $468\pm302$, and $29\pm31$ μM, for LPKN, LPNK, and LPNKN, respectively. This revealed that the first booster immunization significantly promoted the maturation of antibody avidity. Interestingly, after the second booster immunization (on day 40), the avidity of antibodies induced by the three nanovaccines decreased. The $IC_{50}$ was $115\pm162$, $1004\pm1276$, and $132\pm51$M for LPKN, LPNK, and LPNKN, respectively. The avidity of antibodies induced by LPKN and LPNKN was considerably higher over LPNK on all the studied days. Specially, statistical comparison suggested that the end-point avidity of antibodies elicited by LPKN and LPNKN was significantly higher than that induced by LPNK, and no significant differences existed between LPKN and LPNKN (FIG. 19B).

IgG Subclass Distribution of Anti-Nicotine Antibodies

Subtype distribution of anti-nicotine IgG antibodies induced by the nanovaccines on day 40 was assayed. As shown in FIGS. 20A-20E, IgG1 was the dominant subtype among all four subtypes for all the three nanovaccines with different hapten localizations. In concordance with the total IgG titers, LPNKN induced higher titers of all four IgG subtypes over LPKN and LPNKN, especially for IgG1 and IgG2a. Interestingly, although the total IgG titers of LPKN and LPNK were very close (FIG. 18A), LPNK generated significantly higher levels of IgG2a than LPKN. The relative magnitude of Th1 versus Th2 immune response induced by nanovaccines was assessed by the Th1/Th2 index. The Th1/Th2 indexes for LPKN, LPNK, and LPNKN were $0.043\pm0.042$, $0.430\pm0.288$, and $0.191\pm0.136$, respectively, which were all significantly less than 1. This indicated that the immune responses induced by the nanovaccines, regardless of hapten localizations, was Th2-skewed (humoral response dominated). Interestingly, LPNKN and LPNK resulted in a more balanced Th1-Th2 response than LPKN.

Pharmacokinetic Efficacy of the Nicotine Nanovaccines

Pharmacokinetic efficacy of nanovaccines with different hapten localizations was tested in mice. Mice were received a dose of 0.06 mg/kg nicotine for 3 min on day 42. Serum nicotine levels were shown in FIG. 21A. The blank group had a serum nicotine level of 12.5 ng/ml. Compared to the blank group, the nicotine levels of LPKN, LPNK and LPNKN increased by 79.2%, 20%, and 192.0%, respectively. This indicated that LPNKN had the best ability to retain nicotine in serum. Nicotine levels in the brain were shown in FIG. 21B. The brain nicotine level in the blank group was 98.8 ng/g. The percent reductions in brain nicotine levels were 49.4%, 41.3%, and 66.9% for LPKN, LPNK, and LPNKN, respectively. This suggested that LPNKN had the best ability of blocking nicotine from entering the brain.

Safety of the Nicotine Nanovaccines

Figures 22A, 22Y:
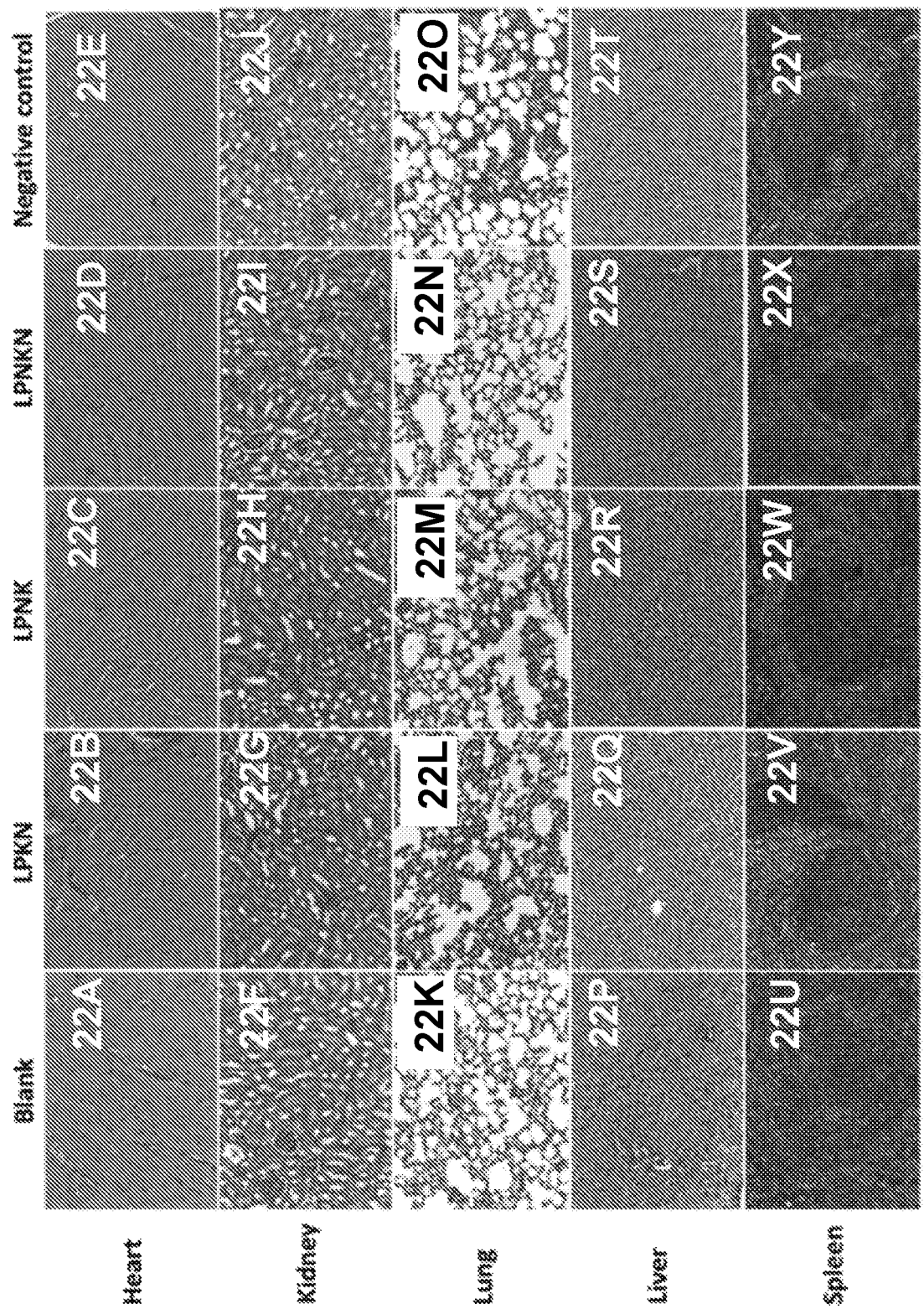
FIGS. 22A-22Y show images of H&E staining of the sections of major organs including heart, kidney, lung, liver, and spleen harvested from the mice immunized with different nicotine vaccines.

The safety of nanovaccines was evaluated histopathologically (FIGS. 22A-22Y). Major organs of mice, including heart, kidney, lung, liver, and spleen, were stained with H&E and examined. No significant differences were detected between the blank (PBS) and the three nanovaccine groups, in all the examined organs. Moreover, no detectable difference was observed among the nanovaccines with different hapten localizations. These results suggest the nanovaccines, regardless of hapten localization, were fairly safe.

Discussion

Nicotine vaccines remain a promising strategy for treating and/or preventing nicotine addiction. Conjugate vaccines are the most prevalent and studied types of nicotine vaccines. However, current nicotine conjugate vaccines are limited by their intrinsic shortcomings, including low nicotine loading capacity, low bioavailability, poor recognition and uptake by immune cells, and difficulty in incorporation of adjuvants, limit their immunological efficacy. [9, 25]. Nanoparticles have been widely studied for delivery of drugs and vaccines. [33-37] Nanoparticles are able to maintain the activity of payloads and enhance delivery efficiency. In addition, high payload loading capacity, improved bioavailability, and controlled payload release can be achieved by nanoparticles. [38-41]. This Example demonstrates the immunogenicity and efficacy of lipid-polymeric nanoparticle-based nicotine nanovaccines can be improved by modulating the hapten localization.

Figure 21A:
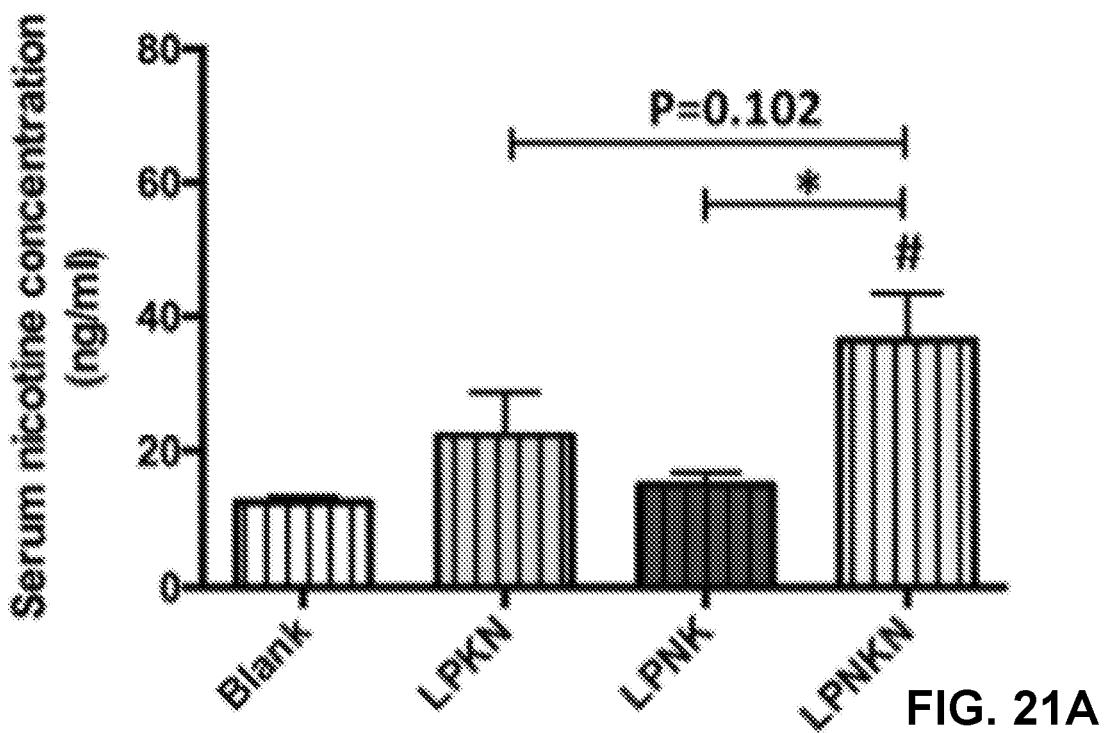
FIGS. 21A-21B show graphs demonstrating the pharmacokinetic efficacy of nanovaccines with different hapten localizations. Nicotine levels in the serum (FIG. 21A) and brain (FIG. 21B) of mice after challenged with 0.06 mg/kg nicotine for 3 min were analyzed. Data were reported as means±standard error. Significantly different compared to the blank group: #$p<0.05$, ###$p<0.001$. Significantly different: * $p<0.05$.
Figure 21B:
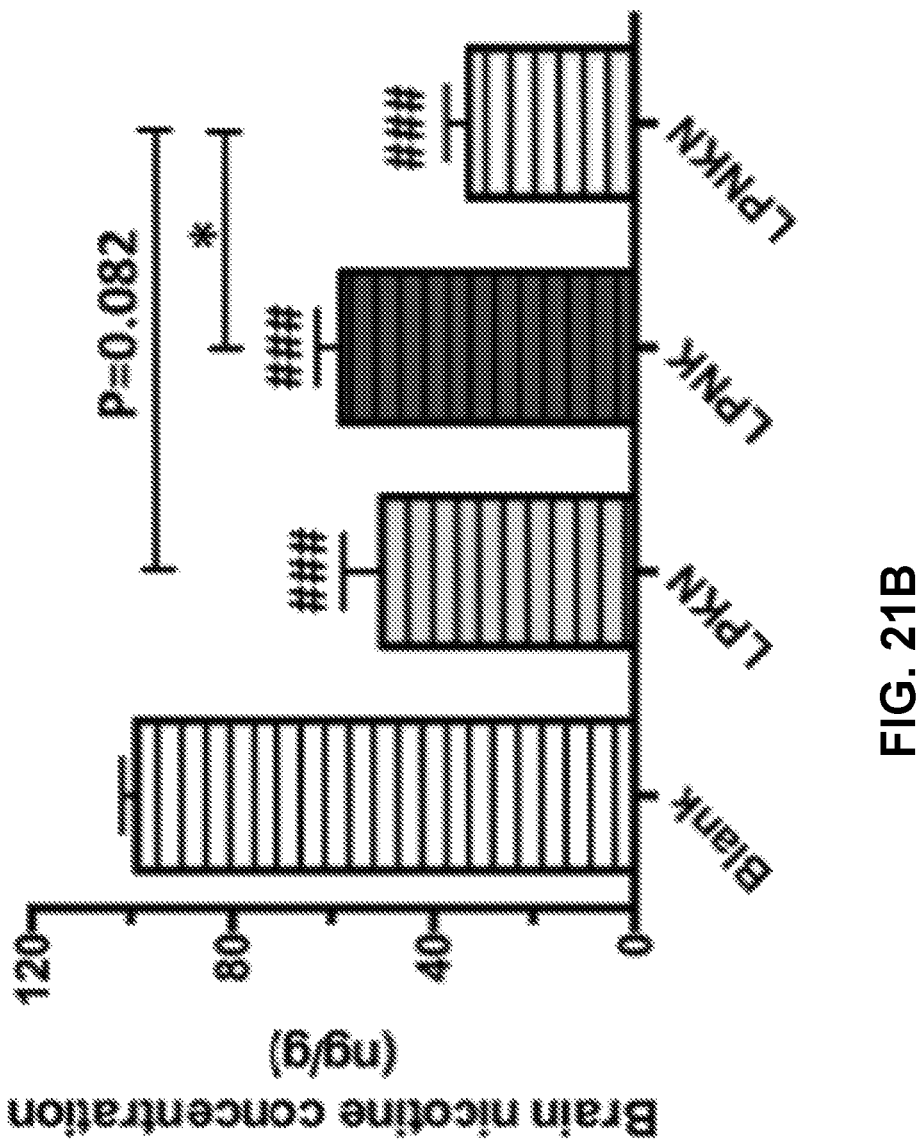

LPNKN induced significantly higher anti-nicotine antibody titers than LPKN and LPNK, while the antibody levels of LPKN and LPNK were comparable (FIG. 18A), which suggests that nanovaccines with Nic-haptens conjugated onto both the stimulating protein and the nanoparticle surface, instead of only on one, can increase efficacy of the nanovacine as compared to current nicotine nanovaccines. LPNKN induced the lowest anti-KLH antibody titers among the nanovaccines tested with other hapten localizations. LPNKN had the greatest immunogenicity among the nanovaccines tested and elicited the greatest anti-nicotine antibody titers and the lowest anti-KLH antibody titers. PNKN had significantly greater avidity than that by LPNK (FIGS. 19A-19B). This indicated that hapten localization appeared to affect anti-nicotine antibody's avidity. It was also observed that hapten location influenced IgG subtypes. All three nanovaccines tested induced Th2-skewed humoral responses (Th1/Th2 indexes significantly less than 1), which is desirable as the efficacy of reducing the rewarding effects of nicotine is dependent on the magnitude of the humoral response. Consistent with the immunogenicity and avidity data, LPNKN resulted in a better pharmacokinetic efficacy of retaining nicotine in serum and blocking nicotine from entering the brain than LPKN and LPNK (FIGS. 21A-21B). This suggested the efficacy of nicotine nanovaccines was improved by conjugating Nic-haptens to both stimulating protein and nanoparticle surface.

REFERENCES FOR EXAMPLE 1

[1] Tobacco, Fact Sheet Number 339. World Health Organization; 2015. [2] Benowitz N L. Nicotine addiction. N Engl J Med. 2010; 362:2295-303.

[3] Prochaska J J, Benowitz N L. The Past, Present, and Future of Nicotine Addiction Therapy. Annu Rev Med. 2016; 67:467-86.

[4] Hughes J R, Keely J, Naud S. Shape of the relapse curve and long-term abstinence among untreated smokers. Addiction. 2004; 99:29-38.

[5] Paolini M, De Biasi M. Mechanistic insights into nicotine withdrawal. Biochem Pharmacol. 2011; 82:996-1007.

[6] Stead L F, Perera R, Bullen C, Mant D, Hartmann-Boyce J, Cahill K, et al. Nicotine replacement therapy for smoking cessation. Cochrane db Syst Rev. 2012.

[7] Piper M E, Federman E B, McCarthy D E, Bolt O M, Smith S S, Fiore M C, et al. Efficacy of bupropion alone and in combination with nicotine gum. Nicotine Tob Res. 2007; 9:947-54.

[8] Koegelenberg C F N, Noor F, Bateman E D, van Zyi-Smit R N, Bruning A, O'Brien J A, et al. Efficacy of Varenicline Combined With Nicotine Replacement Therapy vs Varenicline Alone for Smoking Cessation A Randomized Clinical Trial. Jama-J Am Med Assoc. 2014; 312:155-61.

[9] Pentel P R, LeSage M G. New Directions in Nicotine Vaccine Design and Use. Adv Pharmacol. 2014; 69:553-80.

[10] Raupach T, Hoogsteder P H, Onno van Schayck C P. Nicotine vaccines to assist with smoking cessation:current status of research. Drugs. 2012; 72:e1-16.

[11] Goniewicz M L, Delijewski M. Nicotine vaccines to treat tobacco dependence. Hum Vacc Immunother. 2013; 9:13-25.

[12] Keyler D E, Roiko S A, Earley C A, Murtaugh M P, Pentel P R. Enhanced immunogenicity of a bivalent nicotine vaccine. Int Immunopharmacol. 2008; 8:1589-94.

[13] McCiuskie M J, Thorn J, Mehelic P R, Kolhe P, Bhattacharya K, Finneman J I, et al. Molecular attributes of conjugate antigen influence function of antibodies induced by anti-nicotine vaccine in mice and non-human primates. Int Immunopharmacol. 2015; 25:518-27.

[14] Miller K D, Roque R, Clegg C H. Novel Anti-Nicotine Vaccine Using a Trimeric Coiled-Coil Hapten Carrier. Plos One. 2014; 9.

[15] De Blasi M, Mclaughlin I, Perez E E, Crooks P A, Dwoskin L P, Bardo M T, et al. Scientific overview: 2013 BBC plenary symposium on tobacco addiction. Vol. 141; pg 107. (2014). Drug Alcohol Depen. 2014; 141:107-117.

[16] Hatsukami D K, Jorenby D E, Gonzales D, Rigotti N A, Glover E D, Oncken C A, et al. Immunogenicity and Smoking-Cessation Outcomes for a Novel Nicotine Immunotherapeutic. Clin Pharmacol Ther. 2011; 89:392-9.

[17] Cornuz J, Zwahlen S, Jungi W F, Osterwalder J, Klingler K, van Melle G, et al. A Vaccine against Nicotine for Smoking Cessation: A Randomized Controlled Trial. Plos One. 2008; 3.

[18] Pryde D C, Jones L H, Gervais D P, Stead D R, Blakemore D C, Selby M D, et al. Selection of a Novel Anti-Nicotine Vaccine: Influence of Antigen Design on Antibody Function in Mice. Plos One. 2013; 8.

[19] de Villiers S H L, Lindblom N, Kalayanov G, Gordon S, Baraznenok I, Malmerfelt A, et al. Nicotine hapten structure, antibody selectivity and effect relationships: Results from a nicotine vaccine screening procedure. Vaccine. 2010; 28:2161-8.

[20] Chen X Y, Pravetoni M, Bhayana B, Pentel P R, Wu M X. High immunogenicity of nicotine vaccines obtained by intradermal delivery with safe adjuvants. Vaccine. 2012; 31:159-64.

[21] McCiuskie M J, Pryde D C, Gervais D P, Stead D R, Zhang N L, Benoit M, et al. Enhancing immunogenicity of a 3' aminomethylnicotine-D T-conjugate anti-nicotine vaccine with CpG adjuvant in mice and non-human primates. Int Immunopharmacol. 2013; 16:50-6.

[22] Lockner J W, Lively J M, Collins K C, Vendruscolo J C M, Azar M R, Janda K D. A Conjugate Vaccine Using Enantiopure Hapten Imparts Superior Nicotine-Binding Capacity. J Med Chem. 2015; 58:1005-11.

[23] Collins K C, Janda K D. Investigating Hapten Clustering as a Strategy to Enhance Vaccines against Drugs of Abuse. Bioconjug Chem. 2014; 25:593-600.

[24] Hu Y, Zheng H, Huang W, Zhang C M. A novel and efficient nicotine vaccine using nano-lipoplex as a delivery vehicle. Hum Vacc Immunother. 2014; 10:64-72.

[25] Zheng H, Hu Y, Huang W, de Villiers S, Pentel P, Zhang J F, et al. Negatively Charged Carbon Nanohorn. Nanotechnol. 2015; 11:2197-210.

[26] Zhao Z, Hu Y, Haerle R, Devine M, Raleigh M, Pentel P, et al. A nanoparticle-based nicotine vaccine and the influence of particle size on its immunogenicity and efficacy. Nanomed-Nanotechnol. 2016.

[27] Jacob N T, Lockner J W, Schlosburg J E, Ellis B A, Eubanks L M, Janda K D. Investigations of Enantiopure Nicotine Haptens Using an Adjuvanting Carrier in Anti-Nicotine Vaccine Development. J Med Chem. 2016; 59:2523-9.

[28] Parra J, Abad-Somovilla A, Mercader J V, Iaton T A, Abad-Fuentes A. Carbon nanotube-protein carriers enhance size-dependent self-adjuvant antibody response to haptens. J Control Release. 2013; 170:242-51.

[29] Sloat B R, Sandoval M A, Hau A M, He Y, Cui Z. Strong antibody responses induced by protein antigens conjugated onto the surface of lecithin-based nanoparticles. J Control Release. 2010; 141:93-100.

[30] Jalah R, Torres O B, Mayorov A V, Li F, Antoline J F, Jacobson A E, et al. Efficacy, but not antibody titer or affinity, of a heroin hapten conjugate vaccine correlates with increasing hapten densities on tetanus toxoid, but not on $CRM_{197}$ carriers. Bioconjug Chem. 2015; 26:1041-53.

[31] Pravetoni M, Keyler D E, Pidaparthi R R, Carroll F I, Runyon S P, Murtaugh M P, et al. Structurally distinct nicotine immunogens elicit antibodies with non-overlapping specificities. Biochem Pharmacol. 2012; 83:543-50.

[32] de Villiers S H L, Cornish K E, Troska A J, Pravetoni M, Pentel P R. Increased efficacy of a trivalent nicotine vaccine compared to a dose-matched monovalent vaccine when formulated with alum. Vaccine. 2013; 31:6185-93.

[33] Thangavel S, Yoshitomi T, Sakharkar M K, Nagasaki Y. Redox nanoparticle increases the chemotherapeutic efficiency of pioglitazone and suppresses its toxic side effects. Biomaterials. 2016; 99:109-23.
[34] Liu et. al. Multifunctional aptamer-based nanoparticles for targeted drug delivery to circumvent cancer resistance. Biomaterials. 2016; 91:44-56.
[35] Qian Y, Jin H L, Qiao S, Dai V F, Huang C, Lu L S, et al. Targeting dendritic cells in lymph node with an antigen peptide-based nanovaccine for cancer immunotherapy. Biomaterials. 2016; 98:171-83.
[36] Van S Y, Rolfe B E, Zhang B, Mohammed V H, Gu W Y, Xu Z P. Polarized immune responses modulated by layered double hydroxides nanoparticle conjugated with CpG. Biomaterials. 2014; 35:9508-16.
[37] Rosalia R A, Cruz U, van Duikeren S, Tromp A T. Silva A L, Jiskoot W, et al. CD40-targeted dendritic cell delivery of PLGA-nanoparticle vaccines induce potent anti-tumor responses. Biomaterials. 2015; 40:88-97. [38] Chen M C, Sonaje K, Chen K J, Sung H W. A review of the prospects for polymeric nanoparticle platforms in oral insulin delivery. Biomaterials. 2011; 32:9826-38.
[39] Mandai B, Bhattacharjee H, Mittal N, Sah H, Balabathula P, Thoma L A, et al. Core-shell-type lipid-polymer hybrid nanoparticles as a drug delivery platform. Nanomed-Nanotechnol. 2013; 9:474-91.
[40] Grobmyer S R, Zhou G V, Gutwein L G, Iwakuma N, Sharma P, Hochwald S N. Nanoparticle delivery for metastatic breast cancer. Nanomed-Nanotechnol. 2012; 8:S21-S30.
[41] Park K. Controlled drug delivery systems: Past forward and future back. J Control Release. 2014; 190:3-8. [42] Zhang L F, Granick S. How to stabilize phospholipid liposomes (using nanoparticles). Nano Lett. 2006; 6:694-8.
[43] Zhao P F, Zheng M B, Vue ex, Luo Z V, Gong P, Gao G H, et al. Improving drug accumulation and photothermal efficacy in tumor depending on size of ICG loaded lipid-polymer nanoparticles. Biomaterials. 2014; 35:6037-46.
[44] Mueller M, Reichardt W, Koerner J, Groettrup M. Coencapsulation of tumor lysate and CpG-ODN in PLGA-microspheres enables successful immunotherapy of prostate carcinoma in TRAMP mice. J Control Release. 2012; 162:159-166.
[45] Wang Q, Tan M T, Keegan B P, Barry M A, Heffernan M J. Time course study of the antigen-specific immune response to a PLGA microparticle vaccine formulation. Biomaterials. 2014; 35:8385-93.
[46] Shen K Y, Liu H Y, Li H J, Wu C C, Liou G G, Chang Y C, et al. A novel liposomal recombinant lipoimmunogen enhances anti-tumor immunity. J Control Release. 2016; 233:57-63.
[47] Nakazawa T, Nagatsuka S, Yukawa O. Effects of Membrane Stabilizing Agents and Radiation on Liposomal Membranes. Drug Exp Clin Res.1986; 12:831-5.
[48] Ibricevic A, Guntsen S P, Zhang K, Shrestha R, Liu Y J, Sun J Y, et al. PEGylation of cationic, shell-crosslinked-knedel-like nanoparticles modulates inflammation and enhances cellular uptake in the lung. Nanomed-Nanotechnol. 2013; 9:912-22.
[49] Pelaz B, del Pino P, Maffre P, Hartmann R, Gallego M, Rivera-Fernandez S, et al. Surface Functionalization of Nanoparticles with Polyethylene Glycol: Effects on Protein Adsorption and Cellular Uptake. Acs Nano. 2015; 9:6996-7008.
[50] Mickler F M, Vachutinsky Y, Oba M, Miyata K, Nishiyama N, Kataoka K, et al. Effect of integrin targeting and PEG shielding on polyplex micelle internalization studied by live-cell imaging. J Control Release 2011; 156:364-73.
[51] Moser M, Murphy K M. Dendritic cell regulation of TH1-TH2 development. Nat Immunol. 2000; 1:199-205.

Example 2

Introduction

Tobacco smoking remains the leading cause of preventable diseases and premature deaths; it is responsible for nearly 6 million deaths and huge economic losses each year worldwide. [1, 2] Despite the use of pharmacological treatments, e.g., nicotine replacement therapy and nicotine agonists/antagonists, only a small percentage of treated smokers (10-25%) will successfully quit smoking in the end. [3-5] Therefore, more efficient approaches are needed to combat tobacco addiction.

Nicotine vaccines that induce the production of antibodies that specifically bind to nicotine in serum, thereby blocking its entrance into the brain, have been presented as an attractive strategy to treat nicotine addiction. [6, 7] In the past decades, many nicotine vaccines were reported to achieve high immunogenicity and pharmacokinetic efficacy in preclinical trials. [8-11] However, all human clinical trials of conjugate nicotine vaccines to date have not achieved the expected efficacies. [12] The phase 2 clinical studies of NicVax and NicQβ revealed that while the overall smoking cessation rate was not enhanced compared to the placebo group, the top 30% of subjects that had the highest antibody titers showed improved quit rate. [13, 14]. This indicates the need for inducement of more antibodies to generate vaccination efficacy. Though multiple approaches have been explored to strengthen their immunogenicity—including the design of hapten structure, [15, 16] modulation of linker position and composition, [8] selection of carrier proteins, [10] use of different adjuvants, [17] application of multivalent vaccines, [18-21] and optimization of administration routes [22]—traditional conjugate nicotine vaccines still suffer from several shortcomings. These shortcomings include poor recognition and internalization by immune cells, fast degradation, difficulty in integration with molecular adjuvants, and short immune persistence, all of which limit the immunogenic outcomes. [23]

Figure 24:
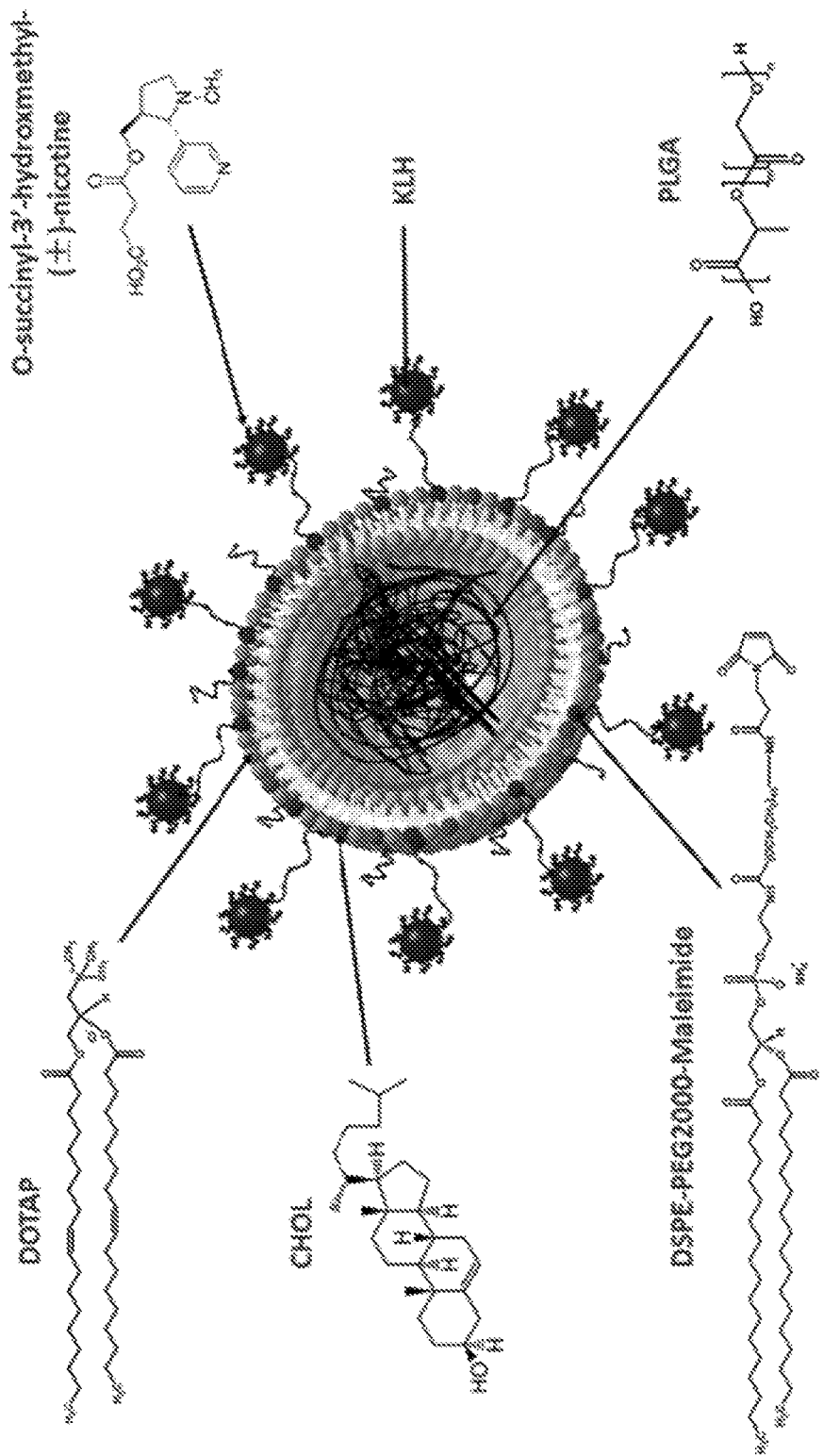
FIG. 24 shows a schematic illustration of the structure of nanovaccine NPs. PLGA NP serves as a scaffold that is capable of supporting the outside lipid layer and stabilizing the vaccine delivery system. The DSPE-PEG2000-Maleimide component of the lipid layer enables the association of carrier protein (KLH) onto the surface of lipid-PLGA NPs. Nic-haptens are conjugated to KLH to be immunogenic.

This Example demonstrates aspects of a lipid-poly(lactic-co-glycolic acid) (lipid-PLGA) hybrid nanoparticle (NP)-based nicotine vaccine to improve the immunogenicity of the conjugate nicotine vaccine. As shown in FIG. 24, multiple hapten-protein conjugates were conjugated to the surface of one hybrid NP to form the NP-based nanovaccine. Considering that hapten density may play an important role in the recognition of nanovaccine particles by immune cells, we also investigated the influence of hapten density on the immunogenicity of the nicotine nanovaccines. Various nanovaccine NPs with different hapten density were fabricated and characterized in terms of physicochemical properties and epitope density. The in vitro uptake of hapten-protein conjugate and nanovaccine particles was studied in immature dendritic cells. The immunogenicity and pharmacokinetic efficacy of three nanovaccines representing the low-, medium-, and high-hapten density were tested in mice. Finally, the safety of the nanovaccines was evaluated by histopathological analysis.

Materials and Methods

Materials

Lactel® 50:50 PLGA was purchased from Durect Corporation (Cupertino, Calif., USA). 2,4,6-trinitrobenzenesulfonic acid (TNBSA) was purchased from Thermo Fisher Scientific Inc. (Rockford, Ill., USA). 1,2-Dioleoyl-3-trimethylammonium-propane (DOTAP), cholesterol (CHOL), 1,2-distearoyl-sn-glycero-3-phosphoethanolamine-N-[maleimide(polyethylene glycol)-2000] (ammonium salt) (DSPE-PEG2000-maleimide), and 1,2-diphytanoyl-snglycero-3-phosphoethanolamine-N-(7-nitro-2-1,3-benzoxadiazol-4-yl) (ammonium salt) (NBD-PE) were purchased from Avanti Polar Lipids Inc. (Alabaster, Ala., USA). Nic-hapten was purchased from Toronto Research Chemicals (North York, ON, Canada). All other chemicals were of analytical grade.

Preparation of Lipid-PLGA NPs

PLGA NPs were prepared using a double emulsion solvent evaporation method. In brief, 50 mg of PLGA was dissolved in 2 mL of dichloromethane (oil phase). Two hundred µL of ultrapure water was added to the oil phase and mixed by vortex. The mixture was emulsified by sonication for 10 min using a Branson M2800H Ultrasonic Bath sonicator (Danbury, Conn., USA). The resultant primary emulsion was added dropwise to 12 mL of 0.5% w/v poly(vinyl alcohol) solution under continuous stirring. The suspension was emulsified again by sonication using a sonic dismembrator (Model 500; Fisher Scientific, Pittsburgh, Pa., USA) at an amplitude of 70% for 40 s. The resultant secondary emulsion was stirred overnight to allow complete dichloromethane evaporation. PLGA NPs were collected by centrifugation at 10,000 g, 4° C. for 30 min (Beckman Coulter Avanti J-251, Brea, Calif., USA). Pellets were washed three times using ultrapure water. The final suspension was freeze-dried (LABCONCO Freezone 4.5, Kansas City, Mo.), and NPs were stored at 2° C. for later use. Lipid-PLGA NPs were assembled using a film-hydration-sonication method as described previously. [40] In brief, 15 mg of lipid mixture dissolved in chloroform consisting of DOTAP, DSPE-PEG2000-maleimide, and CHOL was evaporated to form a lipid film. One and a half mL of pre-heated 0.01 M PBS (pH 7.4, 60° C.) was added to hydrate the lipid film. The resultant suspension was mixed vigorously and cooled down to room temperature, followed by sonication for 5 min in a Branson M2800H Ultrasonic Bath sonicator. Fifteen mg of PLGA NPs suspended in DI water (10 mg/ml) was added and mixed with the above liposome suspension. Subsequently, the mixture was sonicated in an ice-water bath using a bath sonicator for 5 min. Lipid-PLGA NPs were collected by centrifugation at 10,000 g, 4° C. for 30 min, freeze-dried, and stored at 2° C. for later use.

Assembly of Nicotine Vaccine NPs with Different Hapten Densities

Nic-KLH conjugates were synthesized using a carbodiimide-mediated reaction. In brief, Nic-hapten of various equivalents of KLH was mixed with appropriate amounts of EDC and Sulfo-NHS in activation buffer (0.1 M MES, 0.5 M NaCl, pH 6.0) and incubated at room temperature for 15 min. The mixture was added to 5 mg of KLH, which was dissolved in coupling buffer (0.1 M sodium phosphate, 0.15 M NaCl, pH 7.2). After the overnight reaction, unconjugated Nic-hapten and byproducts were eliminated by dialyzing against 0.01 M PBS (pH 7.4) at room temperature for 24 h. The number of Nic-haptens on Nic-KLH was determined by measuring the difference in the number of remaining lysine groups on the surface of KLH before and after hapten conjugation using a TNBSA based method. In brief, KLH and Nic-KLH conjugates were prepared at a concentration of 1 mg/mL. Two hundred µL of the protein solution was taken and mixed with 200 µL of 4% $NaHCO_3$ solution. Two hundred µL of 0.1% TNBSA solution was added to the mixture and incubated at 37° C. for 1 h, and the absorbance was read at 335 nm. Hapten density of KLH was calculated from the differences between the O.D. of the control and the conjugates.

Nanovaccine NPs were assembled by attaching Nic-KLH conjugates onto the surface of lipid-PLGA hybrid NPs via a thiol-maleimide-mediated method. In brief, an appropriate amount of Traut's reagent was added to 3 mg of Nic-KLH, which was dissolved in 0.1 M pH 8.0 bicarbonate buffer and incubated for 1 h. Nic-KLH was attached to lipid-PLGA NPs by reacting to the thiolated Nic-KLH with the appropriate amount of lipid-PLGA NPs in 0.1 M pH 8.0 bicarbonate buffer for 2 h. NPs were collected by centrifugation at 10,000 g, 4° C. for 30 min. Unattached Nic-KLH in the supernatant was quantified by the BCA assay. The lipid layer of hybrid NPs was labeled by NBD-PE, and the number of lipid-PLGA NPs was counted by flow cytometry. Hapten density (number of haptens per NP) was approximated by the following formula, $D_{nic} = (AF_{Nic-KLH} * M_{Nic-KLH} * D_{Nic-KLH} * N_A)/N_{NPs}$, where $D_{nic}$, $AF_{Nic-KLH}$, $M_{Nic-KLH}$, $D_{Nic-KLH}$, $N_A$, and $N_{NPs}$ represent hapten density per NP, Nic-KLH association efficiency, moles of KLH associated on 1 mg of NPs, hapten density of Nic-KLH, Avogadro constant, and NP number per 1 mg of NPs, respectively. Vaccine NPs were lyophilized and stored at 2° C. for later use.

Characterization of NPs

The successful assembly of nanovaccine NPs was validated using CLSM. Fluorescent vaccine NPs—in which the lipid layer, PLGA layer, and KLH were labeled by Nile red, NBD, and AF350, respectively—were prepared according to a similar method as described above with minor modifications. In brief, PLGA NPs containing Nile red were fabricated by a double emulsion solvent evaporation method, wherein the appropriate amount of Nile red was dissolved in the oil phase. The lipid layer was labelled by adding 5% w/w of NBD-PE into the lipid mixture. AF350 was conjugated to KLH through an EDC-mediated reaction. NPs were imaged by a Zeiss LSM 510 Laser Scanning Microscope (Carl Zeiss, German).

The morphology of NPs was studied using TEM. NP samples were negatively stained for 60 s using freshly prepared 1% phosphotunstic acid. The processed NP samples were imaged on a JEOL JEM 1400 Transmission Electron Microscope (JEOL Ltd., Tokyo, Japan).

The physicochemical properties of NPs, including particle size and zeta potential, were measured by the Dynamic Light Scattering method and Laser Doppler Micro-electrophoresis method, respectively. NPs that were suspended in ultrapure water (1 mg/mL) were analyzed on a Malvern Nano ZS Zetasizer (Malvern Instruments Ltd, Worcestershire, United Kingdom).

Cellular Uptake of Vaccine Particles by Dendritic Cells (DCs)

The uptake of vaccine particles by DCs was quantitatively measured by flow cytometry. AF647, a model of Nichapten, was used instead of Nic-hapten to prepare vaccine particles in order to provide fluorescence. JAWSII (ATCC® CRL-11904™) immature DCs were cultured in alpha minimum essential medium (80% v/v) supplemented with ribonucleosides, deoxyribonucleosides, 4 mM L-glutamine, 1 mM sodium pyruvate, 5 ng/mL murine GM-CSF, and fetal bovine serum (20% v/v) at 37° C., 5% $CO_2$. Cells were seeded into 24-well plates at a concentration of $2 \times 10^6$/well and cultured for 24 h. The original medium was replaced with fresh medium containing various vaccine particles. After incubation for 2 h, the medium was immediately removed, and the cells were washed three times with 0.01 M pH 7.4 PBS. Cells were detached from the culture plates using Trypsin/EDTA solution and centrifuged at 200 g for 10 min. Cell pellets were re-suspended in 0.01 M pH 7.4 PBS. Samples were immediately analyzed on a flow cytometer (BD FACSAria I, BD, Franklin Lakes, N.J., USA).

The uptake and intracellular distribution of vaccine particles were qualitatively determined by CLSM. Cells were seeded into a 2-well chamber slide at a concentration of $2 \times 10^5$/chamber, and cultured overnight. The original medium was replaced with 2 mL of fresh medium containing various vaccine particles. After incubation for 2 h, the medium was discarded, and the cells were washed three times using 0.01 M pH 7.4 PBS. One mL of freshly prepared 4% (w/v) paraformaldehyde was added to each well to fix the cells for 15 min. The fixed cells were washed three times with PBS and were made permeable by adding 0.5 mL of 0.1% (v/v) Triton™ X-100 for 15 min. After washing the cells three times again using PBS, the nuclei of cells were stained with DAPI. The intracellular distribution of NPs was visualized on a Zeiss LSM 510 Laser Scanning Microscope.

Immunization of Mice with Nicotine Vaccines

All animal studies were carried out following the National Institutes of Health (NIH) guidelines for animal care and use. Female Balb/c mice (6-7 weeks of age, 16-20 g, 8 per group) were immunized subcutaneously on Days 0, 14, and 28 with vaccines of negative control (KLH associated lipid-PLGA NPs), Nic-KLH with alum, low-density nanovaccine, low-density nanovaccine with alum, medium-density nanovaccine, medium-density nanovaccine with alum, high-density nanovaccine, and high-density nanovaccine with alum. For vaccine groups without alum adjuvant, the mice were injected with vaccine particles (containing 25 μg of protein antigen) that were suspended in 200 μL of 0.01 M pH 7.4 PBS. In the vaccine with alum adjuvant groups, the mice were injected with vaccine particles (containing 25 μg of protein antigen) that were suspended in 100 μL of PBS and mixed with 100 μL of alum (10 mg/mL), and the mixture was used to immunize mice. Blood samples were collected on Days 0, 12, 26, 40, and 54.

Measurement of Nicotine-Specific IgG Antibodies (NicAb) Titer, Nicotine-Specific IgG Subclass Antibody Titer, and Anti-Carrier Protein Antibody Titer.

The NicAb titers in serum were determined by ELISA as described previously. [37] Titers of IgG subclasses were measured using the similar ELISA protocol, except that anti-mouse IgG1 HRP, IgG2a HRP, IgG2b HRP and IgG3 HRP were used as the secondary antibodies. The Th1/Th2 indexes were calculated according to the formula, Th1/Th2 index=(IgG3+IgG2a)/2IgG1. Anti-KLH antibody titers were measured using a similar ELISA protocol as that used for anti-nicotine specific antibody measurement, except that KLH was used as the coating material. Antibody titer was defined as the dilution factor at which absorbance at 450 nm declined to half maximal.

Pharmacokinetic Study in Mice

Female Balb/c mice (6-7 weeks of age, 16-20 g, 4-5 per group) were immunized with the same protocol as described in the previous context. On Day 54, mice were administrated with 0.03 mg/Kg nicotine subcutaneously. Mice were euthanized under anesthesia 4 min after nicotine challenge, and the blood and brain were collected. Nicotine contents in serum and brain tissues were analyzed by GC/MS according to a method reported previously. [19]

Preliminary Evaluation of Nanovaccine Safety

The safety of the nicotine nanovaccines was preliminarily evaluated in mice by monitoring the body weight change and histopathological analysis. To investigate the body weight change during the study, mice were weighed before primary immunization and once a week after that. Histopathological analysis of tissues from immunized mice, including heart, kidney, liver, spleen, and stomach, was performed to examine the lesions caused by the administration of nanovaccine NPs. In brief, different mouse organs were fixed with 10% formalin, followed by cutting the organs according to a standard protocol. Tissue blocks were then embedded in paraffin, and the routine sections were stained with hematoxylin and eosin. The stained sections were imaged on a Nikon Eclipse E600 light microscope, and pictures were captured using a Nikon DS-Fi1 camera.

Statistical Analysis

Comparison between two groups was performed by unpaired student's t-test. Comparisons among multiple groups were conducted by one-way ANOVA followed by Tukey's HSD analysis. Differences were considered significant at p-values less than 0.05.

Results

Validation of the Conjugate Chemistry and Characterization of the Structure of Nanovaccine NPs The nanovaccine NPs assembled in this study are supposed to have a structure composed of a PLGA core, a lipid shell, and multiple O-succinyl-3'-hydroxymethyl-(±)-nicotine (Nic)-keyhole limpet hemocyanin (KLH) conjugates. Confocal laser scanning microscopy (CLSM) was applied to characterize the nanovaccine structure and verify the conjugate chemistry of hapten. The PLGA, lipid, and KLH layers were labeled with Nile Red, NBD, and AF350 fluorescence, respectively. As shown in FIGS. 25A-25D, almost all the particles were co-labeled with the three fluorescence, indicating that lipids were successfully coated around PLGA NPs to form a hybrid coreshell structure, and KLH was associated to the surface of NPs with very high efficiency. Meanwhile, AF350 was a model of Nic-hapten, having similar size and the same reactive group (NHS ester). In this study, Nic-hapten was attached to KLH by the EDC/NHS-mediated conjugate chemistry, in which the carboxylic groups of Nic were activated by EDC/NHS to form semi-stable Nic-NHS esters that could readily react with the amino groups of KLH. AF350 was conjugated to KLH efficiently, validating the feasibility of the hapten conjugate chemistry.

Figure 26B:
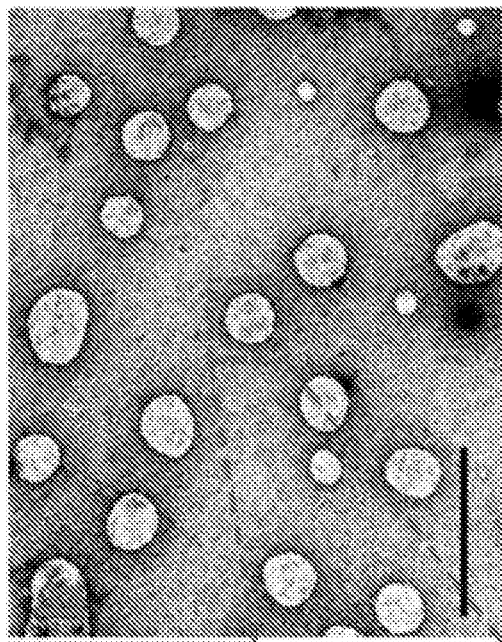
FIGS. 26A-26D show TEM images of PLGA NPs (FIG. 26A), liposome NPs (FIG. 26B), lipid-PLGA hybrid NPs (FIG. 26C), and nanovaccine NPs (FIG. 26D), which demonstrate the morphological properties of NPs involved in the preparation of nanovaccine NPs. Scale bars in all the TEM images represent 200 nm.
Figure 26D:
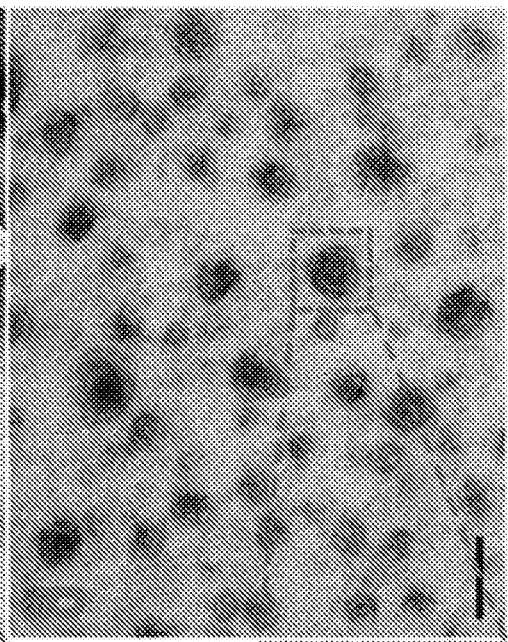
Figure 26A:
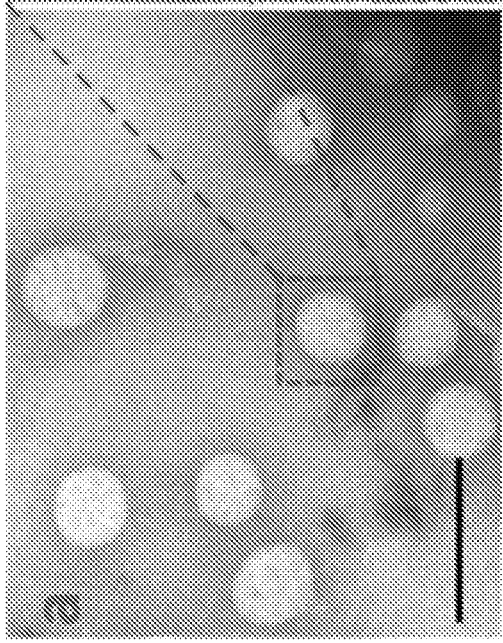
Figure 26C:
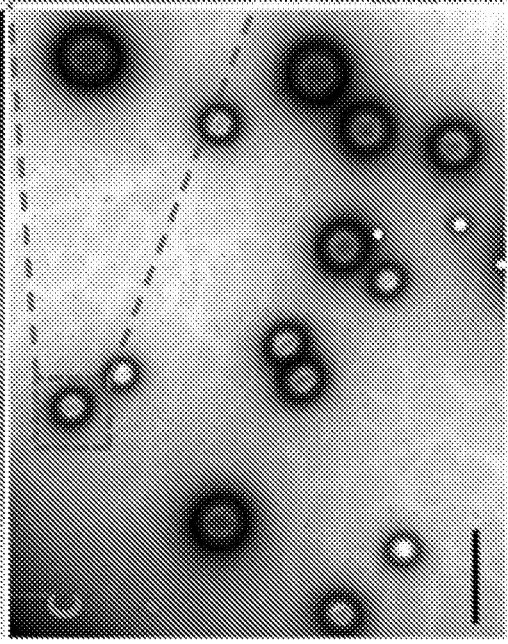
Figure 27:
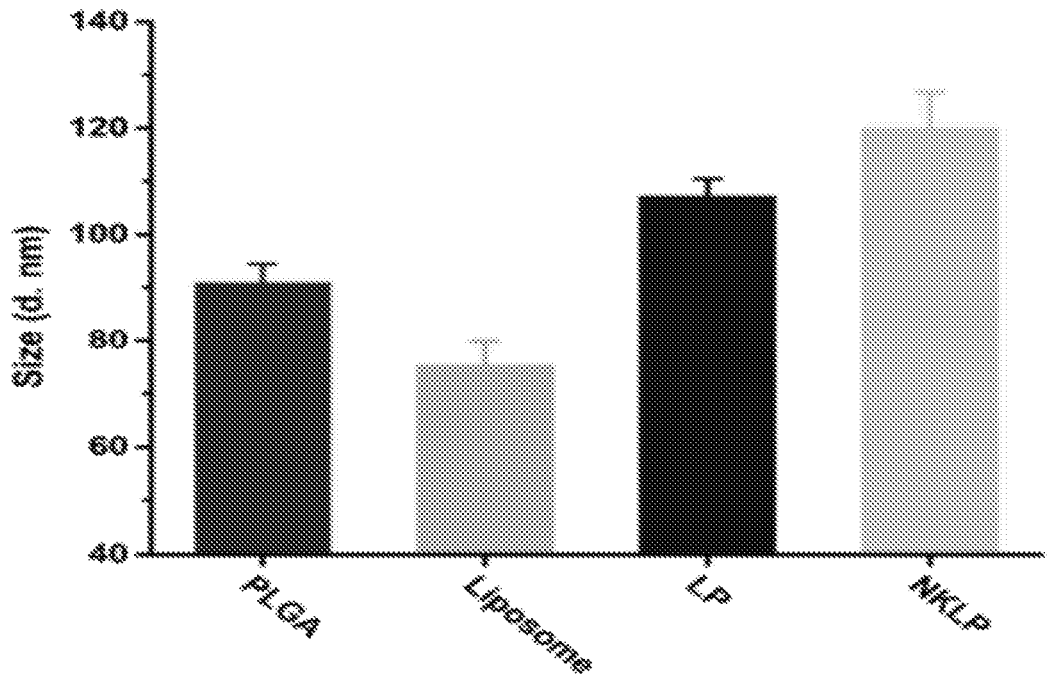
FIG. 27 shows a graph demonstrating the average size of the NPs shown in FIGS. 26A-26D.
Figure 28:
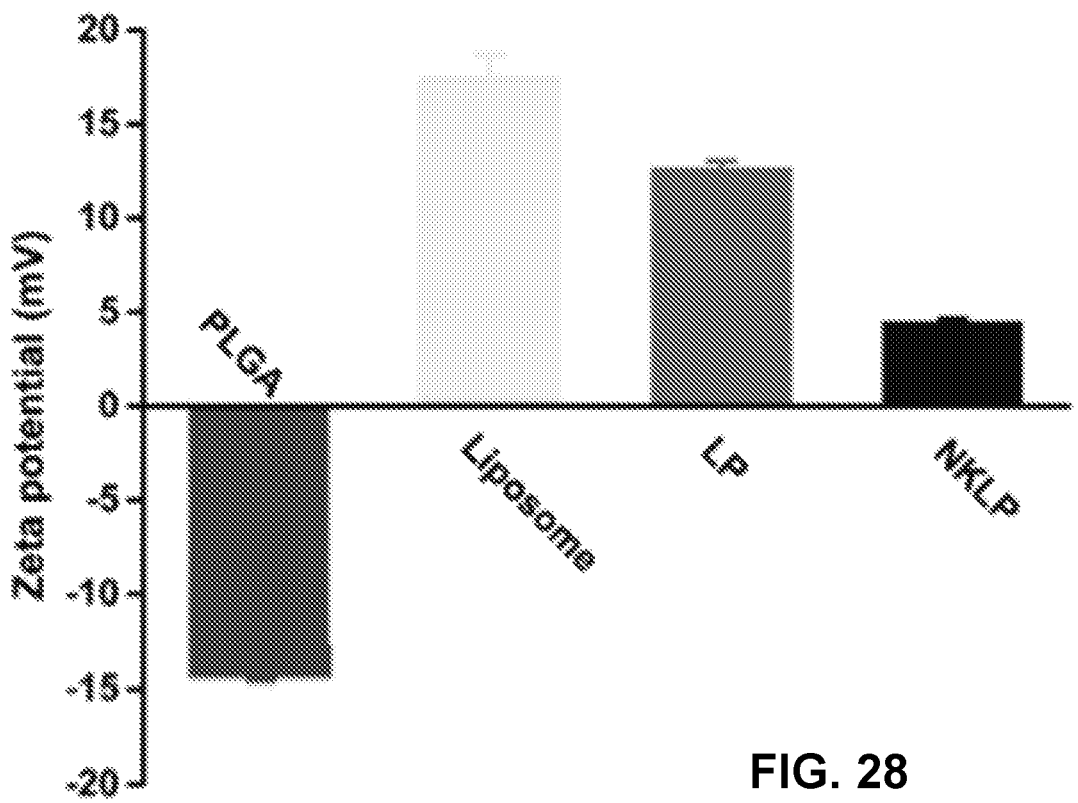
FIG. 28 shows a graph demonstrating the zeta potential of the NPs shown in FIGS. 26A-26D.

The structure of the nanovaccine NPs was further investigated using transmission electron microscopy (TEM). FIGS. 26A-26D shows the TEM images exhibiting the morphology of PLGA NPs, liposomes, lipid-PLGA hybrid NPs, and nanovaccine NPs. All four NPs were of spherical shapes. A distinguishing core-shell structure, which was shown as a bright PLGA core and a dark lipid shell, was observed on Lipid-PLGA NPs (FIG. 26C), indicating the successful coating of lipids onto PLGA NPs. As shown in FIG. 26D, multiple black dots, which were Nic-KLH conjugates, were located on the surface of hybrid NPs, confirming the efficient association of Nic-KLH. KLH is a large carrier protein that is composed of KLH1 and KLH2 subunits, both of which are around 400 kDa. [27] The large size makes it visible in the TEM images. The average size of NPs increased from 90.8 nm to 107.0 nm upon lipid coating and further increased to 121.3 nm after Nic-KLH associating (FIG. 27). The zeta potential of NPs changed from −14.3 mV of PLGA NPs to 12.6 mV of Lipid-PLGA NPs and then to 4.16 mV of nanovaccine NPs (FIG. 28), as the liposome is positively charged (FIG. 28) and Nic-KLH is negatively charged (data not shown).

Preparation and Characterization of Nanovaccines with Different Hapten Density

Figure 29:
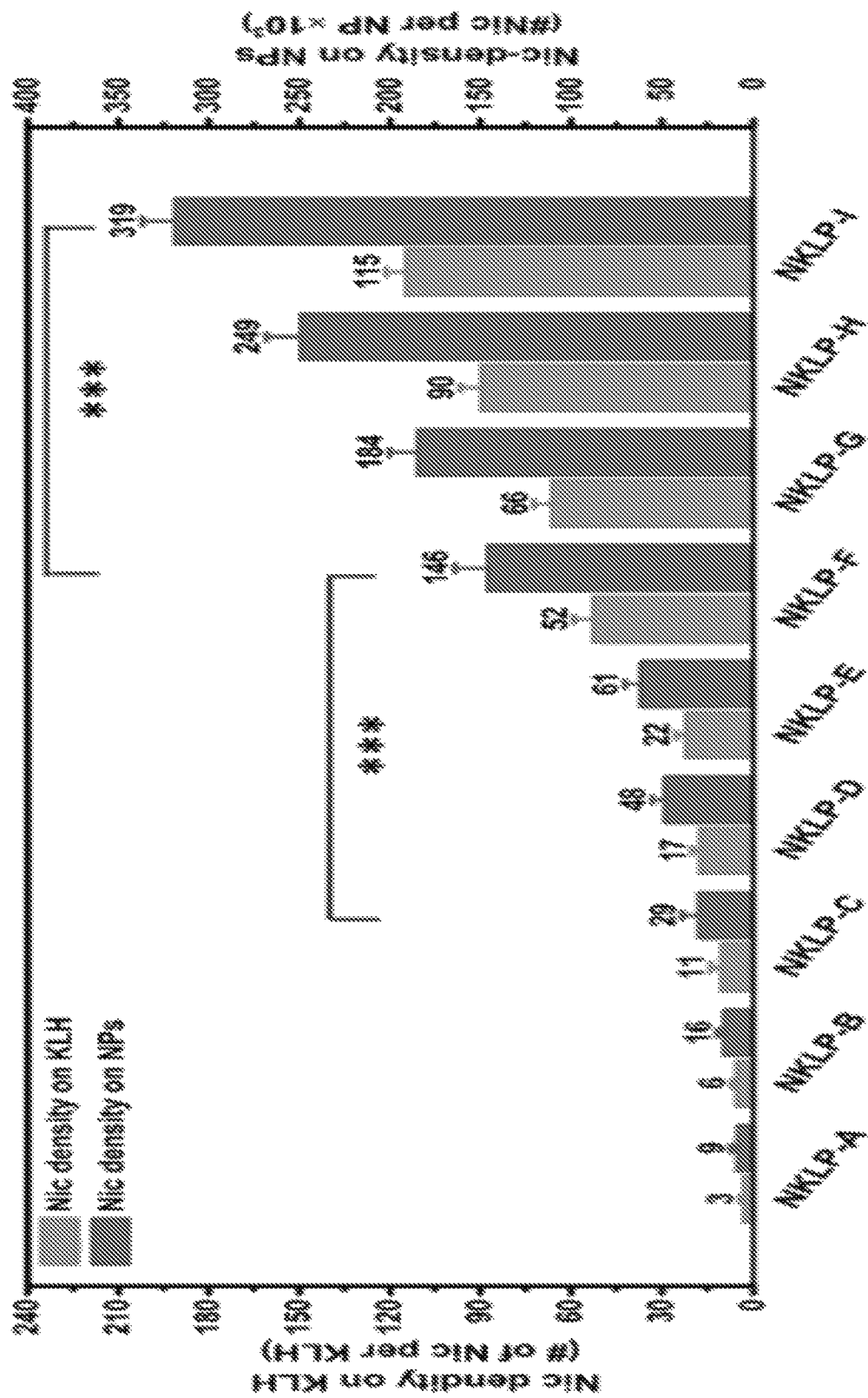
FIG. 29 shows a graph demonstrating the hapten density of different nanovaccines, which were prepared using various molar ratios of Nic-hapten to KLH. *** indicates hapten density on NPs are significantly different (p-value <0.001). NKLP-A, B, C, D, E, F, G, H, I represent nanovaccines which were prepared using increased Nic/KLH molar ratios.

Various molar excess of Nic-hapten to KLH was applied for the conjugating reaction of hapten on KLH. The hapten density of the prepared nanovaccines is shown in FIG. 29. The increased hapten density from NKLP-A to NKLP-I verified the feasibility of modulating the Nic hapten density by changing the molar ratios of hapten to KLH in the preparation process. To date, most reported hapten-protein conjugate nicotine vaccines have hapten density ranging from 2 to 100 per monomer protein, [10, 28, 29] depending on the available lysine groups and conjugate chemistry. Each NKLP-C, NKLP-F, and NKLP-I nanovaccine NP carried approximately $29 \times 10^3$, $146 \times 10^3$, and $319 \times 10^3$ Nic haptens, respectively, which correspond to 11, 52, and 115 haptens per KLH; statistical analysis revealed that these three hapten densities are significantly different ($p<0.001$). Thus in this study, NKLP-C, NKLPF, and NKLP-I were selected as low-, medium-, and high-density nanovaccines for in vivo immunogenicity study.

Figure 30:
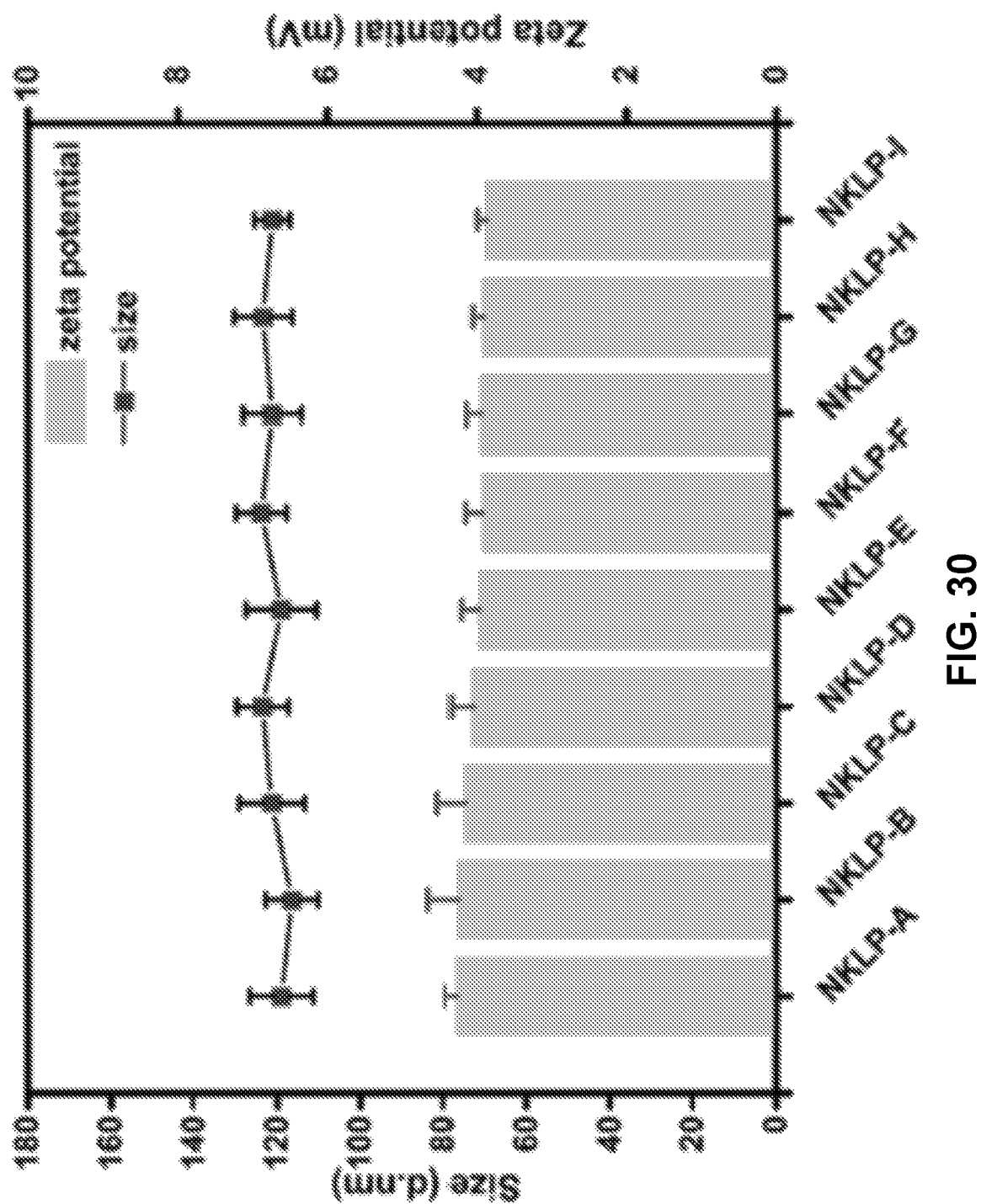
FIG. 30 shows a graph demonstrating the average diameter and zeta potential of various NPs. No significant differences in average size detected for all the nanovaccine NPs with different hapten density. NKLP-A, B, C, D, E, F, G, H, I represent nanovaccines which were prepared using increased Nic/KLH molar ratios.

The physicochemical properties of different hapten density nanovaccines were characterized and shown in FIG. 30 and Table 32. The average zeta potentials of NKLP-C, NKLP-F, and NKLP-I nanovaccine NPs were 4.16 mV, 3.92 mV, and 3.86 mV, respectively. The positively charged surface of nanovaccine NPs will enhance their interaction with the negatively charged surface of immune cells, [30] thereby promoting cellular uptake of the nanovaccines.

Figure 31:
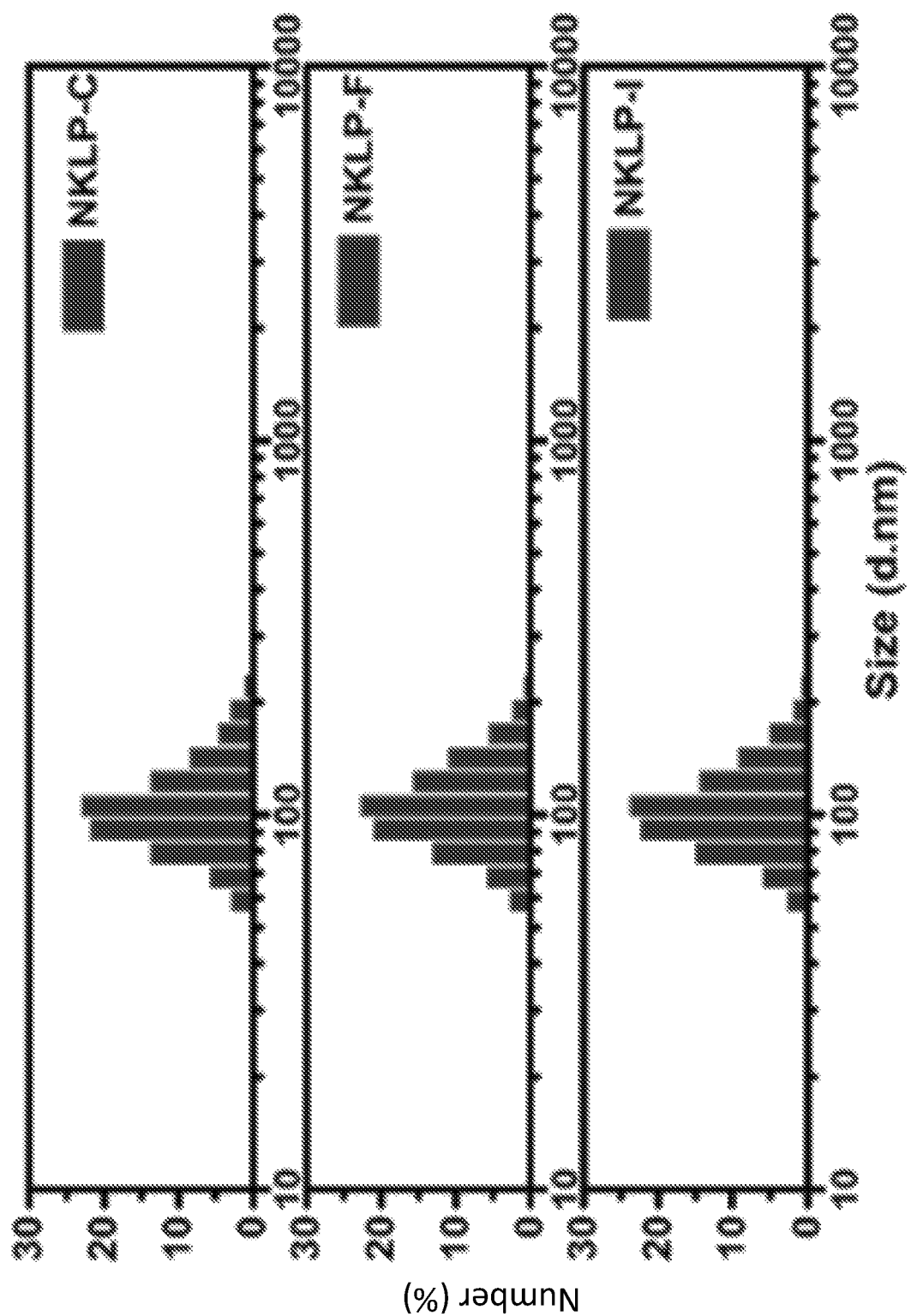
FIG. 31 shows a graph demonstrating the size distribution of three representative nanovaccine NPs used for immunization of mice. NKLP-C, F, I represent nanovaccines which were prepared using increased Nic/KLH molar ratios.
Figure 33:
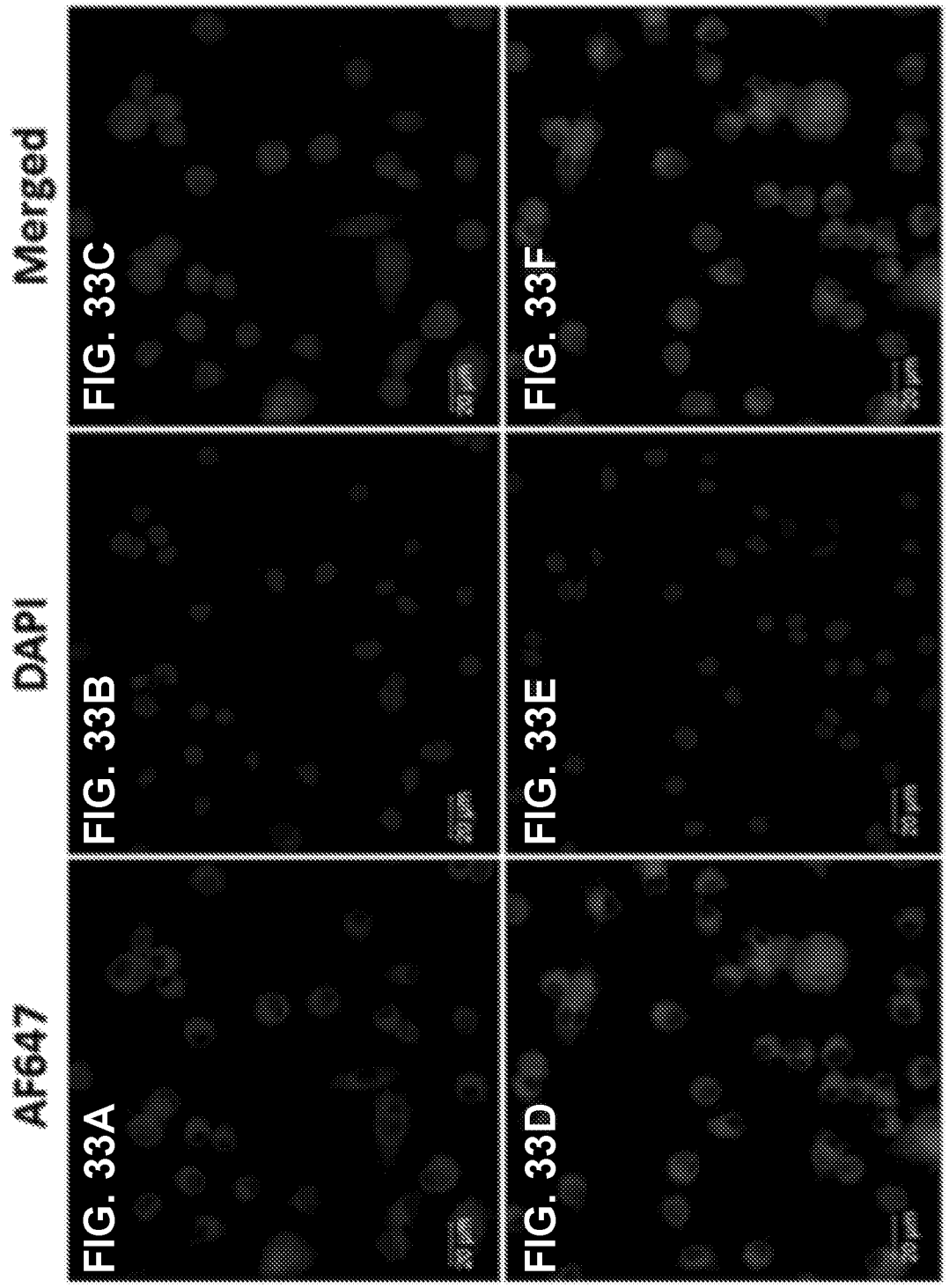
FIGS. 33A-33F shows CLSM images demonstrating the uptake of nanovaccine and conjugate vaccine particles by dendritic cells. AF647 was conjugated to KLH as a model of Nic-hapten. Cells were treated with nanovaccine or conjugate vaccine particles containing equal amounts of KLH for 2 h. Scale bars represent 20 μm.

The average size of NKLP-C, NKLP-F, and NKLP-I was 121.3 nm, 123.8 nm, and 121.2 nm, respectively. According to FIG. 31, all three nanovaccine NPs exhibited narrow size distributions, with most of the NPs less than 200 nm, which were in agreement with the small PDI (0.21-0.24, FIG. 32) and uniform size in the TEM images (FIG. 26D).

It has been reported that size is a critical parameter influencing the efficacy of nanoparticle vaccines. Particles of 20-200 nm will efficiently enter the lymphatic system, while by contrast, particles that are larger than 200-500 nm do not efficiently enter lymph capillaries in a free form. [31-33] The size of the nanovaccines in this study was relatively optimal and will hopefully result in high immunogenicity.

Cellular Uptake of Nanovaccine NPs by Dendritic Cells (DCs)

Figure 34:
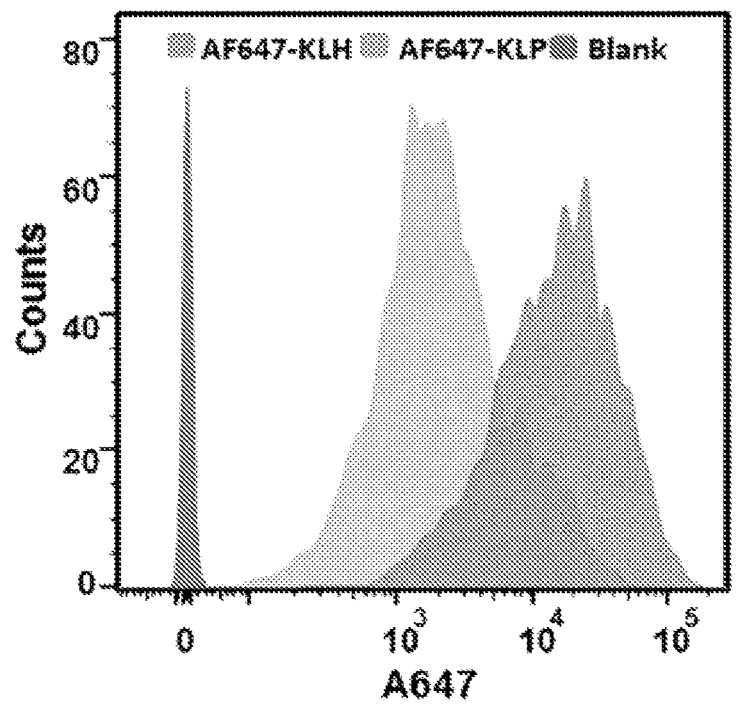
FIG. 34 shows a graph demonstrating a representative intensity distribution of AF647 fluorescence in dendritic cells. AF647 was conjugated to KLH as a model of Nic-hapten. Cells were treated with nanovaccine or conjugate vaccine particles containing equal amounts of KLH for 2 h.
Figure 35:
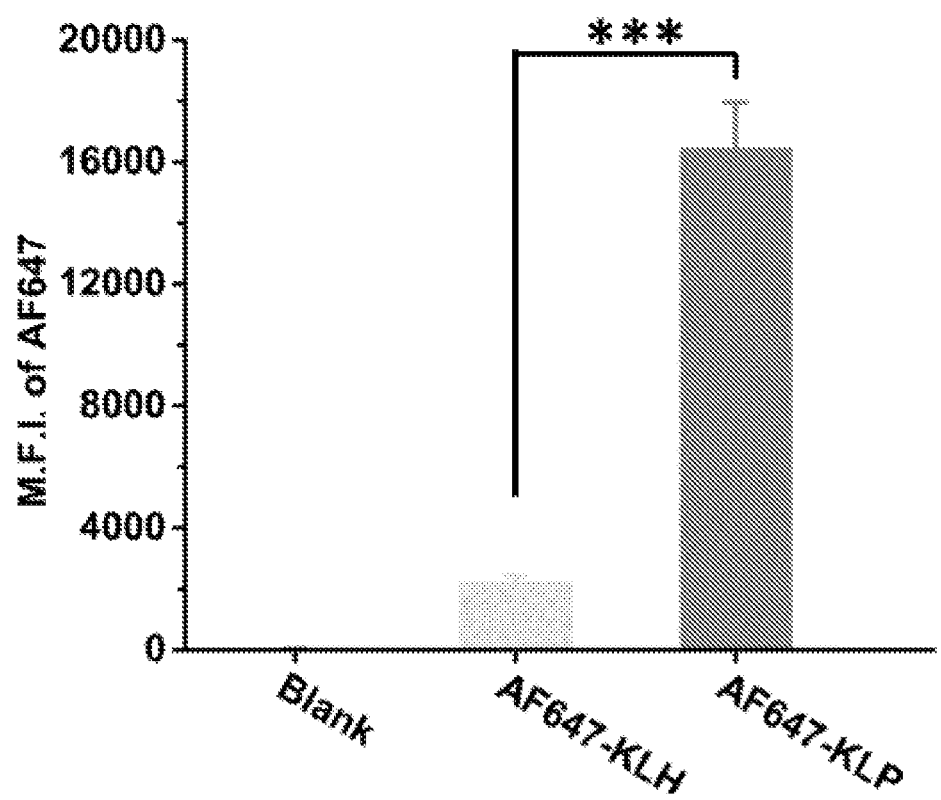
FIG. 35 shows a graph demonstrating the mean fluorescence intensity (M.F.I) of AF647 in cells corresponding to (FIG. 34). *** indicates that AF647 fluorescence intensity was significantly higher in AF647-KLP group than in AF647-KLH group ($p<0.001$). AF647 was conjugated to KLH as a model of Nic-hapten. Cells were treated with nanovaccine or conjugate vaccine particles containing equal amounts of KLH for 2 h.
Figure 36B:
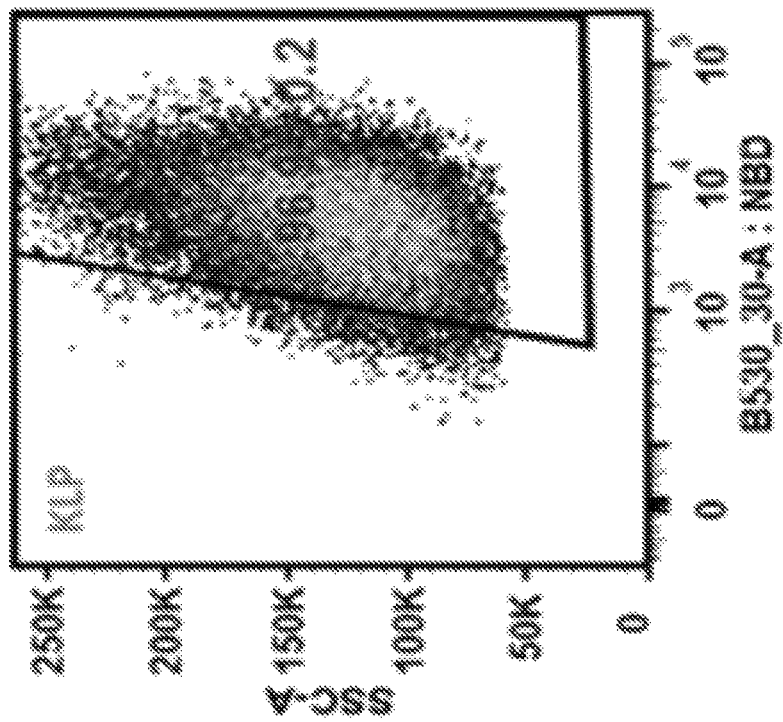
FIGS. 36A-36E show graphs demonstrating recorded events which indicated that most of the studied cells (>95%) had taken up NPs of KLP, NKLP-C, NKLP-F, and NKLP-I, after 2 hours' incubation. The percentages of positive cells are shown overlaid on the graphs. NPs were labeled by adding NBD to the lipid layer, and cells were treated with equal amounts of different hapten density nanovaccine NPs.
Figure 36A:
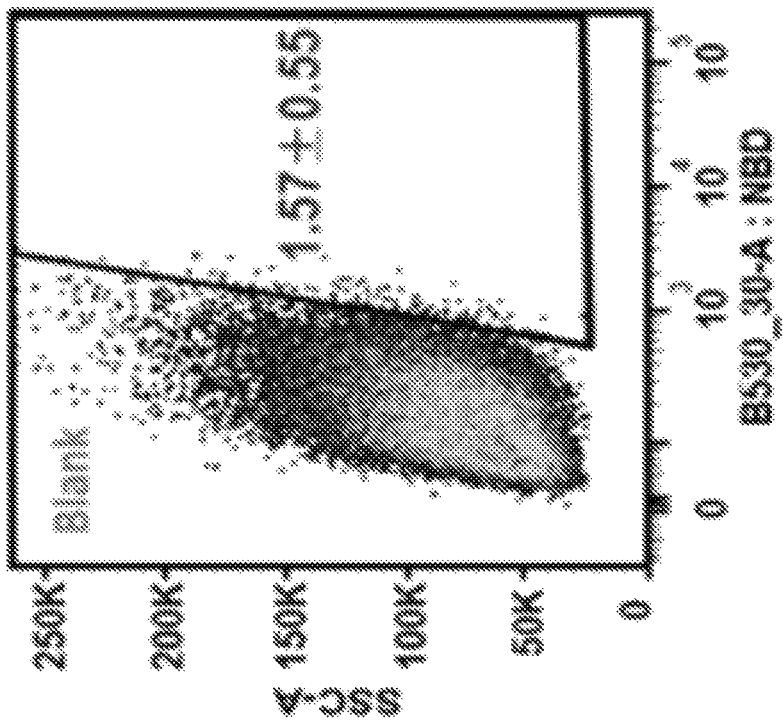
Figure 36D:
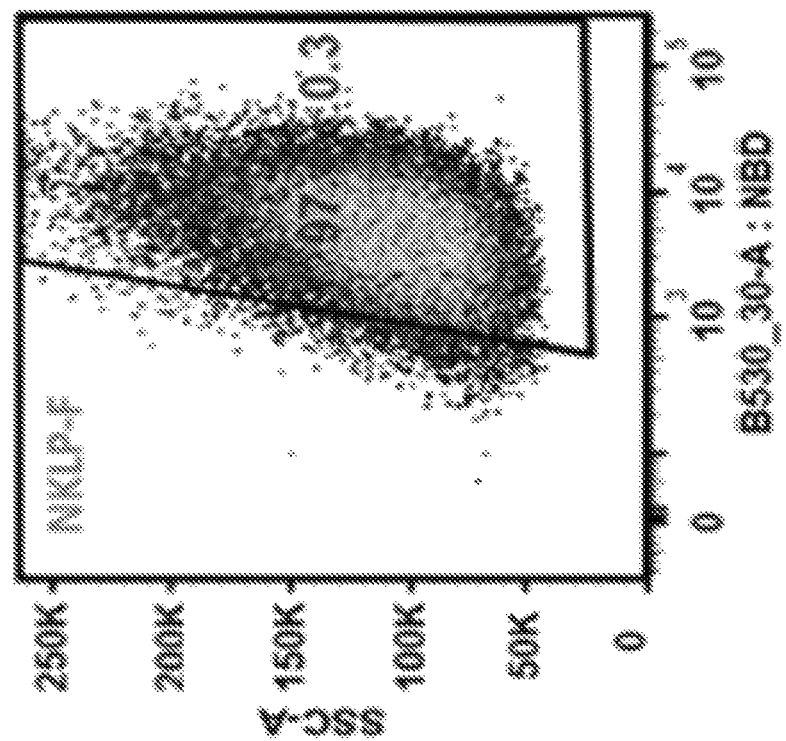
Figure 36C:
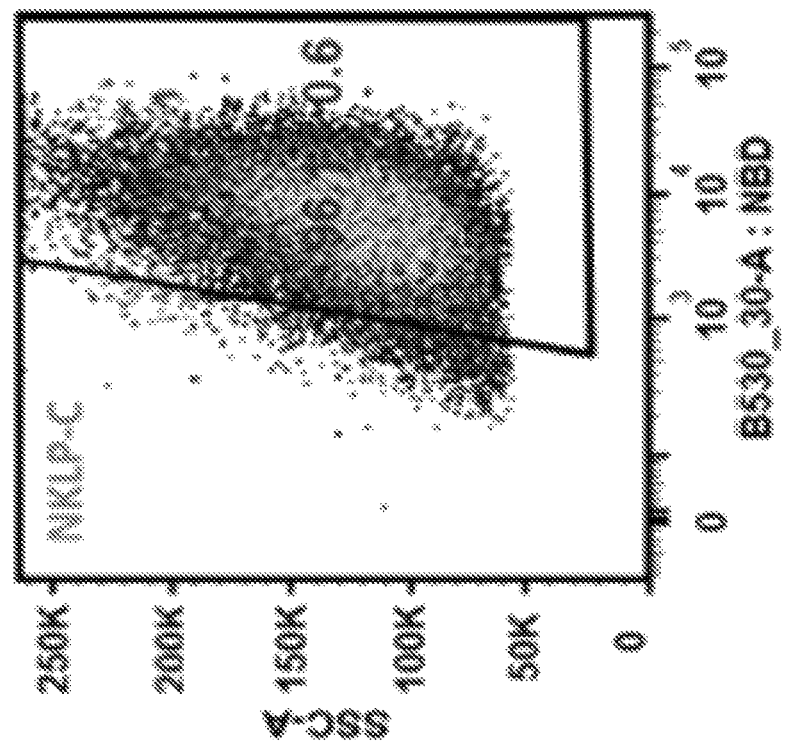
Figure 36E:
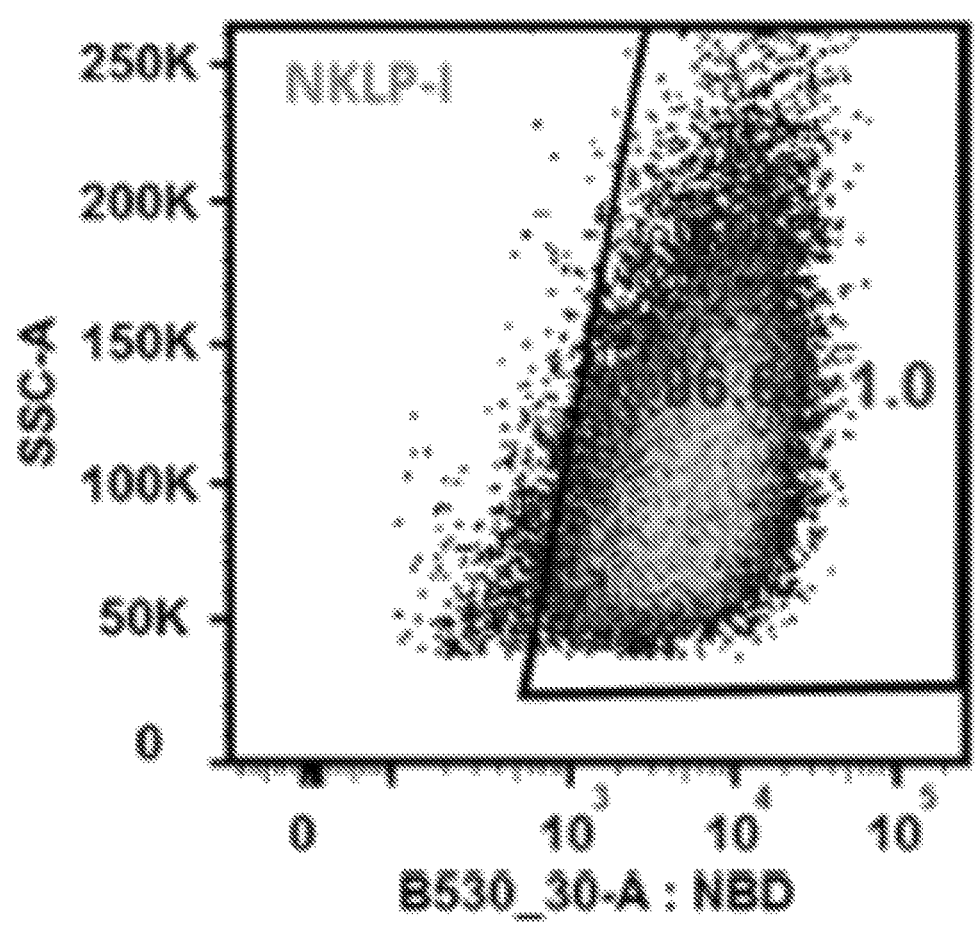

Efficient capture, internalization, and processing of nicotine containing antigens by DCs largely determine the outcomes of vaccination. Traditional nicotine-protein conjugate vaccines suffer from the disadvantage of poor recognition and internalization by immune cells. Here, we compared the uptake of nanovaccine NPs (AF647-KLP) to nicotine-KLH conjugate vaccine particles (AF647-KLH) by DCs. Nic-hapten was substituted by AF647 to render KLH fluorescent, and the density of AF647 on KLH of either AF647-KLH or AF647-KLP was identical. As shown in FIG. 34 and FIG. 35, the mean fluorescence intensity (M.F.I.) of AF647 in the AF647-KLP group was over 500% more than that in the AF647-KLH group, suggesting that more protein antigens were taken up by DCs in the nanovaccine NP group within the same time. The uptake and distribution of particles in DCs were also examined by CLSM. As shown in FIGS. 33A-33F, in agreement with the flow cytometry results, brighter AF647 fluorescence was observed in the AF647-KLP group compared to the AF647-KLH group, indicating again that DCs took up antigens more efficiently when treated with AF647-KLP. The internalization of more protein antigens by DCs enhanced by the lipid-PLGA NP delivery vehicles will benefit many of the immunogenic outcomes of nicotine nanovaccines. The uptake and processing of protein antigens is a critical prerequisite for T helper cell formation, which is necessary for B cell activation in humoral immunity. [23, 34] Therefore, the more protein antigens internalized by DCs, the more T helper cells may be generated, causing more B cells to be activated, and finally leading to a better immunogenic efficacy of nicotine vaccines.

Figure 37:
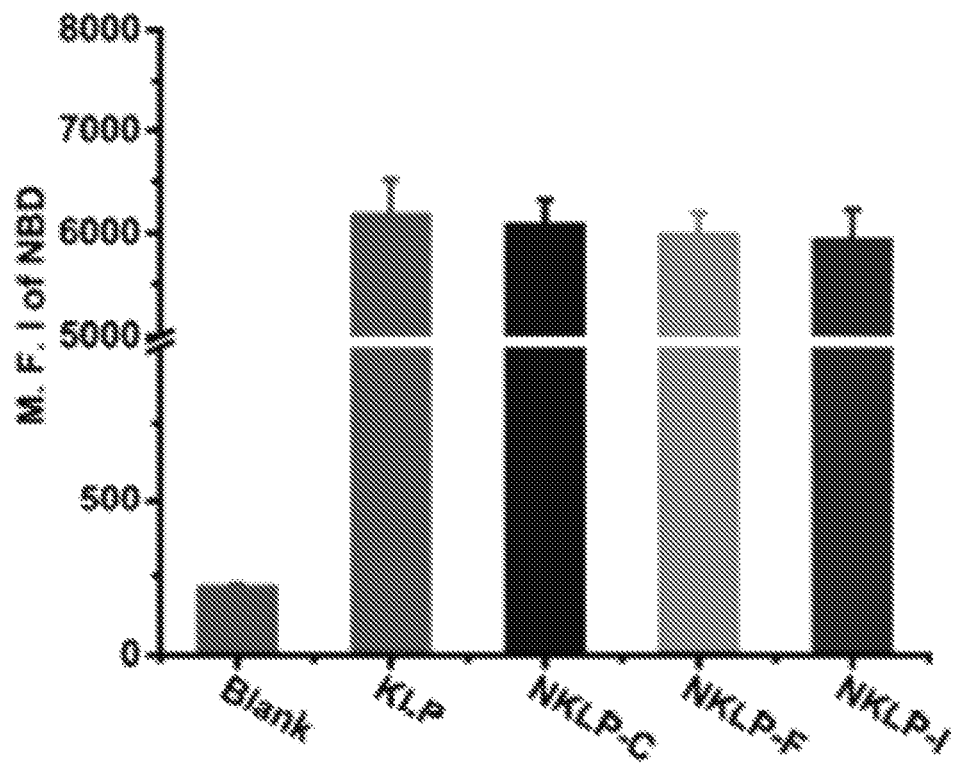
FIG. 37 shows a graph demonstrating M.F.I of AF647 in cells after internalizing NPs for 2 h. NPs were labeled by adding NBD to the lipid layer, and cells were treated with equal amounts of different hapten density nanovaccine NPs.
Figures 38A, 38B:
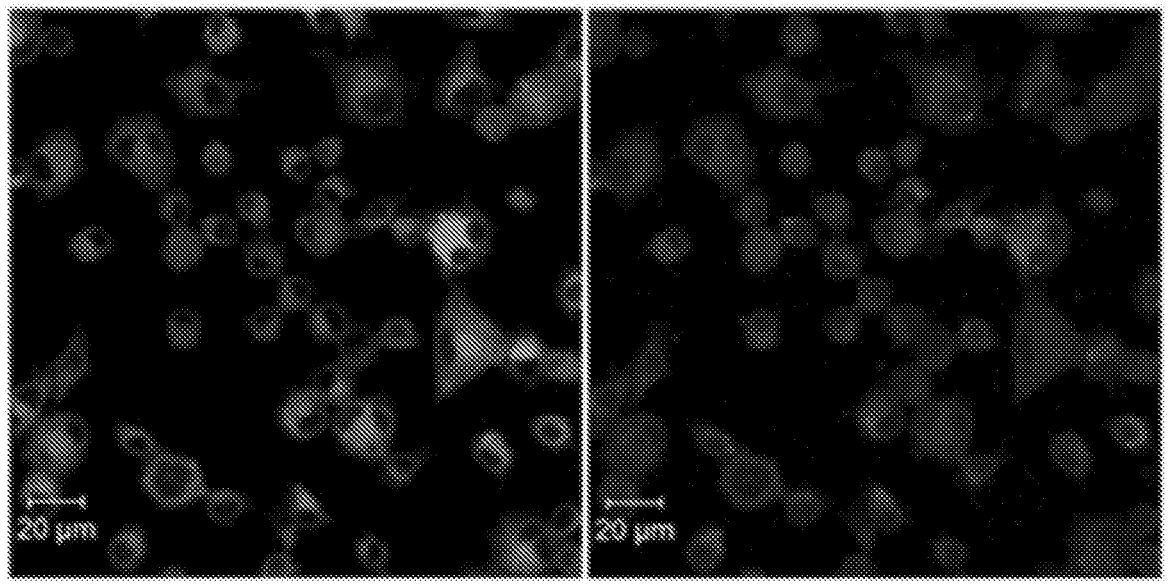
FIGS. 38A-38D show CLSM images of cells treated with fluorescent nanovaccine NPs for 2 h, in which the lipid layer was labeled by NBD and AF647 was used as a model of Nic hapten.
Figures 38C, 38D:
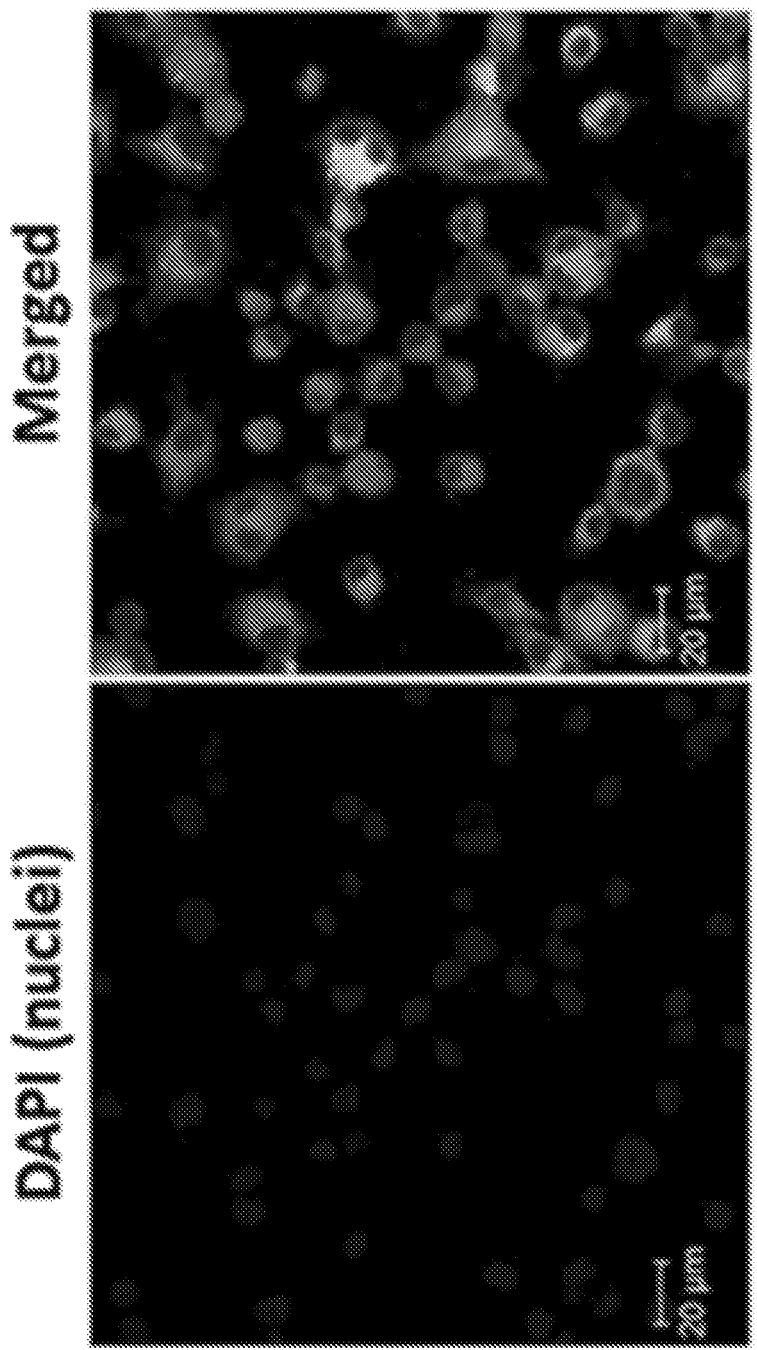

The uptake of different hapten density nanovaccine NPs by DCs was characterized. As shown in FIGS. 36A-36E, for all the nanovaccine groups, including KLP (non-hapten-conjugated nanovaccine), NKLP-C, NKLP-F, and NKLP-1, over 96% of the cells were stained by the NBD fluorescence within 2 h. This demonstrated that all the nanovaccine NPs, regardless of hapten density, were rapidly taken up by dendritic cells. Furthermore, as demonstrated in FIG. 37, the M.F.I. of NBD of blank cells was less than 250, while by contrast, the values were around 6000 for all four nanovaccine groups and no marked difference was detected in terms of NBD fluorescence intensity. This indicated that DCs could take up all different hapten density nanovaccine NPs efficiently, and hapten density would not influence this process discriminately. The uptake of nanovaccine NPs was further confirmed by CLSM, shown in FIGS. 38A-38D, in which the lipid-PLGA NPs and KLH were labeled by NBD and AF647, respectively. Co-localized, bright green and red fluorescence showing simultaneously in all recorded cells verified that the DCs rapidly and efficiently took up the nanovaccine NPs. Despite the similar uptake behavior of different hapten density nanovaccine NPs by DCs, Nic hapten density is expected to impact the recognition and activation of nicotine-specific B cells, and thereby influencing the efficacy of nanovaccines.

Immunogenicity of Different Hapten Density Nicotine Nanovaccines

A nicotine vaccine aims to induce the production of specific antibodies that bind to nicotine and thereby block its entry into the brain. Previous studies have shown that the pharmacokinetic efficacy of nicotine vaccines closely correlates with the antibody concentration elicited. [11, 35] The phase 2 clinical trials of NicVax revealed that only the top 30% of subjects with the highest antibody titers showed improved smoking cessation rates compared to the placebo. [13] Therefore, the presence of high antibody titers is one of the most critical factors influencing the efficacy of nicotine vaccines, and thus it is necessary to be high enough to ensure the vaccination efficacy.

Figure 39:
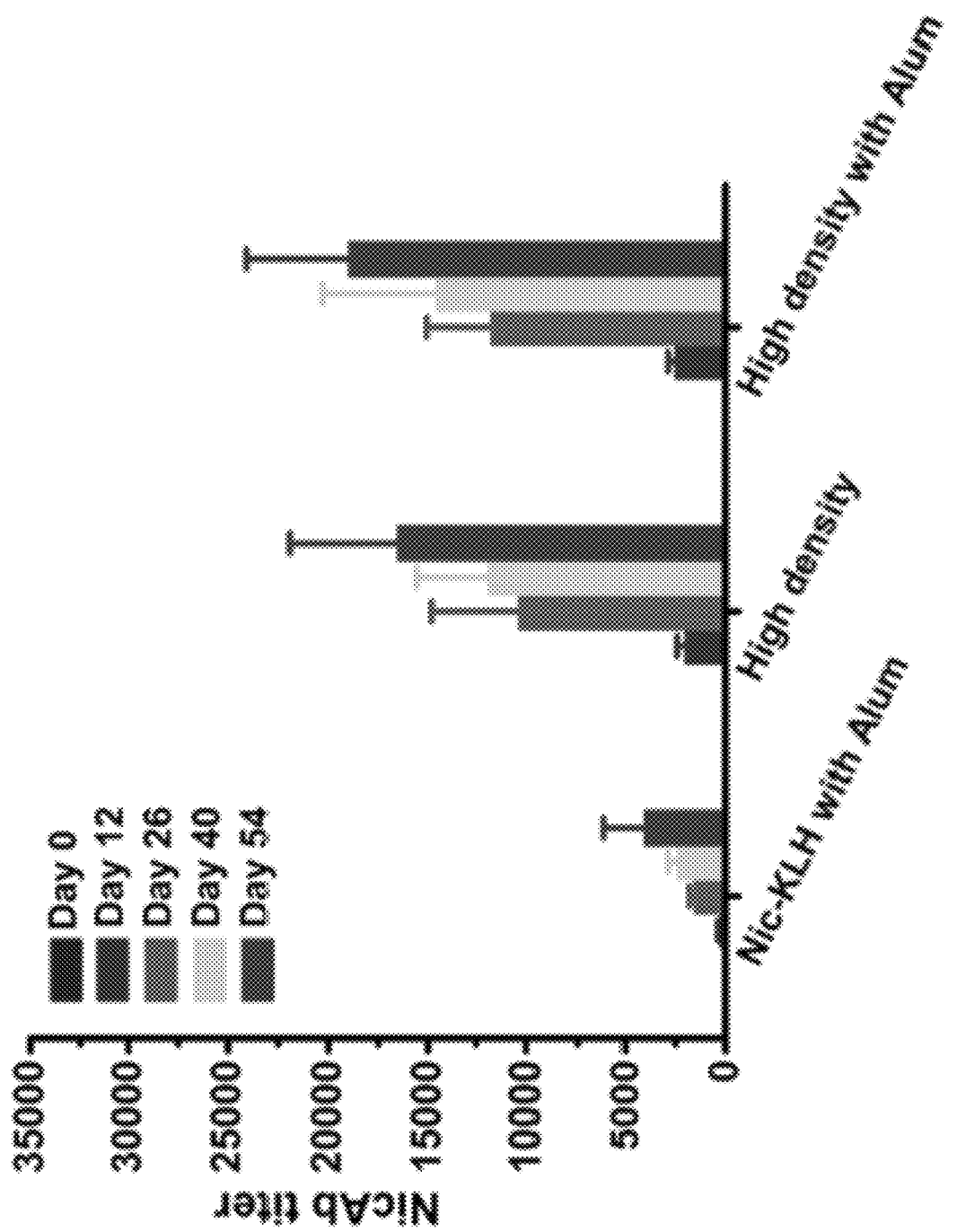
FIG. 39 shows a graph demonstrating a time-course of nicotine-specific antibody (NicAb) titers in response to the Nic-KLH conjugate vaccine and high-density nanovaccines, both of which had identical hapten density.
Figure 40:
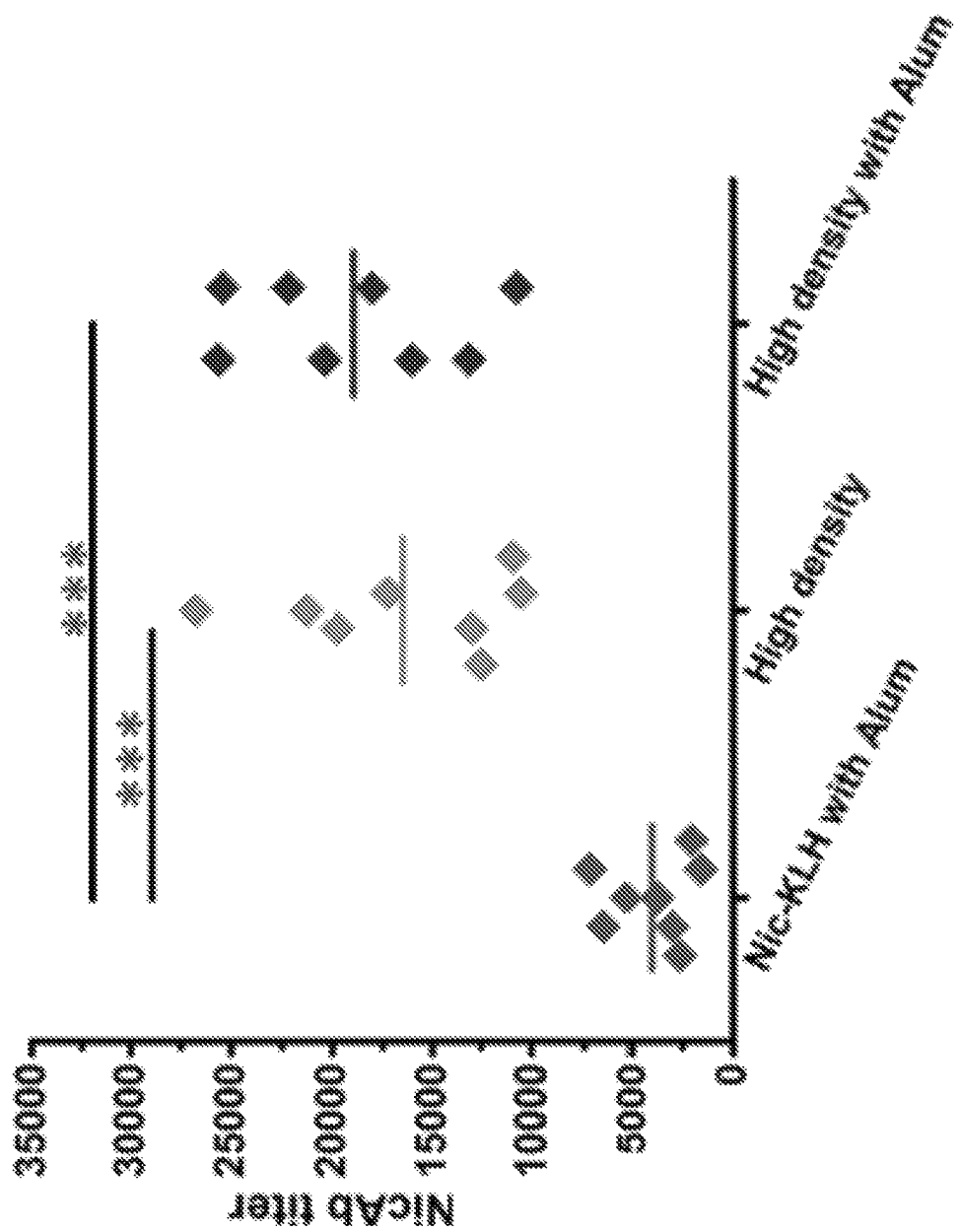
FIG. 40 shows a graph demonstrating the statistical comparison of the NicAb titers of the Nic-KLH and high-density nanovaccine groups on day 54. Each diamond represents NicAb titer of each mouse, and the colorful straight lines show the average NicAb titer of each group. *** $p<0.001$.
Figure 41:
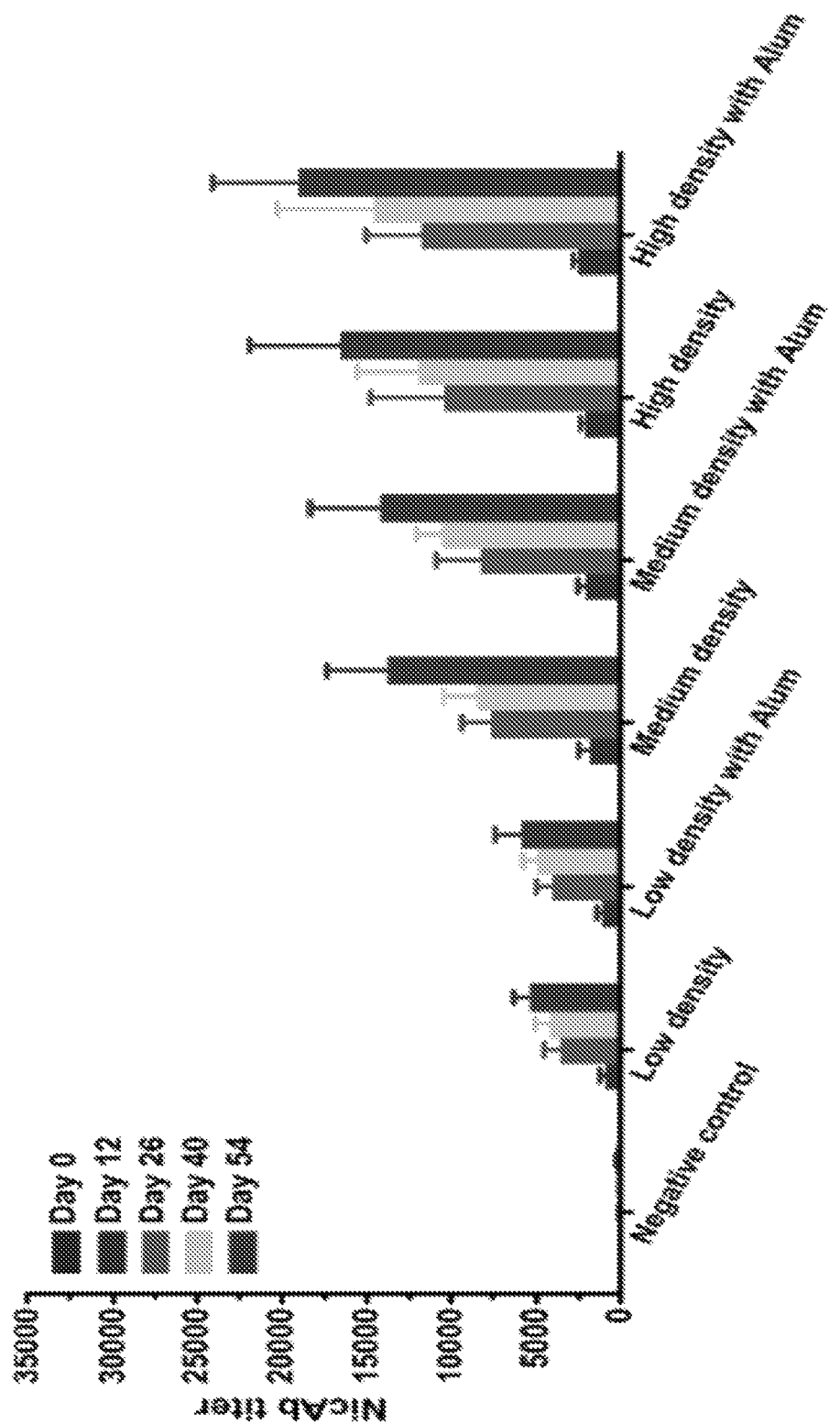
FIG. 41 shows a graph demonstrating a time-course of NicAb titers in response to different hapten density nanovaccines.
Figure 42:
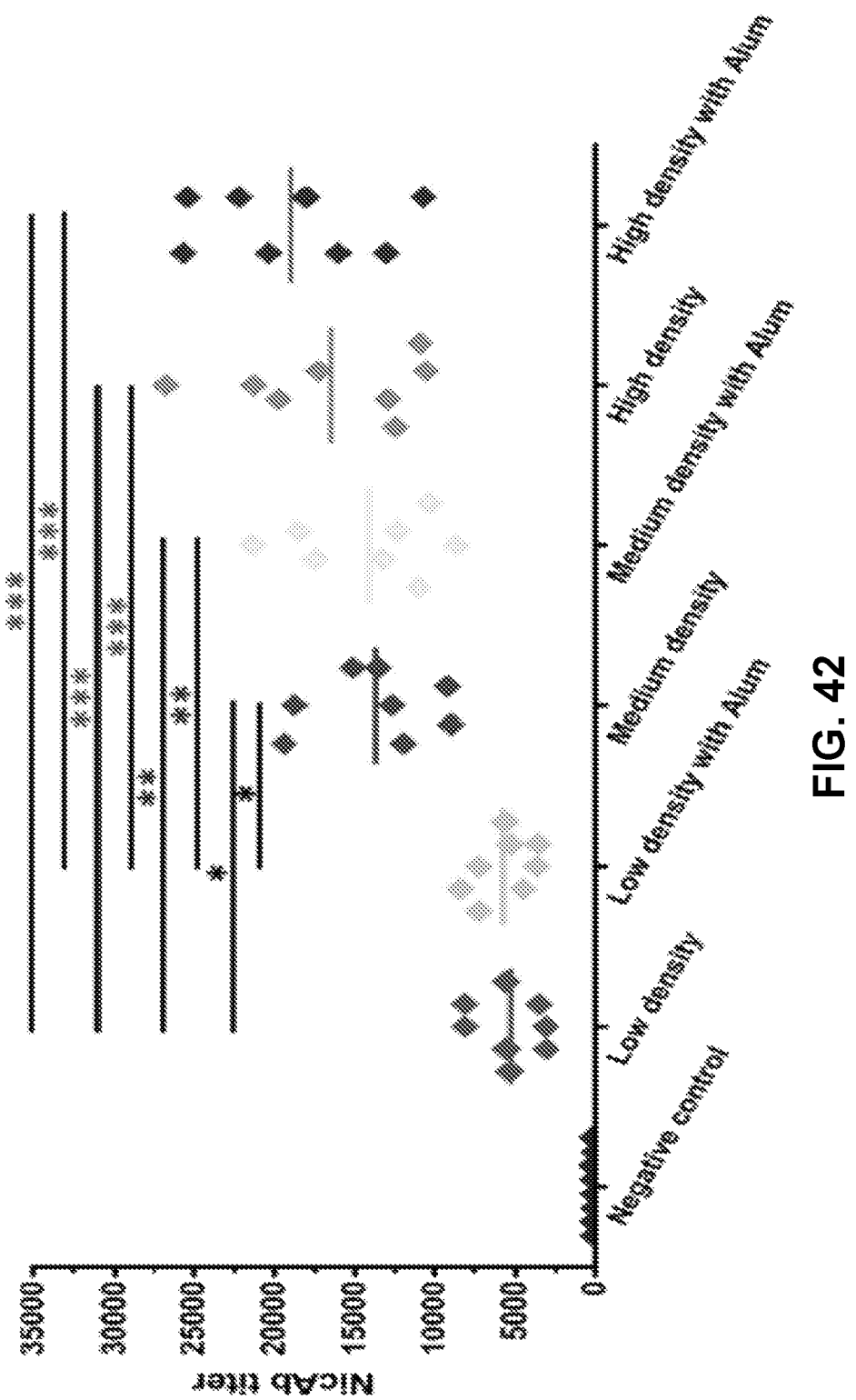
FIG. 42 shows a graph demonstrating the statistical analysis of the NicAb titers of different hapten density nanovaccines on day 54. Significantly different: * $p<0.05$,  $p<0.01$, * $p<0.001$.

FIG. 39 and FIG. 41 show the time-course results of anti-nicotine antibody titers, demonstrating that administration of all nicotine vaccines resulted in a steady increase of anti-nicotine IgG antibody titers along the study period. Particularly a sharp increase was observed after the first boost injection (on Day 26). In this study, the hapten density of the Nic-KLH conjugate vaccine and high-density nanovaccine were identical. The antibody titers in the high-density nanovaccine with or without alum groups were much higher (4-10 fold) than that in the Nic-KLH with Alum group in all the studied days (FIG. 39 and FIG. 40). This enhanced immunogenicity was in agreement with the enhanced internalization of antigens by the lipid-PLGA hybrid NP delivery system (FIG. 34). These results were consistent with previous reports. It was reported that a tetrahedral DNA nanostructure delivery system could effectively enhance antigen uptake and induce strong and long-lasting antibody responses against antigens. [36] In our previous study, we reported that using liposomes and nanohorn supported liposomes as delivery vehicles of Nic-BSA conjugate vaccines could result in stronger immune responses than Nic-BSA conjugate vaccine alone. [37, 38] The ability of different hapten density nanovaccines to induce nicotine-specific antibodies was then compared. As shown in FIG. 41, the high-density nanovaccine induced the highest antibody titers compared to the low- and medium-density nanovaccines along the entire study period. At the end of the study (on Day 54), the average antibody titer of the low-density without alum group was 5300, and increased by 7%, 159%, 166%, 211%, and 257% to 5700, 13700, 14100, 16500, and 18900, in groups of low-density with alum, medium-density with and without alum, high-density with and without alum, respectively. As shown in FIG. 42, statistical analysis revealed that there were significant differences between the high-/medium-density groups and low-density groups, regardless of the presence of alum or not ($p<0.05$). Although no statistically significant differences were observed between the high- and medium-density groups ($p>0.05$), the high-density nanovaccines resulted in more responders of high antibody titers. Specifically, based on a cutoff of antibody titer >15000, the percentage of high-titer responders was 37.5%, 37.5%, 50%, and 75% in medium-density with and without alum groups, high-density with and without alum groups, respectively. The increased immunogenicity of nanovaccines with higher hapten density could be attributed to the evidence that the nanovaccine NPs with more haptens would have more chances to be recognized by naïve B cells, thereby activating more nicotine-specific B cells and strengthening the immune response. These results are not completely consistent with previous studies reporting the influence of hapten density on the efficacy of nicotine-protein conjugate vaccines. Miller et al. reported that nicotine 6-hexanoic acid-KLH conjugate nicotine vaccine generated higher antibody titers with a density of 100 compared to 22. [10] In another study, McCluskie et al. showed that stronger immune responses were obtained with 5-aminoethoxy-nicotine-CRM conjugate vaccines having hapten density of 11-18, with weaker responses above the range and more variable responses below the range. [28] Pravetoni et al. reported that the antibody titer was highest with a hapten/KLH ratio of 700:1 in a 1-SNic-KLH conjugate vaccine. [21]

Figure 43:
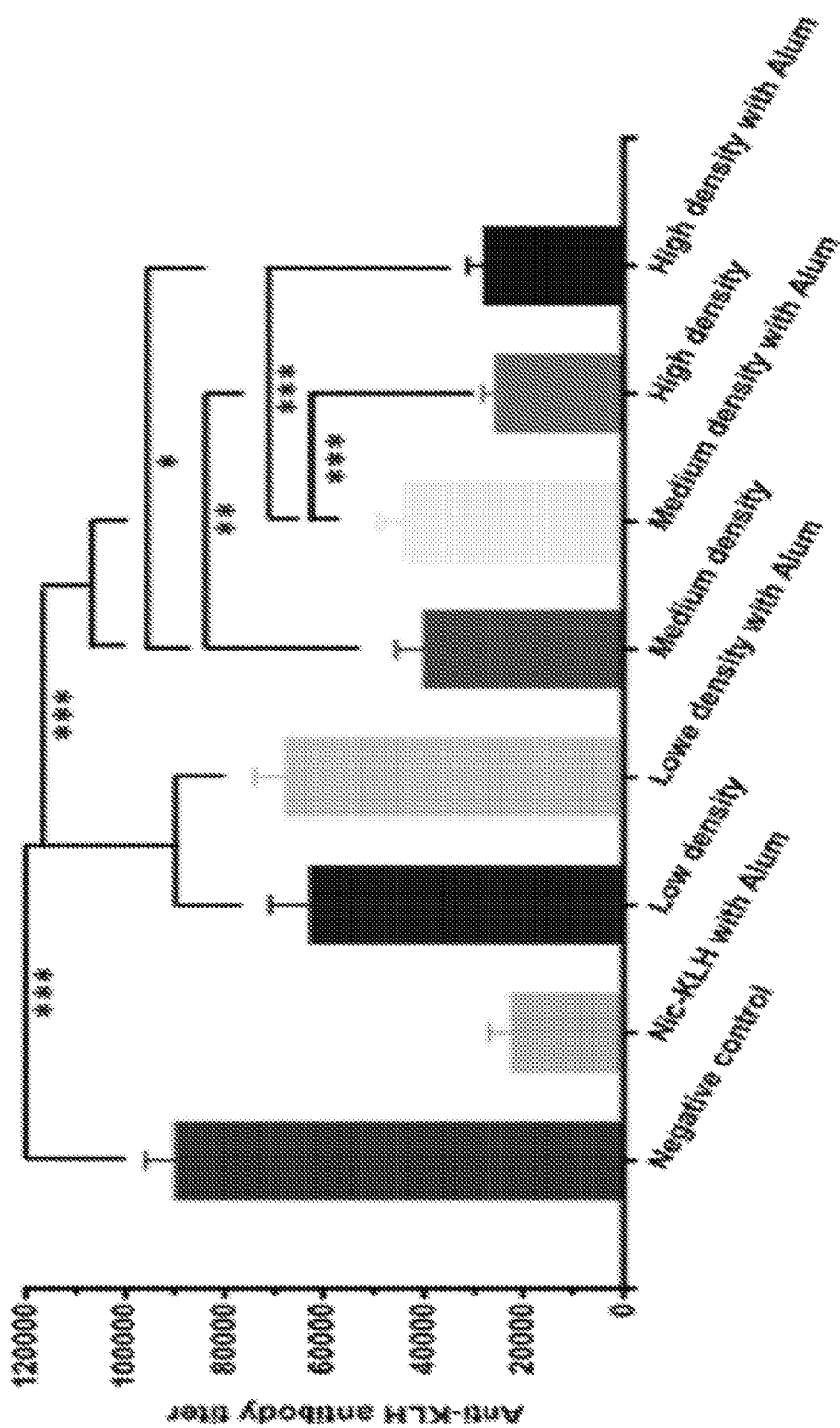
FIG. 43 shows a graph demonstrating anti-KLH antibody titers determined by ELISA. Significantly different: * $p<0.05$,  $p<0.01$, * $p<0.001$.
Figure 44:
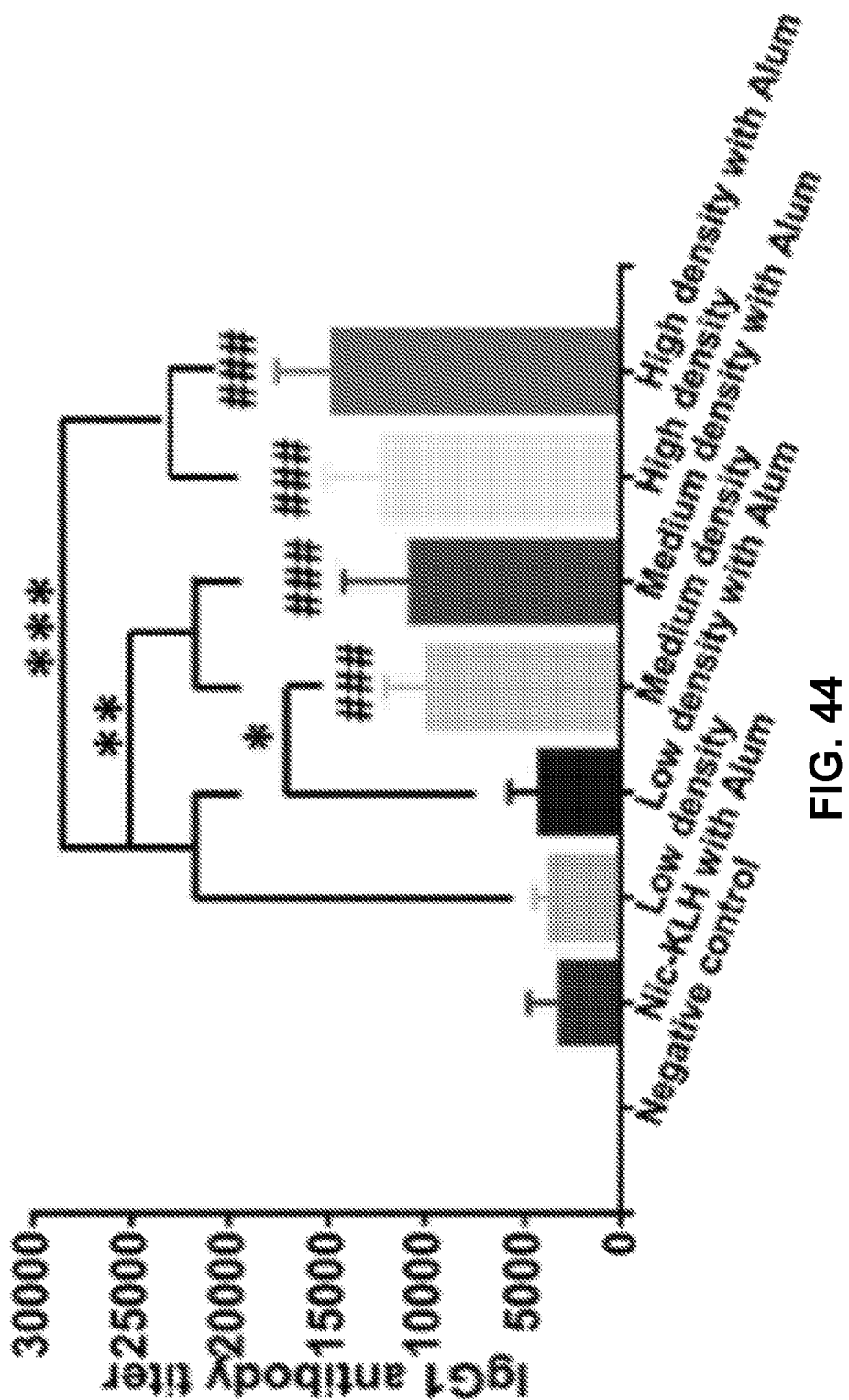
FIG. 44 shows a graph demonstrating the IgG1 antibody titer. Significantly different compared to Nic-KLH with Alum group: ###$p<0.001$; * $p<0.001$,  $p<0.01$, * $p<0.05$.
Figure 45:
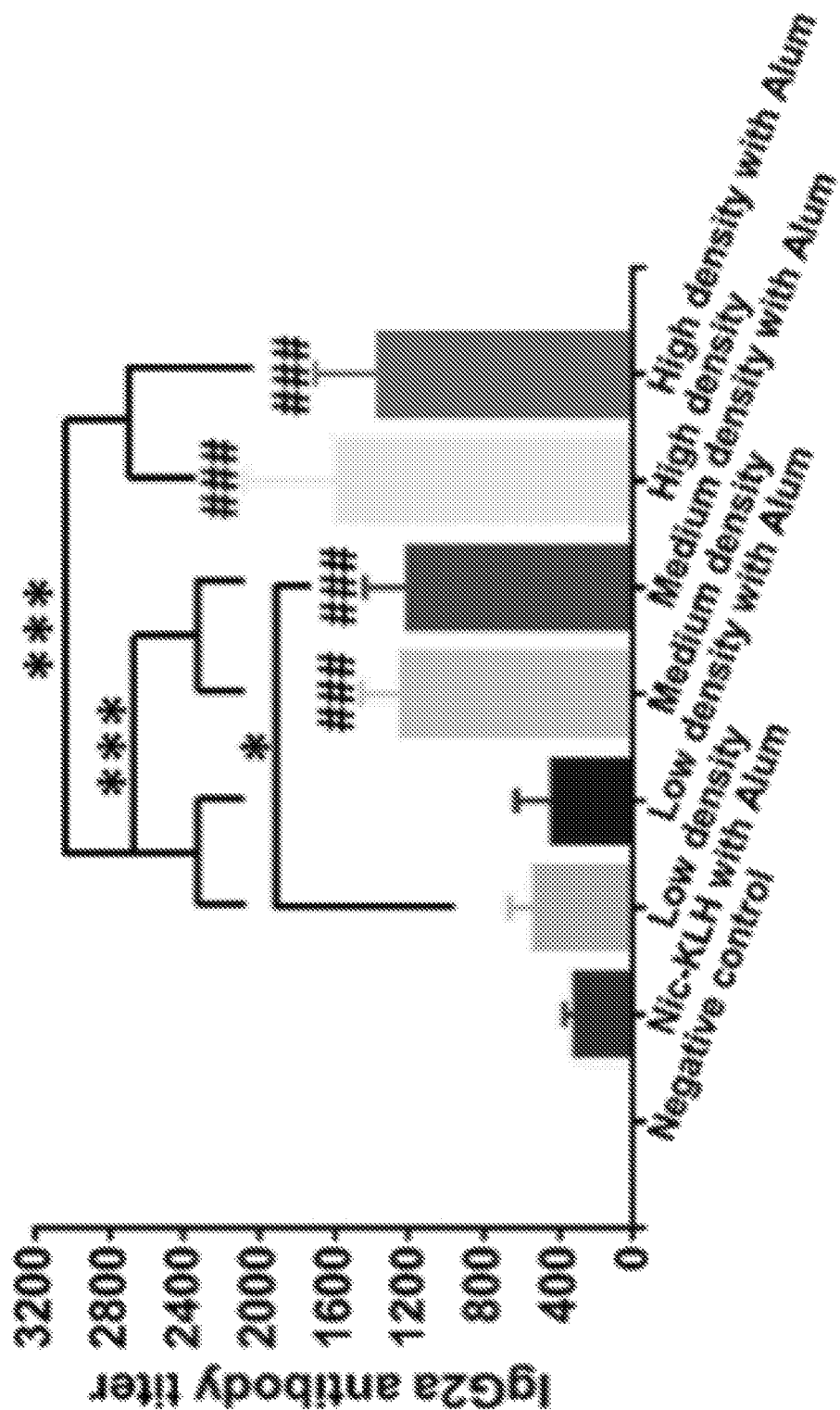
FIG. 45 shows a graph demonstrating the IgG2a antibody titer. Significantly different compared to Nic-KLH with Alum group: ###$p<0.001$; * $p<0.001$,  $p<0.01$, * $p<0.05$.
Figure 46:
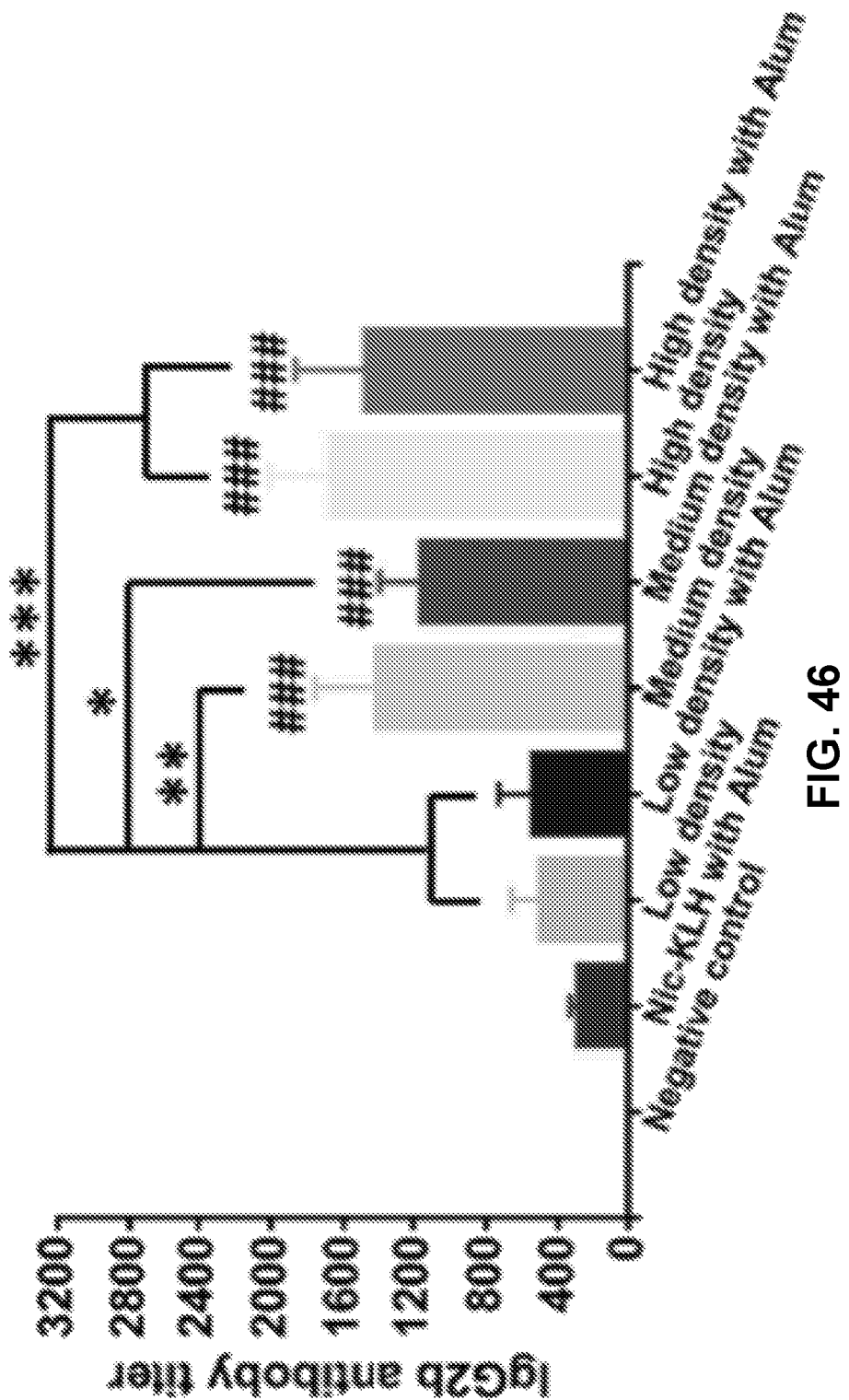
FIG. 46 shows a graph demonstrating the IgG2b antibody titer. Significantly different compared to Nic-KLH with Alum group: ###$p<0.001$; * $p<0.001$,  $p<0.01$, * $p<0.05$.
Figure 47:
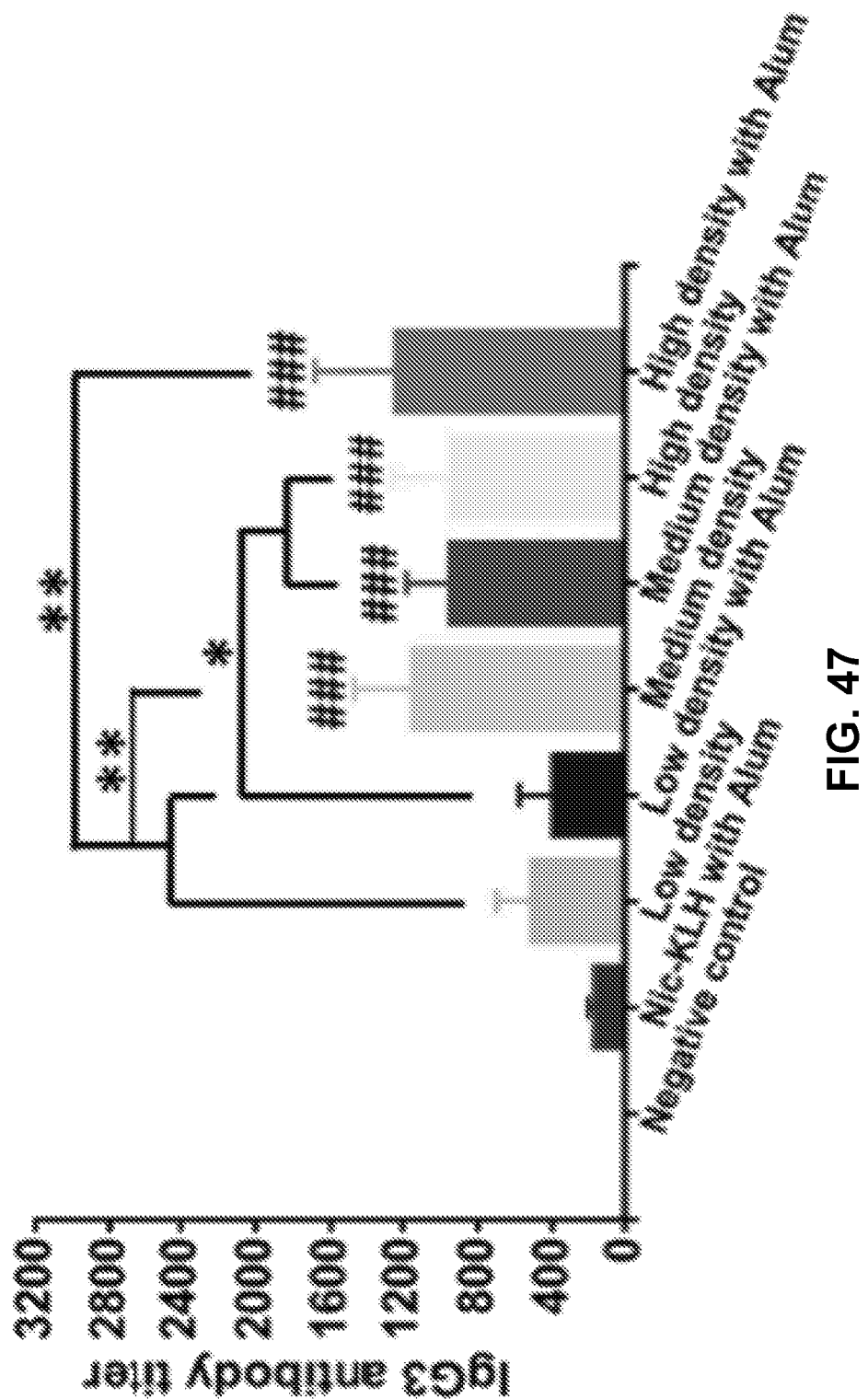
FIG. 47 shows a graph demonstrating IgG3 antibody titer. ###$p<0.001$; * $p<0.001$,  $p<0.01$, * $p<0.05$.

The titers of anti-KLH antibody were measured to evaluate the influence of hapten density of nanovaccines on the production of carrier protein specific antibodies. As shown in FIG. 43, the anti-KLH antibody titer of the negative control group, in which no hapten was conjugated, was around 90000. Interestingly, in contrast, the anti-KLH antibody titers were reduced by 30.6%, 24.5%, 55.4%, 51.3%, 71.8%, and 68.6% in groups of low-density, low-density with alum, medium-density, medium-density with alum, high-density, and high-density with alum, respectively. This indicated that the anti-carrier protein antibody titers decreased with the increase of hapten density. Statistical analysis revealed significant differences in the anti-KLH antibody titers of different hapten density nanovaccine groups ($p<0.05$). This is probably because hapten conjugation masks the immunogenic epitopes on the carrier protein surface. A low anti-carrier protein antibody titer is considered beneficial for the vaccine design in this study, as anti-carrier protein antibodies may neutralize the carrier protein on the surface of nanovaccine particles and influence the efficacy of nicotine nanovaccines.

The titers of IgG subclasses, including IgG1, IgG2a, IgG2b, and IgG3, were measured to provide further insights into the distribution of anti-nicotine IgG antibodies. As shown in FIGS. 44-47, IgG1 was the dominant subtype for all the nicotine vaccines, accounting for around 80% of the total IgG. The high- and medium-density nanovaccines induced remarkably higher antibody titers of all four IgG subclasses than the low-density nanovaccine and Nic-KLH conjugate vaccine. The Th1/Th2 indexes of immune responses induced by the nicotine vaccines were calculated based on the results of antibody titers of IgG subclasses. [39] As shown in FIG. 48, the Th1/Th2 indexes of all the nicotine vaccines, including Nic-KLH conjugate vaccine and nanovaccines, were significantly lower than 1, indicating that the immune responses induced by the nicotine vaccines were Th2-skewed (humoral response). The small Th1/Th2 indexes may be valuable to the performance of the nicotine nanovaccines, as the efficacy of reducing the rewarding effects of nicotine largely depends on the magnitude of humoral response.

Pharmacokinetic Efficacy of Different Hapten Density Nicotine Nanovaccines

Figure 49A:
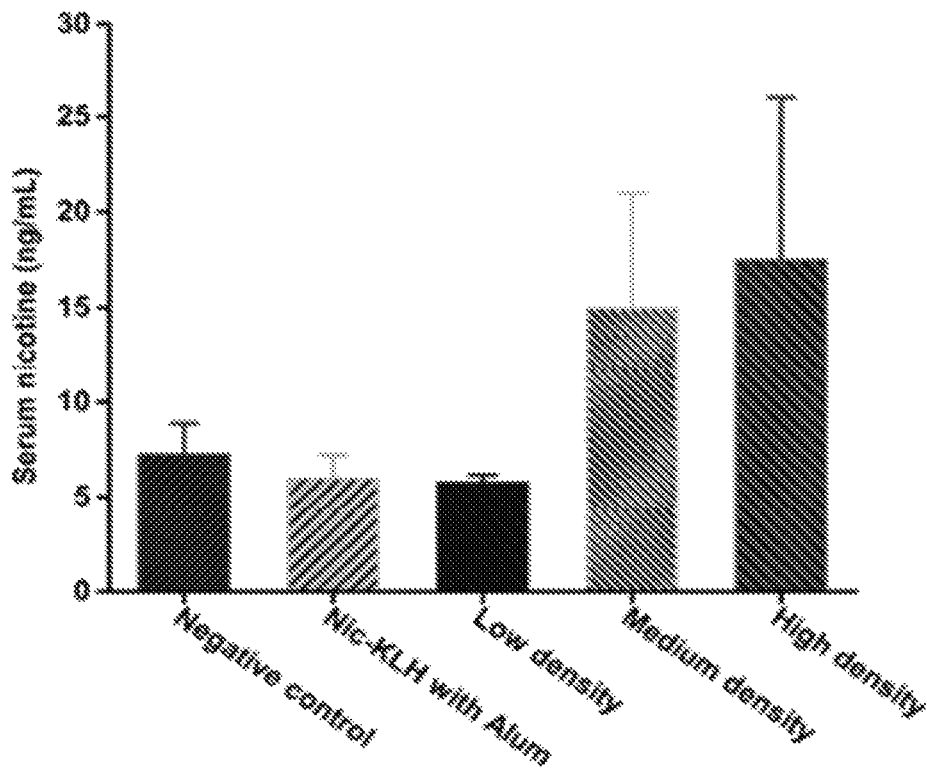
FIGS. 49A-49B demonstrate nicotine distribution in the (FIG. 49A) serum and (FIG. 49B) brain of immunized mice. Serum and brain tissues of mice were collected 4 min after administration of 0.03 mg/kg nicotine subcutaneously on day 54, and nicotine contents in tissues were analyzed. * and ** indicate significant differences compared to the negative control group, * $p<0.05$, ** $P<0.01$; #$P<0.05$.
Figure 49B:
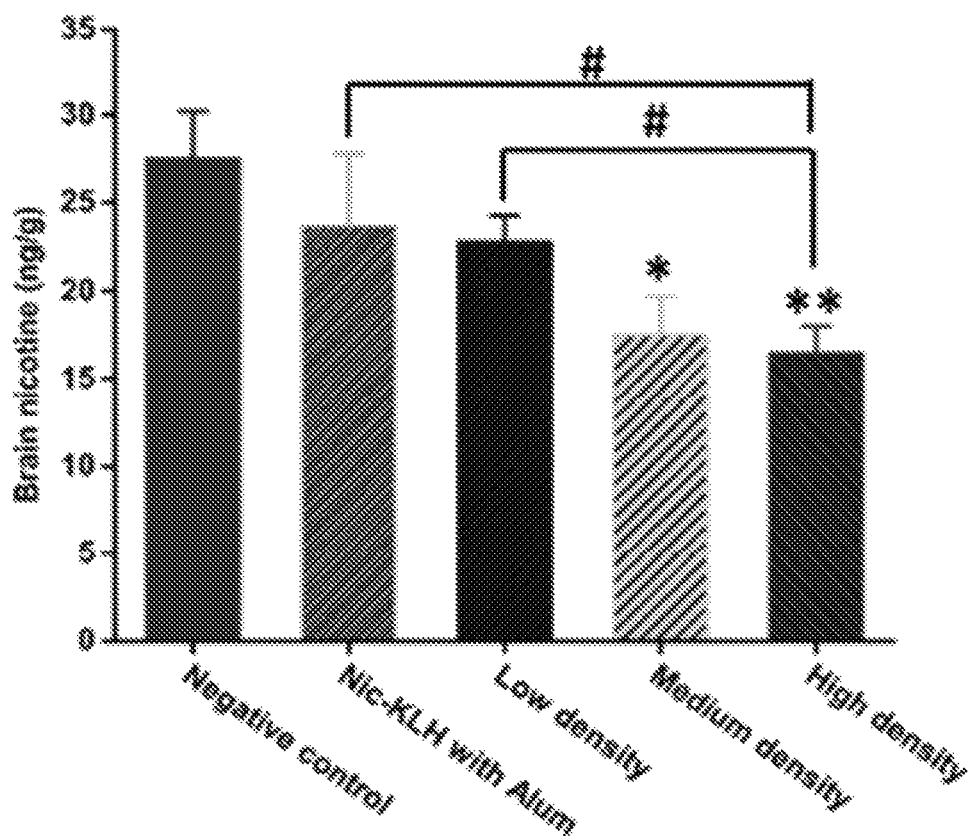

Nicotine vaccines are designed to retain nicotine in serum and block it from entering the brain. As shown in FIG. 49A, the serum nicotine level was 5.75 ng/mL for the low-density nanovaccine group and increased by 160% and 204% to 15.0 ng/mL and 17.5 ng/mL for the medium- and high-density nanovaccine groups, respectively. This suggests the medium- and high-density nanovaccines had better efficacy in retaining nicotine in serum than the low-density nanovaccine, and particularly, the high-density nanovaccine exhibited the best efficacy. FIG. 49B shows the results of brain nicotine levels in mice vaccinated with different hapten density nanovaccines. The brain nicotine levels of Nic-KLH with alum group, low-density group, medium-density group, and high-density group, were reduced by 14.0%, 17.2%, 36.7%, and 40.0% compared to that of the negative control group. Statistical analysis revealed that the brain nicotine level for the high-density nanovaccine group was significantly lower than that of the Nic-KLH with alum group, suggesting that the use of lipid-PLGA hybrid NPs as delivery vehicles considerably enhanced the pharmacokinetic efficacy of the conjugate nicotine vaccine. In addition, the medium- and high-density nanovaccines resulted in considerably higher brain nicotine reduction than the low density nanovaccine, and statistical analysis showed that the high-density nanovaccine had a significantly lower brain nicotine level than the low-density nanovaccine. This indicated that the high-density nanovaccine exhibited the best efficacy in blocking nicotine from entering the brain. Together with the results of serum and brain nicotine levels, the high-density nanovaccine was considered to have the best pharmacokinetic efficacy.

Preliminary Safety of Nicotine Nanovaccines

Figure 51:
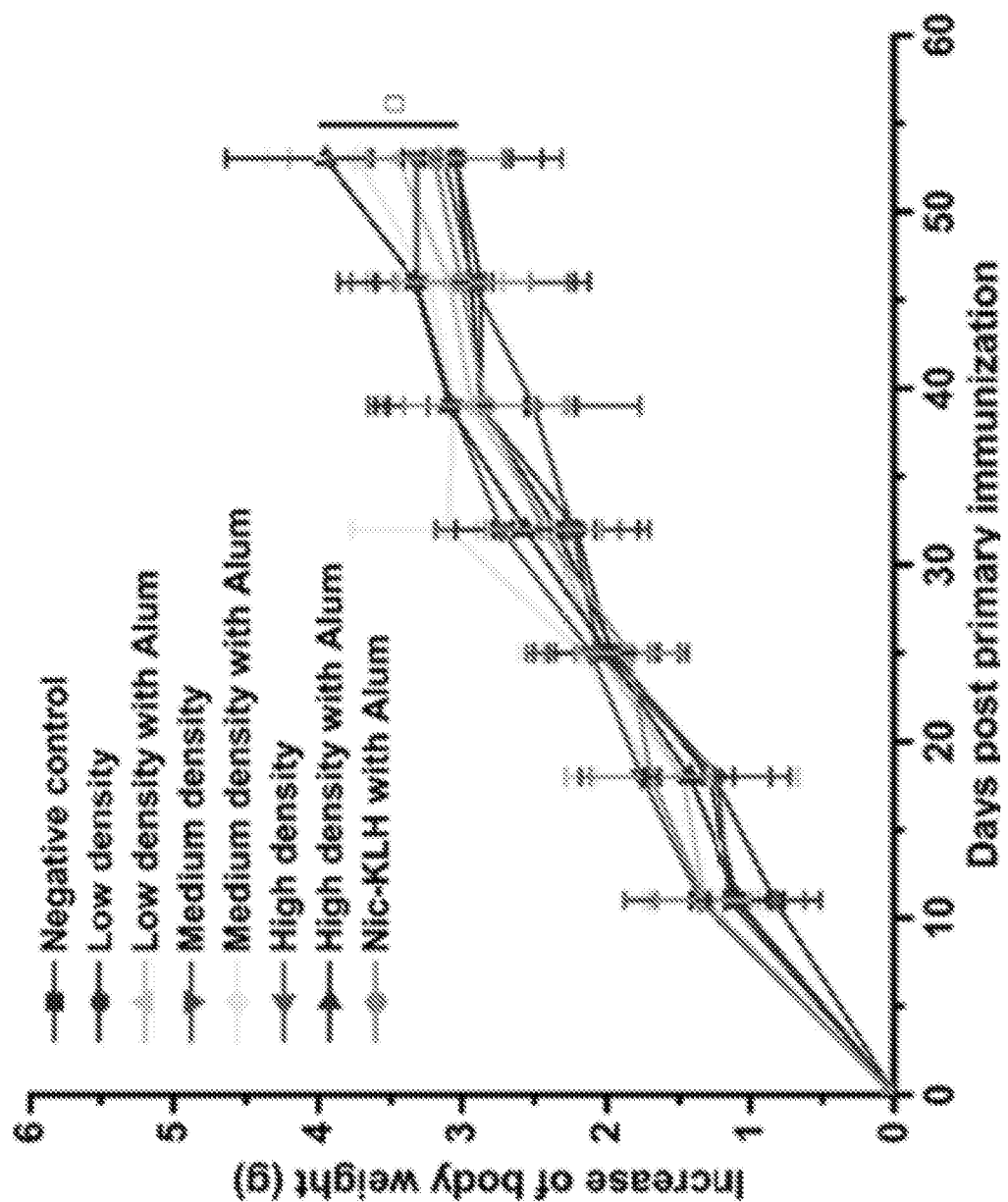
FIG. 51 shows a graph demonstrating the increase of body weight during the immunization study. The box symbol indicates that no significant differences among multiple groups were found for all seven measurements.

Mouse organs, including heart, kidney, liver, lung, and spleen, were examined by histopathological analysis after administration of nicotine vaccines. FIGS. 50A-50T shows the representative histopathological images of the negative control group, Nic-KLH with alum group, and high density with and without alum groups. As for the three different hapten density nanovaccines, mouse organs exhibited similar characteristics, thus here, we only show the results of the high-density nanovaccine groups as a representative. The histopathological review revealed no significant lesions in the five organs of mice of each treatment and control groups. Mouse body weight was monitored as an indicator of vaccine safety along the study period. As shown in FIG. 51, no body weight losses were detected for all the groups, and statistical analysis suggested that no significant differences were observed among all the groups, indicating that the administration of nicotine vaccines did not impose apparent adverse impacts on mouse growth. The above preliminary safety results proved that the lipid-PLGA NP based nicotine nanovaccines, regardless of hapten density, are of distinguishing safety.

Summary

In this study, different hapten density nicotine nanovaccines using lipid-polymeric NPs as delivery vehicles were synthesized and characterized in vitro and in vivo. The in vitro results suggested that all nanovaccine NPs, regardless of hapten density, were taken up by dendritic cells. Moreover, nanovaccine NPs were internalized by dendritic cells more efficiently compared to the hapten-KLH conjugate particles in terms of internalized antigens. The in vivo immunization study in mice indicated that the nanovaccine resulted in a 570% higher antibody titer than the Nic-KLH conjugate vaccine at a similar hapten density. Furthermore, the medium- and high-density nanovaccines exhibited significantly higher immunogenicity compared to the low-density nanovaccine. In addition, although no significant differences in antibody titers were detected between the high- and medium-density nanovaccines, the high-density nanovaccine resulted in more responders of high antibody titers (>15000). The pharmacokinetic study in mice suggested that the high hapten density nanovaccine had the best efficacy in blocking nicotine from entering the brain. The histopathological study showed that none of the different hapten density nanovaccines caused any apparent toxic effects to mouse organs. All these findings suggest that the immunogenicity of the lipid-polymeric NP based nicotine nanovaccines can be enhanced by modulating hapten density.

REFERENCES FOR EXAMPLE 2

[1] Benowitz, N. L. (2010) Nicotine Addiction. New Engl J Med 362, 2295-2303.
[2] Lockner, J. W., Lively, J. M., Collins, K. C., Vendruscolo, J. C. M., Azar, M. R., and Janda, K. D. (2015) A Conjugate Vaccine Using Enantiopure Hapten Imparts Superior Nicotine-Binding Capacity. J Med Chem 58, 1005-1011.
[3] McCarthy, D. E., Piasecki, T. M., Lawrence, D. L., Jorenby, D. E., Shiffman, S., Fiore, M. C., and Baker, T. B. (2008) A randomized controlled clinical trial of bupropion SR and individual smoking cessation counseling. Nicotine Tob Res 10, 717-729.
[4] Stapleton, J. A., Watson, L., Spirling, L. I., Smith, R., Milbrandt, A., Ratcliffe, M., and Sutherland, G. (2008) Varenicline in the routine treatment of tobacco dependence: a pre-post comparison with nicotine replacement therapy and an evaluation in those with mental illness. Addiction 103, 146-154.
[5] Carpenter, M. J., Jardin, B. F., Burris, J. L., Mathew, A. R., Schnoll, R. A., Rigotti, N. A., and Cummings, K. M. (2013) Clinical Strategies to Enhance the Efficacy of Nicotine Replacement Therapy for Smoking Cessation: A Review of the Literature. Drugs 73, 407-426.
[6] Raupach, T., Hoogsteder, P. H., and Onno van Schayck, C. P. (2012) Nicotine vaccines to assist with smoking cessation: current status of research. Drugs 72, e1-16.
[7] Shen, X. Y., Orson, F. M., and Kosten, T. R. (2012) Vaccines Against Drug Abuse. Clin Pharmacol Ther 91, 60-70.
[8] Pryde, D. C., Jones, L. H., Gervais, D. P., Stead, D. R., Blakemore, D. C., Selby, M. D., Brown, A. D., Coe, J. W., Badland, M., Beal, D. M., Glen, R., Wharton, Y., Miller, G. J., White, P., Zhang, N. L., Benoit, M., Robertson, K., Merson, J. R., Davis, H. L., and McCluskie, M. J. (2013) Selection of a Novel Anti-Nicotine Vaccine: Influence of Antigen Design on Antibody Function in Mice. Plos One 8.
[9] Hieda, Y., Keyler, D. E., VandeVoort, J. T., Kane, J. K., Ross, C. A., Raphael, D. E., Niedbalas, R. S., and Pentel, P. R. (1997) Active immunization alters the plasma nicotine concentration in rats. J Pharmacol Exp Ther 283, 1076-1081.
[10] Miller, K. D., Roque, R., and Clegg, C. H. (2014) Novel Anti-Nicotine Vaccine Using a Trimeric Coiled-Coil Hapten Carrier. Plos One 9.
[11] Pravetoni, M., Keyler, D. E., Raleigh, M. D., Harris, A. C., LeSage, M. G., Mattson, C. K., Pettersson, S., and Pentel, P. R. (2011) Vaccination against nicotine alters the distribution of nicotine delivered via cigarette smoke inhalation to rats. Biochem Pharmacol 81, 1164-1170.
[12] De Biasi, M., McLaughlin, I., Perez, E. E., Crooks, P. A., Dwoskin, L. P., Bardo, M. T., Pentel, P. R., and Hatsukami, D. (2014) Scientific overview: 2013 BBC plenary symposium on tobacco addiction. Drug Alcohol Depen 141, 107-117.
[13] Hatsukami, D. K., Jorenby, D. E., Gonzales, D., Rigotti, N. A., Glover, E. D., Oncken, C. A., Tashkin, D. P., Reus, V. I., Akhavain, R. C., Fahim, R. E. F., Kessler, P. D., Niknian, M., Kalnik, M. W., and Rennard, S. I. (2011) Immunogenicity and Smoking-Cessation Outcomes for a Novel Nicotine Immunotherapeutic. Clin Pharmacol Ther 89, 392-399.
[14] Cornuz, J., Zwahlen, S., Jungi, W. F., Osterwalder, J., Klingler, K., van Melle, G., Bangala, Y., Guessous, I., Muller, P., Willers, J., Maurer, P., Bachmann, M. F., and Cerny, T. (2008) A Vaccine against Nicotine for Smoking Cessation: A Randomized Controlled Trial. Plos One 3.
[15] Meijler, M. M., Matsushita, M., Altobelli, L. J., Wirsching, P., and Janda, K. D. (2003) A new strategy for improved nicotine vaccines using conformationally constrained haptens. J Am Chem Soc 125, 7164-7165.
[16] de Villiers, S. H. L., Lindblom, N., Kalayanov, G., Gordon, S., Baraznenok, I., Malmerfelt, A., Marcus, M. M., Johansson, A. M., and Svensson, T. H. (2010) Nicotine hapten structure, antibody selectivity and effect relationships: Results from a nicotine vaccine screening procedure. Vaccine 28, 2161-2168.
[17] Lockner, J. W., Ho, S. O., McCague, K. C., Chiang, S. M., Do, T. Q., Fujii, G., and Janda, K. D. (2013) Enhancing nicotine vaccine immunogenicity with liposomes. Bioorg Med Chem Lett 23, 975-978.
[18] Cornish, K. E., de Villiers, S. H. L., Pravetoni, M., and Pentel, P. R. (2013) Immunogenicity of Individual Vaccine Components in a Bivalent Nicotine Vaccine Differ According to Vaccine Formulation and Administration Conditions. Plos One 8.
[19] de Villiers, S. H. L., Cornish, K. E., Troska, A. J., Pravetoni, M., and Pentel, P. R. (2013) Increased efficacy of a trivalent nicotine vaccine compared to a dose-matched monovalent vaccine when formulated with alum. Vaccine 31, 6185-6193.
[20] Keyler, D. E., Roiko, S. A., Earley, C. A., Murtaugh, M. P., and Pentel, P. R. (2008) Enhanced immunogenicity of a bivalent nicotine vaccine. Int Immunopharmacol 8, 1589-94.

[21] Pravetoni, M., Keyler, D. E., Pidaparthi, R. R., Carroll, F. I., Runyon, S. P., Murtaugh, M. P., Earley, C. A., and Pentel, P. R. (2012) Structurally distinct nicotine immunogens elicit antibodies with non-overlapping specificities. Biochem Pharmacol 83, 543-550.
[22] Chen, X. Y., Pravetoni, M., Bhayana, B., Pentel, P. R., and Wu, M. X. (2012) High immunogenicity of nicotine vaccines obtained by intradermal delivery with safe adjuvants. Vaccine 31, 159-164.
[23] Pentel, P. R., and LeSage, M. G. (2014) New Directions in Nicotine Vaccine Design and Use. Adv Pharmacol 69, 553-580.
[24] Pejawar-Gaddy, S., Kovacs, J. M., Barouch, D. H., Chen, B., and Irvine, D. J. (2014) Design of Lipid Nanocapsule Delivery Vehicles for Multivalent Display of Recombinant Env Trimers in HIV Vaccination. Bioconjugate Chem 25, 1470-1478.
[25] Daglioglu, C., and Okutucu, B. (2016) Synthesis and Characterization of AICAR and DOX Conjugated Multifunctional Nanoparticles as a Platform for Synergistic Inhibition of Cancer Cell Growth. Bioconjugate Chem 27, 1098-1111.
[26] Kim, C. S., Mout, R., Zhao, Y. L., Yeh, Y. C., Tang, R., Jeong, Y., Duncan, B., Hardy, J. A., and Rotello, V. M. (2015) Co-Delivery of Protein and Small Molecule Therapeutics Using Nanoparticle-Stabilized Nanocapsules. Bioconjugate Chem 26, 950-954.
[27] Harris, J. R., and Markl, J. (1999) Keyhole limpet hemocyanin (KLH): a biomedical review. Micron 30, 597-623.
[28] McCluskie, M. J., Thorn, J., Mehelic, P. R., Kolhe, P., Bhattacharya, K., Finneman, J. I., Stead, D. R., Piatchek, M. B., Zhang, N. L., Chikh, G., Cartier, J., Evans, D. M., Merson, J. R., and Davis, H. L. (2015) Molecular attributes of conjugate antigen influence function of antibodies induced by anti-nicotine vaccine in mice and non-human primates. International Immunopharmacology 25, 518-527.
[29] Collins, K. C., and Janda, K. D. (2014) Investigating Hapten Clustering as a Strategy to Enhance Vaccines against Drugs of Abuse. Bioconjugate Chem 25, 593-600.
[30] Foged, C., Brodin, B., Frokjaer, S., and Sundblad, A. (2005) Particle size and surface charge affect particle uptake by human dendritic cells in an in vitro model. Int J Pharm 298, 315-322.
[31] Bachmann, M. F., and Jennings, G. T. (2010) Vaccine delivery: a matter of size, geometry, kinetics and molecular patterns. Nat Rev Immunol 10, 787-796.
[32] Reddy, S. T., van der Vlies, A. J., Simeoni, E., Angeli, V., Randolph, G. J., O'Neill, C. P., Lee, L. K., Swartz, M. A., and Hubbell, J. A. (2007) Exploiting lymphatic transport and complement activation in nanoparticle vaccines. Nat Biotechnol 25, 1159-1164.
[33] Oussoren, C., Zuidema, J., Crommelin, D. J., and Storm, G. (1997) Lymphatic uptake and biodistribution of liposomes after subcutaneous injection. II. Influence of liposomal size, lipid compostion and lipid dose. Biochim Biophys Acta 1328, 261-72.
[34] Banchereau, J., and Steinman, R. M. (1998) Dendritic cells and the control of immunity. Nature 392, 245-252.
[35] Maurer, P., Jennings, G. T., Willers, J., Rohner, F., Lindman, Y., Roubicek, K., Renner, W. A., Muller, P., and Bachmann, M. F. (2005) Frontline: A therapeutic vaccine for nicotine dependence: preclinical efficacy, and phase I safety and immunogenicity. Eur J Immunol 35, 2031-2040.
[36] Liu, X. W., Xu, Y., Yu, T., Clifford, C., Liu, Y., Yan, H., and Chang, Y. (2012) A DNA Nanostructure Platform for Directed Assembly of Synthetic Vaccines. Nano Lett 12, 4254-4259.
[37] Zheng, H., Hu, Y., Huang, W., de Villiers, S., Pentel, P., Zhang, J. F., Dorn, H., Ehrich, M., and Zhang, C. M. (2015) Negatively Charged Carbon Nanohorn Supported Cationic Liposome Nanoparticles: A Novel Delivery Vehicle for Anti-Nicotine Vaccine. J Biomed Nanotechnol 11, 2197-2210.
[38] Hu, Y., Zheng, H., Huang, W., and Zhang, C. M. (2014) A novel and efficient nicotine vaccine using nanolipoplex as a delivery vehicle. Hum Vacc Immunother 10, 64-72.
[39] Visciano, M. L., Tagliamonte, M., Tornesello, M. L., Buonaguro, F. M., and Buonaguro, L. (2012) Effects of adjuvants on IgG subclasses elicited by virus-like Particles. J Transl Med 10.
[40] Hu, Y., Ehrich, M., Fuhrman, K., and Zhang, C. M. (2014) In vitro performance of lipid-PLGA hybrid nanoparticles as an antigen delivery system:lipid composition matters. Nanoscale Res Lett 9.

Example 3

Introduction

Tobacco smoking continues to be the leading preventable cause of disease, disability, and death worldwide.[1] Every year in the United States alone, more than 480,000 people die from tobacco smoking.[2] Current pharmacological medications for smoking cessation are only partially successful and associated with the risk of serious side effects.[3] Nicotine vaccines that can generate nicotine-specific antibodies capable of sequestering nicotine in serum and blocking nicotine from entering the brain have shown to be a promising approach to treating nicotine addiction.[4, 5] Several conjugate nicotine vaccines have reached various stages of clinical trials.[6, 7] Despite the prominent results in preclinical and early-stage clinical trials, no conjugate nicotine vaccines have proven overall enhanced smoking cessation rate, mainly due to their insufficient and highly variable antibody titers.[5, 8, 9]

In other Examples herein and elsewhere, other next-generation nanoparticle-based nicotine vaccines have been developed that can have improved immunogenicity over conjugate nicotine vaccines. [10-13]. These next-generation nanoparticle-based nicotine nanovaccines have many unique superiorities, such as high bioavailability, enhanced recognition and uptake by immune cells, long immunological persistence, high specificity, and ease of incorporation with adjuvants. In particular, a lipid-polymeric hybrid nanoparticle-based nicotine nanovaccine (NanoNicVac for abbreviation) was demonstrated to result in significantly higher immunological efficacy than the conjugate nicotine vaccine. [12] In addition, we previously demonstrated that the immunogenicity of NanoNicVac could be improved by modulating the particle size[12], hapten density [Example 2 herein], and hapten localization [Example 1 herein].

Immunologically speaking, an efficient T cell immunity is essential for the generation of an effective humoral immune response against nicotine. [14, 15] The Maturation of nicotine-specific B cells to antibody-secreting cells involves two pivotal T-cell-dependent processes. The two processes are the formation of T-helper cells and the interaction between T-helper cells and B cells, both of which only occur via presentation of peptidic antigens on the major histocompatibility complex (MHC) of antigen presenting cells.[5, 16]

Basically, an effective T cell immunity makes the humoral immune response against nicotine specific, fervent, and long-lasting.[17] In this sense, a stimulating protein that provides peptidic antigens can be important for a nanoparticle-based nicotine nanovaccine.[18] Incorporation of different stimulating proteins into a nanoparticle-based nicotine nanovaccine may cause the different effectiveness of T cell immunity, thus leading to different immunological efficacy.

Figure 52:
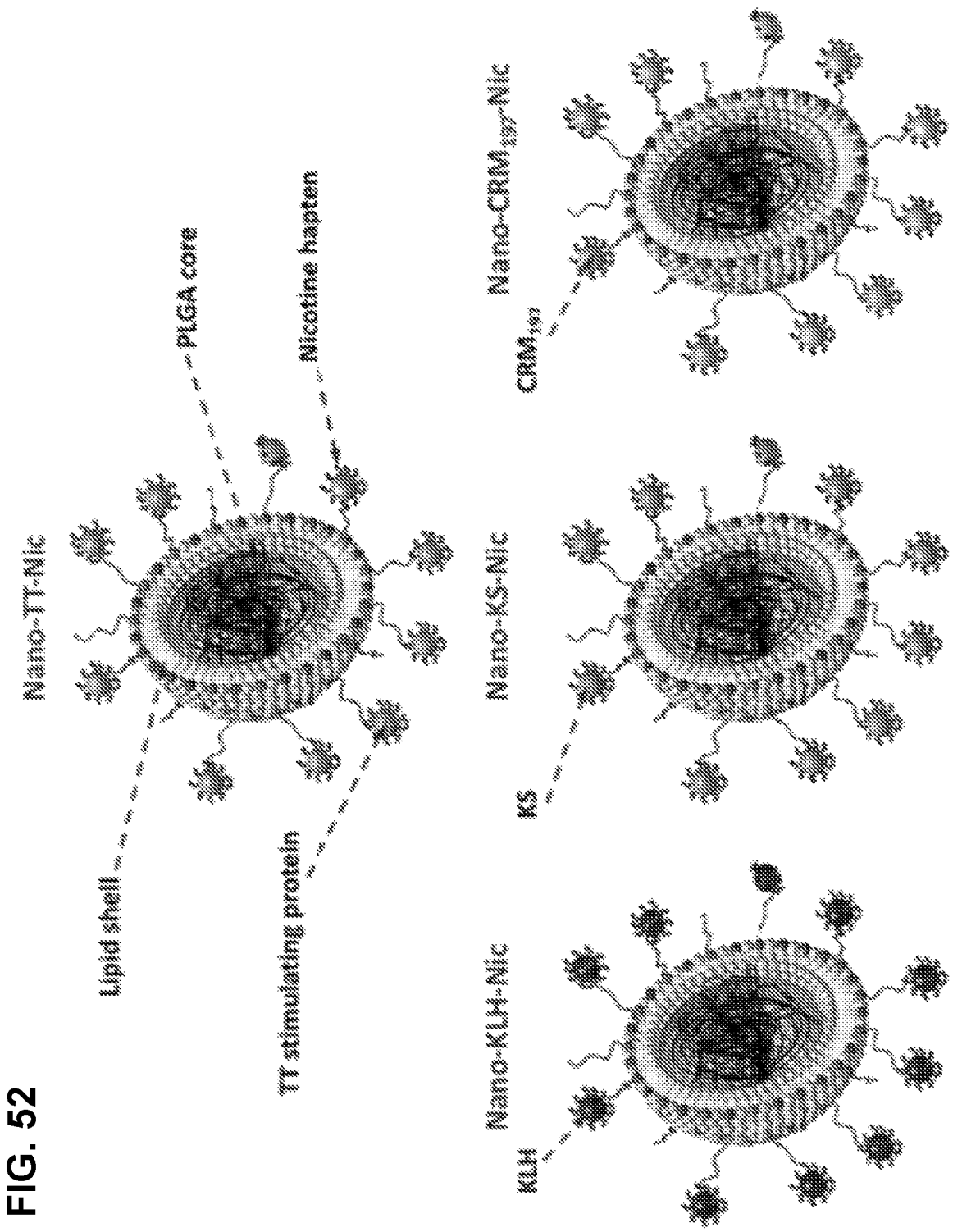
FIG. 52 shows a schematic demonstrating a hybrid nanoparticle-based nicotine nanovaccine (NanoNicVac) carrying different stimulating proteins.
Figures 55A, 55B, 55C, 55D, 55E, 55F:
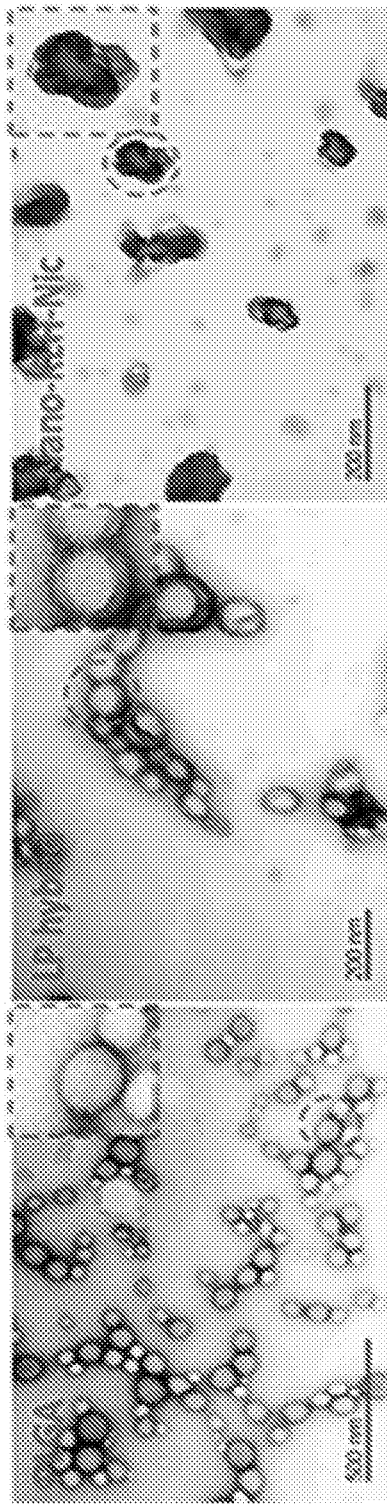
FIGS. 55A-55F shows TEM images demonstrating the morphological characteristics of NanoNicVac nanoparticles.
Figures 56A, 56B:
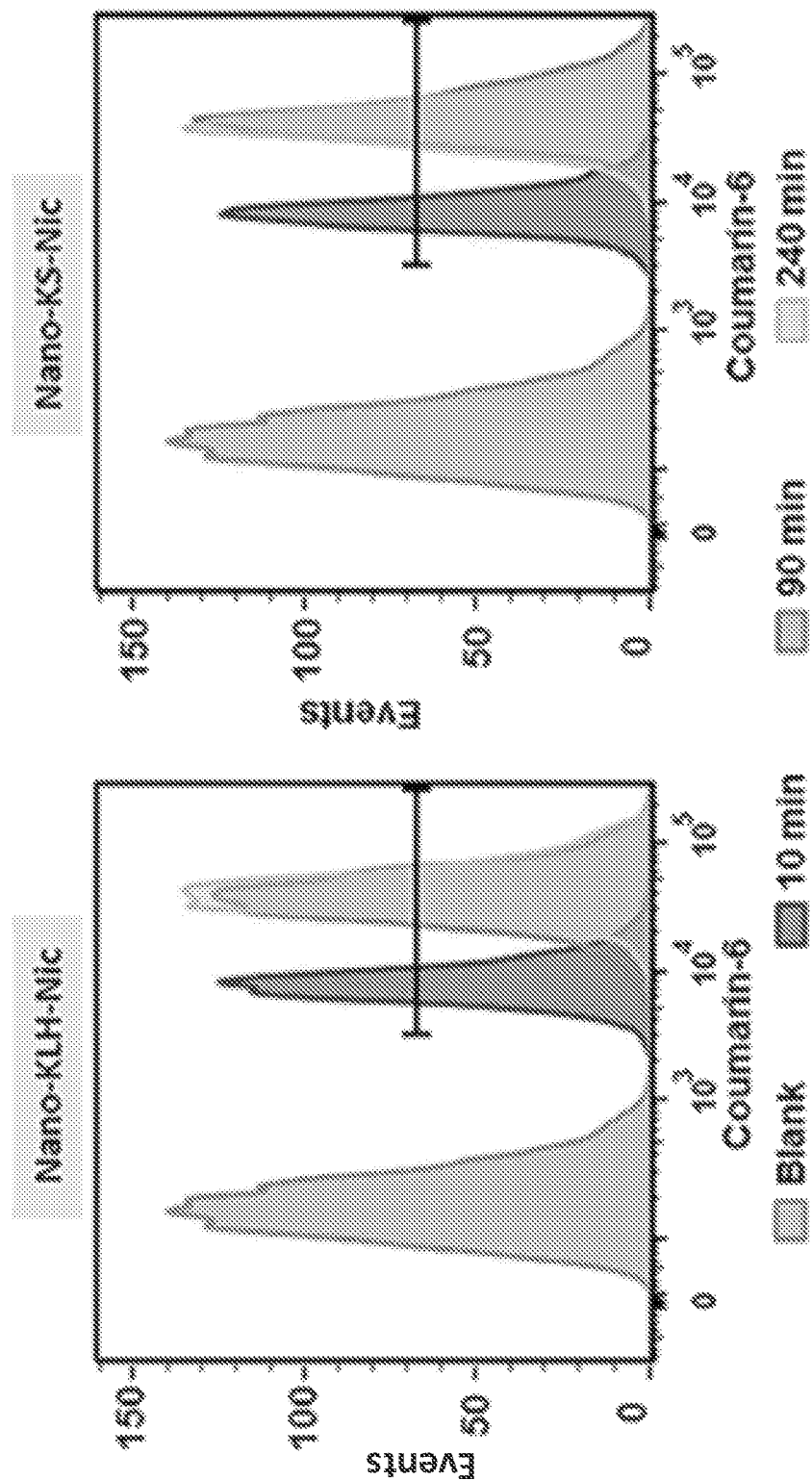
FIGS. 56A-56D show graphs demonstrating the CM-6 intensity distribution of cells treated with NanoNicVac conjugated with different stimulating proteins.
Figures 56C, 56D:
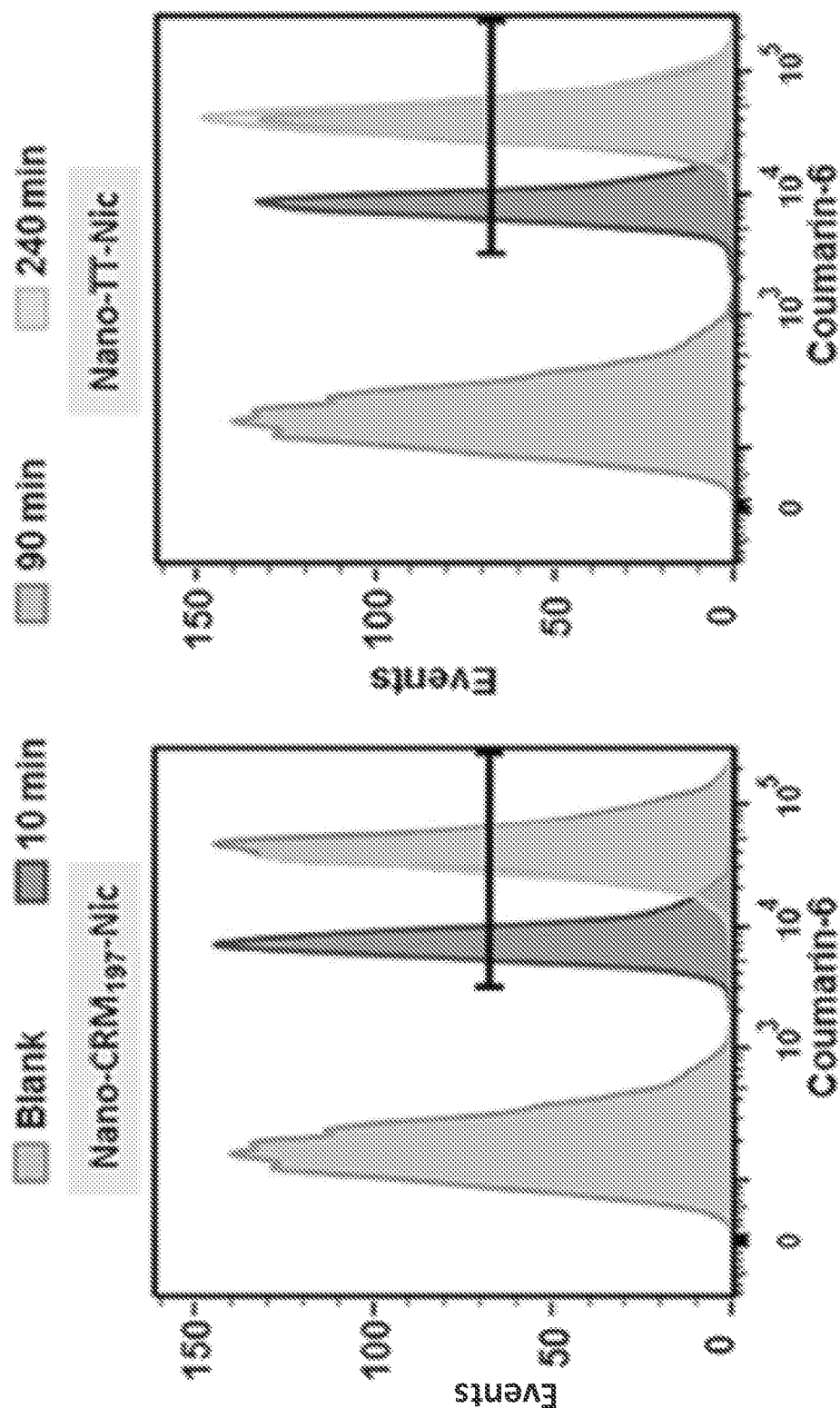

In this Example, potent stimulating proteins were incorporated into NanoNicVac to boost the immunological efficacy. Specifically, four candidate proteins, keyhole limpet hemocyanin (KLH) multimer, [19] KLH subunit (KS), [20] cross-reacting material ($CRM_{197}$), [21] and tetanus toxoid (TT), [22] all of which have been reported to be highly-immunogenic and widely used as stimulating proteins, were conjugated to NanoNicVac to study the impact of stimulating proteins on the immunogenicity and pharmacokinetic efficacy of NanoNicVac. NanoNicVac with different stimulating proteins (FIG. 52) were prepared and characterized. The cellular uptake and processing of NanoNicVac particles were studied in dendritic cells. The immunogenicity and efficacy of NanoNicVac were tested in mice. The results showed that a boosted immunological efficacy was achieved by the conjugation of $CRM_{197}$ or TT, making NanoNicVac be a promising candidate against nicotine addiction.

Materials and Methods

Materials

Lactel® (50:50 poly(lactic-co-glycolic acid) (PLGA)) was purchased from Durect Corporation (Cupertino, Calif., USA). 1,2-Dioleoyl-3-trimethylammonium-propane (DOTAP), cholesterol (CHOL), 1,2-diphytanoyl-sn-glycero-3-phosphoethanolamine-N-(7-nitro-2-1,3-benzoxadiazol-4-yl) (ammonium salt) (NBD-PE), and 1,2-distearoyl-snglycero-3-phosphoethanolamine-N-[maleimide (polyethylene glycol)-2000] (ammonium salt) (DSPE-PEG2000-maleimide) were purchased from Avanti Polar Lipids (Alabaster, Ala., USA). 0-Succinyl-3'-hydroxymethyl-(±)-nicotine (Nic) was purchased from Toronto Research Chemicals (North York, ON, Canada). KLH multimer, KLH subunit, Alexa Fluor® 647 NHS ester (AF647), Fluor® 350 NHS ester (AF350), 1-Ethyl-3-[3-dimethylaminopropyl] carbodiimide hydrochloride (EDC), and N-hydroxysulfosuccinimide (Sulfo-NHS) were purchased from Thermo Fisher Scientific (Rockford, Ill., USA). TT was purchased from Statens Serum Institut (Copenhagen, Denmark). $CRM_{197}$ was a gift from Fina Biosolutions (Rockville, Md., USA). All other chemicals were of analytical grade.

Fabrication of Lipid-Polymeric Hybrid Nanoparticles

PLGA nanoparticles were fabricated using a nanoprecipitation method. In brief, 60 mg of PLGA was dissolved in 3 ml of acetone to form the organic phase. The PLGA-in-acetone solution was injected perpendicularly into 10 ml of 0.5% (w/v) PVA aqueous solution by a vertically mounted syringe pump with magnetic stir agitation (1200 rpm). The resultant suspension was continuously stirred under vacuum for 6 hours to eliminate acetone. PLGA nanoparticles were collected by centrifugation at 10,000 g, 4° C. for 45 min.

Liposomes were fabricated with a hydration-sonication method. In brief, 15 mg of lipid mixture, which was composed of DOTAP, DSPE-PEG2000-maleimide, and CHOL at a molar ratio of 90:5:5, was placed under vacuum to form a lipid film. The film was hydrated with 1 mL of pre-heated 0.01 M phosphate buffer saline (PBS). The resultant suspension was sonicated for 2 min to form liposomes.

Lipid-polymeric hybrid nanoparticles were assembled by coating liposomes onto PLGA nanoparticles using a sonication method. In brief, 15 mg of liposomes in PBS (3 mg/mL) was mixed with 60 mg of PLGA nanoparticles. The mixture was sonicated using a Branson 1800 Ultrasonic Cleaner for 8 min. The resultant lipid-polymeric hybrid nanoparticles were collected by centrifugation at 10,000 g, 4° C. for 30 min.

Synthesis and Characterization of Nic-Stimulating Protein Conjugates

Nic-stimulating protein conjugates (Nic-KLH, Nic-KS, Nic-$CRM_{197}$, and Nic-TT) were synthesized using an EDC/NHS-mediated reaction. In brief, an appropriate amount of Nic-haptens was dissolved in 0.5 mL activation buffer (0.1 M MES, 0.5 M NaCl, pH 6.0). EDC and NHS (EDC:NHS:Nic-hapten=10:10:1) were subsequently added. The mixture was incubated at room temperature for 30 min to activate Nic-haptens. Ten mg of stimulating proteins that were dissolved in 3 mL of coupling buffer (0.1 M PBS, pH 7.4) were mixed with the activated Nic-haptens. The reaction was allowed to proceed for 10 hours, and unconjugated Nic-haptens were eliminated by dialysis. The Nic-hapten loading in Nic-stimulating protein conjugates were estimated by a 2,4,6-trinitrobenzene sulfonic acid (TNBSA)-based method. [11] In brief, stimulating proteins and Nic-stimulating protein conjugates were prepared at a concentration of 1 mg/mL. Two hundred μL of the protein solution was mixed with 200 μL of 4% $NaHCO_3$ solution. Two hundred μL of 0.1% TNBSA solution was added to the mixture and incubated at 37° C. for 1 h, and the absorbance was read at 335 nm. Glycine was used an amino standard. Hapten density was calculated from the differences between the O.D. of the control and the conjugates.

Assembly of NanoNicVac Particles

NanoNicVac were assembled by a thiol-maleimide-mediated reaction. In brief, an appropriate amount of Traut's reagent was added to 6 mg of Nic-stimulating protein conjugates that were dissolved in 2 mL of 0.01 M PBS. The mixture was incubated at room temperature for 1 h to form thiolated Nic-stimulating protein conjugates. The activated conjugates were added to 75 mg of lipid-polymeric hybrid nanoparticles and incubated for 2 hours. NanoNicVac nanoparticles were separated by centrifugation at 10,000 g, 4° C. for 30 min. Unconjugated Nic—stimulating protein conjugates in the supernatants were quantified by the bicinchoninic acid assay.

Characterization of Nanoparticles

The morphology of nanoparticles was characterized by transmission electron microscopy (TEM). Nanoparticles were negatively stained with 1% phosphotungstic acid and imaged on a JEM 1400 transmission electron microscope. The conjugation of protein antigens to the surface of hybrid nanoparticles was verified by confocal laser scanning microscopy (CLSM). Fluorescent NanoNicVac particles, in which the PLGA core, lipid-shell, and stimulating proteins were labeled by Nile Red, NBD, and AF350, respectively, were imaged on a Zeiss LSM 510 laser scanning microscope. The average size and zeta-potential of nanoparticles were measured on a Malvern Nano ZS Zetasizer.

In Vitro Study of the Uptake and Processing of NanoNicVac by DCs

JAWSII (ATCC® CRL-11904™) immature dendritic cells were cultured in alpha minimum essential medium supplemented with 5 ng/mL murine GM-CSF and fetal bovine serum (20%) at 37° C. with 5% $CO_2$. Coumarin-6 (CM-6)-labeled NanoNicVac nanoparticles were prepared by encapsulating 1% (w/w) CM-6 in the PLGA core during the nanoprecipitation process. AF647-labeled NanoNicVac particles were fabricated by conjugating AF647-stimulating protein conjugates to nanoparticles. The uptake of NanoNicVac particles was quantitatively studied by flow cytometry assay (FCA). In brief, cells ($2\times10^6$/well) were seeded into 6-well plates and cultured overnight. Cells were treated with 50 µg of CM-6-labeled NanoNicVac particles for 10, 90, or 240 min. The medium was removed, and the cells were washed three times using PBS. Cells were detached from plates by trypsinization and re-suspended in PBS. Samples were immediately analyzed on a FACSAria I flow cytometer. The uptake and processing of NanoNicVac particles were qualitatively studied by CLSM. In brief, cells ($2\times10^5$/chamber) were seeded into 2-well chamber slides and cultured overnight. Cells were treated with 50 µg of AF647-labeled NanoNicVac particles for 10 or 90 min. At 90 min, the medium containing NPs were replaced with fresh medium, and the cells were continuously incubated until 240 min. Cells were fixed with 4% (w/v) paraformaldehyde. The nuclei of cells were stained by DAPI according to a standard protocol provided by the supplier. Cells were imaged on a Zeiss LSM 510 laser scanning microscope.

In Vivo Study of the Immunogenicity and Efficacy of NanoNicVac in Mice Female Balb/c mice (6-7 weeks, 5-6 per group) were immunized with nicotine vaccines or blank (PBS) on days 0, 14, and 28. For NanoNicVac groups, mice were injected with 200 µL of nanovaccines (Nano-KLH-Nic, Nano-KS-Nic, Nano-CRM$_{197}$-Nic, and Nano-TT-Nic) containing 25 µg of protein antigens. For the Nic-TT conjugate group, mice were immunized with a mixture of 25 µg Nic-TT and 40 µg Alum that were dissolved in 200 µL of PBS. For the blank group, mice were injected with 200 µL of sterilized PBS. Blood samples were collected on days 0, 12, 26, and 40.

Titers of anti-nicotine antibody, anti-nicotine IgG subclass antibody (IgG1, IgG2a, IgG2b, and IgG3), and anti-stimulating protein antibody in the serum were assayed by an enzyme-linked immunosorbent assay (ELISA) using a method reported previously. [12] Antibody titer was defined as the dilution factor at which absorbance at 450 nm dropped to half maximal.

The affinity and specificity of anti-nicotine antibodies induced by nicotine vaccines were estimated by a competition ELISA method. In brief, serum samples were diluted to a factor at which the absorbance at 450 nm was around 1.0. Inhibitors (nicotine, cotinine, nornicotine, nicotine-N-oxide, and acetylcholine) with concentrations of $10^{-2}$ to $10^{-6}$ M were serially prepared. Inhibitor samples were added to plates that were coated with Nic-BSA, and serum samples were subsequently added. The following steps were the same as in measuring anti-nicotine antibody titers. Percent inhibition was calculated at each inhibitor concentration, and the concentration at which 50% inhibition was achieved ($IC_{50}$) was determined. Pooled serum samples were used for specificity estimation.

The pharmacokinetic efficacy of nicotine nanovaccines in blocking nicotine from entering the brain of mice was conducted using a method reported previously. Balb/c mice (6-7 weeks, 5-6 per group) were immunized as described in the previous context. On day 42, mice were dosed 0.06 mg/kg of nicotine subcutaneously. After 3 mins, mice were sacrificed, and the brain and blood tissues were collected. The nicotine levels in the brain and serum samples were measured using a GC/MS method as reported previously.

[23]

Assessment of the Safety of NanoNicVac by Histopathological Examination

On day 42, major organs of immunized mice, including heart, liver, spleen, kidney, and lung, were extracted and stored in 10% formalin. The organs were processed by a hematoxylin and eosin staining method. Tissue blocks were imaged on a Nikon Eclipse E600 light microscope.

Statistical Analysis

Data were expressed as means±standard error of the mean (MSE) unless specified. Comparisons among multiple groups were conducted with one-way ANOVA followed by Tukey's HSD test. Differences were considered significant when p-values were less than 0.05.

Results

Morphological and Physicochemical Properties of NanoNicVac Conjugated with Different Stimulating Proteins.

CLSM was applied to characterize the structure of NanoNicVac nanoparticles conjugated with different stimulating proteins. The PLGA core, lipid shell, and stimulating proteins were labeled by Nile Red, NBD, and AF-350, respectively. The co-localization of red, green, and blue fluorescence on most of the particles (FIGS. 53A-53D and FIGS. 54A-54L) suggested the successful and efficient assembly of NanoNicVac particles. The morphology of nanoparticles was characterized by TEM. As shown in FIGS. 54A-54F, a "core-shell" structure was shown on lipidpolymeric (LP) hybrid nanoparticles. Upon conjugation of Nic-stimulating protein conjugates, a dark layer, which was formed by protein antigens, was observed on all four NanoNicVac nanoparticles. This further verified the efficient conjugation of protein antigens to hybrid nanoparticle surface.

The physicochemical properties of NanoNicVac were also characterized. As shown in FIG. 2 all four NanoNicVac nanoparticles exhibited narrow size distributions. This narrow size distribution is in concordance with the uniform size shown in the TEM images (FIGS. 55A-55F) and the low PDI indexes (FIG. 72). Specifically, the average size of Nano-KLH-Nic (167.2 nm) and Nano-KS-Nic (153.2 nm) was slightly larger than that of Nano-CRM197-Nic (125.2 nm) and Nano-TT-Nic (136.6 nm) (FIG. 72). The four NanoNicVac nanoparticles, regardless of stimulating proteins, were negatively charged (indicated by the negative zeta-potentials shown in FIG. 72), which was probably caused by the conjugation of negatively-charged Nic-stimulating protein conjugates. The conjugation efficiency of Nic-stimulating protein conjugates was 87.6±7.9%, 83.2±11.3%, 90.0±7.6%, and 84.3±9.4% for Nano-KLH-Nic, Nano-KS-Nic, Nano-CRM197-Nic, and Nano-TT-Nic, respectively (FIG. 72). Meanwhile, the loading contents of Nic-haptens on NanoNicVac particles were 0.88±0.07, 0.93±0.12, 0.84±0.07, and 0.81±0.09 µg Nic/mg nanoparticle, respectively. This suggested that the four NanoNicVac nanoparticles had similar hapten loading contents.

Cellular Uptake and Processing of NanoNicVac by Dendritic Cells.

Figure 57:
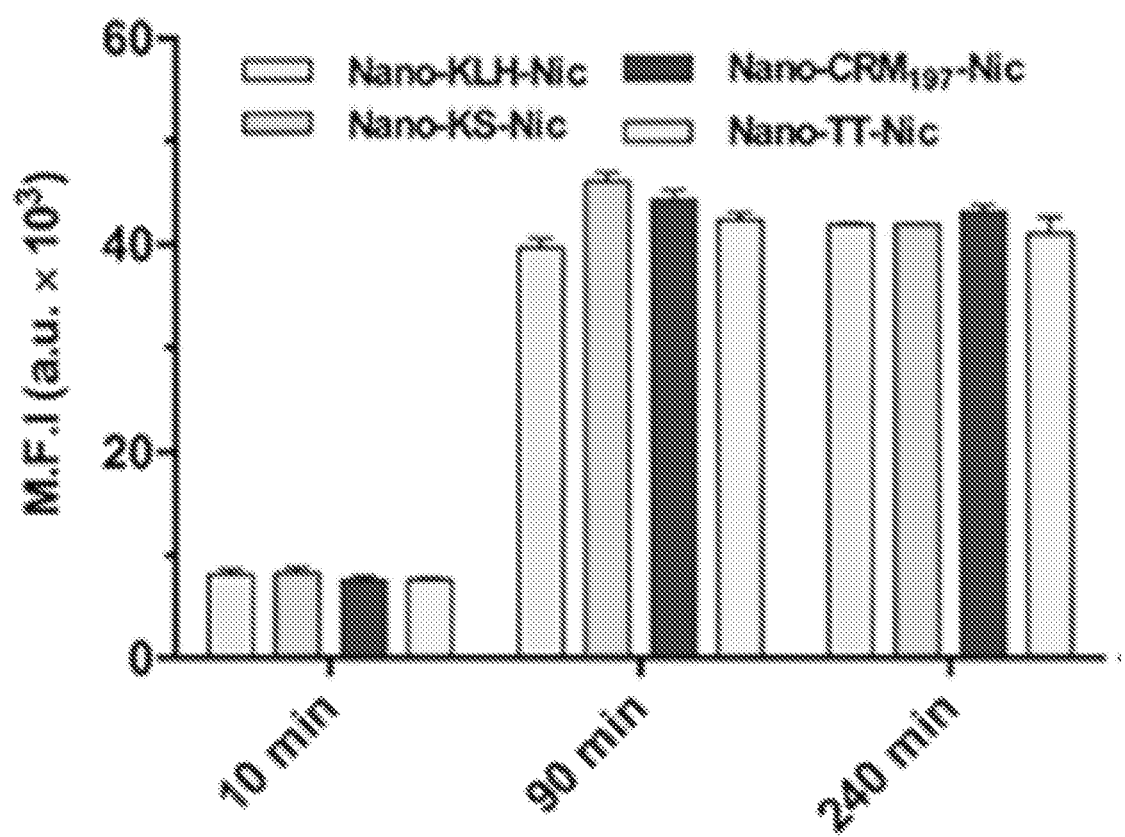
FIG. 57 shows a graph demonstrating the M.F.I. of CM-6 fluorescence in cells treated with CM-6 labeled NanoNicVac nanoparticles for 10, 90, and 240 min, which evidences cellular uptake and processing of NanoNicVac conjugated with different stimulating proteins.

The uptake efficiency of NanoNicVac nanoparticles by dendritic cells were studied by FCA. As shown in FIGS. 56A-56D, >95.3% of the studied cells had taken up nanoparticles in all four NanoNicVac groups after being incubated with nanoparticles for 10 min. This revealed that NanoNicVac nanoparticles could be internalized by dendritic cells efficiently in a short period of time. As shown in FIG. 57, indicated by the significantly increased mean fluorescence intensity (M. F. I.) of CM-6, NanoNicVac nanoparticles were continuously internalized from 10 to 90 min. However, the M. F. I. of CM-6 at 240 min was similar to that at 90 min, suggesting that the uptake of NanoNicVac was saturated after 90 min. Meanwhile, all four NanoNicVac, regardless of stimulating proteins, had a similar cellular uptake efficiency, as they exhibited comparable M. F. I. of CM-6 at all the studied time points.

Figures 58A, 58B, 58C:
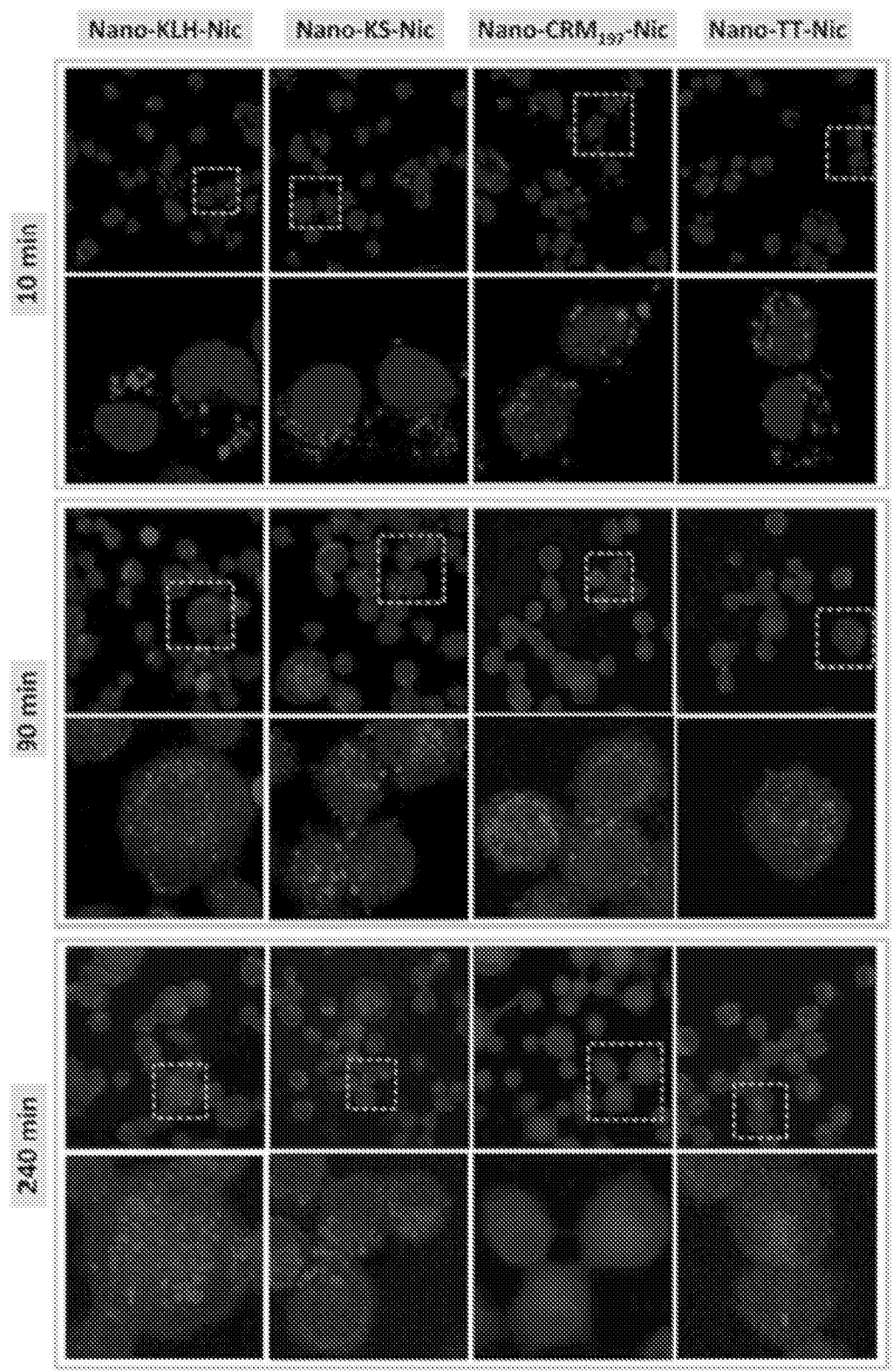
FIGS. 58A-58C show panels of images demonstrating processing of protein antigens carried by NanoNicVac particles. Protein antigens on NanoNicVac particles were labeled by AF647. Cells were treated with NanoNicVac particles for 10 (FIG. 58A) or 90 (FIG. 58B) min. The medium containing particles were replaced with fresh medium at 90 min, and cells were continuously incubated until 240 min (FIG. 58C).

The processing of stimulating proteins carried by NanoNicVac was studied using CLSM (FIGS. 58A-58C). The stimulating proteins on NanoNicVac particles were labeled by AF647. At 10 min, the AF647 fluorescence displayed as individual dots in cells, revealing that the stimulating proteins had not been processed. At 90 min, a substantial amount of AF647 fluorescence was found to spread throughout the cells. This suggested that the stimulating proteins began to be processed to small peptidic antigens. At 240 min, a substantial percent of AF647 fluorescence was still observed to display as individual dots in the Nano-KLH-Nic and Nano-KS-Nic groups, indicating the KLH and KS stimulating proteins had not been completely processed. Interestingly, less red individual dots were found in cells treated with Nano-$CRM_{197}$-Nic and Nano-TT-Nic, suggesting that the $CRM_{197}$ and TT stimulating proteins were efficiently processed to small peptidic antigens. NanoNicVac conjugated with $CRM_{197}$ and TT appeared to be processed more efficiently than that conjugated with KLH and KS.

Immunogenicity of NanoNicVac Conjugated with Different Stimulating Proteins Against Nicotine.

Figure 59:
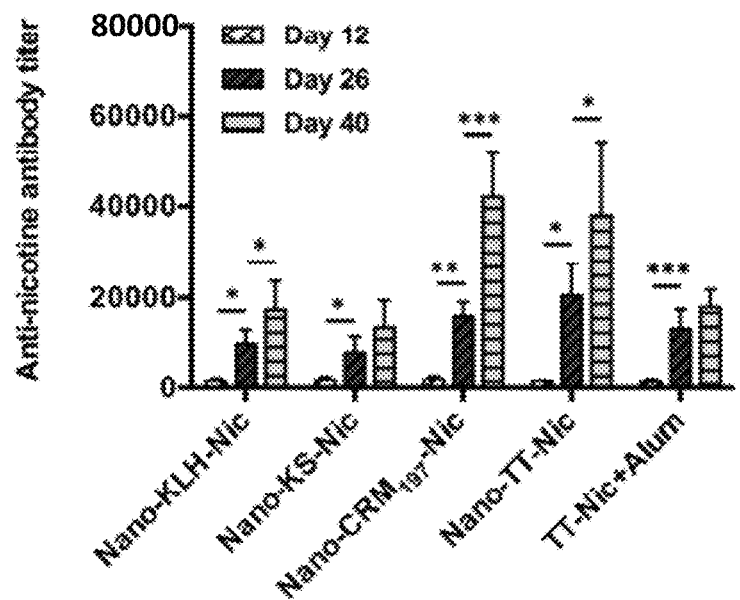
FIG. 59 shows a graph demonstrating a time-course of the anti-nicotine antibody titers induced by NanoNicVac. Significantly different: * $p<0.05$,  $p<0.01$, * $p<0.001$.
Figure 60:
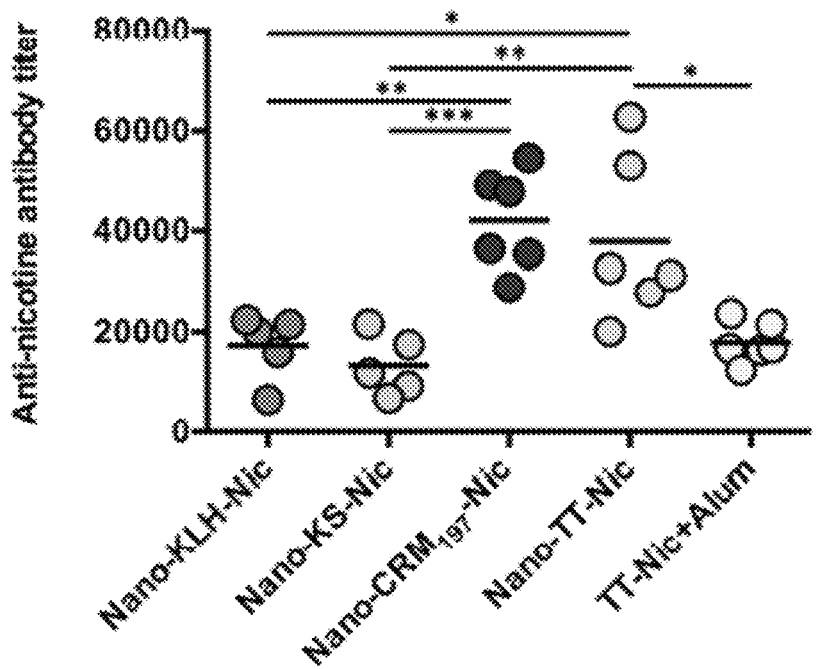
FIG. 60 shows a graph demonstrating end-point anti-nicotine antibody titers of individual mice on day 40. Significantly different: * $p<0.05$,  $p<0.01$, * $p<0.001$.

The immunogenicity of NanoNicVac against nicotine was tested in Balb/c mice. As shown in FIG. 59, comparable anti-nicotine antibody titers were found in all the nicotine vaccine groups 12 days after the primary immunization (on day 12). The anti-nicotine antibody levels significantly increased in all vaccine groups 12 days after the first booster immunization (on day 26). Twelve days after the second booster immunization (on day 40), the anti-nicotine antibody titers increased by $7.5 \times 10^3$, $5.6 \times 10^3$, $26.3 \times 10^3$, $17.5 \times 10^3$, and $4.8 \times 10^3$ in Nano-KS-Nic, Nano-$CRM_{197}$-Nic, Nano-TT-Nic, and Nic-TT+alum groups, respectively, compared to that on day 26. The second booster immunization boosted antibody titers in the groups of Nano-$CRM_{197}$-Nic and Nano-TT-Nic more remarkably than in the other groups. The end-point anti-nicotine antibody titers of individual mice on day 40 were shown in FIG. 60. Compared to TT-Nic+alum, Nano-TT-Nic induced a significantly higher antinicotine antibody titer ($p<0.05$). This suggested that conjugating hapten-protein conjugates to hybrid nanoparticle surface would enhance the immunogenicity of the conjugate nicotine vaccine. The titers of Nano-$CRM_{197}$-Nic and Nano-TT-Nic were comparable ($p>0.91$), and were significantly higher than that of Nano-KLH-Nic and Nano-KS-Nic ($p<0.05$). This indicated NanoNicVac conjugated with $CRM_{197}$ and TT had an enhanced immunogenicity against nicotine over NanoNicVac carrying KLH or KS.

Subclass distribution of anti-nicotine IgG antibodies elicited by NanoNicVac

Figure 61:
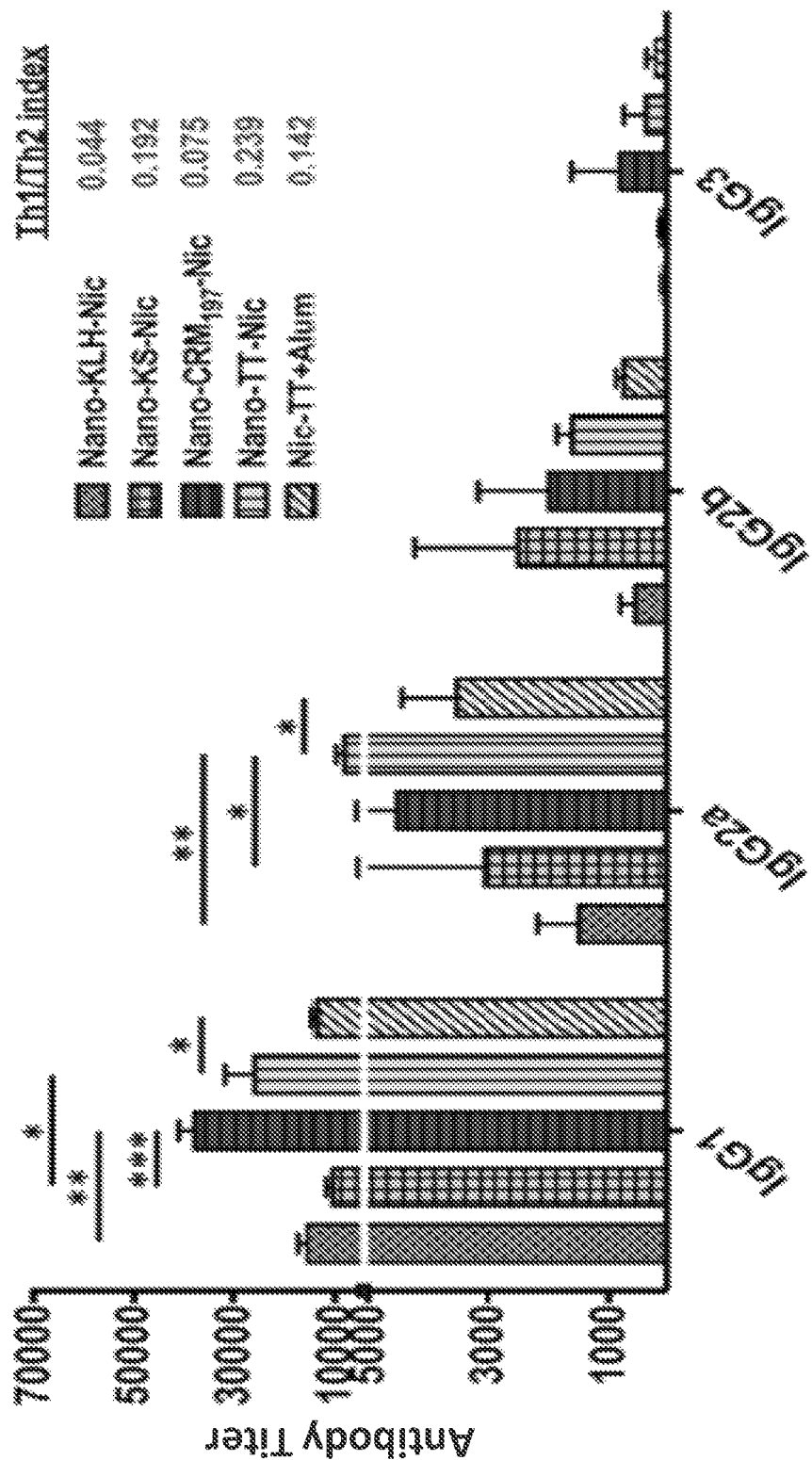
FIG. 61 shows a graph demonstrating titers of anti-nicotine IgG subclass antibodies and the Th1/Th2 indexes induced by NanoNicVac on day 40. Significantly different: * $p<0.05$,  $p<0.01$, * $p<0.001$.

The titers of anti-nicotine IgG subclass antibodies on day 40 were assayed and presented in FIG. 61. For all vaccine groups, IgG1 and IgG3 were the most and least dominant subtypes, respectively. Compared to Nic-TT conjugate vaccine, Nano-TT-Nic resulted in higher titers of all four IgG subtypes, especially IgG1 and IgG2a, which is consistent with our previous reports. [12] Nano-$CRM_{197}$-Nic and Nano-TT-Nic induced higher levels of IgG1, IgG2a, and IgG3 than Nano-KLH-Nic and Nano-KS-Nic. Specifically, Nano-$CRM_{197}$-Nic generated a highest IgG1 titer among the four NanoNicVac vaccines. The IgG1 titer of Nano-$CRM_{197}$-Nic was significantly higher than that of Nano-KLH-Nic and Nano-KS-Nic ($p<0.01$). Nano-TT-Nic induced a highest IgG2a titer among the four NanoNicVac vaccines. And the IgG2a titer of Nano-TT-Nic was significantly higher than that of Nano-KLH-Nic and Nano-KS-Nic ($p<0.05$). Interestingly, although the overall IgG titer of Nano-KLH-Nic is slightly higher than that of Nano-KS-Nic (FIG. 60), Nano-KLH-Nic had a higher IgG1 titer but lower IgG2a and IgG2b titers compared to Nano-KS-Nic. The Th1/Th2 indexes were 0.044, 0.192, 0.075, 0.239, and 0.142 for Nano-KLH-Nic, Nano-KS-Nic, Nano-$CRM_{197}$-Nic, Nano-TT-Nic, and Nic-TT+alum, respectively. All the values were considerably less than 1, indicating that the immune responses induced by all the nicotine vaccines were skewed toward Th2 (humoral response). Interestingly, the indexes of Nano-TT-Nic and Nano-KS-Nic were considerably larger than that of Nano-KLH-Nic and Nano-$CRM_{197}$-Nic, indicating that Nano-TT-Nic and Nano-KS-Nic resulted in more balanced Th1/Th2 responses than Nano-KLH-Nic and Nano-$CRM_{197}$-Nic.

Anti-Stimulating Protein Antibody Levels Induced by NanoNicVac Carrying Different Stimulating Proteins.

Figure 62:
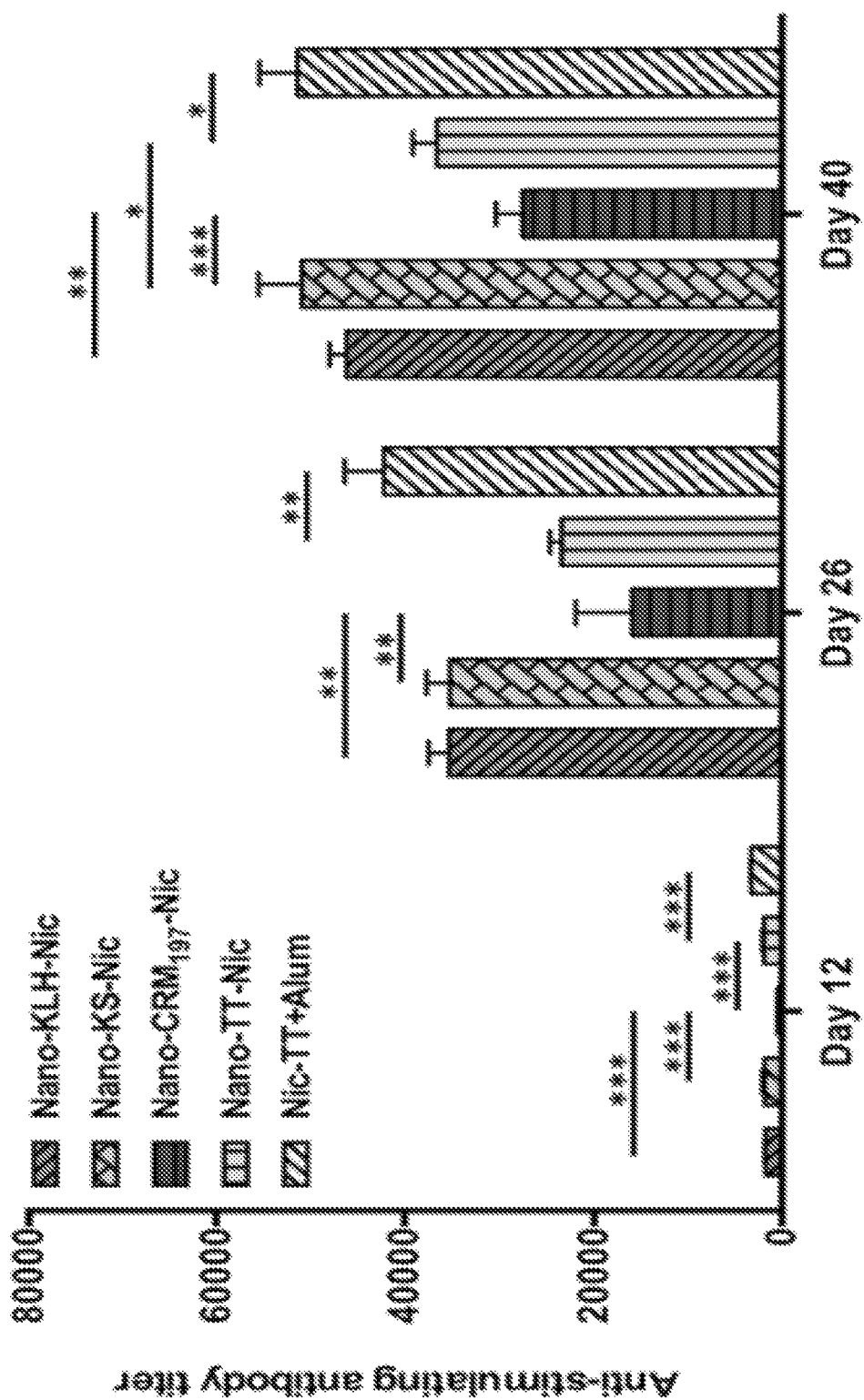
FIG. 62 shows a graph demonstrating a time-course of anti-stimulating protein antibody titers induced by NanoNicVac with different stimulating proteins. Significantly different: * $p<0.05$,  $p<0.01$, * $p<0.001$.

The anti-stimulating protein antibody titers were assayed and shown in FIG. 62. Similar to anti-nicotine antibody titers, the anti-stimulating protein antibody titers were increased after each immunization. On day 12, the anti-stimulating protein antibody titers were $(1.8\pm0.1)\times10^3$, $(1.9\pm0.2)\times10^3$, $(0.5\pm0.1)\times10^3$, $(1.9\pm0.1)\times10^3$, and $(3.3\pm0.1)\times10^3$, for Nano-KLH-Nic, Nano-KS-Nic, Nano-$CRM_{197}$-Nic, Nano-TT-Nic, and Nic-TT+alum, respectively. On day 26, the titers increased to be $(35.3\pm2.2)\times10^3$, $(35.2\pm2.5)\times10^3$, $(16.0\pm6.0)\times10^3$, $(23.5\pm12.8)\times10^3$, and $(42.2\pm4.2)\times10^3$, respectively. On day 40, the titers further aclined to be $(46.2\pm1.8)\times10^3$, $(50.9\pm4.6)\times10^3$, $(27.5\pm0.2.9)\times10^3$, $(36.6\pm2.5)\times10^3$, and $(51.4\pm4.0)\times10^3$, respectively. On all the studied days, Nano-TT-Nic induced significantly lower anti-stimulating protein antibody titers compared to Nic-TT+alum ($p<0.05$).

Among the four NanoNicVac carrying different stimulating proteins, Nano-$CRM_{197}$-Nic and Nano-TT-Nic elicited considerably lower anti-stimulating protein levels than Nano-KLH-Nic and Nano-KS-Nic, especially on days 26 and 40.

Affinity of Anti-Nicotine Antibodies Generated by NanoNicVac.

Figure 63:
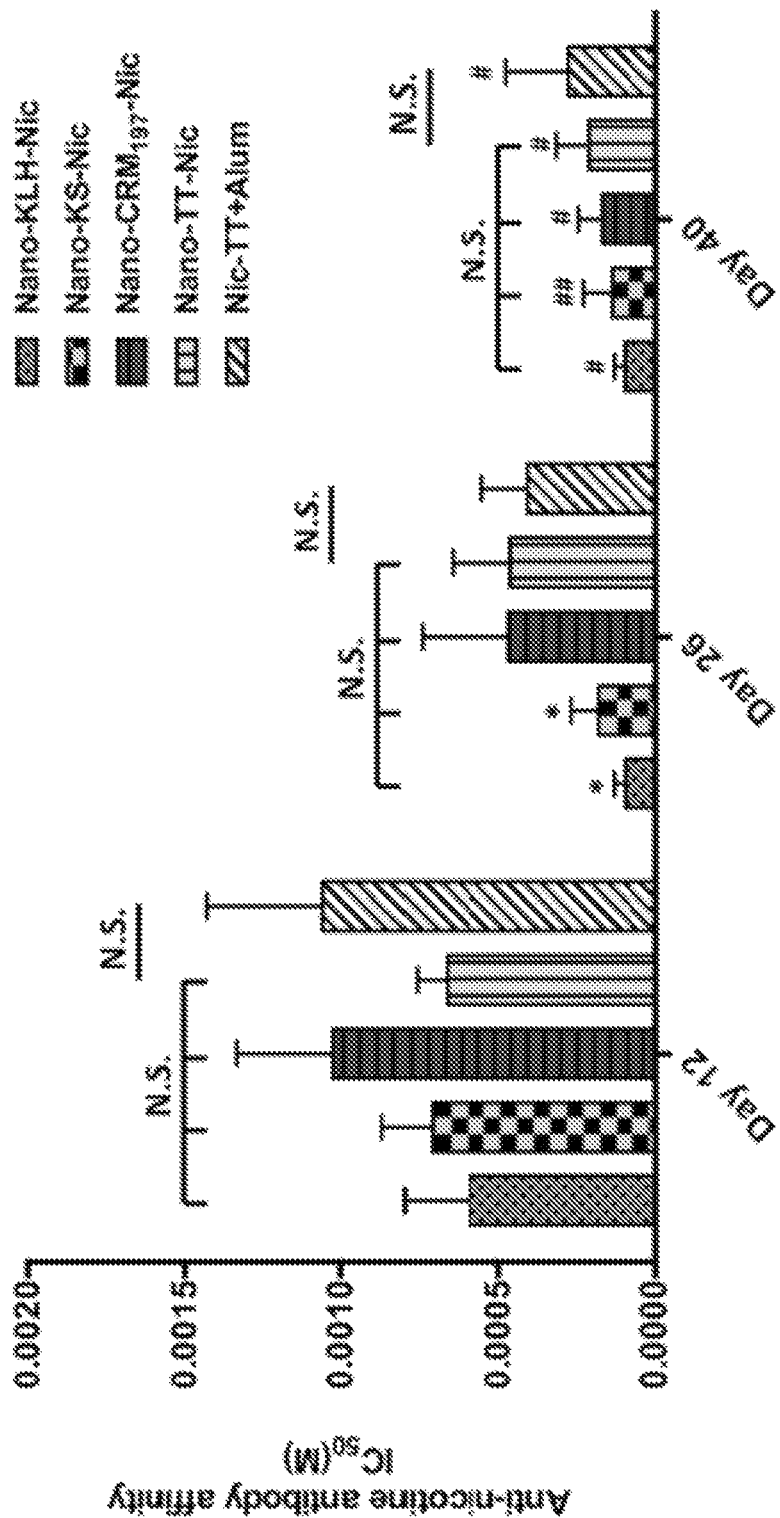
FIG. 63 shows a graph demonstrating the affinity of anti-nicotine antibodies induced by nicotine vaccines estimated by competition ELISA. N.S. indicated no significant differences were found among groups ($p>0.55$).
Figure 64:
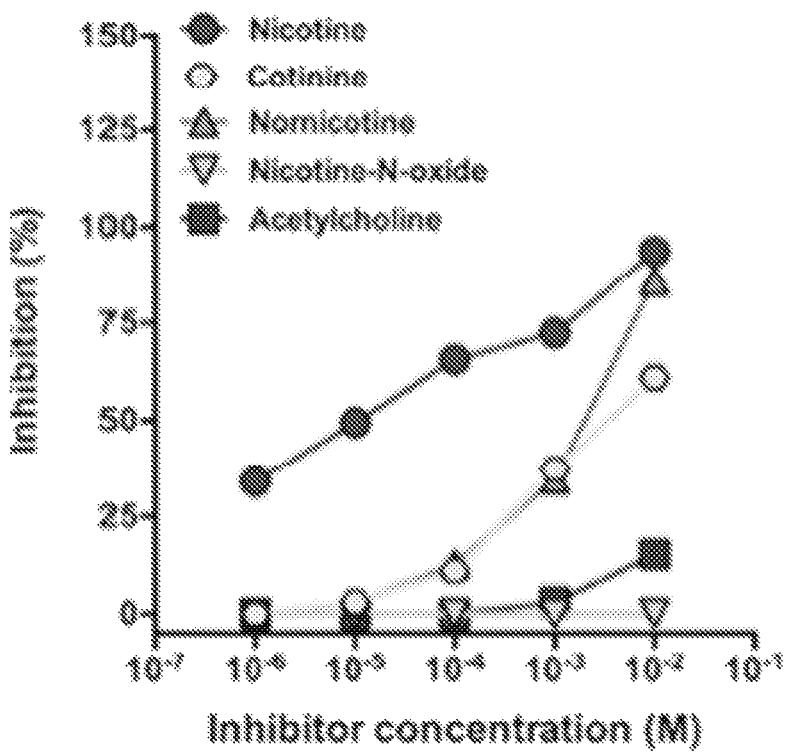
FIG. 64 shows a graph demonstrating the specificity of anti-nicotine antibodies induced by NanoNicVac conjugated with KLH as tested by inhibition with different inhibitors. Does-dependent inhibitions of nicotine binding by various inhibitors in Nano-KLH-Nic were estimated by competition ELISA.
Figure 65:
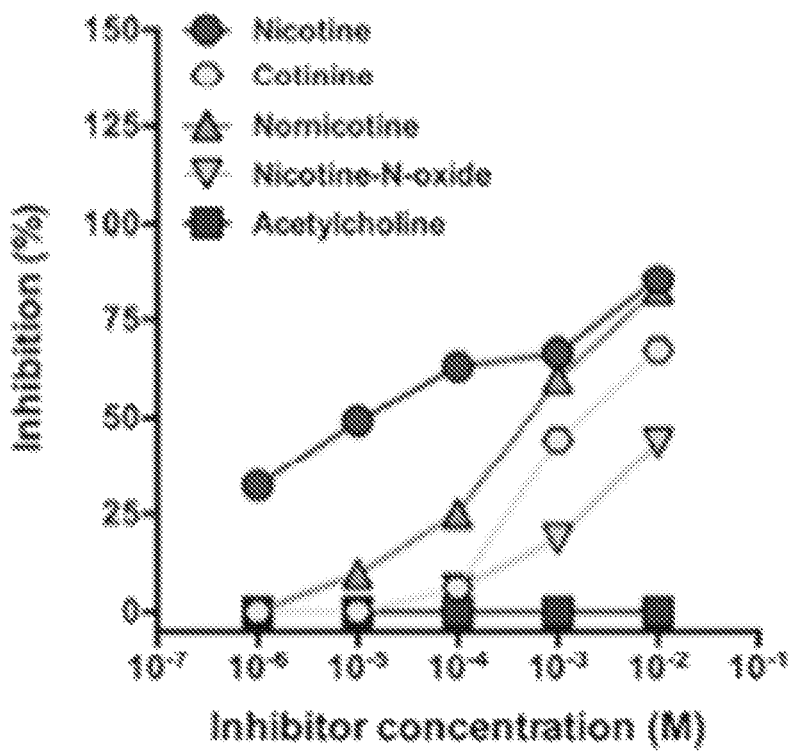
FIG. 65 shows a graph demonstrating the specificity of anti-nicotine antibodies induced by NanoNicVac conjugated with KS as tested by inhibition with different inhibitors. Does-dependent inhibitions of nicotine binding by various inhibitors in Nano-KS-Nic were estimated by competition ELISA.
Figure 66:
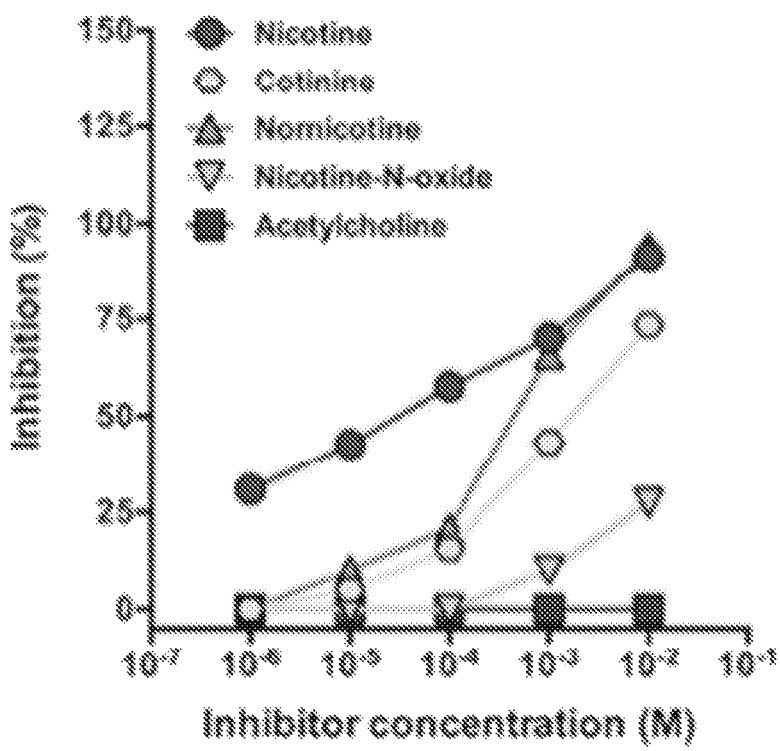
FIG. 66 shows a graph demonstrating the specificity of anti-nicotine antibodies induced by NanoNicVac conjugated with $CRM_{197}$ as tested by inhibition with different inhibitors. Does-dependent inhibitions of nicotine binding by various inhibitors in Nano-$CRM_{197}$-Nic were estimated by competition ELISA.
Figure 67:
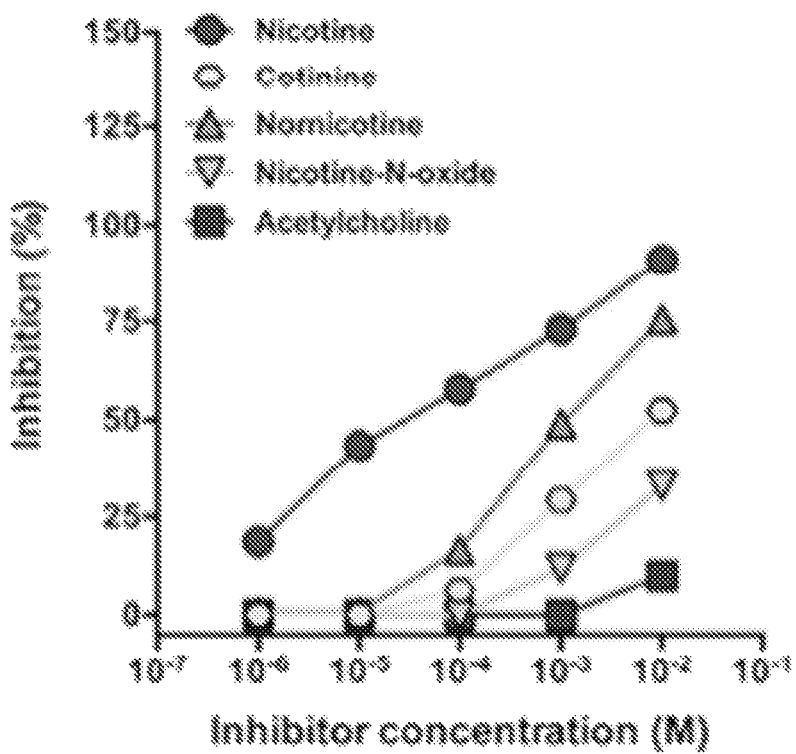
FIG. 67 shows a graph demonstrating the specificity of anti-nicotine antibodies induced by NanoNicVac conjugated with TT as tested by inhibition with different inhibitors. Does-dependent inhibitions of nicotine binding by various inhibitors in Nano-TT-Nic were estimated by competition ELISA.

The affinity of anti-nicotine antibodies elicited by NanoNicVac carrying different stimulating proteins was estimated by competition ELISA on days 12, 26, and 40 (FIG. 63). The affinity of antibodies was increased after each immunization in all the nicotine vaccine groups, except that the affinity in the Nano-KLH-Nic group slightly decreased after the second booster immunization. On day 40, the $IC_{50}$ of nicotine was 96±35, 137±92, 167±78, 212±103, and 277±199 μM for Nano-KLH-Nic, Nano-KS-Nic, Nano-$CRM_{197}$-Nic, Nano-TT-Nic, and Nic-TT+alum, respectively. The antibodies induced by Nano-TT-Nic had a comparable affinity to that elicited by Nic-TT+alum ($p>0.99$). Nano-KLH-Nic resulted in a highest average antibody affinity, but the differences among the four NanoNicVac were not significant ($p>0.92$). Interestingly, the maturation of anti-nicotine antibody affinity exhibited different patterns in the four NanoNicVac groups. Specifically, the maturation of antibody affinity in the Nano-KLH-Nic and Nano-KS-Nic groups was significantly completed after the first booster immunization, and the second booster immunization did not remarkably enhance the antibody affinity. In contrast, the anti-nicotine antibody affinity was gradually matured in the Nano-$CRM_{197}$-Nic and Nano-TT-Nic groups, and both the first and second booster immunizations remarkably promoted the affinity maturation.

Specificity of Anti-Nicotine Antibodies Elicited by NanoNicVac.

Figures 68, 69:
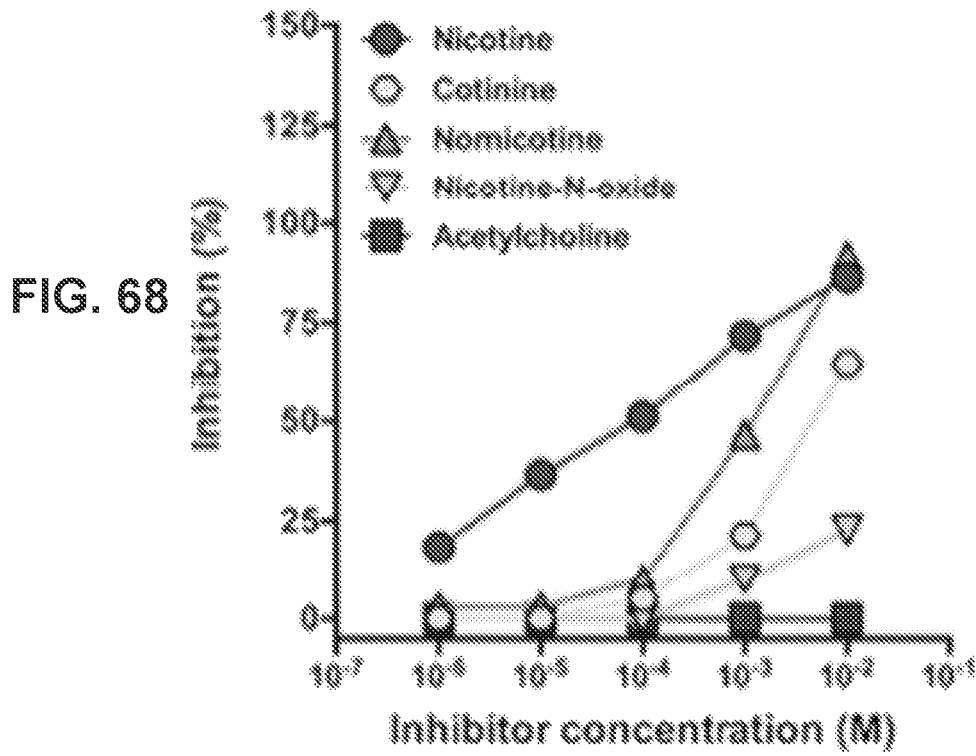
FIG. 68 shows a graph demonstrating the specificity of anti-nicotine antibodies induced by Nic-TT conjugate vaccine as tested by inhibition with different inhibitors. Does-dependent inhibitions of nicotine binding by various inhibitors in Nic-TT+alum were estimated by competition ELISA.
FIG. 69 shows a table demonstrating the percent ligand cross-reactivity defined as ($IC_{50}$ of nicotine/$IC_{50}$) of inhibitors).

The specificity of anti-nicotine antibodies on day 40 was assayed by competition ELISA. The dose-dependent inhibitions of nicotine binding by nicotine metabolites (cotinine, nornicotine, and nicotine-N-oxide) and endogenous nicotine receptor ligand (acetylcholine) were shown in FIGS. 64-68. As shown in FIGS. 64-68, in all the nicotine vaccine groups, the anti-nicotine antibodies had the highest relative affinity to nicotine. A somewhat lower affinity was detected to the inactive nicotine metabolite (cotinine) and active but minor nicotine metabolite (nornicotine) in all nicotine vaccine groups. Specifically, the cross-reactivity between nicotine and cotinine was less than 2%, and that between nicotine and nornicotine was less than 7%, in all groups (FIG. 69). Meanwhile, the antibodies elicited by all the nicotine vaccines had little affinity to the inactive nicotine metabolite (nicotine-N-oxide) and endogenous nicotine receptor ligand (acetylcholine). The cross-reactivity between nicotine and nicotine-N-oxide/acetylcholine was less than 1% in all groups (FIG. 69). The anti-nicotine antibodies generated by NanoNicVac, regardless of stimulating protein, exhibited high specificity for nicotine.

Figure 70A:
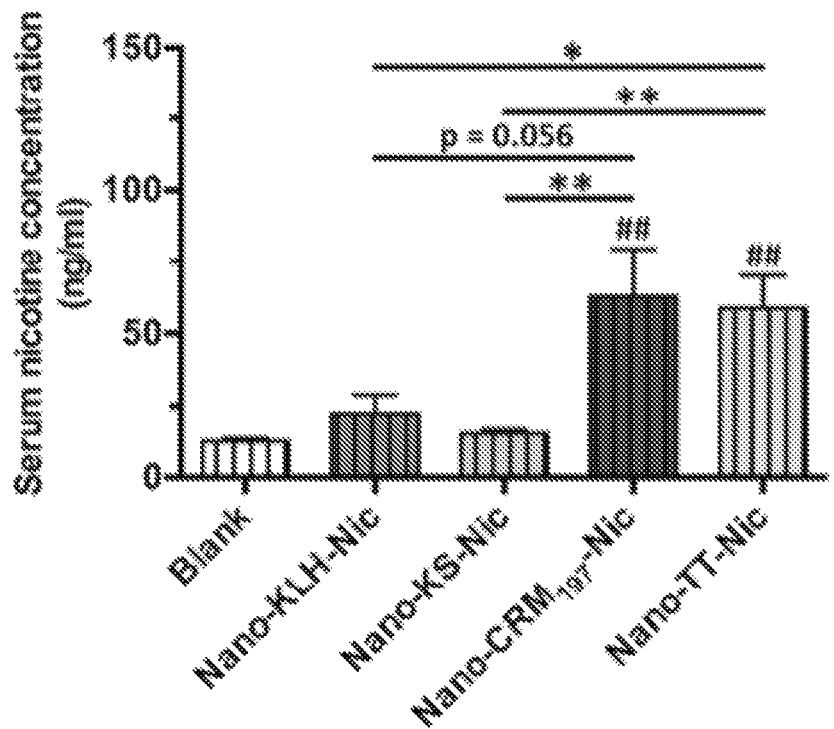
FIGS. 70A-70B show graphs demonstrating pharmacokinetic efficacy of NanoNicVac conjugated with different stimulating proteins. The nicotine levels in the serum (FIG. 70A) and brain (FIG. 70B) of mice were analyzed after challenging the mice with 0.06 mg/kg nicotine subcutaneously for 3 min. Significantly different compared to the blank group: ##$p<0.01$, ###$p<0.001$. Significantly different: * $p<0.05$, ** $p<0.01$.
Figure 70B:
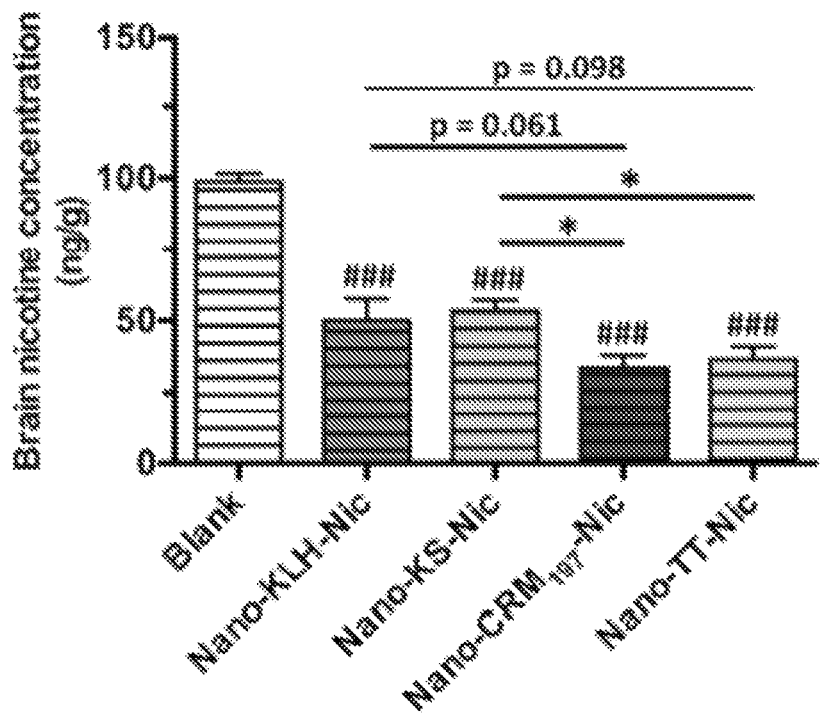

Pharmacokinetic Efficacy of NanoNicVac Conjugated with Different Stimulating Proteins The ability of NanoNicVac in retaining nicotine in serum and blocking nicotine from entering the brain of mice was studied. FIG. 70A shows the serum nicotine levels of mice after being challenged with 0.06 mg/kg nicotine subcutaneously for 3 mins. More nicotine was retained in serum after immunization with NanoNicVac, regardless of stimulating proteins. Compared to that of the blank group, the serum nicotine levels of Nano-KLH-Nic, Nano-KS-Nic, Nano-$CRM_{197}$-Nic, and Nano-TT-Nic increased by 79.2%, 21.6%, 403.7%, and 370.7%, respectively. Nano-$CRM_{197}$-Nic and Nano-TT-Nic exhibited considerably better abilities in sequestering nicotine in the serum of mice than Nano-KLH-Nic and Nano-KS-Nic. The brain nicotine levels of mice after being treated with nicotine were shown in FIG. 70B. NanoNicVac groups, regardless of stimulating proteins, had significantly lower brain nicotine concentrations than the blank group ($p<0.001$). Specifically, the brain nicotine levels reduced by 48.5%, 45.9%, 65.2%, and 63.1% in Nano-KLH-Nic, Nano-KS-Nic, Nano-$CRM_{197}$-Nic, and Nano-TT-Nic groups, compared to that in the blank group. Nano-$CRM_{197}$-Nic and Nano-TT-Nic had a significantly better efficacy in reducing nicotine from entering the brain of mice than Nano-KS-Nic ($p<0.05$). Meanwhile, Nano-$CRM_{197}$-Nic and Nano-TT-Nic also exhibited a considerably better ability in reducing the brain nicotine contents than Nano-KLH-Nic. Overall, NanoNicVac conjugated with $CRM_{197}$ and TT had an enhanced efficacy in sequestering nicotine in serum and blocking nicotine from entering the brain of mice than NanoNicVac conjugated with KLH and KS.

Safety of NanoNicVac Carrying Different Stimulating Proteins

The safety of NanoNicVac was evaluated by histopathological analysis. FIGS. 71A-71Y shows the images of major organs of mice after being treated with the blank (PBS) or NanoNicVac conjugated with different stimulating proteins. No significant differences on all the studied organs were found between the blank group and all NanoNicVac groups. Also, all the NanoNicVac, regardless of stimulating proteins, exhibited similar characteristics on all the major organs. This indicated the four NanoNicVac conjugated with different stimulating proteins did not cause detectable lesions to mouse organs and were relatively safe.

Discussion

Conventional hapten-protein conjugate nicotine vaccines tested in human clinical trials have not proven enhanced overall smoking cessation rate so far.[5-7] In our previous work, we suggested a novel strategy to improve the immunological efficacy of conjugate nicotine vaccines by using biodegradable lipid-polymeric hybrid nanoparticles as delivery vehicles.[12, 13] The hybrid nanoparticle-based nicotine nanovaccine (NanoNicVac) was demonstrated to have a significantly higher immunogenicity than the conjugate nicotine vaccine. In addition, it was demonstrated that the immunogenicity of NanoNicVac could be enhanced by modulating the particle size, hapten density [Example 2 herein], and hapten localization [Example 1 herein]. In this Example, a series of NanoNicVac in which various potent stimulating proteins were conjugated was developed and their physicochemical properties, cellular uptake and processing by immune cells, immunogenicity, and pharmacokinetic efficacy were evaluated. It was demonstrated in this Example that enhanced immunological efficacy could be achieved by conjugating $CRM_{197}$ or TT to NanoNicVac, making NanoNicVac capable of being a next-generation nanoparticle-based immunotherapeutic against nicotine addiction.

The ELISA results revealed that NanoNicVac conjugated with TT (Nano-TT-Nic) exhibited a significantly higher immunogenicity against nicotine over Nic-TT+alum conjugate vaccine even in the absence of alum adjuvant. This data is in agreement with a previous report that Nano-KLH-Nic was more immunogenic against nicotine than the Nic-KLH conjugate. [12] Also, this data further proved our hypothesis that the use of hybrid nanoparticles as delivery vehicles might improve the immunogenicity of conjugate nicotine vaccines. The higher immunogenicity of Nano-TT-Nic over Nic-TT may be attributed to the better recognition and internalization by immune cells. The conjugation of multiple TT-Nic to one hybrid nanoparticle may increase the availability of antigens for uptake, thus contributing to an enhanced antigen internalization. Meanwhile, the immune system prefers to recognize and take up particulate pathogens (such as bacteria and virus) and is relatively invisible to small soluble protein antigens. [24-26] The stable and spherical lipid-polymeric hybrid nanoparticles [27-31] endowed Nano-TT-Nic with a particulate property that is a mimic of particulate pathogens. This particulate nature together with the optimal particle size (~100 nm) is beneficial for the improved recognition and uptake by immune cells. [12, 32]

Efficient uptake and processing of NanoNicVac by antigen presenting cells (like dendritic cells and macrophages) is a prerequisite for the generation of a potent immune response. [5, 33, 34] The in vitro data revealed that NanoNicVac conjugated with different stimulating proteins were similarly taken up but differently processed by dendritic cells. All NanoNicVac developed in this study, regardless of stimulating proteins, were found to be internalized rapidly and efficiently. The rapid and efficient internalization of vaccine particles may provide sufficient amounts of antigens for processing, and thus contributes to the generation of a quick immune response. The CLSM data suggested that Nano-CRM197-Nic and Nano-TT-Nic, especially Nano-$CRM_{197}$-Nic, were processed more efficiently than Nano-KLH-Nic and Nano-KS-Nic. This higher effectiveness of antigen processing may be attributed to the smaller size and lower structural complexity of the $CRM_{197}$ and TT stimulating proteins. KS has a molecular weight of about 400 kDa, and KLH multimer is an assembled form of multiple KS.

[35] Both have a relatively high structural complexity due to the large size. In contrast, CRM197 and TT have a molecular weight of about 150 kDa and about 59 kDa, respectively. The relatively small size makes them have a relatively low structural complexity.[36, 37] Immunological speaking, the generation of an effective humoral immune response involves two T-cell-dependent processes, the formation of T-helper cells and the interaction between B cells and T-helper cells, both of which only occur via the presentation of peptidic antigens on the MHC of antigen presenting cells.[16, 38] Thus, the efficient processing of protein antigens to peptidic antigens may enhance the T-cell-dependent processes, subsequently leading to a potent humoral immune response.

The immunogenicity data revealed that Nano-CRM$_{197}$-Nic and Nano-TT-Nic could induce significantly higher antinicotine antibody titers and considerably lower anti-stimulating protein antibody titers than Nano-KLH-Nic and Nano-KS-Nic. The lower antibody titers against stimulating proteins induced by Nano-CRM$_{197}$-Nic and Nano-TT-Nic may be caused by the relatively smaller size of CRM$_{197}$ and TT. Compared with the larger KS and KLH multimer, the smaller CRM$_{197}$ and TT had less immunogenic epitopes available for B cells, thus producing less anti-stimulating protein antibodies. A lower anti-stimulating protein antibody level is desirable in nicotine vaccine design, as the anti-stimulating protein antibodies may neutralize the vaccine particles that are injected during booster immunizations. This neutralization may cause wastages and impair the efficacy of nicotine vaccines. [13, 39] Noticeably, the levels of anti-nicotine antibodies induced by NanoNicVac were in concordance with the effectiveness of antigen processing by dendritic cells. As discussed in the previous context, the efficient processing of protein antigens that were carried by Nano-CRM$_{197}$-Nic and Nano-TT-Nic would result in a potent T-cell immunity and contribute to an enhanced immunogenicity against nicotine. Interestingly, the second booster immunization boosted the anti-nicotine antibody titers in the Nano-CRM$_{197}$-TT and Nano-TT-Nic groups more remarkably than in the Nano-KLH-Nic and Nano-KS-Nic groups. Although we do not have direct evidences to show the mechanism, the following facts may fairly explain the finding. On one hand, the higher effectiveness of Nano-CRM$_{197}$-Nic and Nano-TT-Nic in generating a T-cell immunity may enhance the humoral immune response, resulting in more anti-nicotine antibodies to be generated. On the other hand, Nano-CRM$_{197}$-Nic and Nano-TT-Nic had lower anti-stimulating protein antibody titers than Nano-KLH-Nic and Nano-KS-Nic after the first booster immunization. The lower anti-stimulating protein antibody levels may neutralize less vaccine particles administered in the second booster immunization, and thus leave more vaccine particles available for inducing the production of anti-nicotine antibodies. In agreement with the data of anti-nicotine antibody titer, affinity, and specificity, the pharmacokinetic data suggested that NanoNicVac conjugated with CRM$_{197}$ and TT exhibited better abilities in sequestering nicotine in serum and blocking nicotine from entering the brain than NanoNicVac conjugated with KLH and KS.

Summary

In summary, a series of hybrid nanoparticle based nicotine nanovaccines (NanoNicVac) were developed in this Example by conjugating potent stimulating proteins (KLH, KS, CRM$_{197}$, and TT) to the nanoparticle surface. Although all the four NanoNicVac were taken up by dendritic cells efficiently, NanoNicVac conjugated with CRM$_{197}$ and TT were processed more efficiently than that conjugated with KLH and KS. In addition, compared to NanoNicVac carrying KLH and KS, NanoNicVac conjugated with CRM$_{197}$ and TT induced remarkably higher anti-nicotine antibody titers and considerably lower anti-stimulating protein antibody levels. Meanwhile, the anti-nicotine antibodies induced by all four NanoNicVac, regardless of stimulating proteins, exhibited high affinity and specificity to nicotine. Also, NanoNicVac conjugated with CRM$_{197}$ and TT had better pharmacokinetic efficacies in blocking nicotine from entering the brain of mice than NanoNicVac conjugated with KLH and KS. This Example illustrated the necessity of selecting potent stimulating proteins in maximizing the immunological efficacy of the nicotine nanovaccine. The findings can potentially be applied in the development of other drug abuse and nanoparticle-based vaccines. Furthermore, NanoNicVac with boosted immunological efficacy can be be effective for treating nicotine addiction.

REFERENCES FOR EXAMPLE 3

[1] Benowitz N L. Nicotine addiction. N Engl J Med. 2010; 362:2295-303.
[2] Prochaska J J, Benowitz N L. The Past, Present, and Future of Nicotine Addiction Therapy. Annual Review of Medicine, Vol 67. 2016; 67:467-86.
[3] Polosa R, Benowitz N L. Treatment of nicotine addiction: present therapeutic options and pipeline developments. Trends Pharmacol Sci. 2011; 32:281-9.
[4] Moreno A Y, Janda K D. Immunopharmacotherapy: Vaccination strategies as a treatment for drug abuse and dependence. Pharmacology Biochemistry and Behavior. 2009; 92:199-205.
[5] Pentel P R, LeSage M G. New Directions in Nicotine Vaccine Design and Use. Emerging Targets & Therapeutics in the Treatment of Psychostimulant Abuse. 2014; 69:553-80.
[6] Cornuz J, Zwahlen S, Jungi W F, Osterwalder J, Klingler K, van Melle G, et al. A Vaccine against Nicotine for Smoking Cessation: A Randomized Controlled Trial. Plos One. 2008; 3.
[7] Hatsukami D K, Jorenby D E, Gonzales D, Rigotti N A, Glover E D, Oncken C A, et al. Immunogenicity and Smoking-Cessation Outcomes for a Novel Nicotine Immunotherapeutic. Clinical Pharmacology & Therapeutics. 2011; 89:392-9.
[8] Goniewicz M L, Delijewski M. Nicotine vaccines to treat tobacco dependence. Hum Vaccin Immunother. 2013; 9:13-25.
[9] Raupach T, Hoogsteder P H, Onno van Schayck C P. Nicotine vaccines to assist with smoking cessation: current status of research. Drugs. 2012; 72:e1-16.
[10] Hu Y, Zheng H, Huang W, Zhang C M. A novel and efficient nicotine vaccine using nano-lipoplex as a delivery vehicle. Hum Vacc Immunother. 2014; 10:64-72.
[11] Zheng H, Hu Y, Huang W, de Villiers S, Pentel P, Zhang J F, et al. Negatively Charged Carbon Nanohorn Supported Cationic Liposome Nanoparticles: A Novel Delivery Vehicle for Anti-Nicotine Vaccine. Journal of Biomedical Nanotechnology. 2015; 11:2197-210.
[12] Zhao Z, Hu Y, Hoerle R, Devine M, Raleigh M, Pentel P, et al. A nanoparticle-based nicotine vaccine and the influence of particle size on its immunogenicity and efficacy. Nanomedicine. 2016.
[13] Hu Y, Smith D, Frazier E, Hoerle R, Ehrich M, Zhang C. The next-generation nicotine vaccine: a novel and potent hybrid nanoparticle-based nicotine vaccine. Biomaterials. 2016; 106:228-39.

[14] Crotty S. A brief history of T cell help to B cells. Nat Rev Immunol. 2015; 15:185-9.
[15] Abbas A K, Murphy K M, Sher A. Functional diversity of helper T lymphocytes. Nature. 1996; 383:787-93.
[16] Collins K C, Janda K D. Investigating Hapten Clustering as a Strategy to Enhance Vaccines against Drugs of Abuse. Bioconjugate Chemistry. 2014; 25:593-600.
[17] Jacob N T, Lockner J W, Schlosburg J E, Ellis B A, Eubanks L M, Janda K D. Investigations of Enantiopure Nicotine Haptens Using an Adjuvanting Carrier in Anti-Nicotine Vaccine Development. Journal of Medicinal Chemistry. 2016; 59:2523-9.
[18] Fraser C C, Altreuter D H, Ilyinskii P, Pittet L, LaMothe R A, Keegan M, et al. Generation of a universal CD4 memory T cell recall peptide effective in humans, mice and non-human primates. Vaccine. 2014; 32:2896-903.
[19] Bi S G, Bailey W, Brisson C. Performance of Keyhole Limpet Hemocyanin (KLH) as an Antigen Carrier for Protein Antigens Depends on KLH Property and Conjugation Route. Journal of Immunology. 2016; 196.
[20] Zhong T Y, Arancibia S, Born R, Tampe R, Villar J, Del Campo M, et al. Hemocyanins Stimulate Innate Immunity by Inducing Different Temporal Patterns of Proinflammatory Cytokine Expression in Macrophages. Journal of Immunology. 2016; 196:4650-62.
[21] McCluskie M J, Thorn J, Gervais D P, Stead D R, Zhang N L, Benoit M, et al. Anti-nicotine vaccines: Comparison of adjuvanted CRM197 and Qb-VLP conjugate formulations for immunogenicity and function in non-human primates. International Immunopharmacology. 2015; 29:663-71.
[22] Haile C N, Kosten T A, Shen X Y, O'Malley P W, Winoske K J, Kinsey B M, et al. Altered Methamphetamine Place Conditioning in Mice Vaccinated With a Succinyl-Methamphetamine-Tetanus-Toxoid Vaccine. American Journal on Addictions. 2015; 24:748-55.
[23] de Villiers S H L, Cornish K E, Troska A J, Pravetoni M, Pentel P R. Increased efficacy of a trivalent nicotine vaccine compared to a dose-matched monovalent vaccine when formulated with alum. Vaccine. 2013; 31:6185-93.
[24] Storni T, Kundig T M, Senti G, Johansen P. Immunity in response to particulate antigen-delivery systems. Adv Drug Deliver Rev. 2005; 57:333-55.
[25] Benne N, van Duijn J, Kuiper J, Jiskoot W, Slutter B. Orchestrating immune responses: How size, shape and rigidity affect the immunogenicity of particulate vaccines. J Control Release. 2016; 234:124-34.
[26] De Temmerman M L, Rejman J, Demeester J, Irvine D J, Gander B, De Smedt S C. Particulate vaccines: on the quest for optimal delivery and immune response. Drug Discov Today. 2011; 16:569-82.
[27] Zheng M B, Yue C X, Ma Y F, Gong P, Zhao P F, Zheng C F, et al. Single-Step Assembly of DOX/ICG Loaded Lipid-Polymer Nanoparticles for Highly Effective Chemo-photothermal Combination Therapy. Acs Nano. 2013; 7:2056-67.
[28] Zhang L F, Chan J M, Gu F X, Rhee J W, Wang A Z, Radovic-Moreno A F, et al. Self-assembled lipid-polymer hybrid nanoparticles: A robust drug delivery platform. Acs Nano. 2008; 2:1696-702.
[29] Hu Y, Hoerle R, Ehrich M, Zhang C M. Engineering the lipid layer of lipid-PLGA hybrid nanoparticles for enhanced in vitro cellular uptake and improved stability. Acta Biomater. 2015; 28:149-59.
[30] Hu Y, Zhao Z M, Ehrich M, Fuhrman K, Zhang C M. In vitro controlled release of antigen in dendritic cells using pH-sensitive liposome-polymeric hybrid nanoparticles. Polymer. 2015; 80:171-9.
[31] Hadinoto K, Sundaresan A, Cheow W S. Lipid-polymer hybrid nanoparticles as a new generation therapeutic delivery platform: A review. Eur J Pharm Biopharm. 2013; 85:427-43.
[32] Bachmann M F, Jennings G T. Vaccine delivery: a matter of size, geometry, kinetics and molecular patterns. Nat Rev Immunol. 2010; 10:787-96.
[33] Metlay J P, Pure E, Steinman R M. Control of the Immune-Response at the Level of Antigen-Presenting Cells—a Comparison of the Function of Dendritic Cells and Lymphocytes-B. Adv Immunol. 1989; 47:45-116.
[34] Banchereau J, Steinman R M. Dendritic cells and the control of immunity. Nature. 1998; 392:245-52.
[35] Harris J R, Markl J. Keyhole limpet hemocyanin (KLH): a biomedical review. Micron. 1999; 30:597-623.
[36] Broker M, Costantino P, DeTora L, McIntosh E D, Rappuoli R. Biochemical and biological characteristics of cross-reacting material 197 (CRM197), a non-toxic mutant of diphtheria toxin: Use as a conjugation protein in vaccines and other potential clinical applications. Biologicals. 2011; 39:195-204.
[37] Pichichero M E. Protein carriers of conjugate vaccines Characteristics, development, and clinical trials. Hum Vacc Immunother. 2013; 9:2505-23.
[38] Liu X W, Xu Y, Yu T, Clifford C, Liu Y, Yan H, et al. A DNA Nanostructure Platform for Directed Assembly of Synthetic Vaccines. Nano Lett. 2012; 12:4254-9.
[39] Skolnick P. Biologic Approaches to Treat Substance-Use Disorders. Trends Pharmacol Sci. 2015; 36:628-35.

Example 4

Introduction

Tobacco use continues to be the leading cause of preventable death worldwide, resulting in more than 6 million deaths and immeasurable economic loss each year [1]. It has been widely recognized that nicotine is the major component that is responsible for tobacco addiction [2]. Although, conventional pharmacotherapies [3] including nicotine replacement therapy, varenicline, and bupropion prove to be effective in treating nicotine addiction, the overall abstinence rate is highly limited and these therapies are more or less accompanied with adverse effects [4-6]. Therefore, there is an urgent need for a more effective and safer treatment method for nicotine addiction. In recent years, nicotine vaccines, which can induce the production of nicotine-specific antibodies and prevent nicotine entry into the brain, have exhibited great potential as a new-generation therapy to help people quit smoking [7]. Nicotine is a small compound and cannot induce immune response on its own; and thus it has to be associated with bigger molecules, such as proteins, for it to be immunogenic [8]. Following the above rationale, traditional nicotine vaccines share a common trait, in that nicotine haptens are covalently conjugated to proteins [9]. These vaccines prove effective in producing nicotine specific antibodies, and some of them have even advanced into clinical trials [10, 11]. However, such a nicotine-protein conjugate design has some drawbacks, which may limit the treatment efficacy of the resulting vaccines. Firstly, antigen presenting cells (APCs), such as dendritic cell (DC), macrophage, and B cell, prefer to capture and internalize particulate antigens [12], including virus, bacteria, and nanoparticles, instead of soluble protein antigens; secondly, if not impossible, nicotine-protein conjugate vaccines can hardly co-deliver antigens and adjuvant molecules to target immune cells, in contrast, nanoparticles-based vaccine can relative easily achieve such a co-delivery [13]; and lastly, carrier proteins themselves are immunogenic, which may result in wastage of the nicotine-protein conjugate vaccine for eliciting antibodies against the protein rather than nicotine.

In order to overcome the above shortcomings of the traditional nicotine-protein conjugate vaccines, in this study, we designed a novel lipid-PLGA hybrid nanoparticle-based nicotine vaccine (NanoNiccine). The major components of this vaccine are a PLGA core, a lipid surface layer, keyhole limpet hemocyanin (KLH) in the core, monophosphoryl lipid A (MPLA) as a molecular adjuvant in the lipid layer, and nicotine haptens covalently linked to the outer surface of the lipid layer. Different from the traditional nicotine-protein conjugate vaccine [14-16], KLH in the PLGA core of NanoNiccine solely served as a supplier of T cell antigens, instead of a carrier protein. This may reduce the possibility of generating antibodies against KLH. Another advantage of this design is that molecular adjuvants, such as MPLA [17], and CpG oligodeoxynucleotides (CpG ODNs) [18] can be co-delivered with antigens to immune cells, which may increase the magnitude of immune response. The immunogenicity of NanoNiccine and the traditional nicotine vaccine using KLH as a carrier protein (i.e. positive control) was studied in mice. The results showed that NanoNiccine generated a much higher titer of antibodies against nicotine than the traditional Nic-KLH conjugate vaccine.

EXPERIMENTAL SECTION

Materials

Lactel® 50:50 PLGA was purchased from Durect Corporation (Cupertino, Calif.). Fetal bovine serum (FBS), granulocyte macrophage-colony stimulating factor (GM-CSF) recombinant mouse protein, Alpha minimum essential medium, trypsin/EDTA, and Alexa Fluor® 647 hydrazide were purchased from Life Technologies Corporation (Grand Island, N.Y.). The anti-mouse IgG from goat, anti-mouse IgG1, IgG2a, IgG2b, IgG3 HRP, and anti-goat IgG-HRP were procured from Alpha Diagnostic Intl (San Antonio, Tex.). TMB one component microwell substrate was procured from SouthernBiotech (Birmingham, Ala.). Lipids, including 1,2-dioleoyl-3-trimethylammonium-propane (DOTAP), 1,2-distearoyl-sn-glycero-3-phosphoethanolamine-N-[carboxy(polyethylene glycol)-2000] (ammonium salt) ((DSPE-PEG2000) carboxylic acid), cholesterol, MPLA and 1,2-diphytanoyl-sn-glycero-3-phosphoethanolamine-N-(7-nitro-2-1,3-benzoxadiazol-4-yl) (ammonium salt) (NBD PE) were purchased from Avanti Polar Lipids, Inc. (Alabaster, Ala.). Poly(vinyl alcohol) (PVA, MW 89,000-98,000), dichloromethane (DCM), and bovine serum albumin (BSA) were purchased from Sigma-Aldrich Inc. (Saint Louis, Mo.). Alexa Fluor® 647 Hydrazide, KLH, Imject™ Alum Adjuvant (Alum), 1-ethyl-3-[3-dimethylaminopropyl] carbodiimide hydrochloride (EDC), and sulfo-NHS were purchased from Thermo Fisher Scientific Inc. (Rockford, Ill.). JAWSII (ATCC® CRL-11904™) immature dendritic cells were purchased from ATCC (Manassas, Va.). (San Diego, Calif.). Rac-trans 3'-aminomethyl nicotine was purchased from Toronto Research Chemicals Inc. (Toronto, Canada). All other chemicals were of analytical grade.

Synthesis of KLH-Containing PLGA Nanoparticles

PLGA nanoparticles were prepared using a reported double emulsion solvent evaporation method with modifications [19-21]. Briefly, PLGA (30 mg) was dissolved in DCM (1 mL), followed by mixing with 100 µL of KLH (20 mg/mL) for 2 min using a vortex mixer. The resultant mixture was emulsified in Branson B1510DTH Ultrasonic Cleaner (Branson, Danbury, Conn.) for 10 min. The primary emulsion was added drop-wise into 100 mL PVA (0.5% (w/v)), and continuously stirred for 10 min at 500 rpm. The above suspension was emulsified by sonication using a sonic dismembrator (Model 500; Fisher Scientific, Pittsburgh, Pa.) at 50% amplitude for 120 s. The secondary emulsion was stirred overnight to allow DCM to evaporate. Large particles were removed after the mixture sat undisturbed at room temperature for 30 min. Nanoparticles in suspension were collected by centrifugation at 10,000 g, 4° C. for 60 min using an Eppendorf centrifuge (Eppendorf, Hauppauge, N.Y.). The pellet was suspended in 10 mL phosphate buffered saline (PBS) buffer (pH 7.4) and stored at 2° C. until future use.

Assembly of NanoNiccine

Lipid-PLGA nanoparticles were assembled using a method as described in previous reports. [20, 22] The lipid film containing 0.25 mg MPLA, 2.83 mg DOTAP, 3.08 mg (DSPE-PEG2000) carboxylic acid, and 0.1 mg cholesterol was hydrated with 1 mL of 55° C. pre-warmed PBS buffer. The resulting liposome suspension was vigorously mixed using a vortex mixer for 2 min, followed by sonication for 5 min, using a Branson B1510DTH Ultrasonic Cleaner (Branson, Danbury, Conn.) and then cooled to room temperature. The prepared liposome was added into the above prepared KLH-containing PLGA nanoparticles and pre-homogenized for 15 min using a Branson B1510DTH Ultrasonic Cleaner, followed by sonication for 5 min in an ice bath using a sonic dismembrator at 15% amplitude (pulse on 20 s, pulse off 50 s). The acquired lipid-PLGA nanoparticles were dialyzed against 500 mL activation buffer (0.1M MES, 0.5M NaCl, pH 6.0) for 2 h. EDC (4.1 mg) and sulfo-NHS (11.3 mg) were added into the hybrid nanoparticle suspension and allowed to react for 20 min at room temperature. The activated nanoparticles were dialyzed against 1000 mL PBS buffer (100 mM sodium phosphate, 150 mM NaCl; pH 7.2) for 30 min. After dialysis, 4.1 mg rac-trans 3'-aminomethyl nicotine was incubated with the above nanoparticle suspension at room temperature for 4 h. The remaining impurities were removed by dialysis against PBS buffer (pH 7.4) for 12 h. The assembled NanoNiccine was stored at 4° C. until future use.

Synthesis of Nicotine-KLH Conjugate Vaccine

KLH (4 mg) dissolved in 2 mL activation buffer (0.1M MES, 0.5M NaCl, pH 6.0) was incubated with 1 mg EDC and 2.8 mg sulfo-NHS for 20 min. The activated KLH was transferred to an Amicon Ultra 15 mL centrifugal filter unit (NMWL, 50 KDa), and purified by centrifugation at 5000 g for 20 min. The purified KLH was suspended in 2 mL PBS buffer (100 mM sodium phosphate, 150 mM NaCl; pH 7.2) and reacted with 1 mg rac-trans 3'-aminomethyl nicotine at room temperature for 4 h. The resultant mixture was then transferred to the centrifugal filter unit mentioned above and centrifuged at 5000 g for 20 min in order to remove the nicotine. The purified nicotine-KLH conjugate was suspended in 2 mL PBS buffer (pH 7.4) and stored at 4° C. until future use.

Synthesis of Nicotine-Bovine Serum Albumin (Nic-BSA) Conjugate

Bovine serum albumin (BSA) (10 mg) dissolved in 5 mL activation buffer (0.1M MES, 0.5M NaCl, pH 6.0) was incubated with 2 mg EDC and 5.6 mg sulfo-NHS for 20 min. The activated BSA was transferred to an Amicon Ultra-15 Centrifugal Filter Unit (NMWL, 30 KDa), and purified by centrifugation at 5000 g for 20 min. The purified BSA was suspended in 5 mL PBS buffer (100 mM sodium phosphate, 150 mM NaCl; pH 7.2) and reacted with 2 mg rac-trans 3′-aminomethyl nicotine at room temperature for 4 h. The resultant mixture was then transferred to the centrifugal filter unit mentioned above and centrifuged at 5000 g for 20 min in order to remove nicotine. The purified nicotine-KLH conjugate was suspended in 5 mL PBS buffer (pH 7.4) and stored at 4° C. until future use.

Synthesis of Alexa 647 Labeled KLH

KLH (4 mg) dissolved in 2 mL activation buffer (0.1M MES, 0.5M NaCl, pH 6.0) was incubated with 1 mg EDC and 2.8 mg sulfo-NHS for 20 min. The activated KLH was transferred to an Amicon Ultra 15 mL centrifugal filter unit (NMWL, 50 KDa), and purified by centrifugation at 5000 g for 20 min. The purified KLH was suspended in 2 mL PBS buffer (100 mM sodium phosphate, 150 mM NaCl; pH 7.2) and reacted with 0.1 mg Alexa Fluor® 647 Hydrazide at room temperature for 4 h. The resultant mixture was then transferred to the centrifugal filter unit mentioned above and centrifuged similarly in order to remove the excess Alexa Fluor® 647 hydrazide. The purified Alexa 647-KLH conjugate was suspended in 2 mL PBS buffer (pH 7.4), lyophilized, and stored at 4° C. until future use.

Characterization of Physicochemical Properties of Nanoparticles

The nanoparticles assembly above were diluted ten times in PBS buffer (pH 7.0). The physicochemical properties including particle size (diameter, nm) and surface charge (zeta potential, mV) were measured at room temperature using a Malvern Nano-ZS zetasizer (Malvern Instruments Ltd, Worcestershire, United Kingdom).

Imaging Hybrid Nanoparticles Using Confocal Laser Scanning Microscopy (CLSM)

A Zeiss LSM 510 Laser Scanning Microscope (Carl Zeiss, German) was used to image NanoNiccine containing Alexa Fluor® 647 hydrazide-labeled KLH and NBD PE-labeled lipid shells. Fluorescently labeled NanoNiccine was formed using the same method for regular NanoNiccine, except that KLH was replaced with Alexa 647—KLH, and 0.1 mg NBD PE was added to the existing lipids.

Imaging Nanoparticles Using Transmission Electrical Microscopy (TEM)

Nanoparticle suspensions (0.5 mg/mL), including KLH-containing PLGA nanoparticles, MPLA-containing liposomes, and NanoNiccine nanoparticles, were dropped onto a 300-mesh Formvar-coated copper grid. After standing for 10 min, the remaining suspension was carefully removed with wipes, and the samples were negatively stained using fresh 1% phosphotungstic acid for 20 s, and washed with ultrapure water twice. The dried samples were imaged on a JEOL JEM 1400 transmission electron microscope (JEOL Ltd., Tokyo, Japan).

Flow cytometry (FACS) measurement of the uptake of lipid-PLGA hybrid NPs by DCs JAWSII (ATCC® CRL-11904™) immature DCs from ATCC were cultured with alpha minimum essential medium (80% v/v) including ribonucleosides, deoxyribonucleosides, 4 mM L-glutamine, 1 mM sodium pyruvate and 5 ng/mL murine GM-CSF, along with fetal bovine serum (20% v/v) at 37° C., 5% $CO_2$ in CytoOne® 35×10 mm TC dish (USA Scientific Inc., Ocala, Fla.). Alexa 647 and NBD PE labeled NanoNiccine (100 µg) was added into each dish containing $2\times10^6$ cells, and incubated for 5, 30, 60, and 120 min, respectively. After incubation, the medium was immediately removed and cells were washed five times with PBS buffer (pH 7.4). Cells were detached from the culture plate using trypsin/EDTA solution and centrifuged at 200 g for 10 min, and cell pellets were suspended in 2 mL PBS buffer (pH 7.4). Cell samples were immediately analyzed by flow cytometer (BD FACSAria I, BD, Franklin Lakes, N.J.).

Imaging Uptake of Lipid-PLGA Hybrid NPs by DCs Using CLSM

Cells were cultured in a 2 well chamber slide (Thermo Fisher Scientific Inc., Rd, Rockford, Ill.) using the same method described above. To investigate the uptake of hybrid NPs by DCs, 100 µg of freshly prepared NanoNiccine (labeled with Alexa Fluor® 647 Hydrazide and NBD PE) was incubated with $4\times10^5$ cells for 5, 30, 60, and 120 min, respectively. After incubation, the medium was immediately removed and cells were washed five times with PBS buffer (pH 7.4). Freshly prepared 4% (w/v) paraformaldehyde (2 mL) was added into each well, and cells were fixed for 15 min. This was followed by washing three times with PBS buffer (pH 7.4). Fixed cells were labeled with DAPI Fluoromount-G® (SouthernBiotech, Birmingham, Ala.). Cell samples were covered with a glass cover. Images were acquired using a Zeiss LSM 880 Laser Scanning Microscope (Carl Zeiss, Germany).

Active Immunization of Mice with Nicotine Vaccines

All animal studies were carried out following the National Institutes of Health (NIH) guidelines for animal care and use. Animal protocols were approved by the Institutional Animal Care and Use Committee (IACUC) at Virginia Polytechnic Institute and State University (VT). Groups of n=8 female BALB/c mice (6-7 weeks, 16-20 g) were immunized by subcutaneous (s.c.) injections on days 0 (primary injection), 14 (1st booster), and 28 (2nd booster) with PBS (pH 7.4), Nic-KLH conjugate vaccine (with 4 mg Alum), NanoNiccine without nicotine hapten (with 4 mg Alum), NanoNiccine with MPLA (without Alum), NanoNiccine containing no MPLA but adjuvanted with 4 mg Alum, and NanoNiccine containing MPLA and adjuvanted with 4 mg Alum (all the vaccine constructs contained a total amount of 40 µg KLH). Following vaccine administration, blood samples (~200 µL) were collected on days -2, 13, 27, 35, and 55 via retro orbital puncture from each mouse. Sera were collected from blood by centrifugation and stored at −80° C.

Measurement of Specific Anti-Nicotine IgG and Anti-KLH IgG Antibodies Using Enzyme-Linked Immunosorbent Assay (ELISA)

Mice sera were analyzed according to the ELISA procedure described in previous publications with proper modifications [23]. Briefly, Nic-BSA was used as the coating material for anti-Nic IgG measurement, and KLH was used as the coating material for anti-KLH measurement. MICROLON® 96 well plates (Greiner BioOne, Longwood, Fla.) were coated with Nic-BSA conjugate or KLH (10 µg/mL in carbonate buffer, 0.05 M, pH 9.6, 100 µL/well) and incubated at 25° C. for 5 h. The plates were washed with PBS-Tween (0.1%) and distilled water for three times, followed by blocking with 300 µL Pierce® protein-free T20 blocking buffer for 12 h. After washing, 100 µL of each dilution (1:25, 1:125, 1:625, 1:3125, 1:15625, 1:78125, and 1:390625) of serum from each mouse was incubated in plates at 25° C. for 2 h. The plates were washed again, and incubated for 1 h with 100 µL anti-mouse IgG. The pates were washed as before, and incubated with 100 µL Anti-Goat IgG-HRP (1:5000) (Alpha Diagnostic Intl, San Antonio, Tex.) for 1 h. After washing as before, 100 µL of TMB one component microwell substrate was added into each well and incubated for 10 min, and the reaction was stopped by adding 100 µL of 0.5% (v/v) $H_2SO_4$. The absorbance for each well was recorded at 450 nm. Titer was defined as the dilution factor at which OD450 fell to half of the maximal.

Measurement of Specific Anti-Nicotine IgG Subtype Antibodies Using ELISA

Anti-Nic IgG antibodies, of different subtypes, including IgG1, IgG2a, IgG2b, and IgG3 from the 55th day sera were measured using ELISA. The ELISA protocol for anti-nicotine IgG subtypes measurement was the same as above, except that 100 µL (1:10000 diluted) anti-Mouse IgG1 HRP, Anti-Mouse IgG2a HRP, Anti-Mouse IgG2b HRP, and Anti-Mouse IgG3 HRP were directly applied after coating with Nic-BSA for 2 h. After reacting with 100 µL TMB One Component Microwell Substrate for 10 min, the reaction was stopped by the addition of 100 µL of 0.5% (v/v) H2SO4. The absorbance for each well was recorded at 450 nm. Titer was defined as the dilution factor at which OD450 fell to half of the maximal.

Th1/Th2 Index Calculation

As described in a previous work [8], Th1:Th2 index was calculated as ([IgG2a+IgG3]/2)/(IgG1) for each immunization groups. According to such calculations, an index value less than one represents a Th2 polarization; and a value greater than one represents a Th1 polarization.

Histopathological Examination

Mice immunized with PBS, Nic-KLH, NanoNiccine with MPLA, with Alum, and with both MPLA and Alum were scarified, and their tissues, including heart, lung, kidney, spleen, liver, and stomach were harvested and fixed in 10% buffered formalin. Haemotoxylin and eosin (H&E) staining was carried out within two weeks after organ harvest according to the method described before [8]. Sections were examined by light microscopy on an Olympus CKX41 inverted microscope and images were captured using an INFINITY 1 camera.

Data Analysis

Antibody titers were compared among groups using one way ANOVA and comparisons among paired groups were analyzed with Tukey's honest significant difference (HSD). The difference is considered as significant when a P-value is less than 0.05. Each measurement was carried out at least thrice, and the results were expressed as mean±standard deviation.

Results

Morphological and Structural Study of NanoNiccine by CLSM and TEM

Figure 73:
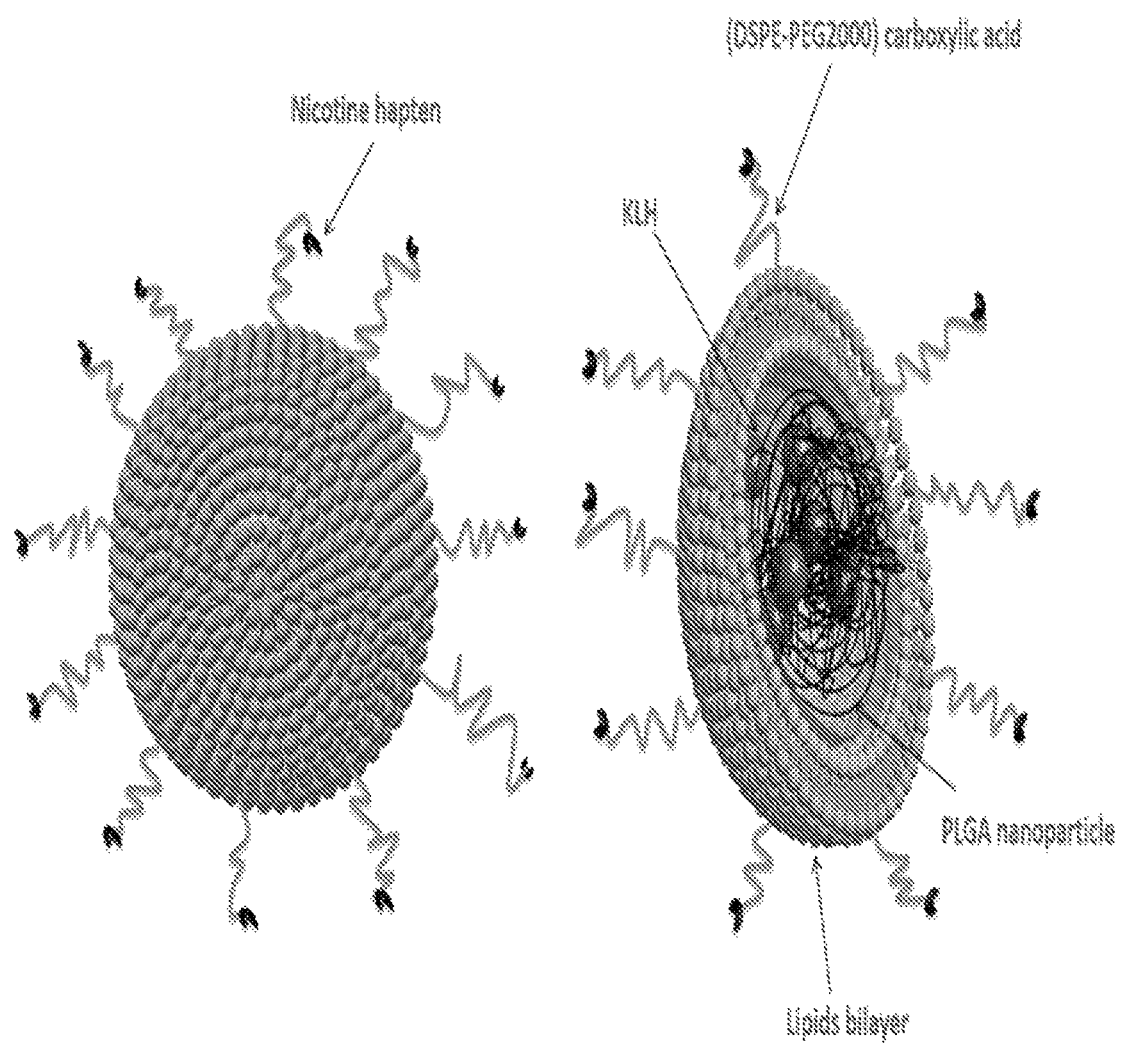
FIG. 73 shows schematic illustration of lipid-PLGA nanoparticle based nicotine vaccine—NanoNiccine. This nicotine vaccine is composed of KLH containing PLGA core, a lipid layer (formed by DOTAP, cholesterol, MPLA, and DSPE-PEG (2000) carboxylic acid), and rac-trans 3'-aminomethyl nicotine covalently linked to the outer terminal of DSPE-PEG (2000) carboxylic acid.
Figure 74:
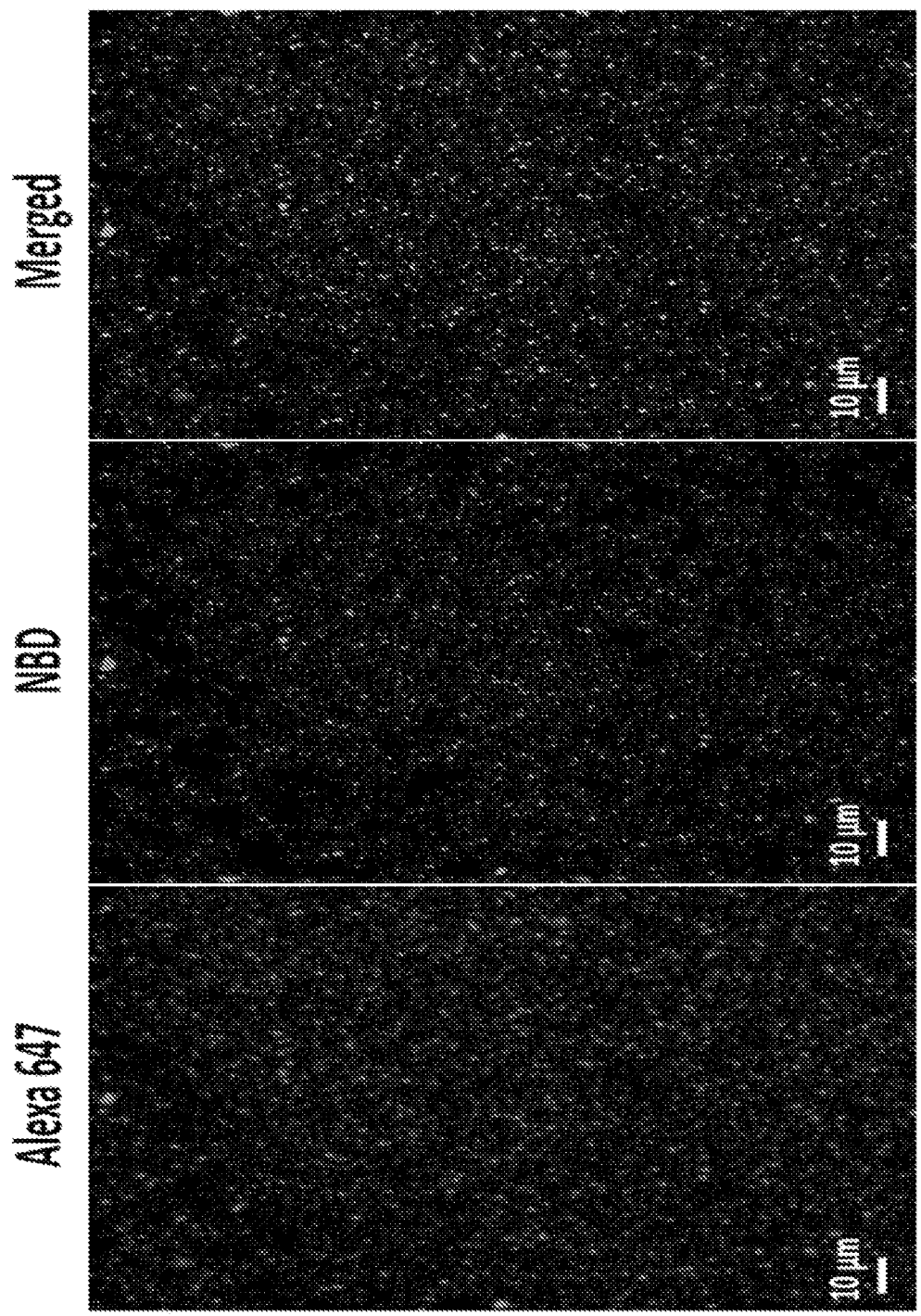
FIGS. 74A-74C show confocal image of NanoNiccine particles, in which the lipid layer was labeled with NBD PE (green color) (FIG. 74B) and PLGA core encapsulated Alexa 647-labeled KLH (red color) (FIG. 74A). Red dots display PLGA core, which contains KLH, and green dots display lipid layer. The merged image is shown in FIG. 74C. The scale bars represent 10 μm.
Figure 75:
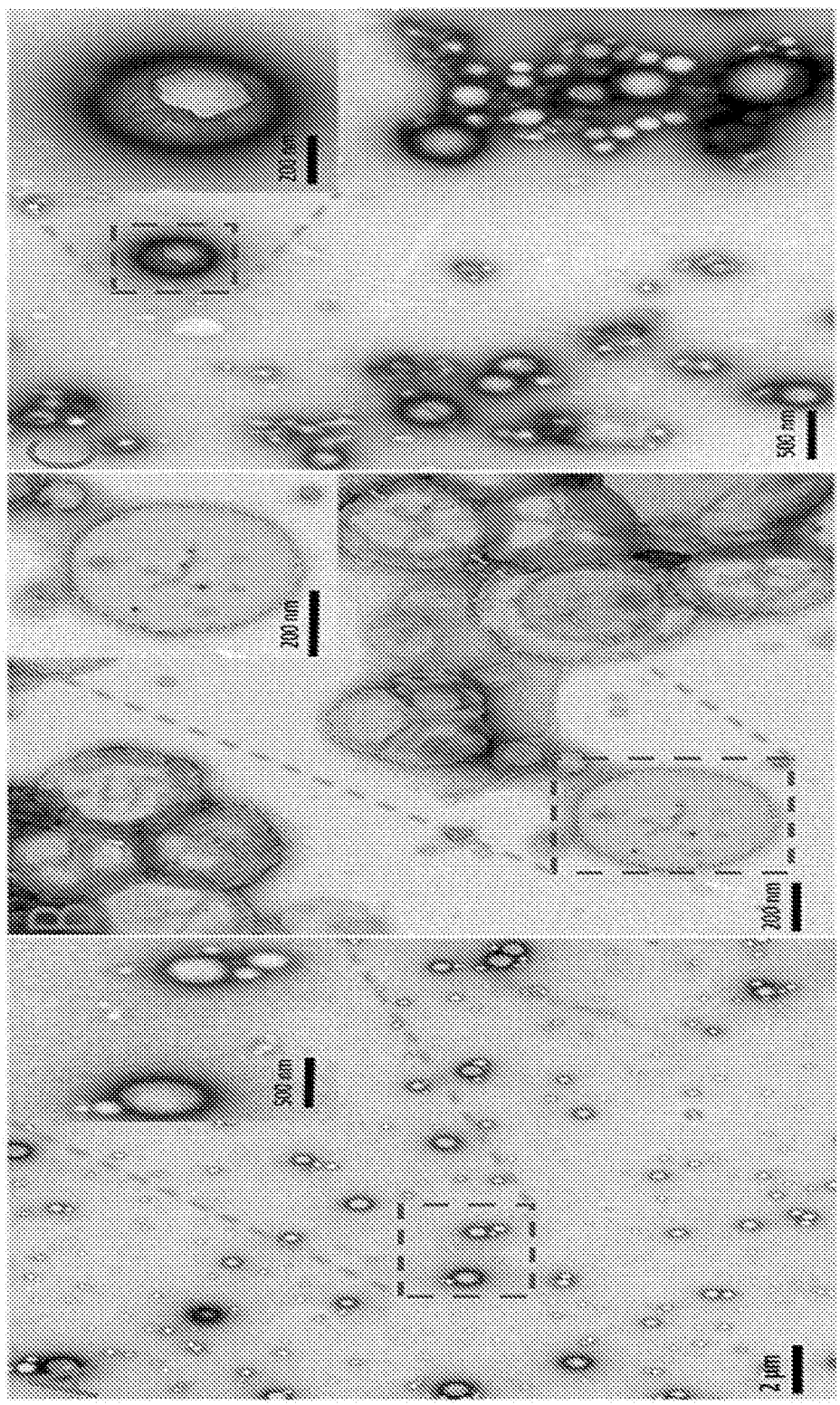
FIGS. 75A-75C show TEM image of nanoparticles.

As illustrated in FIG. 73, NanoNiccine was assembled by conjugating nicotine haptens to the surface of previously well characterized lipid-PLGA hybrid nanoparticles [20]. The morphology and structure of NanoNiccine were investigated by CLSM and TEM. For the CLSM study, structural components of NanoNiccine, including KLH in the PLGA core and the lipid layer, were labeled with Alexa 647 (red color) and NBD PE (green color), respectively. As shown in FIGS. 74A-74C, both Alexa 647 and NBD were expressed on almost all NanoNiccine particles, indicating that a hybrid core-shell structure was formed on the majority of NanoNiccine particles. In addition, the size of most NanoNiccine particles was in nano-range, reflecting the high structural uniformity of the vaccine produced by the protocol described in this study. To study the structural details of NanoNiccine, nanoparticles, including PLGA nanoparticles, liposomes, and NanoNiccine were negatively stained and examined by TEM. PLGA nanoparticles displayed a spherical structure with a mean size of around 250 nm in diameter (FIG. 75A). Similar to PLGA nanoparticles, liposomes were also spherically shaped with a diameter of around 300 nm (FIG. 75B). As shown in FIG. 75C, NanoNiccine particles also displayed a spherical morphology and their sizes were close to that of both the PLGA nanoparticles and the liposomes. However, the difference between the NanoNiccine particles and the PLGA nanoparticles or liposomes, was that the NanoNiccine particles clearly exhibited a hybrid structure, in which a white solid core was surrounded by a thin layer of gray membrane. This suggested that the PLGA nanoparticles and liposomes were successfully hybridized via sonication to form the NanoNiccine particles.

Characterization of Physicochemical Properties of NanoNiccine Particles

Figure 76:
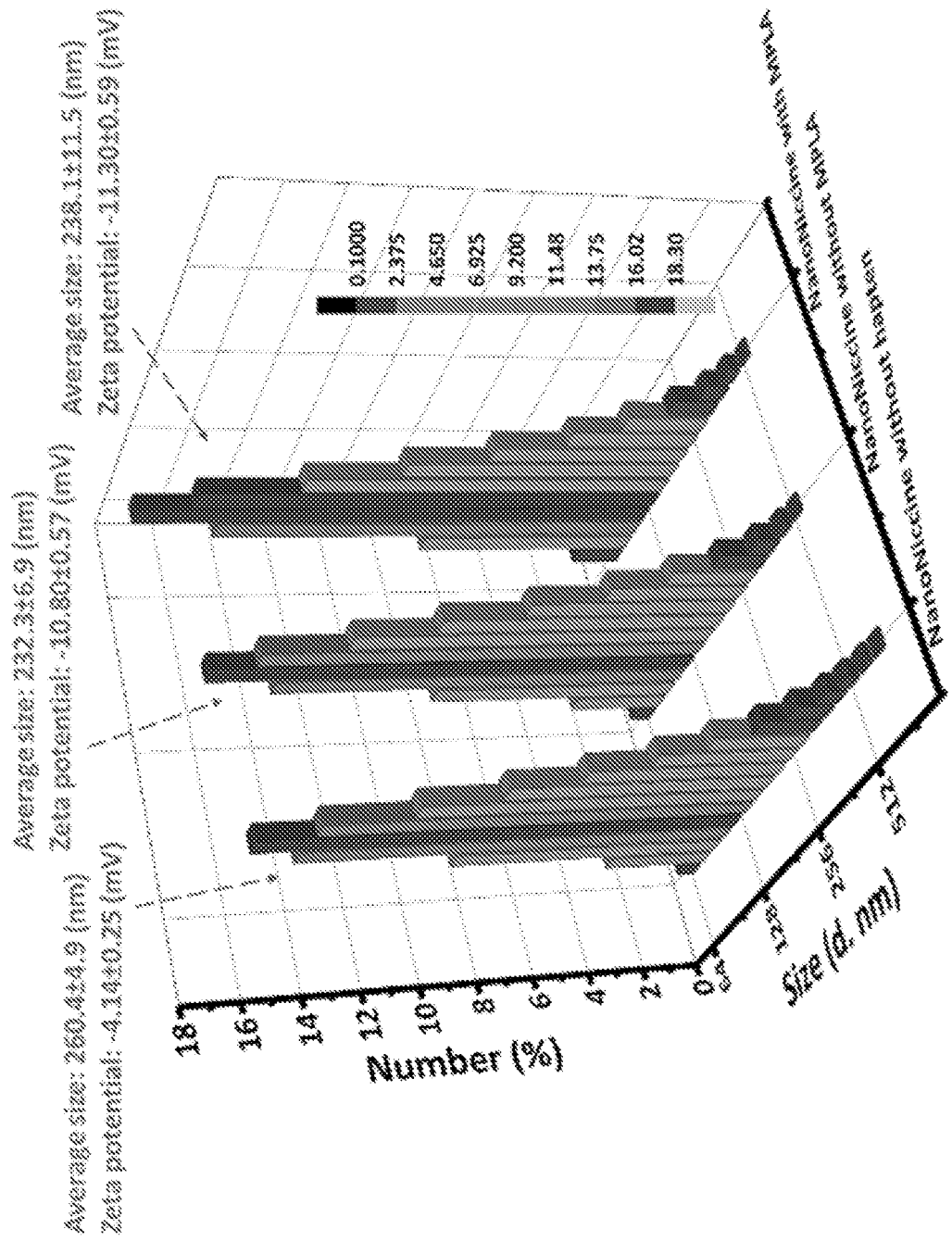
FIG. 76 shows Zeta potential and size distributions of nanoparticles. Newly prepared nanoparticles, including NanoNiccines without nicotine hapten, without MPLA, and with MPLA, were suspended in PBS buffer (pH 7.0), and their physicochemical properties (zeta potential and particle size) were measured by Malvern Nano-ZS zetasizer.

Physicochemical properties, such as mean particle size, size distribution, and surface charge (represented by zeta potential) were characterized for NanoNiccine particles without nicotine hapten (i.e. blank NanoNiccine), with MPLA, without MPLA. As shown in FIG. 76, blank NanoNiccine, NanoNiccine without MPLA, and NanoNiccine with MPLA have average sizes of 260.4±4.9 nm, 232.3±6.9 nm, and 238.1±11.5 nm, respectively. Consistent with the results acquired by CLSM and TEM, the size distributions of all the three particles were in a narrow range with a center at around 150 nm, demonstrating that the majority of the NanoNiccine particles were of a uniform size. Zeta potentials of blank NanoNiccine, NanoNiccine without MPLA, and NanoNiccine with MPLA were −4.14±0.25 mV, −10.80±0.57 mV, and −11.30±0.59 mV, respectively, indicating that all the three particles carried a net negative charge on their surface. The difference in surface charges between blank NanoNiccine and the other two particles might be due to the presence of nicotine haptens on the other two.

Uptake of NanoNiccine Particles by DCs

Figure 77:
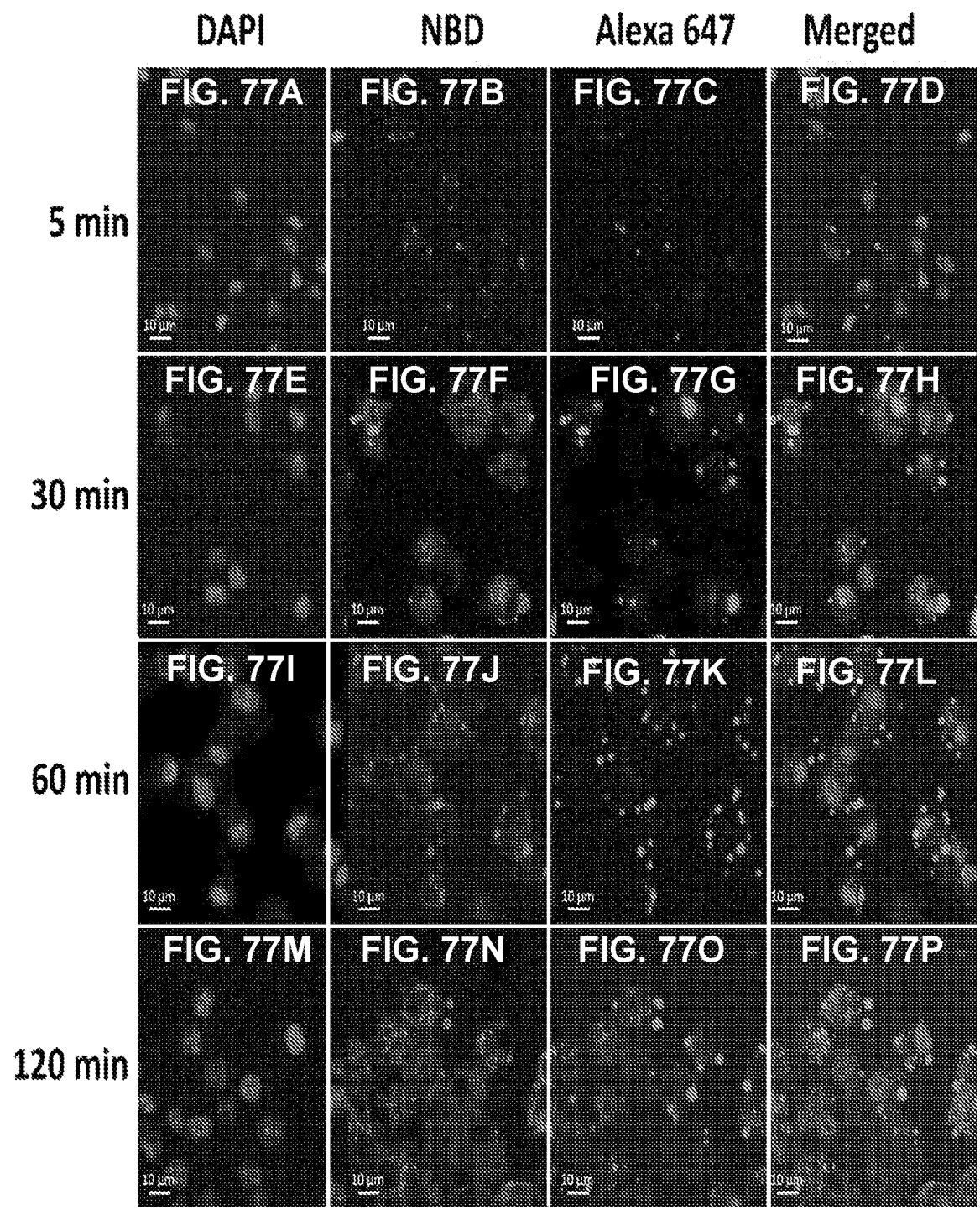
FIGS. 77A-77P show images demonstrating NanoNiccine uptake and degradation by dendritic cells using CLSM. Dendritic cells ($4 \times 10^5$) in a culture chamber were treated with 100 µg fluorescently labeled (lipid layer was marked by NBD PE and PLGA core contained Alexa 647-KLH) NanoNiccine for 5, 30, 60, and 120 min. Scale bars represent 10 µm.

To elicit an immune response, antigens have to be internalized and processed by APCs [24]. Therefore, the uptake of NanoNiccine by APCs is of great importance to its immunological outcome. In this study, the uptake of NanoNiccine by DCs was investigated by flow cytometry (FACS). Mouse DCs ($2\times10^6$) in a culture dish were treated with 100 µg NanoNiccine (particles were fluorescently labeled with both Alexa 647 and NBD). The percentage of cells that internalized NanoNiccine as well as the relative amount taken up by the DCs were then monitored. As shown in the top panel of FIGS. 77A-77P, the uptake of NanoNiccine by the DCs was time-dependent; the percentages of cells that internalized NanoNiccine particles were 1.83%, 57.3%, 93.9%, and 96.3% at 5, 30, 60, and 120 min, respectively. Both Alexa 647 and NBD were detected in NanoNiccine treated DCs, indicating that NanoNiccine hybrid particles as a whole were internalized by the DCs. The relative amount of NanoNiccine internalized by DCs was also recorded by measuring the fluorescence intensity of both Alexa 647 and NBD in DCs. As shown in FIGS. 77A-77P, the fluorescence intensity of both Alexa 647 and NBD increased with time, in which the NBD median intensity increased from 108 at 5 min to 3236 at 120 min, and that of Alexa 647 increased from 35 at 5 min to 1140 at 120 min. Within 115 min, median intensities of both Alexa 647 and NBD increased by about 30 times. The percentages of DCs that were emitting NBD and Alexa 647 after 120 min treatment were as high as 96.2% and 98.8%, respectively.

The in vitro cellular uptake of NanoNiccine was also studied using confocal microscopy. DCs ($4\times10^5$) placed in a cell chamber were incubated with 100 µg fluorescently marked NanoNiccine particles (KLH was labeled with Alexa 647 and the lipid layer was labeled with NBD) for 5, 30, 60, and 120 min, respectively. As shown in FIGS. 77A-77P, in concordance with the results from the FACS study, the number of cells that internalized NanoNiccine and the amount internalized were both found to increase with time. In addition, NanoNiccine particles with a hybrid structure were internalized as a whole entity. After a treatment period of 5 min, NanoNiccine was detected in few cells, and its amount in each cell was quite limited, which was reflected by the dim fluorescence in both NBD and Alexa647 channels. In contrast, after 60 min treatment, NanoNiccine was observed in most of the DCs, and the quantity was found to increase considerably. In addition, we found that the degradation of NanoNiccine in the DCs might occur in a step-wise and time-dependent manner. At 30 min, the lipid layer was removed from NanoNiccine, which was reflected by the wide dispersion of NBD. For KLH in the PLGA core, in the first 60 min, the red fluorescence was confined within the vesicles, indicating that the major portion of PLGA core stayed intact. However, by 120 min, large portion of the PLGA particles was degraded and Alexa 647-labeled KLH was released, leading to a wide distribution of red fluorescence in the DCs.

Nicotine-Specific IgG Antibody Titer Induced by Nicotine Vaccines

Figure 78:
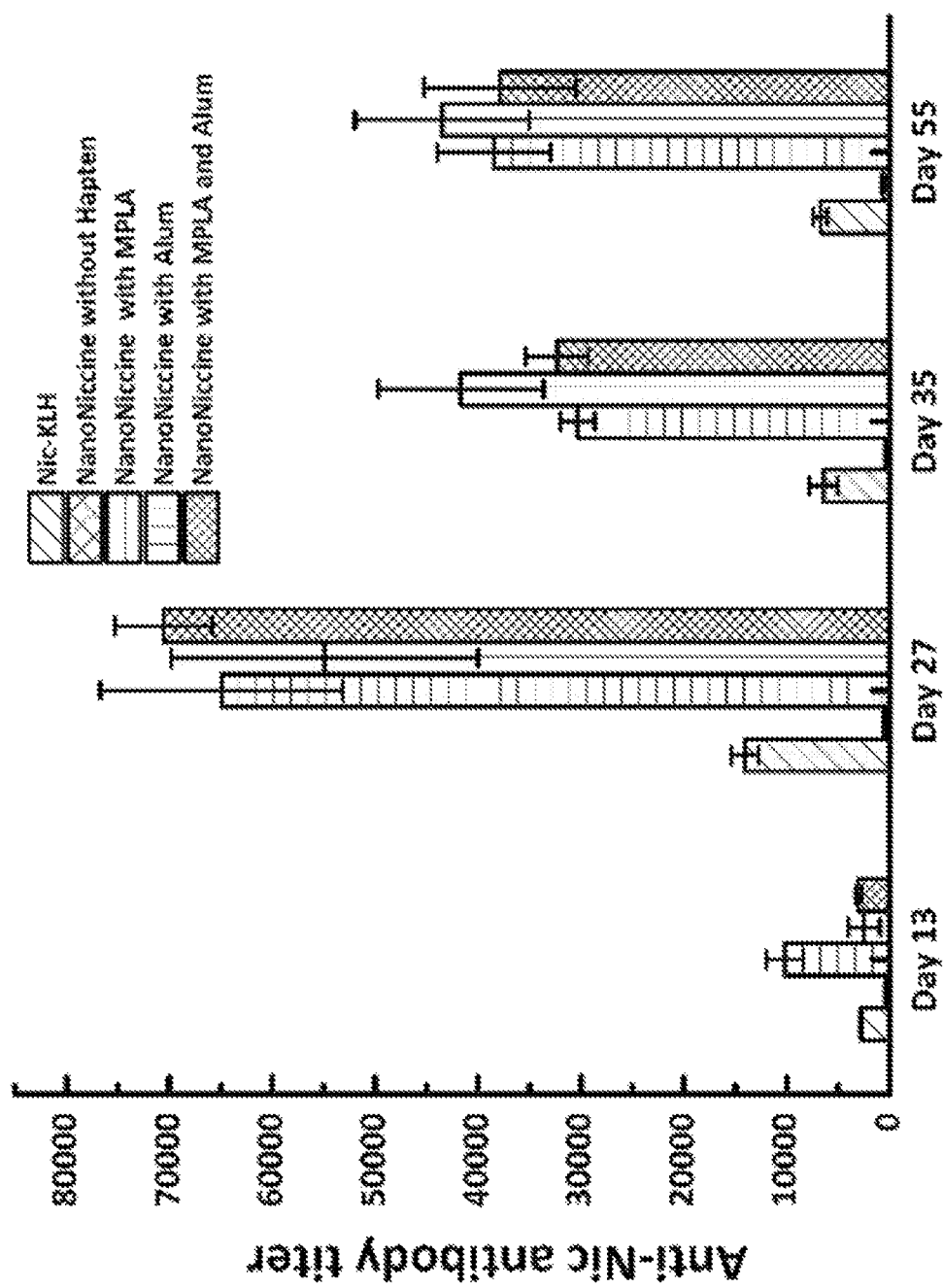
FIG. 78 shows time course of nicotine-specific antibodies titers elicited by Nic-KLH, NanoNiccines without hapten, with MPLA, with Alum, and with MPLA and Alum. Each group of eight mice was injected with vaccines containing 40 µg KLH on days 0, 14, and 28. Nicotine specific antibodies in mice sera from days 13, 27, 35, and 55 were measured using ELISA. ** means P-value <0.01.

On days 0, 14, and 28, each group of eight mice was immunized with PBS (negative control), Nic-KLH (positive control), NanoNiccines without hapten, with MPLA, with Alum, and with MPLA and Alum, respectively. Anti-Nic IgG from sera on days 13, 27, 35, and 55 were measured. No anti-Nic antibody was detected in mice immunized with PBS at any of the time points. As shown in FIG. 78, 13 days after the primary injection, NanoNiccine with MPLA elicited antibody titer as high as $10.2\pm1.8\times10^3$, which was significantly higher than those in the other four groups. No anti-Nic antibody was detected in the mice injected with NanoNiccine without nicotine hapten.

The first booster injection enormously promoted nicotine antibody production among all nicotine vaccines, except NanoNiccine without hapten. Thirteen days after the first booster injection, the antibody titer reached $14.0\pm1.3\times10^3$, $65.0\pm11.8\times10^3$, $54.9\pm14.9\times10^3$, and $70.5\pm4.7\times10^3$ for Nic-KLH, NanoNiccines with MPLA, Alum, and with MPLA and Alum groups, respectively. No anti-Nic antibody was detected in the group without nicotine hapten. The fold increase in the antibody titer after the first booster was found to be 4, 5.3, 21.4, and 22.3, in the Nic-KLH group, the NanoNiccines with MPLA, with Alum, with MPLA and Alum group, respectively. The immunogenicity of NanoNiccine with all the formulations, except in that without hapten, was stronger than the Nic-KLH conjugate vaccine. As compared to Nic-KLH, NanoNiccine with MPLA, with Alum, and with MPLA and Alum generated an anti-Nic antibody titer 4.6, 3.9, and 5 times higher, respectively.

Seven days after the second booster injection, the antibody titers of Nic-KH, NanoNiccines with MPLA, with Alum, and with MPLA and Alum, dropped to $6.4\pm1.4\times103$, $30.3\pm1.6\times10^3$, $41.7\pm8.1\times10^3$, and $32.3\pm3.1\times10^3$, respectively. However, anti-Nic antibody titers of NanoNiccine groups were still significantly higher than that of Nic-KLH.

On day 55, no significant changes in anti-Nic antibody titer were detected from those on day 35 among all vaccine groups. Titers in mice treated with Nic-KH, NanoNiccines with MPLA, with Alum, and with MPLA and Alum, were $6.7\pm0.7\times10^3$, $38.4\pm5.5\times10^3$, $43.5\pm8.5\times10^3$, and $37.8\pm7.4\times10^3$, respectively. NanoNiccine groups maintained a superiorly higher antibody titer than that of Nic-KLH. Within the NanoNiccine groups, the anti-Nic antibody titers did not significantly differ from one another.

KLH Specific IgG Antibody Titer Induced by Nicotine Vaccines

Figure 79:
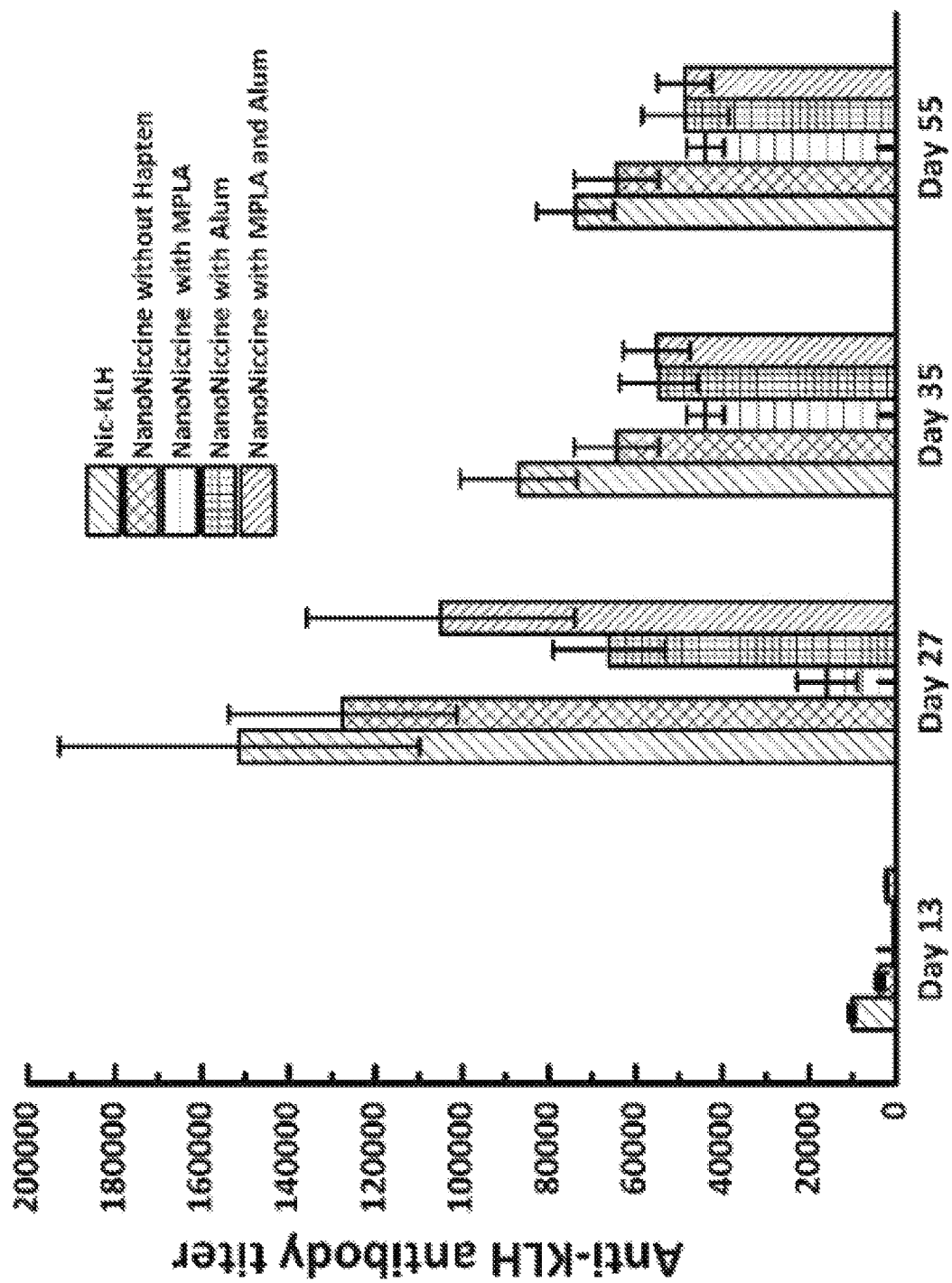
FIG. 79 shows time course of KLH specific antibodies elicited by Nic-KLH, NanoNiccines without hapten, with MPLA, with Alum, and with MPLA and Alum. Each group of eight mice was injected with vaccines containing 40 µg KLH on days 0, 14, and 28. KLH specific antibodies in mice sera from days 13, 27, 35, and 55 were measured using ELISA. ** means P-value <0.01.

Anti-KLH antibody titers were measured using the same sera as for the anti-Nic antibody assay. No anti-KLH antibody was detected in the mice immunized with PBS at any time points. As shown in FIG. 79, on day 13, anti-KLH antibody titers of $10.1\pm0.8\times10^3$, $3.9\pm1.0\times10^3$, $462\pm51$, $596\pm111$, and $2.2\pm0.3\times10^3$ were found for Nic-KLH, NanoNiccines without hapten, with MPLA, with Alum, and with MPLA and Alum, respectively. Nic-KLH generated a significantly higher anti-KLH antibody titer as compared to all the NanoNiccine groups. On day 27, anti-KLH antibody titers increased to $151.3\pm41.5\times10^3$, $127.6\pm26.2\times10^3$, $16.0\pm6.9\times10^3$, $66.2\pm12.9\times10^3$, and $104.9\pm30.9\times10^3$ for Nic-KLH, NanoNiccines without hapten, with MPLA, with Alum, and with MPLA and Alum, respectively. Despite the tremendous increase, anti-KLH antibody titer of NanoNiccine with MPLA was still significantly lower than all other vaccine formulations. On day 35, anti-KLH antibody titers of Nic-KLH, NanoNiccines without hapten, with Alum, and with MPLA and Alum group considerably decreased to $87.0\pm13.5\times10^3$, $64.4\pm9.7\times10^3$, $54.7\pm9.0\times10^3$, and $55.1\pm7.6\times10^3$, respectively. In contrast, the anti-KLH antibody titer of NanoNiccine with MPLA increased significantly to $44.0\pm4.3\times10^3$. The anti-KLH antibody titer of Nic-KLH was significantly higher than those in all the NanoNiccine groups. On day 55, similar to the anti-Nic antibody titer, anti-KLH titers stayed close to these on day 35, which were $73.9\pm8.9\times10^3$, $64.4\pm9.7\times10^3$, $44.0\pm4.3\times10^3$, $48.5\pm10.1\times10^3$, and $48.7\pm6.3\times10^3$, respectively. Nic-KLH maintained a significantly higher anti-KLH titer than the NanoNiccine groups. In addition, no significant difference in the anti-KLH antibody titer was detected among the NanoNiccine groups.

Figure 80:
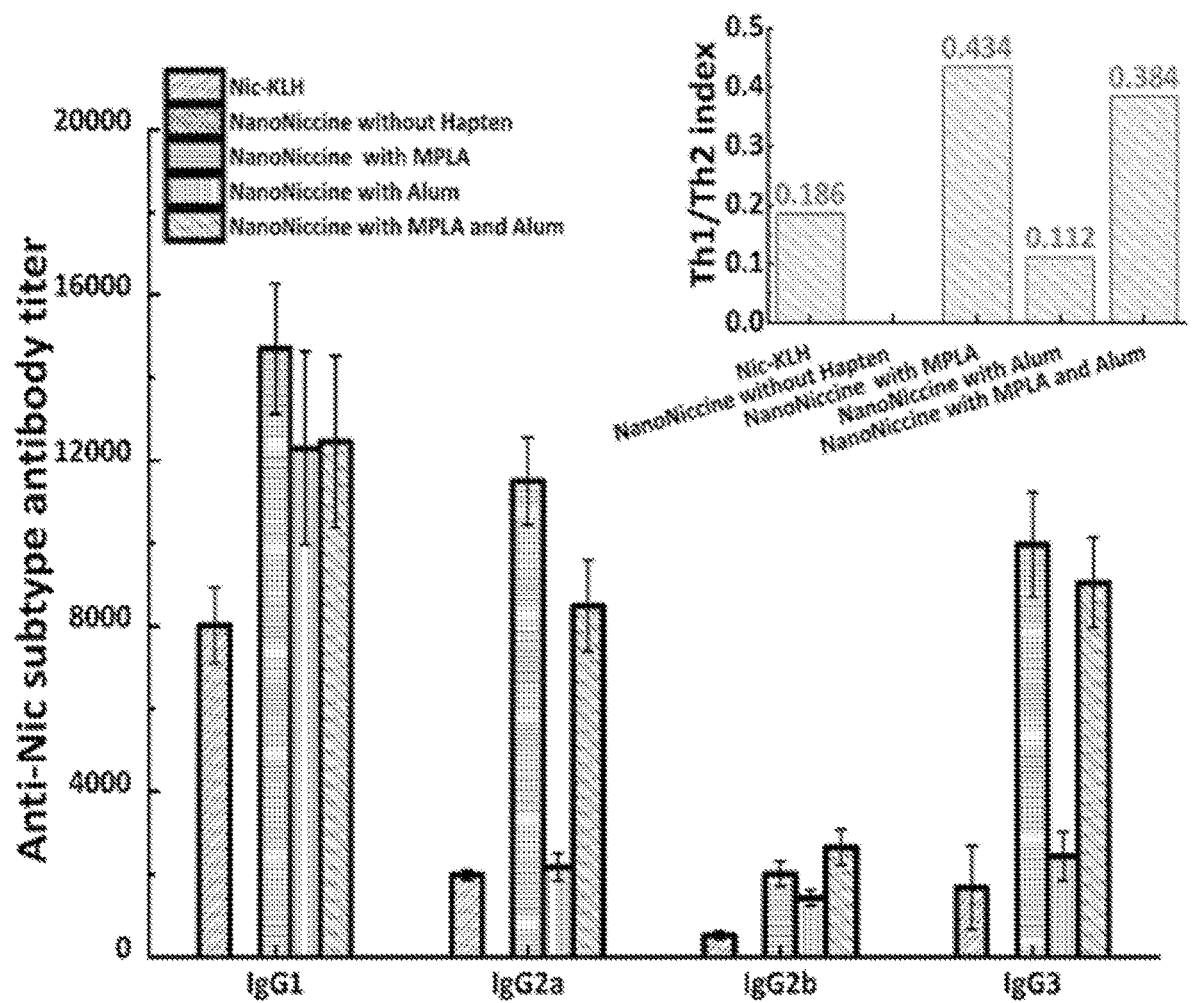
FIG. 80 shows titers of anti-Nic IgG1, IgG2a, IgG2b, and IgG3 from sera of day 55. Based on subtype antibody titer, the Th1/Th2 index, which indicates dominance of antibody response and cell mediated response, was calculated using equation, Th1/Th2 index=([IgG2a+IgG3]/2)/(IgG1).

Titers of Anti-Nicotine Antibody of Different Subtypes Induced by Nicotine Vaccines For all the nicotine vaccine groups, titers of anti-nicotine subtype antibodies from sera on day 55 were assayed. As shown in FIG. 80, no antibody titer of any subtype was detected in the NanoNicine without hapten group, and all the other vaccines generated antibody subtypes at various levels. IgG1 and IgG2b were the most dominant and the least dominant antibody subtype, respectively, among all the vaccine groups. In agreement with the total IgG titer results, Nic-KLH generated significantly lower titers of all subtypes compared to those in most of the NanoNiccine groups. For IgG1, Nic-KLH, NanoNiccines with MPLA, with Alum, and with MPLA and Alum, achieved titers of $8.0\pm0.9\times10^3$, $14.7\pm1.6\times10^3$, $12.3\pm2.3\times10^3$, and $12.4\pm2.1\times10^3$, respectively. For IgG2a, Nic-KLH, NanoNiccines with MPLA, with Alum, and with MPLA and Alum, achieved anti-KLH antibody titer of $2.0\pm0.1\times10^3$, $11.5\pm1.1\times10^3$, $2.2\pm0.3\times10^3$, and $8.5\pm1.1\times10^3$, respectively. The titers of IgG2b were $0.5\pm0.1\times10^3$, $2.0\pm0.3\times10^3$, $1.4\pm0.2\times10^3$, and $2.6\pm0.4\times10^3$ for Nic-KLH, NanoNiccines with MPLA, with Alum, and with MPLA and Alum, respectively. The four vaccines attained IgG3 titers of $1.7\pm1.0\times10^3$, $10.0\pm1.3\times10^3$, $2.4\pm0.6\times10^3$, and $9.0\pm1.1\times10^3$, respectively. To evaluate the relative magnitude of antibody response and cell-mediated response, the Th1/Th2 index was also calculated based on the titers of the different subtype antibodies. The Th1/Th2 indices are demonstrated in FIG. 80, inset. It was found that the Th1/Th2 indices achieved by all the nicotine vaccines were less than one. Among these vaccines, NanoNiccine with Alum achieved the lowest Th1/Th2 index of 0.112, while that with MPLA achieved the highest index of 0.434.

In Vivo Toxicity of NanoNiccine

Mice injected with PBS and nicotine vaccines were sacrificed on day 57. Major organs from the mice, including heart, lung, kidney, spleen, stomach, and liver were stored in 10% formalin. These organs were stained with H&E and examined under microscope within two weeks after harvest. As shown in FIGS. 81A-81DD, no significant difference was detected between the mice treated with PBS and those treated with nicotine vaccines, in all the examined organs, thus indicating the safety of NanoNiccines.

Discussion

Nicotine vaccines, exhibiting great potential as a future treatment against tobacco addition, have been intensively investigated [25]. Previous studies on development of nicotine vaccine mainly focused on improving the nicotine epitope, screening carrier protein, selecting adjuvants, and optimizing injection routes [14, 26, 27]. Despite the differences in nicotine vaccine design among various research groups, they were structurally similar to one another, that is nicotine haptens were covalently conjugated to a carrier protein [28]. To a great extent, such a design was inspired by the idea that small molecules, like nicotine, heroin, and cocaine, are unable to elicit an immune response on their own, and have to be associated with larger and more complex molecules to be immunogenic [29]. In animal trials, some of the traditional nicotine-protein conjugate vaccines were discovered to be highly immunogenic and could effectively block the entry of nicotine into the brain [30, 31]. In addition, some of them achieved encouraging results in early stages of clinical trials [32]. However, these vaccines are associated with some innate defects, which may limit their immunological efficacy and future improvement. The first problem of these vaccines is that there may exist immune response targets not only on the nicotine molecule, but also on amino acid sequences on the carrier protein. Given the much greater variations in structure and composition of a carrier protein as compared to those of the nicotine hapten, large quantities of polyclonal antibodies may be generated against the carrier protein. This may undermine the specificity of the nicotine vaccine, which is supposed to produce only nicotine specific antibodies. Moreover, vaccine conjugate may be drained to produce carrier protein specific antibodies, resulting in its lowered utilization efficiency. Thirdly, co-delivery of increasingly important molecular adjuvants by nicotine-protein conjugate vaccine is difficult [33, 34], thereby limiting the ability for further improving the immunogenicity of the vaccine.

Figure 82:
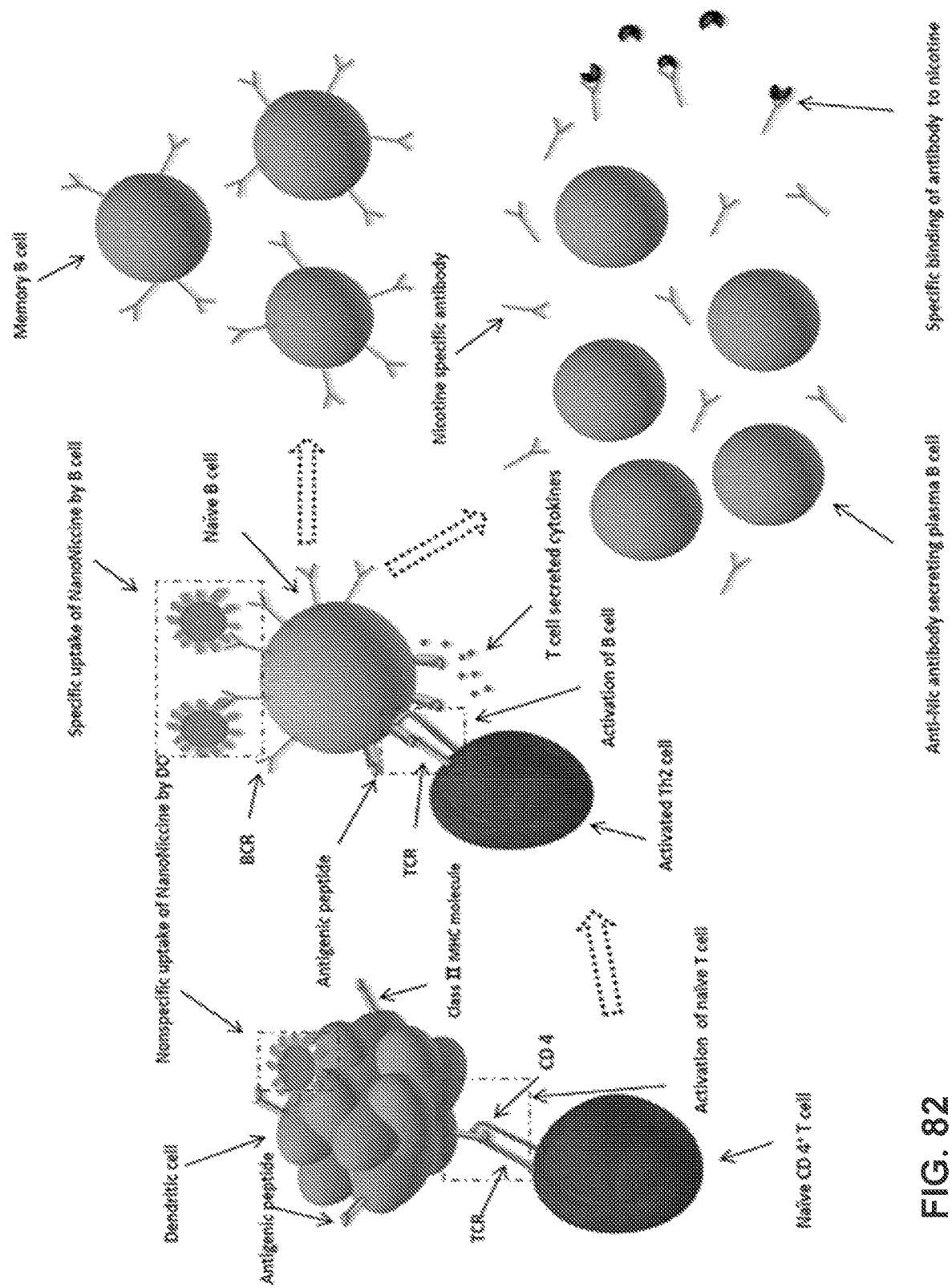
FIG. 82 shows schematic illustration of antibody production induced by NanoNiccine.

To overcome the shortcomings of the traditional nicotine protein conjugate vaccines, in this study, a lipid-PLGA nanoparticle based nicotine vaccine—NanoNiccine was invented. Core-shell hybrid nanoparticles have been intensively studied as delivery systems for anti-cancer drugs and vaccines [35-38]. These hybrid nanoparticles proved highly biocompatible and biodegradable. As shown in FIG. 82, the nicotine haptens and protein (KLH) are no longer covalently conjugated; instead, nicotine haptens are linked to the outer surface of the hybrid nanoparticle and KLH is enclosed within the PLGA core. As shown in FIG. 82, NanoNiccine may minimize the exposure of the protein to immune cells, and effectively present nicotine haptens to the immune system, thereby improving the specificity of the vaccine. Different from the traditional nicotine vaccines, protein in NanoNiccine does not act as a carrier for nicotine, but serves solely as an antigenic peptide supplier to bridge the interaction between DC, B cell, and T cell [39].

The assembly of the hybrid nanoparticle based nicotine vaccine in this study primarily involved three steps: the first step was PLGA nanoparticle formation, followed by lipid-PLGA assembly, and the last step involved conjugating nicotine epitope onto the hybrid nanoparticles. The whole process and components appeared to be complex, however, each step was easy to perform. Moreover, according to previous studies [20, 40], the physicochemical properties of the vaccine particles were controllable. Lipid-PLGA hybrid nanoparticle has proven to be an excellent delivery system for vaccines and anti-cancer drugs [41]. In addition, all the components of NanoNiccine in this study exhibited good safety for animals or human use [42-46].

The lipid layer of NanoNiccine was composed of three lipids, including DOTAP, DSPE-PEG(2000)COOH, and cholesterol. Each of the three lipids has its unique function. DOTAP [47], as a cationic lipid, may strengthen the association between the lipid layer and the negatively charged PLGA core via electrostatic attraction. The carboxylic acid groups on DSPE-PEG(2000)COOH serve as the ligand for conjugating nicotine epitope. Cholesterol acts as a stabilizer in the lipid layer to improve the stability of NanoNiccine [48]. As reported in our previous work [40], PEGylated lipid-PLGA hybrid nanoparticles are resistant to the harsh physiological environment. PEGylation may enable prolonged circulation of NanoNiccine and improve the bioavailability of the vaccine to immune cells. Since the adaptive immune system has evolved to recognize highly repetitive structures in antigens [49], the repetitive copies of the nicotine epitopes on the surface of NanoNiccine may allow its fast and effective recognition by immune cells, thereby leading to rapid development of immune response. Another important feature of NanoNiccine is that it can co-deliver molecular adjuvants [50], such as Toll-like receptor 9 (TLR 9) agonists (CpG ODNs), TLR 4 agonist (MPLA) and antigens. CpG ODNs can be easily enclosed within the PLGA core, and MPLA can be readily incorporated into the lipid layer. The incorporation of these molecular adjuvants may further improve the immunogenicity of NanoNiccine.

To be functional, the formation of core-shell hybrid structure is critical for NanoNiccine. Both CLSM and TEM images of NanoNiccine confirmed the formation of the hybrid structure. In our previous studies [20, 40], it was found that the hybrid structures of lipid-PLGA nanoparticles can be built via sonication mediated fusion, which was used in this study. Moreover, the hybrid nanoparticles proved to be highly stable under physiological conditions over time [40]. As illustrated in Scheme 2, to elicit immune response, NanoNiccine needs to be recognized through the cognate interaction between nicotine hapten on the lipid layer and B cell receptors [51], which is followed by cellular uptake of the vaccine particle. Therefore, the core-shell hybrid structure is of great importance to the immunological outcome of NanoNiccine. In this study, the prevalent existence of hybrid nanoparticles in both CLSM and TEM images demonstrated the high effectiveness and robustness of the hybrid nanoparticle assembly process.

For antibody response, vaccines need to be internalized and processed by APCs [39]. It has been discovered that APCs, especially DCs [52], preferably take up antigens with dimensions comparable to that of bacteria and viruses. Therefore, to facilitate the uptake of vaccine particles by immune cells, the size of NanoNiccine was designed to be within the nano-range. The results from the size distribution study confirmed that the three NanoNiccine particles, regardless of the formulation, had an average size of around 250 nm. Another advantage of a nano-sized vaccine is that the vaccine particles can freely drain from the site of injection into the lymph node [53], where they can extensively interact with the immune cells, thereby enhancing immune response. The FACS analysis showed that up to 96% of the DCs internalized NanoNiccine particles within 120 min, and there was a 30-fold increase in its uptake from 5 to 120 min, demonstrating that the physicochemical properties of NanoNiccine were quite favorable for cellular uptake. Rapid internalization of NanoNiccine by the DCs may lead to faster antibody production and reduce its nonspecific clearance during circulation.

Another pivotal step of antibody response development is antigen processing by APCs [39]. As shown in Scheme 2, after uptake by APCs, the protein (KLH) enclosed inside the PLGA core needs to be released and processed into antigenic peptides before being presented to the T helper cells. Therefore, the time that taken for antigen processing may also influence the outcome of the immune response. Previous studies showed that considerable amount of antigens was released from hybrid nanoparticle within 24 h in PBS buffer or human serum [54]. The antigen release might be faster in DCs than that in buffers, because DCs have some efficient mechanisms for antigens processing [55]. Although, we do not have direct evidence to show the degradation of hybrid nanoparticles in DCs, KLH, stained with Alexa 647 (red color), was not likely to diffuse out of hybrid nanoparticles due to its big size [56]. Therefore, it is highly possible that the widely distributed KLH in DCs at 120 min shown in FIGS. 77M-77P was released from hybrid nanoparticles after their degradation. This indicates that the proteins in NanoNiccine can be rapidly released and processed, which may allow rapid development of immune response.

The potent immunogenicity of NanoNiccine with MPLA was reflected by the significantly higher anti-nicotine antibody titer than that elicited by Nic-KLH after primary injection. Based on the minimal anti-KLH antibody titer shown in FIG. 79, it is highly possible that such high anti-nicotine antibody titers could largely be accredited to the ability of NanoNiccine to stimulate the immune system in a highly specific way. Interestingly, NanoNiccine administered with Alum did not achieve an anti-Nic antibody titer as high as the one without Alum. This might be caused by the depot effect of Alum [57], which may slow the movement of NanoNiccine particles and limit the interaction of NanoNiccine with the immune cells. Alum has long been used as a vaccine adjuvant due to its ability to strongly promote immune response [58]. The potent adjuvanticity of Alum was demonstrated by the tremendous increase in the anti-Nic antibody titer after the first booster. Despite the lower anti-Nic antibody titer after the primary injection, NanoNiccines with Alum achieved a level of antibody comparable to that with only MPLA. However, the level of anti-KLH antibody also considerably increased after the second injection of NanoNiccine supplemented with Alum. It is possible that KLH was released from some NanoNiccine particles, which were degraded after being retained by Alum for a long time. In contrast, NanoNiccine without Alum still maintained a significantly lower level of anti-KLH antibody titer compared to other vaccine formulations.

Surprisingly, the second booster injection did not increase antibody level in any of the vaccine formulations. In contrast, anti-Nic antibody titers of all vaccine groups considerably dropped after the third vaccine injection. Although, the exact mechanism is unknown, it is possible that the anti-Nic antibody already exceeded the threshold level of the immune response after the first booster injection and the immune system was insensitive to the nicotine vaccine at the third injection. Meanwhile, the IgG antibody in mice has a half-life of around one week [59], and this can also partially explain the sharp decrease in anti-Nic antibody concentration. Similar to the anti-Nic antibody, a large decrease in anti-KLH antibody was also detected in most vaccines after the second injection. However, anti-KLH antibody concentration significantly increased after the third injection of NanoNiccine with MPLA. The seemingly confusing results are in agreement with the above explanation that the immune system was tolerant to the NanoNiccine vaccines after high antibody levels were reached. It is possible the increase in anti-KLH antibody level after the third injection of NanoNiccine with MPLA is simply because the anti-KLH antibody level still did not reach the threshold level after the second injection.

As discussed above, NanoNiccine may have extended half-life after injection due to its ability to evade nonspecific clearance. Due to the short half-life of IgG, anti-Nic antibody level from the 55th day sera was supposed to be lower than that from the 35th day. On the contrary, anti-Nic antibody level from all NanoNiccine groups increased slightly in the final sera, indicating that the NanoNiccine particles could exist long enough to maintain a high level of anti-Nic antibody for a long term.

MPLA [60], as a molecular adjuvant, was incorporated into the lipid layer of NanoNiccine to promote the immune response. Although Alum has been conventionally used as a vaccine adjuvant for many years due to its strong adjuvanticity and acceptable safety, it has a couple of problems that have already been discussed in a previous study, including causing lesions at the site of injection, poorly defined adjuvant mechanism, and causing neurological complications [61]. In addition, as shown in the results, NanoNiccine with MPLA achieved a comparable level of anti-Nic antibody as NanoNiccine adjuvanted with Alum. Therefore, MPLA might be used as a candidate to replace Alum as an adjuvant for NanoNiccine. To study the polarity of the immune response induced by NanoNiccines, the Th1/Th2 index was calculated [62-64]. The low Th1/Th2 index in NanoNiccine supplemented with Alum substantiated that that Alum is a potent adjuvant for antibody production [58], which was reflected by the lower Th1/Th2 indices in vaccines supplemented with Alum. As reported in previous studies, MPLA primarily promotes cell mediated immune response instead of a antibody response [65, 66]. It was found that NanoNiccine with MPLA as the sole adjuvant had a Th1/Th2 index of 0.434, indicating that the immune response induced by this vaccine was Th2 skewed (which means that the antibody response was dominant).

Safety is always the most important criterion taken into consideration while to evaluating a vaccine. All the components in NanoNiccine, including KLH, nicotine hapten, MPLA, and lipid-PLGA hybrid nanoparticles have proved to be safe in previous studies [14, 67-69]. The histopathological examination on major organs of NanoNiccine immunized mice confirmed its safety.

Conclusion

In summary, we successfully constructed a lipid-PLGA hybrid nanoparticle based nicotine vaccine (NanoNiccine). NanoNiccine was designed to improve the specificity of the generated antibody and lengthen the immune response. The cellular uptake studies showed that NanoNiccine possessed physicochemical properties that enable a fast and efficient uptake by the DCs. Results from trials in mice showed that NanoNiccine exhibited superior immunogenicity compared to nicotine-protein conjugate vaccine. NanoNiccine could effectively minimize the generation of antibodies against KLH and tremendously promote the production of anti-Nic antibodies. The low Th1/Th2 index of NanoNiccine indicated that it could dominantly induce antibody response. Lastly, the histopathological examination of the major organs of the vaccinated mice demonstrated that NanoNiccine possessed excellent safety. Based on all reported results, NanoNiccine holds great promise as a candidate vaccine against nicotine addiction.

REFERENCES FOR EXAMPLE 4

[1] G. A. Giovino, S. A. Mirza, J. M. Samet, P. C. Gupta, M. J. Jarvis, N. Bhala, et al. Tobacco use in 3 billion individuals from 16 countries: an analysis of nationally representative cross-sectional household surveys. Lancet 380 (2012) 668-79.
[2] N. L. Benowitz. Nicotine addiction. N Engl J Med 362 (2010) 2295-303.
[3] T. Raupach, C. P. van Schayck. Pharmacotherapy for smoking cessation: current advances and research topics. CNS Drugs 25 (2011) 371-82.
[4] J. T. Hays, J. O. Ebbert. Varenicline for tobacco dependence. N Engl J Med 359 (2008) 2018-24.
[5] E. J. Mills, P. Wu, I. Lockhart, K. Wilson, J. O. Ebbert. Adverse events associated with nicotine replacement therapy (NRT) for smoking cessation. A systematic review and meta-analysis of one hundred and twenty studies involving 177,390 individuals. Tob Induc Dis 8 (2010) 8.
[6] R. Richmond, N. Zwar. Review of bupropion for smoking cessation. Drug Alcohol Rev 22 (2003) 203-20.
[7] P. R. Pentel, M. G. LeSage. New directions in nicotine vaccine design and use. Adv Pharmacol 69 (2014) 553-80.
[8] H. Zheng, Y. Hu, W. Huang, S. de Villiers, P. Pentel, J. Zhang, et al. Negatively Charged Carbon Nanohorn Supported Cationic Liposome Nanoparticles: A Novel Delivery Vehicle for Anti-Nicotine Vaccine. J Biomed Nanotechnol 11 (2015) 2197-210.
[9] D. K. Hatsukami, S. Rennard, D. Jorenby, M. Fiore, J. Koopmeiners, A. de Vos, et al. Safety and immunogenicity of a nicotine conjugate vaccine in current smokers. Clin Pharmacol Ther 78 (2005) 456-67.
[10] D. K. Hatsukami, D. E. Jorenby, D. Gonzales, N. A. Rigotti, E. D. Glover, C. A. Oncken, et al. Immunogenicity and smoking-cessation outcomes for a novel nicotine immunotherapeutic. Clin Pharmacol Ther 89 (2011) 392-9.
[11] E. H. Cerny, T. Cerny. Vaccines against nicotine. Hum Vaccin 5 (2009) 200-5.
[12] T. Storni, T. M. Kundig, G. Senti, P. Johansen. Immunity in response to particulate antigen-delivery systems. Adv Drug Deliv Rev 57 (2005) 333-55.
[13] S. Hamdy, P. Elamanchili, A. Alshamsan, O. Molavi, T. Satou, J. Samuel. Enhanced antigen-specific primary CD4+ and CD8+ responses by codelivery of ovalbumin and toll-like receptor ligand monophosphoryl lipid A in poly(D,L-lactic-co-glycolic acid) nanoparticles. J Biomed Mater Res A 81 (2007) 652-62.
[14] D. E. Keyler, S. A. Roiko, C. A. Earley, M. P. Murtaugh, P. R. Pentel. Enhanced immunogenicity of a bivalent nicotine vaccine. Int Immunopharmacol 8 (2008) 1589-94.
[15] M. J. McCluskie, D. C. Pryde, D. P. Gervais, D. R. Stead, N. Zhang, M. Benoit, et al. Enhancing immunogenicity of a 3' aminomethylnicotine-DT-conjugate antinicotine vaccine with CpG adjuvant in mice and non-human primates. Int Immunopharmacol 16 (2013) 50-6.
[16] M. G. LeSage, D. E. Keyler, P. R. Pentel. Current status of immunologic approaches to treating tobacco dependence: vaccines and nicotine-specific antibodies. AAPS J 8 (2006) E65-75.
[17] V. Mata-Haro, C. Cekic, M. Martin, P. M. Chilton, C. R. Casella, T. C. Mitchell. The vaccine adjuvant monophosphoryl lipid A as a TRIF-biased agonist of TLR4. Science 316 (2007) 1628-32.
[18] R. D. Weeratna, M. J. McCluskie, Y. Xu, H. L. Davis. CpG DNA induces stronger immune responses with less toxicity than other adjuvants. Vaccine 18 (2000) 1755-62.
[19] Y. Y. Yang, H. H. Chia, T. S. Chung. Effect of preparation temperature on the characteristics and release profiles of PLGA microspheres containing protein fabricated by double-emulsion solvent extraction/evaporation method. J Control Release 69 (2000) 81-96.
[20] Y. Hu, R. Hoerle, M. Ehrich, C. Zhang. Engineering the lipid layer of lipid-PLGA hybrid nanoparticles for enhanced in vitro cellular uptake and improved stability. Acta Biomater 28 (2015) 149-59.
[21] R. A. Jain. The manufacturing techniques of various drug loaded biodegradable poly(lactide-co-glycolide) (PLGA) devices. Biomaterials 21 (2000) 2475-90.
[22] Y. Hu, Z. Zhao, M. Ehrich, K. Fuhrman, C. Zhang. controlled release of antigen in dendritic cells using pH-sensitive liposome-polymeric hybrid nanoparticles. Polymer (Guildf) 80 (2015) 171-9.
[23] Y. Hu, H. Zheng, W. Huang, C. Zhang. A novel and efficient nicotine vaccine using nano-lipoplex as a delivery vehicle. Hum Vaccin Immunother 10 (2014) 64-72.
[24] J. P. Metlay, E. Pure, R. M. Steinman. Control of the immune response at the level of antigen-presenting cells: a comparison of the function of dendritic cells and B lymphocytes. Adv Immunol 47 (1989) 45-116.
[25] M. Sliwinska-Mosson, I. Zielen, H. Milnerowicz. New trends in the treatment of nicotine addiction. Acta Pol Pharm 71 (2014) 525-30.
[26] S. H. de Villiers, N. Lindblom, G. Kalayanov, S. Gordon, I. Baraznenok, A. Malmerfelt, et al. Nicotine hapten structure, antibody selectivity and effect relationships: results from a nicotine vaccine screening procedure. Vaccine 28 (2010) 2161-8.
[27] A. R. Ottney. Nicotine conjugate vaccine as a novel approach to smoking cessation. Pharmacotherapy 31 (2011) 703-13.
[28] J. Hartmann-Boyce, K. Cahill, D. Hatsukami, J. Cornuz. Nicotine vaccines for smoking cessation. Cochrane Database Syst Rev (2012) CD007072.
[29] K. V. Singh, J. Kaur, G. C. Varshney, M. Raje, C. R. Suri. Synthesis and characterization of hapten-protein conjugates for antibody production against small molecules. Bioconjug Chem 15 (2004) 168-73.
[30] D. H. Malin. Nicotine dependence: studies with a laboratory model. Pharmacol Biochem Behav 70 (2001) 551-9.
[31] A. Y. Moreno, M. R. Azar, N. A. Warren, T. J. Dickerson, G. F. Koob, K. D. Janda. A critical evaluation of a nicotine vaccine within a self-administration behavioral model. Mol Pharm 7 (2010) 431-41.
[32] R. E. Fahim, P. D. Kessler, M. W. Kalnik. Therapeutic vaccines against tobacco addiction. Expert Rev Vaccines 12 (2013) 333-42.
[33] R. L. Coffman, A. Sher, R. A. Seder. Vaccine adjuvants: putting innate immunity to work. Immunity 33 (2010) 492-503.
[34] S. de Jong, G. Chikh, L. Sekirov, S. Raney, S. Semple, S. Klimuk, et al. Encapsulation in liposomal nanoparticles enhances the immunostimulatory, adjuvant and anti-tumor activity of subcutaneously administered CpG ODN. Cancer Immunol Immunother 56 (2007) 1251-64.

[35] M. Zheng, C. Yue, Y. Ma, P. Gong, P. Zhao, C. Zheng, et al. Single-step assembly of DOX/ICG loaded lipid—polymer nanoparticles for highly effective chemo-photothermal combination therapy. ACS Nano 7 (2013) 2056-67.

[36] K. Hadinoto, A. Sundaresan, W. S. Cheow. Lipid-polymer hybrid nanoparticles as a new generation therapeutic delivery platform: a review. Eur J Pharm Biopharm 85 (2013) 427-43.

[37] J. Cheng, B. A. Teply, I. Sherifi, J. Sung, G. Luther, F. X. Gu, et al. Formulation of functionalized PLGA-PEG nanoparticles for in vivo targeted drug delivery. Biomaterials 28 (2007) 869-76.

[38] L. Zhang, J. M. Chan, F. X. Gu, J. W. Rhee, A. Z. Wang, A. F. Radovic-Moreno, et al. Self-assembled lipid—polymer hybrid nanoparticles: a robust drug delivery platform. ACS Nano 2 (2008) 1696-702.

[39] J. Banchereau, R. M. Steinman. Dendritic cells and the control of immunity. Nature 392 (1998) 245-52.

[40] Y. Hu, M. Ehrich, K. Fuhrman, C. Zhang. In vitro performance of lipid-PLGA hybrid nanoparticles as an antigen delivery system:lipid composition matters. Nanoscale Res Lett 9 (2014) 434.

[41] B. Mandal, H. Bhattacharjee, N. Mittal, H. Sah, P. Balabathula, L. A. Thoma, et al. Core-shell-type lipid-polymer hybrid nanoparticles as a drug delivery platform. Nanomedicine 9 (2013) 474-91.

[42] H. I. Chang, M. K. Yeh. Clinical development of liposome-based drugs: formulation, characterization, and therapeutic efficacy. Int J Nanomedicine 7 (2012) 49-60.

[43] J. M. Lu, X. Wang, C. Marin-Muller, H. Wang, P. H. Lin, Q. Yao, et al. Current advances in research and clinical applications of PLGA-based nanotechnology. Expert Rev Mol Diagn 9 (2009) 325-41.

[44] P. H. Hoogsteder, D. Kotz, P. I. van Spiegel, W. Viechtbauer, O. C. van Schayck. Efficacy of the nicotine vaccine 3'-AmNic-rEPA (NicVAX) co-administered with varenicline and counselling for smoking cessation: a randomized placebo-controlled trial. Addiction 109 (2014) 1252-9.

[45] D. Miles, H. Roche, M. Martin, T. J. Perren, D. A. Cameron, J. Glaspy, et al. Phase III multicenter clinical trial of the sialyl-TN (STn)-keyhole limpet hemocyanin (KLH) vaccine for metastatic breast cancer. Oncologist 16 (2011) 1092-100.

[46] M. S. Duthie, H. P. Windish, C. B. Fox, S. G. Reed. Use of defined TLR ligands as adjuvants within human vaccines. Immunol Rev 239 (2011) 178-96.

[47] M. Mansourian, A. Badiee, S. A. Jalali, S. Shariat, M. Yazdani, M. Amin, et al. Effective induction of anti-tumor immunity using p5 HER-2/neu derived peptide encapsulated in fusogenic DOTAP cationic liposomes co-administrated with CpG-ODN. Immunol Lett 162 (2014) 87-93.

[48] T. Nakazawa, S. Nagatsuka, O. Yukawa. Effects of membrane stabilizing agents and radiation on liposomal membranes. Drugs Exp Clin Res 12 (1986) 831-5.

[49] M.F. Bachmann, G. T. Jennings. Vaccine delivery: a matter of size, geometry, kinetics and molecular patterns. Nat Rev Immunol 10 (2010) 787-96.

[50] F. Steinhagen, T. Kinjo, C. Bode, D. M. Klinman. TLR-based immune adjuvants. Vaccine 29 (2011) 3341-55.

[51] R. Medzhitov, C. A. Janeway, Jr. Innate immune recognition and control of adaptive immune responses. Semin Immunol 10 (1998) 351-3.

[52] S. T. Reddy, M. A. Swartz, J. A. Hubbell. Targeting dendritic cells with biomaterials: developing the next generation of vaccines. Trends Immunol 27 (2006) 573-9.

[53] S. T. Reddy, A. Rehor, H. G. Schmoekel, J. A. Hubbell, M. A. Swartz. In vivo targeting of dendritic cells in lymph nodes with poly(propylene sulfide) nanoparticles. J Control Release 112 (2006) 26-34.

[54] (!!! INVALID CITATION !!!).

[55] I. Mellman, R. M. Steinman. Dendritic cells: specialized and regulated antigen processing machines. Cell 106 (2001) 255-8.

[56] J. R. Harris, J. Markl. Keyhole limpet hemocyanin (KLH): a biomedical review. Micron 30 (1999) 597-623.

[57] H. HogenEsch. Mechanisms of stimulation of the immune response by aluminum adjuvants. Vaccine 20 Suppl 3 (2002) S34-9.

[58] M. Kool, K. Fierens, B. N. Lambrecht. Alum adjuvant: some of the tricks of the oldest adjuvant. J Med Microbiol 61 (2012) 927-34.

[59] P. Vieira, K. Rajewsky. The half-lives of serum immunoglobulins in adult mice. Eur J Immunol 18 (1988) 313-6.

[60] C. R. Casella, T. C. Mitchell. Putting endotoxin to work for us: monophosphoryl lipid A as a safe and effective vaccine adjuvant. Cell Mol Life Sci 65 (2008) 3231-40.

[61] L. Tomljenovic, C. A. Shaw. Aluminum vaccine adjuvants: are they safe? Curr Med Chem 18 (2011) 2630-7.

[62] M. Moser, K. M. Murphy. Dendritic cell regulation of TH1-TH2 development. Nat Immunol 1 (2000) 199-205.

[63] L. J. Cruz, P. J. Tacken, R. Fokkink, C. G. Figdor. The influence of PEG chain length and targeting moiety on antibody-mediated delivery of nanoparticle vaccines to human dendritic cells. Biomaterials 32 (2011) 6791-803.

[64] M. A. Shahbazi, T. D. Fernandez, E. M. Makila, X. Le Guevel, C. Mayorga, M. H. Kaasalainen, et al. Surface chemistry dependent immunostimulative potential of porous silicon nanoplatforms. Biomaterials 35 (2014) 9224-35.

[65] P. Moingeon, J. Haensler, A. Lindberg. Towards the rational design of Th1 adjuvants. Vaccine 19 (2001) 4363-72.

[66] F. Sarti, G. Perera, F. Hintzen, K. Kotti, V. Karageorgiou, O. Kammona, et al. In vivo evidence of oral vaccination with PLGA nanoparticles containing the immunostimulant monophosphoryl lipid A. Biomaterials 32 (2011) 4052-7.

[67] J. M. Chan, L. Zhang, K. P. Yuet, G. Liao, J. W. Rhee, R. Langer, et al. PLGA-lecithin-PEG core-shell nanoparticles for controlled drug delivery. Biomaterials 30 (2009) 1627-34.

[68] T. Kamphuis, T. Meijerhof, T. Stegmann, J. Lederhofer, J. Wilschut, A. de Haan. Immunogenicity and protective capacity of a virosomal respiratory syncytial virus vaccine adjuvanted with monophosphoryl lipid A in mice. PLoS One 7 (2012) e36812.

[69] Y. Dong, S. S. Feng. Methoxy poly(ethylene glycol)-poly(lactide) (MPEG-PLA) nanoparticles for controlled delivery of anticancer drugs. Biomaterials 25 (2004) 2843-9.

Example 5

Introduction

Tobacco smoking has constantly been the leading cause of preventable death for decades, resulting in tremendous socioeconomic burden worldwide [1]. Due to the less than desired efficacy of current pharmacotherapies, more potent and safer medications are needed to treat tobacco addiction [2]. Nicotine vaccine, which can induce production of nicotine-specific antibodies and sequester nicotine in the blood, has been widely considered a promising candidate therapy for smoking cessation [3].

In a previous study, we invented a hybrid nanoparticle-based nicotine vaccine (NanoNiccine), which could potently produce nicotine-specific antibodies [4]. As compared to the conventional protein-nicotine conjugate vaccine, NanoNiccine was able to produce a significantly higher titer anti-nicotine antibodies (ANAs). It has been found that a higher titer of ANAs was associated with a better treatment efficacy on smoking cessation [5, 6]. Therefore, one of the major tasks in developing a nicotine vaccine is to improve its immunogenicity [4, 7]. Traditionally, vaccines are co-administered with adjuvants to enhance their immunogenicity [8]. It is likely to promote the immunogenicity of NanoNiccine by introducing a desirable adjuvant.

Currently, the most commonly used vaccine adjuvants for human use are aluminum salts (Alum) [9]. Although, Alum can strongly augment immune response against poorly immunogenic vaccines, increasingly concerns have been raised over their safety [10]. The first problem with Alum is that their mechanism of action is poorly understood, making it difficult to predict and discover the potential adverse effects [11]. Secondly, some studies revealed that Alum were associated with some serious autoimmune diseases in humans [12]. Thirdly, it has long been documented that Alum have negative impact on the human nervous system [13], and this problem might be more profound for a nicotine vaccine, which may require multiple injections. Fourthly, the most commonly observed detrimental outcome of Alum is lesion caused by their long-term persistence at the site of injection [14]. Moreover, according to our previous findings (not published), due to the depot effect of Alum [15], a considerable amount of NanoNiccine was retained at the site of injection, which may result in limited interaction of the vaccine particles and the immune cells. In addition, the intact hybrid structure of NanoNiccine is essential for its immunogenicity[4] and long-term retention of the vaccine at the site of injection by Alum may eventually lead to the disintegration of the hybrid structure, undermining the utilization efficiency of NanoNiccine. Therefore, there is great necessity to replace Alum with a suitable adjuvant to avoid Alum-related side effects as well as to improve the immunogenicity of NanoNiccine.

Among these adjuvants, toll-like receptor 9 (TLR9) agonists [16], CpG DNAs, might be an adjuvant of choice for NanoNiccine. In recent years, CpG DNAs have emerged as new generation of vaccine adjuvants due to their potent ability to safely promote immunogenicity for vaccines[17]. It was found that CpG DNAs via TLR9 mediated cellular response could tremendously promote activation of B cells, and dendritic cells (DCs), leading to accelerated immune cell proliferation and enhanced secretion of cytokines, chemokines, and antibodies [18, 19].

Compared to Alum, the mechanism in the adjuvanticity of CpG DNAs is well understood and no major side effects have been discovered when using CpG DNAs as vaccine adjuvants in animals [20]. It was also reported that CpG DNA, as an aqueous soluble adjuvant, could be enclosed within the poly lactic-co-glycolic acid (PLGA) core without bringing extra engineering challenges [21]. Moreover, delivering CpG DNAs with the PLGA core is also immunologically sound, because most of the TLR 9 are intracellularly distributed [22, 23], and CpG DNA may effectively interact with these receptors, following its release from the nanoparticle in the endosomes of the immune cells.

In this study, to study the influence of CpG DNA on the immunogenicity of NanoNiccine, the vaccine harboring CpG ODN 1555 or CpG ODN 1826 [24, 25] or a combination of the two was assembled. The physicochemical properties of these vaccines, including particle size and surface charge, were measured. The cellular uptake of the NanoNiccines by DCs were also studied. Lastly, the immunogenicity of these NanoNiccines was evaluated in mice. It was found that both CpG ODN 1555 and CpG ODN 1826 could significantly improve the titer of ANAs in mice. Surprisingly, we observed that a combination of CpG ODN 1555 and CpG ODN 1826 exerted suppressive effect on the immunogenicity of NanoNiccine.

Materials and Methods

Materials

Lipids, including 1,2-dioleoyl-3-trimethylammonium-propane (DOTAP), 1,2-distearoyl-sn-glycero-3-phosphoethanolamine-N-[carboxy(polyethylene glycol)-2000] (ammonium salt) ((DSPE-PEG2000) carboxylic acid), cholesterol, and 1,2-diphytanoyl-sn-glycero-3-phosphoethanolamine-N-(7-nitro-2-1,3-benzoxadiazol-4-yl) (ammonium salt) (NBD PE) were purchased from Avanti Polar Lipids, Inc. (Alabaster, Ala.). Lactel® 50:50 PLGA was purchased from Durect Corporation (Cupertino, Calif.). Fetal bovine serum (FBS), Granulocyte macrophage-colony stimulating factor (GM-CSF) recombinant mouse protein, Alpha minimum essential medium, trypsin/EDTA, and Alexa Fluor® 647 hydrazide were purchased from Life Technologies Corporation (Grand Island, N.Y.). Poly (vinyl alcohol) (PVA, MW 89,000-98,000), dichloromethane (DCM), and bovine serum albumin (BSA) were purchased from Sigma-Aldrich Inc. (Saint Louis, Mo.). Alexa Fluor® 647 hydrazide (Alexa 647), Keyhole limpet hemocyanin (KLH), Imject™ Alum Adjuvant (Alum), 1-ethyl-3-[3-dimethylaminopropyl] carbodiimide hydrochloride (EDC), and sulfo-NHS were purchased from Thermo Fisher Scientific Inc. (Rockford, Ill.). JAWSII (ATCC® CRL-11904™) immature dendritic cell was purchased from ATCC (Manassas, Va.). (San Diego, Calif.). Rac-trans 3'-aminomethyl nicotine (Nic) was purchased from Toronto Research Chemicals Inc. (Toronto, Canada). Goat Anti-Mouse IgG, Rabbit Anti-Goat IgG HRP conjugate, Goat Anti-Mouse IgG1 HRP conjugate, Goat Anti-Mouse IgG2a HRP conjugate, Goat Anti-Mouse IgG2b HRP conjugate, and Goat Anti-Mouse IgG3 HRP conjugate were purchased from Alpha Diagnostic Intl. Inc. (San Antonio, Tex.). TMB One Component Microwell Substrate was purchased from SouthernBiotech (Birmingham, Ala.). CpG ODN 1555 (GCTAGACGTTAGCGT) and CpG ODN 1826 (TCCATGACGTTCCTGACGTT) were synthesized by Integrated DNA Technologies (Coralville, Iowa). All other chemicals were of analytical grade.

Synthesis of PLGA Nanoparticles Containing KLH and CpG ODNs

PLGA nanoparticles were fabricated according to previous reports with proper modifications [26, 27]. Briefly, PLGA (30 mg) was dissolved in DCM (1 mL), followed by mixing with 100 µL phosphate buffered saline (PBS) buffer containing 2 mg KLH and 1.6 mg CpG ODN 1555 or CpG ODN 1826 or CpG ODN combinations. The resultant mixture was emulsified in Branson B1510DTH Ultrasonic Cleaner (Branson, Danbury, Conn.) for 10 min. The primary emulsion was added drop-wise into 100 mL PVA (0.5% (w/v)), and continuously stirred for 10 min at 500 rpm. The above suspension was emulsified through sonication using a sonic dismembrator (Model 500; Fisher Scientific, Pittsburgh, Pa.) at 70% amplitude for 30 s. The secondary emulsion was stirred overnight to allow DCM to evaporate. PLGA nanoparticles in suspension were collected by centrifugation at 10,000 g, 4° C. for 60 min using an Eppendorf centrifuge. (Eppendorf, Hauppauge, N.Y.). The pellet was suspended in 10 mL phosphate buffered saline (PBS) buffer (pH 7.4) and stored at 4° C. for later use.

Fabricating Liposomes and Assembly of NanoNiccine

Liposome was fabricated using a previously reported method [27]. Briefly, lipid film containing 2.83 mg DOTAP, 3.08 mg (DSPE-PEG2000) carboxylic acid, and 0.1 mg cholesterol was hydrated with 1 mL 55° C. pre-warmed PBS buffer. After vigorous vortex for 2 min, the lipids suspension was sonicated by a Branson B1510DTH Ultrasonic Cleaner (Branson, Danbury, Conn.) for 5 min and cooled to room temperature. The above prepared liposomes and PLGA nanoparticles were mixed by vortex and sonicated for 15 min using a Branson B1510DTH Ultrasonic Cleaner, followed by 5 min sonication in an ice bath using a sonic dismembrator at 15% amplitude (pulse on 20 s, pulse off 50 s). The formed lipid-PLGA nanoparticles were dialyzed against 1000 mL activation buffer (0.1M MES, 0.5M NaCl, pH 6.0) for 2 h. 4.1 mg EDC and 11.3 mg sulfo-NHS were reacted with the hybrid nanoparticle suspension for 20 min at room temperature. The activated nanoparticles were dialyzed against 1000 mL coupling buffer (100 mM sodium phosphate, 150 mM NaCl; pH 7.2) for 30 min, followed by incubating with 4.1 mg rac-trans 3'-aminomethyl nicotine for 4 h. Impurities were removed by dialysis against PBS buffer (pH 7.4) for 12 h. The assembled NanoNiccine was stored at 4° C. for future use.

Synthesis of Nic-BSA as ELISA Coating Material

Nic-BSA was synthesized according to a method described in a previous study [4]. Briefly, 10 mg BSA dissolved in 5 mL buffer (0.1M MES, 0.5M NaCl, pH 6.0) was incubated with 2 mg EDC and 5.6 mg sulfo-NHS for 20 min. The activated BSA was reacted with 2 mg rac-trans 3'-aminomethyl nicotine at room temperature for 3 h. Impurities were removed by dialysis (NMWL, 6000-8000) against 2000 mL PBS buffer (pH 7.4) for 12 h at room temperature. The purified Nic-BSA conjugate was stored at 4° C. for future use.

Synthesis of Alexa 647-KLH Conjugate

Alexa 647-KLH conjugate was synthesized using a method described in a previous study [4]. 4 mg KLH dissolved in 2 mL activation buffer (0.1M MES, 0.5M NaCl, pH 6.0) was incubated with 1 mg EDC and 2.8 mg sulfo-NHS for 20 min. The activated KLH was reacted with 0.1 mg Alexa Fluor® 647 hydrazide at room temperature for 4 h. The excessive Alexa 647, EDC, and Sulfo-NHS were removed by dialysis against 2000 mL PBS (pH 7.4) for 12 h. The purified Alexa 647-KLH conjugate was lyophilized and stored at 4° C. for future use.

Characterization of Physicochemical Properties of NanoNiccines

NanoNiccines with different types of CpG ODNs were diluted by 10 fold in PBS buffer (pH 7.0). The physicochemical properties including particle size (diameter, nm) and surface charge (zeta potential, mV) were measured at room temperature using a Malvern Nano-ZS zetasizer (Malvern Instruments Ltd, Worcestershire, United Kingdom).

Morphological Study of NanoNiccine by Confocal Laser Scanning Microscopy (CLSM)

Fluorescently labeled NanoNiccine was assembled using the methods as described for regular NanoNiccine with proper modifications. To label the core-shell structure of NanoNiccine, Alexa 647—KLH was used to replace KLH, and NBD PE was added into the lipids. A Zeiss LSM 880 Laser Scanning Microscope (Carl Zeiss, German) was used to image the fluorescently labeled NanoNiccine.

Morphological Study of NanoNiccine by Transmission Electrical Microscopy (TEM)

Nanoparticles were examined by TEM using a method as described in a previous article [27]. PLGA nanoparticles, liposomes, and NanoNiccine nanoparticles were dropped onto a 300-mesh Formvar-coated copper grid. After standing 10 min, the remaining suspension was carefully removed with wipes, and the samples were negatively stained using fresh 1% phosphotunstic acid for 20 s and washed with ultrapure water twice. The dried samples were imaged on a JEOL JEM 1400 Transmission Electron Microscope (JEOL Ltd., Tokyo, Japan).

Study of Cellular Uptake of NanoNiccine by DCs Using (CLSM)

$5 \times 10^5$ DCs cultured in 2 well chamber slide (Thermo Fisher Scientific Inc., Rd, Rockford, Ill.) were treated with 100 μg of Alexa 647 and NBD labeled NanoNiccine containing no CpG DNA (NanoNiccine), NanoNiccine containing CpG ODN 1555 (NanoNiccine 1555), and NanoNiccine containing CpG ODN 1826 (NanoNiccine 1826) for 30 min, 60 min, and 90 min, respectively. After incubation, the medium was immediately removed and cells were washed 5 times with PBS buffer (pH 7.4). Freshly prepared 4% (w/v) paraformaldehyde (2 mL) was added into each well, and cells were fixed for 15 min, followed by washing 3 times with PBS buffer (pH 7.4). Fixed cells were labeled with DAPI Fluoromount-G® (SouthernBiotech, Birmingham, Ala.). Images were acquired using a Zeiss LSM 880 Laser Scanning Microscope (Carl Zeiss, Germany).

Immunizing Mice with Nicotine Vaccines

All animal studies were carried out following the National Institutes of Health guidelines for animal care and use. Animal protocols were approved by the Institutional Animal Care and Use Committee at Virginia Polytechnic Institute and State University. Groups of n=5 female BALB/c mice (8-10 weeks, 16-20 g) were immunized by subcutaneous (s.c.) injection on days 0 (Primary injection), 14 (booster injection) with PBS buffer (pH 7.4), NanoNiccine, NanoNiccine containing 20 μg CpG ODN 1555 (NanoNiccine 1555), NanoNiccine containing 20 μg CpG ODN 1826 (NanoNiccine 1826), NanoNiccine with 10 μg CpG ODN 1555 and 10 μg CpG ODN 1826 (NanoNiccine MixL); and NanoNiccine containing 20 μg CpG ODN 1555 and 20 μg CpG ODN 1826 (NanoNiccine MixH). All the vaccine constructs contained total amount of 25 μg KLH. Following vaccine administration, blood samples (~200 μl) were collected on days −2, 13, 28, and 35 via retroorbital puncture from each mouse. Sera centrifuged from blood were stored at −80° C.

Measurement of Titers of Specific Anti-Nicotine IgG and Anti-KLH IgG Antibodies Using Enzyme-Linked Immunosorbent Assay (ELISA)

Mice sera were analyzed according to the ELISA procedure described in previous publications with minor modifications [4, 5, 28]. Nic-BSA and KLH were used as coating material for measurement of anti-Nic IgG and anti-KLH IgG, respectively. MICROLON® 96 well plates (Greiner BioOne, Longwood, Fla.) were coated with Nic-BSA conjugate or KLH (10 μg/mL in carbonate buffer, 0.05 M, pH 9.6, 100 μL/well) and incubated at 25° C. for 5 h. The plates were washed with PBS-Tween 20 (0.1%) for 3 times and distilled water for 3 times, followed by blocking with 300 μL Pierce® protein-free T20 blocking buffer for 12 h. After washing, 100 µL of each dilution (1:25, 1:125, 1:625, 1:3125, 1:15625, 1:78125 and 1:390625) of serum from each mouse was incubated in plates at 25° C. for 2 h. The plates were washed again, and incubated with 100 µL Anti-Mouse IgG from goat (1:5000) for 1 h. The plates were washed as before, and incubated with 100 µL Rabbit Anti-Goat IgG-HRP (1:5000) for 1 h. After washing as before, 100 µL of TMB One Component Microwell Substrate was added into each well and incubated for 10 min, and the reaction was stopped by adding 100 µL of 0.5% (v/v) H2SO4. The absorbance for each well at 450 nm was recorded. Titer was defined as the dilution factor at which OD450 falls to half of the maximal.

Measurement of specific anti-nicotine IgG subtype antibodies using ELISA

Subtype anti-Nic IgG antibodies, including IgG1, IgG2a, IgG2b, and IgG3 from day 13, day 28, and day 35 sera were measured using ELISA. Subtype antibodies were measured using an ELISA method exactly described in a previous article.

Histopathological Examination

Mice immunized with NanoNiccine, NanoNiccine 1555, NanoNiccine 1826, NanoNiccine MixL, and NanoNiccine MixH were scarified on day 37. Mice organs, including heart, kidney, spleen, liver, and stomach were harvested and stored in 10% buffered formalin. The organs were treated with H&E staining using a method as described before. Sections were examined by light microscopy on an Olympus CKX41 Inverted Microscope and images were captured using an INFINITY 1 camera.

Data Analysis

Titers of anti-Nic IgG and anti-KLH IgG were compared among groups using one way ANOVA and comparisons among paired groups were analyzed with Tukey's HSD. The difference is considered as significant when P-value is less than 0.05. Each measurement was carried out at least three times, and the results were expressed as mean±standard deviation.

Results and Discussion

Characterization of morphology and physicochemical properties of NanoNiccines

In recently years, nicotine vaccine has emerged as a novel and promising strategy to treat nicotine addiction [6]. Results from previous clinical trials showed that nicotine vaccine was effective in helping smokers quit smoking [29]. However, all the past clinical trials failed due to the unsatisfactory abstinence rates [30]. The failure of these vaccines might be attributed to their innate defects, including low specificity, poor immunogenicity, and short-lasting antibody response [31, 32]. To overcome the shortcomings of the traditional nicotine-protein conjugate vaccine, in a previous work, we invented a lipid-PLGA hybrid nanoparticle-based nicotine vaccine (NanoNiccine). In mice trials, NanoNiccine demonstrated superiorly higher specificity and stronger immunogenicity than a nicotine-KLH conjugate vaccine. In the previous study, Alum was used as the adjuvant for NanoNiccine. However, according to our findings (not published) and other reports [10, 33], Alum as the adjuvant may not be optimal for NanoNiccine due to lesions and other adverse side effects.

Figure 83C:
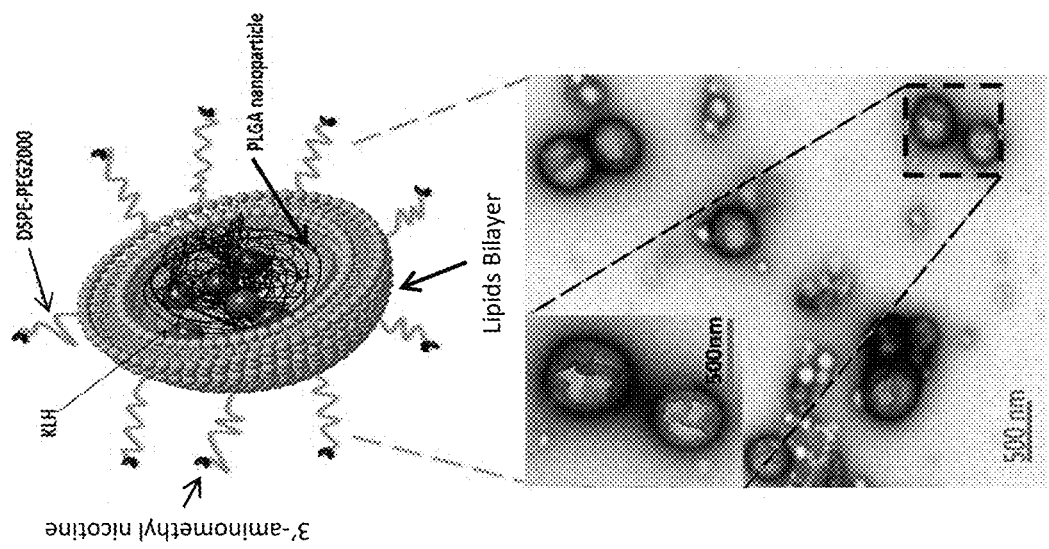
FIGS. 83A-83C show schematic illustrations and TEM images of (FIG. 83A) PLGA nanoparticle, (FIG. 83B) liposome, and (FIG. 83C) NanoNiccine. NanoNiccine was constructed by hybridization of PLGA nanoparticle and liposome, followed by conjugation with 3'-aminomethyl nicotine.
Figure 83B:
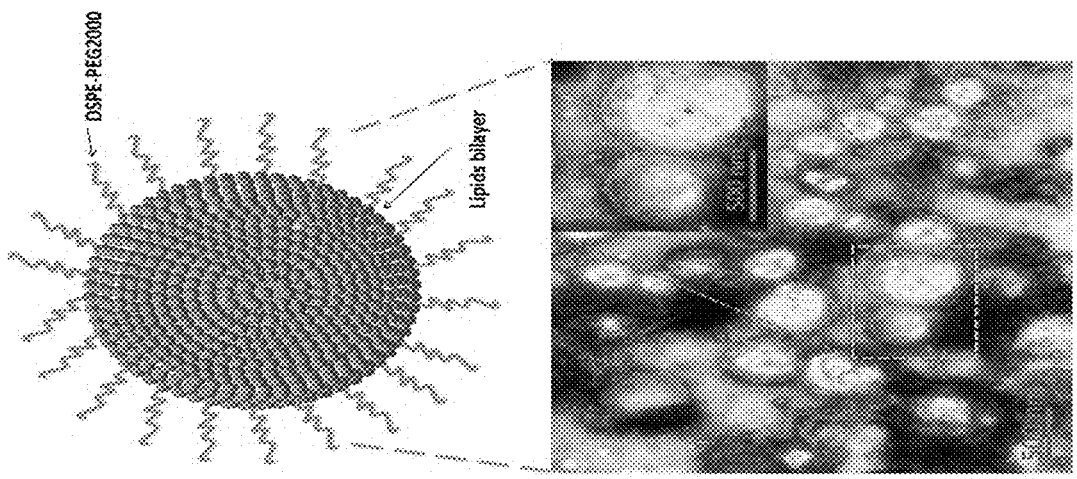
Figure 83A:
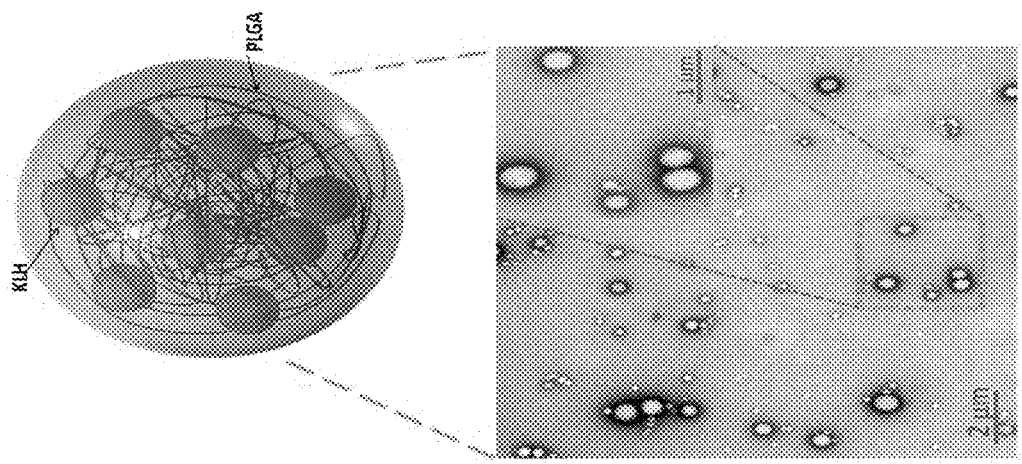

In this study, to avoid Alum related problems, NanoNiccines enclosing CpG DNAs as the adjuvant were constructed. As shown in FIGS. 83A-83C, NanoNiccine was assembled from PLGA nanoparticle and liposome. Due to its favorable properties, including biocompatibility, biodegradability, and controlled release, PLGA nanoparticle has been widely used as a carrier for anti-cancer drugs, and vaccines [34, 35]. In this study, PLGA nanoparticles were fabricated via a conventional double emulsion and solvent evaporation technique [36]. As shown in FIG. 83A, KLH was enclosed within the PLGA nanoparticle to serve as a source of antigenic peptides to the immune cells [37]. As discussed in a previous research [4], this design is fundamentally different from that of the traditional nicotine-protein conjugate vaccines and is expected to considerably improve the specificity of the nicotine vaccine. The TEM images (FIG. 83A) showed that the KLH enclosing PLGA nanoparticles were spherically shaped with a particle size at around 200-300 nm. Another major component of NanoNiccine is the lipid layer, which covers the PLGA nanoparticle. Liposomes of different formulations have a long history of acting as delivery systems for anti-cancer drugs and antigens [38-40]. In this study, liposomes were formed from DOTAP, DSPE-PEG (2000) COOH, and cholesterol through a lipid film rehydration technique [27]. DSPE-PEG (2000) COOH could function to improve the stability of nanoparticles as well as provide the reactive carboxylic group for conjugation with the nicotine hapten [4, 41]. As shown in FIG. 83B, liposomes also had a spherical shape with a diameter at around 300-500 nm. To take the advantages of both PLGA nanoparticles and liposomes, NanoNiccine was designed to use the lipid-PLGA hybrid nanoparticles as delivery system [4, 27]. However, NanoNiccine was not just a simple physical combination of PLGA nanoparticle and liposome, the practical functions of the two structural components were fully considered. For instance, the lipid layer can minimize premature degradation of the PLGA nanoparticle from enzymes as well as facilitate cellular uptake of nanoparticles by the immune cells [27, 42, 43]. In addition, if necessary, the lipid layer can carry molecular adjuvants, such as monophosphoryl lipid A (MPLA) [4, 44, 45], to further enhance the immunogenicity of NanoNiccine. The quantity of DSPE-PEG (2000) COOH in the lipid layer is tunable [27], which makes the density of the nicotine epitope on the surface of NanoNiccine adjustable, thus making the immunogenicity of NanoNiccine controllable [46]. This is especially useful when users need different levels of treatment. For the PLGA core, it can serve as a rigid support to improve the stability of lipid layer [26]. In addition, it can prevent KLH from degradation by proteinases as well as permit controlled release of the antigen and adjuvants [47, 48]. Moreover, in this study, CpG DNAs as molecular adjuvants were harbored within PLGA core to augment the immune response [49]. The TEM image of NanoNiccine (FIG. 83C) clearly showed that the vaccine had a hybrid structure, in which a thin and grey lipid layer was coating on a white and solid PLGA core. Similar to both liposome and PLGA nanoparticle, NanoNiccine also had a round shape. In addition, NanoNiccine had a size very close to the PLGA nanoparticle, which was at around 300 nm, indicating that the size of NanoNiccine was primarily decided by the size of the PLGA nanoparticles. Previous studies also showed that the dimension of the core-shell hybrid nanoparticles was largely dependent on the size of the core part [26, 27, 50].

To further validate the assembly of NanoNiccine, the vaccine particle was fluorescently marked, in which the lipid layer was labeled with NBD (green color) and KLH in the PLGA core was stained with Alexa 647 (red color). The confocal image (FIGS. 84A-84C) of NanoNiccine particles showed that the majority of the particles were simultaneously labeled by NBD and Alexa 647, indicating a hybrid structure was successfully constructed in NanoNiccine. Also consistent with the TEM image of NanoNiccine, the confocal picture of NanoNiccine showed that most of the vaccine particles had a particle size within nano-range. The prevalent existence of the hybrid nanoparticle displayed in FIGS. 84A-84C also demonstrated the high robustness of the nanoparticle formation technique applied in this study.

Figure 85:
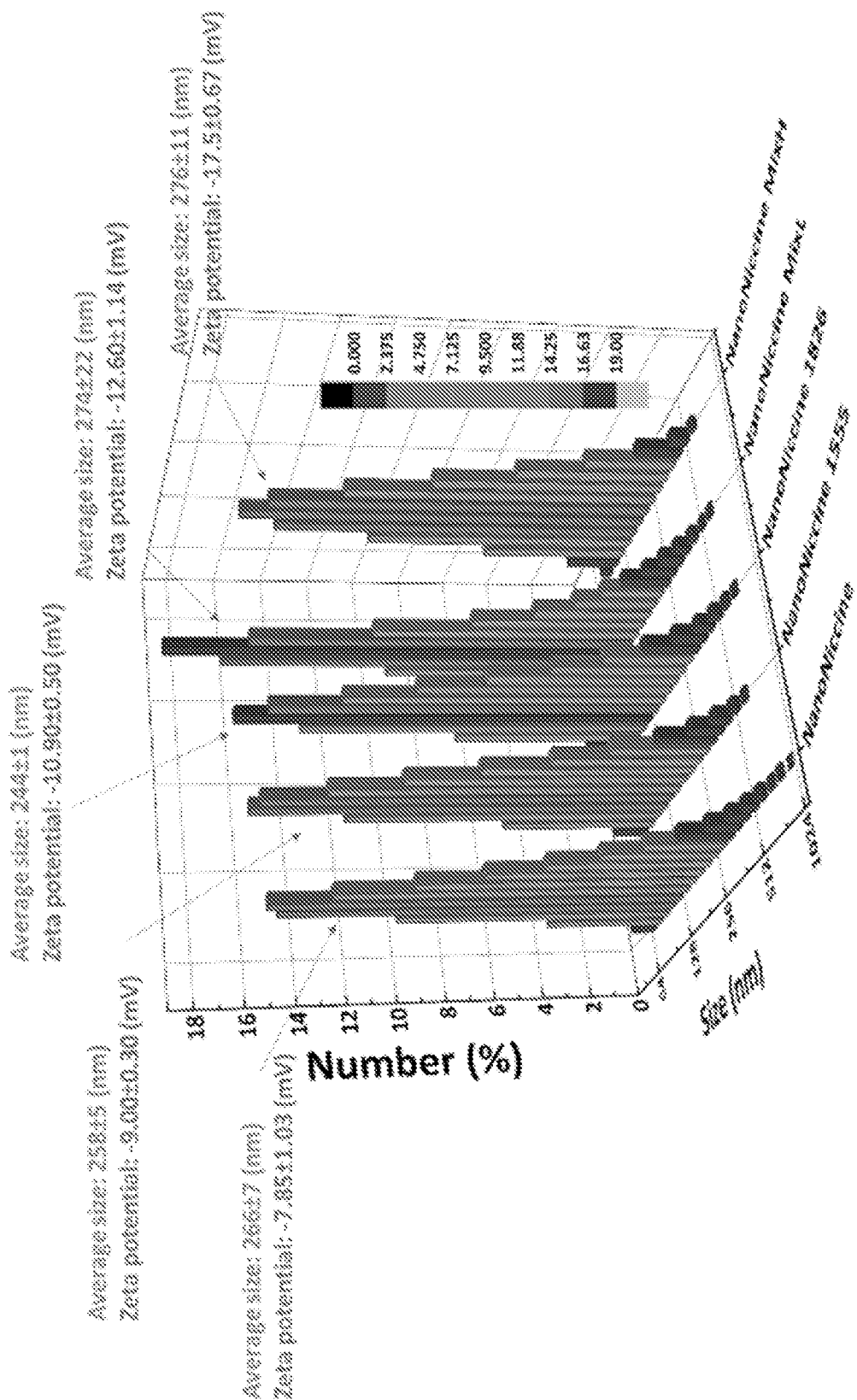
FIG. 85 shows size distribution, mean size, and surface charge of NanoNiccine, NanoNiccine 1555, NanoNiccine 1826, NanoNiccine MixL, and NanoNiccine MixH. Vaccine nanoparticles were freshly made, and physicochemical properties were characterized by zeta sizer.

NanoNiccine with different formulations, including the one without CpG DNA (NanoNiccine), with CpG ODN 1555 (NanoNiccine 1555), with CpG ODN 1826 (NanoNiccine 1826), with low quantities of CpG ODN 1555 and CpG ODN 1826 (NanoNiccine MixL), and with high quantities of CpG ODN 1555 and CpG ODN 1826 (NanoNiccine MixH), were constructed. The physicochemical properties, such as size distribution, particle mean size, and surface charge were characterized for these vaccines. As shown in FIG. 85, NanoNiccines regardless of the formulations had similar size distributions, which were centered at 128 nm. In agreement with the finding from the confocal images and the TEM images, the majority of the particles had a size less than 1000 nm. The mean sizes of NanoNiccine, NanoNiccine 1555, NanoNiccine 1826, NanoNiccine MixL, and NanoNiccine MixH were 266±7 nm, 258±5 nm, 244±1 nm, 274±22 nm, and 276±11 nm, respectively. It was reported that immune cells, such as DCs, internalize nano-sized antigens with a higher efficiency than larger particles [51]. Therefore, the nan-range size of NanoNiccine may facilitate its uptake by the immune cells. Moreover, small particles may move more easily into the lymph node, where vaccines can extensively interact DCs and B cells [52]. Another important physicochemical properties of NanoNiccine is the quantity of surface charges it carries. Typically, researchers use zeta potential to represent the relative amount of surface charges that particles carry [53]. As shown in FIG. 85, zeta potentials of −7.85±1.03 mV, −9.00±0.30 mV, −10.90±0.50 mV, −12.60±1.14 mV, −17.50±0.67 mV were detected for NanoNiccine, NanoNiccine 1555, NanoNiccine 1826, NanoNiccine MixL, and NanoNiccine MixH, respectively. The negative value of the zeta potential indicated that the surface of NanoNiccine particles carried a net negative charge. As discussed before, the zeta potential of hybrid nanoparticles were greatly influenced by the components of the lipids layer [26]. In this study, it was likely that the negative surface charges were contributed by the carboxylic acid group on the distant terminal of DSPE-PEG (2000) COOH [54]. As displayed in FIG. 85, zeta potential varied with the type and quantity of CpG DNAs, the zeta potential might also be affected by the CpG DNAs in the PLGA core. As we know that DNA carries negative charge, which might explain the lower zeta potential of NanoNiccine MixH than that of NanoNiccine MixL.

Cellular Uptake of NanoNiccines by Dendritic Cells

Figure 86A:
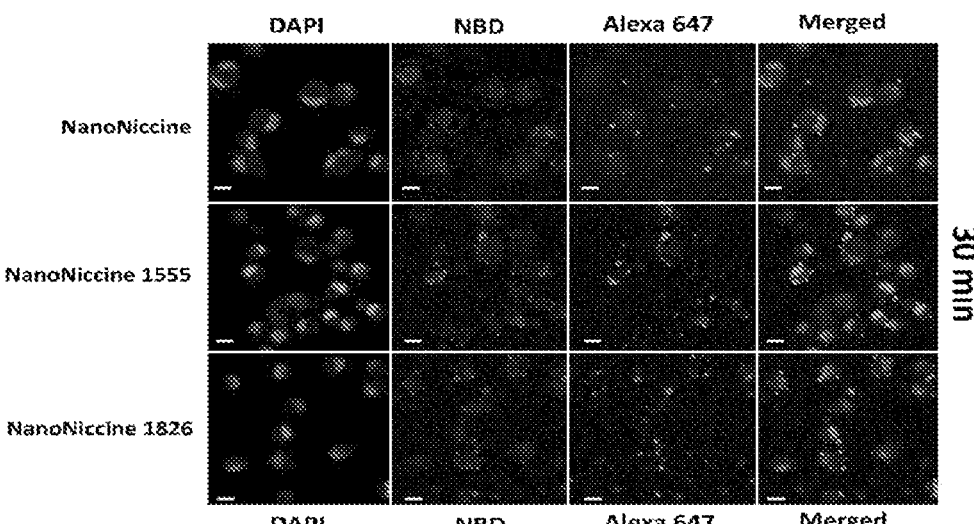
FIGS. 86A-86C show panels of confocal images of uptake of NanoNiccine, NanoNiccine 1555, and NanoNiccine 1826 by DCs. $5 \times 10^5$ DCs in chamber slides were treated with 100 µg NBD and Alexa 647 labeled vaccine particles for 30 min (FIG. 86A), 60 min (FIG. 86B), and 90 min (FIG. 86C), respectively. Excessive particles in the slides were removed and images of vaccine particles in DCs were acquired using a Zeiss LSM 880 confocal microscope. Scale bars represent 10 µm.
Figure 86B:
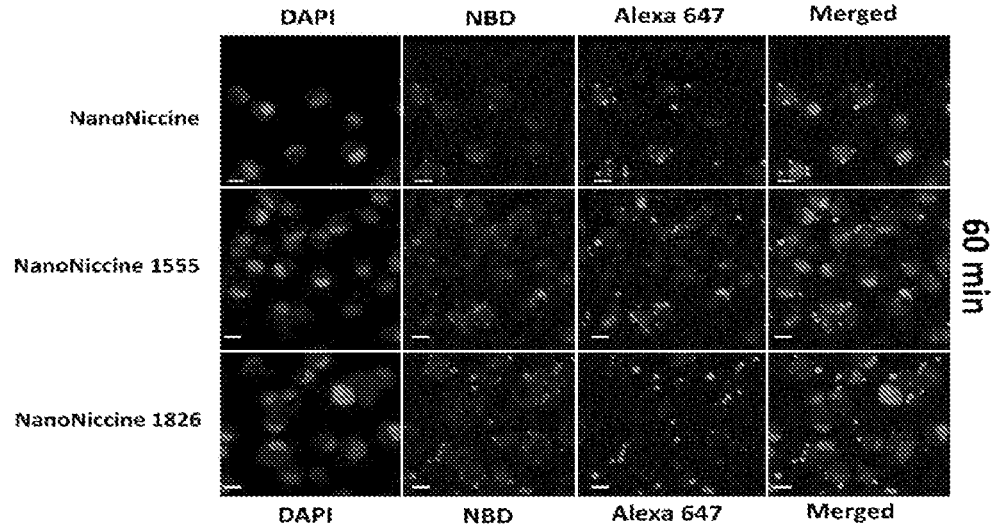
Figure 86C:
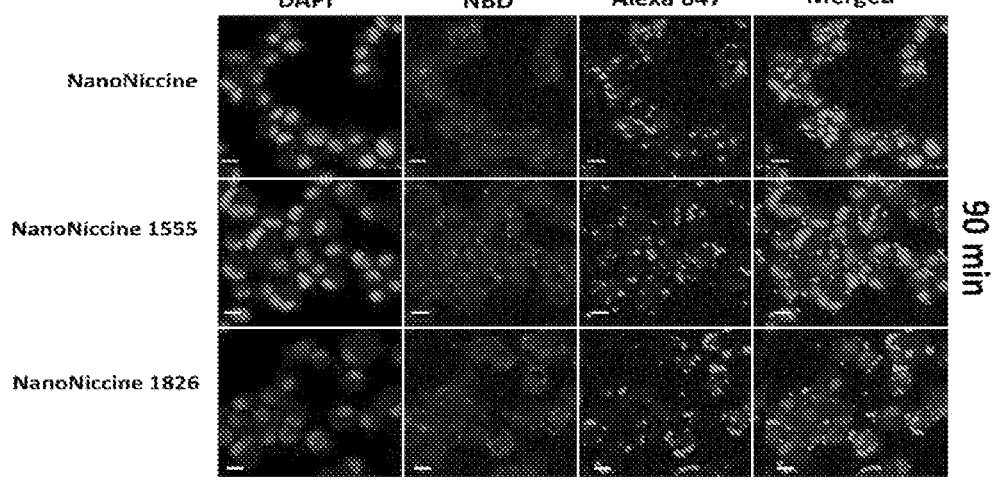

The first step in inducing antibody immune response involves uptake and processing of antigens by antigen presenting cells (APC), including macrophage and DCs [55, 56]. Although macrophage can also internalize and process antigens, it primarily functions to destroy foreign substances and minimize the potential threats brought by invaders [57, 58]. In contrast, DC can process and present antigens in a more immunologically professional and efficient way [59, 60]. After internalization by DC, antigens will be processed into antigenic peptides, which will be subsequently presented to T helper cells, leading to activation of T helper cells [55]. Therefore, the way how DCs internalize and process antigens may have profound impact on the outcome of the immune response. In the study, the uptake of NanoNiccine, NanoNiccine 1555, and NanoNiccine 1826 by the DCs were investigated using both CLSM and FACS. Vaccine particles were marked with NBD PE in the lipid layer and Alexa 647 in the PLGA core. As shown in FIGS. 86A-86C, uptake of the vaccine particles by the DCs was time-dependent. The quantities of vaccine particles regardless of the formulations that were internalized by the DCs increased from 30 min to 90 min, suggesting that the DCs were capable of continuously capturing multiple vaccine particles. It was also observed that the DCs appeared to take up the three vaccine particles at close rate, which could be explained by the similar physicochemical properties of the three nanoparticles. Another important finding shown in FIG. 86A-86C was that both green fluorescence and red fluorescence were detected in the particles internalized by the DCs, suggesting that hybrid vaccine particles were internalized by DCs as a whole entity. This was consistent with results from a previous study [4], in which both the core part and shell part of the vaccine particles were detected in the DCs. As discussed before, keeping the hybrid structure intact during cellular uptake was of pivotal importance to the immunological outcome of this hybrid nanoparticle-based nicotine vaccine [4]. As we know that to induce antibody response, epitopes on the surface of antigens need to be recognized by the B cell receptors (BCRs), which will lead to antigen uptake and processing [61]. Therefore, the vaccine particles need to hold high structural stability under physiological conditions in order to allow cognate interaction between the nicotine epitopes and the BCRs. Results from this study and previous studies demonstrated that lipid-PLGA hybrid nanoparticle had a strong stability [27, 50]. Although this study did not address the uptake of NanoNiccine by B cells, we would expect that the hybrid vaccine particles will also be internalized by B cells with an integral structure. Besides particle uptake, FIGS. 87A-87C also showed degradation of the nanoparticles in the DCs, which was reflected by the increasing amount of red and green fluorescence released from the nanoparticles and distributed over the cells between 30 min and 90 min. These findings illustrated that the DCs could process these nanoparticles in an efficient way. Efficient antigen processing can positively contribute to development of immune response in multiple ways. For example, the released antigens and adjuvants from nanoparticles may expedite the maturation of the DCs, improving their ability in presenting antigenic peptides to T helper cells [62]. Meanwhile, fast antigen processing may also enable the DCs in peripheral tissue to migrate more rapidly into the lymph node, where they can communicate with T helper cells and B cells more extensively [63].

Anti-Nic and Anti-KLH IgG Titer in Mice Immunized with Nicotine Vaccines

Figures 87A, 87B:
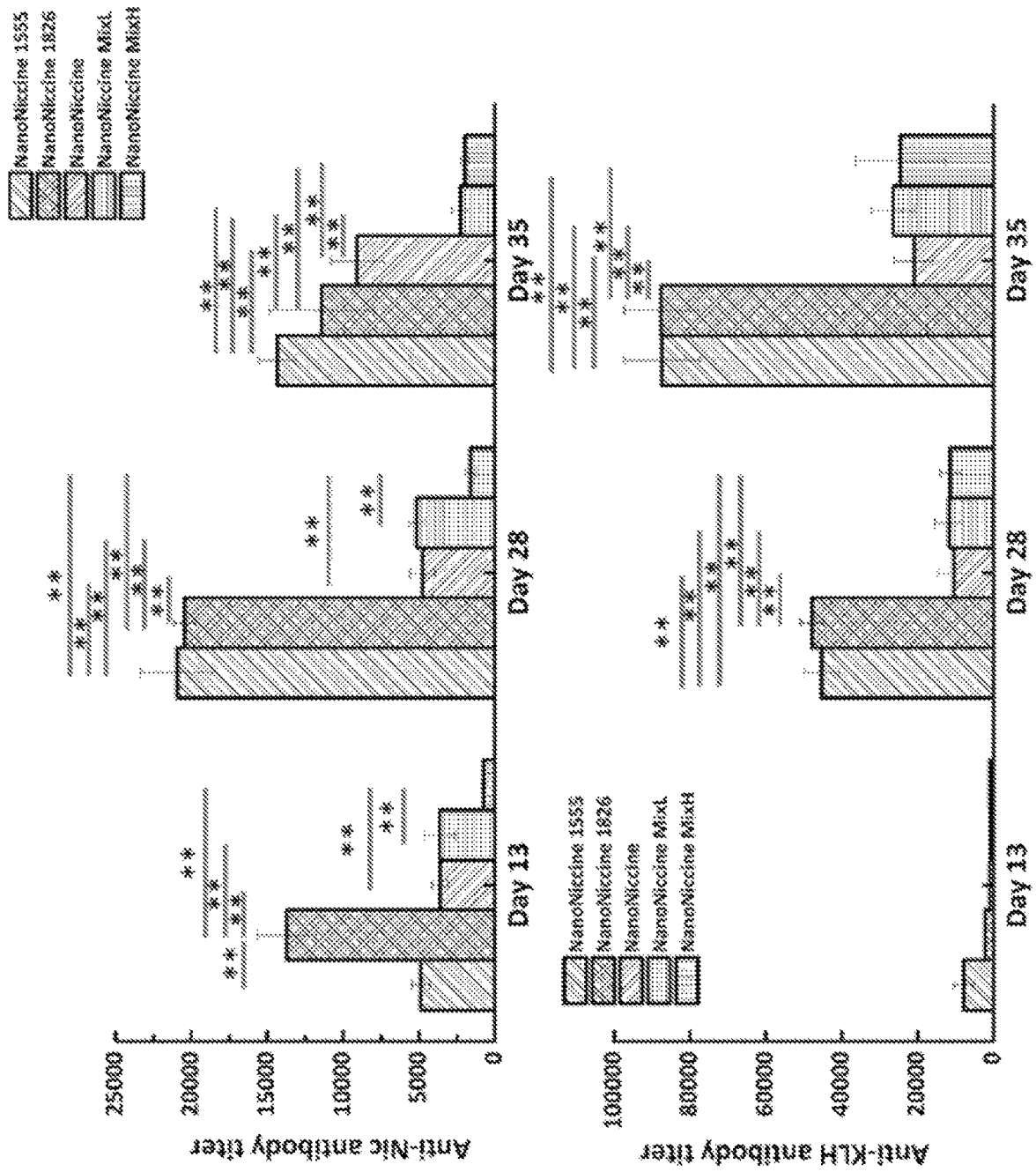
FIGS. 87A-87B show Anti-Nic IgG antibody titer (FIG. 87A) and Anti-KLH IgG antibody titer (FIG. 87B) in mice with NanoNiccine, NanoNiccine 1555, NanoNiccine 1826, NanoNiccine MixL and NanoNiccine MixH, respectively. Mice were injected with vaccine particles containing 25 µg KLH on day 0 (primary injection) and day 14 (booster injection). Antibody titer in sera on day −2, 13, 28, and 35 were assayed using ELISA. ** means that P-value is less than 0.01.

A nicotine vaccine works by inducing the immune system to produce nicotine-specific antibodies, which can bind with nicotine molecules in the blood and prevent them from crossing the blood-brain barrier [64]. IgG is the most abundant antibody in human serum, thus holds great responsibility for sequestering nicotine in the serum. As we know, IgG has only two binding sites for antigens [65], and theoretically it can only capture two nicotine molecules at a time. Low level of anti-Nic IgG might be rapidly saturated by the relatively larger quantity of nicotine inhaled via smoking, resulting in less than desired treatment efficacy of a nicotine vaccine. Therefore, to trap more nicotine in the serum, higher level of anti-Nic IgG needs to be generated by augmenting the antibody response against a nicotine vaccine. To elevate the immune response, the most common strategy is to supplement adjuvant into vaccines [66]. Traditionally, Alum, as a potent adjuvant, is added into many vaccines to improve their immunogenicity [67]. However, Alum was associated with a couple of adverse side effects, including lesions at injection sites, negative impact on the nervous system, and induction of autoimmune disease [33]. In addition, we found that Alum could limit the interaction between the NanoNiccine particles and immune cells. Therefore, in this study, to avoid the potential problems caused by Alum as well as to improve immunogenicity of NanoNiccine, CpG DNAs, including CpG ODN 1555 and CpG ODN 1826, were enclosed within the PLGA core as adjuvants. Native NanoNiccine, NanoNiccines containing single type of CpG DNA (NanoNiccine 1555 and NanoNiccine 1826), and mixtures of CpG DNAs (NanoNiccine MixL and NanoNiccine MixH) were administered into mice subcutaneously on day 0 and day 14. Anti-Nic antibody titer and anti-KLH antibody titer from blood on day 0, day, 13, day 28, and day 35 were assayed using ELISA. As shown in FIG. 87A, the anti-Nic IgG titer was tremendously affected by the type of nicotine vaccines. On day 13, NanoNiccine 1826 achieved an anti-Nic IgG titer as high as 13731±1937, which was significantly higher than those induced by the other vaccine formulations. As the control group, NanoNiccine achieved an anti-Nic IgG titer of 3613±558, which was 280% lower than that elicited by NanoNiccine 1826. In contrast, NanoNiccine 1555 only achieved a titer of 4882±586, which was 30% higher than NanoNiccine. Surprisingly, on day 13, NanoNiccine MixL and NanoNiccine MixH obtained anti-Nic titers as low as 3649±1033 and 740±132, respectively.

According to the results from previous research on nicotine vaccine, antibody titers may significantly increase after second injection [5, 28]. On day 28, as expected, anti-Nic IgG titers for NanoNiccine 1555 and NaoNiccine 1826 were considerably increased to 20931±2416 and 20455±734, which were 320% and 49% higher than those on day 13. In agreement with results from previous studies [68, 69], CpG ODN 1555 and CpG ODN 1826 in NanoNiccine significantly augmented the immune response in mice. Compared to that of the native NanoNiccine, NanoNiccine 1555 and NanoNiccine 1826 produced 3.3-fold higher and 3.2-fold higher antibody, respectively. Unexpectedly, NanoNiccine MixL and NanoNiccine MixH continued to have low titers of 5163±477 and 1615±309, respectively. As agonists of TLR 9, CpG DNAs with varying sequences may target different types of TLR 9 in the immune cells [17, 18, 70]. Therefore, to explore the possible synergistic effect of CpG ODN 1555 and CpG ODN 1826 on the immunogenicity of NanoNiccine, mice were administered with NanoNiccine MixL and NanoNiccine MixH, which contained different quantities of CpG DNA mixtures. However, due to some unknown mechanisms, neither NanoNiccine MixL nor NanoNiccine MixH achieved a higher titer of anti-Nic IgG than that of the native NanoNiccine. On contrary, it seems that the immunogenicity of NanoNiccine was inhibited by supplementing the mixtures of CpG ODN 1555 and CpG ODN 1826, which was reflected by the significantly lower antibody titer in mice that received either NanoNiccine MixL or NanoNiccine MixH than those received either NanoNiccine 1555 or NanoNiccine 1826. More surprisingly, NanoNiccine MixH induced an anti-Nic titer of 1615±309, which was significantly lower than that of the native NanoNiccine group. It was reported that coadministration of 50 μg CpG ODN mixtures and Alum together with rPfs25 (a protein antigen) produced 30-fold higher antibody response than rPfs25 with Alum in mice [71]. However, it needs to be aware that the antigens, delivery systems, and types of CpG DNAs, and supplement of Alum were different between this study and the previous study. These differences might contribute to the discrepancies in the impact of CpG ODN mixture on the immune response. We speculate that that co-delivery of the CpG ODN 1555 and CpG ODN 1826 using nanoparticles into immune cells may cause immunity suppression, resulting in the lowered immune response.

On day 35, the titers of anti-Nic IgG from the mice treated with NanoNiccine 1555 and NanoNiccine 1826 dropped to 14351±1184 and 11433±3464, respectively. Similar phenomenon was found in a previous study [4], in which the antibody titer dropped significantly one week after the second booster injection. As discussed before, the immune response induced by the booster injection of the adjuvanted NanoNiccine might exceed its threshold level, leading to a sharp decrease in the antibody level shortly after the strong stimulation. Despite the drop in the antibody level, it was observed that a high antibody level persisted in the mice for a long period of time [4].

In this study, we also monitored the anti-KLH IgG level in mice. As introduced before, one of the most attractive features of NanoNiccine was that it could largely reduce production of the anti-KLH antibodies, thus improving the specificity of nicotine vaccine [4]. As shown in FIG. 87B, consistent with previous results, minimal levels of anti-KLH antibody were produced by all the vaccines after primary injection. Similar to the past results [4], titers of anti-KLH antibody considerably increased in all the vaccine groups two weeks after the second injection. It was possible that part of the vaccine particles degraded before being captured by the immune cells, causing KLH release from the PLGA core and the elevated levels of anti-KLH antibody. As reported by other researchers, CpG DNAs promote immune response partly by enhancing secretion of chemokines and cytokines from DCs, B cells, and other immune cells [72, 73]. This may explain the considerably higher levels of anti-KLH IgG in groups of NanoNiccine 1555 (45320±4791) and NanoNiccine 1826 (47898±3013) than NanoNiccine (10365±4031) after the booster injection. Interestingly, NanoNiccine MixL and NanoNiccine MixH produced anti-KLH IgG titers of 11723±3764 and 11339±2618, respectively, which were significantly lower than either NanoNiccine 1555 or NanoNiccine 1826. This finding substantiated that co-delivery of CpG ODN 1826 and CpG ODN 1555 could inhibit the immune response, which also resulted in the limited immune repose to nicotine antigen.

Percentages of Subclass Anti-Nic IgGs in Mice Injected with Nicotine Vaccines

In this study, subclass anti-Nic IgGs, including IgG1, IgG2a, IgG2b, IgG3, in sera from days 13, 28, and 35 were measured. As shown in FIG. 88, nicotine vaccines with various formulations induced dramatically different constitutions of the subclass IgGs in the mice. On day 35, 21%, 19%, and 20% IgG1 were detected in the mice immunized with NanoNiccine 1555, NanoNiccine 1826, and NanoNiccine, respectively. In contrast, no IgG1 were detected in the mice treated with either NanoNiccine MixL or NanoNiccine MixH. These results suggested that the mixtures of CpG ODN 1555 and CpG ODN 1826 might suppress IgG1 production in the mice. In addition, percentages of the subclass IgGs changed considerably with time in the mice injected with all the vaccine formulations, except for NanoNiccine 1555. Although, its titer percentage varied with time, IgG2 was found to be the most dominant subclass IgG in all vaccine groups at any time. Especially in the mice treated with NanoNiccine MixH, only IgG2a and IgG2b were detected. It has been reported that the average percentages of IgG1, IgG2, IgG3, and IgG4 in human serum were around 66%, 24%, 7% and 3%, respectively [74-76]. Apparently, the percentage of the subclass anti-Nic IgGs in the mice treated with these nicotine particles did not follow the regular pattern. It was reported that IgG production could be restricted to IgG2 in response to bacteria antigens [77]. These hybrid nanoparticle-based nicotine vaccines with a particulate nature might be treated by immune system in the way that is for bacteria, which might explain the dominant production of IgG2. The percentages of subclass IgGs may also partly explain the decrease in anti-Nic IgG level in the mice immunized with NanoNiccine 1555, NanoNiccine 1826, and NanoNiccine MixL in contrast to the stable level of anti-Nic IgG treated with NanoNiccine MixH. It was found that the average half-life for IgG1, IgG2, IgG4 was 21 days; and for IgG3 was 7.1 days [78]. The higher percentage of IgG3 in the mice treated with the NanoNiccine 1555, NanoNiccine 1826, and NanoNiccine MixL might lead to a faster decrease in the overall IgG level than that in the mice injected with NanoNiccine MixH. However, it is worth noting that the overall IgG level could be affected by multiple factors, including the type of adjuvants, persistence of vaccine particle in the body, half-life of the antibody secreting B cells, and percentages of subclass IgGs, etc.

Histopathological Study on Organs of Mice Immunized Nicotine Vaccines

Safety is always the top concern in developing a vaccine. The components of NanoNiccine, such as DOTAP, PLGA, cholesterol, DSPE-PEG(2000) COOH, KLH, nicotine epitope, and the CpG ODNs have already demonstrated good safety in other studies [25, 79-85]. In this study, in order to evaluate the safety of NanoNiccines, the major organs, including heart, liver, kidney, stomach, and spleen, were harvested from mice injected with NanoNiccines and PBS buffer. The organs were treated with H&E staining, and were examined with a microscope. As shown in FIGS. 89A-89JJ, no detectable abnormity was found in organs of the mice treated with the vaccines. These results were in agreement with previous safety study on NanoNiccine [4], indicating that NanoNiccine with or without CpG ODNs were not toxic for in vivo use.

Conclusions

In summary, in this study, NanoNiccines containing CpG ODN 1555 or CpG ODN 1826, or mixtures of CpG ODN 1555 and CpG ODN 1826 were constructed. Study on the physicochemical properties and morphology of NanoNiccine showed that NanoNiccine was a nano-sized particle with a lipid surface layer and a PLGA core. Results from the in vitro particle uptake study showed that NanoNiccines regardless of their constitutions demonstrated rapid cellular uptake by the DCs. Study on the immunogenicity of the NanoNiccine formulations showed that the incorporation of CpG ODN 1555 or CpG ODN 1826 could significantly promote the immune response against NanoNiccine. However, combined supplement of the two CpG ODNs led to a suppressed antibody response. Lastly, histopathological study on the organs of the immunized with the nicotine vaccines proved the good safety of CpG ODNs containing NanoNiccines.

REFERENCES FOR EXAMPLE 5

[1] J. M. Samet. Tobacco smoking: the leading cause of preventable disease worldwide. Thorac Surg Clin, 23 (2013), pp. 103-12.

[2] K. Cahill, S. Stevens, R. Perera, T. Lancaster. Pharmacological interventions for smoking cessation: an overview and network meta-analysis. Cochrane Database Syst Rev, 5 (2013), pp. CD009329.

[3] P. R. Pentel, M. G. LeSage. New directions in nicotine vaccine design and use. Adv Pharmacol, 69 (2014), pp. 553-80.

[4] Y. Hu, D. Smith, E. Frazier, R. Hoerle, M. Ehrich, C. Zhang. The next-generation nicotine vaccine: a novel and potent hybrid nanoparticle-based nicotine vaccine. Biomaterials, 106 (2016), pp. 228-39.

[5] H. Zheng, Y. Hu, W. Huang, S. de Villiers, P. Pentel, J. Zhang, et al. Negatively Charged Carbon Nanohorn Supported Cationic Liposome Nanoparticles: A Novel Delivery Vehicle for Anti-Nicotine Vaccine. J Biomed Nanotechnol, 11 (2015), pp. 2197-210.

[6] T. Raupach, P. H. Hoogsteder, C. P. Onno van Schayck. Nicotine vaccines to assist with smoking cessation: current status of research. Drugs, 72 (2012), pp. e1-16.

[7] D. K. Hatsukami, D. E. Jorenby, D. Gonzales, N. A. Rigotti, E. D. Glover, C. A. Oncken, et al. Immunogenicity and smoking-cessation outcomes for a novel nicotine immunotherapeutic. Clin Pharmacol Ther, 89 (2011), pp. 392-9.

[8] L. A. Brito, P. Malyala, D. T. O'Hagan. Vaccine adjuvant formulations: a pharmaceutical perspective. Semin Immunol, 25 (2013), pp. 130-45.

[9] E. Oleszycka, E. C. Lavelle. Immunomodulatory properties of the vaccine adjuvant alum. Curr Opin Immunol, 28 (2014), pp. 1-5.

[10] N. Petrovsky, J. C. Aguilar. Vaccine adjuvants: current state and future trends. Immunol Cell Biol, 82 (2004), pp. 488-96.

[11] B. N. Lambrecht, M. Kool, M. A. Willart, H. Hammad. Mechanism of action of clinically approved adjuvants. Curr Opin Immunol, 21 (2009), pp. 23-9.

[12] L. Tomljenovic, C. A. Shaw. Mechanisms of aluminum adjuvant toxicity and autoimmunity in pediatric populations. Lupus, 21 (2012), pp. 223-30.

[13] C. A. Shaw, L. Tomljenovic. Aluminum in the central nervous system (CNS): toxicity in humans and animals, vaccine adjuvants, and autoimmunity. Immunol Res, 56 (2013), pp. 304-16.

[14] P. R. Pittman. Aluminum-containing vaccine associated adverse events: role of route of administration and gender. Vaccine, 20 Suppl 3 (2002), pp. S48-50.

[15] E. De Gregorio, E. Tritto, R. Rappuoli. Alum adjuvanticity: unraveling a century old mystery. Eur J Immunol, 38 (2008), pp. 2068-71.

[16] J. Vollmer, A. M. Krieg. Immunotherapeutic applications of CpG oligodeoxynucleotide TLR9 agonists. Adv Drug Deliv Rev, 61 (2009), pp. 195-204.

[17] C. Bode, G. Zhao, F. Steinhagen, T. Kinjo, D. M. Klinman. CpG DNA as a vaccine adjuvant. Expert Rev Vaccines, 10 (2011), pp. 499-511.

[18] D. M. Klinman. Immunotherapeutic uses of CpG oligodeoxynucleotides. Nat Rev Immunol, 4 (2004), pp. 249-58.

[19] J. M. Roda, R. Parihar, W. E. Carson, 3rd. CpG-containing oligodeoxynucleotides act through TLR9 to enhance the NK cell cytokine response to antibody-coated tumor cells. J Immunol, 175 (2005), pp. 1619-27.

[20] R. D. Weeratna, M. J. McCluskie, Y. Xu, H. L. Davis. CpG DNA induces stronger immune responses with less toxicity than other adjuvants. Vaccine, 18 (2000), pp. 1755-62.

[21] Y. Krishnamachari, S. M. Geary, C. D. Lemke, A. K. Salem. Nanoparticle delivery systems in cancer vaccines. Pharm Res, 28 (2011), pp. 215-36.

[22] H. Hemmi, O. Takeuchi, T. Kawai, T. Kaisho, S. Sato, H. Sanjo, et al. A Toll-like receptor recognizes bacterial DNA. Nature, 408 (2000), pp. 740-5.

[23] T. A. Khan, S. T. Reddy. Immunological principles regulating immunomodulation with biomaterials. Acta Biomater, 10 (2014), pp. 1720-7.

[24] V. B. Joshi, S. M. Geary, B. R. Carrillo-Conde, B. Narasimhan, A. K. Salem. Characterizing the antitumor response in mice treated with antigen-loaded polyanhydride microparticles. Acta Biomater, 9 (2013), pp. 5583-9.

[25] T. Sato, T. Shimosato, A. Ueda, Y. Ishigatsubo, D. M. Klinman. Intrapulmonary Delivery of CpG Microparticles Eliminates Lung Tumors. Mol Cancer Ther, 14 (2015), pp. 2198-205.

[26] Y. Hu, M. Ehrich, K. Fuhrman, C. Zhang. In vitro performance of lipid-PLGA hybrid nanoparticles as an antigen delivery system:lipid composition matters. Nanoscale Res Lett, 9 (2014), pp. 434.

[27] Y. Hu, R. Hoerle, M. Ehrich, C. Zhang. Engineering the lipid layer of lipid-PLGA hybrid nanoparticles for enhanced in vitro cellular uptake and improved stability. Acta Biomater, 28 (2015), pp. 149-59.

[28] Y. Hu, H. Zheng, W. Huang, C. Zhang. A novel and efficient nicotine vaccine using nano-lipoplex as a delivery vehicle. Hum Vaccin Immunother, 10 (2014), pp. 64-72.

[29] S. Tonstad, E. Heggen, H. Giljam, P. A. Lagerback, P. Tonnesen, L. D. Wikingsson, et al. Niccine®, a nicotine vaccine, for relapse prevention: a phase II, randomized, placebo-controlled, multicenter clinical trial. Nicotine Tob Res, 15 (2013), pp. 1492-501.

[30] P. Skolnick. Biologic Approaches to Treat Substance-Use Disorders. Trends Pharmacol Sci, 36 (2015), pp. 628-35.

[31] J. W. Lockner, S. O. Ho, K. C. McCague, S. M. Chiang, T. Q. Do, G. Fujii, et al. Enhancing nicotine vaccine immunogenicity with liposomes. Bioorg Med Chem Lett, 23 (2013), pp. 975-8.

[32] S. H. de Villiers, N. Lindblom, G. Kalayanov, S. Gordon, I. Baraznenok, A. Malmerfelt, et al. Nicotine hapten structure, antibody selectivity and effect relationships: results from a nicotine vaccine screening procedure. Vaccine, 28 (2010), pp. 2161-8.

[33] L. Tomljenovic, C. A. Shaw. Aluminum vaccine adjuvants: are they safe? Curr Med Chem, 18 (2011), pp. 2630-7.

[34] S. Naahidi, M. Jafari, F. Edalat, K. Raymond, A. Khademhosseini, P. Chen. Biocompatibility of engineered nanoparticles for drug delivery. J Control Release, 166 (2013), pp. 182-94.

[35] F. Danhier, E. Ansorena, J. M. Silva, R. Coco, A. Le Breton, V. Preat. PLGA-based nanoparticles: an overview of biomedical applications. J Control Release, 161 (2012), pp. 505-22.

[36] E. Cohen-Sela, M. Chorny, N. Koroukhov, H. D. Danenberg, G. Golomb. A new double emulsion solvent diffusion technique for encapsulating hydrophilic molecules in PLGA nanoparticles. J Control Release, 133 (2009), pp. 90-5.

[37] I. Mellman, R. M. Steinman. Dendritic cells: specialized and regulated antigen processing machines. Cell, 106 (2001), pp. 255-8.

[38] R. A. Schwendener. Liposomes as vaccine delivery systems: a review of the recent advances. Ther Adv Vaccines, 2 (2014), pp. 159-82.

[39] T. Lian, R. J. Ho. Trends and developments in liposome drug delivery systems. J Pharm Sci, 90 (2001), pp. 667-80.

[40] H. W. Wang, P. L. Jiang, S. F. Lin, H. J. Lin, K. L. Ou, W. P. Deng, et al. Application of galactose-modified liposomes as a potent antigen presenting cell targeted carrier for intranasal immunization. Acta Biomater, 9 (2013), pp. 5681-8.

[41] H. Otsuka, Y. Nagasaki, K. Kataoka. PEGylated nanoparticles for biological and pharmaceutical applications. Adv Drug Deliv Rev, 55 (2003), pp. 403-19.

[42] G. Pasut, D. Paolino, C. Celia, A. Mero, A. S. Joseph, J. Wolfram, et al. Polyethylene glycol (PEG)-dendron phospholipids as innovative constructs for the preparation of super stealth liposomes for anticancer therapy. J Control Release, 199 (2015), pp. 106-13.

[43] S. Salmaso, P. Caliceti. Stealth properties to improve therapeutic efficacy of drug nanocarriers. J Drug Deliv, 2013 (2013), pp. 374252.

[44] V. Mata-Haro, C. Cekic, M. Martin, P. M. Chilton, C. R. Casella, T. C. Mitchell. The vaccine adjuvant monophosphoryl lipid A as a TRIF-biased agonist of TLR4. Science, 316 (2007), pp. 1628-32.

[45] J. K. Eby, K. Y. Dane, C. P. O'Neil, S. Hirosue, M. A. Swartz, J. A. Hubbell. Polymer micelles with pyridyl disulfide-coupled antigen travel through lymphatics and show enhanced cellular responses following immunization. Acta Biomater, 8 (2012), pp. 3210-7.

[46] W. Liu, Y. H. Chen. High epitope density in a single protein molecule significantly enhances antigenicity as well as immunogenicity: a novel strategy for modern vaccine development and a preliminary investigation about B cell discrimination of monomeric proteins. Eur J Immunol, 35 (2005), pp. 505-14.

[47] L. J. Cruz, P. J. Tacken, R. Fokkink, B. Joosten, M. C. Stuart, F. Albericio, et al. Targeted PLGA nano- but not microparticles specifically deliver antigen to human dendritic cells via DC-SIGN in vitro. J Control Release, 144 (2010), pp. 118-26.

[48] J. Wu, T. Kong, K. W. Yeung, H. C. Shum, K. M. Cheung, L. Wang, et al. Fabrication and characterization of monodisperse PLGA-alginate core-shell microspheres with monodisperse size and homogeneous shells for controlled drug release. Acta Biomater, 9 (2013), pp. 7410-9.

[49] H. Shirota, D. M. Klinman. Recent progress concerning CpG DNA and its use as a vaccine adjuvant. Expert Rev Vaccines, 13 (2014), pp. 299-312.

[50] Y. Hu, Z. Zhao, M. Ehrich, K. Fuhrman, C. Zhang. controlled release of antigen in dendritic cells using pH-sensitive liposome-polymeric hybrid nanoparticles. Polymer (Guildf), 80 (2015), pp. 171-9.

[51] B. Slutter, W. Jiskoot. Sizing the optimal dimensions of a vaccine delivery system: a particulate matter. Expert Opin Drug Deliv, 13 (2016), pp. 167-70.

[52] P. Sandev, L. J. Ochyl, J. J. Moon. Biomaterials for nanoparticle vaccine delivery systems. Pharm Res, 31 (2014), pp. 2563-82.

[53] W. S. Cho, F. Thielbeer, R. Duffin, E. M. Johansson, I. L. Megson, W. MacNee, et al. Surface functionalization affects the zeta potential, coronal stability and membranolytic activity of polymeric nanoparticles. Nanotoxicology, 8 (2014), pp. 202-11.

[54] C. Salvador-Morales, L. Zhang, R. Langer, O. C. Farokhzad. Immunocompatibility properties of lipid-

[55] J. Banchereau, R. M. Steinman. Dendritic cells and the control of immunity. Nature, 392 (1998), pp. 245-52.

[56] L. Martinez-Pomares, S. Gordon. Antigen presentation the macrophage way. Cell, 131 (2007), pp. 641-3.

[57] B. K. Yang, Y. A. Gu, Y. T. Jeong, H. Jeong, C. H. Song. Chemical characteristics and immuno-modulating activities of exo-biopolymers produced by Grifola frondosa during submerged fermentation process. Int J Biol Macromol, 41 (2007), pp. 227-33.

[58] D. R. Schmidt, W. J. Kao. The interrelated role of fibronectin and interleukin-1 in biomaterial-modulated macrophage function. Biomaterials, 28 (2007), pp. 371-82.

[59] J. A. Villadangos, L. Young. Antigen-presentation properties of plasmacytoid dendritic cells. Immunity, 29 (2008), pp. 352-61.

[60] E. S. Trombetta, I. Mellman. Cell biology of antigen processing in vitro and in vivo. Annu Rev Immunol, 23 (2005), pp. 975-1028.

[61] J. Eckl-Dorna, F. D. Batista. BCR-mediated uptake of antigen linked to TLR9 ligand stimulates B-cell proliferation and antigen-specific plasma cell formation. Blood, 113 (2009), pp. 3969-77.

[62] L. Siewe, M. Bollati-Fogolin, C. Wickenhauser, T. Krieg, W. Muller, A. Roers. Interleukin-10 derived from macrophages and/or neutrophils regulates the inflammatory response to LPS but not the response to CpG DNA. Eur J Immunol, 36 (2006), pp. 3248-55.

[63] G. J. Randolph, J. Ochando, S. Partida-Sanchez. Migration of dendritic cell subsets and their precursors. Annu Rev Immunol, 26 (2008), pp. 293-316.

[64] M. G. LeSage, D. E. Keyler, P. R. Pentel. Current status of immunologic approaches to treating tobacco dependence: vaccines and nicotine-specific antibodies. AAPS J, 8 (2006), pp. E65-75.

[65] G. Vidarsson, G. Dekkers, T. Rispens. IgG subclasses and allotypes: from structure to effector functions. Front Immunol, 5 (2014), pp. 520.

[66] K. M. Lima, S. A. dos Santos, J. M. Rodrigues, Jr., C. L. Silva. Vaccine adjuvant: it makes the difference. Vaccine, 22 (2004), pp. 2374-9.

[67] R. K. Gupta. Aluminum compounds as vaccine adjuvants. Adv Drug Deliv Rev, 32 (1998), pp. 155-72.

[68] D. M. Klinman, H. Xie, B. E. Ivins. CpG oligonucleotides improve the protective immune response induced by the licensed anthrax vaccine. Ann N Y Acad Sci, 1082 (2006), pp. 137-50.

[69] H. L. Davis, R. Weeratna, T. J. Waldschmidt, L. Tygrett, J. Schorr, A. M. Krieg. CpG DNA is a potent enhancer of specific immunity in mice immunized with recombinant hepatitis B surface antigen. J Immunol, 160 (1998), pp. 870-6.

[70] D. M. Klinman, S. Klaschik, T. Sato, D. Tross. CpG oligonucleotides as adjuvants for vaccines targeting infectious diseases. Adv Drug Deliv Rev, 61 (2009), pp. 248-55.

[71] C. Coban, K. J. Ishii, A. W. Stowers, D. B. Keister, D. M. Klinman, N. Kumar. Effect of CpG oligodeoxynucleotides on the immunogenicity of Pfs25, a Plasmodium falciparum transmission-blocking vaccine antigen. Infect Immun, 72 (2004), pp. 584-8.

[72] S. J. Gibson, J. M. Lindh, T. R. Riter, R. M. Gleason, L. M. Rogers, A. E. Fuller, et al. Plasmacytoid dendritic cells produce cytokines and mature in response to the TLR7 agonists, imiquimod and resiquimod. Cell Immunol, 218 (2002), pp. 74-86.

[73] J. D. Marshall, K. Fearon, C. Abbate, S. Subramanian, P. Yee, J. Gregorio, et al. Identification of a novel CpG DNA class and motif that optimally stimulate B cell and plasmacytoid dendritic cell functions. J Leukoc Biol, 73 (2003), pp. 781-92.

[74] F. Shakib, D. R. Stanworth. Human IgG subclasses in health and disease. (A review). Part II. Ric Clin Lab, 10 (1980), pp. 561-80.

[75] M. van der Giessen, E. Rossouw, T. A. van Veen, E. van Loghem, B. J. Zegers, P. C. Sander. Quantification of IgG subclasses in sera of normal adults and healthy children between 4 and 12 years of age. Clin Exp Immunol, 21 (1975), pp. 501-9.

[76] Q. Pan, L. Hammarstrom. Molecular basis of IgG subclass deficiency. Immunol Rev, 178 (2000), pp. 99-110.

[77] D. J. Barrett, E. M. Ayoub. IgG2 subclass restriction of antibody to pneumococcal polysaccharides. Clin Exp Immunol, 63 (1986), pp. 127-34.

[78] A. Morell, W. D. Terry, T. A. Waldmann. Metabolic properties of IgG subclasses in man. J Clin Invest, 49 (1970), pp. 673-80.

[79] T. H. Chuang, C. Y. Lai, P. H. Tseng, C. J. Yuan, L. C. Hsu. Development of CpG-oligodeoxynucleotides for effective activation of rabbit TLR9 mediated immune responses. PLoS One, 9 (2014), pp. e108808.

[80] P. H. Hoogsteder, D. Kotz, P. I. van Spiegel, W. Viechtbauer, O. C. van Schayck. Efficacy of the nicotine vaccine 3'-AmNic-rEPA (NicVAX) co-administered with varenicline and counselling for smoking cessation: a randomized placebo-controlled trial. Addiction, 109 (2014), pp. 1252-9.

[81] T. A. Kosten, X. Y. Shen, B. M. Kinsey, T. R. Kosten, F. M. Orson. Attenuation of cocaine-induced locomotor activity in male and female mice by active immunization. Am J Addict, 23 (2014), pp. 604-7.

[82] C. Wang, X. Cheng, Y. Sui, X. Luo, G. Jiang, Y. Wang, et al. A noticeable phenomenon: thiol terminal PEG enhances the immunogenicity of PEGylated emulsions injected intravenously or subcutaneously into rats. Eur J Pharm Biopharm, 85 (2013), pp. 744-51.

[83] H. I. Chang, M. K. Yeh. Clinical development of liposome-based drugs: formulation, characterization, and therapeutic efficacy. Int J Nanomedicine, 7 (2012), pp. 49-60.

[84] A. L. Silva, P. C. Soema, B. Slutter, F. Ossendorp, W. Jiskoot. PLGA particulate delivery systems for subunit vaccines: linking particle properties to immunogenicity. Hum Vaccin Immunother, (2016), pp. 0.

[85] G. Ott, M. Singh, J. Kazzaz, M. Briones, E. Soenawan, M. Ugozzoli, et al. A cationic sub-micron emulsion (MF59/DOTAP) is an effective delivery system for DNA vaccines. J Control Release, 79 (2002), pp. 1-5.

Example 6

Introduction

As the leading cause of preventable death in the United States, tobacco use results in tremendous social and economic problems [1]. These include 480,000 deaths per year, more than $170 billion in direct medical care for adults, and more than $156 billion in lost of productivity due to premature death and exposure to secondhand smoke [2].

Because of the highly addictive nature of nicotine [3], smoking cessation without medical interventions is an extremely difficult if not impossible mission for most smokers [4]. Even with the assistance from the currently available therapies, the long-term smoking abstinence rate is unacceptably low [4]. Therefore, there is an urgent need for developing novel and more effective treatments against tobacco addiction. Among the new ideas, nicotine vaccine, which can induce production of nicotine-specific antibody, has proven promising in treating smoking addiction [5, 6]. However, the conventional protein-nicotine conjugate vaccines are associated with some innate drawbacks [7, 8], including low immunogenicity, low specificity, and short immune persistence, all of which severely limit their treatment efficacy. To overcome these disadvantages, a novel nanoparticle based-nicotine vaccine (NanoNiccine) [9], was invented in our group. Structurally, NanoNiccine is mainly comprised of a PLGA core and a lipid bilayer. The PLGA core functions as a vehicle for delivery and controlled release of the T-cell antigens, such as keyhole limpet hemocyanin (KLH) [10], tetanus toxoid [11], CRM197 [12], and diphtheria toxin [13]. The PLGA core can also enclose hydrophilic molecular adjuvants, such as CpG oligodeoxynucleotides (ODNs) that target the intracellular toll-like receptors [14, 15]. In addition, the PLGA core serves as a rigid support for the lipid envelop to improve the overall stability of the hybrid nanoparticle [9, 16]. In contrast, the lipid bilayer can deliver hydrophobic molecular adjuvant, such as monophosphoryl lipid A (MPLA) that the toll-like receptors on the surface of the immune cells [17, 18]. In addition, the lipid layer plays as a shield for the PLGA core and its payloads against the harsh physiological environment during circulation in body [19, 20]. Another important function of the lipid layer is that the polyethylene glycol (PEG) molecule with terminal reactive groups, such as carboxylic acid group, amide group, and melaimide group, can provide linking sites for nicotine haptens [9, 16, 21]. As discussed before, the conjugation of the nicotine epitopes on the surface of the NanoNiccine and the delivery of the T-cell antigens within the PLGA core rendered NanoNiccine highly specific and effective in producing antibodies against nicotine [9].

Immunogenicity is one of the most vital factors that govern the efficacy of a nicotine vaccine [22]. The immunogenicity of a nicotine vaccine can be determined by measuring the concentrations of the nicotine-specific antibody in the animals immunized with the vaccine [23]. Researchers typically use anti-nicotine antibody titer to represent the immunogenicity of a nicotine vaccine [21, 24]. In both preclinical trials in animals and clinical trials in human, it was found that a higher nicotine antibody titer in serum was associated with a better immunological outcome [25, 26]. Therefore, the treatment efficacy of a nicotine vaccine is very likely to be improved by augmenting its ability to produce a higher titer of nicotine-specific antibodies. In the traditional nicotine vaccine development, researchers were able to enhance the production of the anti-nicotine antibodies by different means, such as optimizing the carrier proteins [27], selecting better nicotine epitopes [28], improving adjuvants [29], etc. Owing to the unique structure of NanoNiccine, besides these traditional strategies, the immunogenicity of NanoNiccine may be promoted by improving its physicochemical properties, including vaccine particle size [30], particle surface charge [20], degree of PEGylation in the lipid layer [19], etc. As reported in a previous study, the stability and cellular uptake of the lipid-PLGA hybrid nanoparticle was affected by the concentration of PEG molecule in the lipid layer [19]. In addition, highly repetitive and dense epitopes in a vaccine can enhance its immunogenicity [31, 32]. In NanoNiccine, the density of the nicotine epitope is decided by the number of the reactive groups on the terminal of the PEG molecule. It is possible to modulate the density of the nicotine epitopes by controlling the concentration of the PEG molecule in the lipid layer, thereby tuning the immunogenicity of NanoNiccine.

In this study, we assembled lipid-PLGA hybrid nanoparticles with varying concentrations of DSPE-PEG(2000)COOH in the lipid layer. The structural integrity of these hybrid nanoparticles was examined. It was found that liposome containing 2.5%, 5%, 12.5%, and 20% DSPE-PEG(2000)COOH formed stable hybrid structure with the PLGA nanoparticles. In contrast, liposome with 30% DSPE-PEG(2000)COOH failed to form a stable hybrid nanoparticle of an integral core-shell structure. Subsequently, nicotine epitopes were conjugated to the hybrid nanoparticles with distinct degrees of PEGylation to synthesize NanoNiccines with differing nicotine epitope densities. The immunogenicity of these vaccines as well as their ability to block the entry of nicotine into the brain were evaluated in mice. The results showed that NanoNiccine with 20% DSPE-PEG(2000)COOH (NanoNiccine 20.0) in the lipid layer achieved the highest anti-nicotine antibody titer. Consistent with its immunogenicity, nicotine pharmacokinetics study in mice demonstrated that NanoNiccine 20.0 could reduce the entry of nicotine more effectively than other vaccines with lower degrees of PEGylation.

Materials and Methods

Materials

Lactel® 50:50 PLGA was purchased from Durect Corporation (Cupertino, Calif.). JAWSII (ATCC® CRL-11904™) immature dendritic cell was purchased from ATCC (Manassas, Va.). Fetal bovine serum (FBS), granulocyte macrophage-colony stimulating factor (GM-CSF) recombinant mouse protein, Alpha minimum essential medium, trypsin/EDTA, and Alexa Fluor® 647 hydrazide were purchased from Life Technologies Corporation (Grand Island, N.Y.). Poly (vinyl alcohol) (PVA, MW 89,000-98,000), dichloromethane (DCM), and bovine serum albumin (BSA) were purchased from Sigma-Aldrich Inc. (Saint Louis, Mo.). Alexa Fluor® 647 hydrazide (Alexa 647), Keyhole Limpet Hemocyanin (KLH), 1-ethyl-3-[3-dimethylaminopropyl] carbodiimide hydrochloride (EDC), and sulfo-NHS were purchased from Thermo Fisher Scientific Inc. (Rockford, Ill.). Lipids, including monophosphoryl lipid A (MPLA), 1,2-dioleoyl-3-trimethylammonium-propane (DOTAP), 1,2-distearoyl-sn-glycero-3-phosphoethanolamine-N-[carboxy(polyethylene glycol)-2000] (ammonium salt) ((DSPE-PEG2000) carboxylic acid), cholesterol, and 1,2-di phytanoyl-sn-glycero-3-phosphoethanolamine-N-(7-nitro-2-1, 3-benzoxadiazol-4-yl) (ammonium salt) (NBD PE) were purchased from Avanti Polar Lipids, Inc. (Alabaster, Ala.). Rac-trans 3'-aminomethyl nicotine was purchased from Toronto Research Chemicals Inc. (Toronto, Canada). CpG oligonucleotide 1826 (CpG ODN 1826) with a sequence of 5'-tccatgacgttcctgacgtt-3' was synthesized by Integrated DNA Technologies (Coralville, Iowa). Anti-mouse IgG, anti-goat IgG, and TMB substrate were purchased from Alpha Diagnostic Intl., Inc. (San Antonio, Tex.). All other chemicals were of analytical grade.

PLGA Nanoparticle Fabrication

PLGA nanoparticles containing immunological effectors, including KLH, CpG ODN 1826, were formed via a method described in previous studies with proper modifications [9, 19, 33]. Briefly, 30 mg PLGA dissolved in 1 mL DCM was emulsified with 1.2 mg KLH and 0.6 mg CpG ODN 1826 in 100 µL phosphate-buffered saline (PBS) buffer (10 mM, pH 7.4) using a Branson B1510DTH Ultrasonic Cleaner (Branson, Danbury, Conn.) for 10 min. This primary emulsion was added drop-wise into 100 mL PVA (0.5% (w/v)), followed by 10 mins stirring at 500 rpm. The above mixture was further sonicated using a sonic dismembrator (Model 500; Fisher Scientific, Pittsburgh, Pa.) at 70% amplitude for 30 s. The secondary emulsion was stirred overnight to allow evaporation of DCM. Large particles precipitated and were removed after the mixture sat at room temperature for 30 min. Nanoparticles in the suspension were recovered by centrifugation at 10,000 g, 4° C. for 60 min using an Eppendorf centrifuge (Eppendorf, Hauppauge, N.Y.). The collected nanoparticles were suspended in 10 mL phosphate buffered saline (PBS) buffer (pH 7.4) and stored at 4° C. for later use.

Liposome Formation

Liposomes with different concentrations of DSPE-PEG (2000)COOH were formed a via lipid film rehydration and sonication technique [9, 19, 20]. Briefly, lipid films containing 0.2 mg MPLA, and 6 mg other lipids, including DOTAP, DSPE-PEG(2000)COOH, cholesterol, with molar ratios of 92.5:2.5:5.0 (Liposome 2.5), 90:5.0:5.0 (Liposome 5.0), 82.5:12.5:5.0 (Liposome 12.5), 75.0:20.0:5.0 (Liposome 20.0), 65.0:30.0:5.0 (Liposome 30.0) were hydrated with 1 mL 55° C. pre-warmed PBS buffer (pH 7.4). The lipid mixture was vortexed for 2 min, followed by 5 min sonication using a Branson B1510DTH Ultrasonic Cleaner (Branson, Danbury, Conn.) to form liposomes with differing degrees of PEGylation. The formed liposomes were stored at 4° C. for later use.

Lipid-PLGA Hybrid Nanoparticle Assembly and NanoNiccine Synthesis

Lipid-PLGA hybrid nanoparticles with degrees of PEGylation of 2.5% (Hybrid 2.5), 5.0% (Hybrid 5.0), 12.5% (Hybrid 12.5), 20.0% (Hybrid 20.0), and 30.0% (Hybrid 30.0) were assembled via a sonication aided fusion technique described before [9, 19]. The PLGA nanoparticles and the liposomes prepared above were mixed and pre-homogenized for 15 min using a Branson B1510DTH Ultrasonic Cleaner, followed by 5 min sonication in an ice bath using a sonic dismembrator at 15% amplitude (pulse on 20 s, pulse off 50 s). Rac-trans 3'-aminomethyl nicotine (Nic) conjugated to Hybrid 2.5, Hybrid 5.0, Hybrid 12.5, and Hybrid 20.0 to form NanoNiccine 2.5, NanoNiccine 5.0, NanoNiccine 12.5, and NanoNiccine 20.0, respectively. NanoNiccine was synthesized using a previously described method with proper modifications [9]. Briefly, the hybrid nanoparticles were dialyzed against 500 mL activation buffer (0.1M MES, 0.5M NaCl, pH 6.0) for 2 h. 6.3 mg EDC and 17.3 mg sulfo-NHS were added into the hybrid nanoparticle suspension and reacted for 20 min at room temperature. The hybrid nanoparticles in the activation buffer were dialyzed against 1000 mL coupling buffer (100 mM sodium phosphate, 150 mM NaCl; pH 7.2) for 30 min. 6.3 mg Nic was reacted with the activated hybrid nanoparticles in the coupling buffer for 4 h. Impurities were removed by dialysis against PBS buffer (pH 7.4) for 12 h. The assembled NanoNiccine was stored at 4° C. for future use.

Assembly of Fluorescently Labeled Hybrid Nanoparticles

The assembly process of fluorescently labeled hybrid nanoparticles was similar to that for regular hybrid nanoparticles described above, except that KLH in PLGA nanoparticle was labeled with Alexa Fluor® 647 Hydrazide and the lipid layer was labeled with NBD PE. KLH was labeled with Alexa 647 using a method described in a previous study [19]. These fluorescently marked vaccine particles did not contain either CpG ODN 1826 or MPLA.

Measuring the Association Rate of the Lipids and the PLGA Nanoparticles

To calculate the association rate of lipids and PLGA in the hybrid nanoparticles, the NBD intensity in the liposome, and Alexa 647 intensity in the PLGA nanoparticle were measured prior to the hybrid nanoparticle assembly. After hybrid nanoparticle assembly and purification via centrifugation, intensities of both NBD in the lipid layer and Alexa 647 in the PLGA core were recorded. The relative intensity ratios of NBD to Alexa 647 were calculated for hybrid nanoparticles with varying degrees of PEGylation.

Characterization of Physicochemical Properties of Nanoparticles and NanoNiccine

Physicochemical properties, including surface charge, mean particle size, and size distribution of nanoparticles and NanoNiccine were characterized using a Malvern Nano-ZS zetasizer (Malvern Instruments Ltd, Worcestershire, United Kingdom).

Morphological Study of Nanoparticles and NanoNiccines Using a Transmission Electrical Microscopy (TEM)

TEM images of liposome, PLGA nanoparticle, hybrid nanoparticles, and NanoNiccines were acquired using a method described in previous studies with proper modifications [9, 19]. Briefly, particles in PBS buffer were dropped onto a 300-mesh Formvar-coated copper grid. After standing 10 min, the remaining suspension was carefully removed with wipes, and the samples were negatively stained using fresh 1% phosphotunstic acid for 20 s and washed with ultrapure water twice. The dried samples were imaged on a JEOL JEM 1400 Transmission Electron Microscope (JEOL Ltd., Tokyo, Japan).

Imaging endocytosis of lipid-PLGA hybrid NPs by dendritic cell (DC) using CLSM

JAWSII (ATCC® CRL-11904™) immature DCs from ATCC were cultured in a 2 well chamber slide (Thermo Fisher Scientific Inc., Rd, Rockford, Ill.) using the method reported before with minor modifications [9, 19]. For study on uptake of newly made hybrid nanoparticles with differing degrees of PEGylation, $5 \times 10^5$ DCs were incubated with 100 µg fluorescently labeled hybrid particles for 30 min, 60 min, and 120 min, respectively. For study on uptake of nanoparticles that were stored at 4° C. in PBS buffer for 30 days, $5 \times 10^5$ DCs were incubated with 100 µg hybrid particles for 180 min. After incubation, sample processing was similar to that described before [9]. Briefly, the medium was immediately removed and cells were washed 5 times with PBS buffer (pH 7.4). Freshly prepared 4% (w/v) paraformaldehyde (2 mL) was added into each well, and cells were fixed for 15 min, followed by washing 3 times with PBS buffer (pH 7.4). Fixed cells were labeled with DAPI Fluoromount-G® (SouthernBiotech, Birmingham, Ala.). Cell samples were covered with a glass cover. Images were acquired using a Zeiss LSM 880 Laser Scanning Microscope (Carl Zeiss, Germany).

Study of Uptake of Lipid-PLGA Hybrid Nanoparticles by DC Via Flow Cytometry

DCs were cultured in CytoOne® 35×10 mm TC dish (USA Scientific Inc., Ocala, Fla.) using the same method reported before [19]. For study on uptake of newly made hybrid particles with various degrees of PEGylation, $2 \times 10^6$ DCs were incubated with 200 µg fluorescently labeled hybrid nanoparticles for 30 min, 60 min, and 120 min, respectively. For study on uptake of nanoparticles stored at 4° C. in PBS buffer for 30 days, $2 \times 10^6$ DCs were incubated with 200 μg fluorescently labeled hybrid nanoparticles for 180 min. After incubation, sample processing was the same as described before [19]. Briefly, the medium was immediately removed and cells were washed 5 times with PBS buffer (pH 7.4). Cells were detached from culture plate using trypsin/EDTA solution and centrifuged at 200 g for 10 min, and cell pellets were suspended in 2 mL PBS buffer (pH 7.4). Cell samples were immediately analyzed by a flow cytometer (BD FACSAria I, BD, Franklin Lakes, N.J.).

Immunizing Mice with NanoNiccine

All animal studies were carried out following the National Institutes of Health guidelines for animal care and use. Animal protocols were approved by the Institutional Animal Care and Use Committee at Virginia Polytechnic Institute and State University. Groups of n=5 female BALB/c mice (8-10 weeks) were immunized by subcutaneous (s.c.) injection on day 0 (primary injection) and day 14 (booster injection) with PBS buffer (10 mM, pH 7.4) (negatively control), NanoNiccine 2.5, NanoNiccine 5.0, NanoNiccine 12.5, and NanoNiccine 20.0, respectively. All the vaccine constructs contained total quantity of 25 μg KLH. Blood samples (~200 μl) were collected on days -2, 13, 28, and 35 via retroorbital puncture from each mouse. Sera centrifuged from blood were stored at -80° C.

Measurement of Specific Anti-Nicotine IgG and Anti-KLH IgG Antibodies Using Enzyme-Linked Immunosorbent Assay (ELISA)

The mice sera were analyzed according to the ELISA procedure described in previous publications with proper modifications [9, 21]. Briefly, Nic-BSA was used as coating material for anti-Nic IgG measurement, and KLH was used as coating material for anti-KLH measurement. Nic-BSA was synthesized using protocols described in a previous study [9]. MICROLON® 96 well plates (Greiner BioOne, Longwood, Fla.) were coated with Nic-BSA conjugate or KLH (10 μg/mL in carbonate buffer, 0.05 M, pH 9.6, 100 μL/well) and incubated at 25° C. for 5 h. The plates were washed with PBS-Tween (0.1%) for 3 times and distilled water for 3 times, followed by blocking with 300 μL Pierce® protein-free T20 blocking buffer for 12 h. After washing, 100 μL of each dilution (1:25, 1:125, 1:625, 1:3125, 1:15625, 1:78125, and 1:390625) of serum from each mouse was incubated in plates at 25° C. for 2 h. The plates were washed again, and incubated with 100 μL Anti-Mouse IgG from goat (1:5000) from Alpha Diagnostic Intl (San Antonio, Tex.) for 1 h. The pates were washed as before, and incubated with 100 μL Anti-Goat IgG-HRP (1:5000) (Alpha Diagnostic Intl, San Antonio, Tex.) for 1 h. After washing as before, 100 μL of TMB One Component Microwell Substrate (SouthernBiotech, Birmingham, Ala.) was added into each well and incubated for 10 min, and the reaction was stopped by adding 100 μL of 0.5% (v/v) $H_2SO_4$. The absorbance for each well at 450 nm was recorded. Titer was defined as the dilution factor at which OD450 fell to half of the maximal.

Evaluation of the Pharmacokinetic Efficacy of NanoNiccine in Mice

On day 37, the mice immunized with NanoNiccines and the mice in the negative control group were administered with 0.06 mg/kg nicotine subcutaneously. The mice were sacrificed 4 min post nicotine challenge, and brain tissues were collected. Nicotine contents in the brain tissues were analyzed by gas chromatography/mass spectrometry according to a method reported previously [34].

Histopathological Examination

The mice immunized with PBS or NanoNiccines were scarified on day 37, and their tissues, including heart, lung, kidney, spleen, liver, and stomach were harvested and fixed in 10% buffered formalin. H&E staining was carried out according to the method described before [9]. Sections were examined by light microscopy on an Olympus CKX41 Inverted Microscope and images were captured using an INFINITY 1 camera.

Data Analysis

Particle size of the hybrid nanoparticles, fluorescence ratios in the hybrid nanoparticles, antibody titers, brain nicotine concentration were compared among groups using one way ANOVA and comparisons among paired groups were analyzed with Tukey's HSD. The difference is considered as significant when P-value is less than 0.05. Each measurement was carried out at least three times, and the results were expressed as mean±standard deviation.

Results

Figure 90A:
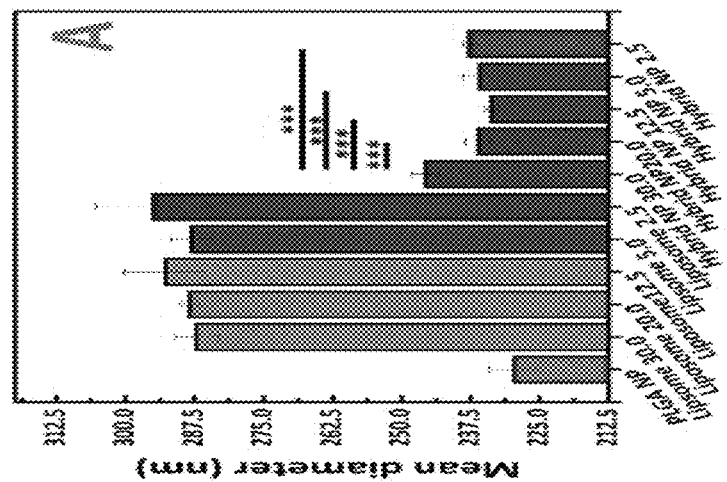
FIGS. 90A-90C show characterization of physicochemical properties of nanoparticles. Particle mean size (FIG. 90A) and surface charge (FIG. 90B) of different nanoparticles. NBD/Alexa 647 intensity ratios in the hybrid nanoparticles (FIG. 90C). For fluorescence labeling, the lipid layer was labeled with NBD (green color) and the PLGA core was labeled with Alexa 647 (red color). ***means that p-value is less than 0.001.
Figure 90B:
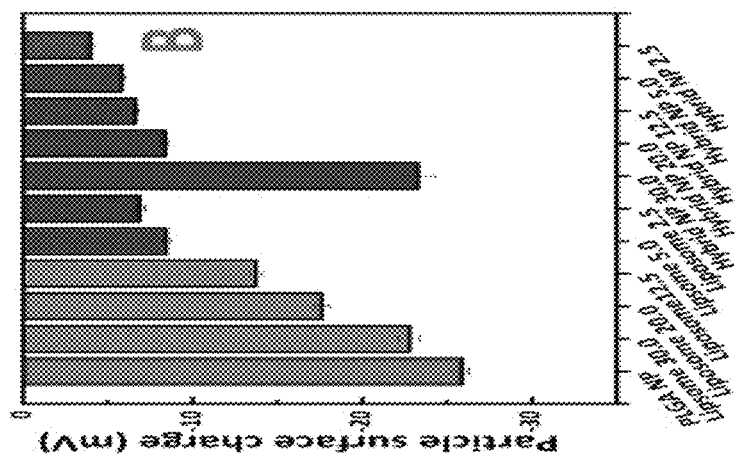

Characterization of physicochemical properties and morphology of the nanoparticles The lipid-PLGA hybrid nanoparticle in this study was assembled by sonication aided fusion of liposome with PLGA nanoparticle [19]. Prior to the hybrid nanoparticle assembly, liposome was formed via lipid film hydration and sonication. As shown in FIG. 90A, the mean sizes of liposomes with 30% (Liposome 30.0), 20% (Liposome 20.0), 12.5% (Liposome 12.5), 5% (Liposome 5.0), and 2.5% (Liposome 2.5) DSPE-PEG(2000)COOH were 287.08±3.96 nm, 288.33±1.63 nm, 292.77±7.45 nm, 288±3.71 nm, and 294.9±10.48 nm, respectively. As shown in FIG. 90B, the surface charges represented by zeta potential of Liposome 30.0, Liposome 20.0, Liposome 12.5, Liposome 5.0, and Liposome 2.5 were -22.77±0.65 mV, -17.6±0.44 mV, -13.73±0.35 mV, -8.43±0.25 mV, and -6.83±0.35 mV, respectively. In the meantime, the PLGA nanoparticle was fabricated via double emulsion and solvent evaporation [19]. As shown in FIG. 90A and FIG. 90B, the mean size of the PLGA nanoparticle was 229.6±4.5 nm and its mean surface charge was -25.88±0.42 mV. The physicochemical properties of the lipid-PLGA hybrid nanoparticles were also characterized. Also illustrated in FIG. 90A, the hybrid nanoparticles with 30% (Hybrid 30.0), 20% (Hybrid 20.0), 12.5% (Hybrid 12.5), 5% (Hybrid 5.0), and 2.5% (Hybrid 2.5) PEGylation had a mean size of 245.6±2.6 nm, 236.1±2.3 nm, 233.7±1.3 nm, 235.8±3.0 nm, and 237.7±1.1 nm, respectively. As shown in FIG. 90B, the surface charges of Hybrid 30.0, Hybrid 20.0, Hybrid 12.5, Hybrid 5.0, and Hybrid 2.5 were -23.30±1.02 mV, -8.39±0.24 mV, -6.59±0.21 mV, -5.80±0.20 mV, and -3.99±0.22 mV, respectively.

Figure 90C:
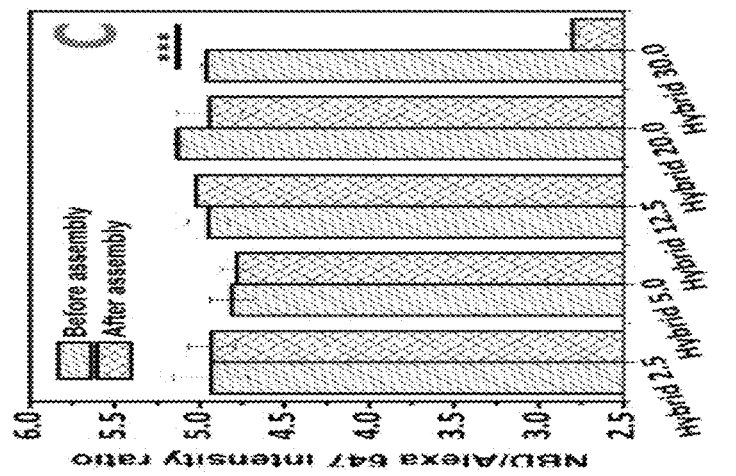
Figure 91:
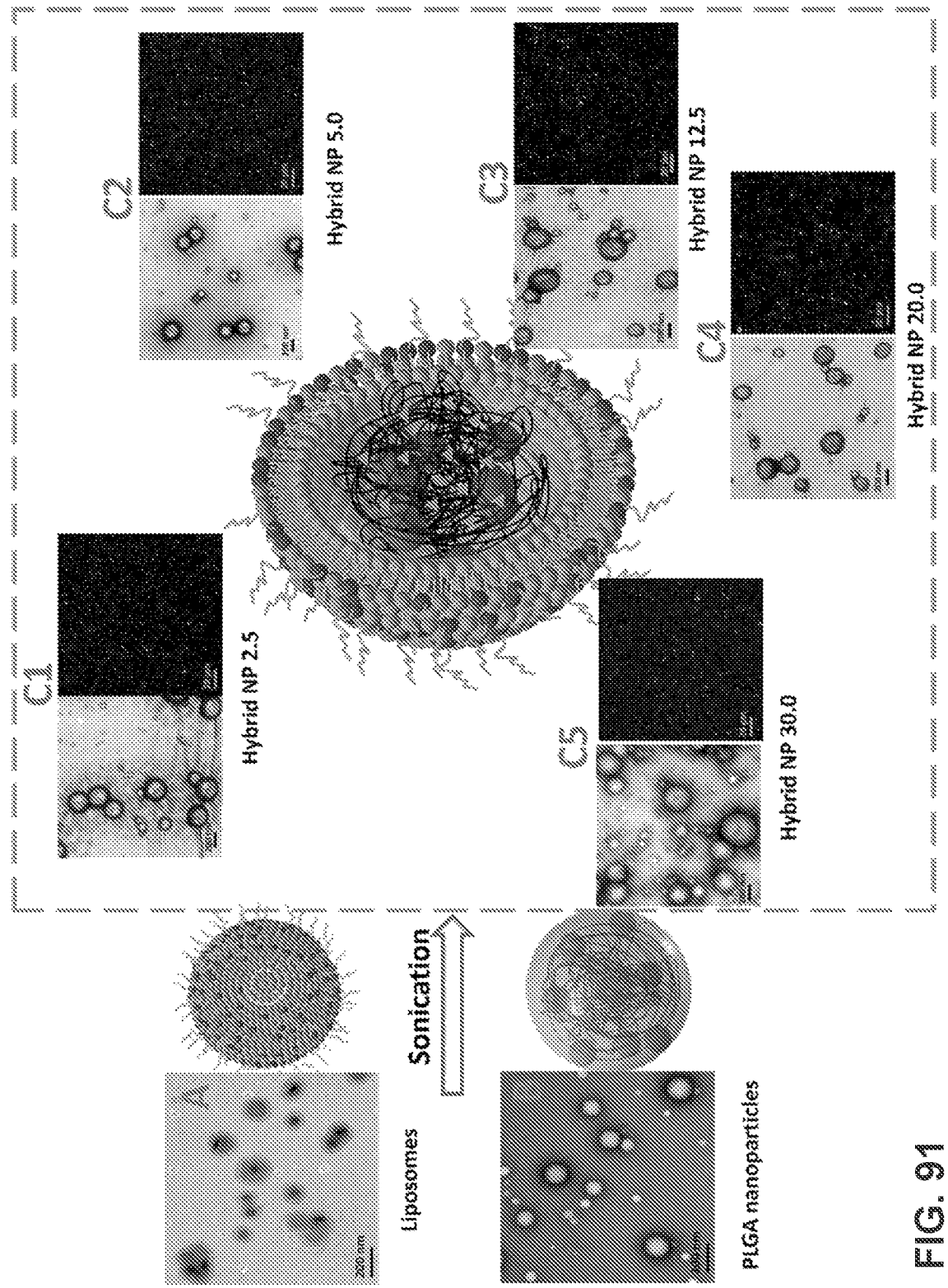
FIG. 91 shows morphology of nanoparticles. TEM images of Liposome (A), PLGA nanoparticle (B). TEM (left) and confocal images (right) of Hybrid 2.5 (C1), Hybrid 5.0 (C2), Hybrid 12.5 (C3), Hybrid 20.0 (C4), and Hybrid 30.0 (C5). The scale bars represent 200 nm in the TEM images and 20 µm in the confocal images.

The morphologies of the nanoparticles were examined using a TEM (FIG. 91). Consistent with the size results measured above, the TEM micrographs (Panel A-PanelC5) showed that the particles, including the liposome, the PLGA nanoparticle, and the hybrid nanoparticles, had a diameter at around 200 nm. In FIG. 91, panel A, a distinct bilayer structure with a thickness of 10 nm was observed in the liposomes. In agreement with previous findings [19, 20], the PLGA nanoparticles exhibited a solid and spherical structure with a narrow size distribution (FIG. 91, Panel B). After sonication, liposomes of different degrees of PEGylation were coated onto the PLGA nanoparticle as an exterior shell. As shown in FIG. 91, Panels C1-C5, a lipid layer (the black ring on the surface of the hybrid nanoparticles) was observed in all the lipid-PLGA hybrid nanoparticles with the exception of Hybrid 30.0. As also detected in previous studies [19, 35], the size of the hybrid nanoparticle was largely decided by that of the PLGA nanoparticle. All the hybrid nanoparticles in this study had a size distribution similar to that of the PLGA nanoparticles. This was also supported by the close mean particle sizes of the two particles (FIG. 90A). However, the lipid layer of Hybrid 30.0 (FIG. 91, Panel C5) looked differently from that of the other hybrid nanoparticles (FIG. 91, Panels C1-C4). The color of the lipid ring in Hybrid 30.0 was apparently lighter than those of the other hybrid nanoparticles, which might be caused by the less quantity of lipids in the lipid layer. In addition, the confocal images of the hybrid nanoparticles supported speculation that Hybrid 30.0 had a less quantity of lipids in the lipid layer than others'. As described in a previous studies [9, 36], labeled with NBD in the lipid layer and Alexa 647 in the PLGA core, hybrid nanoparticles displayed as yellow dots under a confocal microscope. In this study, the majority of the hybrid nanoparticles in the confocal images from FIG. 91, Panels C1-C4 exhibited yellow color, which resulted from the combination of the green color (NBD) emitted from the lipid layer and the red color (Alexa 647) emitted from the PLGA core. In contrast, only red color was detected in most of the Hybrid 30.0 particles in FIG. 91, Panel C5, indicating that red florescence from the PLGA core was dominant. Moreover, the mean size and surface charge of Hybrid 30.0 did not follow the patterns of the other hybrid nanoparticles (FIG. 90A and FIG. 90B). The size of Hybrid 30.0 with a value at around 245 nm was significantly bigger than those of the other hybrid nanoparticles, which shared a particle size at around 235 nm. The surface charge of Hybrid 30.0 was un-proportionally low compared to the others'. To explain these abnormalities, the hybrid nanoparticles were labeled with Alexa 647 in the PLGA core, and NBD in the lipid layer. As shown in FIG. 90C, NBD/Alexa 647 ratio in Hybrid 20.0, Hybrid 12.5, Hybrid 5.0, and Hybrid 2.5 was not significantly different from that before hybrid nanoparticle assembly. In contrast, Hybrid 30.0 had a significantly lower NBD/Alexa 647 ratio than that before its assembly. It was possible that the lipid layer may not be able to associate with the PLGA core firmly due to its instability caused by the high concentration of DSPE-PEG(2000)COOH. Because of its instability, Hybrid 30.0 was not used in subsequent study.

In Vitro Uptake of Newly Assembled Hybrid Nanoparticles by Dendritic Cell

Figure 92A:
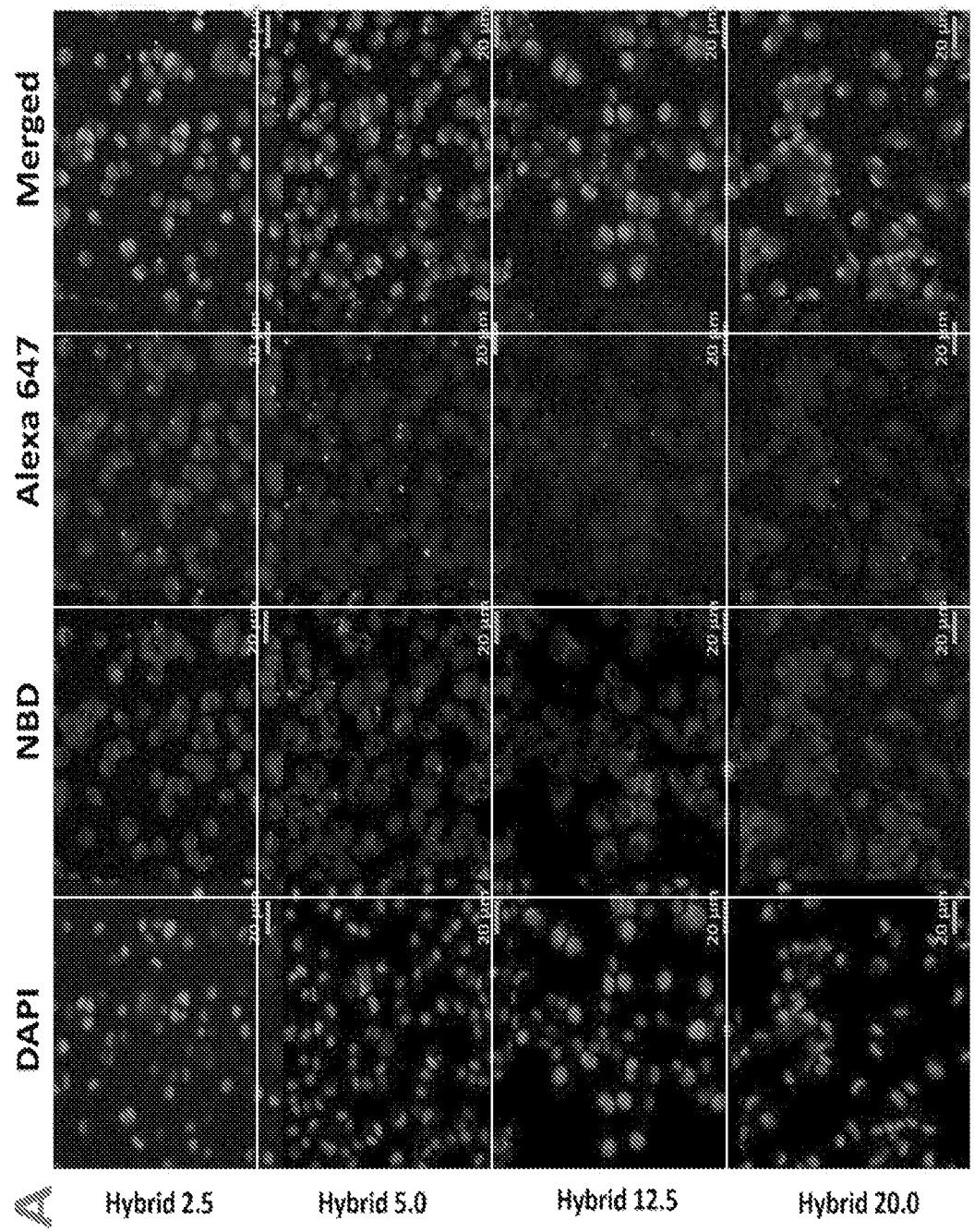
FIGS. 92A-92C shows panels of confocal images of the uptake of the newly-made hybrid nanoparticles by dendritic cells. 100 µg newly-assembled hybrid nanoparticles (the lipid layer was labeled with NBD and the PLGA core was labeled with Alexa 647), including Hybrid 2.5, Hybrid 5.0, Hybrid 12.5, and Hybrid 20.0, were incubated with $5 \times 10^5$ dendritic cells for 30 min (FIG. 92A), 60 min (FIG. 92B), and 120 min (FIG. 92C), respectively. The images were captured using a Zeiss LSM 510 confocal microscope. The scale bars represent 20 µm.
Figure 92B:
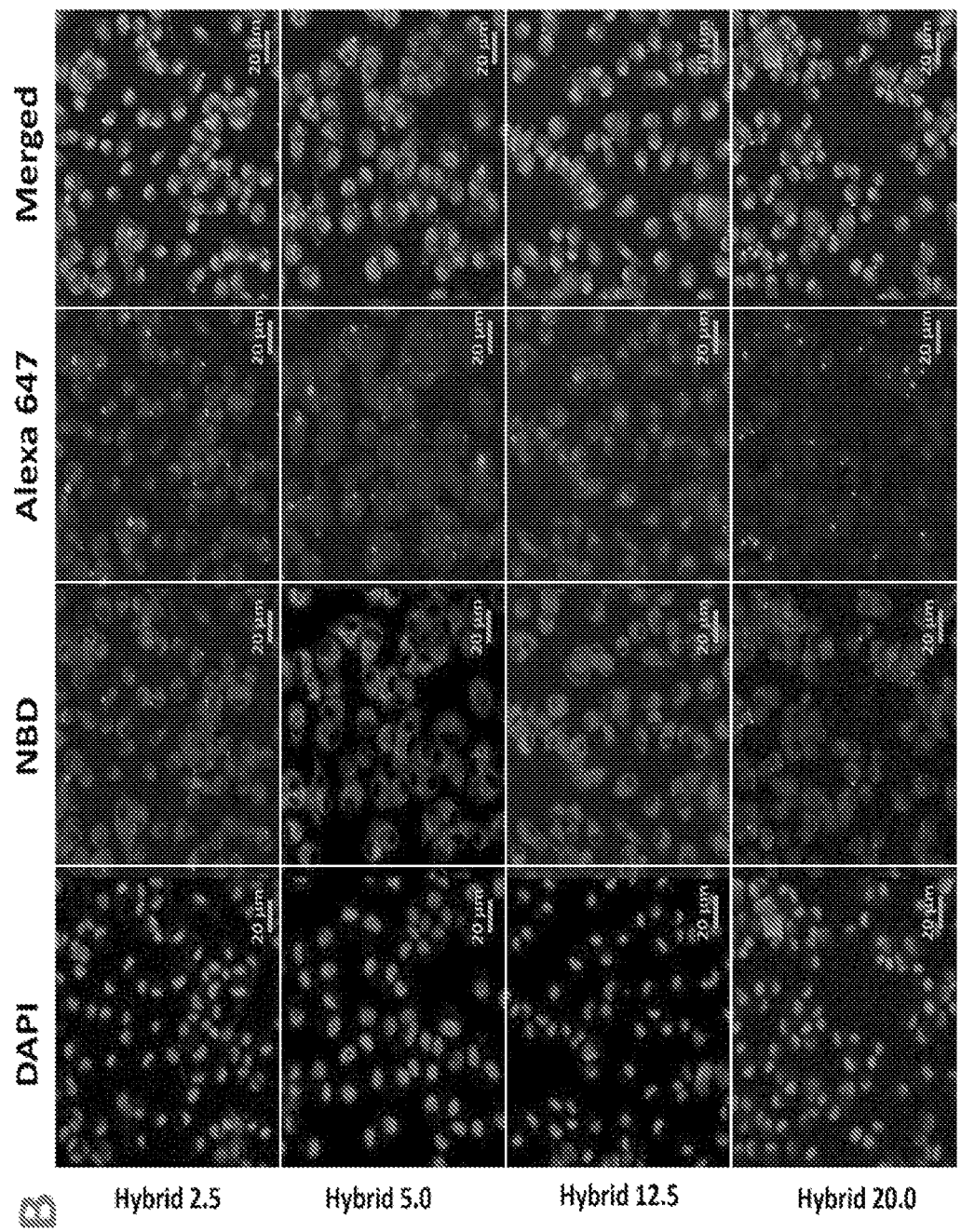
Figure 92C:
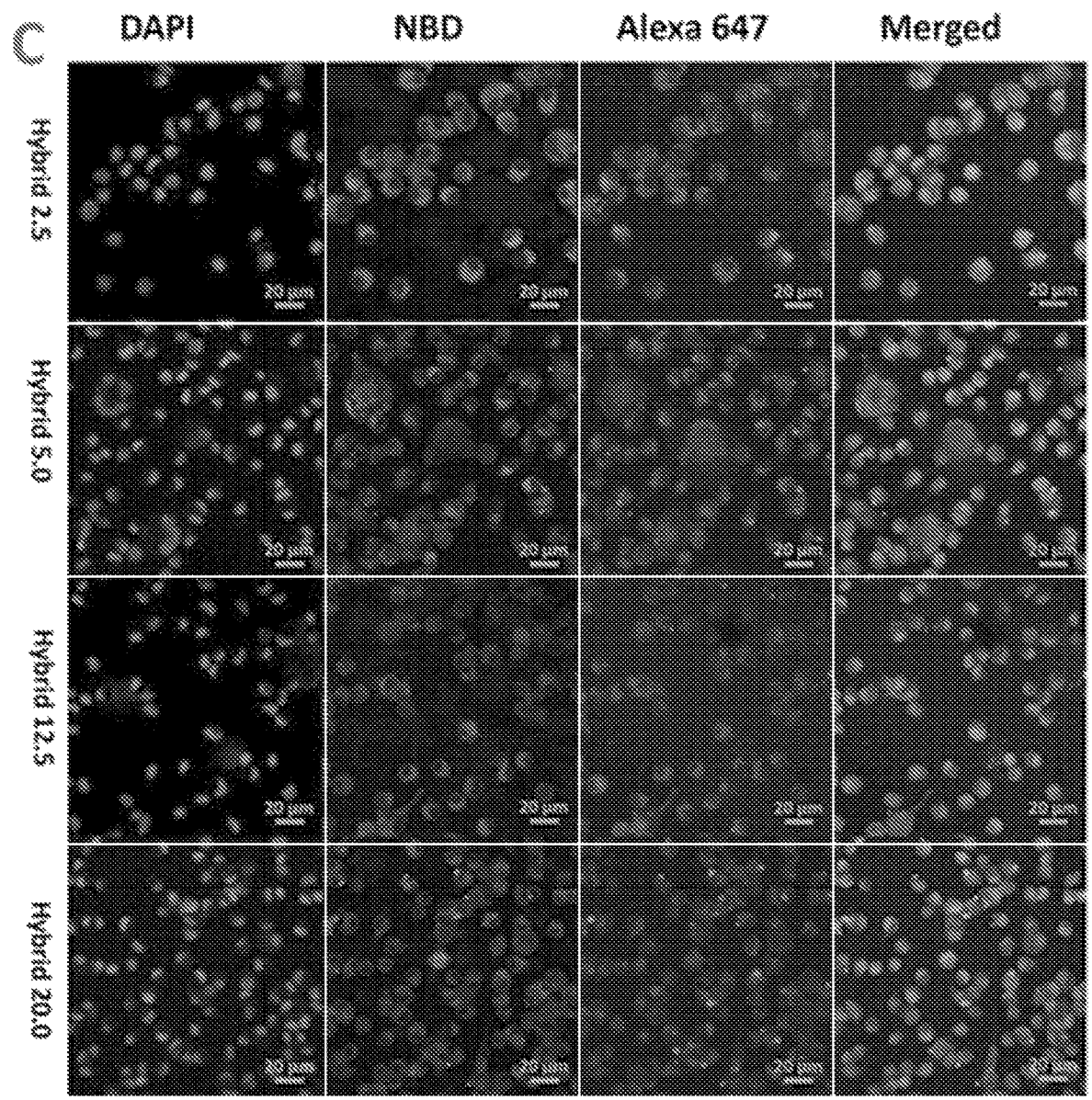
Figures 93A, 93B, 93C, 93D, 93E, 93F:
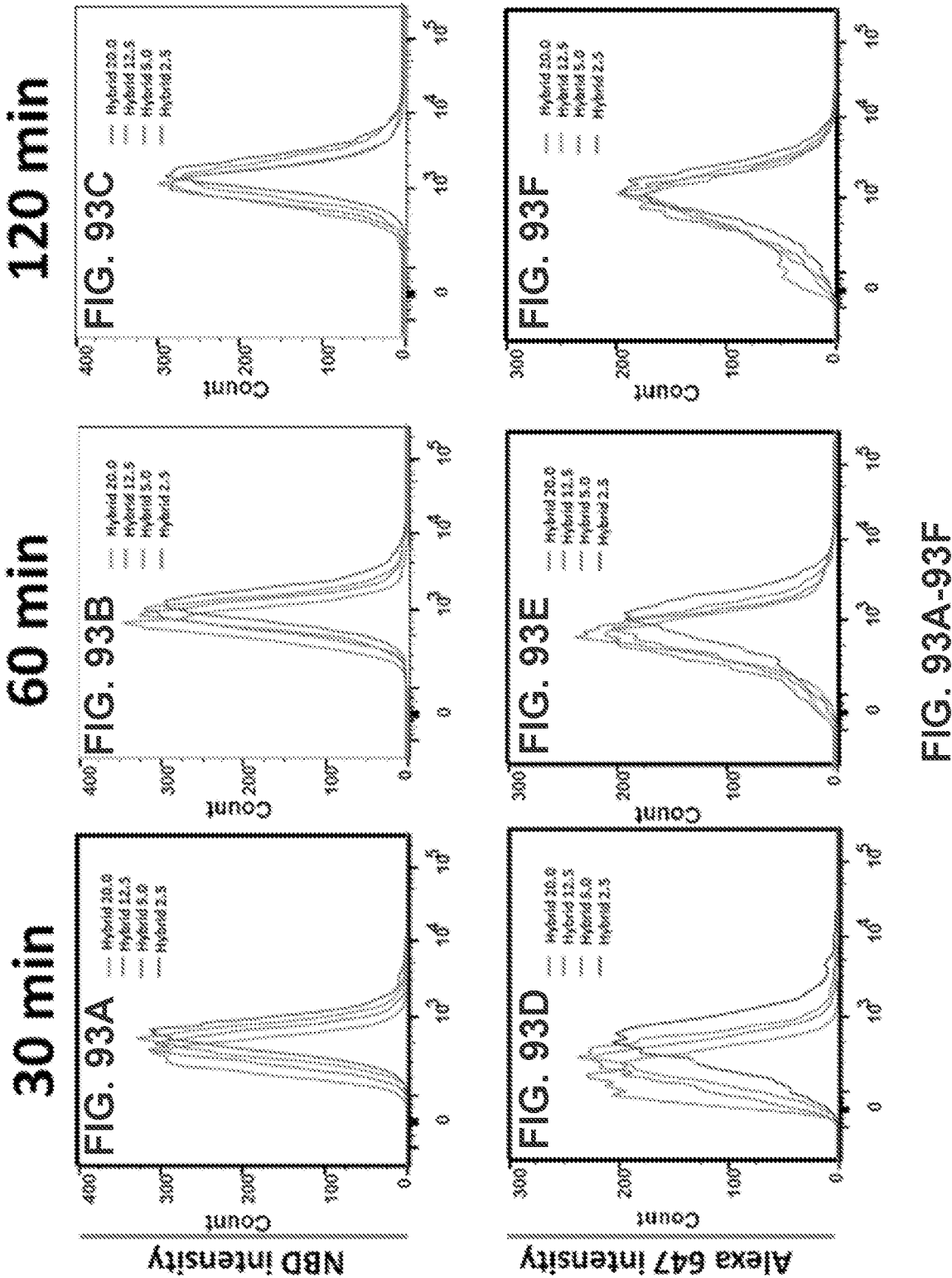
FIGS. 93A-93F show plots of the counts uptake of newly-assembled hybrid nanoparticles by dendritic cells using a flow cytometer. $2 \times 10^6$ dendritic cells in a petri dish were incubated with 200 µg hybrid nanoparticles of various degrees of PEGylation for 30 min, 60 min, and 120 min, respectively. The fluorescence intensities of NBD and Alexa 647 emitting from the nanoparticles in the dendritic cells were recorded using a flow cytometer.

The influence of PEGylation on the uptake of hybrid nanoparticle by dendritic cells was investigated. $5\times10^5$ dendritic cells in each slide chamber were incubated with 100 µg hybrid nanoparticles (the lipid layer was labeled with NBD and KLH in the PLGA core was labeled with Alexa 647), including Hybrid 20.0, Hybrid 12.5, Hybrid 5.0, and Hybrid 2.5, for 30 min, 60 min, and 120 min, respectively. Strikingly, the confocal images in the panel of FIG. 92A showed that all the dendritic cells internalized hybrid nanoparticles regardless of the degree of PEGylation within 30 min. In addition, as illustrated in the panels of FIG. 92A to FIG. 92C, the quantity of the hybrid nanoparticle internalized by the dendritic cells increased with time, which was reflected by the increasingly brighter fluorescence in both the NBD channel and the Alexa 647 channel. In addition, the uptake rate of hybrid nanoparticles was inversely correlated with the degree of PEGylation at all time points. The dendritic cells took up hybrid nanoparticle with a lower PEGylation more rapidly than that with a higher PEGylation.

Figure 94A:
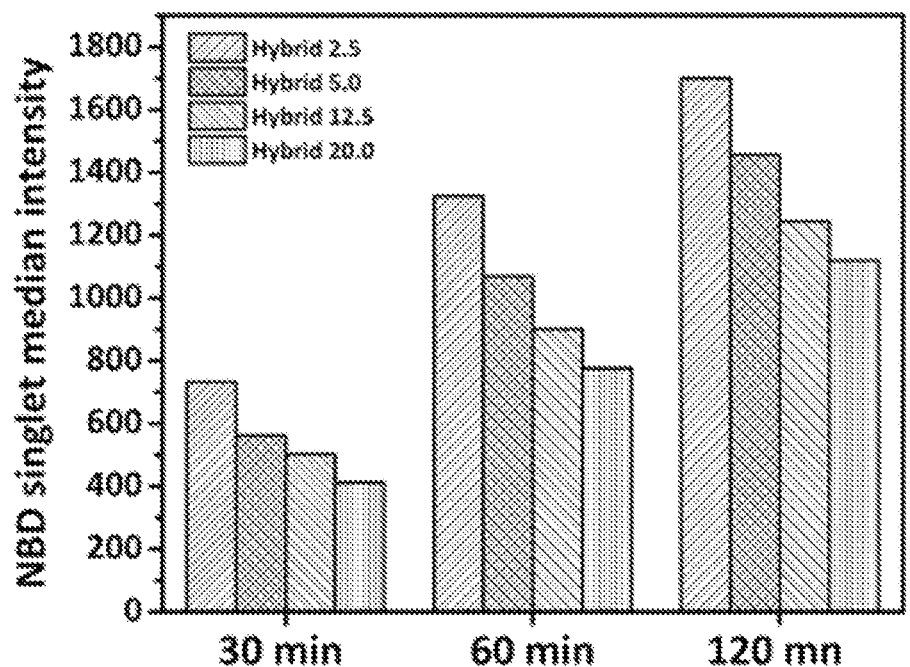
FIGS. 94A-94B show bar graphs demonstrating the uptake of the newly-assembled hybrid nanoparticles by dendritic cells using a flow cytometer. $2 \times 10^6$ dendritic cells in a petri dish were incubated with 200 µg hybrid nanoparticles of various degrees of PEGylation for 30 min, 60 min, and 120 min, respectively. The fluorescence intensities of NBD and Alexa 647 emitting from the nanoparticles in the dendritic cells were recorded using a flow cytometer.
Figure 94B:
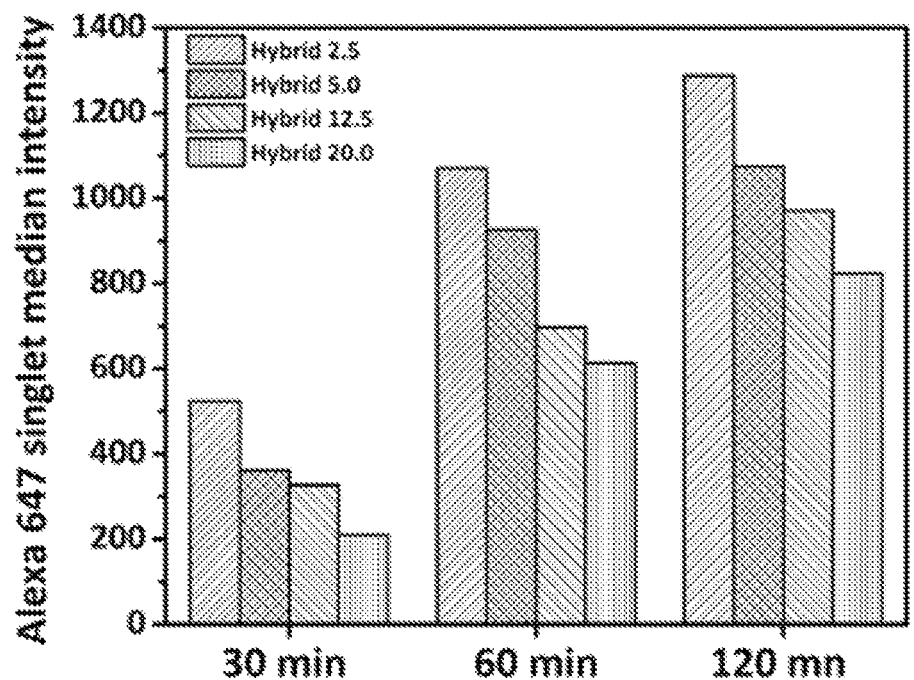

To quantitatively study their uptake, the fluorescence intensities of both NBD and Alexa 647 emitted from the hybrid nanoparticles internalized into the dendritic cells were recorded by a flow cytometer. $2\times10^6$ dendritic cells in each petri dish were incubated with 200 µg of differently PEGylated hybrid nanoparticles for 30 min, 60 min, and 120 min, respectively. In agreement with the findings from the confocal micrographs, the quantity of the hybrid nanoparticles captured by dendritic cells increased with time, which was illustrated by the right-shifting fluorescence intensity curve in FIGS. 93A-93F. It was also detected that a lower concentration of DSPE-PEG(2000)COOH in the lipid layer resulted in a more positively shifted fluorescence intensity curve, indicating the dendritic cells preferred to internalize the hybrid nanoparticles of less DSPE-PEG(2000)COOH. The median fluorescence intensity from a single cell (FIGS. 94A-94B) also substantiated that the dendritic cells could continuously internalize the hybrid nanoparticles and PEGylation hindered their cellular uptake. From 30 min to 120 min, the singlet median intensity increased at least 131% for all the hybrid nanoparticles. Hybrid 2.5, Hybrid 5.0, Hybrid 12.5, and Hybrid 20.0 had decreasing NBD singlet median intensities of 1699, 1456, 1244, and 1120, respectively, at 120 min. However, it is worth noting that the fluorescence intensity curves from different hybrid nanoparticles tended to overlap with each other over time, indicating that the differences in the quantity of the internalized hybrid nanoparticles captured by the dendritic cells were decreasing. The singlet median intensities also showed the same tendency. For example, Hybrid 2.5 had a 77.9% higher NBD singlet median intensity than that Hybrid 20.0 at 30 min, but it dropped to 70.6% and 51.7% at 60 min and 120 min, respectively.

Figure 95:
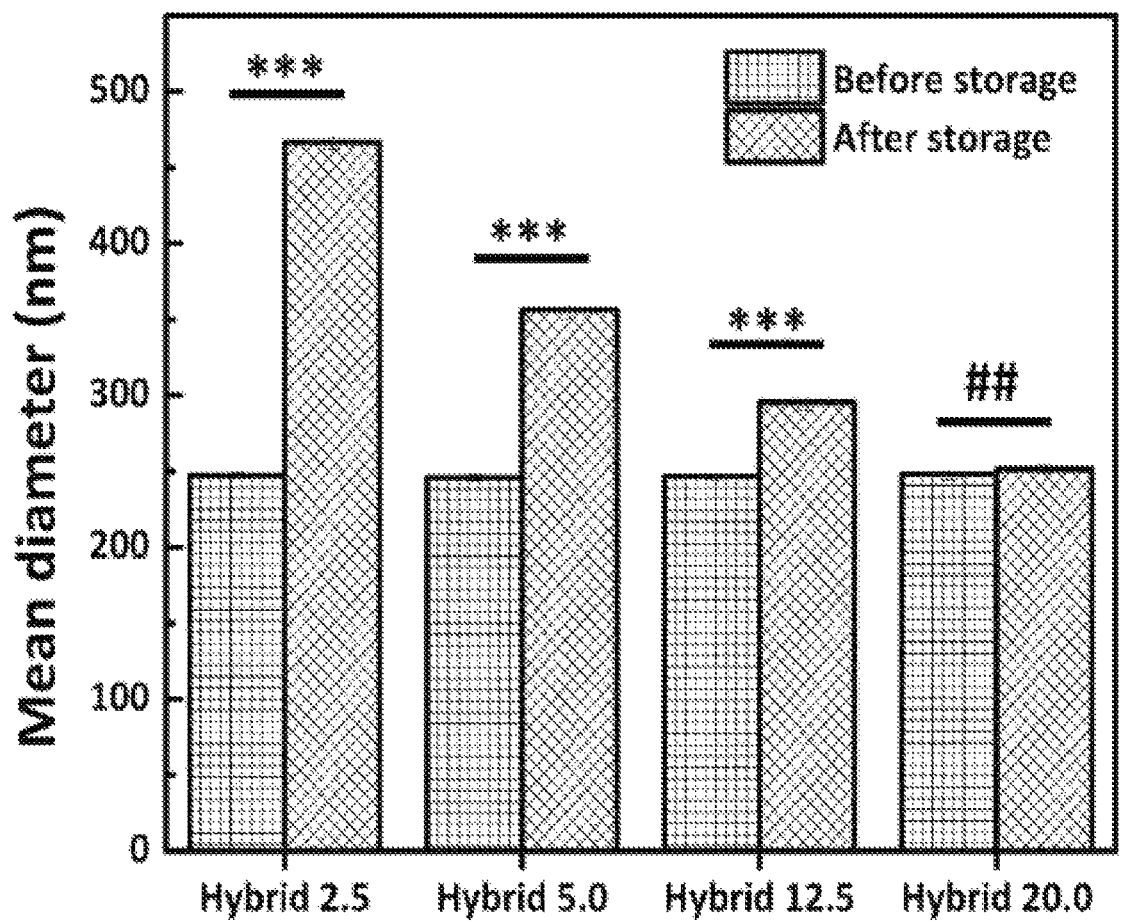
FIG. 95 shows a graph demonstrating the change in particle size of the hybrid nanoparticle after storage. The hybrid nanoparticle (stained with NBD and Alexa 647), including Hybrid 20.0, Hybrid 12.5, Hybrid 5.0, and Hybrid 2.5 were stored under 4° C. in PBS buffer for 30 days. The mean sizes of the particles were recorded before and after storage. *** means that p-value is less than 0.001 and ## means that P-value is higher than 0.05.
Figures 96A, 96P:
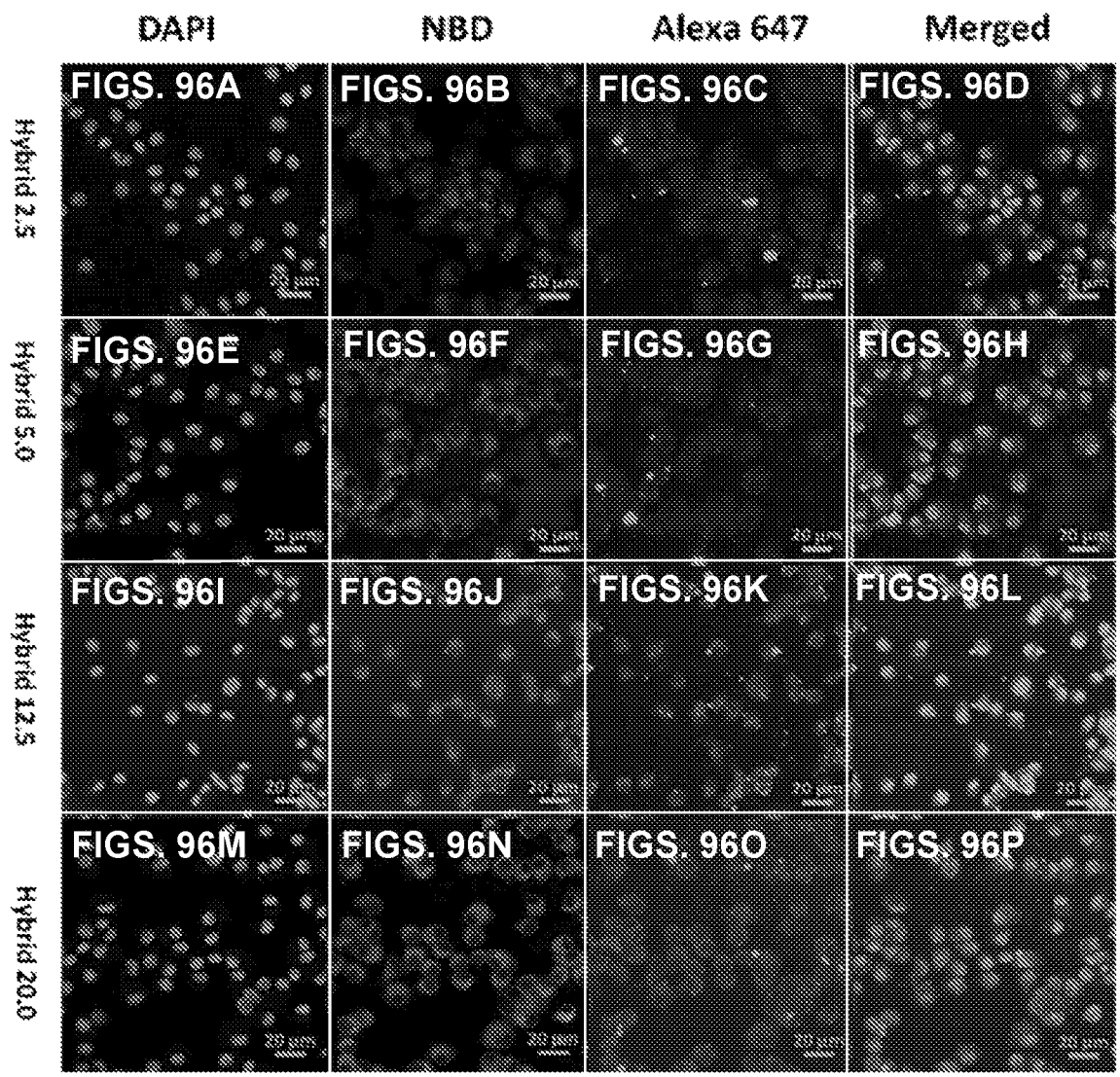
FIGS. 96A-96P shows the uptake of the stored hybrid nanoparticles by dendritic cells. $5 \times 10^5$ dendritic cells were incubated with 100 µg hybrid nanoparticles with different degrees of PEGylation for 180 min. The image of cellular uptake of nanoparticles was captured by a confocal microscope $2 \times 10^6$ dendritic cells were treated with 200 µg of the stored nanoparticles for 180 min.

Impact of Long-Term Storage on Size of Hybrid Nanoparticles and their Cellular Uptake The hybrid nanoparticles (labeled with NBD in the lipid layer and Alexa 647 in the PLGA core) were stored under 4° C. in PBS buffer for 30 days. The mean particle sizes of these nanoparticles were recorded before and after storage. As shown in FIG. 95, newly made hybrid nanoparticles, including Hybrid 20.0, Hybrid 12.5, Hybrid 5.0, and Hybrid 2.5, had a mean particle size of 247.4±1.9 nm, 246.1±2.6 nm, 246.7±2.0 nm, and 248.3±4.0 nm, respectively. After storage, the mean size of Hybrid 12.5, Hybrid, 5.0, and Hybrid 2.5 significantly increased to 295.5±5.2 nm, 356.2±5.9 nm, and 466.7±4.4, respectively. In contrast, the mean size of Hybrid 20.0 only slightly changed to 251.5±2.8 nm, which was not significantly different from that of the fresh Hybrid 20.0.

Figures 97A, 97B, 97C:
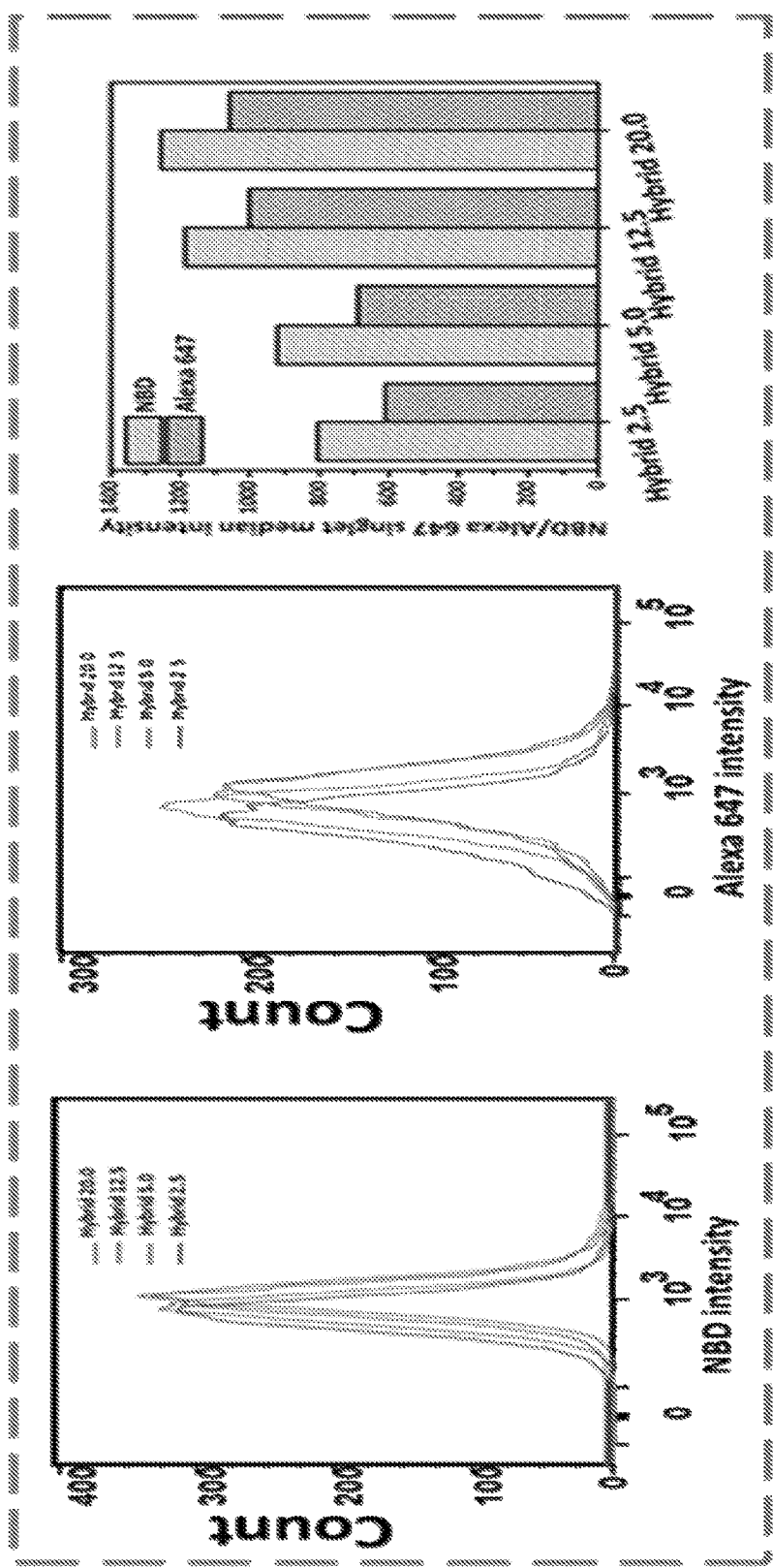
FIGS. 97A-97C show graphs demonstrating the fluorescence intensities of NBD and Alexa emitting from nanoparticles in dendritic cells were recorded by a flow cytometer whose images are shown in FIGS. 96A-96P.

The influence of the change in size of the stored hybrid nanoparticles on their cellular uptake by dendritic cells was investigated. $5\times10^5$ dendritic cells in each chamber slide were incubated with 100 µg of the stored hybrid nanoparticles for 180 min. As shown in FIGS. 96A-96P and 97A-97C, the change in particle size had a great impact on the uptake of nanoparticles by dendritic cells. The increased size of hybrid nanoparticles, especially Hybrid 2.5 and Hybrid 5.0, resulted in apparently impeded cellular uptake. In contrast, Hybrid 20.0, which didn't undergo significant size change, were internalized more rapidly than the others. The uptake of the stored hybrid nanoparticles was further studied using a flow cytometry. Consistent with the confocal results in FIGS. 96A-96P, the fluorescence intensity curve in FIGS. 97A-97B showed that the stored hybrid nanoparticle with a higher PEGylation level was taken up by dendritic cells more rapidly than that a with lower PEGylation level. In addition, the singlet median intensities of both NBD and Alexa 647 in FIG. 97C also revealed that the quantity of the internalized nanoparticles was inversely correlated with the particle size, which significantly increased in nanoparticles with low degrees of PEGylation after storage.

Figure 98:
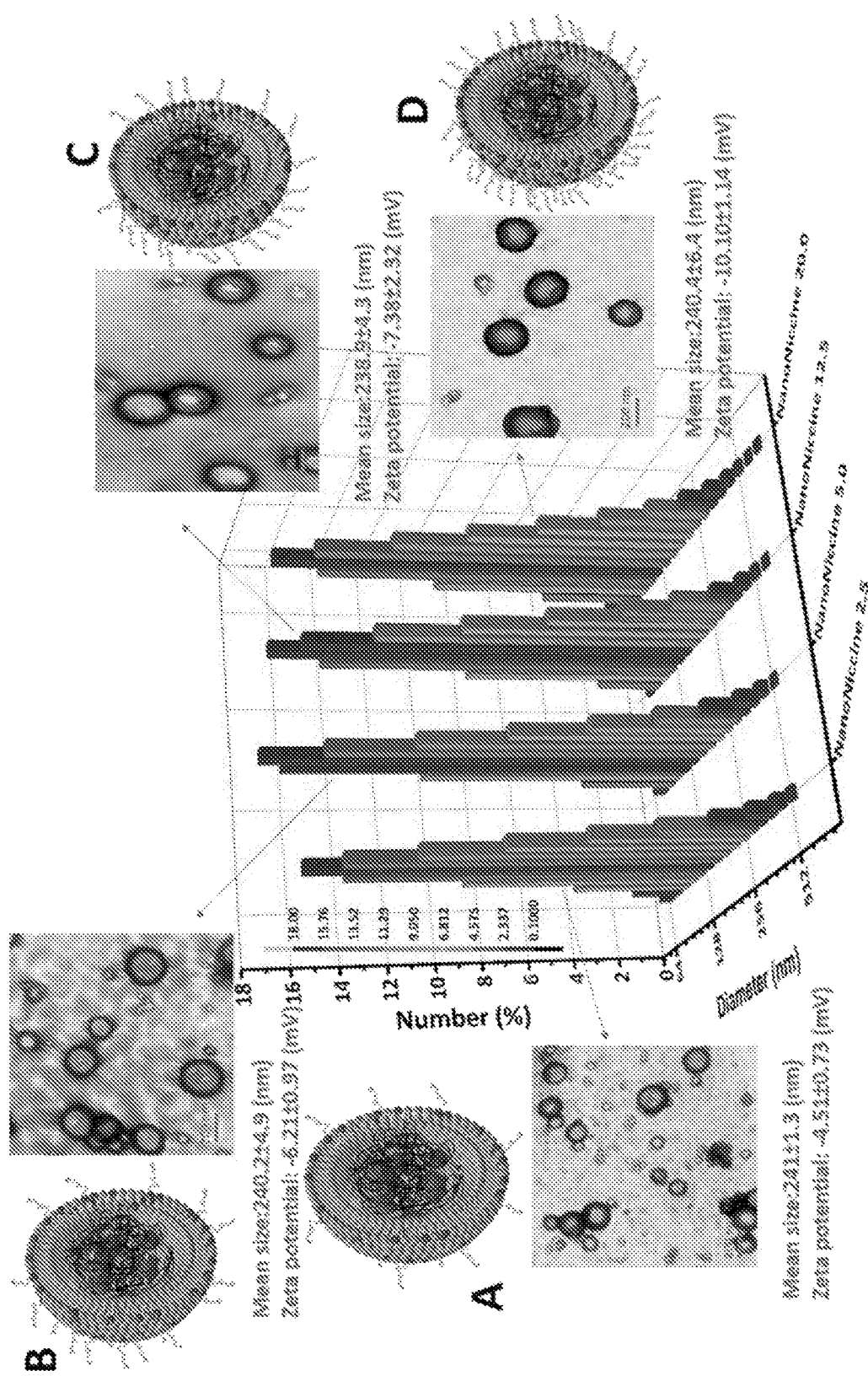
FIG. 98 shows characterization of the physicochemical properties and morphology of NanoNiccines. NanoNiccines with different densities of nicotine epitope were schematically illustrated. Their corresponding size distribution, mean particle size, surface charge, and TEM images were shown. (A) NanoNiccine 2.5, (B) NanoNiccine 5.0, (C) NanoNiccine 12.5, (D) NanoNiccine 20.0. The scale bars in the TEM images represent 200 nm.

Characterization of the Physicochemical Properties and Morphology of NanoNiccines NanoNiccines with different nicotine epitope densities were assembled by conjugating rac-trans 3'-aminomethyl nicotine onto the hybrid nanoparticles with various quantities of DSPE-PEG(2000)COOH. Their physicochemical properties, including particle mean size, size distribution, and surface charge, were measured. In addition, the TEM images of NanoNiccines were captured to study morphology of NanoNiccines. As shown in FIG. 98, all the NanoNiccines had similar size distributions, which peaked at around 150 nm. NanoNiccines with different nicotine epitope densities had very similar mean sizes, which were 241±1.3 nm, 240±4.9 nm, 238.9±4.3 nm, and 240.4±6.4 nm for NanoNiccine 2.5, NanoNiccine 5.0, NanoNiccine 12.5, and NanoNiccine 20.0, respectively. The zeta potentials of NanoNiccine 2.5, NanoNiccine 5.0, NanoNiccine 12.5, and NanoNiccine 20.0 were −4.51±0.73 mV, −6.21±0.97 mV, −7.38±2.32 mV, and −10.10±1.14 mV, respectively. All the NanoNiccine particles in TEM micrographs (FIGS. 96A-96P) displayed a core-shell structure with a particle size at around 200 nm.

Nicotine and KLH Specific IgG Antibody Titers Induced by NanoNiccines

Figure 99A:
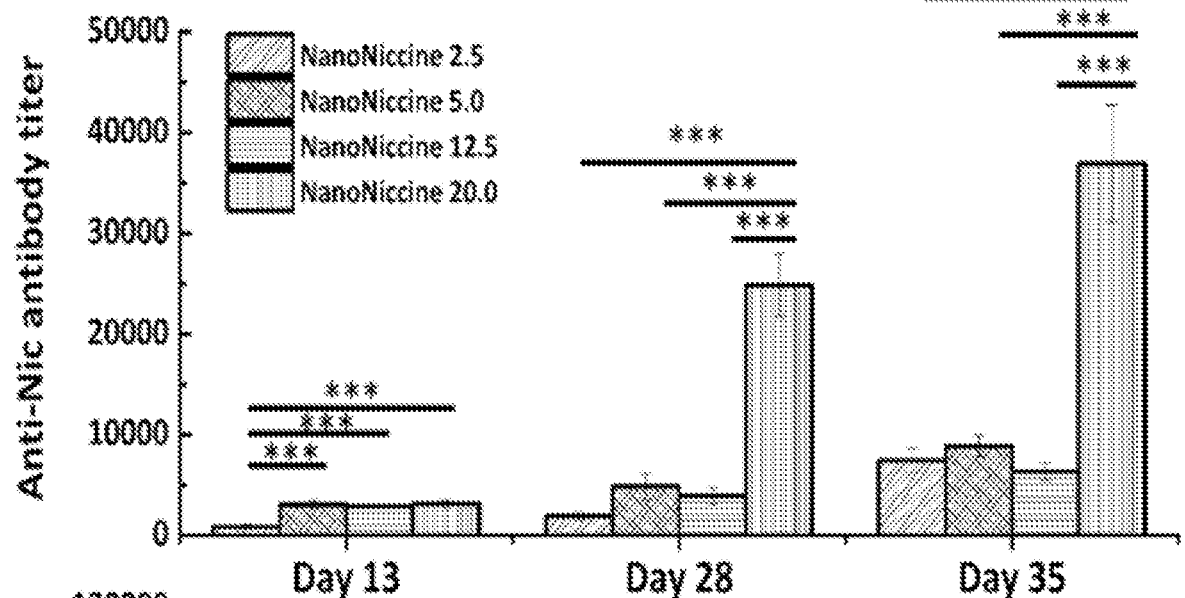
FIGS. 99A-99B show graphs demonstrating the time course of anti-nicotine IgG titer and anti-KLH IgG titer in mice immunized with NanoNiccines. Each group of 5 mice were injected with NanoNiccines containing 25 µg KLH on days 0, 14. The titers of anti-nicotine IgG and anti-KLH IgG in mice sera from days 13, 28, and 35 were measured using ELISA. *** means that P-value is less than 0.001.

Each group of five mice were injected with PBS buffer (negative control), NanoNiccine 2.5, NanoNiccine 5.0, NanoNiccine 12.5, and NanoNiccine 20.0 on day 0 and day 14, respectively. Nicotine-specific IgG titers from the sera on days −2, 13, 28, and 35 were measured. No anti-nicotine IgG or anti-KLH IgG was detected in the sera before immunization. In addition, neither anti-nicotine IgG nor anti-KLH IgG was detected in the mice treated with PBS buffer at any time point. As shown in FIG. 99A, different levels of anti-nicotine antibody titer were produced by NanoNiccines with varying epitope densities. On day 13, NanoNiccine 2.5, NanoNiccine 5.0, NanoNiccine 12.5, and NanoNiccine 20.0 induced anti-nicotine IgG titers of 864±221, 3085±438, 2920±133, and 3158±379, respectively. Two weeks after the booster injection, NanoNiccine 20.0 achieved a titer of 24872±3103, which was significantly higher than 1935±368, 4865±1292, and 3918±853 that were induced by NanoNiccine 2.5, NanoNiccine 5.0, and NanoNiccine 12.5, respectively. On day 35, anti-nicotine IgG titers in the mice immunized with NanoNiccine 2.5, NanoNiccine 5.0, NanoNiccine 12.5, and NanoNiccine 20.0 rose to 7459±1184, 8874±1085, and 6316±864, and 36945±5793, respectively.

Figure 99B:
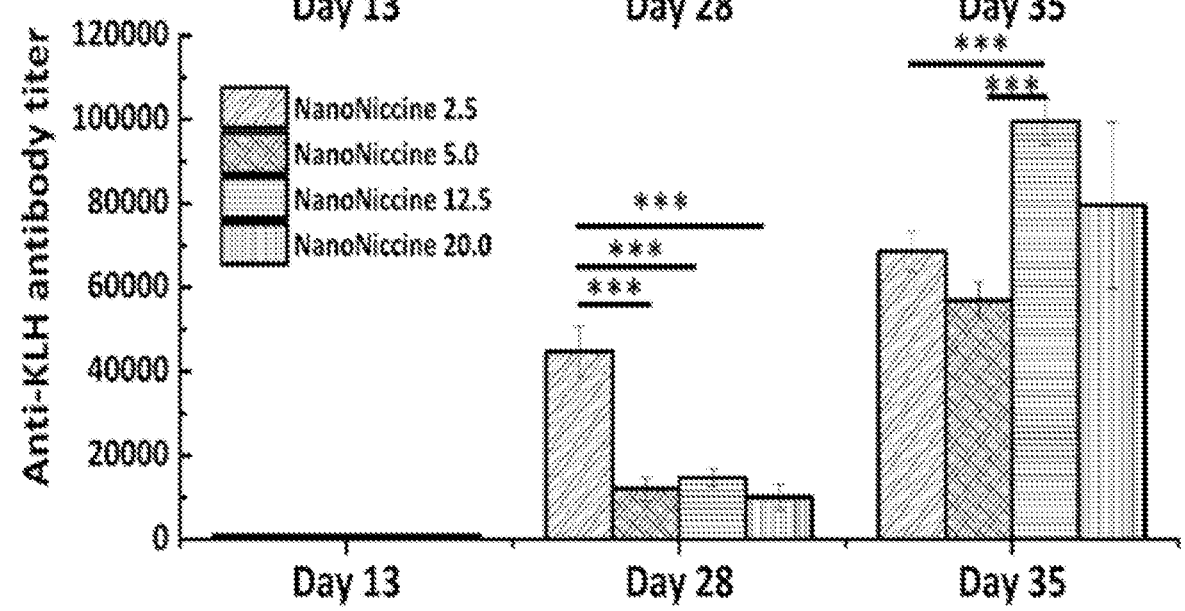

The titers of IgG against KLH were also measured (FIG. 99B). On day 13, the titers of anti-KLH IgG were 1070±286, 1044±195, 1054±204, and 1002±172 for NanoNiccine 2.5, NanoNiccine 5.0, NanoNiccine 12.5, and NanoNiccine 20.0, respectively. 14 days after the booster injection (day 28), anti-KLH antibody titers remarkably increased to 44681±6010, 12123±2705, 14715±2147, and 10082±2982 in the mice immunized with NanoNiccine 2.5, NanoNiccine 5.0, NanoNiccine 12.5, and NanoNiccine 20.0, respectively. NanoNiccine 2.5 produced a significantly higher titer of anti-KLH in the mice than those the other NanoNiccines on day 28. Increased levels of anti-KLH antibody were observed on day 35 for all the vaccine groups, in which NanoNiccine 2.5 group increased to 68586±4751, NanoNiccine 5.0 group increased to 56849±4505, NanoNiccine 12.5 group increased to 99512±5423, and NanoNiccine 20.0 group increased to 79567±19837. Unexpectedly, anti-KLH IgG titer was significantly higher in NanoNiccine 12.5 group than those in either NanoNiccine 5.0 group or NanoNiccine 20.0 group.

Brain Nicotine Concentrations in Mice

Figure 100:
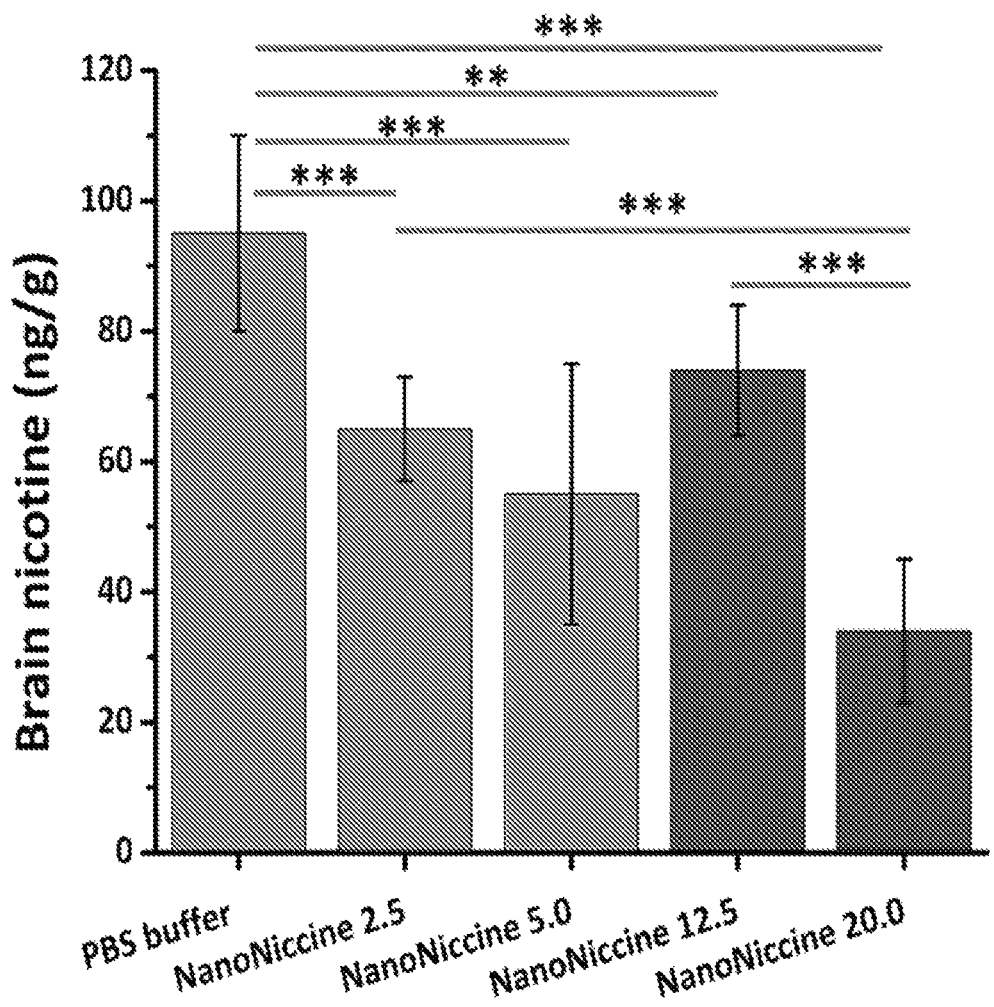
FIG. 100 shows a graph demonstrating brain nicotine concentrations. The mice that received either PBS buffer or NanoNiccines on day 0 and day 14 were subcutaneously injected with 0.06 mg/kg nicotine on day 37, and the brain nicotine concentrations were analyzed.  means P-value is less than 0.05 and * means P-value is less than 0.001.
Figures 101A, 101B, 101C, 101D, 101E:
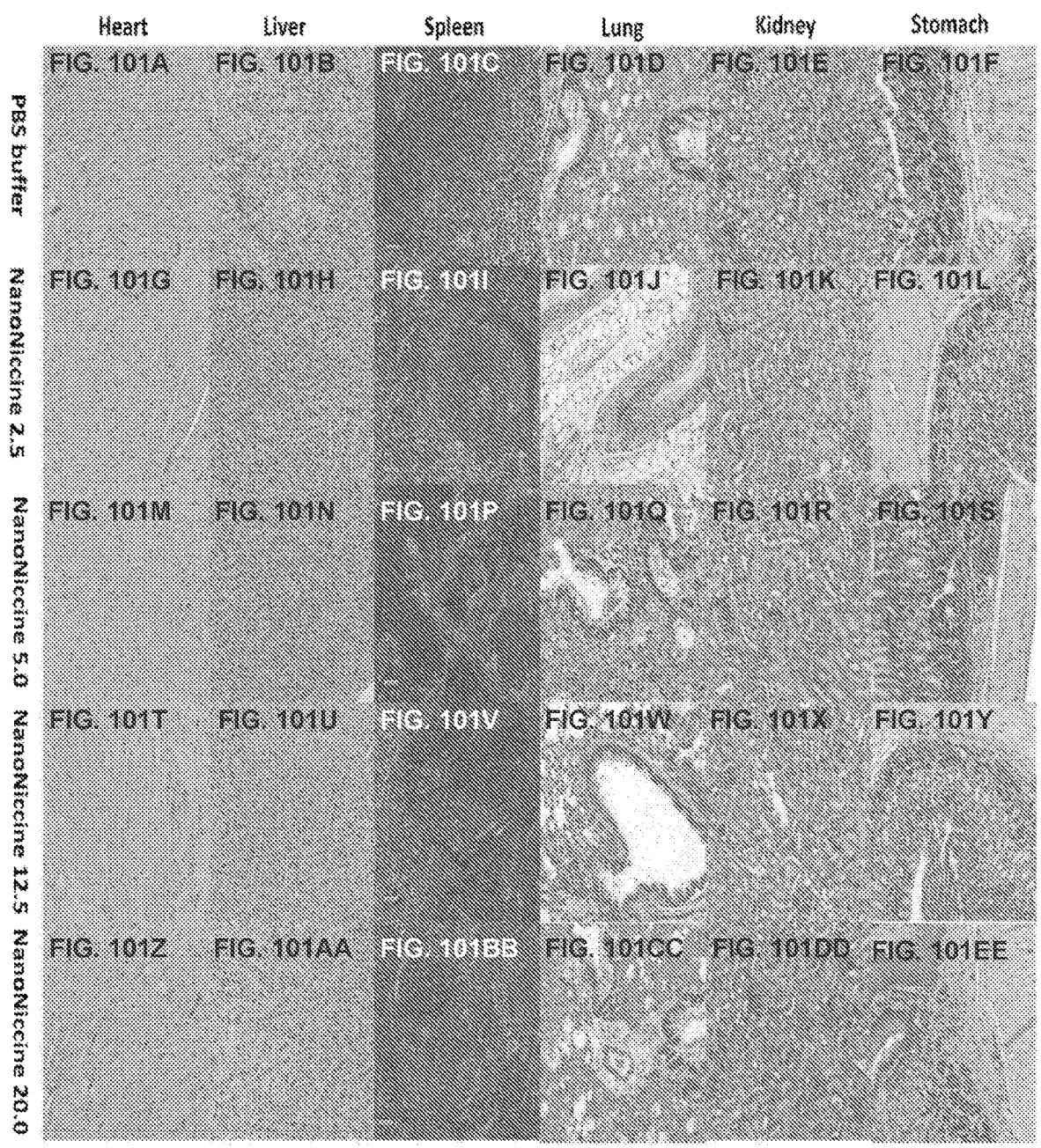
FIGS. 101A-101EE show images of H&E staining of the sections of the main organs from the mice. The mice received either PBS buffer or NanoNiccines were sacrificed on day 37, and their main organs, including heart, liver, spleen, lung, kidney, and stomach were harvested for vaccine toxicity study. Scale bars represent 200 µm.

The mice that were treated with PBS buffer or NanoNiccines were subcutaneously administered with 0.06 mg/kg nicotine on day 37. And 4 mins post nicotine injection, the mice were sacrificed and their brain tissues were harvested for analyzing the brain nicotine concentration. As shown in FIG. 100, immunization with NanoNiccines regardless of the epitope densities resulted in a significantly lower brain nicotine concentration in the mice than that in the negative control. The negative control group had a brain nicotine concentration as high as 95±15 ng/g. In contrast, the mice immunized with NanoNiccine 2.5, NanoNiccine 5.0, NanoNiccine 12.5, and NanoNiccine 20.0 had a brain nicotine concentration of 65±8 ng/g, 55±20 ng/g, 74±10 ng/g, and 34±11 ng/g, respectively. It was also observed that the brain nicotine level was related with the epitope density. It appears that NanoNiccine with a denser epitope tended to result in a lower brain nicotine concentration. However, the mean brain nicotine concentration in the mice treated with NanoNiccine 12.5 was higher than that from either NanoNiccine 5.0 group or NanoNiccine 20.0 group.

Histopathology

On day 37, the mice treated with either PBS buffer or NanoNiccines were sacrificed. The main organs, including heart, liver, spleen, lung, kidney, and stomach, were harvested for toxicity study. As shown in FIGS. 101A-101EE, no abnormality in the major organs was detected in the mice received NanoNiccines as compared to those from the mice treated with PBS buffer.

Discussion

Due to the severe loss in life and economy caused by tobacco smoking, researchers have been actively developing therapies for smoking cessation. Currently, the most widely used medications are pharmacotherapies [37-39], including nicotine replacement therapy, varenicline, and bupropion. Although, these therapies proved somewhat effective in facilitating smoking cessation, the overall efficacy is limited [40]. In addition, some safety issues are associated with these therapies [38, 39, 41]. Therefore, it is necessary and urgent to invent safer and more efficacious therapies against tobacco use.

Nicotine vaccine, which can induce production of nicotine-specific antibodies in human body, has proven promising in promoting smoking cessation [6]. In a previous study, a lipid-PLGA hybrid nanoparticle based nicotine vaccine (NanoNiccine) was invented in our group [9]. NanoNiccine demonstrated good safety and potent immunogenicity in mice. Since NanoNiccine is still in its early design, there is plenty of room to improve its efficacy. Among the factors that govern the efficacy of a nicotine vaccine, immunogenicity is of vital importance [24, 42]. It is possible to improve the immunogenicity of NanoNiccine by optimizing the nicotine epitope density [32], by co-delivering different types of molecular adjuvants, such as CpG ODNs [43], MPLA [44], by optimizing the vaccine particle size [30], by introducing specific ligands [45], such as monoclonal antibodies, that target receptors on immune cells for more specific and effective cell-vaccine interaction, etc. The structure of NanoNiccine mimics those of viruses to induce immune response in human. More often than not, virus carries highly repetitive molecular structures on their particle surface [46] and the immune system can efficiently respond to these structures. In NanoNiccine, it is the nicotine epitope that serves as the repetitive structure. Therefore, it might be possible to improve the immunogenicity of NanoNiccine by optimizing the density of nicotine epitope on its surface.

In this study, the nicotine epitope density was modulated by adjusting the quantity of DSPE-PEG(2000)COOH in the lipid layer. The PEG molecules in the hybrid nanoparticle could play as a shield between the nanoparticle and harsh physiological environment to minimize nanoparticle degradation during circulation [47]. However, PEG may exert steric hindrance to the interaction between nanoparticles and immune cells [48, 49]. As observed in a previous study [19], a higher degree of PEGylation resulted in a lower rate of cellular uptake. Therefore, increasing the quantity of DSPE-PEG(2000)COOH for a higher nicotine epitope density may not necessarily improve the immunogenicity of NanoNiccine. The stability of the hybrid structure in NanoNiccine is critical to its immunogenicity [9]. It was reported that high concentration of the PEG molecules caused instability in liposomes [50, 51]. Therefore, it has to be sure that increasing the concentration of DSPE-PEG(2000)COOH in the lipid layer does not undermine the stability of the hybrid structure. In this study, the results showed that Hybrid 30.0 with 30% DSPE-PEG(2000)COOH in the lipid layer failed to form a stable core-shell hybrid structure, suggesting that the degree of PEGylation in the lipid layer had an upper limit. In contrast, the liposomes with PEGylation of 2.5%, 5.0%, 12.5%, and 20% were able to form a hybrid structure with the PLGA nanoparticles. The particle sizes of Hybrid 2.5, Hybrid 5.0, Hybrid 12.5, and Hybrid 20.0 were slightly bigger (less than 10 nm) than that of the PLGA nanoparticle. This difference in size was caused by the thickness of the lipid shell [35]. The highly linear surface charges on Hybrid 2.5, Hybrid 5.0, and Hybrid 12.5 suggested that DSPE-PEG (2000)COOH with a negatively charged carboxylic group existed in the hybrid nanoparticles with linear concentrations.

As mentioned above, PEGylating hybrid nanoparticles might hinder the interaction between immune cells and the hybrid nanoparticles. Indeed, the increase in the degree of PEGylation negatively affected the cellular uptake of the newly-made hybrid nanoparticles in this study. However, it is also worth noting that the differences in the quantities of the internalized hybrid nanoparticles by the dendritic cells were decreasing with time. Although high degree of PEGylation hindered cellular uptake of the newly-assembled nanoparticles, it appeared to facilitate uptake of the stored hybrid nanoparticles. As found before, hybrid nanoparticle aggregated with each other to form bigger particles during storage, leading to a slowed cellular uptake [19]. In this study, the hybrid nanoparticles with more PEGs in the lipid layer had a smaller size increase after storage. It is likely that a higher concentration of DSPE-PEG(2000)COOH in the hybrid nanoparticles could more effectively limit the contact between the particles, thereby reducing the particle aggregation.

NanoNiccine was assembled by conjugating the nicotine epitope to the surface of the hybrid nanoparticles. The similar sizes of the different NanoNiccines suggested that the assembly process had a minimal impact on the particle size. Like the hybrid nanoparticles, the surface charge of NanoNiccine decreased with the increasing degree of PEGylation. It was found that the net negative charge on hybrid nanoparticles might cause electrostatic repulsion with the negative charge on the membrane of the immune cells, leading to a slowed cellular uptake [20]. Therefore, NanoNiccine with a higher nicotine epitope density may be disadvantageous in the interaction with immune cells as compared to those with lower nicotine epitope densities.

However, the antibody titer induced by NanoNiccines demonstrated that NanoNiccine 20.0 with the highest nicotine epitope density induced a significantly higher anti-nicotine antibody titer than the others' after the booster injection. Given the disadvantageous surface properties of NanoNiccine 20.0, its high nicotine epitope density was likely to be responsible for its stronger immunogenicity. It is well known that uptake of antigen by B cells is mediated by the cognate binding of the epitopes on an antigen to the B cell receptors [52]. The higher nicotine epitope density on NanoNiccine 20.0 may enable more efficient uptake of NanoNiccine 20.0 than the others with lower nicotine epitope densities. In addition, part of the intracellular signals for B cell activation is generated by the crosslinking of B cell receptors with epitopes of an antigen [53, 54]. A denser epitope on NanoNiccine may allow more extensive and effective B cell receptor crosslinking to produce stronger signals for B cell activation.

Interestingly, the comparison of the immunogenicity of NanoNiccine 2.5, NanoNiccine 5.0, and NanoNiccine 12.5 was complicated. On day 13, NanoNiccine 5.0 and NanoNiccine 12.5 produced similar levels of anti-nicotine antibody titer, which was significantly higher than that of NanoNiccine 2.5. However, on day 35, the anti-nicotine antibody titer induced by NanoNiccine 12.5 was lower in than those by either NanoNiccine 2.5 or NanoNiccine 5.0. This phenomenon might be an outcome of the competing effects of multiple factors, including the surface charge, the physical hindrance caused by the PEG, and the epitope density that might affect the particle uptake and B cell activation. It was possible that after the primary immunization, the low nicotine density on NanoNiccine 2.5 caused inefficient activation of B cells, which led to its lower titer of anti-nicotine IgG. However, electrostatic repulsion and physical hindrance caused by its high PEG density might limit the immunogenicity of NanoNiccine 12.5 after the booster injection. But for NanoNiccine 20.0, the favorable effect provided by the high epitope density always outweighed the negative effect exerted by the negative surface charge and PEG caused physical hindrance.

As discussed in a previous study [9], one of the important features of NanoNiccine was that it could minimize the production of antibody against T-cell antigen, improving its specificity. In agreement with the previous results, the levels of anti-KLH antibody generated by NanoNiccines were minimal after the primary injection. The increase in the titer of anti-KLH antibody after the booster injection might be caused by the released KLH from NanoNiccine particles, which degraded after long-term circulation. It is interesting that the level of anti-KLH antibody was inversely correlated to the level of anti-nicotine antibody. It was likely that the NanoNiccine particles that induced a lower level of anti-nicotine antibody could not be efficiently captured by the immune cells and eventually released the enclosed KLH after degradation, resulting in the increased level of anti-KLH antibody.

Nicotine in tobacco is widely considered the primary substance that is responsible for smoking addition [55]. The treatment efficacy of a nicotine vaccine is largely influenced by its ability to reduce the quantity of nicotine that enters into the brain [5, 56]. The significantly lower quantity of nicotine in the brain of the immunized mice as compared to that in the negative control demonstrated that NanoNiccine regardless of the epitope density could effectively block the entry of nicotine into the brain. In addition, the ability of NanoNiccine to reduce the brain nicotine concentration was highly consistent with their capability in producing anti-nicotine antibodies. The mice with a lower titer of anti-nicotine antibody had a higher nicotine concentration in the brain. Such a correlation between the antibody titer and the nicotine pharmacokinetics was also widely observed in other studies [34, 56]. Generally, a higher nicotine epitope density in NanoNiccine resulted in a lower brain nicotine concentration. However, NanoNiccine 12.5, which blocked less nicotine outside the brain than that by NanoNiccine 2.5 and NanoNiccine 5.0, was an "abnormality". The weaker ability of NanoNiccine 12.5 to reduce the brain nicotine level was accurately predicted by its lower anti-nicotine antibody level in the blood. Therefore, the choice of nicotine epitope density is not simply a matter of "the higher the better" or "the lower the better". It requires a careful consideration of the overall influence of the epitope density on the hybrid structural integrity, physicochemical properties, interaction with the immune cells, etc.

Safety is always the top priority when developing a vaccine. All the components of NanoNiccine, including the nicotine epitope [57], lipids [58], PLGA [59], KLH [60], and CpG ODN [15], were either approved by the FDA for pharmaceutical use or tested with good safety in clinical trials. Results from previous studies also showed that NanoNiccine did not cause any detectable toxicity to the immunized mice [9]. According to the histopathological results, no aberrant changes were observed in the major organs of the immunized mice. These results indicated that NanoNiccine did not cause toxicity to mice and was safe to use.

Conclusion

In summary, the lipid-PLGA hybrid nanoparticles with 2.5%, 5.0%, 12.5%, 20.0%, and 30% PEGylation were constructed. The hybrid nanoparticle with 30% PEGylation failed to form a stable hybrid structure. In addition, dendritic cells internalized the newly-made hybrid nanoparticle with a lower PEGylation more rapidly than that with a higher PEGylation. However, hybrid nanoparticle with more PEGs in the lipid layer could more effectively reduce aggregation than those with less PEGs during storage. NanoNiccines with varying nicotine epitope densities were assembled by decorating the nicotine epitope onto the surface of the hybrid nanoparticles. The highest anti-nicotine antibody titer was achieved in the mice immunized with NanoNiccine 20.0 that had a 20% PEGylation in its lipid layer. In addition, the lowest brain nicotine concentration was also detected in the NanoNiccine 20.0-immunized mice, suggesting that 20% PEGylation was optimal for the immunogenicity of NanoNiccine. Lastly, no safety issues were detected in the mice immunized with any of the NanoNiccine formulations.

REFERENCES FOR EXAMPLE 6

[1] A. Jamal, I. T. Agaku, E. O'Connor, B. A. King, J. B. Kenemer, L. Neff. Current cigarette smoking among adults—United States, 2005-2013. MMWR Morb. Mortal. Wkly. Rep., 63 (2014), pp. 1108-12.

[2] The Health Consequences of Smoking-50 Years of Progress: A Report of the Surgeon General. Atlanta (Ga.) 2014.

[3] M. R. Picciotto, P. J. Kenny. Molecular mechanisms underlying behaviors related to nicotine addiction. Cold Spring Harb. Perspect. Med., 3 (2013), pp. a012112.

[4] K. Cahill, S. Stevens, T. Lancaster. Pharmacological treatments for smoking cessation. JAMA, 311 (2014), pp. 193-4.

[5] P. Skolnick. Biologic Approaches to Treat Substance-Use Disorders. Trends Pharmacol. Sci., 36 (2015), pp. 628-35.

[6] T. Raupach, P. H. Hoogsteder, C. P. Onno van Schayck. Nicotine vaccines to assist with smoking cessation: current status of research. Drugs, 72 (2012), pp. e1-16.

[7] O. C. van Schayck, K. Horstman, E. Vuurman, G. de Wert, D. Kotz. Nicotine vaccination—does it have a future? Addiction, 109 (2014), pp. 1223-5.

[8] B. Kinsey. Vaccines against drugs of abuse: where are we now? Ther. Adv. Vaccines, 2 (2014), pp. 106-17.

[9] Y. Hu, D. Smith, E. Frazier, R. Hoerle, M. Ehrich, C. Zhang. The next-generation nicotine vaccine: a novel and potent hybrid nanoparticle-based nicotine vaccine. Biomaterials, 106 (2016), pp. 228-39.

[10] J. R. Harris, J. Markl. Keyhole limpet hemocyanin (KLH): a biomedical review. Micron, 30 (1999), pp. 597-623.

[11] K. Lockyer, F. Gao, J. P. Derrick, B. Bolgiano. Structural correlates of carrier protein recognition in tetanus toxoid-conjugated bacterial polysaccharide vaccines. Vaccine, 33 (2015), pp. 1345-52.

[12] H. R. Shinefield. Overview of the development and current use of CRM(197) conjugate vaccines for pediatric use. Vaccine, 28 (2010), pp. 4335-9.

[13] M. Broker, P. Costantino, L. DeTora, E. D. McIntosh, R. Rappuoli. Biochemical and biological characteristics of cross-reacting material 197 CRM197, a non-toxic mutant of diphtheria toxin: use as a conjugation protein in vaccines and other potential clinical applications. Biologicals, 39 (2011), pp. 195-204.

[14] J. P. Pradere, D. H. Dapito, R. F. Schwabe. The Yin and Yang of Toll-like receptors in cancer. Oncogene, 33 (2014), pp. 3485-95.

[15] M.F. Sanchez Vallecillo, G. V. Ullio Gamboa, S. D. Palma, M.F. Harman, A. L. Chiodetti, G. Moron, et al. Adjuvant activity of CpG-ODN formulated as a liquid crystal. Biomaterials, 35 (2014), pp. 2529-42.

[16] H. Zheng, Y. Hu, W. Huang, S. de Villiers, P. Pentel, J. Zhang, et al. Negatively Charged Carbon Nanohorn Supported Cationic Liposome Nanoparticles: A Novel Delivery Vehicle for Anti-Nicotine Vaccine. J. Biomed. Nanotechnol., 11 (2015), pp. 2197-210.

[17] H. P. Patil, S. Murugappan, W. ter Veer, T. Meijerhof, A. de Haan, H. W. Frijlink, et al. Evaluation of monophosphoryl lipid A as adjuvant for pulmonary delivered influenza vaccine. J. Control. Release, 174 (2014), pp. 51-62.

[18] A. L. Siefert, M. J. Caplan, T. M. Fahmy. Artificial bacterial biomimetic nanoparticles synergize pathogen-associated molecular patterns for vaccine efficacy. Biomaterials, 97 (2016), pp. 85-96.

[19] Y. Hu, R. Hoerle, M. Ehrich, C. Zhang. Engineering the lipid layer of lipid-PLGA hybrid nanoparticles for enhanced in vitro cellular uptake and improved stability. Acta Biomater., 28 (2015), pp. 149-59.

[20] Y. Hu, M. Ehrich, K. Fuhrman, C. Zhang. In vitro performance of lipid-PLGA hybrid nanoparticles as an antigen delivery system:lipid composition matters. Nanoscale Res. Lett., 9 (2014), pp. 434.

[21] Y. Hu, H. Zheng, W. Huang, C. Zhang. A novel and efficient nicotine vaccine using nano-lipoplex as a delivery vehicle. Hum. Vaccin. Immunother., 10 (2014), pp. 64-72.

[22] D. K. Hatsukami, S. Rennard, D. Jorenby, M. Fiore, J. Koopmeiners, A. de Vos, et al. Safety and immunogenicity of a nicotine conjugate vaccine in current smokers. Clin. Pharmacol. Ther., 78 (2005), pp. 456-67.

[23] D. E. Keyler, S. A. Roiko, C. A. Earley, M. P. Murtaugh, P. R. Pentel. Enhanced immunogenicity of a bivalent nicotine vaccine. Int. Immunopharmacol., 8 (2008), pp. 1589-94.

[24] P. R. Pentel, M. G. LeSage. New directions in nicotine vaccine design and use. Adv. Pharmacol., 69 (2014), pp. 553-80.

[25] J. Cornuz, S. Zwahlen, W. F. Jungi, J. Osterwalder, K. Klingler, G. van Melle, et al. A vaccine against nicotine for smoking cessation: a randomized controlled trial. PLoS One 3 (2008), pp. e2547.

[26] Y. Hieda, D. E. Keyler, S. Ennifar, A. Fattom, P. R. Pentel. Vaccination against nicotine during continued nicotine administration in rats: immunogenicity of the vaccine and effects on nicotine distribution to brain. Int. J. Immunopharmacol., 22 (2000), pp. 809-19.

[27] M. J. McCluskie, J. Thorn, D. P. Gervais, D. R. Stead, N. Zhang, M. Benoit, et al. Anti-nicotine vaccines: Comparison of adjuvanted CRM197 and Qb-VLP conjugate formulations for immunogenicity and function in non-human primates. Int. Immunopharmacol., 29 (2015), pp. 663-71.

[28] S. H. de Villiers, N. Lindblom, G. Kalayanov, S. Gordon, I. Baraznenok, A. Malmerfelt, et al. Nicotine hapten structure, antibody selectivity and effect relationships: results from a nicotine vaccine screening procedure. Vaccine, 28 (2010), pp. 2161-8.

[29] M. J. McCluskie, D. C. Pryde, D. P. Gervais, D. R. Stead, N. Zhang, M. Benoit, et al. Enhancing immunogenicity of a 3' aminomethylnicotine-DT-conjugate anti-nicotine vaccine with CpG adjuvant in mice and non-human primates. Int. Immunopharmacol., 16 (2013), pp. 50-6.

[30] V. B. Joshi, S. M. Geary, A. K. Salem. Biodegradable particles as vaccine delivery systems: size matters. AAPS J., 15 (2013), pp. 85-94.

[31] S. Thrane, C. M. Janitzek, S. Matondo, M. Resende, T. Gustaysson, W. A. de Jongh, et al. Bacterial superglue enables easy development of efficient virus-like particle based vaccines. J. Nanobiotechnology, 14 (2016), pp. 30.

[32] W. Liu, Y. H. Chen. High epitope density in a single protein molecule significantly enhances antigenicity as well as immunogenicity: a novel strategy for modern vaccine development and a preliminary investigation about B cell discrimination of monomeric proteins. Eur. J. Immunol., 35 (2005), pp. 505-14.

[33] I. Kim, H. J. Byeon, T. H. Kim, E. S. Lee, K. T. Oh, B. S. Shin, et al. Doxorubicin-loaded porous PLGA microparticles with surface attached TRAIL for the inhalation treatment of metastatic lung cancer. Biomaterials, 34 (2013), pp. 6444-53.

[34] S. H. de Villiers, K. E. Cornish, A. J. Troska, M. Pravetoni, P. R. Pentel. Increased efficacy of a trivalent nicotine vaccine compared to a dose-matched monovalent vaccine when formulated with alum. Vaccine, 31 (2013), pp. 6185-93.

[35] L. Zhang, J. M. Chan, F. X. Gu, J. W. Rhee, A. Z. Wang, A. F. Radovic-Moreno, et al. Self-assembled lipid—polymer hybrid nanoparticles: a robust drug delivery platform. ACS Nano, 2 (2008), pp. 1696-702.

[36] Y. Hu, Z. Zhao, M. Ehrich, K. Fuhrman, C. Zhang. In vitro controlled release of antigen in dendritic cells using pH-sensitive liposome-polymeric hybrid nanoparticles. Polymer (Guildf), 80 (2015), pp. 171-9.

[37] L. F. Stead, R. Perera, C. Bullen, D. Mant, J. Hartmann-Boyce, K. Cahill, et al. Nicotine replacement therapy for smoking cessation. Cochrane Database Syst. Rev., 11 (2012), pp. CD000146.

[38] K. Cahill, L. F. Stead, T. Lancaster. Nicotine receptor partial agonists for smoking cessation. Cochrane Database Syst. Rev., (2010), pp. CD006103.

[39] J. Hughes, L. Stead, T. Lancaster. Antidepressants for smoking cessation. Cochrane Database Syst. Rev., (2004), pp. CD000031.

[40] T. Raupach, C. P. van Schayck. Pharmacotherapy for smoking cessation: current advances and research topics. CNS Drugs, 25 (2011), pp. 371-82.

[41] E. J. Mills, P. Wu, I. Lockhart, K. Wilson, J. O. Ebbert. Adverse events associated with nicotine replacement therapy (NRT) for smoking cessation. A systematic review and meta-analysis of one hundred and twenty studies involving 177,390 individuals. Tob. Induc. Dis., 8 (2010), pp. 8.

[42] R. E. Fahim, P. D. Kessler, M. W. Kalnik. Therapeutic vaccines against tobacco addiction. Expert Rev. Vaccines, 12 (2013), pp. 333-42.

[43] M. Gursel, I. Gursel. Development of CpG ODN Based Vaccine Adjuvant Formulations. Methods Mol. Biol., 1404 (2016), pp. 289-98.

[44] G. R. Matyas, A. V. Mayorov, K. C. Rice, A. E. Jacobson, K. Cheng, M. R. Iyer, et al. Liposomes containing monophosphoryl lipid A: a potent adjuvant system for inducing antibodies to heroin hapten analogs. Vaccine, 31 (2013), pp. 2804-10.

[45] I. Caminschi, K. Shortman. Boosting antibody responses by targeting antigens to dendritic cells. Trends Immunol., 33 (2012), pp. 71-7.

[46] M. F. Bachmann, R. M. Zinkernagel. The influence of virus structure on antibody responses and virus serotype formation. Immunol. Today, 17 (1996), pp. 553-8.

[47] N. J. Butcher, G. M. Mortimer, R. F. Minchin. Drug delivery: Unravelling the stealth effect. Nat. Nanotechnol., 11 (2016), pp. 310-1.

[48] H. Yang, J. J. Morris, S. T. Lopina. Polyethylene glycol-polyamidoamine dendritic micelle as solubility enhancer and the effect of the length of polyethylene glycol arms on the solubility of pyrene in water. J. Colloid. Interface Sci., 273 (2004), pp. 148-54.

[49] S. Moffatt, R. J. Cristiano. Uptake characteristics of NGR-coupled stealth PEI/pDNA nanoparticles loaded with PLGA-PEG-PLGA tri-block copolymer for targeted delivery to human monocyte-derived dendritic cells. Int. J. Pharm., 321 (2006), pp. 143-54.

[50] O. Garbuzenko, Y. Barenholz, A. Priev. Effect of grafted PEG on liposome size and on compressibility and packing of lipid bilayer. Chem. Phys. Lipids, 135 (2005), pp. 117-29.

[51] S. Sriwongsitanont, M. Ueno. Physicochemical properties of PEG-grafted liposomes. Chem. Pharm. Bull. (Tokyo), 50 (2002), pp. 1238-44.

[52] A. M. Avalos, H. L. Ploegh. Early BCR Events and Antigen Capture, Processing, and Loading on MHC Class II on B Cells. Front. Immunol., 5 (2014), pp. 92.

[53] J. M. Dal Porto, S. B. Gauld, K. T. Merrell, D. Mills, A. E. Pugh-Bernard, J. Cambier. B cell antigen receptor signaling 101. Mol. Immunol., 41 (2004), pp. 599-613.

[54] M. Reth, J. Wienands. Initiation and processing of signals from the B cell antigen receptor. Annu. Rev. Immunol., 15 (1997), pp. 453-79.

[55] N. L. Benowitz, J. E. Henningfield. Reducing the nicotine content to make cigarettes less addictive. Tob. Control., 22 Suppl 1 (2013), pp. i14-7.
[56] M. J. McCluskie, J. Thorn, P. R. Mehelic, P. Kolhe, K. Bhattacharya, J. I. Finneman, et al. Molecular attributes of conjugate antigen influence function of antibodies induced by anti-nicotine vaccine in mice and non-human primates. Int. Immunopharmacol., 25 (2015), pp. 518-27.
[57] P. H. Hoogsteder, D. Kotz, P. I. van Spiegel, W. Viechtbauer, O. C. van Schayck. Efficacy of the nicotine vaccine 3'-AmNic-rEPA (NicVAX) co-administered with varenicline and counselling for smoking cessation: a randomized placebo-controlled trial. Addiction, 109 (2014), pp. 1252-9.
[58] D. Simberg, S. Weisman, Y. Talmon, Y. Barenholz. DOTAP (and other cationic lipids): chemistry, biophysics, and transfection. Crit Rev Ther. Drug Carrier. Syst., 21 (2004), pp. 257-317.
[59] F. Danhier, E. Ansorena, J. M. Silva, R. Coco, A. Le Breton, V. Preat. PLGA-based nanoparticles: an overview of biomedical applications. J. Control. Release, 161 (2012), pp. 505-22.
[60] D. Tuse, N. Ku, M. Bendandi, C. Becerra, R. Collins, Jr., N. Langford, et al. Clinical Safety and Immunogenicity of Tumor-Targeted, Plant-Made Id-KLH Conjugate Vaccines for Follicular Lymphoma. Biomed. Res. Int., 2015 (2015), pp. 648143.

Example 7

Introduction

Nicotine vaccines that can induce nicotine-specific antibody production in human and prevent the entry of nicotine into the brain, has been widely considered a promising therapy for smoking cessation [1-3]. Traditionally, nicotine vaccines are prepared by conjugating nicotine epitopes to various carrier proteins [4]. However, due to the fact that peptide sequences on the carrier proteins may also be targeted by the immune system, these vaccines may generate antibodies against the carrier proteins [5, 6]. This may not only lower the specificity of the immune response, but may also waste the vaccine for producing irrelevant antibodies. To overcome these defects, a lipid-poly(lactic-co-glycolic acid) (PLGA) hybrid nanoparticle-based nicotine vaccine (NanoNiccine) was generated [7]. This vaccine exhibited an improved immunogenicity and specificity as compared to those of the traditional nicotine-keyhole limpet hemocyanin (Nic-KLH) conjugate vaccines. It is well accepted that the concentration of nicotine-specific antibody in the blood is one of the key factors that govern the efficacy of a nicotine vaccine [8, 9]. Higher anti-nicotine antibody concentrations were often associated with lower nicotine levels in the brain [10, 11]. Therefore, the immunological efficacy of NanoNiccine may be improved by enhancing its immunogenicity.

Traditionally, the immunogenicity of a vaccine can be promoted by introducing proper adjuvants [12]. Due to its strong immune-potentiating effect and good safety record, aluminum salts (Alum) have been used for more than 70 years and until recently represented the only adjuvant approved in the United States [13]. Although the mechanisms underlying the immune-promoting effect of Alum are not well elucidated, it has been proposed that adsorption of antigen onto Alum could increase their uptake and stability at the site of injection [14]. In addition, it is believed that Alum is an effective adjuvant because it enable antigens to remain in the body for a period of long time, which results in a prolonged and effective stimulation to the immune system [15, 16]. The adjuvanticity of Alum may also come from its ability to induce a local pro-inflammatory reaction [13, 17, 18]. Alum has been reported to potently enhance the immunogenicity of a wide range of soluble antigens, including hepatitis B surface antigen [19], anthrax recombinant protective antigen [20], recombinant *Streptococcus pneumoniae* antigen [21], etc. Although nanoparticle-based vaccines have been extensively studied [22-24], the adjuvanticity of Alum on these vaccines is scarcely reported.

Because Alum is capable of triggering profoundly polarized antibody response [25] and the efficacy of a nicotine vaccine is largely dictated by the concentration of anti-nicotine antibody that it can induce [26], Alum has been commonly used as the adjuvant of choice in many traditional nicotine-protein conjugate vaccines [27, 28]. Indeed, Alum tremendously promoted the immunogenicity of these vaccines. It is possible that Alum can also serve as an adjuvant for improving the immunological performance of NanoNiccine.

In this Example, the influence of Alum on the immunogenicity of NanoNiccine as well as its ability to prevent the entry of nicotine into the brain in mice.

Materials and Methods

Materials

Lactel® 50:50 PLGA was purchased from Durect Corporation (Cupertino, Calif.). Fetal bovine serum (FBS), granulocyte macrophage-colony stimulating factor (GM-CSF) recombinant mouse protein, alpha minimum essential medium, and trypsin/EDTA were purchased from Life Technologies Corporation (Grand Island, N.Y.). The anti-mouse IgG from goat and anti-goat IgG-HRP were procured from Alpha Diagnostic Intl (San Antonio, Tex.). TMB one component microwell substrate was procured from SouthernBiotech (Birmingham, Ala.). Lipids, including monophosphoryl lipid A (MPLA), 1,2-dioleoyl-3-trimethylammonium-propane (DOTAP), 1,2-distearoyl-sn-glycero-3-phosphoethanolamine-N-[amino(polyethylene glycol)-2000] (ammonium salt) (DSPE-PEG(2000) amine), cholesterol and 1,2-diphytanoyl-sn-glycero-3-phosphoethanolamine-N-(7-nitro-2-1,3-benzoxadiazol-4-yl) (ammonium salt) (NBD PE) were purchased from Avanti Polar Lipids, Inc. (Alabaster, Ala.). Poly(vinyl alcohol) (PVA), dichloromethane (DCM), and bovine serum albumin (BSA) were purchased from Sigma-Aldrich Inc. (Saint Louis, Mo.). Alexa Fluor® 647 hydrazide, KLH, 1-ethyl-3-[3-dimethylaminopropyl] carbodiimide hydrochloride (EDC), and sulfo-NHS were purchased from Thermo Fisher Scientific Inc. (Rockford, Ill.). Alhydrogel® adjuvant was purchased from InvivoGen (San Diego, Calif.). JAWSII (ATCC® CRL-11904™) immature dendritic cells were purchased from ATCC (Manassas, Va.). 6-carboxymethylureido nicotine (CMUNic) was obtained as a gift, other chemicals were of analytical grade.

Fabrication of KLH-Containing PLGA Nanoparticles

PLGA nanoparticles that contained KLH were prepared according to a previously reported method with minor modifications [7, 29]. Briefly, PLGA (40 mg) was dissolved in DCM (1 mL), followed by mixing with 60 μL of KLH (20 mg/mL) for 5 min using a vortex mixer. The resultant mixture was emulsified in a Branson B1510DTH Ultrasonic Cleaner (Branson, Danbury, Conn.) for 5 min. The primary emulsion was added drop-wise into 14 mL PVA (0.5% (w/v)), and continuously stirred for 2 min at 500 rpm. The above suspension was emulsified by sonication using a sonic dismembrator (Model 500; Fisher Scientific, Pittsburgh, Pa.) at 70% amplitude for 30 s. The secondary emulsion was stirred overnight to allow DCM to evaporate. Nanoparticles in the suspension were collected by centrifugation at 10,000 g, 4° C. for 60 min using an Eppendorf centrifuge (Eppendorf, Hauppauge, N.Y.). The pellet was suspended in 10 mL phosphate buffered saline (PBS) buffer (pH 7.4) and stored at 4° C. until future use.

Assembly of NanoNiccine

NanoNiccine was assembled according to a previously reported method with minor modifications [7]. Briefly, a lipid film containing MPLA (0.45 mg), DOTAP (3.82 mg), DSPE-PEG(2000) amine (4.07 mg), and cholesterol (0.14 mg) was hydrated with 1 mL of 55° C. pre-warmed PBS buffer (pH 7.4). The resulting liposome suspension was vigorously mixed using a vortex mixer for 2 min, followed by sonication for 2 min, using a Branson B1510DTH Ultrasonic Cleaner (Branson, Danbury, Conn.) and then cooled to room temperature. The prepared liposome was added into the above prepared KLH-containing PLGA nanoparticles and pre-homogenized for 10 min using a Branson B1510DTH Ultrasonic Cleaner, followed by sonication for 5 min in an ice bath using a sonic dismembrator at 15% amplitude (pulse on 20 s, pulse off 50 s). The assembled lipid-PLGA nanoparticles were dialyzed against 500 mL coupling buffer (100 mM sodium phosphate, 150 mM NaCl; pH 7.2) for 2 h. EDC (5.6 mg), sulfo-NHS (15.4 mg) and CMUNic (8.5 mg) in 1 mL activation buffer (0.1M MES, 0.5M NaCl, pH 6.0) were incubated for 20 min at room temperature. The activated CMUNic was incubated with the above hybrid nanoparticle suspension at room temperature for 4 h. The remaining impurities were removed by dialysis against 5000 mL PBS buffer (pH 7.4) for 12 h. The synthesized NanoNiccine was stored at 4° C. until future use.

Synthesis of CMUNic-Bovine Serum Albumin (CMUNic-BSA) Conjugate

CMUNic (2 mg), EDC (2 mg), and sulfo-NHS (5.5 mg) in 1 mL activation buffer (0.1M MES, 0.5M NaCl, pH 6.0) were incubated for 20 min at room temperature. The activated CMUnic was incubated with BSA (10 mg) in 5 mL coupling buffer at room temperature for 4 h. The CMUNic-BSA conjugate was dialyzed against 500 mL PBS buffer (pH 7.4) for 12 h at room temperature. The purified CMUNic-BSA conjugate was stored at 4° C. until future use.

Synthesis of Alexa 647-Labeled KLH

Alexa 647-labeled KLH was prepared using a previously reported method with proper modifications [7]. The impurities were removed by dialysis against 2000 mL PBS buffer (pH 7.4) in darkness for 12 h. The purified Alexa 647-KLH conjugate was lyophilized, and stored at 4° C. until future use.

Characterization of Physicochemical Properties of Nanoparticles

The nanoparticles, including liposome, PLGA nanoparticle, and NanoNiccine were diluted ten times in PBS buffer (pH 7.0). The physicochemical properties including particle size (diameter, nm) and surface charge (zeta potential, mV) were measured at room temperature using a Malvern Nano-ZS zetasizer (Malvern Instruments Ltd, Worcestershire, United Kingdom).

Imaging Nanoparticles Using Transmission Electron Microscopy (TEM)

TEM images of nanoparticles were acquired using a method as previously reported with proper modifications [7, 29]. Briefly, nanoparticles were dropped onto a 300-mesh formvar-coated copper grid. After standing for 5 min, the remaining suspension was carefully removed with wipes, and the samples were negatively stained using fresh 1% phosphotungstic acid for 30 s. The dried samples were imaged on a JEOL JEM 1400 transmission electron microscope (JEOL Ltd., Tokyo, Japan).

Imaging Uptake of NanoNiccine by DCs Using CLSM

CLSM images of uptake of NanoNiccine by DCs were captured using a method described before with minor modifications [7]. Briefly, DCs were cultured in a 2 well chamber slide (Thermo Fisher Scientific Inc., Rd, Rockford, Ill.) using the same method described above. To investigate the influence of Alum on the uptake of NanoNiccine by the DCs, 100 µg of freshly prepared NanoNiccine (labeled with Alexa Fluor® 647 hydrazide and NBD PE) with various mass ratios of Alum (0:1, 0.5:1, 1:1, 2:1, and 4:1) was incubated with $7 \times 10^5$ cells for 180 min. After incubation, the medium was immediately removed and the cells were washed five times with PBS buffer (pH 7.4). Freshly prepared 4% (w/v) paraformaldehyde (2 mL) was added into each well, and cells were fixed for 15 min. This was followed by washing three times with PBS buffer (pH 7.4). Fixed cells were labeled with DAPI Fluoromount-G® (SouthernBiotech, Birmingham, Ala.). Cell samples were covered with a glass cover. Images were acquired using a Zeiss LSM 880 Laser Scanning Microscope (Carl Zeiss, Germany).

Measurement of NanoNiccine Release from Alum

Two mg NanoNiccine particles (without nicotine hapten and MPLA) labeled with Alexa 647 was thoroughly mixed with different quantities of Alum (1 mg, 2 mg, 4 mg, and 8 mg) using a vortex mixer for 5 min. After incubating for 0, 2, 4, 8, 24, and 48 h in darkness, the released NanoNiccine particles were separated from the NanoNiccine-Alum mixture by centrifugation at 200 g for 20 min. Three hundred microliter of the supernatant that contained the released NanoNiccine was transferred to a black 96-well plate and the fluorescence intensity was measured using a Synergy HTX Multi-Mode Microplate Reader (BioTek Instruments, Inc., Winooski, Vt.) with the excitation wavelength at 620 nm and the emission wavelength at 680 nm. The percentage of the released NanoNiccine was calculated using the following equation: NanoNiccine released (%)=total fluorescence intensity from the supernatant/total fluorescence intensity from 2 mg native NanoNiccine.

Active Immunization of Mice with NanoNiccine

Immunizing mice with NanoNiccine was carried out according to a previously described method with proper modifications [3, 7]. Briefly, groups of n=5 female BALB/c mice (8-10 weeks, 16-20 g) were immunized via subcutaneous (s.c.) injection on days 0 (primary injection), 14 (1st booster), and 28 ($2^{nd}$ booster) with PBS buffer (negative control), and NanoNiccine supplemented with 0, 125, 250, 500, and 1000 µg Alum (NanoNiccine contained a total amount of 20 µg KLH). Following vaccine administration, blood samples (about 200 µL) were collected from each mouse on days −2, 13, 27, and 42 via retro orbital puncture. Sera were collected from blood by centrifugation and stored at −80° C. Measurement of specific anti-CMUNic IgG using enzyme-linked immunosorbent assay (ELISA) Mice sera were analyzed according to the ELISA procedure described in previous publications with proper modifications [3, 7]. Briefly, CMUNic-BSA was used as the coating material for anti-CMUNic IgG measurement. MICROLON® 96 well plates (Greiner BioOne, Longwood, Fla.) were coated with CMUNic-BSA conjugate (10 µg/mL in carbonate buffer, 0.05 M, pH 9.6, 100 µL/well) and incubated at room temperature for 5 h. The plates were washed with PBS-Tween (0.1%) and distilled water for three times, followed by blocking with 300 µL Pierce® protein-free T20 blocking buffer for 12 h. After washing, 100 µL of each dilution (100, 500, 2500, 12500, and 62500) of serum from each mouse was incubated in plates at room temperature for 2 h. The plates were washed again, and incubated for 1 h with 100 µL antimouse IgG. The pates were washed as before, and incubated with 100 µL anti-goat IgG-HRP (1:5000) (Alpha Diagnostic Intl, San Antonio, Tex.) for 1 h. After washing as before, 100 µL of TMB one component microwell substrate was added into each well and incubated for 10 min, and the reaction was stopped by adding 100 µL of 0.5% (v/v) H2SO4. The absorbance for each well was recorded at 450 nm. Titer was defined as the dilution factor at which OD450 fell to half of the maximal.

Evaluation of the Pharmacokinetic Efficacy of NanoNiccine in Mice

On day 45, both the mice immunized with NanoNiccine-Alum mixtures and the mice in the negative control group were injected with 0.1 mg/kg nicotine subcutaneously. Mice were sacrificed 4 min post nicotine challenge, and their brain tissues were collected. Nicotine contents in the brain tissues were analyzed by gas chromatography/mass spectrometry according to a method reported previously [30].

Histopathological Examination

The mice injected with PBS and the mice treated with NanoNiccine-Alum mixtures were scarified, and their organs, including heart, lung, kidney, spleen, liver, and stomach were harvested and fixed in 10% buffered formalin. Haemotoxylin and eosin (H&E) staining was carried out according to the method described before [3, 7]. Sections were examined by a light microscopy on an Olympus CKX41 inverted microscope and images were captured using an INFINITY 1 camera.

Data Analysis

The antibody titers and the brain nicotine concentrations were compared among groups using one way ANOVA and comparisons among paired groups were analyzed with Tukey's honest significant difference (HSD). The difference is considered as significant when a P-value is less than 0.05. Each measurement was carried out at least thrice, and the results were expressed as mean±standard deviation.

Results

Physicochemical Properties and Morphology of Nanoparticles

Figure 102A:
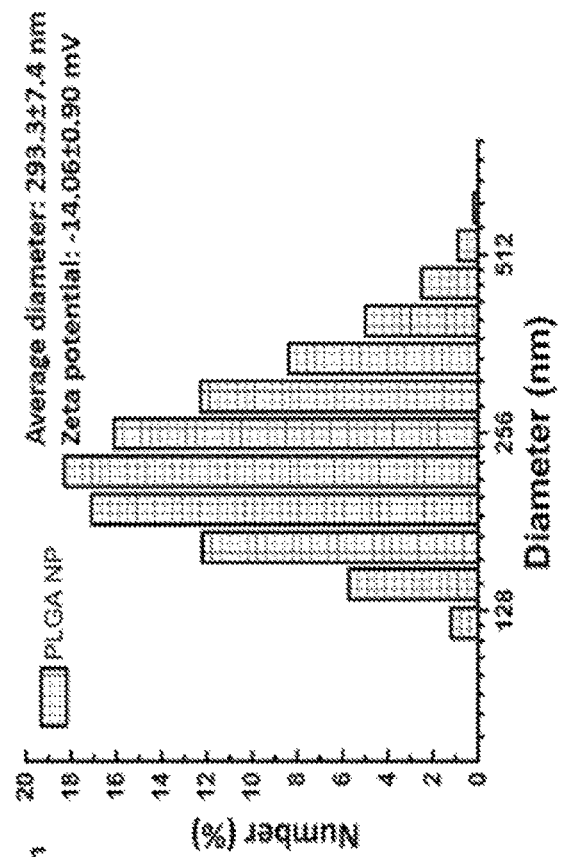
FIGS. 102A-102C shows graphs demonstrating the size distribution, zeta potential, and morphology of the nanoparticles. Newly-prepared nanoparticles, including liposome, PLGA nanoparticle, and NanoNiccine particle were suspended in PBS buffer (pH 7.0) and their physiochemical properties, including mean size, size distribution, and surface charge (represented by zeta potential), were measured by a Malvern Nano-ZS zetasizer.
Figure 102B:
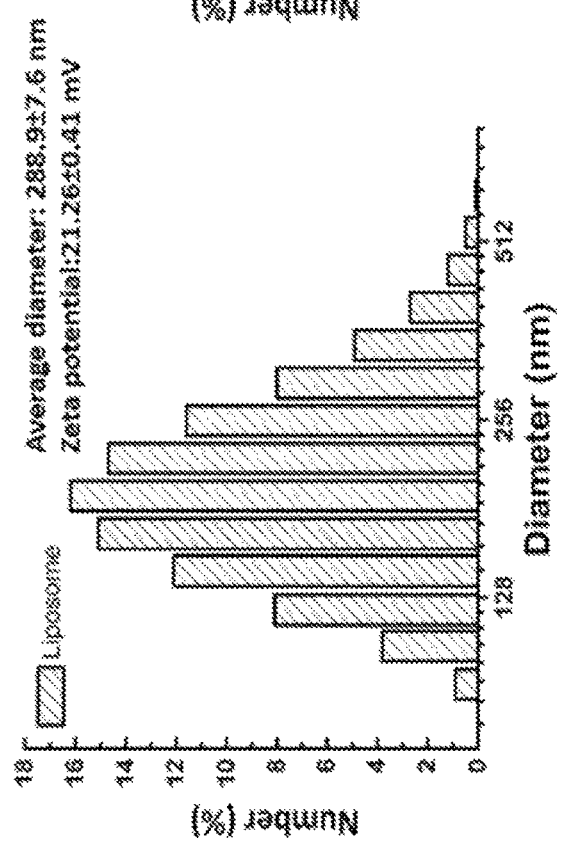
Figure 102C:
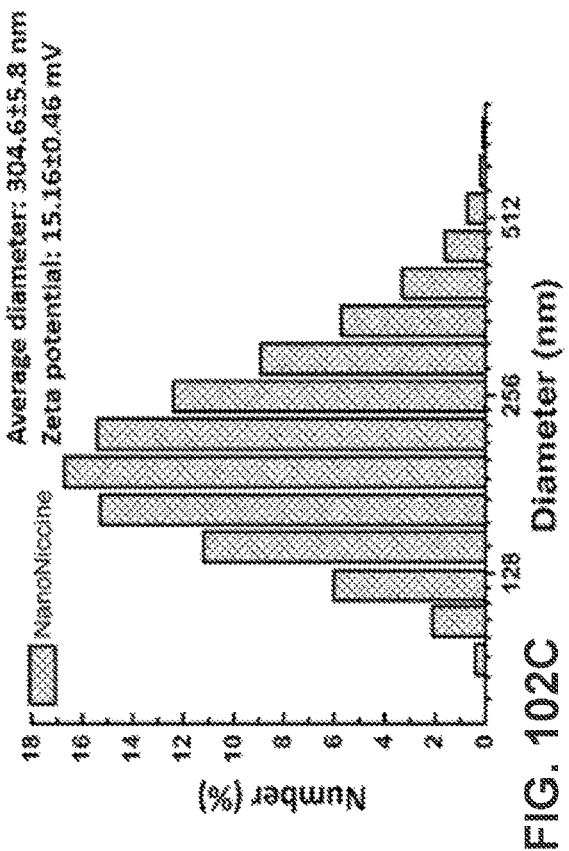
Figure 103A:
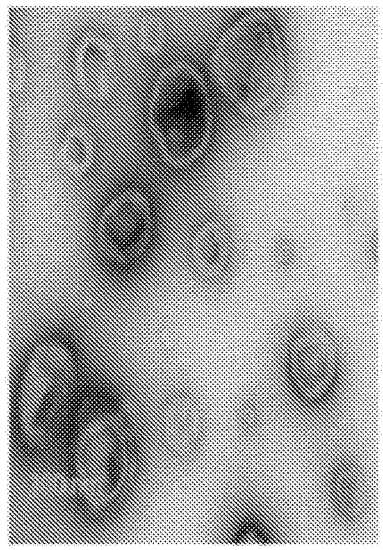
FIGS. 103A-103C show TEM images of the nanoparticles characterized in FIGS. 102A-102C. The nanoparticles were negatively stained and their morphologies were examined by a TEM. The scale bars represent 200 nm.
Figure 103B:
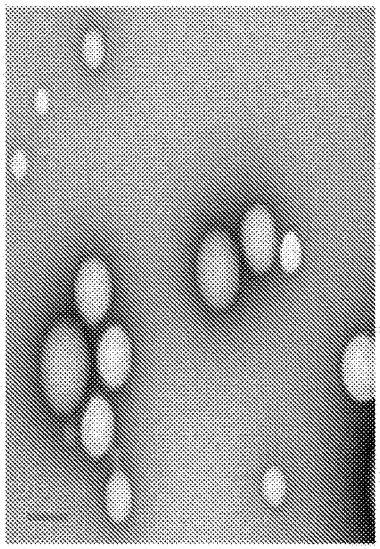
Figure 103C:
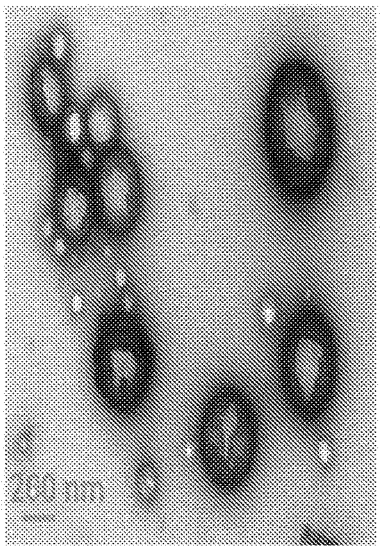

The lipid-PLGA hybrid nanoparticle, the main structure of NanoNiccine, was prepared via sonication medicated fusion of liposome and PLGA nanoparticle [7, 29]. NanoNiccine was assembled by conjugating CMUNic hapten onto the surface of the lipid-PLGA hybrid nanoparticle. The physicochemical properties, including mean size, size distribution, and zeta potential, were characterized for liposome, PLGA nanoparticle, and NanoNiccine. As shown in FIGS. 102A-102C, liposome, PLGA nanoparticle, and NanoNiccine had a mean size of 288.9±7.6 nm, 293.3±7.4 nm, and 304.6±5.8 nm, respectively. The three nanoparticles shared a similar size distribution, which had a center at around 200 nm. The surface charges, which were represented by the zeta potentials, were 21.26±0.41 mV, −14.06±0.90 mV, and 15.16±0.46 mV for liposome, PLGA nanoparticle, and NanoNiccine respectively. The morphology of the three nanoparticles were also examined using a TEM. Also shown in FIGS. 103A-103C, consistent with the size distributions, most of the three nanoparticles had a size at around 200 nm. A spherical two-layer membrane structure was detected in most of the liposome particles. In contrast, the PLGA nanoparticles did not have a membrane and exhibited a solid and spherical morphology. In agreement with previous findings [7], most of the NanoNiccine particles displayed a core-shell hybrid structure, which resulted from the coating of the lipid layer onto the PLGA nanoparticle.

TEM Images of NanoNiccine-Alum Mixtures

Figure 104A:
FIGS. 104A-104D show TEM images of NanoNiccine-Alum mixtures. Newly-prepared NanoNiccine was thoroughly mixed with Alum at Alum/NanoNiccine mass ratios of (FIG. 104A) 0.5:1, (FIG. 104B) 1:1, (FIG. 104C) 2:1, and (FIG. 104D) 4:1. The NanoNiccine-Alum mixtures were negatively stained and their images were captured by a TEM. The scale bars represent 200 nm.
Figure 104B:
Figure 104C:
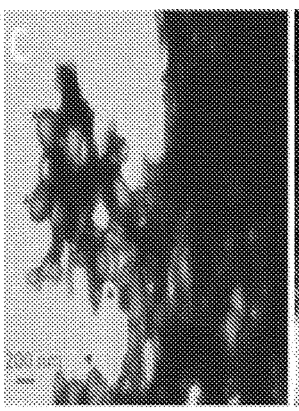
Figure 104D:

NanoNiccine particles were mixed with Alum at Alum/NanoNiccine mass ratios (ANMRs) of 0.5:1, 1:1, 2:1, and 4:1, respectively. Shortly after the blending, the images of the NanoNiccine-Alum mixtures were captured using a TEM. The NanoNiccine particles (marked with red arrows in FIGS. 104A-104D) had a similar size as those in FIGS. 102A-102C. As shown in FIG. 104A, part of the NanoNiccine particles were entrapped with in the Alum particles, while some were not. In contrast, FIGS. 104B-104D showed that the majority of the NanoNiccine particles were entangled with the Alum particles at ANMRs of 1:1, 2:1, and 4:1. It is worth noting that some of the unentrapped NanoNiccine particles (the zoom-in image in FIG. 104A) exhibited a damaged core-shell structure. By contrast, the NanoNiccine particles in FIGS. 103A-103C had a smooth membrane surface. It appears that part of the lipid membrane on these Alum-treated NanoNiccine particles was ripped off.

Release of NanoNiccine Particle from Alum

Figure 105:
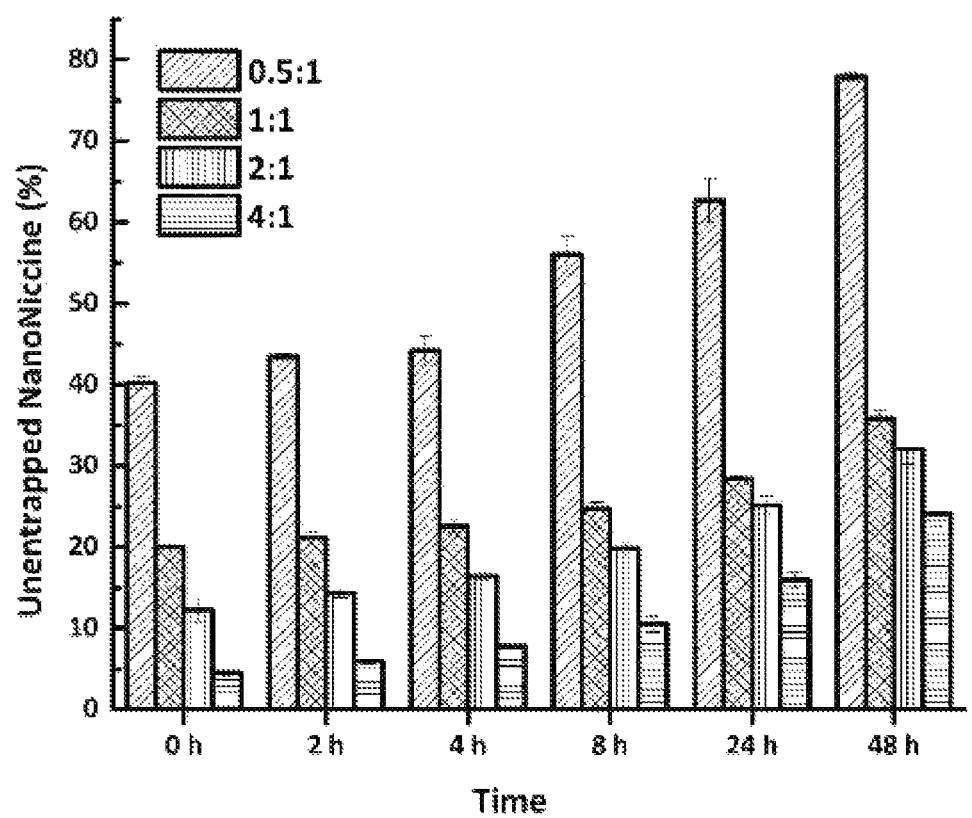
FIG. 105 shows a graph demonstrating the time course release of NanoNiccine from Alum. Alexa 647-labeled NanoNiccine particle (without CMUNic) was thoroughly mixed Alum at Alum/NanoNiccine mass ratios of 0.5:1, 1:1, 2:1, and 4:1. The released NanoNiccine at specific time points were separated from the NanoNiccine-Alum mixture via centrifugation and the fluorescence intensity of the released NanoNiccine was recorded.
Figure 106A:
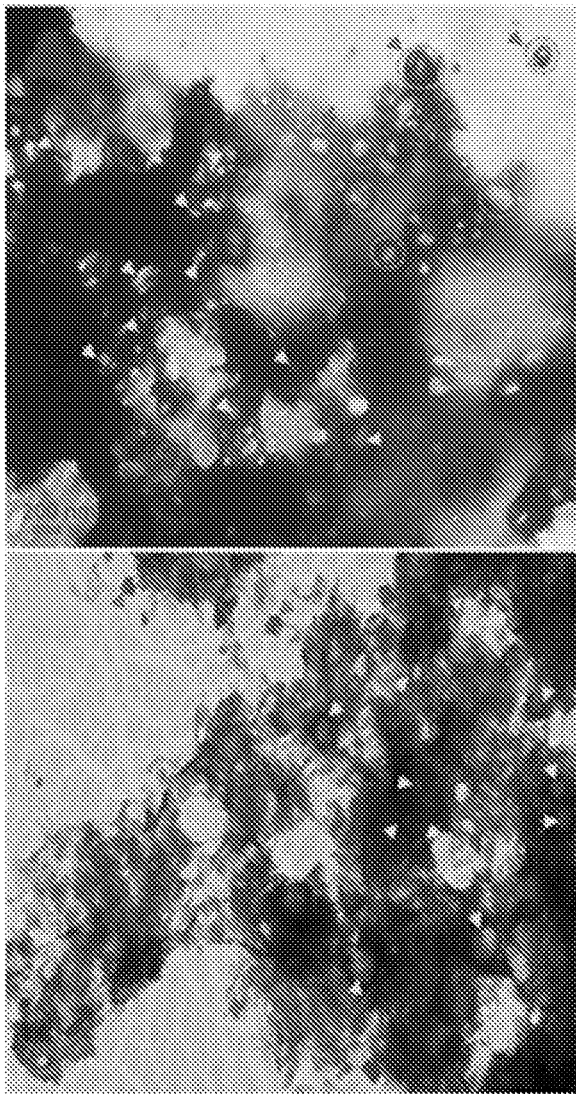
FIGS. 106A-106D show TEM images of NanoNiccine release from Alum. Newly-prepared NanoNicine was thoroughly mixed with Alum at Alum/NanoNiccine mass ratios of 0.5:1 (FIG. 106A), 1:1 (FIG. 106B), 2:1 (FIG. 106C), and 4:1 (FIG. 106D). The mixtures were incubated for 48 h and the images of NaoNiccine-Alum mixture were captured using a TEM. The scale bars represent 200 nm.
Figure 106B:
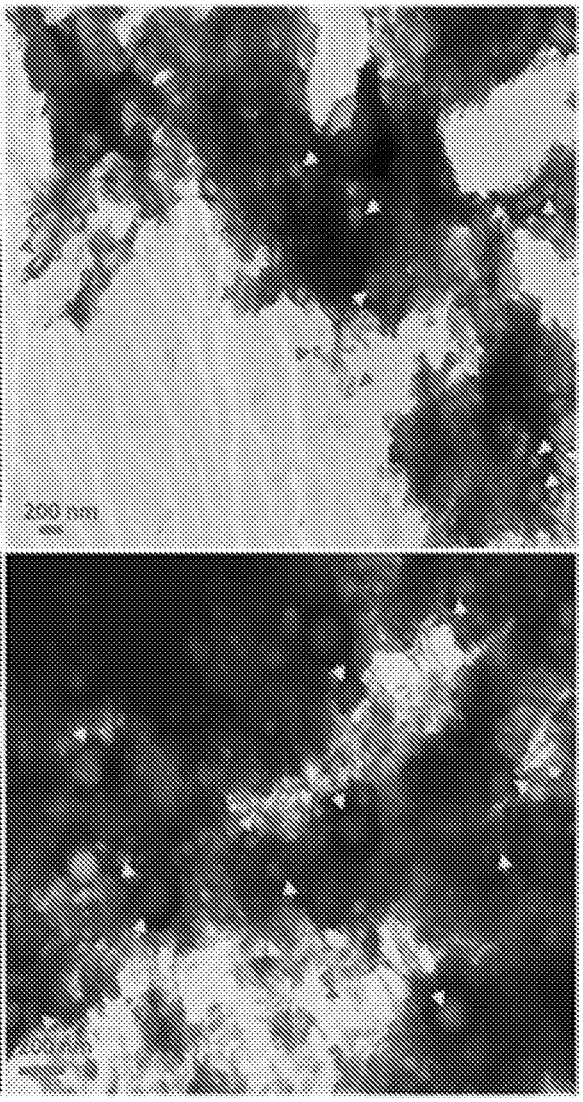
Figure 106C:
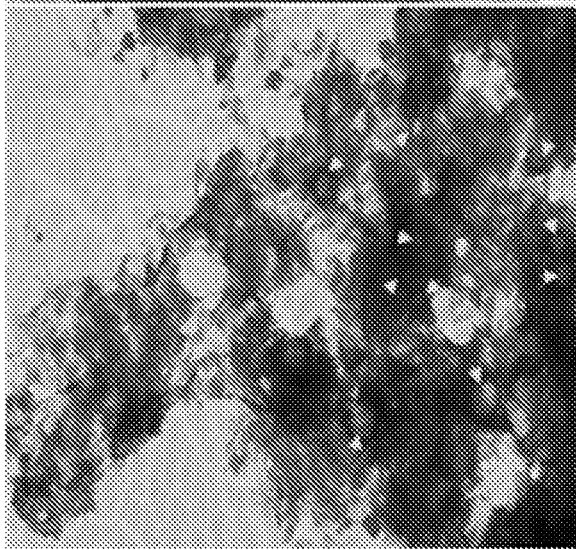
Figure 106D:
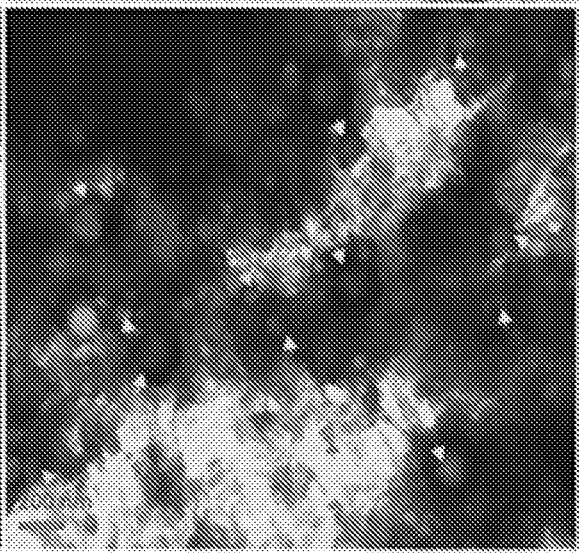

Alexa 647-labeled NanoNiccine were thoroughly mixed with Alum at ANMRs of 0.5:1, 1:1, 2:1, and 4:1. The unentrapped NanoNiccine particles were recovered via centrifugation and their relative quantities in terms of fluorescence intensities were measured at 0, 2, 4, 8, 24, 48 h. As shown in FIG. 105, a higher ANMR resulted in more NanoNiccine entrapped within the Alum. It was detected that right after blending NanoNiccine with Alum (0 h), 59.7%, 80.0%, 87.8%, and 95.8% of the NanoNiccine particles were entrapped within the Alum at ANMRs of 0.5:1, 1:1, 2:1, and 4:1, respectively. This was substantiated by the images of the NanoNiccine-Alum mixtures in FIGS. 104A-104D. During incubation, part of the NanoNiccine particles was released from the Alum. We found that the quantity of the released NanoNiccine was time-dependent regardless of the ANMR. From 0 h to 48 h, the percentage of the unentrapped NanoNiccine increased 37.6%, 15.8%, 19.9%, and 19.6% at ANMRs of 0.5:1 1:1, 2:1, and 4:1, respectively. However, at 48 h, as much as 75.9%, 67.9%, and 64.2%, 22.1% were still entrapped within the Alum at ANMRs of 4:1, 2:1, 1:1, and 0.5:1, respectively.

NanoNiccine release from the Alum was also examined under a TEM. After incubation for 48 h, the images of NanoNiccine-Alum mixtures were captured. As shown in FIGS. 106A-106D, considerable amount of NanoNiccine particles were entangled with the Alum (marked by the yellow arrows) at all the ANMRs. In agreement with the results in FIG. 105, the quantity of the unentrapped NanoNiccine (marked with the red arrows) was negatively correlated with the ANMR. At ANMR of 0.5:1, a large portion of NanoNiccine particles were not enclosed within the Alum. By contrast, the majority of the NanoNiccine particles were entrapped within the Alum at ANMRs of 1:1, 2:1, and 4:1. As shown in FIG. 105A, the lipid layer of many released NanoNiccine particles (marked with the green circles) was missing. However, part of the NanoNiccine particles (marked with the blue arrows) still maintained an intact lipid-PLGA hybrid structure in FIG. 105A. These findings indicated that NanoNiccine particles were retained within the Alum for a longer time at a higher ANMR.

Morphology and Physiochemical Properties of the Alum-Treated NanoNiccine

The influence of Alum on the structure and the physicochemical properties of NanoNiccine was studied. As shown in FIGS. 107A-107E, the TEM images of NanoNiccine that were incubated for 48 h with Alum at ANMRs of (FIG. 107A) 0:1, (FIG. 107B) 0.5:1, (FIG. 107C) 1:1, (FIG. 107D) 2:1, and (FIG. 107E) 4:1, were captured. The NanoNiccine particles that were not mixed with Alum (FIG. 107A) exhibited a core-shell hybrid structure (the black halo surrounding the white core) as the newly prepared particles shown in FIGS. 103A-103O. By contrast, regardless of the ANMR, some particles in the groups that were treated with Alum did not display the core-shell structure. This was consistent with the findings shown in FIG. 106A, in which the lipid layer of some of the unentrapped particles was ripped off. In FIGS. 107B-107E, it was shown that a larger portion of particles lost the lipid membrane at a higher ANMR.

Figure 108A:
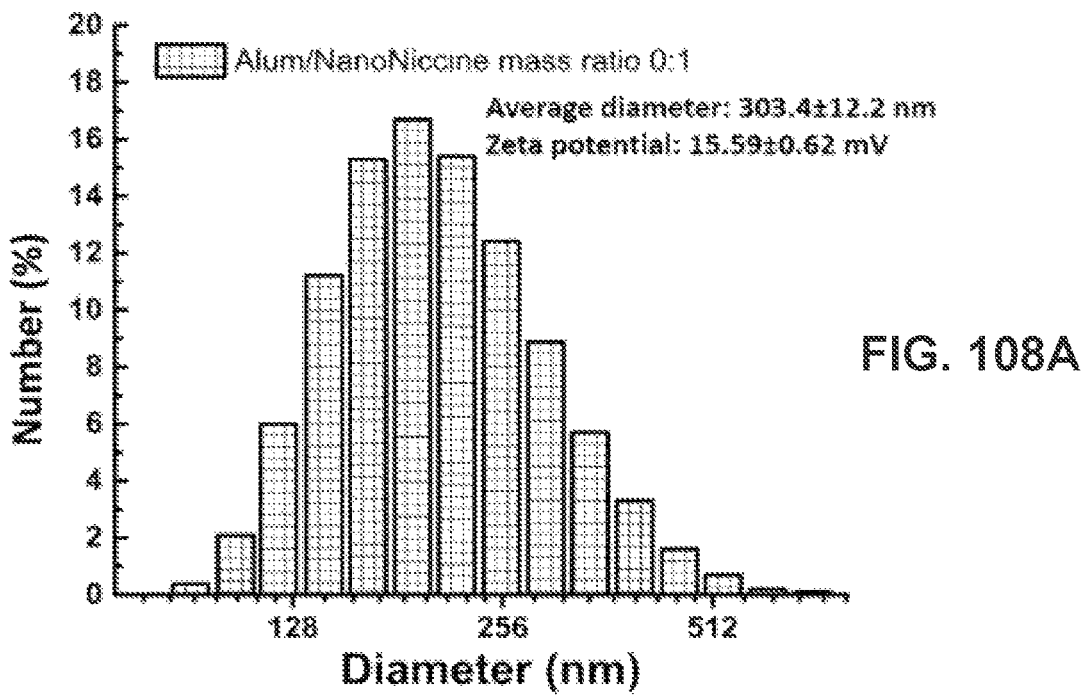
FIGS. 108A-108D show graphs demonstrating physicochemical properties of NanoNiccine that were released from NanoNiccine-Alum mixture. Newly prepared NanoNiccine was thoroughly mixed with Alum at Alum/NanoNiccine mass ratios of (FIG. 108A) 0:1, (FIG. 108B) 0.5:1, (FIG. 108C) 1:1, (FIG. 108D) 2:1, and (FIG. 108E) 4:1. The mixtures were incubated for 48 h, followed by recovery of the released NanoNiccine via centrifugation (washed 3 times with $H_2O$). The mean size, size distribution, and zeta potential of the released NanoNiccine were measured by a Malvern Nano-ZS zetasizer.
Figure 108B:
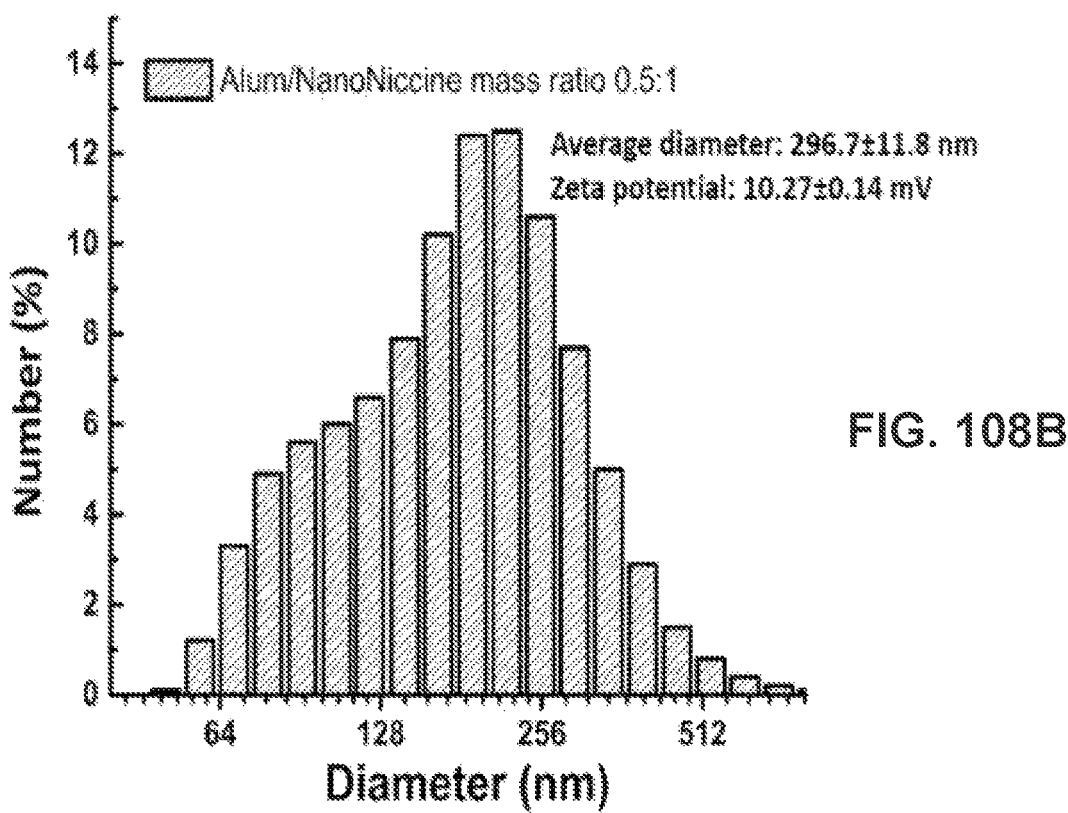
Figure 108C:
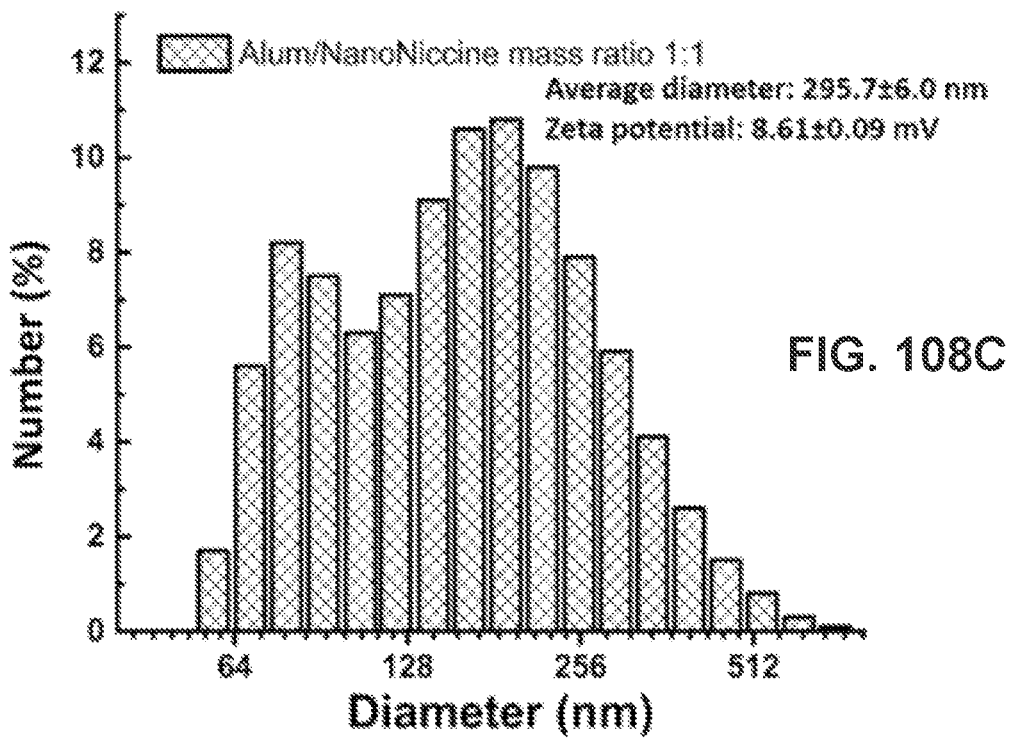
Figure 108D:
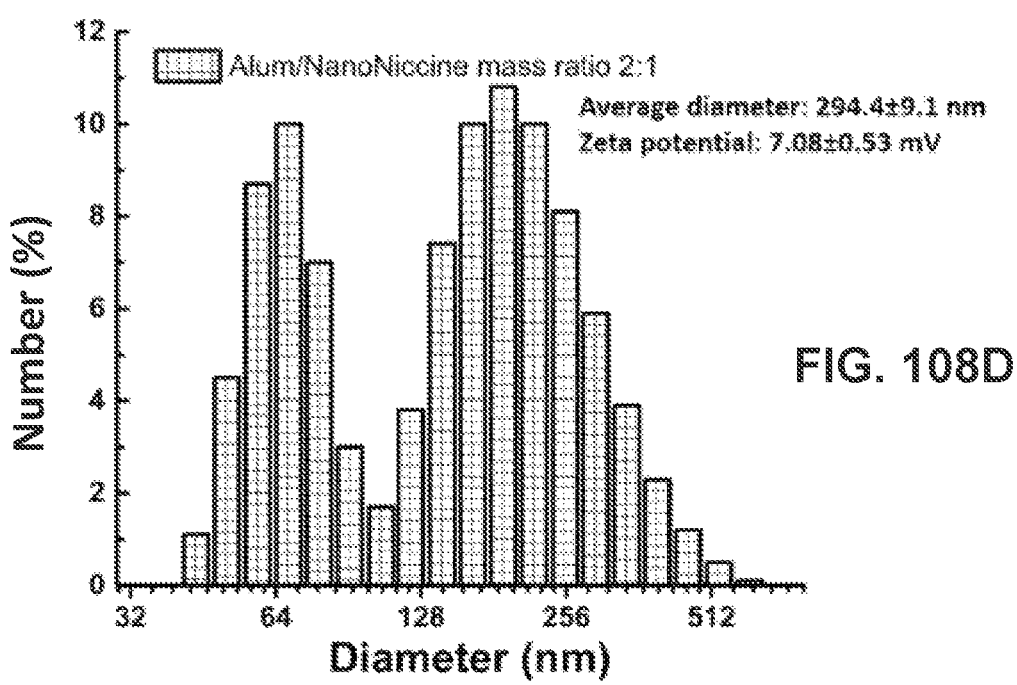
Figure 108E:
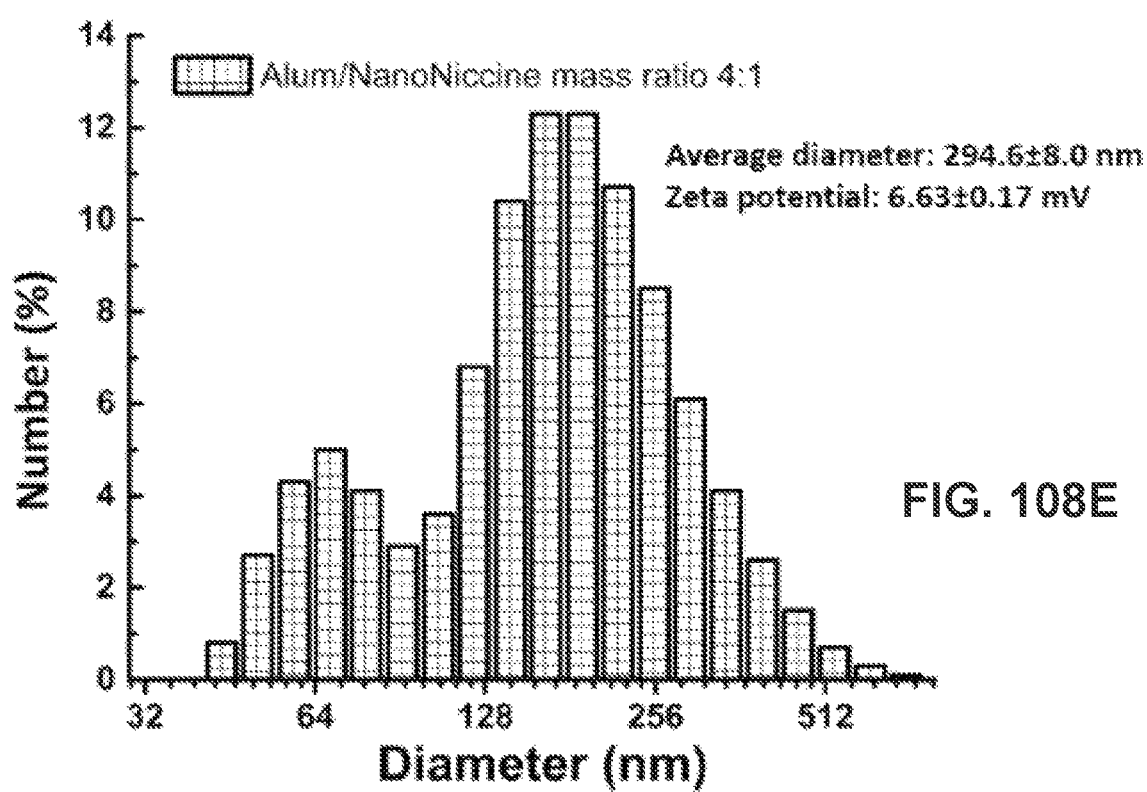

The surface charge and particle size of the NanoNiccine were also recorded after incubation with Alum. As shown in FIGS. 108A and 108E, NanoNiccine particles treated Alum at ANMRs of 0:1, 0.5:1, 1:1, 2:1, and 4:1 had an average diameter of 303.4±12.2 nm, 296.7±11.8 nm, 295.7±6.0 nm, 294.4±9.1 nm, and 294.6±8.0 nm, respectively. NanoNiccine that was not treated with Alum exhibited a similar size distribution as that of the newly prepared particles shown in FIGS. 102A-102C and 103A-103C. In contrast, the size distributions of the Alum-treated NanoNiccine particles changed considerably as compared to that of the newly formed NanoNiccine. In addition, zeta potentials of 15.59±0.62 mV, 10.27±0.14 mV, 8.61±0.09 mV, 7.08±0.53 mV, and 6.63±0.17 mV were recorded for the recovered particles at ANMRs of 0:1, 0.5:1, 1:1, 2:1, and 4:1, respectively. It seems that the zeta potential of the unentrapped NanoNiccine particles was negatively correlated with the ANMR. The positive surface charge of the NanoNiccine particles was mainly contributed by the cationic lipids in the lipid layer. And removal of the lipid layer would expose PLGA core, which was negatively charged. It is possible more NanoNiccine particles lost their lipid layer in a higher concentration of Alum, resulting in the decreased zeta potentials with the increased ANMRs. These findings showed that blending NanoNiccine with Alum could lead to removal of the lipid layer of the particles.

Cellular Uptake of Alum-Treated NanoNiccine

Fluorescently-labeled NanoNiccine particles (Alexa 647 in the PLGA core and NBD in the lipid layer) were blended with Alum at ANMRs of 0:1, 0.5:1, 1:1, 2:1, and 4:1. The uptake of fluorescently-labeled NanoNiccine (the PLGA core was labeled with Alexa 647 and the lipid layer was labeled with NBD) by DCs was studied using a confocal microscope. NanoNiccine-Alum mixture containing 100 µg NanoNiccine was incubated with $7 \times 10^5$ DCs for 180 min. As shown in FIGS. 109A-109T, fluorescence in both the NBD and Alexa 647 channels were much brighter in group without Alum than all the other groups, reflecting that DCs captured considerably more NanoNiccine that was not blended with Alum than those mixed with Alum. In addition, it showed that the quantity of the internalized NanoNiccine was negatively correlated with ANMR, which was demonstrated by the dimmer NBD and Alexa 647 fluorescence in cells treated with NanoNiccine in higher concentrations of Alum. These results demonstrated that mixing NanoNiccine with Alum could remarkably hinder the uptake of NanoNiccine particles by DCs.

Figure 110:
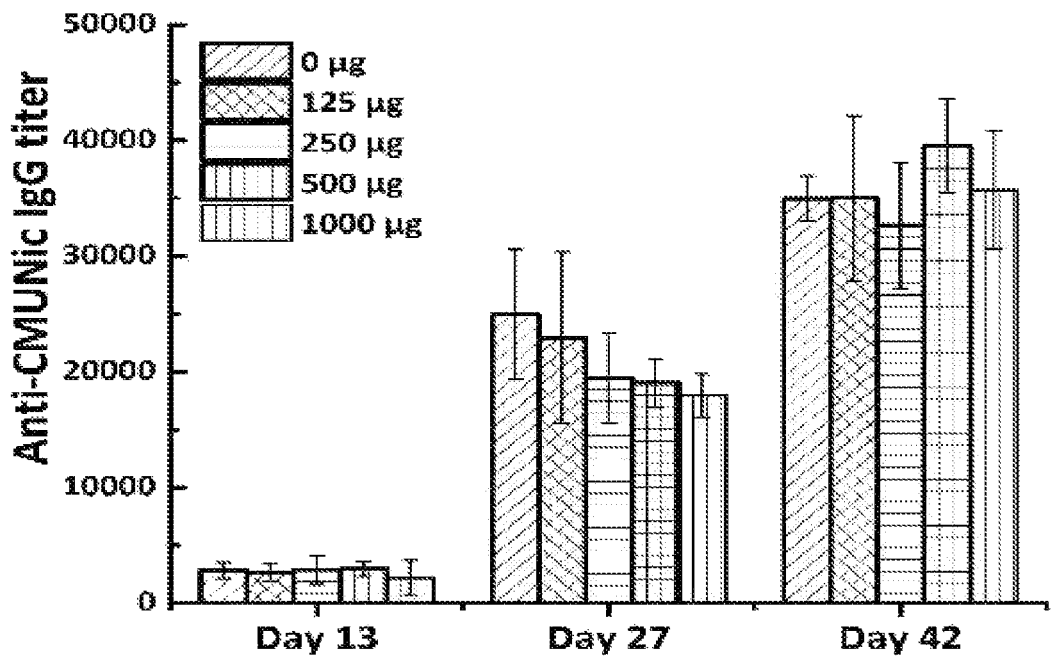
FIG. 110 shows a graph demonstrating a time course of CMUNic-specific IgG titers elicited by NanoNiccine adjuvanted with various quantities of Alum. On days 0, 14, and 28, 5 mice in each group were immunized with NanoNiccine (each dose contained 20 µg KLH) that was mixed with 0, 125, 250, 500, and 1000 µg Alum, respectively. Anti-CMUNic IgG titers were assayed for sera collected on days −2, 13, 27, and 42.

On days 0, 14, and 28, each group of five mice were immunized with NanoNiccine (each dose contained 20 µg KLH) that was supplemented with 0, 125, 250, 500, and 1000 µg Alum, respectively. Anti-CMUNic IgG from sera on days −2, 13, 27, and 42 were measured. No anti-CMUNic IgG was detected in mice before vaccine injection. As shown in FIG. 110, the vaccine formulations with different quantities of Alum achieved comparable anti-CMUNic antibody titers in the mice at all the studied time points. On day 13, NanoNiccine with 0, 0.125, 0.25, 0.5, and 1 mg Alum induced antibody titers of 2835±682, 2679±756, 2901±1251, 2965±669, and 2155±1555, respectively. Two weeks after the second injection, the antibody titers significantly increased to 24959±5601, 22976±7430, 19495±3890, 19035±2127, and 17968±1841 in mice treated with 0, 125, 250, 500, and 1000 µg Alum, respectively. Interestingly, although not significant, the antibody titer in the mice was inversely correlated with the quantity of the injected Alum on day 27. The second booster on day 28 further improved the antibody titers to 34980±1962, 35016±7117, 32663±5438, 39564±4042, and 35732±5125 in vaccine groups supplemented with 0, 125, 250, 500, and 1000 µg Alum, respectively.

Brain Nicotine Concentration in Mice Immunized with NanoNiccine

Figure 111:
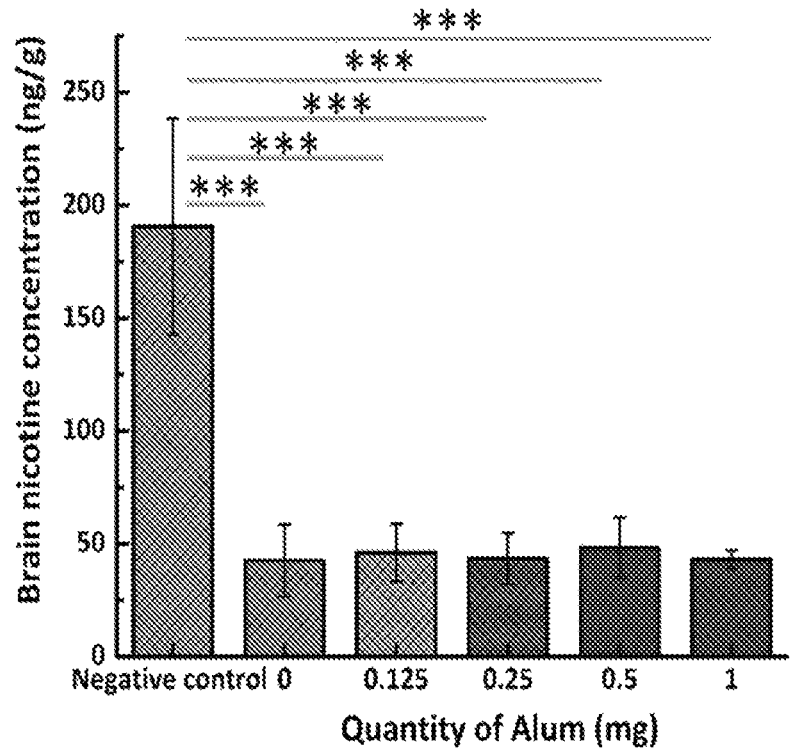
FIG. 111 shows a graph demonstrating brain nicotine level in mice immunized with NanoNiccine. 5 mice in each group were immunize with NanoNiccine (each dose contained 20 µg KLH) that were supplemented with 0, 0.125, 0.25, 0.5, and 1 mg Alum, respectively. Mice injected with PBS buffer were used as the negative control group. On day 45, all the mice were challenged with 0.1 mg/Kg nicotine via subcutaneous injection. 4 min post nicotine challenge, the mice brain tissues were harvested and the brain nicotine concentration was assayed. ***means that P-value is less than 0.001.
Figure 112:
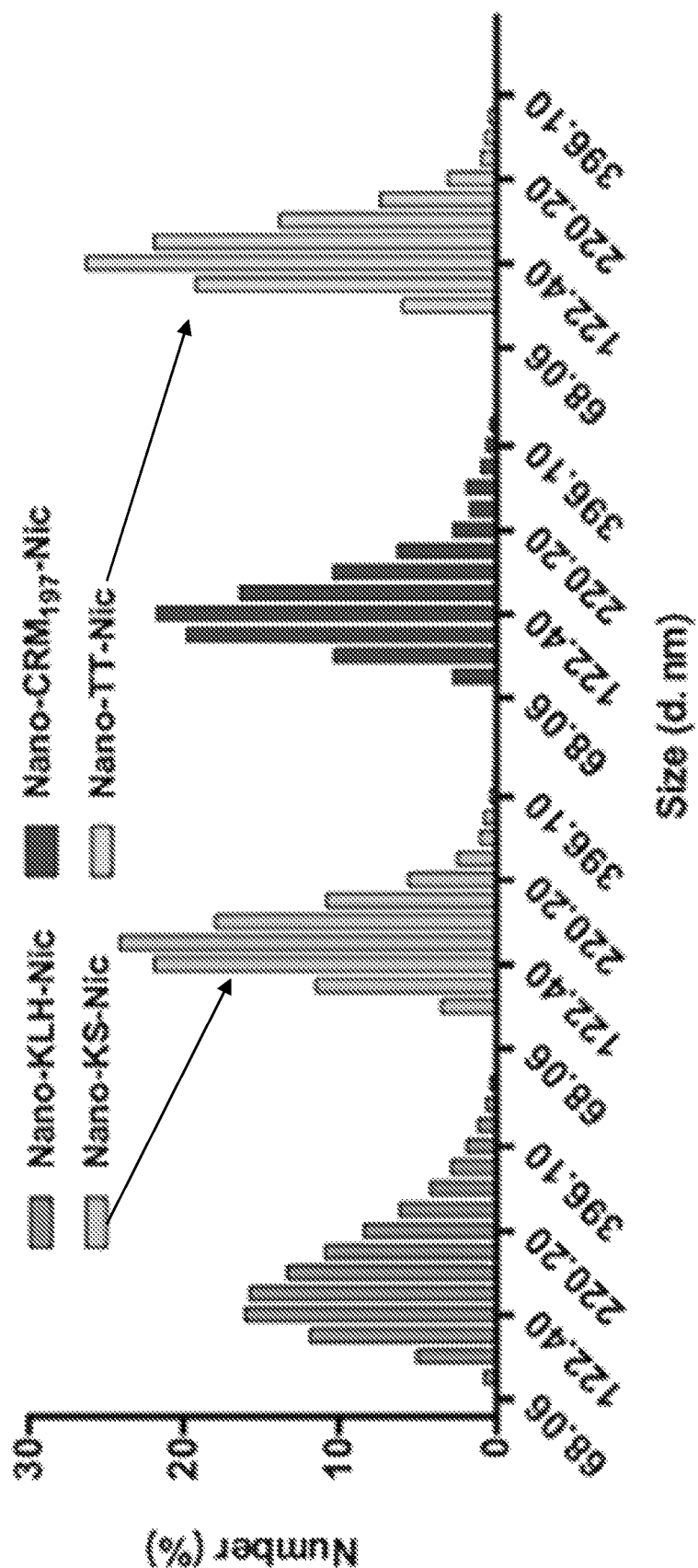
FIG. 112 shows a graph demonstrating the dynamic size distribution of the NanoNicVac nanoparticles.

To evaluate the influence of Alum on the ability of NanoNiccine in blocking the entry of nicotine into the brain, mice immunized with NanoNiccine that was adjuvanted by 0, 0.125, 0.25, 0.5, and 1 mg Alum were subcutaneously injected with 0.1 mg/Kg nicotine. Mice injected with PBS buffer was used as the negative control. As shown in FIG. 111, the brain nicotine concentration in the negative control was as high as 190.6±47.9 ng/g. In contrast, the brain nicotine concentrations were 42.6±15.9, 46.0±12.8, 43.4±11.3, 48.2±11.5, 43.0±4.1 ng/g in mice immunized with NanoNiccine formulations that were adjuvanted with 0, 0.125, 0.25, 0.5, and 1 mg Alum, respectively. Up to 77.4% of reduction in the brain nicotine level was detected in the mice immunized with NanoNiccine without Alum as compared to that in the negative control. Regardless of the quantity of Alum, the brain nicotine concentrations in mice immunized with NanoNiccine were significantly lower than that in the negative control. However, no significant difference was detected in the brain nicotine concentrations in mice treated with NanoNiccine that was supplemented with various quantity of Alum. These results were consistent with the anti-CMUNic antibody concentrations, in which the quantity of Alum did not make significant differences. These results suggested that NanoNiccine was able to achieve significant reduction in the brain nicotine concentration on its own and Alum could not significantly improve the immunological efficacy of NanoNiccine in mice.

Discussion

The ability of a nicotine vaccine to block the entry of nicotine into the brain is of pivotal importance to its treatment efficacy on tobacco addiction [31]. It has been widely observed that higher titers of antinicotine antibody in the immunized subjects were correlated with higher percentages of reduction in the brain nicotine [10, 11]. Therefore, improving the immunogenicity of a nicotine vaccine has been considered an important goal in the vaccine design.

Conventionally, the most efficient way of promoting the immunogenicity of a vaccine is co-administering the vaccine with an adjuvant. To date, due to its potent adjuvanticity and good safety profile, Alum has been the most widely used adjuvant for human vaccines. Interestingly, most of the vaccines that require Alum as the adjuvant are protein, peptide, or inactivated virus-based vaccines, such as HIV vaccine [32], EV71 vaccine[33], tetanus toxoid [34], and diphtheria toxoid [35], etc. In recent years, application of microparticle or nanoparticle-based delivery system for vaccines has been intensively studied [36]. These delivery systems have some unique features, including efficient uptake by the immune cells [37], co-delivery of antigen and adjuvants [38], controlled released of antigen [39], etc., that can considerably improve the immunological outcome of an otherwise poorly immunogenic vaccine. However, study on combination of Alum adjuvant and nanoparticle-delivered vaccine was rarely reported. It might be possible that those vaccines delivered by nanoparticles could achieve a satisfactory immune response own their own. NanoNiccine is a lipid-PLGA hybrid nanoparticle-based nicotine vaccine. Although, in the previous study, we demonstrated that NanoNiccine could produce significantly higher anti-nicotine antibody than a protein-nicotine conjugate vaccine, it might be worth trying to explore the possibility of further improving its immunogenicity by co-administering with Alum. Surprisingly, the supplement of Alum into NanoNiccine did not significantly improve either its immunogenicity or further reduce the brain nicotine concentration as compared to the native NanoNiccine. In previous studies, it was reported that lipid-PLGA hybrid nanoparticle-based delivery system could significantly improve the immunogenicity of antigens [40, 41]. It is possible that nicotine presented by the hybrid nanoparticle already reached a threshold level of immunogenicity, which could not be further improved simply by incorporation of Alum.

It was suggested that adsorption of antigen onto Alum may ensure a high localized concentration of antigen to allow antigen uptake and activation of DCs [18]. However, in this study, tremendously slowed antigen uptake by the DCs was observed in the particles that were mixed with Alum. In addition, the uptake rate of the NannoNiccine nanoparticles was negatively correlated with the quantity of Alum. The slowed particle cellular uptake might be caused by the slowed particle release from Alum. It is possible that unlike soluble antigens, the hybrid nanoparticles could not freely diffuse out of the Alum complex, which might limit the contact between the vaccine particles and the DCs, leading to the hindered cellular uptake. Antigen uptake by DCs is a vital step in the development of an antibody response.

Following antigen uptake, B cells or DCs can process the captured protein into antigenic peptides, which will be subsequently presented to T helper cells for their activation. In addition, antigen uptake is also followed by secretion of cytokines from the immune cells and these cytokines may increase the magnitude of the immune response. Therefore, the impeded antigen uptake by DCs may partially explain the failure of Alum to improve the immunogenicity of NanoNiccine. As discussed in a previous study [7], the integrity of the hybrid structure in NanoNiccine is essential for its immunological efficacy. The PLGA core and the lipid layer have their own distinct functions. For example, the PLGA core mainly serves as a delivery vehicle for harboring the protein antigen, in contrast, the lipid layer can present the nicotine epitopes to B cells. In this study, we observed that mixing NanoNiccine with Alum caused damage to the lipid layer. The damage might occur during the mixing process, because particles with damaged structure were observed in the newly prepared NanoNiccine-Alum mixtures in FIGS. 104A-104D. The incubation of NanoNiccine in Alum might also contributed to the damage, as considerably more particles with stripped lipid layer were detected after 48 h incubation. In addition, the degree of the damage may be correlated with the quantity of Alum, because higher proportions of damaged particles were observed in NanoNiccine-Alum mixtures with higher quantities of Alum. This was also supported by the physicochemical properties of the Alum-treated NanoNiccine particles. The particles recovered from NanoNiccine-Alum mixtures regardless of the quantity of Alum had a similar mean particle size as compared to that of untreated NanoNiccine. Since the dimension of the hybrid nanoparticle was mainly decided by the size of the PLGA core, particles with or without a lipid layer may have similar sizes. By contrast, the average surface charge of the Alum-treated NanoNiccine particles decreased with the increasing quantity of Alum. Since the surface charge of the hybrid nanoparticle is largely influenced by the lipids in the lipid layer [29, 42], such a decrease in the surface charge was very likely caused by the loss of the cationic lipids in the lipid layer. As found in a previous study, the cellular uptake of hybrid nanoparticles was affected by their surface charges, the decrease in the surface charges on the Alum-treated NanoNiccine might also contribute to the slowed uptake of NanoNiccine by the DCs.

In spite of the loss of the lipid layer and the hindered cellular uptake, the NanoNiccine with and without Alum exhibited similar immunological efficacy, which was reflected by the similar levels of anti-nicotine antibody titer and the brain nicotine concentration. It was possible that part of the Alum-treated NanoNiccine particles maintained the core-shell structure and had the ability to produce nicotine specific antibody. In addition, Alum can produce a local pro-inflammatory environment, which can promote DC differentiation and activation, resulting in an enhanced immune response [43-45].

Moreover, the study on the uptake of NanoNiccine was performed in vitro, it did not take the ability of Alum in recruiting the immune cells to the site of injection into consideration [46, 47]. It was likely that more DCs could migrate into the site of injection to capture NanoNiccine that was co-administered with Alum than that without Alum. The final immunological performance of Alum-mixed NanoNiccine was an outcome of the competing effects of the favorable and the unfavorable impacts from Alum.

REFERENCES FOR EXAMPLE 7

[1] Fahim R E, Kessler P D, Kalnik M W. Therapeutic vaccines against tobacco addiction. Expert review of vaccines. 2013; 12:333-42.
[2] Hu Y, Zheng H, Huang W, Zhang C. A novel and efficient nicotine vaccine using nano-lipoplex as a delivery vehicle. Human vaccines & immunotherapeutics. 2014; 10:64-72.
[3] Zhao Z, Hu Y, Hoerle R, Devine M, Raleigh M, Pentel P, et al. A nanoparticle-based nicotine vaccine and the influence of particle size on its immunogenicity and efficacy. Nanomedicine: nanotechnology, biology, and medicine. 2016.
[4] Moreno A Y, Janda K D. Immunopharmacotherapy: vaccination strategies as a treatment for drug abuse and dependence. Pharmacology, biochemistry, and behavior. 2009; 92:199-205.
[5] De Groot A S, Martin W. Reducing risk, improving outcomes: bioengineering less immunogenic protein therapeutics. Clinical immunology. 2009; 131:189-201.
[6] Huleatt J W, Nakaar V, Desai P, Huang Y, Hewitt D, Jacobs A, et al. Potent immunogenicity and efficacy of a universal influenza vaccine candidate comprising a recombinant fusion protein linking influenza M2e to the TLR5 ligand flagellin. Vaccine. 2008; 26:201-14.
[7] Hu Y, Smith D, Frazier E, Hoerle R, Ehrich M, Zhang C. The next-generation nicotine vaccine: a novel and potent hybrid nanoparticle-based nicotine vaccine. Biomaterials. 2016; 106:228-39.

[8] Maurer P, Jennings G T, Willers J, Rohner F, Lindman Y, Roubicek K, et al. A therapeutic vaccine for nicotine dependence: preclinical efficacy, and Phase I safety and immunogenicity. European journal of immunology. 2005; 35:2031-40.

[9] LeSage M G, Keyler D E, Pentel P R. Current status of immunologic approaches to treating tobacco dependence: vaccines and nicotine-specific antibodies. The AAPS journal. 2006; 8: E65-75.

[10] Keyler D E, Roiko S A, Earley C A, Murtaugh M P, Pentel P R. Enhanced immunogenicity of a bivalent nicotine vaccine. International immunopharmacology. 2008; 8:1589-94.

[11] Raupach T, Hoogsteder P H, Onno van Schayck C P. Nicotine vaccines to assist with smoking cessation: current status of research. Drugs. 2012; 72:e1-16.

[12] Alving C R, Peachman K K, Rao M, Reed S G. Adjuvants for human vaccines. Current opinion in immunology. 2012; 24:310-5.

[13] Mbow M L, De Gregorio E, Valiante N M, Rappuoli R. New adjuvants for human vaccines. Current opinion in immunology. 2010; 22:411-6.

[14] Morefield G L, Sokolovska A, Jiang D, HogenEsch H, Robinson J P, Hem S L. Role of 2005; 23:1588-95.

[15] De Gregorio E, Tritto E, Rappuoli R. Alum adjuvanticity: unraveling a century old mystery. European journal of immunology. 2008; 38:2068-71.

[16] Marrack P, McKee A S, Munks M W. Towards an understanding of the adjuvant action of aluminium. Nature reviews Immunology. 2009; 9:287-93.

[17] Goto N, Akama K. Histopathological studies of reactions in mice injected with aluminum-adsorbed tetanus toxoid. Microbiology and immunology. 1982; 26:1121-32.

[18] HogenEsch H. Mechanisms of stimulation of the immune response by aluminum adjuvants. Vaccine. 2002; 20 Suppl 3:S34-9.

[19] Hansen B, Belfast M, Soung G, Song L, Egan P M, Capen R, et al. Effect of the strength of adsorption of hepatitis B surface antigen to aluminum hydroxide adjuvant on the immune response. Vaccine. 2009; 27:888-92.

[20] Berthold I, Pombo M L, Wagner L, Arciniega J L. Immunogenicity in mice of anthrax recombinant protective antigen in the presence of aluminum adjuvants. Vaccine. 2005; 23:1993-9.

[21] Levesque P M, Foster K, de Alwis U. Association between immunogenicity and adsorption of a recombinant Streptococcus pneumoniae vaccine antigen by an aluminum adjuvant. Human vaccines. 2006; 2:74-7.

[22] Rosalia R A, Cruz L J, van Duikeren S, Tromp A T, Silva A L, Jiskoot W, et al. CD40-targeted dendritic cell delivery of PLGA-nanoparticle vaccines induce potent anti-tumor responses. Biomaterials. 2015; 40:88-97.

[23] Sandev P, Ochyl L J, Moon J J. Biomaterials for nanoparticle vaccine delivery systems. Pharmaceutical research. 2014; 31:2563-82.

[24] Lugade A A, Bharali D J, Pradhan V, Elkin G, Mousa S A, Thanavala Y. Single low-dose un-adjuvanted HBsAg nanoparticle vaccine elicits robust, durable immunity. Nanomedicine: nanotechnology, biology, and medicine. 2013; 9:923-34.

[25] Coffman R L, Sher A, Seder R A. Vaccine adjuvants: putting innate immunity to work. Immunity. 2010; 33:492-503.

[26] Pentel P R, LeSage M G. New directions in nicotine vaccine design and use. Advances in pharmacology. 2014; 69:553-80.

[27] Hatsukami D K, Rennard S, Jorenby D, Fiore M, Koopmeiners J, de Vos A, et al. Safety and immunogenicity of a nicotine conjugate vaccine in current smokers. Clinical pharmacology and therapeutics. 2005; 78:456-67.

[28] Fahim R E, Kessler P D, Fuller S A, Kalnik M W. Nicotine vaccines. CNS & neurological disorders drug targets. 2011; 10:905-15.

[29] Hu Y, Hoerle R, Ehrich M, Zhang C. Engineering the lipid layer of lipid-PLGA hybrid nanoparticles for enhanced in vitro cellular uptake and improved stability. Acta biomaterialia. 2015; 28:149-59.

[30] de Villiers S H, Cornish K E, Troska A J, Pravetoni M, Pentel P R. Increased efficacy of a trivalent nicotine vaccine compared to a dose-matched monovalent vaccine when formulated with alum. Vaccine. 2013; 31:6185-93.

[31] Pentel P R, Malin D H, Ennifar S, Hieda Y, Keyler D E, Lake J R, et al. A nicotine conjugate vaccine reduces nicotine distribution to brain and attenuates its behavioral and cardiovascular effects in rats. Pharmacology, biochemistry, and behavior. 2000; 65:191-8.

[32] Tian H, Xiao Y, Zhu M, Chen Y H. HIV epitope-peptides in aluminum adjuvant induced high levels of epitope-specific antibodies. International immunopharmacology. 2001; 1:763-8.

[33] Zhu F C, Liang Z L, Li X L, Ge H M, Meng F Y, Mao Q Y, et al. Immunogenicity and safety of an enterovirus 71 vaccine in healthy Chinese children and infants: a randomised, double-blind, placebo controlled phase 2 clinical trial. Lancet. 2013; 381:1037-45.

[34] Vandermeulen C, Theeten H, Rathi N, Kuriyakose S, Han H H, Sokal E, et al. Decennial administration in young adults of a reduced-antigen content diphtheria, tetanus, acellular pertussis vaccine containing two different concentrations of aluminium. Vaccine. 2015; 33:3026-34.

[35] Baylor N W, Egan W, Richman P. Aluminum salts in vaccines—U S perspective. Vaccine. 2002; 20 Suppl 3:S18-23.

[36] Singh M, Chakrapani A, O'Hagan D. Nanoparticles and microparticles as vaccine-delivery systems. Expert review of vaccines. 2007; 6:797-808.

[37] Kwon Y J, Standley S M, Goh S L, Frechet J M. Enhanced antigen presentation and immunostimulation of dendritic cells using acid-degradable cationic nanoparticles. Journal of controlled release: official journal of the Controlled Release Society. 2005; 105:199-212.

[38] Hamdy S, Elamanchili P, Alshamsan A, Molavi O, Satou T, Samuel J. Enhanced antigen-specific primary CD4+ and CD8+ responses by codelivery of ovalbumin and toll-like receptor ligand monophosphoryl lipid A in poly(D,L-lactic-co-glycolic acid) nanoparticles. Journal of biomedical materials research Part A. 2007; 81:652-62.

[39] Mi F L, Shyu S S, Chen C T, Schoung J Y. Porous chitosan microsphere for controlling the antigen release of Newcastle disease vaccine: preparation of antigen-adsorbed microsphere and in vitro release. Biomaterials. 1999; 20:1603-12.

[40] Hanson M C, Bershteyn A, Crespo M P, Irvine D J. Antigen delivery by lipid-enveloped PLGA microparticle vaccines mediated by in situ vesicle shedding. Biomacromolecules. 2014; 15:2475-81.

[41] Moon J J, Suh H, Polhemus M E, Ockenhouse C F, Yadava A, Irvine D J. Antigen-displaying lipidenveloped PLGA nanoparticles as delivery agents for a Plasmodium vivax malaria vaccine. PloS one. 2012; 7:e31472.

[42] Hu Y, Ehrich M, Fuhrman K, Zhang C. In vitro performance of lipid-PLGA hybrid nanoparticles as an antigen delivery system: lipid composition matters. Nanoscale research letters. 2014; 9:434.

[43] Tritto E, Mosca F, De Gregorio E. Mechanism of action of licensed vaccine adjuvants. Vaccine. 2009; 27:3331-4.

[44] Flach T L, Ng G, Hari A, Desrosiers M D, Zhang P, Ward S M, et al. Alum interaction with dendritic cell membrane lipids is essential for its adjuvanticity. Nature medicine. 2011; 17:479-87.

[45] Kool M, Petrilli V, De Smedt T, Rolaz A, Hammad H, van Nimwegen M, et al. Cutting edge: alum adjuvant stimulates inflammatory dendritic cells through activation of the NALP3 inflammasome. Journal of immunology. 2008; 181:3755-9.

[46] Awate S, Babiuk L A, Mutwiri G. Mechanisms of action of adjuvants. Frontiers in immunology. 2013; 4:114.

[47] McKee A S, Munks M W, MacLeod M K, Fleenor C J, Van Rooijen N, Kappler J W, et al. Alum induces innate immune responses through macrophage and mast cell sensors, but these sensors are not required for alum to act as an adjuvant for specific immunity. Journal of immunology. 2009; 183:4403 14.

[48] Gnjatic S, Sawhney N B, Bhardwaj N. Toll-like receptor agonists: are they good adjuvants? Cancer journal. 2010; 16:382-91.

[49] Ishii K J, Akira S. Toll or toll-free adjuvant path toward the optimal vaccine development. Journal of clinical immunology. 2007; 27:363-71.

[50] Li X, Aldayel A M, Cui Z. Aluminum hydroxide nanoparticles show a stronger vaccine adjuvant activity than traditional aluminum hydroxide microparticles. Journal of controlled release: official journal of the Controlled Release Society. 2014; 173:148-57.

We claim:

1. A nanoparticle comprising:
a polymer core;
a lipid shell, wherein the lipid shell comprises a lipid bilayer comprising dioleoyl trimethylammonium propane (DOTAP) or a derivative thereof, DSPE (1,2-Distearoylphosphatidylethanolamine)-PEG (polyethylene glycol)-maleimide, and cholesterol, wherein the lipid shell encapsulates the polymer core;
a first stimulating molecule, wherein the first stimulating molecule is attached to the outer surface of the lipid shell;
a first nicotine-hapten antigen, wherein the first nicotine-hapten antigen is attached to the first stimulating molecule;
a second nicotine-hapten antigen, wherein the second nicotine-hapten antigen is attached to the outer surface of the lipid shell and wherein the second nicotine-hapten antigen is not attached to the first stimulating molecule; and
optionally, a second stimulating molecule, wherein the second stimulating molecule is attached to a polymer of the polymer core, encapsulated in a polymer of the polymer core, encapsulated in the lipid shell, embedded in the lipid bilayer, attached to the inner surface of the lipid shell, attached to the outer surface of the lipid shell, or any combination thereof.

2. The nanoparticle of claim 1, wherein the polymer core comprises poly(lactic-co-glycolic acid).

3. The nanoparticle of claim 1, wherein
the first stimulating molecule, the second stimulating molecule, or both are each independently selected from the group consisting of: keyhole limpet hemocyanin (KLH) multimer, KLH subunit, tetanus toxoid (TT), cross-reacting material 197 (CRM$_{197}$), bovine serum albumin (BSA), human papillomavirus (HPV) proteins, recombinant P. aeruginosa exoprotein A, recombinant cholera toxin B, outer protein capsid of bacteriophage Qb, a peptide, and any combination thereof.

4. The nanoparticle of claim 1, wherein the first stimulating molecule, the second stimulating molecule, or both are each selected from the group consisting of: a toll-like receptor agonist, a dendritic cell surface molecule agonist, a NOD-like receptor agonist, antigen presenting cell agonist, and any combination. thereof.

5. The nanoparticle of claim 4, wherein the toll-like receptor agonist is selected from a CpG oligodeoxynucleotide, a bacterial lipopolysaccharide, a VSV-G protein, HMGB-1, a TLR-1 agonist, a TLR-2 agonist, a TLR-3 agonist, a TLR-4 agonist, a TLR-5 agonist, a TLR-6 agonist, a TLR-7 agonist, a TLR-8 agonist, a TLR-9 agonist, a TLR-10 agonist, a urate crystal, monophosphoryl lipid A (MPLA), and any combination thereof.

6. The nanoparticle of claim 1, wherein the total density of the first nicotine-hapten and the second nicotine-hapten ranges from about 52 to about 115 nicotine-hapten molecules per nanoparticle.

7. The nanoparticle of claim 1, wherein the diameter of the nanoparticle ranges from about 1 nm to 999 nm.

8. A vaccine formulation comprising:
a nanoparticle of claim 1; and
a pharmaceutically acceptable carrier.

9. The vaccine formulation of claim 8, wherein the first stimulating molecule, the second stimulating molecule, or both are each independently selected from the group consisting of: keyhole limpet hemocyanin (KLH) multimer, KLH subunit, tetanus toxoid (TT), cross-reacting material 197 (CRM$_{197}$), bovine serum albumin (BSA), human papillomavirus (HPV) proteins, recombinant P. aeruginosa exoprotein A, recombinant cholera toxin B, outer protein capsid of bacteriophage Qb, a peptide, and any combination thereof.

10. The vaccine formulation of claim 8, wherein the polymer core comprises poly(lactic-co-glycolic acid).

11. The vaccine formulation of claim 8, wherein the first stimulating molecule, the second stimulating molecule, or both are each selected from the group consisting of: a toll-like receptor agonist, a dendritic cell surface molecule agonist, a NOD-like receptor agonist, antigen presenting cell agonist, and any combination thereof.

12. The vaccine formulation of claim 11, wherein the toll-like receptor agonist is selected from a CpG oligodeoxynucleotide, a bacterial lipopolysaccharide, a VSV-G protein, HMGB-1, a TLR-1 agonist, a TLR-2 agonist, a TLR-3 agonist, a TLR-4 agonist, a TLR-5 agonist, a TLR-6 agonist, a TLR-7 agonist, a TLR-8 agonist, a TLR-9 agonist, a TLR-10 agonist, a urate crystal, monophosphoryl lipid A (MPLA), and any combination thereof.

13. The vaccine formulation of claim 8, wherein the total density of the first nicotine-hapten and the second nicotine-hapten ranges from about 52 to about 115 nicotine-hapten molecules per nanoparticle.

14. The vaccine formulation of claim 8, wherein the diameter of the nanoparticle ranges from about 1 nm to 999 nm.

15. The vaccine formulation of claim 8, wherein the vaccine formulation does not contain Alum.

16. A method of treating nicotine addiction or a symptom thereof in a subject in need thereof, the method comprising:

administering a nanoparticle according to claim 1, to the subject in need thereof.

17. The method of claim 16, wherein the polymer core comprises poly(lactic-co-glycolic acid).

18. The method of claim 16, wherein the first stimulating molecule, the second stimulating molecule, or both are each independently selected from the group consisting of: keyhole limpet hemocyanin (KLH) multimer, KLH subunit, tetanus toxoid (TT), cross-reacting material 197 ($CRM_{197}$), bovine serum albumin (BSA), human papillomavirus (HPV) proteins, recombinant *P. aeruginosa* exoprotein A, recombinant cholera toxin B, outer protein capsid of bacteriophage Qb, a peptide, and any combination thereof.

19. The method of claim 16, wherein the first stimulating molecule, the second stimulating molecule, or both are each selected from the group consisting of: a toll-like receptor agonist, a dendritic cell surface molecule agonist, a NOD-like receptor agonist, antigen presenting cell agonist, and any combination thereof.

20. The method of claim 19, wherein the toll-like receptor agonist is selected from a CpG oligodeoxynucleotide, a bacterial lipopolysaccharide, a VSV-G protein, HMGB-1, a TLR-1 agonist, a TLR-2 agonist, a TLR-3 agonist, a TLR-4 agonist, a TLR-5 agonist, a TLR-6 agonist, a TLR-7 agonist, a TLR-8 agonist, a TLR-9 agonist, a TLR-10 agonist, a urate crystal, monophosphoryl lipid A (MPLA), and any combination thereof.

* * * * *